(12) United States Patent
Wessler et al.

(10) Patent No.: US 8,063,268 B2
(45) Date of Patent: Nov. 22, 2011

(54) TRANSPOSABLE ELEMENTS IN RICE AND METHODS OF USE

(75) Inventors: Susan R. Wessler, Athens, GA (US); Ning Jiang, Athens, GA (US); Zhirong Bao, Seattle, WA (US); Xiaoyu Zhang, Athens, GA (US); Sean R. Eddy, St. Louis, MO (US)

(73) Assignees: Washington University, St. Louis, MO (US); University of Georgia Research Foundation, Inc., Athens, GA (US)

( * ) Notice: Subject to any disclaimer, the term of this patent is extended or adjusted under 35 U.S.C. 154(b) by 709 days.

(21) Appl. No.: 11/775,665

(22) Filed: Jul. 10, 2007

(65) Prior Publication Data

US 2007/0294788 A1 Dec. 20, 2007

Related U.S. Application Data

(63) Continuation of application No. 10/346,198, filed on Jan. 16, 2003, now Pat. No. 7,250,556.

(60) Provisional application No. 60/377,409, filed on May 1, 2002.

(51) Int. Cl.
*C12N 15/82* (2006.01)
*C12N 15/29* (2006.01)
*C12N 15/09* (2006.01)
*A01H 5/00* (2006.01)
*A01H 5/10* (2006.01)

(52) U.S. Cl. ..... 800/291; 800/278; 800/298; 435/320.1; 435/468; 435/419; 536/23.1; 536/23.6

(58) Field of Classification Search .......... None
See application file for complete search history.

(56) References Cited

U.S. PATENT DOCUMENTS

| | | | |
|---|---|---|---|
| 6,420,117 B1 | 7/2002 | Wessler et al. | 435/6 |
| 2002/0199216 A1* | 12/2002 | MacRae | 800/279 |
| 2004/0088761 A1 | 5/2004 | Tanaka et al. | |
| 2005/0125854 A1* | 6/2005 | Kikuchi et al. | 800/278 |

FOREIGN PATENT DOCUMENTS

| | | |
|---|---|---|
| WO | WO0105986 | 1/2001 |
| WO | 01/73036 | 10/2001 |
| WO | WO 01/32881 A1 | 10/2001 |
| WO | WO 03/040363 A1 | 5/2003 |

OTHER PUBLICATIONS

Database EMBL, Oct. 4, 2001, "Oryza Sativa Japonica Group Genomic DNA, Chromosome 6, PAC Clone: P0417D05," Database Accession No. AP004236.
Bureau et al., 1994, "Stowaway: A New Family of Inverted Repeat Elements Associated with the Genes of Both Monocotyledonous and Dicotyledonous Plants," The Plant Cell, 6:907-916.
Feschotte et al., 2000, "Evidence that a Family of Miniature Inverted-Repeat Transposable Elements (MITEs) from the Arabidopsis Thaliana Genome has Arisen from a Pogo-Like DNA Transposon," Molecular Biology and Evolution, 17 (5):730-737.
Han et al., 2000, "New Transposable Elements Identified as Insertions in Rice Transposon TNR1," Genes and Genetic Systems, 75:69-77.
Jarvik et al., 1998, "Characterization of Soymar1, a Mariner Element in Soybean," Genetics, 149:1569-1574.
Taylor et al., 1987, "Isolation and Characterization of a 1.7-kb Transposable Element from a Mutator Line of Maize," Genetics, 117:297-307.
Yang et al., 2001, "Kiddo, a New Transposable Element Family Closely Associated with Rice Genes," Mol. Genet. Genomics, 266:417-424.
Supplementary European Search Report dated Aug. 11, 2008 for EP Application No. 03 70 7441 (3 pages).
Yano, et al., "Hd1, a Major Photoperiod Sensitivity Quantitative Trait Locus in Rice, Is Closely Related to the Arabidopsis Flowering Time Gene Constans", *The Plant Cell*, 12:2473-2483 (2000).
Bureau, et al., "A computer-based systematic survey reveals the predominance of small inverted-repeat elements in wild-type rice genes", 1996 *Proc. Natl. Acad. Sci. USA*, 93:8524-8529.
Casa et al., "The MITE family *Heartbreaker(HBR)*: Molecular markers in maize", 2000 *Proc. Natl. Acad. Sci. USA*, 97(18):10083-10089.
Feschotte et al., "Mariner-like transposases are widespread and diverse in flowering plants", 2002 *Proc. Natl. Acad. Sci. USA*, 99(1):280-285.
Feschotte et al., "Plant Transposable Elements: Where Genetics Meets Genomics", 2002 *Nat. Rev. Genet.*, 3:329-341.
Goff et al., "A Draft Sequence of the Rice Genome (*Oryza sativa* L. ssp. *japonica*)", 2002, *Science*, 296:92-100.
Hirochika, H., "Activation of tobacco retrotransposons during tissue culture", 1993 *EMBO J.*, 12(6):2521-2528.
Hirochika, et al., "Retrotransposons of rice involved in mutations induced by tissue culture", 1996 *Proc. Natl. Acad. Sci. USA*, 93:7783-7788.
Jiang et al., "Insertion Preference of Maize and Rice Minature Inverted Repeat Transposable Elements as Revealed by the Analysis of Nested Elements", 2001 *Plant Cell*, 13:2553-2564.
Jiang et al., "An active DNA transposon family in rice", 2003 *Nature* 421(6919):163-167.
Kawakami, et al., "Identification of a functional transposase of the *Tol2* element, an *Ac*-like element from the Japanese medaka fish, and its transposition in the Zebrafish germ lineage", 2000 *Proc. Natl. Acad. Sci. USA*, 97(21):11403-11408.

(Continued)

Primary Examiner — Brent T Page
(74) Attorney, Agent, or Firm — Pabst Patent Group LLP

(57) ABSTRACT

Disclosed are isolated transposable elements, or isolated DNA sequences which encode a transposase protein or a portion of a transposase protein. The isolated transposable elements or the isolated DNA sequences are members of the mPing/Pong family of transposable elements. The invention also relates to a purified transposase protein, or peptide fragments thereof, encoded by such DNA sequences. Such transposable elements are useful in applications such as the stable introduction of a DNA sequence of interest into a eukaryotic cell. The sequence information disclosed herein is useful in the design of oligonucleotide primers which are useful for the isolation of related members of the mPing/Pong family of transposable elements, or for the detection of transpositions of the transposable elements.

8 Claims, 23 Drawing Sheets

OTHER PUBLICATIONS

Mao, et al., "Rice Transposable Elements: A Survey of 73,000 Sequence-Tagged-Connectors", 2000 *Genome Res.,* 10(7):982-990.

Tarchini et al., "The Complete Sequence of 340 kb of DNA around the Rice *Adhl-Adh2* Region Reveals Interrupted Colinearity with Maize Chromosome 4", 2000 *Plant Cell,* 12:381-391.

Turcotte et al., "Survey of transposable elements from rice genomic sequences", 2001 *Plant J.,* 25(2):169-179.

Yu, et al., "A Draft Sequence of the Rice Genome (*Oryze sativa* L. ssp. *indica*)", 2002 *Science,* 296:79-92.

Zhang, et al., "*P* instability factor: An active maize transposon system associated with the amplification of *Tourist*-like MITEs and a new superfamily of transposases", *Proc. Natl. Acad. Sci. USA,* 98(22):12572-12577, 2001.

* cited by examiner

Figure 2

| Chromosome | Accession number | Position (bp) | Orientation * | Strain |
|---|---|---|---|---|
| 1 | Ap003681 | 9421-9580 | C | Nipponbare |
| 1 | Ap003054 | 27515-27944 | C | Nipponbare |
| 1 | Ap002843 | 144459-1444888 | C | Nipponbare |
| 1 | Ap003453 | 69332-69761 | C | Nipponbare |
| 1 | Ap003253 | 118715-119144 | + | Nipponbare |
| 2 | Ap004049 | 87505-87934 | C | Nipponbare |
| 2 | Ap004752 | 96298-96727 | + | Nipponbare |
| 2 | Ap004062 | 61350-61779 | + | Nipponbare |
| 2 | Ap004255 | 71064-71493 | C | Nipponbare |
| 2 | Ap004071 | 16713-17142 | C | Nipponbare |
| 3 | Ac107315 | 73615-74044 | C | Nipponbare |
| 3 | Ac0107226 | 25272-25701 | + | Nipponbare |
| 3 | Ac607101 | 88446-88875 | C | Nipponbare |
| 3 | Ac083942 | 96505-96934 | + | Nipponbare |
| 3 | Ac093018 | 47331-47760 | + | Nipponbare |
| 4 | Al606456 | 103997-104426 | C | Nipponbare |
| 4 | Al606635 | 64979-65408 | C | Nipponbare |
| 4 | Al606652 | 98400-98829 | C | Nipponbare |
| 4 | Al606656 | 25466-25895 | + | Nipponbare |
| 5 | Ac093919 | 44810-45239 | C | Nipponbare |
| 6 | Ap003618 | 37191-37620 | C | Nipponbare |
| 6 | Ap003572 | 58823-59252 | + | Nipponbare |
| 6 | Ap004329 | 97684-98113 | C | Nipponbare |
| 7 | Ap003753 | 58467-58896 | + | Nipponbare |
| 7 | Ap004384 | 500-929 | + | Nipponbare |
| 8 | Ap004587 | 72873-73302 | + | Nipponbare |

Figure 2 (continued)

| 8 | Ap003925 | 103864-104293 | + | Nipponbare |
|---|---|---|---|---|
| 8 | Ap004617 | 112570-112999 | C | Nipponbare |
| 8 | Ap004463 | 86742-87171 | C | Nipponbare |
| 8 | Ap003860 | 131982-132411 | C | Nipponbare |
| 8 | Ap004692 | 64470-64899 | + | Nipponbare |
| 8 | Ap004562 | 8801-9230 | + | Nipponbare |
| 10 | Al607098 | 91380-91809 | + | Nipponbare |
| 10 | Ac026758 | 8064-8492 | C | Nipponbare |
| 11 | Ac109594 | 104427-104856 | + | Nipponbare |
| 6 | Ab041842 | 2784-3213 | + | Ginbouzu |

* "+" indicates the element is in the same orientation as consensus sequence; "C" indicates that the element is in the complementary orientation compared to consensus sequence.

Figure 4

| Chromosome | Accession number | Position (bp) | Orientation * | Strain |
|---|---|---|---|---|
| 6 | Ap004236 | 89360-94700 | + | Nipponbare |

Figure 5

| Chromosome | Accession number | Position (bp) | Orientation * | Strain |
|---|---|---|---|---|
| 2 | Ap004753 | 59569-64734 | C | Nipponbare |
| 6 | Ap003543 | 25305-32616 | C | Nipponbare |
| 6 | Ap003714 | 8360-13525 | + | Nipponbare |
| 11 | Ac112208 | 124572-129737 | C | Nipponbare |

Figure 6

| Contig number | Position | Orientation* |
|---|---|---|
| 30367 | 42-470 | C |
| 7740 | 6834-7263 | C |
| 2926 | 2509-2938 | C |
| 4745 | 11119-11537 | C |
| 22661 | 954-1372 | + |
| 9483 | 1506-1984 | + |
| 6265 | 3777-4195 | + |
| 43 | 23012-23430 | + |
| 47711 | 1147-1425 | + |
| 79075 | 1-254 | C |
| 11984 | 1-340 | C |
| 74523 | 698-844 | C |

Figure 7

| | | |
|---|---|---|
| Plant | Monocots | Rice (AP003986), Sorghum (AF114171), Barley (AJ001317), Wheat (AF459639), Maize (BH140750) |
| | Dicots | *Arabidopsis* (AC018660), Soybean (AF271796), *L. japonica* (AP004506), Suger beet (BI643302), Medicago (BG585958), Tomato (AW616734), Stevia (BG525000), Peppermint (AW255120), Brassica (BH493441) |
| | Algae | *Physcomitrella patens* (BJ164583), *Porphyra yezoensis* (AV436370) |
| Animal | Invertebrates | *C. elegans* (AF040643), *C. briggsae* (AC090524), *Drosophila* (AE003496), Silkworm (AV404936), Mosquito (AAAB01008967), Ciona (AV996094) |
| | Vertebrates | Zebrafish (AL591210), Mouse (BI247185), Pig (BF191773), Cow (BE668489), Human (AK057237) |
| Fungus | | *F. neoformans* (AC068564), *N. crassa* (NC93G11) |

Sequences were found by tBlastn searches (one GenBank accession number from each species is shown as an example).

Figure 8

| Element | Adapter primer | Size of the fragment from TD | Hit in database | Position of insertion site[1] |
|---|---|---|---|---|
| mPing | Mse1 + A | 89 | Contig482 | 21140 |
| | | 101 | Contig7079 | 5186 |
| | | 119 | Contig10017 | 7552 |
| | | 129 | Contig16063 | 4588 |
| | | 137 | Contig21518 | 1963 |
| | | 148 | Contig24556 | 2216 |
| | | 165 | Contig40966 | 517 |
| | | 173 | Contig4310 | 4497 |
| | | 195 | Contig391 | 157 |
| | | 237 | Contig34913 | 276 |
| | | 247 | Contig65368 | 166 |
| | | 320 | Contig23309 | 338 |
| | Mse1 + C | 126 | Contig909 | 21055 |
| | | 152 | Contig17922 | 3757 |
| | | 172 | Contig17222 | 4466 |
| | | 187 | Contig4708 | 2198 |
| | | 238 | Contig18737 | 4241 |
| | | 244 | Contig42209 | 1029 |
| | | 256 | Contig25343 | 2750 |
| | Mse1 + G | 93 | Contig17946 | 4149 |
| | | 124 | Contig17419 | 2467 |
| | | 136 | Contig23646 | 1322 |
| | | 147 | Contig1408 | 5777 |
| | | 153 | Contig2742 | 15355 |
| | | 189 | Contig17506 | 1995 |
| | | 217 | Contig15096 | 1964 |
| | | 239 | Contig63623 | 327 |
| | | 262 | Contig5138 | 10139 |
| | | 302 | Contig7692 | 1306 |
| | | | Contig22012 | 962 |
| | Mse1 + T | 143 | AL731884[2] | 10135[2] |
| | | 162 | Contig13315 | 1527 |
| | | 164 | Contig2742 | 15355 |
| | | 196 | Contig63668 | 72 |
| | | 230 | Contig10585 | 7471 |
| | | 267 | Contig10749 | 6329 |
| Ping | Mse1 + 0 | 116 | Contig7304 | 8347 |
| | | 141 | Contig2744 | 3314 |
| | | 169 | Contig1031 | 18894 |
| | | 181 | Contig18 | 48390 |
| | | 203 | Contig35873 | 1 |
| | | 224 | Contig3321 | 8382 |
| | | | Contig16311 | 5969 |
| | | | Contig24541 | 2774 |
| | | 257 | Contig494 | 22438 |
| | | 318 | Contig18755 | 2443 |
| | | 340 | Contig51 | 16732 |
| | | 377 | Contig6747 | 193 |

[1] The position of the first nucleotide of the trinucleotide TSD is listed
[2] GenBank accession number for Nipponbare. All others are from 93-11

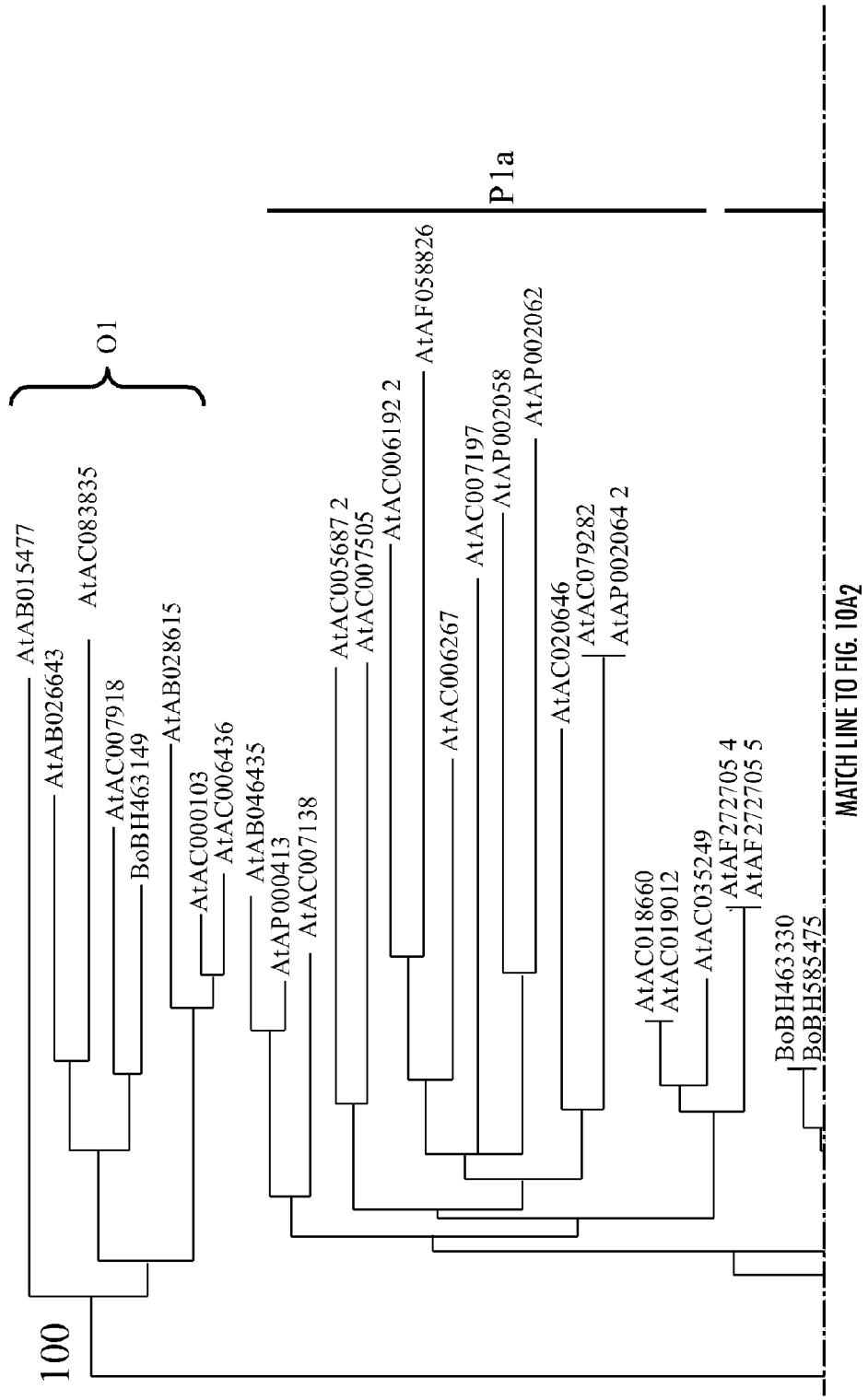
Fig. 10A₁

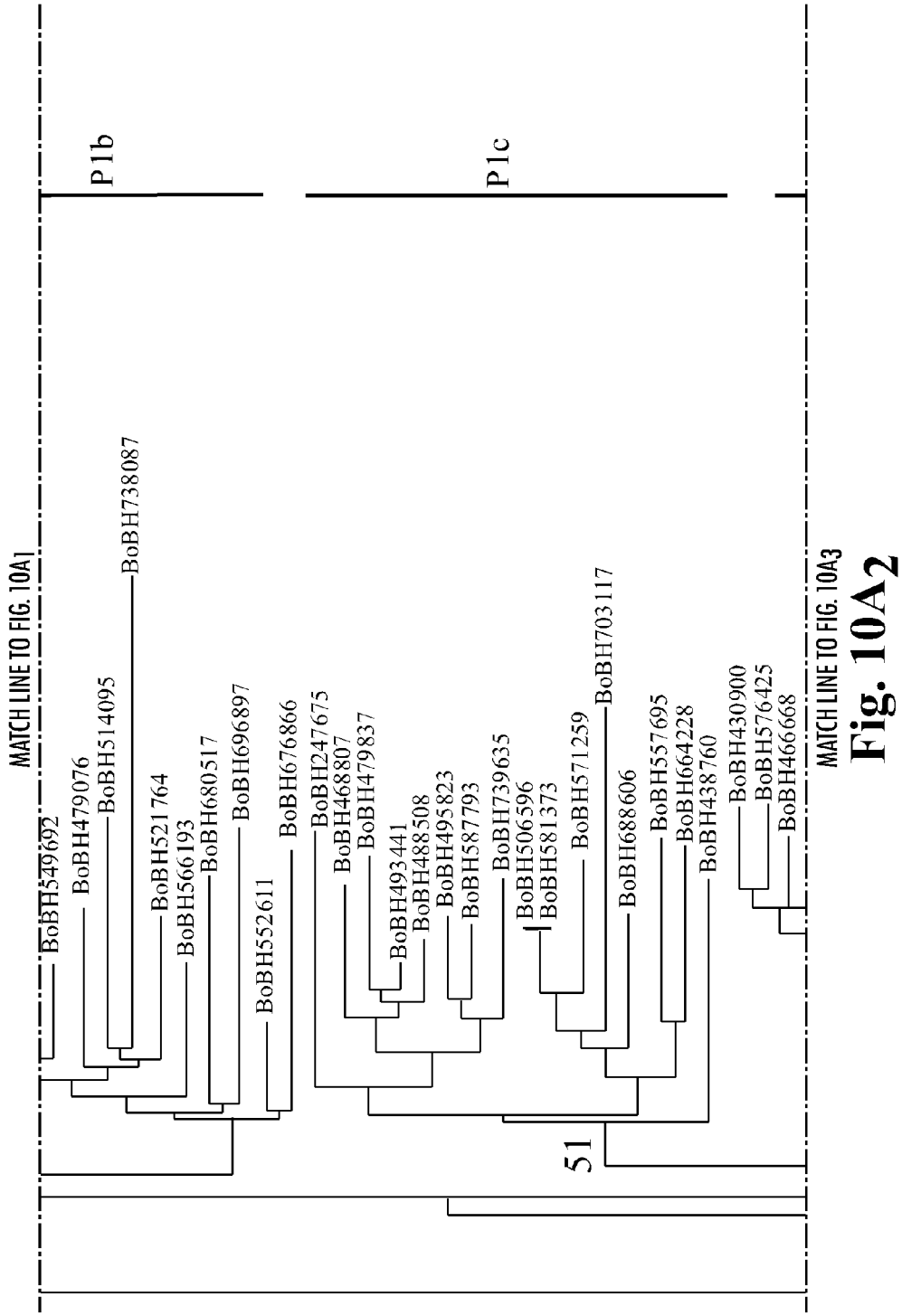
Fig. 10A2

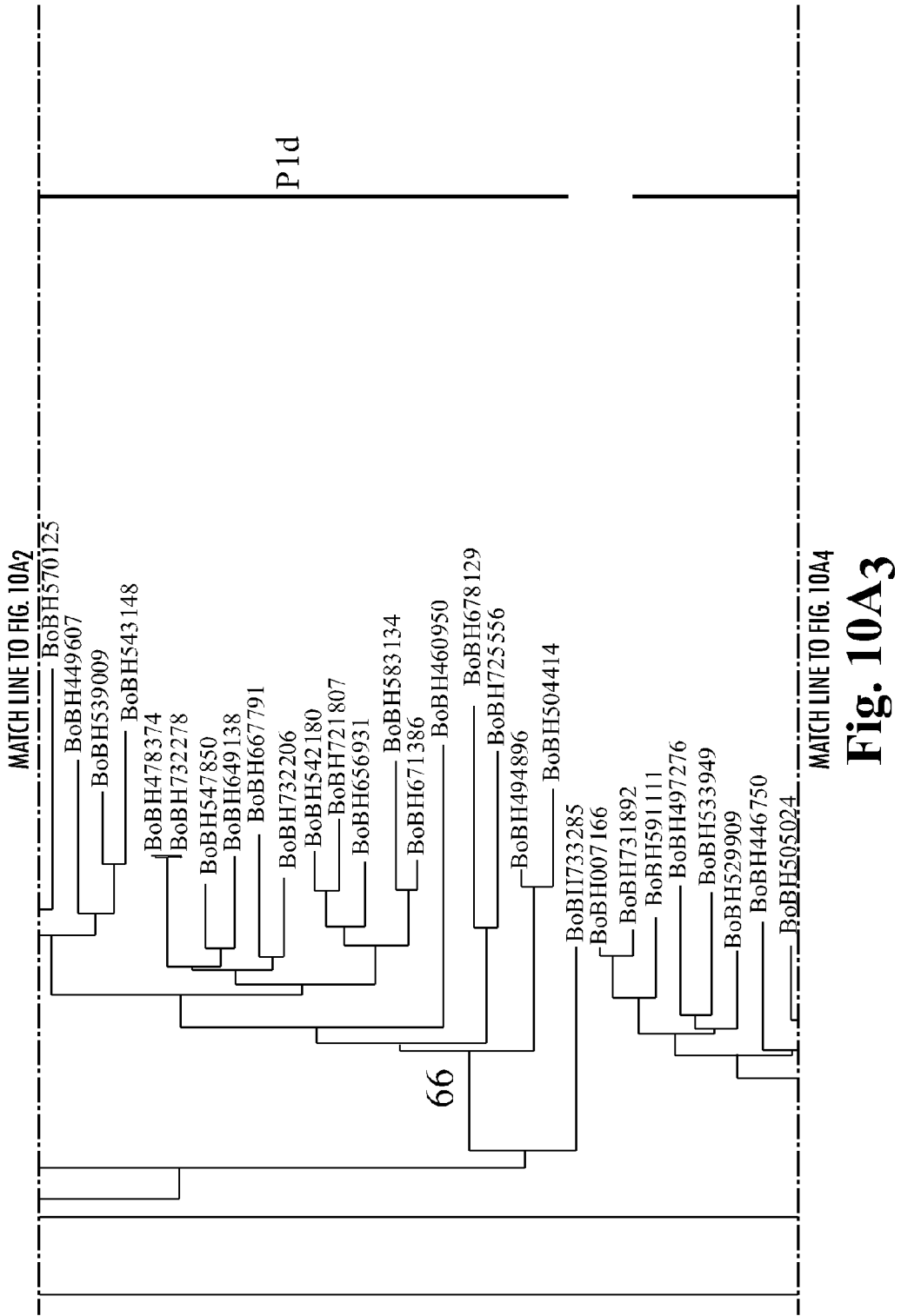

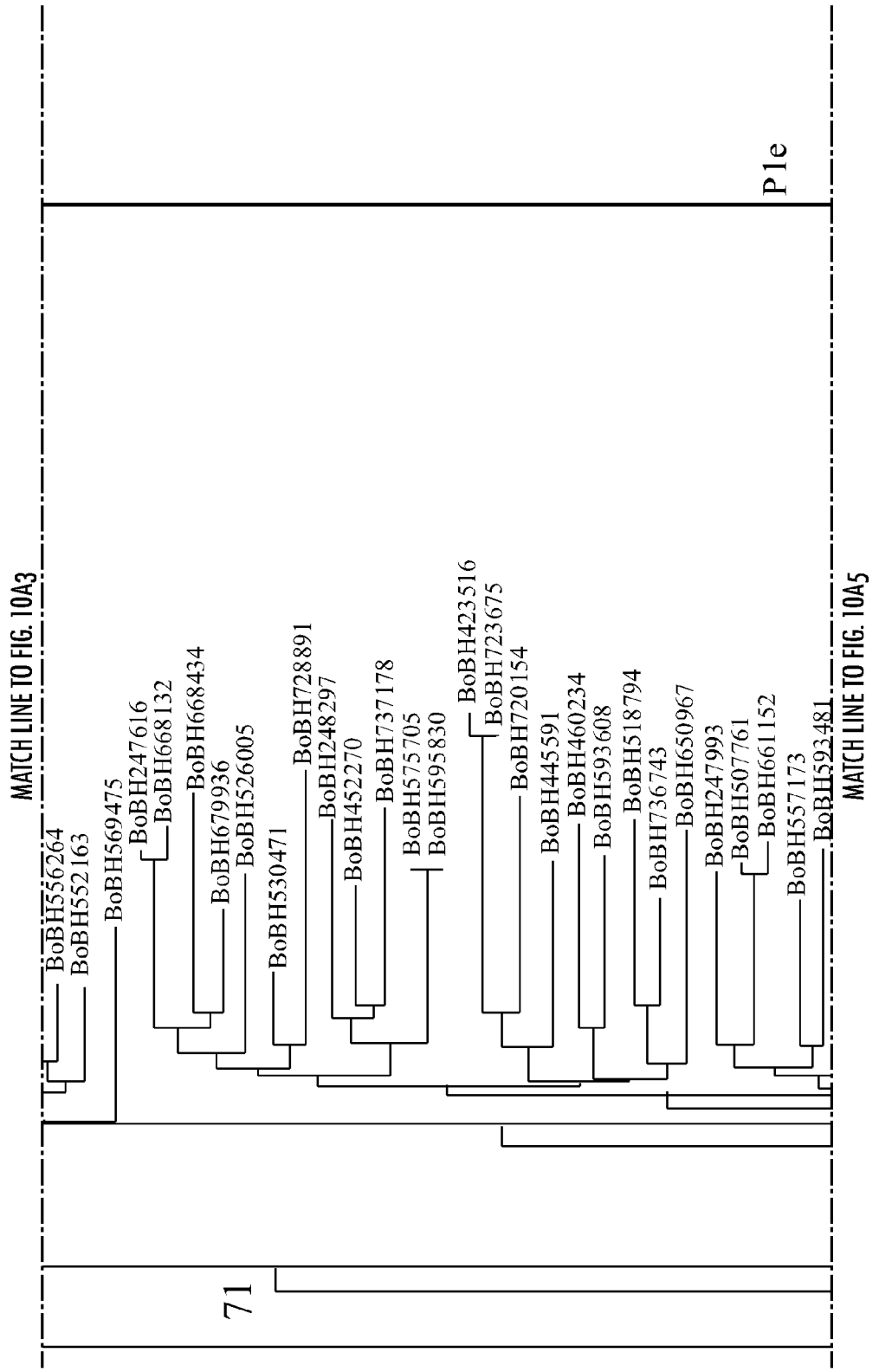

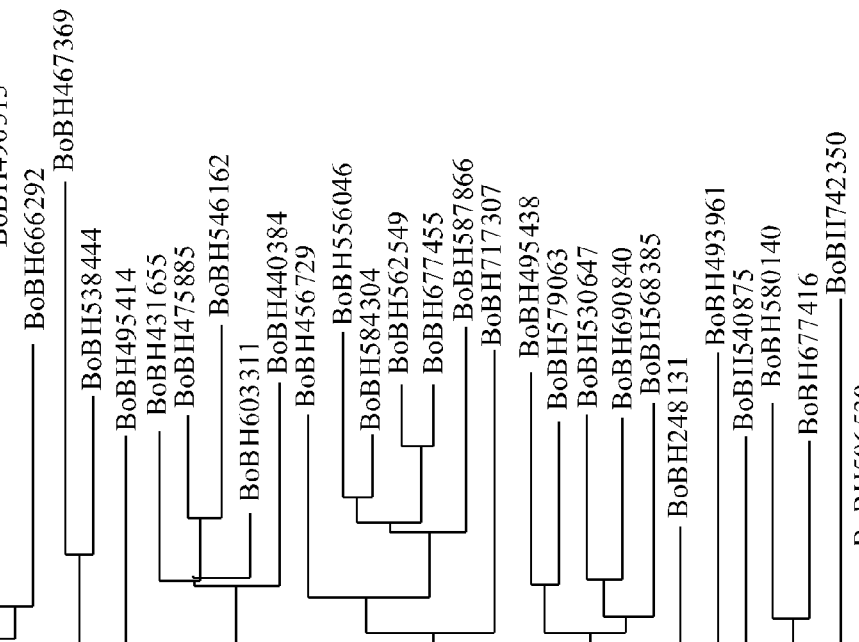

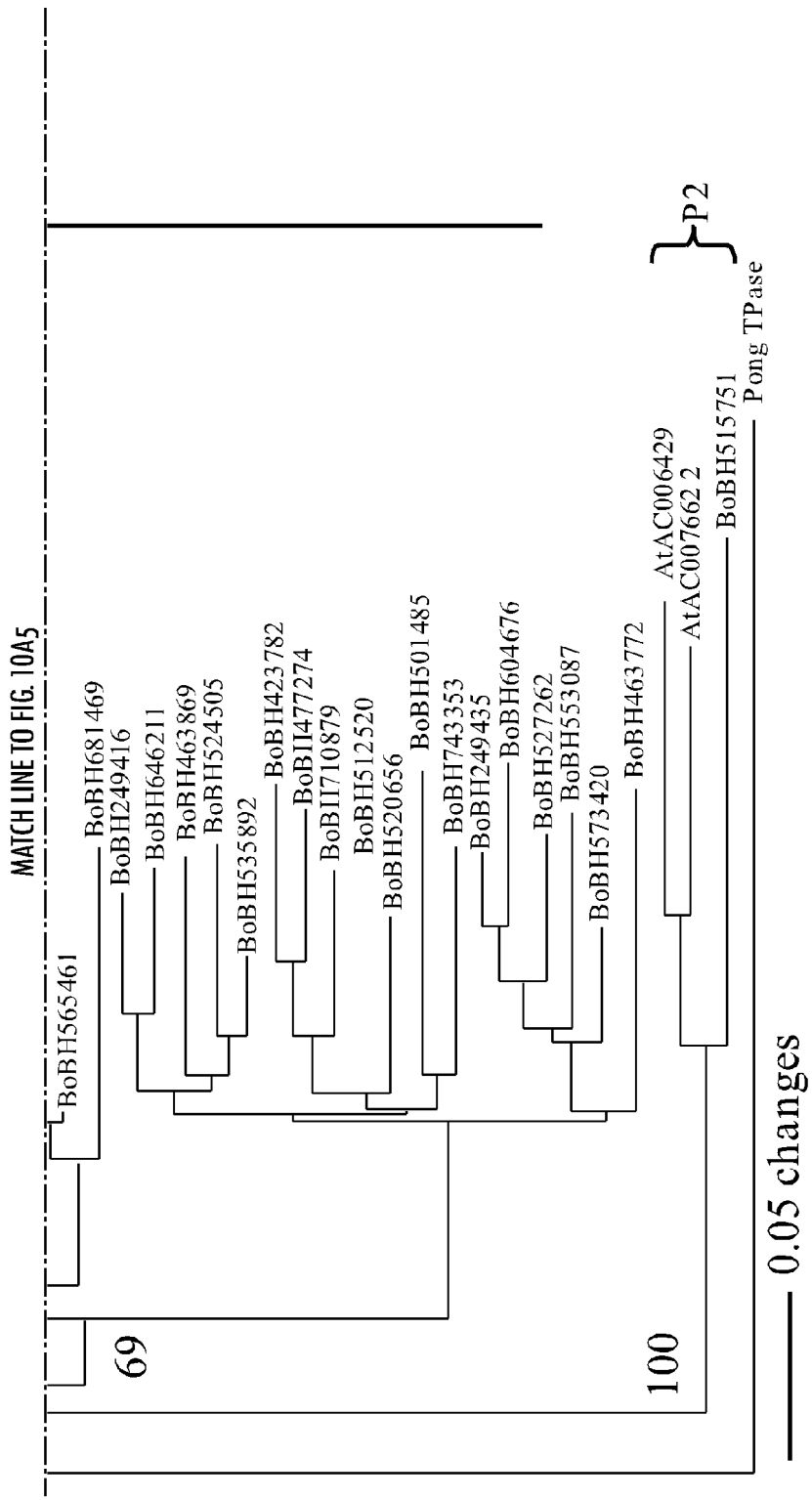
Fig. 10A₆

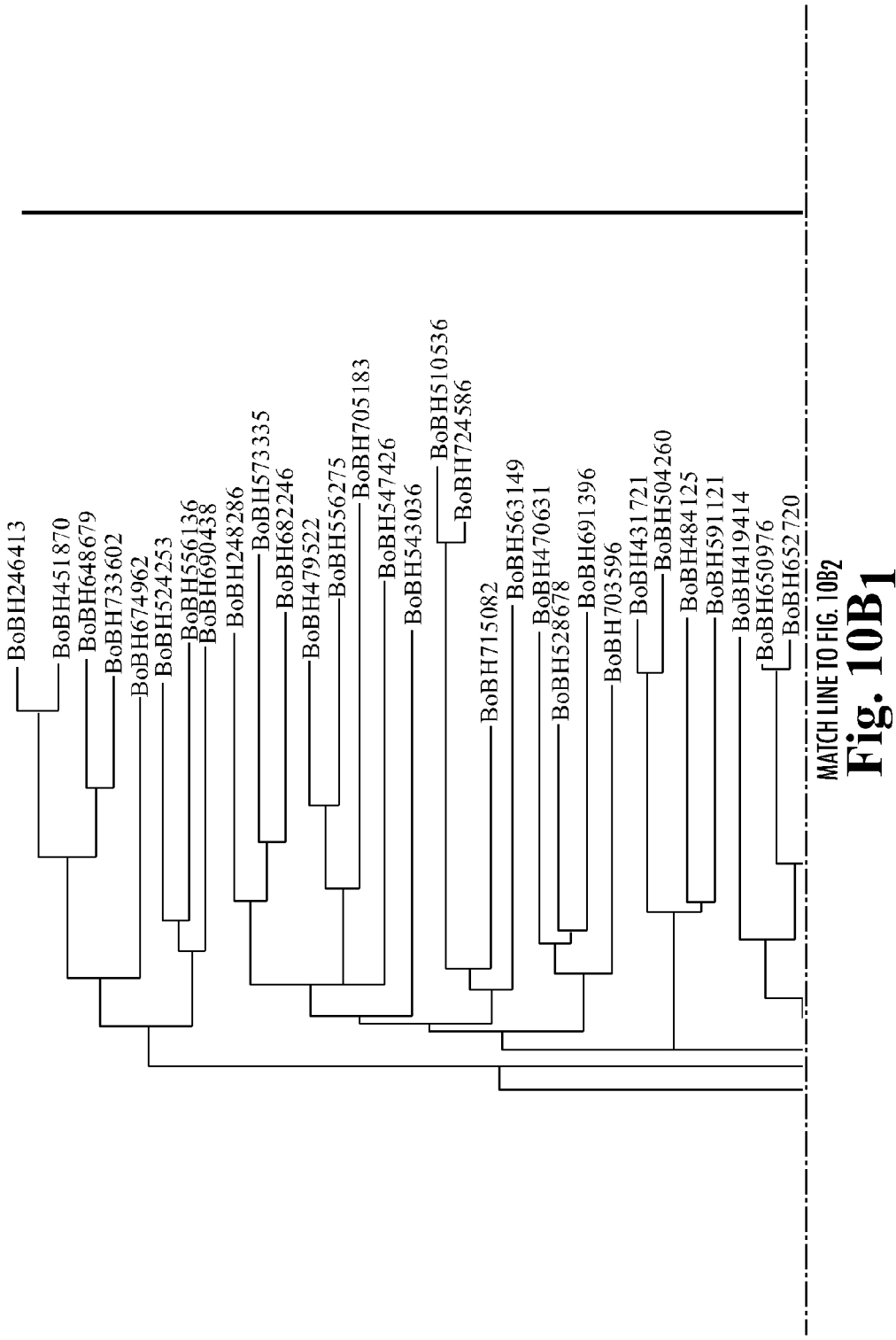

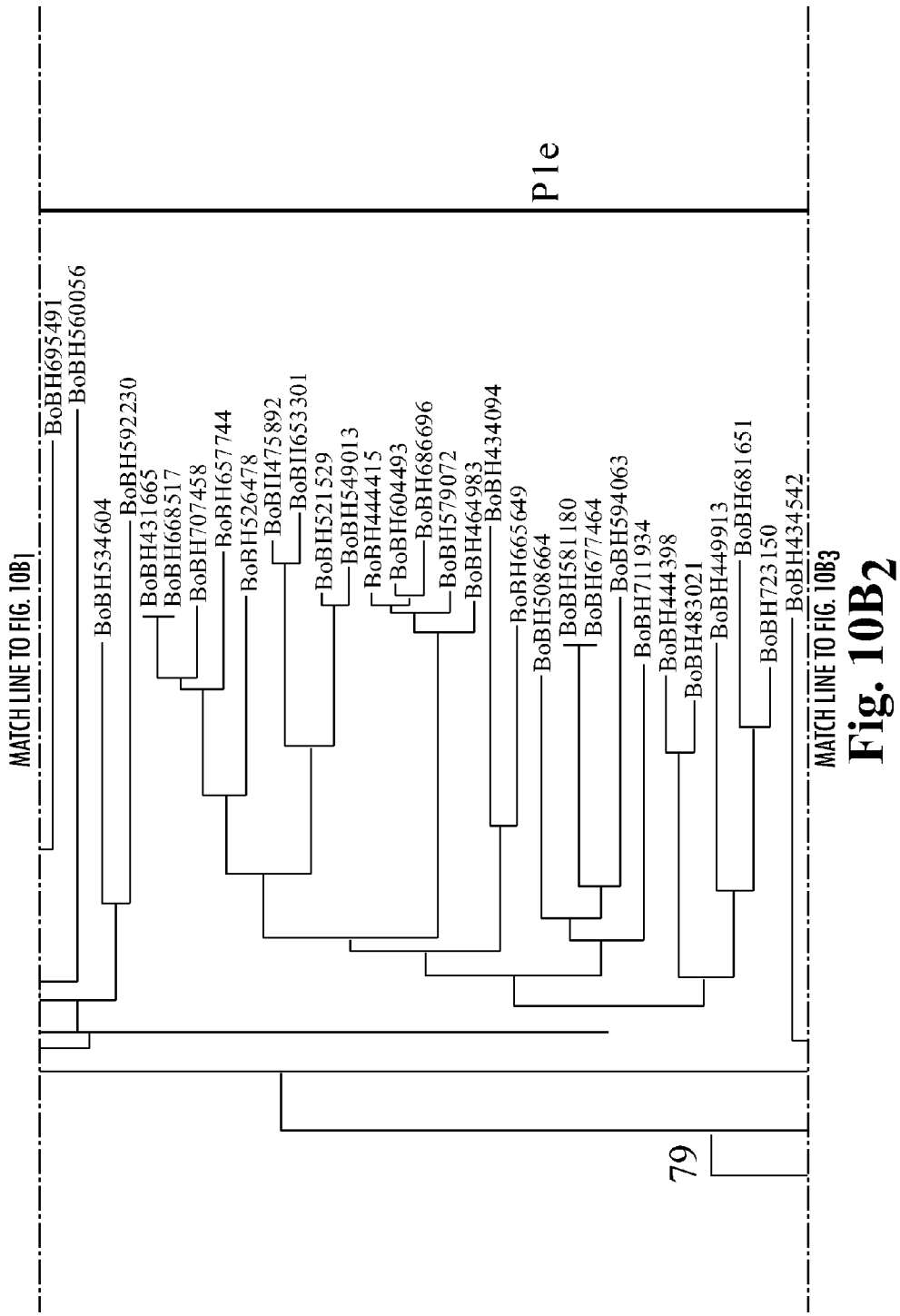
Fig. 10B2

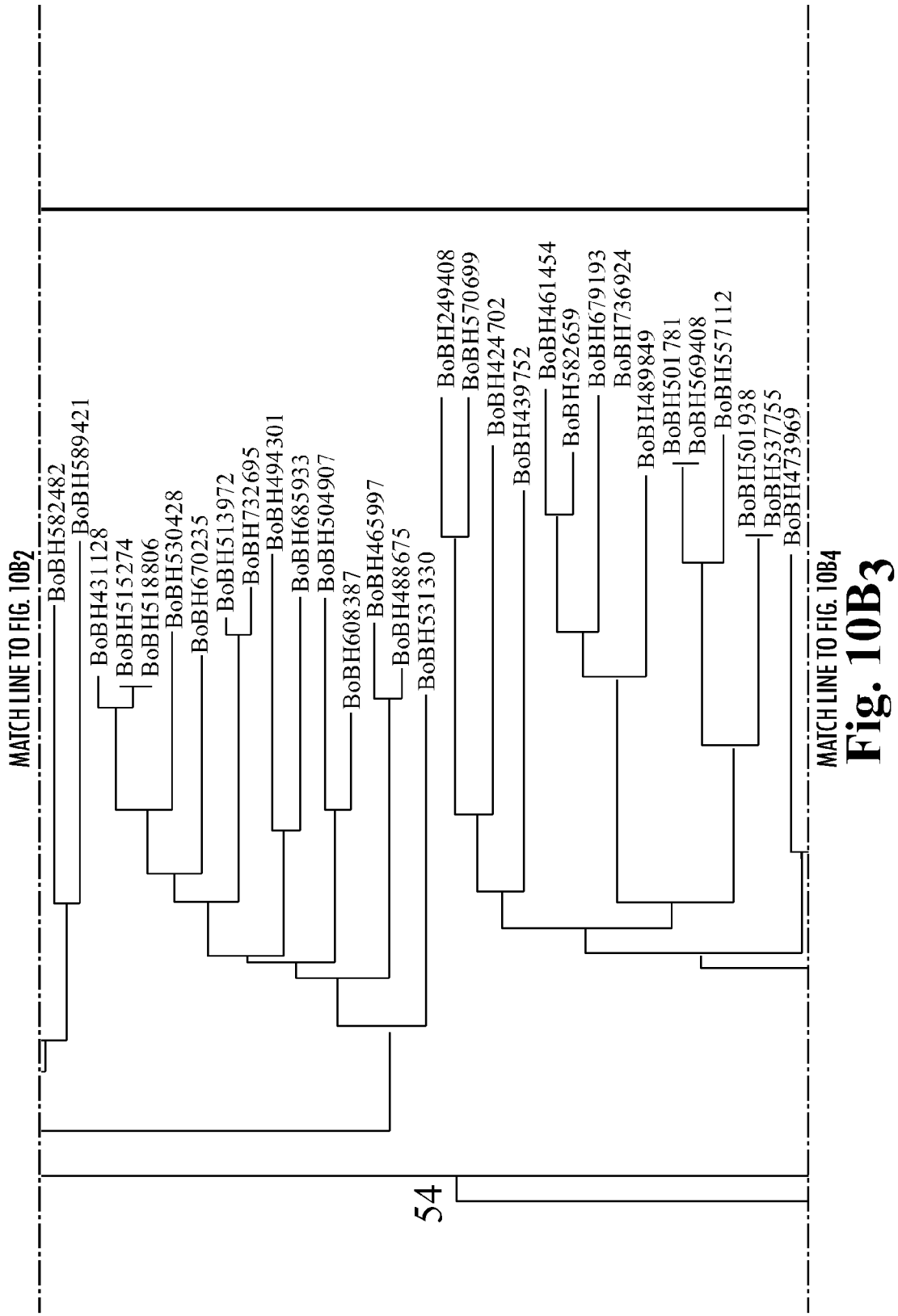
Fig. 10B3

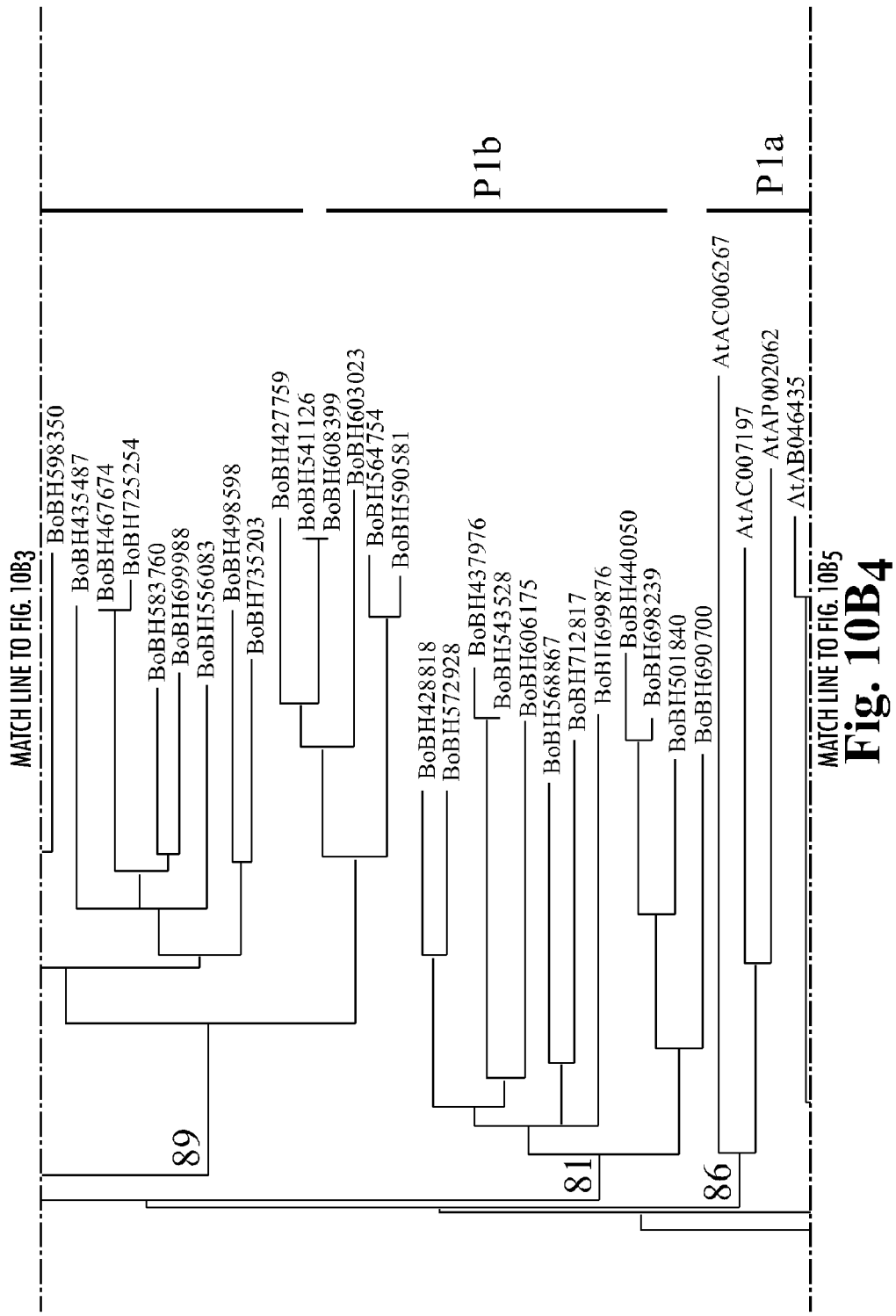
Fig. 10B4

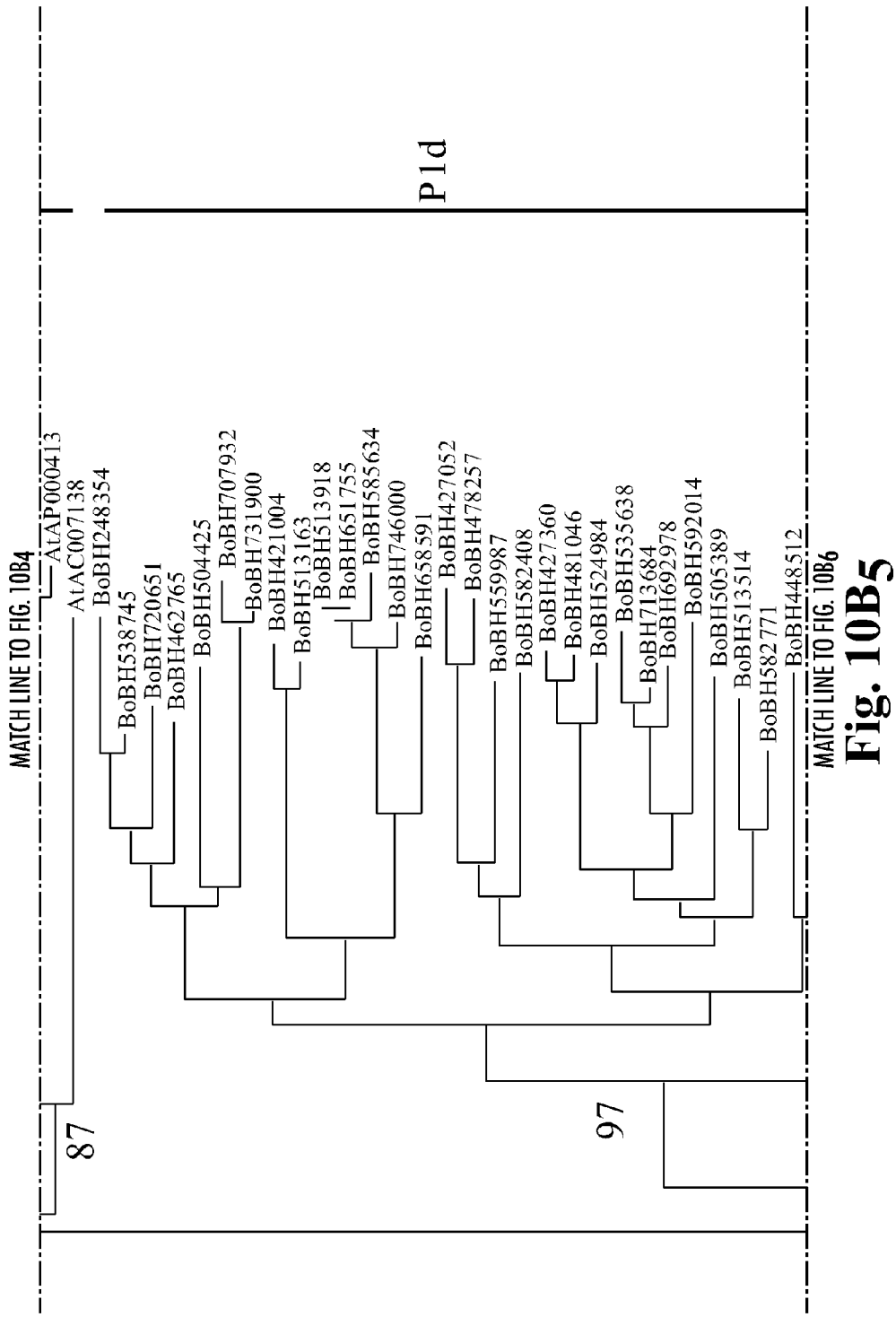
Fig. 10B5

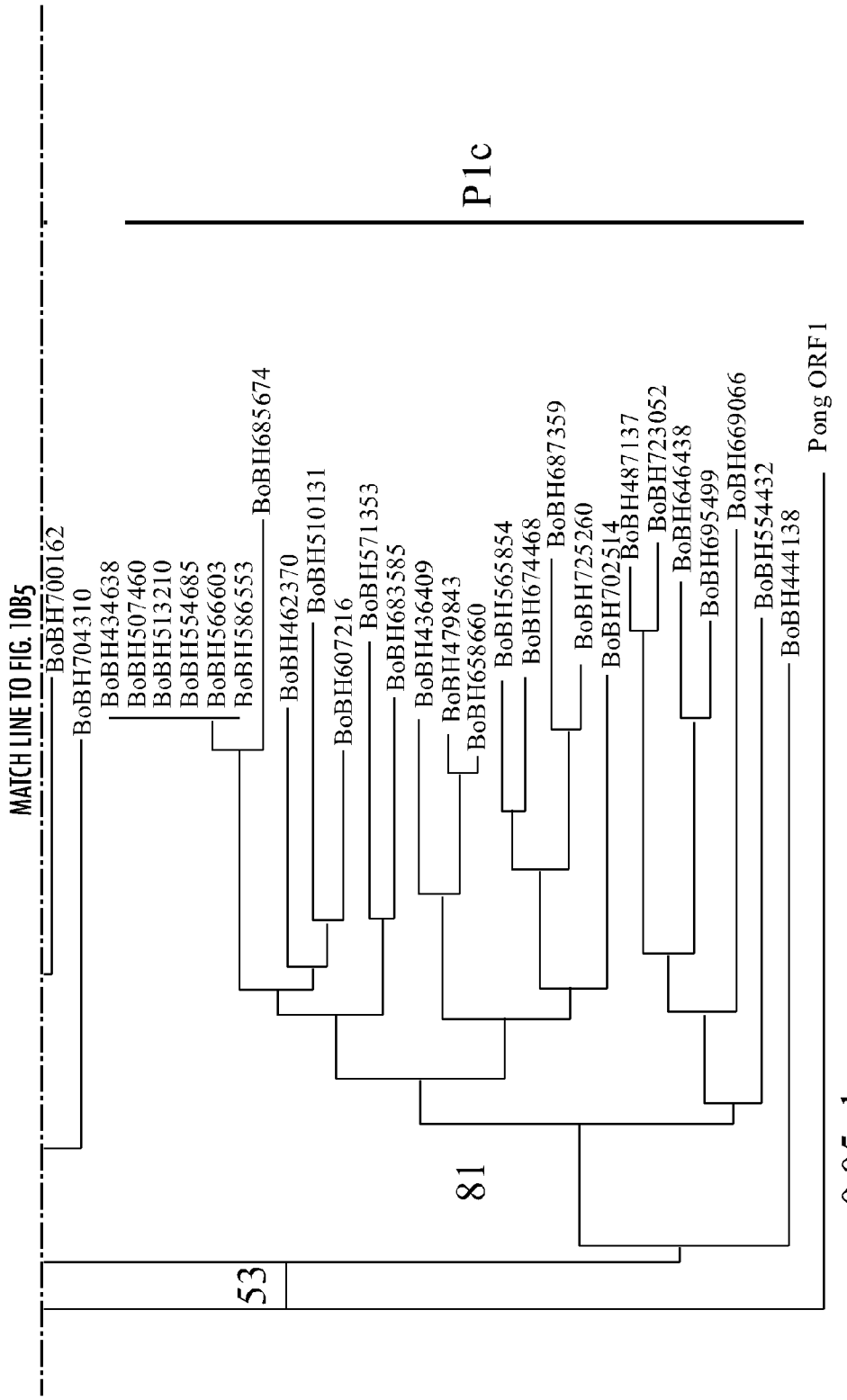
Fig. 10B₆

TRANSPOSABLE ELEMENTS IN RICE AND METHODS OF USE

CROSS REFERENCE TO RELATED APPLICATIONS

This application is a continuation of U.S. application Ser. No. 10/346,198 filed on Jan. 16, 2003, pending, which claims priority to U.S. Provisional Patent Application Ser. No. 60/377,409 filed May 1, 2002.

ACKNOWLEDGMENT OF FEDERAL RESEARCH SUPPORT

This invention was made, at least in part, with funding from the National Science Foundation (DBI 0077709) to SRW. Accordingly, the United States Government has certain rights in this invention.

BACKGROUND OF THE INVENTION

1. Field of the Invention

This invention relates generally to nucleic acid sequences encoding members of the mPing/Pong family of transposable elements. In addition, this invention relates to nucleic acid sequences encoding polypeptides that function as transposases, or polypeptides that interact with transposases to modulate the transposition of members of the mPing/Pong genus of transposable elements.

2. Background Art

Rice is the most important crop for human nutrition in the world. At 430 Mb, rice also has the smallest genome among the agriculturally important cereals, including the genomes of maize, sorghum, barley and wheat (Arumuganathan & Earle, 1991 *Plant Mol. Biol.,* 9: 208-218). For these reasons rice is the focus of several genome sequencing projects in both the public and private sectors (Burr, 2002 *Plant Cell,* 14: 521-523; Goff, et al., 2002 *Science,* 296: 92-100; Yu, et al., 2002 *Science,* 296: 79-92). Computer-assisted analyses of rice genomic sequence indicate that despite its small size, over 40% of the genome is repetitive DNA; most of this is related to transposable elements (Goff, et al., 2002 *Science,* 296: 92-100; Yu, et al., 2002 *Science,* 296: 79-92). Although the largest component of transposable elements in the rice genome is class 1 LTR retrotransposons (14%), the largest group with over 100,000 elements divided into hundreds of families is miniature inverted-repeat transposable elements (MITEs), comprising about 6% of the genome (Tarchini et al., 2000 *Plant Cell,* 12: 381-391; Jiang & Wessler, 2001 *Plant Cell,* 13: 2553-2564). MITEs are the predominant transposable element associated with the noncoding regions of the genes of flowering plants, especially the grasses and have been found in several animal genomes including nematodes, mosquitoes, fish, and humans (reviewed in Feschotte et al., 2002 *Nat. Rev. Genet.,* 3: 329-341).

MITEs are structurally reminiscent of nonautonomous DNA (class 2) elements with their small size (less than 600 bp) and short (10 to 30 bp) terminal inverted repeat (TIR). However, their high copy number (up to 10,000 copies/family) and target-site preference for TA or TAA distinguish them from most previously described nonautonomous DNA elements (Feschotte et al., 2002 *Nat., Rev. Genet.,* 3: 329-341). Nonautonomous elements, which make up a significant fraction of eukaryotic genomes, have been classified into families based on the transposase responsible for their mobility. Classifying MITEs in this way has been problematic because no actively transposing MITE had been reported in any organism. Instead, based on the similarity of their TIRs and their target site duplication (TSD), most of the tens of thousands of plant MITEs have been classified into two superfamilies: Tourist-like MITEs and Stowaway-like MITEs (Jiang & Wessler, 2001 *Plant Cell,* 13: 2553-2564; Turcotte et al., 2001 *Plant J.,* 25: 169-179; Feschotte & Wessler, 2002 *Proc. Natl. Acad. Sci. USA,* 99: 280-285). Recently, evidence has accumulated linking Tourist and Stowaway MITEs with two superfamilies of transposases, PIF/IS5 and Tc1/mariner, respectively (Turcotte et al., 2001 *Plant J.,* 25: 169-179; Feschotte & Wessler, 2002 *Proc. Natl. Acad. Sci. USA,* 99: 280-285; Zhang, et al., *Proc. Natl. Acad. Sci. USA,* 98: 12572-12577).

Activity has not been demonstrated for any of the hundreds of MITE families previously identified in the rice genome, however three families of LTR retrotransposons, Tos10, Tos17, and Tos19, have been shown to transpose in both *japonica* (Nipponbare) and *indica* (C5924) cell culture (Hirochika, et al., 1996 *Proc. Natl. Acad. Sci. USA,* 93: 7783-7788). Similarly, no activity has been associated with the hundreds of MITE families from either plants or animals. Most MITE families are characterized by high copy number (hundreds to thousands per haploid genome) and intra-family sequence identity that is rarely over 95% (Feschotte & Wessler, 2002 *Proc. Natl. Acad. Sci. USA,* 99: 280-285). Since newly amplified elements are usually identical, these families have most likely been inactive for hundreds of thousands or even millions of years. In addition, to date, only a single active DNA transposon, Tol2, has been isolated from a vertebrate (Kawakami, et al., 2000 *Proc. Natl. Acad. Sci. USA,* 97: 11403-8), and no active DNA transposons have been isolated from mammals.

Because no activity has been demonstrated for any of the known MITE families in either plants or animals, there is a need in the art to identify MITEs and related transposable elements that are actively transposing.

SUMMARY OF THE INVENTION

It is an object of the present invention to overcome, or at least alleviate, one or more of the difficulties or deficiencies associated with the prior art. In that regard, the present invention fulfills in part the need to identify new, unique transposable elements capable of actively transposing, at least in plants. The present invention describes a novel genus of Pong-like Transposase Polypeptides (PTPs) and Pong-like Transposable Element (PTE) nucleic acids. The novel genus is the mPing/Pong family of DNA transposable elements, and the Pong family of transposases. Preferably, the mPing/Pong family of DNA transposable elements is capable of actively transposing, and comprises two terminal inverted repeats.

The present invention includes an isolated cell comprising a PTP-encoding nucleic acid, wherein expression of the nucleic acid sequence in the cell results in increased transposition of a mPing/Pong transposable element as compared to a wild type variety of the cell. The invention further comprises an isolated cell comprising a nucleic acid sequence comprising a transposable element of the mPing/Pong family of transposable elements.

The invention provides in some embodiments that the PTP-encoding and PTE nucleic acid are those that are found in members of the genus *Brassica,* or *Oryza.* In another preferred embodiment, the nucleic acid and polypeptide are from a *Brassica oleracea* plant or an *Oryza sativa* plant.

The invention further provides a seed produced by a transgenic plant transformed by a PTP-encoding or PTE containing nucleic acid, wherein the plant is true breeding for increased transposition of a mPing/Pong transposable element as compared to a wild type variety of the plant. The invention further provides a seed produced by a transgenic plant expressing a PTP, wherein the plant is true breeding for increased transposition of a mPing/Pong transposable element as compared to a wild type variety of the plant.

The invention further provides an agricultural product produced by any of the below-described transgenic plants, plant parts or seeds. The invention further provides an isolated PTP as described below. The invention further provides an isolated PTP-encoding nucleic acid, wherein the PTP-encoding nucleic acid codes for a PTP as described below.

The invention further provides an isolated recombinant expression vector comprising a PTP-encoding nucleic acid as described below, wherein expression of PTP from the vector in a host cell results in increased transposition of a mPing/Pong transposable element as compared to a wild type variety of the host cell. The invention further provides an isolated recombinant expression vector comprising a PTE nucleic acid as described below, wherein expression of PTP from the vector in a host cell results in increased transposition of a mPing/Pong transposable element as compared to a wild type variety of the host cell. The invention further provides a host cell containing at least one of the vectors described above and a plant containing the host cell.

The invention further provides a method of producing a transgenic plant with a PTP-encoding nucleic acid or a PTE nucleic acid, wherein expression of the nucleic acid in the plant results in increased transposition of a mPing/Pong transposable element as compared to a wild type variety of the plant comprising: (a) transforming a plant cell with an expression vector comprising a PTP-encoding nucleic acid or a PTE nucleic acid, and (b) generating from the plant cell a transgenic plant. In preferred embodiments, the PTP, PTP coding nucleic acid, and PTE nucleic acid are as described below.

The present invention further provides a method of identifying a novel PTP, comprising (a) raising a specific antibody that binds to a PTP, or fragment thereof as described below; (b) screening putative PTP material with the antibody, wherein specific binding of the antibody to the material indicates the presence of a potentially novel PTP; and (c) identifying from the bound material a novel PTP in comparison to known PTP. Alternatively, hybridization with nucleic acid probes as described below can be used to identify novel PTP-encoding and PTE-containing nucleic acids.

The present invention also provides methods of identifying an active transposable element in a sample, comprising combining an active transposable element with a nucleic acid sequence which hybridizes in 5×SSC at 55° C. to the transposable element and detecting hybridization, thereby identifying the transposable element. In a preferred embodiment, the active transposable element is a member of the mPing/Pong family of transposable elements.

The present invention also provides methods of screening a cell for a transposition of a transposable element, wherein the transposable element is actively transposing, comprising the steps of: a) providing a cell comprising a transposable element, b) inducing a transposition of the transposable element by a transposase comprising a nucleic acid sequence and c) comparing the phenotype of the cell containing the transposition of the transposable element to a wild-type cell not containing a transposition of the transposable element to thereby screen for a cell containing the transposition. In a preferred embodiment, the transposable element is a member of the mPing/Pong family of transposable elements.

BRIEF DESCRIPTION OF THE DRAWINGS

FIG. 2 shows the Accession number of mPing-containing rice sequences in GenBank. The chromosome number, the Accession number, the position, the orientation and the strain of rice are all indicated.

FIG. 4 shows the Accession number of Ping-containing rice sequences in GenBank. The chromosome number, the Accession number, the position, the orientation and the strain of rice are all indicated.

FIG. 5 shows the Accession number of Pong-containing rice sequences in GenBank. The chromosome number, the Accession number, the position, the orientation and the strain of rice are all indicated.

FIG. 6 shows the position of the Pong-containing rice sequences in 93-11 (indica), The contig number, the position, and the orientation of the sequences are all indicated.

FIG. 7 shows a list of organisms that contain Pif-like transposes. Pif-like transposes are present in plants (monocots, dicots, and algae), animals (vertebrates and invertebrates), and fungus.

FIG. 8 shows a list of the new insertion sites of mPing and Pong in the C5924 cell line, where the insertion sites were determined using transposon display.

DETAILED DESCRIPTION OF THE INVENTION

Figure 1:
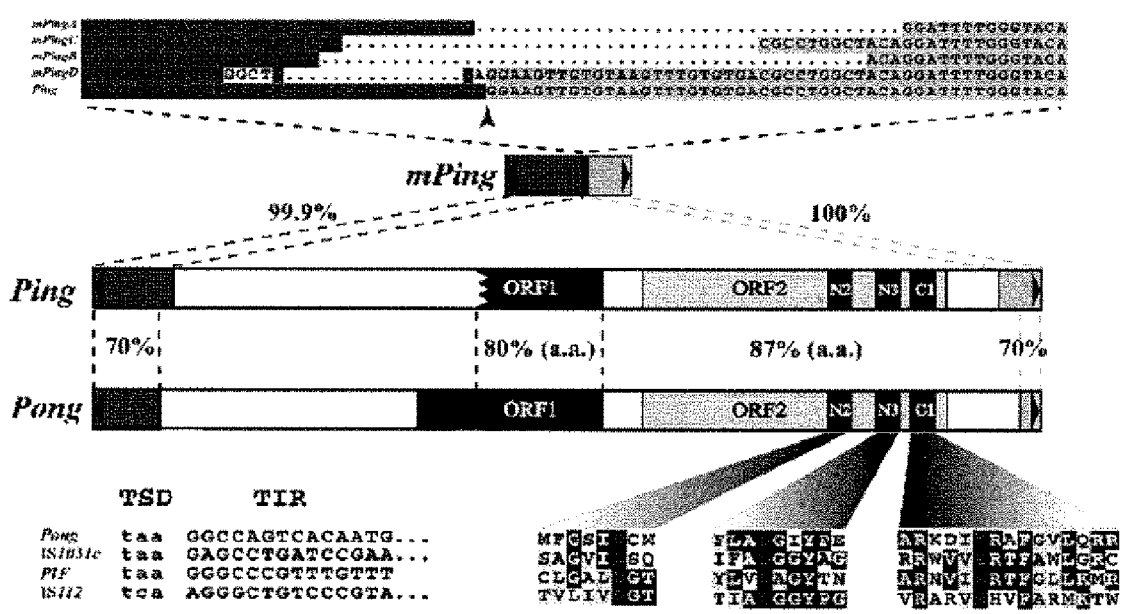
FIG. 1 shows a comparison of mPing, Ping and Pong elements. Black triangles represent TIRs and black boxes represent putative N2, N3 and C1 catalytic domains. The nucleotide sequences of the TIRs/TSDs and amino acid sequences of the catalytic domains of the rice Pong, the maize PIF (Zhang, et al., 2001 Proc. Natl. Acad. Sci. USA, 98: 12572-12577) and the bacterial IS1031c and IS112 elements are shown. The thick vertical black line in mPing stands for internal sequences that differ among the four subtypes derived from Ping. An alignment of this region is at the top. The arrowhead indicates the breakpoint in Ping where 4923 bp of its internal sequence is not shown in alignment.

The present invention provides in certain embodiments an isolated transposable element comprising two terminal inverted repeat nucleic acid sequences, wherein the transposable element is actively transposing. The transposable element of the present invention can be transposed and inserted into various sites on chromosomes. By means of this ability, the transposable element of the present invention can be used as effective means for a variety of genetic techniques. Examples of these practical applications include, but are not limited to, creation of insertion mutant strains, gene mapping, promoter searching, insertion of genetic information, disruption of a specific gene or genes and the like.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 *Glossary of genetics: classical and molecular*, 5th Ed., Berlin: Springer-Verlag; and in *Current Protocols in Molecular Biology*, F. M. Ausubel et al., Eds., Current Protocols, a joint venture between Greene Publishing Associates, Inc. and John Wiley & Sons, Inc. (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

The present invention describes a novel genus of Pong-like Transposase Polypeptides (PTPs) and Pong-like Transposable Element (PTE) nucleic acids. The novel family is the mPing/Pong family of DNA transposable elements, and the Pong family of transposases. Preferably, the mPing/Pong family of DNA transposable elements is capable of actively transposing, and comprises two terminal inverted repeats.

The term "transposable element," as used herein, refers to a DNA sequence whose excision from or insertion into genomic DNA is catalyzed by a functional transposase protein encoded by a non-defective member of the family of transposable elements. A member of the Pong family which encodes a functional transposase and possesses other necessary cis-acting elements (e.g., terminal inverted repeats) falls within this definition. In addition, a transposable element which encodes a defective transposase (e.g., Ping) falls within this definition. Furthermore, a transposable element that does not encode a transposase, but possesses the necessary cis-acting elements (i.e. mPing) falls within this definition. As discussed in greater detail below, such transposable elements that do not encode a functional transposase can be used in conjunction with a helper element (i.e., a member of the mPing/Pong family which encodes a functional transposase) to introduce a DNA sequence of interest into a eukaryotic cell.

The invention also relates to an isolated DNA sequence encoding a functional transposase protein, or a portion of a transposase protein, encoded by a member of the mPing/Pong family. Such a DNA sequence need not retain the ability to transpose in the presence of the encoded transposase protein. A sequence encoding a functional transposase protein can be used to prepare an expression construct which can be used to produce the transposase protein by recombinant DNA methodology. Such a recombinant protein can be over-produced in a eukaryotic (e.g., yeast) or prokaryotic (e.g., *E. coli*) host cell, and subsequently purified by conventional methods.

The active transposase can be used in a variety of ways. For example, as discussed below, the transposase protein or a transposase-producing vector can be co-introduced into a eukaryotic cell with a modified transposon carrying a DNA sequence of interest to catalyze the insertion of the modified transposon into the genomic DNA of the eukaryotic cell. This is an alternative to the co-introduction of a helper construct in eukaryotic cells which do not constitutively produce the mPing/Pong transposase.

In addition, the transposase, or portions thereof, can be used to produce antibodies (monoclonal and polyclonal) reactive with the transposase protein. Methods for the production of monoclonal and polyclonal antibodies are well-known in the art once a purified antigen is available.

As used herein, the terms "active transposable element" and "actively transposing" refer to the capacity of the DNA transposable element to change location within the genome of an organism. Preferably, the change of location occurs at a rate higher than 1 translocation per 1000 years, and more preferably at a rate higher than 1 translocation per 100 years. The transposable element can be induced to change location through cultivating a cell containing a mPing/Pong transposable element and a nucleic acid encoding a functional mPing/Pong transposase in cell culture. Other methods of inducing the translocation of a mPing/Pong transposable element are contemplated.

The present invention describes for the first time that the rice mPing, and Pong elements, and the *Brassica oleracea* Pong elements are actively transposing transposable elements of the PTE superfamily. Table 1 provides a quick reference for the identification of the nucleic acid sequences and amino acid sequences provided herein.

TABLE 1

| Identification | Sequence Identification Numbers |
| --- | --- |
| Nucleotide sequences of mPing in rice | SEQ ID NO: 1, SEQ ID NO: 2, SEQ ID NO: 3, and SEQ ID NO: 4 |
| Nucleotide sequence of Ping in rice | SEQ ID NO: 5 |
| Amino acid sequence of ORF1 of Ping in rice | SEQ ID NO: 6 |
| Amino acid sequence of ORF2 of Ping in rice | SEQ ID NO: 7 |
| Nucleotide sequences of Pong in rice | SEQ ID NO: 8; SEQ ID NO: 9; SEQ ID NO: 10; SEQ ID NO: 11; SEQ ID NO: 14; SEQ ID NO: 22; SEQ ID NO: 27; SEQ ID NO: 31; SEQ ID NO: 47; SEQ ID NO: 50; SEQ ID NO: 53; SEQ ID NO: 57; SEQ ID NO: 62; SEQ ID NO: 79; SEQ ID NO: 82; SEQ ID NO: 87; and SEQ ID NO: 90 |

TABLE 1-continued

| Identification | Sequence Identification Numbers |
|---|---|
| Amino acid sequences of ORF1 of Pong in rice | SEQ ID NO: 12; the contiguous sequence of SEQ ID NOs: 15 and 16; the contiguous sequence of SEQ ID NOs: 23 and 24; SEQ ID NO: 28: the contiguous sequence of SEQ ID NOs: 32 through 36; SEQ ID NO: 48; SEQ ID NO: 51; the contiguous sequence of SEQ ID NOs: 54 and 55; SEQ ID NO: 58; the contiguous sequence of SEQ ID NOs: 63 through 77; SEQ ID NO: 80; the contiguous sequence of SEQ ID NOs: 83 and 84; and SEQ ID NO: 91 |
| Amino acid sequences of ORF2 in Pong in rice | SEQ ID NO: 13; the contiguous sequence of SEQ ID NOs: 17 through 21; the contiguous sequence of SEQ ID NOs: 25 and 26; the contiguous sequence of SEQ ID NOs: 29 and 30; the contiguous sequence of SEQ ID NOs: 37 through 46; SEQ ID NO: 49; SEQ ID NO: 52; SEQ ID NO: 56; the contiguous sequence of SEQ ID NOs: 59 through 61; SEQ ID NO: 78; SEQ ID NO: 81; the contiguous sequence of SEQ ID NOs: 85 and 86; the contiguous sequence of SEQ ID NOs: 88 and 89; and SEQ ID NO: 92 |
| Nucleotide sequences of ORF2 in Pong in Brassica | SEQ ID NO: 93; SEQ ID NO: 96; SEQ ID NO: 99; SEQ ID NO: 102; SEQ ID NO: 104; SEQ ID NO: 107; SEQ ID NO: 109; SEQ ID NO: 111; SEQ ID NO: 113; and SEQ ID NO: 116 |
| Amino acid sequences of ORF2 in Pong in Brassica | the contiguous sequence of SEQ ID NOs: 94 and 95; the contiguous sequence of SEQ ID NOs: 97 and 98; the contiguous sequence of SEQ ID NOs: 100 and 101; SEQ ID NO: 103; the contiguous sequence of SEQ ID NOs: 105 and 106; SEQ ID NO: 108; SEQ ID NO: 110; SEQ ID NO: 112; the contiguous sequence of SEQ ID NOs: 114 and 115; and the contiguous sequence of SEQ ID NOs: 117 through 119 |
| Nucleotide sequences of ORF1 in Pong in Brassica | SEQ ID NO: 120; the contiguous sequence of SEQ ID NOs: 122-123; SEQ ID NO: 125; SEQ ID NO: 127; SEQ ID NO: 129; SEQ ID NO: 131; SEQ ID NO: 133; SEQ ID NO: 135; SEQ ID NO: 138; and SEQ ID NO: 140 |
| Amino acid sequences of ORF1 in Pong in Brassica | SEQ ID NO: 121; SEQ ID NO: 124; SEQ ID NO: 126; SEQ ID NO: 128; SEQ ID NO: 130; SEQ ID NO: 132; SEQ ID NO: 134; the contiguous sequence of SEQ ID NOs: 136 and 137; SEQ ID NO: 139; and SEQ ID NO: 141 |

In preferred embodiments, the PTE comprises a nucleic acid sequence selected from the group consisting of a polynucleotide as defined in SEQ ID NO:1, SEQ ID NO:2, SEQ ID NO:3, and SEQ ID NO:4; and homologs and orthologs thereof. In other preferred embodiments the PTE is selected from the group consisting of a polynucleotide as defined in SEQ ID NO:5; and homologs and orthologs thereof. In other preferred embodiments the PTE is selected from the group consisting of a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; and SEQ ID NO:90; and homologs and orthologs thereof. In still other preferred embodiments, the PTE comprises a nucleic acid sequence selected from the group consisting of a nucleic acid having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; and homologs and orthologs thereof. In other preferred embodiments, the PTE comprises a nucleic acid sequence selected from the group consisting of 1) a polynucleotide encoding a polypeptide as defined in SEQ ID NO:12; the contiguous sequence of SEQ ID NOs:15 and 16; the contiguous sequence of SEQ ID NOs: 23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; 2) a nucleic acid encoding a polypeptide having at least 25% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; and homologs and orthologs thereof. In still other preferred embodiments, the PTE comprises a nucleic acid sequence selected from the group consisting of 1) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs: 29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs: 88 and 89; or SEQ ID NO:92; 2) a nucleic acid encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; and homologs and orthologs thereof.

In other preferred embodiments, the PTE comprises a nucleic acid sequence selected from the group consisting of 1) a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; 2) a nucleic acid having at least 55% sequence identity with a polynucleotide as defined in SEQ ID NO:120;

the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; and orthologs and homologs thereof. In other preferred embodiments, the PTE comprises a nucleic acid sequence selected from the group consisting of 1) a polynucleotide encoding a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; 2) a nucleic acid encoding a polypeptide having at least 60% sequence identity with a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; and homologs and orthologs thereof.

In still other preferred embodiments, the PTE comprises a nucleic acid sequence selected from the group consisting of 1) a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; 2) a nucleic acid having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and homologs and orthologs thereof. In still other preferred embodiments, the PTE comprises a nucleic acid sequence selected from the group consisting of 1) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; 2) a nucleic acid encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and homologs and orthologs thereof.

As used herein, the term polypeptide refers to a chain of at least four amino acids joined by peptide bonds. The chain may be linear, branched, circular or combinations thereof. Accordingly, the present invention provides isolated PTPs selected from the group consisting of PONG_LIKE_1, PONG_LIKE_2, PONG_LIKE_3, PONG_LIKE_4, PONG_LIKE_5a, PONG_LIKE_5b, PONG_LIKE_5c, PONG_LIKE_6, PONG_LIKE_7, PONG_LIKE_8, PONG_LIKE_9, PONG_LIKE_10, and PONG_LIKE_12, and homologs thereof.

In preferred embodiments, the PTP is selected from: 1) a *Oryza sativa* ORF2 polypeptide as defined in SEQ ID NO:13; 2) an *Oryza sativa* PONG_LIKE_1 ORF2 polypeptide as defined in the contiguous sequences of SEQ ID NOs:17 through 21; 3) an *Oryza sativa* PONG_LIKE_2 ORF2 polypeptide as defined in the contiguous sequences of SEQ ID NOs:25-26; 4) an *Oryza sativa* PONG_LIKE_3 ORF2 polypeptide as defined in the contiguous sequences of SEQ ID NOs:29-30; 5) an *Oryza sativa* PONG_LIKE_4 ORF2 polypeptide as defined in the contiguous sequences of SEQ ID NOs:37 through 46; 6) an *Oryza sativa* PONG_LIKE_5a ORF2 polypeptide as defined in SEQ ID NO:49; 7) an *Oryza sativa* PONG_LIKE_5b ORF2 polypeptide as defined in SEQ ID NO:52; 8) an *Oryza sativa* PONG_LIKE_5c ORF2 polypeptide as defined in SEQ ID NO:56; 9) an *Oryza sativa* PONG_LIKE_6 ORF2 polypeptide as defined in the contiguous sequences of SEQ ID NOs:59 through 61; 10) an *Oryza sativa* PONG_LIKE_7 ORF2 polypeptide as defined in SEQ ID NO:78; 11) an *Oryza sativa* PONG_LIKE_8 ORF2 polypeptide as defined in SEQ ID NO:81; 12) an *Oryza sativa* PONG_LIKE_9 ORF2 polypeptide as defined in the contiguous sequences of SEQ ID NOs:85-86; 13) an *Oryza sativa* PONG_LIKE_10 ORF2 polypeptide as defined in the contiguous sequences of SEQ ID NOs:88-89; and 14) an *Oryza sativa* PONG_LIKE_12 ORF2 polypeptide as defined in SEQ ID NO:92, and homologs and orthologs thereof.

In one embodiment, the PTPs and PTEs of the present invention are produced by recombinant DNA techniques. For example, a nucleic acid molecule encoding the transposase polypeptide or a nucleic acid comprising a transposable element is cloned into a vector (as described below), the vector is introduced into a host cell (as described below) and the PTP is expressed in the host cell or the PTE may insert into the genome of the host cell. The PTP or PTE can then be isolated from the cells by an appropriate purification scheme using standard polypeptide purification techniques. For the purposes of the invention, the term "recombinant polynucleotide" refers to a polynucleotide that has been altered, rearranged or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a PTP, or peptide can be synthesized chemically using standard peptide synthesis techniques. Moreover, native PTPs can be isolated from cells (e.g., *Oryza saliva*, or *Brassica oleracea*), for example using an anti-PTP antibody, which can be produced by standard techniques utilizing a PTP or fragment thereof.

The invention further provides an isolated PTP-encoding nucleic acid. The present invention includes PTP-encoding nucleic acids that encode PTPs as described herein. In preferred embodiments, the PTP coding nucleic acid is selected from: 1) Nucleotide sequence of Pong in rice as defined in SEQ ID NO:8; 2) Nucleotide sequence of Pong in rice as defined in SEQ ID NO:9; 3) Nucleotide sequence of Pong in rice as defined in SEQ ID NO:10; 4) Nucleotide sequence of Pong in rice as defined in SEQ ID NO:11; 5) Nucleotide sequence of PONG_LIKE_1 in *Oryza sativa* as defined in SEQ ID NO:14; 6) Nucleotide sequence of PONG_LIKE_2 in *Oryza sativa* as defined in SEQ ID NO:22; 7) Nucleotide sequence of PONG_LIKE_3 in *Oryza sativa* as defined in SEQ ID NO:27; 8) Nucleotide sequence of PONG_LIKE_4 in *Oryza sativa* as defined in SEQ ID NO:31; 9) Nucleotide sequence of PONG_LIKE_5a in *Oryza sativa* as defined in SEQ ID NO:47; 10) Nucleotide sequence of PONG_LIKE_5b in *Oryza sativa* as defined in SEQ ID NO:50; 11) Nucleotide sequence of PONG_LIKE_5c in *Oryza sativa* as defined in SEQ ID NO:53; 12) Nucleotide sequence of PONG_LIKE_6 in *Oryza sativa* as defined in SEQ ID NO:57; 13) Nucleotide sequence of PONG_LIKE_7 in *Oryza sativa* as defined in SEQ ID NO:62; 14) Nucleotide sequence of PONG_LIKE_8 in *Oryza sativa* as defined in SEQ ID NO:79; 15) Nucleotide sequence of PONG_LIKE_9 in *Oryza sativa* as defined in SEQ ID NO:82; 16) Nucleotide sequence of PONG_LIKE_10 in *Oryza sativa* as defined in SEQ ID NO:87; and 17) Nucleotide sequence of PONG_LIKE_12 in *Oryza sativa* as defined in SEQ ID NO:90, and homologs and orthologs thereof. Homologs and orthologs of the nucleotide sequences are defined below. In one preferred embodiment, the nucleic acid and polypeptide are isolated from the plant genus *Brassica*, or *Oryza*. In another preferred embodiment, the nucleic acid and polypeptide are from a *Brassica oleracea* plant, or an *Oryza sativa* plant.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5, ends of the coding region of the gene: at least about 1000 nucleotides of sequence upstream from the 5' end of the coding region and at least about 200 nucleotides of sequence downstream from the 3, end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. In various embodiments, the isolated PTP or PTE nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Brassica oleracea*, or an *Oryza sativa* cell). A nucleic acid is also considered isolated if it has been altered by human intervention, or placed in a locus or location that is not its natural site, or if it is introduced into a cell by agroinfection. Moreover, an "isolated" nucleic acid molecule can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention can be isolated using standard molecular biology techniques and the sequence information provided herein. For example, a nucleic acid molecule comprising a nucleotide sequence of SEQ ID NO:1, SEQ ID NO:2, SEQ ID NO:3, or SEQ ID NO:4; comprising a nucleotide sequence of SEQ ID NO:5; comprising a nucleotide sequence of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; or a nucleic acid molecule comprising a nucleic acid sequence selected from the group consisting of 1) a nucleic acid having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; 2) a polynucleotide encoding a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; 3) a nucleic acid encoding a polypeptide having at least 25% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; 4) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; 5) a nucleic acid encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; 6) a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; 7) a polynucleotide having at least 55% sequence identity with a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; 8) a polynucleotide encoding a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; 9) a nucleic acid encoding a polypeptide having at least 60% sequence identity with a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; 10) a polynucleotide as defined in SEQ ID NO:93; SEQ ID NO:96; SEQ ID NO:99; SEQ ID NO:102; SEQ ID NO:104; SEQ ID NO, 107; SEQ ID NO:109; SEQ ID NO:111; SEQ ID NO:113; or SEQ ID NO:116; 11) a nucleic acid having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; 12) a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:11; SEQ ID NO:113; or SEQ ID NO:116; 13) a nucleic acid encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; or a portion thereof, can be isolated using standard molecular biology techniques and the sequence information provided herein.

In another example, a rice PTP nucleic acid can be isolated from a rice library using all or portion of one of the sequences of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90. In another embodiment, a PTP or PTE nucleic acid can be isolated from the genomic library of an organism using all of a portion of one of the sequences of SEQ ID NO:1; SEQ ID NO:2; SEQ ID NO:3; SEQ ID NO:4; SEQ ID NO:5; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO: 53; SEQ ID NO: 57; SEQ ID NO:62; SEQ ID NO:79; SEQ ID NO:82; SEQ ID NO:87; SEQ ID NO:90; SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; SEQ ID NO:140; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141. Moreover, a nucleic acid molecule encompassing all or a portion of one of the sequences of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:11; SEQ ID NO:113; SEQ ID NO:116; SEQ ID NO:120; the contiguous sequence of SEQ ID NOs: 122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140 can be isolated by the polymerase chain reaction using oligonucleotide primers designed based upon this sequence. For example, mRNA can be isolated from plant cells (e.g., by the guanidinium-thiocyanate extraction procedure of Chirgwin et al. 1979, Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PTP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:1; SEQ ID NO:2; SEQ ID NO:3; SEQ ID NO:4; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; and SEQ ID NO:90. These cDNAs may comprise sequences encoding the PTPs, (i.e., one of the "coding regions" of PONG_LIKE_1 and PONG_LIKE_2), as well as 5' untranslated sequences and 3, untranslated sequences. The PTP coding region of PONG_LIKE_1 comprises nucleotides 3,236-4,585 of SEQ ID NO:14 whereas the PTP coding region of PONG_LIKE_2 comprises nucleotides 968-2,282 of SEQ ID NO:22. It is to be understood that SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; and SEQ ID NO:90 comprise both coding regions for the transposase and 5' and 3' untranslated regions. Alternatively, the nucleic acid molecules of the present invention can comprise only the coding region of any of the sequences in SEQ ID NO:8; SEQ ID NO:9; SEQ ID NO:10 SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; and SEQ ID NO:90 or can contain whole genomic fragments isolated from genomic DNA. The present invention also includes PTP coding nucleic acids that encode PTPs as described herein.

Moreover, the nucleic acid molecule of the invention can comprise a portion of the coding region of one of the sequences in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140 for example, a fragment which can be used as a probe or primer or a fragment encoding a biologically active portion of a PTP. The nucleotide sequences determined from the cloning of the PTP genes from Brassica oleracea, and Oryza sativa allow for the generation of probes and primers designed for use in identifying and/or cloning PTP homologs in other cell types and organisms, as well as PTP homologs from other related species. The portion of the coding region can also encode a biologically active fragment of a PTP.

As used herein, the term "biologically active portion of" a PTP is intended to include a portion, e.g., a domain/motif, of a PTP that participates in the transposition of a transposable element. For the purposes of the present invention, transposition of a transposable element refers to at least the movement of one transposable element in an organism. Methods for quantitating transposition are provided at least in Example 2 below.

The mPing/Pong transposable element may be actively transposing in a number of taxa other than rice and Brassica, i.e. the transposable element may transpose in eukaryotes under the appropriate conditions, thus, it will be recognized by those skilled in the art that the methods disclosed herein relating to plants may be extended to other higher eukaryotes. If the transposase is functional when expressed or otherwise introduced in vertebrate embryos or cells, it will be possible to develop transformation methods based on mPing/Pong elements for non-plant species as well.

Biologically active portions of a PTP include peptides comprising amino acid sequences derived from the amino acid sequence of a PTP, e.g., an amino acid sequence of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141 or the amino acid sequence of a polypeptide identical to a PTP, which include fewer amino acids than a full length PTP or the full length polypeptide which is identical to a PTP, and exhibit at least one activity of a PTP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a PTP. Moreover, other biologically active portions in which other regions of the polypeptide are deleted, can be prepared by recombinant techniques and evaluated for one or more of the activities described herein. Preferably, the biologically active portions of a PTP include one or more selected domains/motifs or portions thereof having biological activity such as a catalytic domain. For example, a catalytic domain of PONG_LIKE_1 spans amino acid residues 199-341 of the contiguous sequence of SEQ ID NOs:17-21, and a catalytic domain of PONG_LIKE_2 spans amino acid residues 193-335 of the contiguous sequence of SEQ ID NOs:25-26. Accordingly, the present invention includes PTPs comprising amino acid residues 199-341 of the contiguous sequence of SEQ ID NOs:15-16 and amino acid residues 193-335 of the contiguous sequence of SEQ ID NOs:25-26.

The invention also provides PTP chimeric or fusion polypeptides. As used herein, a PTP "chimeric polypeptide" or "fusion polypeptide" comprises a PTP operatively linked to a non-PTP. A PTP polypeptide refers to a polypeptide having an amino acid sequence corresponding to a PTP, whereas a non-PTP polypeptide refers to a polypeptide having an amino acid sequence corresponding to a polypeptide which is not substantially identical to the PTP, e.g., a polypeptide that is different from the PTP and is derived from the same or a different organism. As used herein with respect to the fusion polypeptide, the term "operatively linked" is intended to indicate that the PTP and the non-PTP are fused to each other so that both sequences fulfill the proposed function attributed to the sequence used. The non-PTP can be fused to the N-terminus or C-terminus of the PTP. For example, in one embodiment, the fusion polypeptide is a GST-PTP fusion polypeptide in which the PTP sequences are fused to the C-terminus of the GST sequences. Such fusion polypeptides can facilitate the purification of recombinant PTPs. In another embodiment, the fusion polypeptide is a PTP containing a heterologous signal sequence at its N-terminus. In certain host cells (e.g., mammalian host cells), expression and/or secretion of a PTP can be increased through use of a heterologous signal sequence.

Preferably, a PTP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (See, e.g., *Current Protocols in Molecular Biology*, Eds. Ausubel et al. John Wiley & Sons: 1992). Moreover, many expression vectors are commercially available that already encode a fusion moiety (e.g., a GST polypeptide). A PTP-encoding nucleic acid can be cloned into such an expression vector such that the fusion moiety is linked in-frame to the PTP.

Large amounts of the recombinant DNA molecules may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially *Escherichia coli* or *Saccharomyces cerevisiae*. Commonly used prokaryotic hosts include strains of *Escherichia coli*, although other prokaryotes, such as *Bacillus subtilis* or a pseudomonad, may also be used. Eukaryotic host cells include yeast, filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors influence the choice of the host cell.

In addition to fragments and fusion polypeptides of the PTPs described herein, the present invention includes homologs and analogs of naturally occurring PTPs and PTP-encoding nucleic acids, and of naturally occurring PTE nucleic acids. "Homologs" are defined herein as two nucleic acids or polypeptides that have similar, or substantially identical, nucleotide or amino acid sequences, respectively. Homologs include allelic variants, orthologs, paralogs, agonists and antagonists of PTPs as defined hereafter. The term "homolog" further encompasses nucleic acid molecules that differ from one of the nucleotide sequences shown in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO, 109; SEQ ID NO:111; SEQ ID NO:113; and SEQ ID NO:116 (and portions thereof) due to degeneracy of the genetic code and thus encode the same PTP as that encoded by the nucleotide sequences shown in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO: 50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. As used herein a "naturally occurring" PTP refers to a PTP amino acid sequence that occurs in nature. Preferably, a naturally occurring PTP comprises an amino acid sequence selected from the group consisting of SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO; 102; SEQ ID NO:104; SEQ ID NO:107; SEQ ID NO:109; SEQ ID NO:111; SEQ ID NO:113; SEQ ID NO:116; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; and SEQ ID NO:141. Similarly, a "naturally occurring" PTE refers to a PTE nucleic acid sequence that occurs in nature. Preferably, a naturally occurring PTE comprises a nucleic acid sequence selected from the group consisting of SEQ ID NO:1; SEQ ID NO:2; SEQ ID NO:3; SEQ ID NO:4; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; and SEQ ID NO:90. In another embodiment, the naturally occurring PTE comprises a nucleic acid sequence selected from the group consisting of SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; and SEQ ID NO:140. In other embodiments, the naturally occurring PTE comprises a nucleic acid sequence selected from the group of polynucleotides encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; a polynucleotide encoding a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; a polynucleotide encoding a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; and the group of polynucleotides encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116.

In other embodiments, the naturally occurring PTE comprises a nucleic acid sequence selected from the group consisting of 1) a nucleic acid having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82;

SEQ ID NO:87; or SEQ ID NO:90; 2) a nucleic acid encoding a polypeptide having at least 25% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; 3) a nucleic acid encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; 4) a nucleic acid having at least 55% sequence identity with a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; 5) a nucleic acid encoding a polypeptide having at least 60% sequence identity with a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; 6) a nucleic acid having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and 7) a nucleic acid encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. An agonist of the PTP can retain substantially the same, or a subset, of the biological activities of the PTP. An antagonist of the PTP can inhibit one or more of the activities of the naturally occurring form of the PTP.

Nucleic acid molecules corresponding to natural allelic variants and analogs, orthologs and paralogs of a PTP or PTE nucleic acid can be isolated based on their identity to the rice, or *Brassica* PTP and PTE nucleic acids described herein using PTP or PTE nucleic acid sequence, or a portion thereof, as a hybridization probe according to standard hybridization techniques under stringent or moderate hybridization conditions. In an alternative embodiment, homologs of the PTP can be identified by screening combinatorial libraries of mutants, e.g., truncation mutants, of the PTP for PTP agonist or antagonist activity. In one embodiment, a variegated library of PTP variants is generated by combinatorial mutagenesis at the nucleic acid level and is encoded by a variegated gene library. A variegated library of PTP variants can be produced by, for example, enzymatically ligating a mixture of synthetic oligonucleotides into gene sequences such that a degenerate set of potential PTP sequences is expressible as individual polypeptides, or alternatively, as a set of larger fusion polypeptides (e.g., for phage display) containing the set of PTP sequences therein. There are a variety of methods that can be used to produce libraries of potential PTP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential PTP sequences. Methods for synthesizing degenerate oligonucleotides are known in the art. See, e.g., Narang, S. A., 1983, *Tetrahedron* 39:3; Itakura et al., 1984, *Annu. Rev. Biochem.* 53:323; Itakura et al., 1984, *Science* 198:1056; Ike et al., 1983, *Nucleic Acid Res.* 11:477.

In addition, libraries of fragments of the PTP coding regions can be used to generate a variegated population of PTP fragments for screening and subsequent selection of homologs of a PTP. In one embodiment, a library of coding sequence fragments can be generated by treating a double stranded PCR fragment of a PTP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the PTP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PTP homologs. The most widely used techniques which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify PTP homologs (Arkin and Yourvan, 1992, *PNAS* 89:7811-7815; Delgrave et al., 1993, *Polypeptide Engineering* 6(3):327-331). In another embodiment, cell based assays can be exploited to analyze a variegated PTP library, using methods well known in the art. The present invention further provides a method of identifying a novel PTP, comprising (a) raising a specific antibody response to a PTP, or a fragment thereof, as described herein; (b) screening putative PTP material with the antibody, wherein specific binding of the antibody to the material indicates the presence of a potentially novel PTP; and (c) analyzing the bound material in comparison to known PTP, to determine its novelty.

As stated above, the present invention includes PTPs, PTEs and homologs and analogs thereof. To determine the percent sequence identity of two amino acid sequences (e.g., one of the sequences of SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO, 102; SEQ ID NO:104; SEQ ID NO; 107; SEQ ID NO:109; SEQ ID NO:111; SEQ ID NO:113; SEQ ID NO:116; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141) is occupied by the same amino acid residue as the corresponding position in the other sequence (e.g., a mutant form of the sequence selected from the polypeptide of SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141), then the molecules are identical at that position. The same type of comparison can be made between two nucleic acid sequences.

The percent sequence identity between the two sequences is a function of the number of identical positions shared by the sequences (i.e., percent sequence identity numbers of identical positions/total numbers of positions×100). Preferably, the isolated amino acid homologs included in the present invention are at least about 25-30%, preferably at least 30-40%, and more preferably at least about 40-50%, 50-60%, 60-70%, 70-75%, 75-80%, 80-85%, 85-90% or 90-95%, and most preferably at least about 96%, 97%, 98%, 99% or more identical to an entire amino acid sequence shown in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO, 104; SEQ ID NO:107; SEQ ID NO:109; SEQ ID NO:111; SEQ ID NO:113; SEQ ID NO:116; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141. In yet another embodiment, the isolated amino acid homologs included in the present invention are at least about 25-30%, preferably at least 40-50%, and more preferably at least about 50-60%, 60-70%, 70-75%, 75-80%, 80-85%, 85-90% or 90-95%, and most preferably at least about 96%, 97%, 98%, 99% or more identical to an entire amino acid sequence encoded by a nucleic acid sequence shown in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. In other embodiments, the PTP amino acid homologs have sequence identity over at least 15 contiguous amino acid residues, more preferably at least 25 contiguous amino acid residues, and most preferably at least 35 contiguous amino acid residues of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. In one embodiment of the present invention, the homolog has at least about 50-60%, preferably at least about 60-70%, more preferably at least about 70-75%, 75-80%, 80-85%, 85-90% or 90-95%, and even more preferably at least about 95%, 96%, 97%, 98%, 99% or more sequence identity with the conserved region of ORF1 in *Brassica oleracea* (for example, amino acids 1-113 of SEQ ID NO: 121) or the catalytic domain of ORF2 in *Brassica oleracea* (for example, amino acids 1-121 of the contiguous sequence of SEQ ID NOs:94-95).

In preferred embodiments, the PTP amino acid homologs of the present invention comprise an amino acid sequence selected from the group consisting of: 1) an amino acid encoded by a nucleic acid having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; 2) a polypeptide having at least 25% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; 3) a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; 4) a polypeptide encoded by a nucleic acid having at least 55% sequence identity with a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; 5) a polypeptide having at least 60% sequence identity with a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; 6) a polypeptide encoded by a nucleic acid having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and 7) a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116.

In another preferred embodiment, an isolated nucleic acid homolog of the invention comprises a nucleotide sequence which is at least about 40-50%, preferably at least about 50-60%, more preferably at least about 60-70%, 70-75%, 75-80%, 80-85%, 85-90% or 90-95%, and even more preferably at least about 95%, 96%, 97%, 98%, 99% or more identical to a nucleotide sequence shown in SEQ ID NO:1; SEQ ID NO:2; SEQ ID NO:3; SEQ ID NO:4; SEQ ID NO:5; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; and SEQ ID NO:90, or to a portion comprising at least 60 consecutive nucleotides thereof. The preferable length of sequence comparison for nucleic acids is at least 75 nucleotides, and more preferably at least 100 nucleotides. In a further embodiment, the isolated nucleic acid homolog of the invention comprises a nucleotide sequence which is at least 40-50%, preferably at least 50-60%, more preferably at least about 60-70%, 70-75%, 75-80%, 80-85%, 85-90% or 90-95%, and even more preferably at least about 95%, 96%, 97%, 98%, 99% or more identical to a nucleotide sequence as defined in SEQ ID NO:93; SEQ ID NO:96 SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:120; the contiguous sequence of SEQ ID NOs:122-123; SEQ ID NO:125. SEQ ID NO:127; SEQ ID NO:129; SEQ ID NO:131; SEQ ID NO:133; SEQ ID NO:135; SEQ ID NO:138; and SEQ ID NO:140.

In a preferred embodiment, the isolated nucleic acid of the invention comprises a transposable element capable of actively transposing, wherein the transposable element comprises a nucleic acid sequence selected from the group consisting of a nucleic acid having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90.

In a preferred embodiment, the isolated nucleic acid of the invention comprises a transposable element capable of actively transposing, wherein the transposable element comprises a nucleic acid sequence selected from the group consisting of 1) a polynucleotide encoding a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; 2) a nucleic acid encoding a polypeptide having at least 25% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91 and homologs and orthologs thereof.

In another preferred embodiment, the isolated nucleic acid of the invention comprises a transposable element capable of actively transposing, wherein the transposable element comprises a nucleic acid sequence selected from the group consisting of 1) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; 2) a nucleic acid encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; and homologs and orthologs thereof.

In another preferred embodiment, the isolated nucleic acid of the invention comprises a transposable element capable of actively transposing, wherein the transposable element comprises a nucleic acid sequence selected from the group consisting of 1) a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; 2) a nucleic acid having at least 55% sequence identity with a polynucleotide as defined in SEQ ID NO:120; the contiguous sequence of SEQ ID NOs: 122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; and homologs and orthologs thereof.

In another preferred embodiment, the isolated nucleic acid of the invention comprises a transposable element capable of actively transposing, wherein the transposable element comprises a nucleic acid sequence selected from the group consisting of 1) a polynucleotide encoding a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; 2) a nucleic acid encoding a polypeptide having at least 60% sequence identity with a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; and homologs and orthologs thereof.

In another preferred embodiment, the isolated nucleic acid of the invention comprises a transposable element capable of actively transposing, wherein the transposable element comprises a nucleic acid sequence selected from the group consisting of 1) a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; 2) a nucleic acid having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and homologs and orthologs thereof.

In another preferred embodiment, the isolated nucleic acid of the invention comprises a transposable element capable of actively transposing, wherein the transposable element comprises a nucleic acid sequence selected from the group consisting of 1) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; 2) a nucleic acid encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and homologs and orthologs thereof.

It is further preferred that a isolated nucleic acid homolog of the invention encodes a PTP, or portion thereof, that is at least 50% identical to an amino acid sequence of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92 and that functions as a modulator of translocation of a transposable element. In an additional preferred embodiment, the isolated nucleic acid homolog of the invention encodes a PTP, or portion thereof that is at least 75% identical to an amino acid sequence of SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. In a further preferred embodiment, the nucleic acid homolog encodes a PTP that functions as a transposase.

For the purposes of the invention, the percent sequence identity between two nucleic acid or polypeptide sequences may be determined using the "Blast Two Sequences" program available at National Center for Biotechnology Information. A gap opening penalty of 5 and a gap extension penalty of 2 are used for determining the percent identity of two nucleic acids. A gap opening penalty of 11 and a gap extension penalty of 1 are used for determining the percent identity of two polypeptides. All other parameters are set at the default settings. Multiple alignment was performed using the CLUSTALW program available at European Bioinformatics Institute, the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:1; SEQ ID NO:2; SEQ ID NO:3; SEQ ID NO:4; SEQ ID NO:5; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116 under moderate or highly stringent conditions. In another aspect, the invention provides an isolated nucleic acid comprising a polynucleotide that hybridizes under moderately or highly stringent conditions to a polynucleotide encoding a polypeptide of SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141. More particularly, an isolated nucleic acid molecule of the invention is at least 15 nucleotides in length and hybridizes under moderately or highly stringent conditions to the nucleic acid molecule comprising a nucleotide sequence of SEQ ID NO:1; SEQ ID NO:2; SEQ ID NO:3; SEQ ID NO:4; SEQ ID NO:5; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. Alternatively, an isolated nucleic acid molecule of the invention is at least 15 nucleotides in length and comprises a polynucleotide that hybridizes under moderate or stringent conditions to a nucleic acid sequence encoding a polypeptide of SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:11; SEQ ID NO:113; SEQ ID NO:116; SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141. In other embodiments, the nucleic acid is at least 30, 50, 100, 250 or more nucleotides in length.

In one embodiment, an isolated nucleic acid homolog of the invention comprises a nucleotide sequence which hybridizes under moderately stringent conditions to the nucleotide sequence shown in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116, and functions as a modulator of translocation of a transposable element. In another embodiment, an isolated nucleic acid homolog of the invention comprises a nucleotide sequence which hybridizes under highly stringent conditions to the nucleotide sequence shown in SEQ ID NO:1; SEQ ID NO:2; SEQ ID NO:3; SEQ ID NO:4; SEQ ID NO:5; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and is actively transposing.

Various degrees of stringency of hybridization can be employed for studies of cloned sequences isolated as described herein. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H., M. M. Manak, 1987 *DNA Probes*, Stockton Press, New York, N.Y., pp. 169-170, hereby incorporated by reference. In a preferred embodiment, the hybridization is selective for target DNA. As used herein, the term "selective hybridization" or "selectively hybridizing" refers to the ability to discern between the binding of a nucleic acid sequence to a target DNA sequence as compared to other non-target DNA sequences.

As used herein, moderate to high stringency conditions for hybridization are conditions that achieve the same, or about the same, degree of specificity of hybridization as the conditions described herein. As used herein, the term "highly stringent" or "high stringency conditions" comprises hybridizing at 68° C. in 5×SSC/5×Denhardt's solution 0.1% SDS, and washing in 0.2×SSC/0.1% SDS at 65° C. As used herein, the term "moderately stringent" or "moderate stringency conditions" comprise hybridizing at 55° C. in 5×SSC/5×Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. 1989 *Molecular Cloning*, Second Edition, Cold Spring Harbor Laboratory, Plainview, N. Y. Ausubel et al., 1995 *Current Protocols in Molecular Biology*, John Wiley & Sons, NY, N.Y., Meinkoth and Wahl, 1984, *Anal, Biochem.* 138: 267-284; or Tijssen, 1993, *Laboratory Techniques in Biochemistry and Molecular Biology: Hybridization with Nucleic Acid Probes*, Part I, Chapter 2, Elsevier, New York, for further guidance on hybridization conditions.

Specifically, hybridization of immobilized DNA in Southern blots with $^{32}$P-labeled gene specific probes is performed by standard methods (Maniatis et al., 1982 *Molecular Cloning*, Cold Spring Harbor Laboratory, Plainview, N.Y.). In general, hybridization and subsequent washes are carried out under moderate to high stringency conditions that allowed for detection of target sequences with homology to a particular nucleic acid molecule of interest. For double-stranded DNA gene probes, hybridization can be carried out overnight at 20-25° C. below the melting temperature (Tm) of the DNA hybrid in 6×SSPE 5×Denhardt's solution, 0.1% SDS, 0.1 mg/ml denatured DNA. The melting temperature is described by the following formula (Beltz et al., 1983 *Methods of Enzymotogy*, R. Wu, L, Grossman and K Moldave (Eds) Academic Press, New York 100:266-285).

$$Tm=81.5°\ C.+16.6\ \text{Log}\ [Na^+]+0.41(+G+C)-0.61(\%\ \text{formamide})-600/\text{length of duplex in base pairs}.$$

Washes are typically carried out as follows: twice at room temperature for 15 minutes in 1×SSPE, 0.1% SDS (low stringency wash), and once at TM-20° C. for 15 minutes in 0.2× SSPE, 0.1% SDS (moderate stringency wash).

For oligonucleotide probes, hybridization is carried out overnight at 10-20° C. below the melting temperature (Tm) of the hybrid 6×SSPE, 5×Denhardt's solution, 0.1% SDS, 0.1 mg/ml denatured DNA. Tm for oligonucleotide probes is determined by the following formula. TM(° C.)=2(number T/A base pairs+4(number G/C base pairs) (Suggs et al., 1981 *ICB-UCLA Symp. Dev. Biol. Using Purified Genes*, D. D. Brown (Ed.), Academic Press, New York, 23:683-693).

Washes are typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.5× or 1×SSPE, 60° C.; and High, 0.1×SSPE, 65° C.

Preferably, an isolated nucleic acid molecule of the invention that hybridizes in 5×SSC at 55° C. to a transposable element comprising at least a portion of a nucleic acid sequence, prising two terminal inverted repeat nucleic acid sequences, wherein the transposable element in actively transposing. In preferred embodiments, the transposable element comprises a nucleic acid sequence selected from the group consisting of 1) a polynucleotide as defined in SEQ ID NO:1, SEQ ID NO:2, SEQ ID NO:3, or SEQ ID NO:4; 2) a polynucleotide as defined in SEQ ID NO:5; 3) a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; 4) a nucleic acid having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; 5) a polynucleotide encoding a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; 6) a nucleic acid encoding a polypeptide having at least 25% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; 7) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; 8) a nucleic acid encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; 9) a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; 10) a nucleic acid having at least 55% sequence identity with a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; 11) a polynucleotide encoding a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; 12) a nucleic acid encoding a polypeptide having at least 60% sequence identity with a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; 13) a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; 14) a nucleic acid having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; 15) a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; 16) a nucleic acid encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and homologs and orthologs thereof.

In other embodiments, the invention provides for an isolated nucleic acid sequence that hybridizes in 5×SSC at 55° C. to a transposable element comprising a nucleic acid sequence as defined in SEQ ID NO:1; SEQ ID NO:2; SEQ ID NO:3; SEQ ID NO:4; SEQ ID NO:5; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and that corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Oryza*, or *Brassica oleracea* PTE or PTP. In another embodiment, the isolated nucleic acid sequence does not correspond to a naturally occurring nucleic acid molecule.

Using the above-described methods, and others known to those of skill in the art, one of ordinary skill in the art can isolate homologs of the PTPs comprising amino acid sequences shown in, for example, SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:1009; SEQ ID NO:111; SEQ ID NO:113; and SEQ ID NO:116. One subset of these homologs are allelic variants. As used herein, the term "allelic variant" refers to a nucleotide sequence containing polymorphisms that lead to changes in the amino acid sequences of a PTP and that exist within a natural population (e.g., a plant species or variety). Such natural allelic variations can typically result in 1-5% variance in a PTP or PTE nucleic acid. Allelic variants can be identified by sequencing the nucleic acid sequence of interest in a number of different plants, or other organisms, which can be readily carried out by using hybridization probes to identify the same PTP or PTE genetic locus in those organisms. Any and all such nucleic acid variations and resulting amino acid polymorphisms or variations in a PTP or PTE that are the result of natural allelic variation and that do not alter the functional activity of a PTP or PTE, are intended to be within the scope of the invention.

Moreover, nucleic acid molecules encoding PTPs and PTE nucleic acids from the same or other species such as PTP or PTE analogs, orthologs, and paralogs, are intended to be within the scope of the present invention. As used herein, the term "analogs" refers to two nucleic acid sequences that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, *Science* 278(5338):631-637). Analogs, orthologs and paralogs of a naturally occurring PTP can differ from the naturally occurring PTP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98% or even 99% identity or sequence identity with all or part of a naturally occurring PTP amino acid sequence and will exhibit a function similar to a PTP. Preferably, a PTP ortholog of the present invention functions as a modulator of transposition of a transposable element. More preferably, a PTP ortholog modulates the transposition of mPing, Ping or Pong. In another embodiment, the PTP orthologs maintain the ability to participate in the transposition of a transposable element having homology to mPing, Ping or Pong in an organism. In a preferred embodiment, that organism is a plant.

In addition to naturally-occurring variants of a PTP sequence that may exist in the population, the skilled artisan will further appreciate that changes can be introduced by mutation into a nucleotide sequence comprising the polynucleotide of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116, thereby leading to changes in the amino acid sequence of the encoded PTP, without altering the functional activity of the PTP. For example, nucleotide substitutions leading to amino acid substitutions at "non-essential" amino acid residues can be made in a sequence comprising the polynucleotide of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. A "non-essential" amino acid residue is a residue that can be altered from the wild-type sequence of one of the PTPs without altering the activity of said PTP, whereas an "essential" amino acid residue is required for PTP activity. Other amino acid residues, however, (e.g., those that are not conserved or only semi-conserved in the domain having PTP activity) may not be essential for activity and thus are likely to be amenable to alteration without altering PTP activity.

Accordingly, another aspect of the invention pertains to nucleic acid molecules encoding PTPs that contain changes in amino acid residues that are not essential for PTP activity. Such PTPs differ in amino acid sequence from a sequence contained in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116, yet retain at least one of the PTP activities described herein. In one embodiment, the isolated nucleic acid molecule comprises a nucleotide sequence encoding a polypeptide, wherein the polypeptide comprises an amino acid sequence at least about 50% identical to an amino acid sequence of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92. Preferably, the polypeptide encoded by the nucleic acid molecule is at least about 50-60% identical to one of the sequences of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92, more preferably at least about 60-70% identical to one of the sequences of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92, even more preferably at least about 70-75%, 75-80%, 80-85%, 85-90%, 90-95% identical to one of the sequences of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92, and most preferably at least about 96%, 97%, 98%, or 99% identical to one of the sequences of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92. In another embodiment, the isolated nucleic acid molecule comprises a nucleotide sequence encoding a polypeptide, wherein the polypeptide comprises an amino acid sequence at least about 50% identical to an amino acid sequence of SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. Preferably, the polypeptide encoded by the nucleic acid molecule is at least about 50-60% identical to one of the sequences of SEQ ID NO:93; SEQ ID NO:96; SEQ ID NO:99; SEQ ID NO:102; SEQ ID NO; 104; SEQ ID NO:107; SEQ ID NO:109; SEQ ID NO:111; SEQ ID NO:113; or SEQ ID NO:116, more preferably at least about 60-70% identical to one of the sequences of SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116, even more preferably at least about 70-75%, 75-80%, 80-85%, 85-90%, 90-95% identical to one of the sequences of SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116, and most preferably at least about 96%, 97%, 98%, or 99% identical to one of the sequences of SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. The preferred PTP homologs of the present invention participate in the transposition of a transposable element within the genome of an organism.

An isolated nucleic acid molecule encoding a PTP having sequence identity with a polypeptide sequence of SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116 can be created by introducing one or more nucleotide substitutions, additions or deletions into a nucleotide sequence of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116, respectively, such that one or more amino acid substitutions, additions, or deletions are introduced into the encoded polypeptide. Mutations can be introduced into one of the sequences of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO: 113; or SEQ ID NO:116, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PTP is preferably replaced with another amino acid residue from the same side chain family. Alternatively, in another embodiment, mutations can be introduced randomly along all or part of a PTP coding sequence, such as by saturation mutagenesis, and the resultant mutants can be screened for a PTP activity described herein to identify mutants that retain PTP activity. Following mutagenesis of one of the sequences of SEQ ID NO:8; SEQ ID NO:9; SEQ ID NO:10; SEQ ID NO:11; SEQ ID NO:14; SEQ ID NO:22; SEQ ID NO:27; SEQ ID NO: 31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104;

SEQ ID NO:107; SEQ ID NO:109; SEQ ID NO:111; SEQ ID NO:113; or SEQ ID NO:116, the encoded polypeptide can be expressed recombinantly and the activity of the polypeptide can be determined by analyzing the transposition of a member of the mPing/Pong family of transposable elements in a plant expressing the polypeptide.

Additionally, optimized PTP nucleic acids can be created. As used herein, "optimized" refers to a nucleic acid that is genetically engineered to increase its expression in a given organism, or to increase its activity in a given organism. For example, to provide plant optimized PTP nucleic acids, the DNA sequence of the gene can be modified to 1) comprise codons preferred by highly expressed plant genes; 2) comprise an A+T content in nucleotide base composition to that substantially found in plants; 3) form a plant initiation sequence; or 4) eliminate sequences that cause destabilization, inappropriate polyadenylation, degradation, and termination of RNA, or that form secondary structure hairpins or RNA splice sites. Increased expression of PTP nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, *Proc. Natl. Acad. Sci. USA* 88:3324-3328; and Murray et al., 1989, *Nucleic Acids Res.* 17:477-498. Similarly, optimized PTP nucleic acids can be generated for animals or fungi.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A=n=1ZXn-YnXn$ times $100 Z$ where $Xn$=frequency of usage for codon n in the host cell; $Yn$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, a PTP-encoding nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or U) nucleotide is the least preferred codon in dicots whereas the XTA codon is avoided in both monocots and dicots. Optimized PTP nucleic acids of this invention also preferably have CG and TA doublet avoidance indices closely approximating those of the chosen host plant (i.e., *Oryza*, or *Brassica oleracea*). More preferably these indices deviate from that of the host by no more than about 10-15%.

In addition to the nucleic acid molecules encoding the PTPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 50% sequence identity with the polypeptide of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116.

The antisense nucleic acid can be complementary to an entire PTP coding strand, or to only a portion thereof. In one embodiment, an antisense nucleic acid molecule is antisense to a "coding region" of the coding strand of a nucleotide sequence encoding a PTP. The term "coding region" refers to the region of the nucleotide sequence comprising codons that are translated into amino acid residues (e.g., the entire coding region of PONG_LIKE__1 transposase comprises nucleotides 3,236-4,588 of SEQ ID NO:14, and the entire coding region of PONG_LIKE__2 transposase comprises nucleotides 965-2,282 of SEQ ID NO:22). In another embodiment, the antisense nucleic acid molecule is antisense to a "noncoding region" of the coding strand of a nucleotide sequence encoding a PTP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of PTP mRNA, but more preferably is an oligonucleotide which is antisense to only a portion of the coding or noncoding region of PTP mRNA. For example, the antisense oligonucleotide can be complementary to the region surrounding the translation star site of PTP mRNA. An antisense oligonucleotide can be, for example, about 5, 10, 15, 20, 25, 30, 35, 40, 45 or 50 nucleotides in length. Typically, the antisense molecules of the present invention comprise an RNA having 60-100% sequence identity with at least 14 consecutive nucleotides of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116, or a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; SEQ ID NO:92; SEQ ID NO:93; SEQ ID NO:96; SEQ ID NO:99; SEQ ID NO: 102; SEQ ID NO:104; SEQ ID NO:107; SEQ ID NO:109; SEQ ID NO:111; SEQ ID NO:113; or SEQ ID NO:116. Preferably, the sequence identity will be at least 50%, more preferably at least 55%, 60%, 70%, 75%, 80%, 85%, 90%, 95%, 98% and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids. Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The antisense nucleic acid molecules of the invention are typically administered to a cell or generated in situ such that they hybridize with or bind to cellular mRNA and/or genomic DNA encoding a PTP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of a PTP polypeptide. By "ribozyme" is meant a catalytic RNA-based enzyme with ribonuclease activity which is capable of cleaving a single-stranded nucleic acid, such as an mRNA, to which it has a complementary region. Ribozymes (e.g., hammerhead ribozymes described in Haselhoff and Gerlach, 1988, *Nature* 334:585-591) can be used to catalytically cleave PTP mRNA transcripts to thereby inhibit translation of PTP mRNA. A ribozyme having specificity for a PTP-encoding nucleic acid can be designed based upon the nucleotide sequence of a PTP cDNA, as disclosed herein (i.e., SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a PTP-encoding mRNA. See, e.g., U.S. Pat. Nos. 4,987,071 and 5,116,742 to Cech et al. Alternatively, PTP mRNA can be used to select a catalytic RNA having a specific ribonuclease activity from a pool of RNA molecules. See, e.g., Bartel, D. and Szostak, J. W., 1993, *Science* 261:1411-1418. In preferred embodiments, the ribozyme will contain a portion having at least 7, 8, 9, 10, 12, 14, 16, 18 or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116, or a polynucleotide having at least 70% sequence identity with SEQ ID NO:8; SEQ ID NO:9; SEQ ID NO:10; SEQ ID NO:1; SEQ ID NO:14; SEQ ID NO:22; SEQ ID NO:27; SEQ ID NO:31; SEQ ID NO:47; SEQ ID NO:50; SEQ ID NO:53; SEQ ID NO-57; SEQ ID NO:62; SEQ ID NO:79; SEQ ID NO:82; SEQ ID NO:87. SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116, The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3, ends and no gaps. However, dsRNAs having 5' or 3' overhangs of up to 100 nucleotides may be used in the methods of the invention.

As used herein, "complement" and "complementary" refer to the ability of two single stranded nucleic acid fragments to base pair with each other, where an adenine on one nucleic acid fragment will base pair to a thymine on a second nucleic acid fragment and a cytosine on one nucleic acid fragment will base pair to a guanine on a second nucleic acid fragment. Two nucleic acid fragments are complementary to each other when a nucleotide sequence in one nucleic acid fragment can base pair with a nucleotide sequence in a second nucleic acid fragment. For instance, 5'-ATGC and 5'-GCAT are complementary. The term complement and complementary also encompasses two nucleic acid fragments where one nucleic acid fragment contains at least one nucleotide that will not base pair to at least one nucleotide present on a second nucleic acid fragment. For instance the third nucleotide of each of the two nucleic acid fragments 5'-ATTGC and 5'-GCTAT will not base pair, but these two nucleic acid fragments are complementary as defined herein. Typically two nucleic acid fragments are complementary if they hybridize under the conditions referred to herein.

The dsRNA may comprise ribonucleotides or ribonucleotide analogs, such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238:645-650 and Cooney et al., 1988, Science 241: 456-459) and co-suppression (Napoli et al., 1990, Plant Cell 2:279-289) are known in the art. Partial and full-length cDNAs have been used for the co-suppression of endogenous plant genes. See, e.g., U.S. Pat. Nos. 4,801,340, 5,034,323, 5,231,020, and 5,283,184; Van der Kroll et al., 1990, Plant Cell 2:291-299; Smith et al., 1990, Mol. Gen. Genetics 224: 477-481 and Napoli et al., 1990, Plant Cell 2:279-289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95% or more. The introduced sense polynucleotide need not be full length relative to the target gene or transcript. Preferably, the sense polynucleotide will have at least 65% sequence identity with at least 100 consecutive nucleotides of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. The regions of identity can comprise introns and/or exons and untranslated regions. The introduced sense polynucleotide may be present in the plant cell transiently, or may be stably integrated into a plant chromosome or extrachromosomal replicon.

Alternatively, PTP gene expression can be inhibited by targeting nucleotide sequences complementary to the regulatory region of a PTP nucleotide sequence (e.g., a PTP promoter and/or enhancer) to form triple helical structures that prevent transcription of a PTP gene in target cells. See generally, Helene, C., 1991, Anticancer Drug Des. 6(6):569-84; Helene, C. et al., 1992, Ann. N.Y. Acad. Sci. 660:27-36; and Maher, L. J., 1992, Bioassays 14(12):807-15.

In addition to the PTP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; an anti-sense sequence of one of the sequences set forth in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; or naturally occurring mutants thereof. Primers based on a nucleotide sequence of SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; SEQ ID NO:90; SEQ ID NO:93; SEQ ID NO:96; SEQ ID NO:99; SEQ ID NO, 102; SEQ ID NO:104; SEQ ID NO:107; SEQ ID NO:109; SEQ ID NO:111; SEQ ID NO:113; or SEQ ID NO:116, can be used in PCR reactions to clone PTP and PTE homologs. Probes based on the PTP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a PTP, such as by measuring a level of a PTP-encoding nucleic acid, in a sample of cells, e.g., detecting PTP mRNA levels or determining whether a genomic PTP gene has been mutated or deleted.

Such probes may also be used to detect whether a cell contains a PTE, such as by transposon display, or screening a genomic library. Detection of a PTE can comprise using a probe that comprises a nucleic acid sequence which hybridizes in 5×SSC at 55° C. to the transposable element and detecting hybridization, thereby identifying the transposable element. In one embodiment, the transposable element comprises a nucleic acid sequence selected from the group consisting of a polynucleotide as defined in SEQ ID NO:1; SEQ ID NO:2; SEQ ID NO:3; or SEQ ID NO:4. In another embodiment, the transposable element comprises a nucleic acid sequence selected from the group consisting of a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90. In another embodiment, the transposable element comprises a nucleic acid sequence selected from the group consisting of a nucleic acid having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90. In another embodiment, the transposable element comprises a polynucleotide encoding a polypeptide as defined in SEQ ID NO, 12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91. In another embodiment, the transposable element comprises a nucleic acid sequence selected from the group consisting of a nucleic acid encoding a polypeptide having at least 25% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91. In another embodiment, the transposable element comprises a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92. In another embodiment, the transposable element comprises a nucleic acid sequence selected from the group consisting of a nucleic acid encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92. In another embodiment, the transposable element comprises a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140. In another embodiment, the transposable element comprises a nucleic acid sequence selected from the group consisting of a nucleic acid having at least 55% sequence identity with a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140. In another embodiment, the transposable element comprises a polynucleotide encoding a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141. In another embodiment, the transposable element comprises a nucleic acid sequence selected from the group consisting of a nucleic acid encoding a polypeptide having at least 60% sequence identity with a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141. In another embodiment, the transposable element comprises a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:11; SEQ ID NO:113; or SEQ ID NO:116. In another embodiment, the transposable element comprises a nucleic acid sequence selected from the group consisting of a nucleic acid having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. In another embodiment, the transposable element comprises a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. In another embodiment, the transposable element comprises a nucleic acid sequence selected from the group consisting of a nucleic acid encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:11; SEQ ID NO:113; or SEQ ID NO:116.

Such probes can also be used to determine whether a transposition of a transposable element has occurred in a sample or a cell. As used herein, the term "transposition" refers to the change in location of a transposable element in the genome of an organism. Such a transposition can be detected by a number of techniques currently known, or known in the future. One such preferred well-known technique for determining whether a transposition of a transposable element has occurred within a sample, a cell, or an organism is transposon display.

The present invention encompasses a method of screening a cell for a transposition of a transposable element, wherein the transposable element is actively transposing, comprising the steps of a) providing a cell comprising a transposable element, b) inducing a transposition of the transposable element by a transposase encoded by a nucleic acid sequence selected from the group consisting of: i) a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; ii) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; iii) a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and iv) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and c) comparing the phenotype of the cell containing the transposition of the transposable element to a wild-type cell not containing the transposition of the transposable element to thereby screen for a cell containing the transposition.

In one embodiment of the above method, the transposase is encoded by a nucleic acid sequence selected from the group consisting of a polynucleotide having at least 75% identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. In another embodiment, the transposase is encoded by a nucleic acid sequence selected from the group consisting of a polynucleotide encoding a polypeptide having at least 75% identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116.

In another embodiment of the above method, the transposable element comprises a nucleic acid sequence selected from the group consisting of a polynucleotide as defined in SEQ ID NO:1; SEQ ID NO:2; SEQ ID NO:3; or SEQ ID NO:4. In another embodiment, the transposable element comprises a nucleic acid sequence selected from the group consisting of a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90. In another embodiment, the transposable element comprises a nucleic acid sequence selected from the group consisting of a nucleic acid having at least 80% sequence identity with a polynucleotide as defined in SEQ ID NO:8; SEQ ID NO:9; SEQ ID NO:10; SEQ ID NO:111; SEQ ID NO: 4; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90. In another embodiment, the transposable element comprises a nucleic acid sequence selected from the group consisting of 1) a polynucleotide encoding a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91; and 2) a nucleic acid encoding a polypeptide having at least 25% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; or SEQ ID NO:91. In another embodiment, the transposable element comprises a nucleic acid sequence selected from the group consisting of 1) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; and 2) a nucleic acid encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92. In another embodiment, the transposable element comprises a nucleic acid sequence selected from the group consisting of: 1) a polynucleotide as defined in SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140; and 2) a nucleic acid having at least 55% sequence identity with a polynucleotide as defined in SEQ ID NO:120; the contiguous sequence of SEQ ID NOs:122-123; SEQ ID NO:125; SEQ ID NO, 127; SEQ ID NO:129; SEQ ID NO:131; SEQ ID NO:133; SEQ ID NO:135; SEQ ID NO:138; or SEQ ID NO:140. In another embodiment, the transposable element comprises a nucleic acid sequence selected from the group consisting of: 1) a polynucleotide encoding a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141; and 2) a nucleic acid encoding a polypeptide having at least 60% sequence identity with a polypeptide as defined in SEQ ID NO:121; SEQ ID NO:124; SEQ ID NO:126; SEQ ID NO:128; SEQ ID NO:130; SEQ ID NO:132; SEQ ID NO:134; the contiguous sequence of SEQ ID NOs:136 and 137; SEQ ID NO:139; or SEQ ID NO:141. In another embodiment, the transposable element comprises a nucleic acid sequence selected from the group consisting of: 1) a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:11; SEQ ID NO:113; or SEQ ID NO:116; and 2) a nucleic acid having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. In another embodiment, the transposable element comprises a nucleic acid sequence selected from the group consisting of: 1) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and 2) a nucleic acid encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116.

The present invention further contemplates a method of localizing a transposable element nucleic acid sequence, comprising a) providing the genomic DNA of a cell; b) obtaining the nucleic acid sequence of the transposable element nucleic acid sequence and the adjacent genomic DNA, wherein the transposable element nucleic acid sequence comprises a polynucleotide selected from the group consisting of: i) a polynucleotide as defined in SEQ ID NO:1, SEQ ID NO:2, SEQ ID NO:3 SEQ ID NO:4; SEQ ID NO:5; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; ii) a polynucleotide encoding a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13 the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; iii) a polynucleotide comprising at least 20 consecutive nucleotides of any of i) through ii) above; and iv) a polynucleotide complementary to a polynucleotide of any of i) through iii) above; to thereby localize the transposable element nucleic acid sequence. In one embodiment of the above method, the transposable element comprises a polynucleotide encoding a polypeptide having at least 95% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92. In another embodiment, the transposable element comprises a polynucleotide encoding a polypeptide having at least 90% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92. In yet another embodiment, the transposable element comprises a polynucleotide encoding a polypeptide having at least 80% sequence identity with a polypeptide as defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; SEQ ID NO:91; SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92.

In one embodiment of the above method, the cell is not transgenic. In another embodiment, the cell is transgenic. In a further embodiment of the above method, obtaining the nucleic acid sequence of the transposable element nucleic acid sequence and the adjacent DNA comprises performing transposon display. In a preferred embodiment, transposon display is performed as described in U.S. Pat. No. 6,420,117, herein incorporated by reference in its entirety. Preferably, performing transposon display to detect a transposition of a transposable element of the mPing/Pong family of DNA transposable elements comprises the use of one or more nucleic acid sequences selected from the group consisting of a) a polynucleotide as defined in SEQ ID NO, 142; SEQ ID NO:143; SEQ ID NO:148; or SEQ ID NO:149; b) a polynucleotide having a nucleic acid sequence which hybridizes to the nucleic acid sequence of SEQ ID NO:1; SEQ ID NO:2; SEQ ID NO:3; SEQ ID NO:4; SEQ ID NO:5; SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; in 5×SSC at 55° C. and c) a polynucleotide having a nucleic acid sequence which hybridizes to the nucleic acid sequence of SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; SEQ ID NO:116; SEQ ID NO:120; the contiguous sequence of SEQ ID NOs:122-123; SEQ ID NO:125; SEQ ID NO:127; SEQ ID NO:129; SEQ ID NO:131; SEQ ID NO:133; SEQ ID NO:135; SEQ ID NO:138; or SEQ ID NO:140 in 5×SSC at 55° C.

The present invention contemplates a method for making a transgenic cell, comprising transforming a cell with an isolated transposable element, wherein the isolated transposable element comprises a nucleic acid sequence selected from the group consisting of a) a polynucleotide as defined in SEQ ID NO:1, SEQ ID NO:2, or SEQ ID NO:4; b) a polynucleotide as defined SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; c) a polynucleotide as defined in SEQ ID NO:93; SEQ ID NO:96; SEQ ID NO:99; SEQ ID NO:102; SEQ ID NO:104; SEQ ID NO:1107; SEQ ID NO:109; SEQ ID NO:111; SEQ ID NO:113; or SEQ ID NO:116; and d) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116 and orthologs and homologs thereof.

In a preferred embodiment of the above method, the isolated transposable element comprises a nucleic acid sequence selected from the group consisting of a polynucleotide having at least 75% identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. In another preferred embodiment of the above method, the isolated transposable element comprises a nucleic acid sequence selected from the group consisting of a polynucleotide encoding a polypeptide having at least 75% identity with a polypeptide as defined in SEQ ID NO:93; SEQ ID NO:96; SEQ ID NO:99; SEQ ID NO:102; SEQ ID NO:104; SEQ ID NO: 107; SEQ ID NO:109; SEQ ID NO:111; SEQ ID NO:113; or SEQ ID NO:116.

In alternative embodiments, the isolated transposable element comprises a nucleic acid sequence that hybridizes in 5×SSC at 55° C. to any of the polynucleotides as defined above. In other embodiments, the isolated transposable element is modified to include a promoter operatively linked to a foreign nucleic acid flanked by the terminal inverted repeats of the transposable element.

In certain embodiments of the above method, the cell transformed with the isolated transposable element further comprises a transposase protein encoded by a nucleic acid sequence selected from the group consisting of a) a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; b) a polynucleotide having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO: 50; SEQ ID NO:53; SEQ ID NO:57; SEQ ID NO:62; SEQ ID NO:79; SEQ ID NO:82; SEQ ID NO:87; or SEQ ID NO:90; c) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; d) a polynucleotide encoding a polypeptide having at least 90% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; e) a polynucleotide encoding a polypeptide having at least 75% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; t) a polynucleotide encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; g) a polynucleotide as defined SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; h) a polynucleotide having at least 90% sequence identity with a polynucleotide as defined SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; i) a polynucleotide having at least 75% sequence identity with a polynucleotide as defined SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; j) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; k) a polynucleotide encoding a polypeptide having at least 90% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:11; SEQ ID NO:113; or SEQ ID NO:116; and 1) a polynucleotide encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116.

The present invention further encompasses a transposase protein comprising a nucleic acid sequence selected from the group consisting of 1) a polynucleotide which hybridizes in 5×SSC at 55° C. to the polynucleotide as defined in any of a) through 1) above, and 2) a polynucleotide complementary to the polynucleotide as defined in 1).

In another preferred embodiment, the cell transformed with the isolated transposable element further comprises an isolated nucleic acid sequence encoding a transposase protein, wherein the nucleic acid sequence is selected from the group consisting of a) a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; b) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; c) a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and d) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. In one embodiment, the cell transformed with the isolated transposable element further comprises an isolated nucleic acid sequence encoding a transposase protein, wherein the nucleic acid sequence is selected from the group consisting of a polynucleotide having at least 75% identity with a polynucleotide as defined SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. In another embodiment, the cell transformed with the isolated transposable element further comprises an isolated nucleic acid sequence encoding a transposase protein, wherein the nucleic acid sequence is selected from the group consisting of a polynucleotide encoding a polypeptide having at least 75% identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116.

In certain embodiments of the above method, the cell transformed with the isolated transposable element further comprises a transposase protein encoded by an isolated nucleic acid sequence selected from the group consisting of a) a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; b) a polynucleotide having at least 80% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; c) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; d) a polynucleotide encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; e) a polynucleotide as defined SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; f) a polynucleotide having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; g) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and h) a polynucleotide encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116. The present invention further encompasses a transposase protein comprising an isolated nucleic acid sequence selected from the group consisting of a) a polynucleotide which hybridizes in 5×SSC at 55° C. to the polynucleotide as defined in any of a) through g) above, and b) a polynucleotide complementary to the polynucleotide as defined in a).

In a preferred embodiment of the above method, the isolated transposable element and nucleic acid sequence encoding the transposase protein are incorporated into a vector.

The present invention further contemplates a method for making a transgenic cell, comprising transforming a cell with transposase protein comprising an isolated nucleic acid sequence selected from the group consisting of a) a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; b) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92; c) a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and d) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; or SEQ ID NO:116; and homologs and orthologs thereof.

In one embodiment of the above method the nucleic acid sequence comprises a polynucleotide encoding a polypeptide having at least 95% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92. In another embodiment, the nucleic acid sequence comprises a polynucleotide encoding a polypeptide having at least 90% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92. In another embodiment, the nucleic acid sequence comprises a polynucleotide encoding a polypeptide having at least 80% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92. In another embodiment, the nucleic acid sequence comprises a polynucleotide encoding a polypeptide having at least 70% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92. In another embodiment, the nucleic acid sequence comprises a polynucleotide encoding a polypeptide having at least 60% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92. In another embodiment, the nucleic acid sequence comprises a polynucleotide encoding a polypeptide having at least 50% sequence identity with a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92.

In another embodiment of the above method, the nucleic acid sequence comprises a polynucleotide having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. In another embodiment, the nucleic acid sequence comprises a polynucleotide encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116.

In another embodiment of the above method, the nucleic acid sequence is a polynucleotide which hybridizes in 5×SSC at 55° C. to a nucleic acid sequence selected from the group consisting of a) a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90; and b) a polynucleotide encoding a polypeptide as defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92. In another embodiment of the above method, the nucleic acid sequence is a polynucleotide which hybridizes in 5×SSC at 55° C. to a nucleic acid sequence selected from the group consisting of a) a polynucleotide as defined in SEQ ID NO:93; SEQ ID NO:96; SEQ ID NO:99; SEQ ID NO:102; SEQ ID NO:104; SEQ ID NO, 107; SEQ ID NO:109; SEQ ID NO:111; SEQ ID NO:113; and SEQ ID NO:116; and b) a polynucleotide encoding a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116

In still another embodiment of the above method, the nucleic acid sequence is a polynucleotide which hybridizes in 5×SSC at 55° C. to a nucleic acid sequence selected from the group consisting of a polynucleotide having at least 95% sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82;

SEQ ID NO:87; or SEQ ID NO:90. In another embodiment, the nucleic acid sequence is a polynucleotide which hybridizes in 5×SSC at 55° C. to a nucleic acid sequence selected from the group consisting of a polynucleotide having at least 50%, 55%, 60%, 65%, 70%, 75%, 80%, 85%, 90%, 95%, 96%, 97%, 98%, 99% or more sequence identity with a polynucleotide as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO:57; SEQ ID NO:62; SEQ ID NO:79; SEQ ID NO:82; SEQ ID NO:87; or SEQ ID NO:90. In another embodiment, the nucleic acid sequence is a polynucleotide which hybridizes in 5×SSC at 55° C. to a nucleic acid sequence selected from the group consisting of a polynucleotide encoding a polypeptide having at least 95% sequence identity with a polypeptide as defined in SEQ ID NO: 13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; or SEQ ID NO:92. In another embodiment, the nucleic acid sequence is a polynucleotide which hybridizes in 5×SSC at 55° C. to a nucleic acid sequence selected from the group consisting of a polynucleotide encoding a polypeptide having at least 50%, 55%, 60%, 65%, 70%, 75%, 80%, 85%, 90%, 95%, 96%, 97%, 98%, 99% or more sequence identity with a polypeptide as defined in SEQ ID NO, 13; the contiguous sequence of SEQ ID NOs:17 through 21; the contiguous sequence of SEQ ID NOs:25 and 26; the contiguous sequence of SEQ ID NOs: 29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs: 88 and 89; or SEQ ID NO:92.

In another embodiment, the nucleic acid sequence is a polynucleotide which hybridizes in 5×SSC at 55° C. to a nucleic acid sequence selected from the group consisting of a polynucleotide having at least 95% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. In another embodiment, the nucleic acid sequence is a polynucleotide which hybridizes in 5×SSC at 55° C. to a nucleic acid sequence selected from the group consisting of a polynucleotide having at least 75% sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. In another embodiment, the nucleic acid sequence is a polynucleotide which hybridizes in 5×SSC at 55° C. to a nucleic acid sequence selected from the group consisting of a polynucleotide having at least 50%, 55%, 60%, 65%, 70%, 75%, 80%, 85%, 90%, 95%, 96%, 97%, 98%, 99% or more sequence identity with a polynucleotide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. In another embodiment, the nucleic acid sequence is a polynucleotide which hybridizes in 5×SSC at 55° C. to a nucleic acid sequence selected from the group consisting of a nucleic acid encoding a polypeptide having at least 95% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. In another embodiment, the nucleic acid sequence is a polynucleotide which hybridizes in 5×SSC at 55° C. to a nucleic acid sequence selected from the group consisting of a nucleic acid encoding a polypeptide having at least 75% sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116. In another embodiment, the nucleic acid sequence is a polynucleotide which hybridizes in 5×SSC at 55° C. to a nucleic acid sequence selected from the group consisting of a nucleic acid encoding a polypeptide having at least 50%, 55%, 60%, 65%, 70%, 75%, 80%, 85%, 90%, 95%, 96%, 97%, 98%, 99% or more sequence identity with a polypeptide as defined in SEQ ID NO:93; SEQ ID NO:96; SEQ ID NO:99; SEQ ID NO:102; SEQ ID NO:104; SEQ ID NO:107; SEQ ID NO:109; SEQ ID NO:111; SEQ ID NO:113; and SEQ ID NO:116.

The present invention provides a transgenic plant cell transformed by a PTP coding nucleic acid, wherein expression of the nucleic acid sequence in the plant cell results in increased transposition of a transposable element as compared to a wild type variety of the plant cell. In a preferred embodiment, the increase of transposition is 2 fold, more preferably the increase in transposition is 4-fold, and most preferably the increase in transposition is at least 6-fold, 7-fold, 8-fold, 9-fold, 10-fold, 100-fold, or 1000-fold. The present invention further provides for a transgenic plant cell transformed by a PTE nucleic acid, wherein the PTE nucleic acid is capable of active transposition within the genome of the plant cell. The invention further provides transgenic plant parts and transgenic plants containing the plant cells described herein. In preferred embodiments, the transgenic plants and plant parts have increased transposition of a transposable element as compared to a wild type variety of the plant. Plant parts include, but are not limited to, stems, roots, ovules, stamens, leaves, embryos, meristematic regions, callus tissue, gametophytes, sporophytes, pollen, microspores, and the like. Plant cells include germ cells and somatic cells. In one embodiment, the transgenic plant is male sterile. Also provided is a plant seed produced by a transgenic plant transformed by a PTP coding nucleic acid or PTE nucleic acid wherein the seed contains the PTP coding nucleic acid or PTE nucleic acid, and wherein the plant is true breeding for increased transposition of a transposable element as compared to a wild type variety of the plant. The invention further provides a seed produced by a transgenic plant expressing a PTP, wherein the seed contains the PTP, and wherein the plant is true breeding for increased transposition of a transposable element as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like. In other embodiments of the present invention, the plant cell, plant part or plant containing a PTP or PTE is not transgenic.

It is expected that an individual that contains transposable elements in its genome can be used in the present invention. The individual can be an animal, plant, or a fungi, and is preferably a plant. The plant can be a monocot plant or a dicot plant. Seeds and plants comprising a nucleic acid molecule as described are also preferred. More preferred are plants as described, wherein the plant is selected from the group consisting of, soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; millet; flax; potato; pine; walnut; citrus (including oranges, grapefruit etc.); hemp; oak; rice; petunia; orchids; *Arabidopsis*; broccoli; cauliflower; brussel sprouts; onion; garlic; leek; squash; pumpkin; celery; pea; bean (including various legumes); strawberries; grapes; apples; cherries; pears; peaches; banana; palm; cocoa; cucumber; pineapple; apricot; plum; sugar beet; lawn grasses; maple; teosinte; *Tripsacum*; *Coix*; triticale; safflower; peanut; and olive. Most preferably, the plant is selected from the group consisting of rice and *Brassica*. Preferably, when the methods are directed to detecting a polymorphism between the nucleic acid fragments of two individuals, or directed to correlating the presence of an amplified fragment to a phenotype, the two individuals are the same species.

In certain embodiments of the present invention, the methods comprise an intermediate step of producing a progeny plant from a plant cell prior to analyzing the phenotype of the cell. As used herein, "phenotype" is a visible or otherwise measurable property of an individual.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

In particular, a useful method to ascertain the level of transcription of the gene (an indicator of the amount of mRNA available for translation to the gene product) is to perform a Northern blot. For reference, see, for example, Ausubel et al., 1988, Current Protocols in Molecular Biology, Wiley: New York. The information from a Northern blot at least partially demonstrates the degree of transcription of the transformed gene. Total cellular RNA can be prepared from cells, tissues or organs by several methods, all well-known in the art, such as that described in Bormann, E. R. et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. See, for example, Ausubel et al., 1988, Current Protocols in Molecular Biology, Wiley: New York.

The invention further provides an isolated recombinant expression vector comprising a PTP nucleic acid or PTE nucleic acid as described above, wherein expression of the vector in a host cell results in increased transposition of a mPing/Pong transposable element as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, *Gene Expression Technology: Methods in Enzymology* 185, Academic Press, San Diego, Calif. (1990) and Gruber and Crosby, in: *Methods in Plant Molecular Biology and Biotechnology*, Eds. Click and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., PTPs, mutant forms of PTPs, fusion polypeptides, etc.).

The recombinant expression vectors of the invention can be designed for expression of PTPs in prokaryotic or eukaryotic cells. For example, PTP genes can be expressed in bacterial cells such as *C. glutamicum*, insect cells (using baculovirus expression vectors), yeast and other fungal cells (See Romanos, M. A. et al., 1992, *Foreign gene expression in Yeast: a Review*, Yeast 8:423-488; van den Hondel, C. A. M. J. J. et al., 1991, Heterologous gene expression in filamentous fungi, in: *More Gene Manipulations in Fungi*, J. W. Bennet & L. L. Lasure, eds., p. 396-428: Academic Press: San Diego; and van den Hondel, C. A. M. J. J. & Punt, P. J., 1991, *Gene transfer systems and vector development for filamentous fungi, in: Applied Molecular Genetics of Fungi*, Peberdy, J. F. et al., eds., p. 1-28, Cambridge University Press: Cambridge), algae (Falciatore et al., 1999, *Marine Biotechnology* 1(3): 239-251), ciliates of the types: *Holotrichia, Peritrichia, Spirotrichia, Suctoria, Tetrahymena, Paramecium, Col-*

*pidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in PCT Application No. WO 98/01572, and multicellular plant cells (See Schmidt, R. and Willmitzer, L., 1988, *High efficiency Agrobacterium tumefaciens-mediated transformation of Arabidopsis thaliana leaf and cotyledon explants, Plant Cell Rep.* 583-586; *Plant Molecular Biology and Biotechnology*, C Press, Boca Raton, Fla., chapter 6/7, S.71-119 (1993); F. F. White, B. Jenes et al., *Techniques for Gene Transfer*, in: *Transgenic Plants*, Vol. 1, Engineering and Utilization, Eds. Kung And R. Wu, 128-43, Academic Press: 1993; Potrykus, 1991, *Annu. Rev. Plant Physiol. Plant Molec. Biol.* 42:205-225 and references cited therein) or mammalian cells. Suitable host cells are discussed further in Goeddel, *Gene Expression Technology; Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31-40), pMAL (New England Biolabs, Beverly, Mass.) and pRITS (Pharmacia, Piscataway, N.J.) which fuse glutathione S-transferase (GST), maltose E binding polypeptide, or polypeptide A, respectively, to the target recombinant polypeptide. In one embodiment, the coding sequence of the PTP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant PTP unfused to GST can be recovered by cleavage of the fusion polypeptide with thrombin.

Examples of suitable inducible non-fusion *E. coli* expression vectors include pTrc (Amann et al., 1988, Gene 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., *Gene Expression Technology: Methods in Enzymology* 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, *Nucleic Acids Res.* 20:2111-2118). Such alteration of nucleic acid sequences of the invention can be carried out by standard DNA synthesis techniques.

In another embodiment, the PTP expression vector is a yeast expression vector. Examples of vectors for expression in yeast *S. cerevisiae* include pYepSec1 (Baldari, et al., 1987, *EMBO J.* 6:229-234), pMFa (Kurjan and Herskowitz, 1982, *Cell* 30:933-943), pJRY88 (Schultz et al., 1987, *Gene* 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J., 1991, *Gene transfer systems and vector development for filamentous fungi*, in: *Applied Molecular Genetics of Fungi*, J. F. Peberdy, et al., eds., p. 1-28, Cambridge University Press: Cambridge.

Alternatively, the PTPs of the invention can be expressed in insect cells using baculovirus expression vectors. Baculovirus vectors available for expression of polypeptides in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a PTP nucleic acid of the invention is expressed in mammalian cells using a mammalian expression vector. Examples of mammalian expression vectors include pCDM8 (Seed, B., 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. *Molecular Cloning: A Laboratory Manual*, 2nd Ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, Cell 33:741-748), neuron-specific promoters (e.g., the neurofilament promoter; Byrne and Ruddle, 1989, *PNAS* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990, Science 249:374-379) and the fetopolypeptide promoter (Campes and Tilghman, 1989, *Genes Dev.* 3:537-546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, and methotrexate, or in plants that confer resistance towards a herbicide such as glyphosate or glufosinate. Nucleic acid molecules encoding a selectable marker can be introduced into a host cell on the same vector as that encoding a PTP or can be introduced on a separate vector. Cells stably transfected with the introduced nucleic acid molecule can be identified by, for example, drug selection (e.g., cells that have incorporated the selectable marker gene will survive, while the other cells die).

In a preferred embodiment of the present invention, the PTPs or the PTE nucleic acid are introduced in plants and plants cells such as unicellular plant cells (e.g. algae) (See Falciatore et al., 1999, *Marine Biotechnology* 1(3):239-251 and references therein) and plant cells from higher plants (e.g., the spermatophytes, such as crop plants). A PTP or PTE may be "introduced" into a plant cell by any means, including transfection, transformation or transduction, electroporation, particle bombardment, agroinfection, and the like. One transformation method known to those of skill in the art is the dipping of a flowering plant into an *Agrobacteria* solution, wherein the *Agrobacteria* contains the PTP or PTE nucleic acid, followed by breeding of the transformed gametes.

Other suitable methods for transforming or transfecting host cells including plant cells can be found in Sambrook, et al., *Molecular Cloning: A Laboratory Manual.* 2nd Ed., Cold Spring Harbor Laboratory, Cold Spring Harbor Laboratory Press, Cold Spring Harbor, N.Y., 1989, and other laboratory manuals such as *Methods in Molecular Biology*, 1995, Vol. 44, *Agrobacterium protocols*, Ed: Gartland and Davey, Humana Press, Totowa, N.J. As actively transposing DNA elements are a useful tool, it is desirable that PTPs and/or PTEs be introduced into a wide variety of plants like maize, wheat, rye, oat, triticale, rice, barley, soybean, peanut, cotton, rapeseed and canola, *manihot*, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops. These crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a PTP or PTE into a plant is achieved by *Agrobacterium* mediated gene transfer. *Agrobacterium* mediated plant transformation can be performed using for example the GV3101 (pMP90) (Koncz and Schell, 1986, *Mol. Gen. Genet.* 204: 383-396) or LBA4404 (Clontech) *Agrobacterium tumefaciens* strain. Transformation can be performed by standard transformation and regeneration techniques (Deblaere et al., 1994, *Nucl. Acids Res.* 13:4777-4788; Gelvin, Stanton B. and Schilperoort, Robert A, *Plant Molecular Biology Manual*, 2nd Ed.—Dordrecht: Kluwer Academic Publ., 1995.—in Sect., Ringbuc Zentrale Signatur; BT11-P ISBN 0-7923-2731-4; Glick, Bernard R.; Thompson, John E., *Methods in Plant Molecular Biology and Biotechnology*, Boca Raton: CRC Press, 1993 360 S., ISBN 0-8493-5164-2). For example, rapeseed can be transformed via cotyledon or hypocotyl transformation (Moloney et al., 1989, *Plant cell Report* 8:238-242; De Block et al., 1989, *Plant Physiol.* 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, *Plant Cell Report* 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake or via the silicon carbide fiber technique. (See, for example, Freeling and Walbot "*The maize handbook*" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced PTP or PTE nucleic acid may be maintained in the plant cell stably if it is incorporated into a non-chromosomal autonomous replicon or integrated into the plant chromosomes. Alternatively, the introduced PTP or PTE nucleic acid may be present on an extra-chromosomal non-replicating vector and be transiently expressed or transiently active.

In one embodiment, a homologous recombinant microorganism can be created wherein the PTP is integrated into a chromosome, a vector is prepared which contains at least a portion of a PTP gene into which a deletion, addition, or substitution has been introduced to thereby alter, e.g., functionally disrupt, the PTP gene. Preferably, the PTP gene is a *Brassica oleracea*, or *Oryza sativa* PTP gene, but it can be a homolog from a related plant or even from a mammalian, yeast, or insect source. In one embodiment, the vector is designed such that, upon homologous recombination, the endogenous PTP gene is functionally disrupted (i.e., no longer encodes a functional polypeptide; also referred to as a knock-out vector). Alternatively, the vector can be designed such that, upon homologous recombination, the endogenous PTP gene is mutated or otherwise altered but still encodes a functional polypeptide (e.g., the upstream regulatory region can be altered to thereby alter the expression of the endogenous PTP). To create a point mutation via homologous recombination, DNA-NA hybrids can be used in a technique known as chimeraplasty (Cole-Strauss et al., 1999, *Nucleic Acids Research* 27(5):1323-1330 and Kmiec, 1999 *Gene Therapy American Scientist.* 87(3):240-247). Homologous recombination procedures in other organisms are also well known in the art and are contemplated for use herein.

Whereas in the homologous recombination vector, the altered portion of the PTP gene is flanked at its 5' and 3' ends by an additional nucleic acid molecule of the PTP gene to allow for homologous recombination to occur between the exogenous PTP gene carried by the vector and an endogenous PTP gene, in a microorganism or plant. The additional flanking PTP nucleic acid molecule is of sufficient length for successful homologous recombination with the endogenous gene. Typically, several hundreds of base pairs up to kilobases of flanking DNA (both at the 5' and 3' ends) are included in the vector. See, e.g., Thomas, K. R., and Capecchi, M. R., 1987, *Cell* 51:503 for a description of homologous recombination vectors or Strepp et al., 1998, *PNAS*, 95 (8):4368-4373 for cDNA based recombination in *Physcomitrella patens*). The vector is introduced into a microorganism or plant cell (e.g., via polyethylene glycol mediated DNA), and cells in which the introduced PTP gene has homologously recombined with an endogenous PTP gene are selected using art-known techniques.

In another embodiment, recombinant microorganisms can be produced that contain selected systems which allow for regulated expression of the introduced gene. For example, inclusion of a PTP gene on a vector placing it under control of the lac operon permits expression of the PTP gene only in the presence of IPTG. Such regulatory systems are well known in the art.

Whether present in an extra-chromosomal non-replicating vector or a vector that is integrated into a chromosome, the PTP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, *EMBO J.* 3:835) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, *Nucl. Acids Research* 15:8693-8711). Examples of plant expression vectors include those detailed in: Becker, D. et al., 1992, *New plant binary vectors with selectable markers located proximal to the left border, Plant Mol. Biol.* 20: 1195-1197; and Bevan, M. W., 1984, *Binary Agrobacterium vectors for plant transformation*, Nucl. Acid. Res. 12:8711-8721; and *Vectors for Gene Transfer in Higher Plants*; in: *Transgenic Plants, Vol.* 1, *Engineering and Utilization*, eds.: Kung and R. Wu, Academic Press, 1993, S. 15-38.

Gene expression should be operatively linked to an appropriate promoter conferring gene expression in a timely, cell or tissue specific manner. Promoters useful in the expression cassettes of the invention include any promoter that is capable of initiating transcription in a cell.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35 S promoters (Odell et al., 1985, *Nature* 313:810-812), the sX CaMV 35S promoter (Kay et al., 1987, *Science* 236:1299-1302) the Sep1 promoter, the rice actin promoter (McElroy et al., 1990, *Plant Cell* 2:163-171), the *Arabidopsis* actin promoter, the ubiquitin promoter (Christensen et al., 1989, *Plant Molec Biol* 18:675-689); pEmu (Last et al., 1991, *Theor Appl Genet.* 81:581-588), the figwort mosaic virus 355 promoter, the Smas promoter (Velten et al., 1984, *EMBO J* 3:2723-2730), the GRP1-8 promoter, the cinnamyl alcohol dehydrogenase promoter (U.S. Pat. No. 5,683, 439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For a review, see Gatz, 1997, *Annu. Rev. Plant Physiol. Plant Mol. Biol* 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, *Plant J.* 2:397-404), and an ethanol inducible promoter (PCT Application No. WO 93/21334).

In one preferred embodiment of the present invention, the inducible promoter is a stress-inducible promoter. Stress inducible promoters include, but are not limited to, Cor78 (Chak et al., 2000, *Planta* 210:875-883; Hovath et al., 1993, *Plant Physiol.* 103:1047-1053), Cor15a (Artus et al., 1996, *PNAS* 93(23) 13404-09), Rci2A (Medina et al., 2001, *Plant Physiol.* 125:1655-66; Nylander et al., 2001, *Plant Mol. Biol.* 45:341-52; Navarre and Goffeau, 2000, *EMBO J.* 19:2515-24; Capel et al., 1997, *Plant Physiol.* 115:569-76), Rd22 (Xiong et al., 2001, *Plant Cell* 13:2063-83; Abe et al., 1997, *Plant Cell* 9:1859-68; Iwasaki et al., 1995, *Mol. Gen. Genet.* 247:391-8), cDet6 (Lang and Palve, 1992, *Plant Mol. Biol.* 20:951-62), ADH1 (Hoeren et al., 1998, *Genetics* 149:479-90), KAT1 (Nakamura et al., 1995, *Plant Physiol.* 109:371-4), KST1 (Müller-Röber et al., 1995, *EMBO* 14:2409-16), Rha1 (Terryn et al., 1993, *Plant Cell* 5:1761-9; Terryn et al., 1992, *FEBS Lett.* 299(3):287-90), ARSK1 (Atkinson et al., 1997, GenBank Accession # L22302, and PCT Application No. WO 97/20057), PtxA (Plesch et al., GenBank Accession # X67427), SbHRGP3 (Ahn et alt, 1996, *Plant Cell* 8:1477-90), GH3 (Liu et al., 1994, *Plant Cell* 6:645-57), the pathogen inducible PRP1-gene promoter (Ward et al., 1993, *Plant. Mol. Biol.* 22:361-366), the heat inducible hsp80-promoter from tomato (U.S. Pat. No. 5,187,267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, *Mol. Gen. Genet.* 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, *BioEssays* 10:108. Examples of seed preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from canola (U.S. Pat. No. 5,608,152), the USP-promoter from *Vicia faba* (Baeumlein et al., 1991, *Mol Gen Genet.* 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, *Plant Journal*, 2(2): 233-9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the App3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086, 169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, *Cell* 43:729-736).

The invention further provides a recombinant expression vector comprising a PTP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a PTP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, *Antisense RNA as a molecular tool for genetic analysis, Reviews—Trends in Genetics*, Vol. 1(1), and Mol et al., 1990, *FEBS Letters* 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a PTP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Similarly, a PTE nucleic acid can be introduced into any prokaryotic or eukaryotic cell, such as bacterial cells, insect cells, fungal cells, or mammalian cells, algae, ciliates, plant cells, fungi, or other microorganisms. Other suitable host cells are known to those skilled in the art.

A host cell of the invention, such as a prokaryotic or eukaryotic host cell in culture, can be used to produce (i.e., express) a PTP. Accordingly, the invention further provides methods for producing PTPs using the host cells of the invention. In one embodiment, the method comprises culturing the host cell of invention (into which a recombinant expression vector encoding a PTP has been introduced, or into which genome has been introduced a gene encoding a wild-type or altered PTP) in a suitable medium until PTP is produced. In another embodiment, the method encompasses the introduction of a heterologous PTE nucleic acid, the production of a PTP from either an endogenous gene or a heterologous gene, resulting in the transposition of the PTE. In another embodiment, the method further comprises isolating PTPs from the medium or the host cell.

Another aspect of the invention pertains to isolated PTPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of PTP in which the polypeptide is separated from some of the cellular components of the cells in which it is naturally or recombinantly produced. In one embodiment, the language "substantially free of cellular material" includes preparations of a PTP having less than about 30% (by dry weight) of non-PTP material (also referred to herein as a "contaminating polypeptide"), more preferably less than about 20% of non-PTP material, still more preferably less than about 10% of non-PTP material, and most preferably less than about 5% non-PTP material.

When the PTP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of PTP in which the polypeptide is separated from chemical precursors or other chemicals that are involved in the synthesis of the polypeptide. In one embodiment, the language "substantially free of chemical precursors or other chemicals" includes preparations of a PTP having less than about 30% (by dry weight) of chemical precursors or non-PTP chemicals, more preferably less than about 20% chemical precursors or non-PTP chemicals, still more preferably less than about 10% chemical precursors or non-PTP chemicals, and most preferably less than about 5% chemical precursors or non-PTP chemicals. In preferred embodiments, isolated polypeptides, or biologically active portions thereof, lack contaminating polypeptides from the same organism from which the PTP is derived. Typically, such polypeptides are produced by recombinant expression of, for example, a *Brassica oleracea*, or *Oryza sativa* PTP in plants other than *Brassica oleracea*, or *Oryza saliva*, or microorganisms such as *C. glutamicum*, ciliates, algae or fungi.

The nucleic acid molecules, polypeptides, polypeptide homologs, fusion polypeptides, primers, vectors, and host cells described herein can be used in one or more of the following methods: identification of *Brassica oleracea*, or *Oryza sativa* and related organisms; mapping of genomes of organisms related to *Brassica oleracea*, or *Oryza sativa*; identification and localization of *Brassica oleracea*, or *Oryza sativa* sequences of interest; evolutionary studies; determination of PTP and PTE regions required for function; modulation of a PTP activity; modulation of the metabolism of one or more cell functions; modulation of the transmembrane transport of one or more compounds; and modulation of expression of PTP nucleic acids.

The PTP and PTE nucleic acid molecules of the invention have a variety of uses. This invention will be of primary value in the establishment of the first non-transgenic DNA transposable element tagging populations in rice. Such populations will be of value in gene discovery in rice. The mPing/Pong transposable element family will be activated in cell culture and plants regenerated by established procedures. Alternatively, the transposable element family will be activated without using cell culture. Large population of regenerants will be established and mutants identified by visual screening or by biochemical analysis. Mutants will be crossed to wild type plants and the F1 will be selfed. If the F2 population segregates for the mutant phenotype, cells from mutant and wild-type plants will be analyzed by transposon display using the procedures described above to identify mPing or Pong products that co-segregate with the mutant phenotype. These bands will be removed from the gel, reamplified, cloned and sequenced, by established procedures.

In addition, the nucleic acid and amino acid sequences of the present invention can be used to transform plants, thereby inducing the transposition of a transposable element. The present invention therefore provides a transgenic plant transformed by a PTP or PTE nucleic acid, wherein expression of a PTP in the plant results in increased transposition of a transposable element as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, *manihot*, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops, for example.

Accordingly, the invention provides a method of producing a transgenic plant with a PTP coding nucleic acid, wherein expression of the nucleic acid in the plant results in increased transposition of a transposable element as compared to a wild type variety of the plant comprising: (a) introducing into a plant cell an expression vector comprising a PTP nucleic acid, and (b) generating from the plant cell a transgenic plant with an increased transposition of a transposable element as compared to a wild type variety of the plant. Also included within the present invention are methods of producing a transgenic plant with a PTE nucleic acid, wherein expression of a PTP in the plant results in increased transposition of the PTE nucleic acid as compared to a wild type variety of the plant comprising: (a) introducing into a plant cell an expression vector comprising a PTE nucleic acid, and (b) generating from the plant cell a transgenic plant with an increased transposition of the PTE nucleic acid as compared to a wild type variety of the plant. The invention further comprises methods of generating a transgenic plant from the transformed plant cell. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations.

The invention further provides a method of producing a transgenic plant with a PTP-encoding nucleic acid or a PTE nucleic acid, wherein expression of the nucleic acid in the plant results in increased transposition of a mPing/Pong transposable element as compared to a wild type variety of the plant comprising: (a) transforming a plant cell with an expression vector comprising a PTP-encoding nucleic acid or a PTE nucleic acid, and (b) generating from the plant cell a transgenic plant with an increased tolerance to environmental stress as compared to a wild type variety of the plant. In preferred embodiments, the environmental stress is exposure to herbicides, drought, extreme cold or heat, or salt.

The present invention also provides a method of modulating the transposition of a transposable element comprising modifying the expression of a PTP coding nucleic acid in the plant. The plant's level of transposition of a transposable element can be increased or decreased as achieved by increasing or decreasing the expression of a PTP, respectively. Preferably, increasing expression of a PIP increases the plant's level of transposition of a transposable element. Expression of a PTP can be modified by any method known to those of skill in the art. The methods of increasing expression of PTPs can be used wherein the plant is either transgenic or not transgenic. In cases when the plant is transgenic, the plant can be transformed with a vector containing any of the above described PTP coding nucleic acids, or the plant can be transformed with a promoter that directs expression of native PTP in the plant, for example. The invention provides that such a promoter can be tissue specific, developmentally regulated, or stress-inducible. Alternatively, non-transgenic plants can have native PTP expression modified by inducing a native promoter. The expression of PTP nucleic acids as defined in SEQ ID NO:8; SEQ ID NO:9; SEQ ID NO:10; SEQ ID NO:11; SEQ ID NO:14; SEQ ID NO:22; SEQ ID NO:27; SEQ ID NO:31; SEQ ID NO:47; SEQ ID NO:50; SEQ ID NO:53; SEQ ID NO: 57; SEQ ID NO:62; SEQ ID NO: 79; SEQ ID NO:82; SEQ ID NO:87; SEQ ID NO:90 in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275:657).

In a preferred embodiment, transcription of the PTP is modulated using zinc-finger derived transcription factors (ZFPs) as described in Greisman and Pabo, 1997, *Science* 275:657 and manufactured by Sangamo Biosciences, Inc. These ZFPs comprise both a DNA recognition domain and a functional domain that causes activation or repression of a target nucleic acid such as a PTP nucleic acid. Therefore, activating and repressing ZFPs can be created that specifically recognize the PTP promoters described above and used to increase or decrease PTP expression in a plant, thereby modulating the levels of transposition of a transposable element of the plant.

In addition to introducing the PTP and PTE nucleic acid sequences into transgenic plants, these sequences can also be used to identify an organism as being *Brassica oleracea*, *Oryza sativa*, or a close relative thereof. Also, they may be used to identify the presence of *Brassica oleracea*, *Oryza saliva*, or a relative thereof in a mixed population of microorganisms. The invention provides the nucleic acid sequences of a number of *Brassica oleracea*, and *Oryza sativa* genes; by probing the extracted genomic DNA of a culture of a unique or mixed population of microorganisms under stringent conditions with a probe spanning a region of a Brass/ca oleracea, or *Oryza sativa* gene which is unique to this organism, one can ascertain whether this organism is present.

The PTP nucleic acid molecules of the invention are also useful for evolutionary and polypeptide structural studies. By comparing the sequences of the nucleic acid molecules of the present invention to those encoding similar transposase enzymes and transposable elements from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the PTP nucleic acid molecules of the invention may result in the production of PTPs having functional differences from the wild-type PTPs. These polypeptides may be improved in efficiency or activity, may be present in greater numbers in the cell than is usual, or may be decreased in efficiency or activity.

Additionally, the sequences disclosed herein, or fragments thereof, can be used to generate knockout mutations in the genomes of various organisms, such as bacteria, mammalian cells, yeast cells, and plant cells (Girke, T., 1998, *Plant Journal* 15:39-48). The resultant knockout cells can then be evaluated for the effect of the transposition on the phenotype and/or genotype of the mutation. For other methods of gene inactivation, see U.S. Pat. No. 6,004,804 "Non-Chimeric Mutational Vectors" and Puttaraju et al., 1999, *Nature Biotechnology* 17:246-252.

The aforementioned strategies for manipulating PTPs and PTEs resulting in increased transposition of a transposable element are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like *C. glutamicum* expressing PTP nucleic acid and polypeptide molecules and containing PTE nucleic acids such that an increase in transposition of a transposable element is observed.

The present invention also provides antibodies that specifically bind to a PTP, or a portion thereof, as encoded by a nucleic acid described herein. Antibodies can be made by many well-known methods (See, e.g. Harlow and Lane, "*Antibodies; A Laboratory Manual.,*" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. See, for example, Kelly et al., 1992, *Bio/Technology* 10:163-167; Bebbington et al., 1992, *Bio/Technology* 10:169-175.

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "*Antibodies, A Laboratory Manual,*" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., Eds., "*Basic and Clinical Immunology,*" (Lange Medical Publications, Los Altos, Calif., Fourth Edition) and references cited therein, and in Harlow and Lane, "*Antibodies, A Laboratory Manual,*" Cold Spring Harbor Publications, New York, (1988).

Throughout this application, various publications are referenced. The disclosures of all of these publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Computer Assisted Identification of a New, Potentially Active MITE

It was reasoned that a potentially active MITE family would have two distinguishing features, (1) low copy number (i.e. it has not amplified significantly) and (2) low intra-family sequence divergence. The availability of almost half of the Nipponbare genome (~200 Mb) in public databases provided the possibility of identifying such low copy number elements by searching for repeat families with the structural features of MITEs and with very low intra-family sequence divergence. To this end, a two step protocol was employed involving the use of an algorithm to identify repeat families followed by manual screening of the output for a MITE family with virtually identical members. 3200 repeats were identified with RECON, a software package for de novo repeat family identification.

The *japonica* sequences (187 Mb total) were downloaded from rgp.dna.affrc.go.jp on Dec. 24, 2001. The *indica* sequences (361 Mb total) were downloaded from btn.genomics.org.cn/rice on Feb. 25, 2002. The *japonica* sequences were used for a systematic identification of repeat families. The sequences were subject to an all-versus-all comparison using WU-BLASTN2.0 (blast.wustl.edu), with options M=5 N=−11 Q=22 R=11–kap E=0.0001–hspmax 5000 wordmask=dust wordmask=seq maskextra=50. The resulting alignments were then clustered into repeat families using RECON with default options. The sequences of the 1257 repeat families obtained with RECON were further examined individually with programs in the University of Wisconsin Genetics Computer Group program suite (GCG, version 10.1) accessed through Research Computing resources (University of Georgia). 3200 total repeats were found. Sequence #1031, termed miniature Ping or mPing (SEQ ID NO:1), was identified as a Tourist-like miniature repeat transposable element (MITE) because (1) its size (430 bp) falls into the range of known MITEs (80-600 bp; (2) its terminal inverted repeat (TIR) is similar to known Tourist elements; (3) its target site duplication (TSD) is TTA or TAA, which is the same for most Tourist MITEs (FIG. 1; Feschotte et al. 2002 *Nat Rev Genet.,* 3(5):329-41).

The family members of mPing and its related elements in Nipponbare (updated on Feb. 25, 2002) and *indica* cultivar 93-11 were identified by BLAST search (WU-BLASTN 2.0) using the consensus sequence of mPing (SEQ ID NO:1). From this search, two types of putative autonomous elements were recovered, and named Ping and Pong.

Of 36 copies of mPing mined from 270 Mb of Nipponbare sequence, 26 were identical while the remaining seven differed at only a single position. A sequence of a consensus mPing element (SEQ ID NO:1) is presented in the Appendix (see FIG. 2 for the GenBank accession numbers). The element has 15 bp TIRs (positions 1-15 and 415-430) and virtually all elements are flanked by the trinucleotide TSD-TAA/TTA. It is estimated that the entire genome should contain 70 copies of mPing. In contrast, only 8 complete copies and 4 half copies of mPing were found in the 361 Mb of publicly available contig sequence of the *indica* cultivar 93-11 (Table 4). Based on this value, the entire genome of 93-11 is estimated to contain 14 copies of mPing. The 8 complete copies represent two subtypes. Subtype A (SEQ ID NO:1) has 3 members with two identical to the consensus mPing Nipponbare sequence and one differing at a single position. Subtype B (SEQ ID NO:2) has 4 identical members that differ from subtype A by an 11 bp deletion that is centrally located. Subtype C (SEQ ID NO:3) has the same length as subtype A, but the two sequences differ in a centrally located 11 bp region. Subtype D (SEQ ID NO:4) is 450 bp in length. Compared to subtype A, Subtype D has a centrally located 22 bp region that is different from subtype A, and also contains an extra 20 bp in the same region.

Example 2

Transposition of mPing in Cell Culture

No DNA transposons had previously been shown to be active in rice. In fact, the only rice transposable elements shown to be active were LTR retrotransposons that transposed in both *japonica* (Nipponbare) and *indica* (C5924) cell culture lines (Hirochika, 1993 EMBO J., 12: 2521-2528). Transposition of one of these elements, Tos17, was associated with its transcriptional activation in culture (Hirochika, 1993 EMBO J., 12: 2521-2528). To assess whether mPing elements were also activated in the same cell lines, a technique called transposon display was used to detect new mPing insertions that may have occurred during culturing. Transposon display is a modification of the AFLP procedure that generates PCR products that are anchored in a transposable element and in a flanking restriction site (Casa et al., 2000 *Proc. Natl. Acad. Sci. USA,* 93: 8524-8529). Since all of the mPing elements are virtually identical at their ends, element-specific primers located in the subterminal sequence were designed to amplify all family members and flanking host sequence.

Transposon display was performed as described (Casa et al., 2000 *Proc. Nat. Acad. Sci. USA,* 93: 8524-8529, and in U.S. Pat. No. 6,420,117, herein incorporated by reference in its entirety) with the following modifications. For transposon display with each element, two rounds of PCR (pre-selective amplification and selective amplification) were performed. For each PCR reaction, one of the two nested primers (P1 for pre-selective amplification and P2 for selective amplification, P2 is located downstream of Pt) complementary to the sub-terminal sequence of the element was used. P2 was labeled with $^{33}$P so that the resulting PCR products could be visualized following autoradiography. For selective amplification, a "touchdown" protocol was used where the annealing temperature starts 6° C. higher than the final annealing temperature and is reduced to the final temperature through a 1° C. reduction in temperature per cycle. Adapter sequences are as described.

For mPing, the primers used for transposon display were P1: TGT GCA TGA CAC ACC ACT G (SEQ ID NO:142); and P2: CAG TGA AAC CCC CAT TGT CAC (SEQ ID NO:143). The temperature cycling parameters used for pre-selective amplification were 72° C. for 2 minutes, 94° C. for 3 minutes, 94° C. for 45 seconds, 58° C. for 45 seconds, 72° C. for 45 seconds for 30 cycles, with a final cycle of 72° C. for 5 minutes. The temperature cycling parameters used for selective amplification were 94° C. for 3 minutes, 94° C. for 45 seconds, 64-59° C. for 45 seconds, 72° C. for 45 seconds, touchdown, 94° C. for 45 seconds, 58° C. for 45 seconds, 72° C. 45 seconds for 30 cycles, and a final cycle of 72° C. for 5 minutes.

Figure 3:
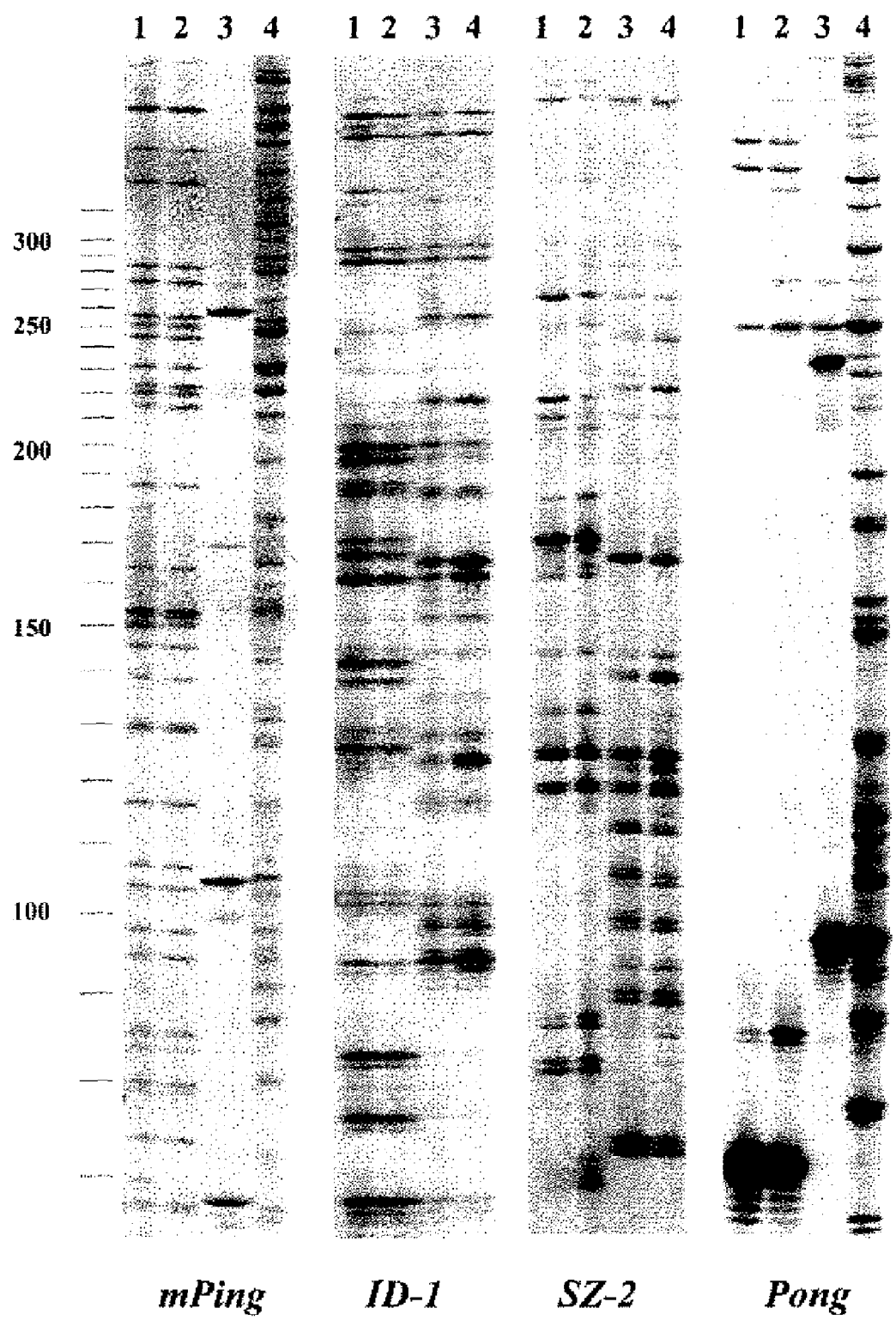
FIG. 3 shows an autoradiograph of transposon display gels of mPing, ID-1, SZ-2, and Pong amplicons with rice genomic DNAs isolated before and after cell culture. The same genomic DNAs (digested and ligated with adapters) were used for each set of primers: 1 Nipponbare; 2, calli of Nipponbare; 3, C5924; 4, Oc cell lines derived from C5924 (Baba, et al., 1986 Plant Cell Physiol., 27: 463-471). The migration of DNA markers is on the left in base pairs.

Comparison of the number of transposon display products amplified from DNAs isolated from Nippponbare (*japonica*) and C5924 (*indica*) plants before culture are consistent with the copy number estimates for mPing family members in the *japonica* and *indica* genomes, respectively (FIG. 3). Whereas the Nipponbare band pattern is the same before and after culture, the C5924 culture line has undergone a dramatic increase in the number of PCR products. To determine whether the difference was due to nonspecific genomic rearrangements in this cell line, transposon display was repeated using the same template DNAs but this time, the mPing primer was replaced with either a primer derived from the consensus sequence of two other rice transposable elements. The primer was derived from a gypsy type LTR retrotransposon, SZ-2, or from another rice MITE, ID-1 (Jiang & Wessler, 2001 *Plant Cell,* 13: 2553-2564).

For ID-1, the primers used for transposon display were P1: TAT GCT GAC ATG GAT CTC (SEQ ID NO:144), and P2: CTC TTR TAG AGA CCC TAT AG (SEQ ID NO:145). The temperature cycling parameters for pre-selective amplification were 72° C. for 2 minutes, 94° C. for 3 minutes, 94° C. for 45 seconds, 52° C. for 45 seconds, 72° C. 45 seconds for 30 cycles, and a final cycle of 72° C. for 5 minutes. The temperature cycling parameters for selective amplification were 94° C. for 3 minutes, 94° C. for 45 seconds, 61-56° C. for 45 seconds, 72° C. for 45 seconds, touchdown, 94° C. for 45 seconds, 55° C. for 45 seconds, 72° C. for 45 seconds for 30 cycles, and a final cycle of 72° C. for 5 minutes.

For SZ-2, the primers used for transposon display were P1: ACG TGG GCG ATT GCG TCT G (SEQ ID NO:146), and P2; TCT GCC TCA AGC CTC TAG TC (SEQ ID NO:147). The temperature cycling parameters for pre-selective amplification were 72° C. for 2 minutes; 94° C. for 3 minutes, 94° C. for 45 seconds, 61° C. for 45 seconds, 72° C. for 45 seconds for 30 cycles, and a final cycle of 72° C. for 5 minutes. The temperature cycling parameters for selective amplification were 94° C. for 3 minutes; 94° C. for 45 seconds, 66-61° C.

for 45 seconds, 72° C. for 45 seconds, touch-down, 94° C. for 45 seconds, 60° C. for 45 seconds, 72° C. for 45 seconds for 30 cycles, and a final cycle of 72° C. for 5 minutes.

In contrast to the mPing transposon display, the ID-1 and SZ-2 amplicons were essentially identical before and after cell culture (see FIG. 3).

Example 3 mPing Targets Low Copy (Genic) Insertion Sites

In several studies, MITEs have been found predominantly in the noncoding regions of genes (Bureau, et al., 1996 Proc. Natl. Acad. Sci. USA, 93:8524-8529; Zhang, et alt, 2000 Proc. Natl. Acad. Sci. USA, 97: 1160-1165; Mao, L. et al., 2000 Genome Res., 10:982-990). They are rarely found in exons or inserted into other classes of repetitive elements. In the absence of actively transposing MITEs, it has not been possible to determine whether this distribution reflects preferential targeting to genic regions or selection against insertion into other regions of the genome. To address this question, 42 amplicons from cell line C5924 were recovered from the transposon display gel, reamplified, subcloned and sequenced.

The new insertion sites were determined from the transposon display gel. DNA fragments were excised from radioactive gels by scratching the dried gel with yellow tips (Stumm et al., 1997, *Elsevier Trends Journals Technical Tips* online, and the tip was placed in 20 µl PCR reaction mix with relevant primers. After a 1 minute incubation, the tips were discarded and the reaction product was reamplified using the same cycling parameters as that of the original reaction. PCR products were resolved in 0.8% agarose gels, fragments were excised, purified (QIAquick, Qiagen, Chatsworth, Calif.) and cloned (TA cloning kit, Invitrogen). DNA templates were sequenced by the Molecular Genetics Instrumentation Facility (University of Georgia). The context of the genomic sequence adjacent to the new insertion was determined using a BLAST search (WU-BLASTN 2.0) of the Nipponbare and 93-11 genomic sequence database. Single copy sequence was defined as a query that results in no more than one hit per genome (except duplicates) with WU-BLASTN 2.0 default parameters.

The sequences indicate that all products were anchored at one end in an mPing element since the primer sequence was always adjacent to the mPing TIR and TSD sequences. To determine insertion sites of the newly transposed elements, sequences flanking the TIR (37 to 268 bp in length) were used to query the 93-11 and Nipponbare sequences. 34 of 42 flanking sequences matched entries from 93-11 contigs while one of the sequences was only found in *japonica* (cv. Nipponbare). Thirty-two of the 35 matches were single copy sequences, and one was in a two-copy sequence (see FIG. 2). The remaining two insertion sites were in or were next to other MITEs that were themselves in single copy sequences. Thus, 34 of 35 new insertions were in single copy regions of the genome. Since about 35 to 40% of the available rice genomic sequence is repetitive, these data provide strong evidence that the mPing family targets low copy (genic) regions of the rice genome.

Example 4

The Amplified Elements

To isolate the complete transposable element associated with each new insertion event, it was necessary to first determine the sequence flanking the other end of the element (that is, the terminus not represented in the transposon display bands). In ordinary circumstances, this can be a tedious and time-consuming task involving techniques like IPCR or the use of genome walker kits. However, the availability of the *indica* sequence made this task routine since sequences at the other end of the transposon were adjacent to the flanking sequences recovered from the BLAST searches mentioned above. Host sequences flanking both ends of the transposon were employed in the design of PCR primers that were used with template DNA from the cell line to recover the entire intervening transposon. Virtually all of the new insertions were either the mPingA element (SEQ ID NO:1), or the closely related subtype B (SEQ ID NO:2); subtype C (SEQ ID NO:3), or subtype D (SEQ ID NO:4).

Example 5

Identification of Candidate Autonomous Elements

Like other MITE families, mPing elements have no coding capacity and as such, are incapable of catalyzing their own transposition. Thus, movement of mPing must be catalyzed by a transposase encoded in trans. To identify putative autonomous elements, the mPing consensus sequence (SEQ ID NO:1) was used to query all available rice genomic sequence for related, longer elements. A single element with remarkable similarity to mPing was found in the Nipponbare sequence, but was absent from the 93-11 draft sequence. This element, called Ping (SEQ ID NO:5), is 5,341 bp in length and shares 253 bp and 177 bp of its terminal sequence with mPing (See FIG. 1 for comparison to mPing; see FIG. 4 for the GenBank accession number). 429 of 430 bp are identical in the two elements, suggesting that mPing has arisen recently from the larger tong element by internal deletion.

Further blast searches using Ping as the query led to the discovery of Pong (SEQ ID NO:8), which is 5,166 bp in length, shares TIRs (the outer 15 bp of its 25 bp TIR are identical to mPing) and similar subterminal regions with mPing and Ping (~70% over ~200 bp and ~40 bp at each end) (See FIG. 1 for comparison). Both Ping and Pong are, like mPing, flanked by 3 bp TSDs of the trinucleotide TAA. While only one copy of Ping was found in Nipponbare (see FIG. 4 for GenBank accession numbers), and there are no copies of Ping in the 93-11 sequence, at least five copies of tong were found in Nipponbare and six copies of Pong were found in 93-11 (see FIGS. 5 and 6 for the GenBank accession numbers). Eight of ten of the Pong elements appear to be full-length and are almost identical (>99% identity), while two copies were truncated.

Example 6

Identification of a New Family of Transposases in Plants and Animals

In addition to their termini, Ping and Pong also share sequence similarity in two blocks of internal sequence corresponding to the two major ORFs of each element (FIG. 1). The predicted size of Ping ORF1 is 172 amino acids (SEQ ID NO:5; positions 2445 to 2663) and 455 amino acids for Pong (SEQ ID NO:8; positions 1630 to 2652), with 80% amino acid identity. ORF2 is predicted to be 455 amino acids for Ping (SEQ ID NO:5; positions 3190 to 4557) and 482 amino acids for Pong (SEQ ID NO:8; positions 2959 to 4407), with 87% amino acid identity. The amino acid sequence of Ping ORF1 is defined in SEQ ID NO:6; the amino acid sequence of Ping ORF2 is defined in SEQ ID NO:7; amino acid sequences of Pong ORF1 are defined in SEQ ID NO:12; the contiguous sequence of SEQ ID NOs:15 and 16; the contiguous sequence of SEQ ID NOs:23 and 24; SEQ ID NO:28; the contiguous sequence of SEQ ID NOs:32 through 36; SEQ ID NO:48; SEQ ID NO:51; the contiguous sequence of SEQ ID NOs:54 and 55; SEQ ID NO:58; the contiguous sequence of SEQ ID NOs:63 through 77; SEQ ID NO:80; the contiguous sequence of SEQ ID NOs:83 and 84; and SEQ ID NO:91; and amino acid sequences of Pong ORF2 are defined in SEQ ID NO:13; the contiguous sequence of SEQ ID NOs:17 through 21; the contiguous sequence of SEQ ID NOs:25 and 26; the contiguous sequence of SEQ ID NOs:29 and 30; the contiguous sequence of SEQ ID NOs:37 through 46; SEQ ID NO:49; SEQ ID NO:52; SEQ ID NO:56; the contiguous sequence of SEQ ID NOs:59 through 61; SEQ ID NO:78; SEQ ID NO:81; the contiguous sequence of SEQ ID NOs:85 and 86; the contiguous sequence of SEQ ID NOs:88 and 89; and SEQ ID NO:92.

When used as queries in tBlastn searches of GenBank, both ORFs yielded numerous hits (E value $e^{-10}$) from a wide range of plants as well as animals and fungi (FIG. 7). ORF2 homologs are abundant in plants, and most frequently found in organisms with large amounts of genomic sequence in databases: 82 hits ($E<e^{-46}$) were from rice, 56 hits ($E<e^{-23}$) were from *Arabidopsis* and over 100 hits ($E<e^{-36}$) were from *Brassica oleracea*. Significantly ORF1 and ORF2 homologs are usually within 2 kb of each other and they are arranged in the same order and orientation as they are in Ping and Pong. Furthermore, several ORF1 and ORF2 pairs are flanked by TIRs and TSDs that are similar to those of Ping and Pong. It is therefore likely that each "pair" of ORF1 and ORF2 homologs belong to the same element.

The function of ORF1 is unclear. It has only very weak sequence similarity to Myb DNA binding domains (Pfam 7.3, E=0.002). The amino acid sequence of ORF2 revealed little about its identity: although it has numerous homologs in tBlastn searches, they were all unknown or hypothetical proteins. The facts that mPing, Ping and tong are flanked by 3-bp TTA TSDs and that mPing is a Tourist-like MITE suggested there was a relationship between Ping/Pong and the recently described PIF/IS5 superfamily (Zhang et al., 2001 *Proc, Natl. Acad. Sci. USA*, 98: 12572-12577). However, the PIF transposase gene was not identified directly in Blast searches as homologous to either of the two ORFs: ORF1 has no homology with PIF transposase, and while ORF2 does have homology to PIF, it does not have the DD47E catalytic motif with the correct spacing as in PIF.

The first clue to the nature of ORF2 came with the finding that many ORF2 homologs are also related to the PIF transposase. Several such homologs served as "bridges" in a multiple alignment in which they connected ORF2 to the PIF transposase. It is obvious in such an alignment that these homologs fall into two groups: the PIF-like group and the Pong-like group. Significantly, the DD47E motif in PIE aligned with a DD35E motif in ORF2. In addition, the residues surround the DDE motifs that form the N2, N3, and C1 catalytic domains are also very well conserved between PIF transposase and ORF2 (FIG. 3). Moreover, like the PIF transposase, ORF2 is also related to IS5-like elements. While PIF-like elements are more closely related to the ISL2 subgroup, Pong-like elements are closer to the IS1031 subgroup. It was therefore concluded that ORF2 is the transposase gene and that the Pong family is a member of the PIF/IS5 superfamily.

Although the two ORFs in Ping and Pong are similar and the mPing elements are clearly derived from Ping, several lines of evidence suggest that Ping is not the autonomous element that mobilizes mPing in C5924 cell culture. Ping was only detected as a single copy in Nipponbare: it is absent in the draft sequence of 93-11 (~84% of the genome) and from 20 of 24 rice cultivars (8 cultivars for each of the following groups: temperate *japonica*, tropical *japonica* and *indica*) tested by PCR, including C5924 itself. Only four temperate *japonicas* were found to harbor Ping: Nipponbare, Gihobyeo, JX 17 and Koshikari. The apparent absence of Ping from all *indica* cultivars tested provides strong evidence that it could not be responsible for the movement of mPing elements in the *indica* cell line. Pong, in contrast, is present in multiple near-identical copies in both *indica* and *japonica*. In addition, ORF1 of Ping (SEQ ID NO:6) appears to be truncated at the N terminus compared to its homologs, lacking at least 60 conserved amino acids (FIG. 1). Truncation also extends to a predicted promoter (94%-100% confidence) which is present upstream of ORF1 in Pong (FIG. 1). Finally, compared to the consensus, the Ping ORF2 (SEQ ID NO:7) contains multiple amino acid substitutions especially in conserved catalytic domains, whereas Pong ORF2 (SEQ ID NO:13) has very few substitutions. These data are consistent with a scenario where Ping is a degenerate non-autonomous element that gave rise to mPing MITEs but that the transposase activity resides in one or more of the Pong elements.

Example 7

Transposition of Pong

If Pong is the autonomous element responsible for the transposition of mPing elements, it should also be capable of transposition. The fact that there are 8 nearly identical copies of Pong in the Nipponbare and 93-11 sequences suggests that Pong, like the mPing repeat, is still actively transposing. By exploiting the sequence differences between Pong and mPing, PCR primers were designed to amplify Pong elements but not mPing in a transposon display assay. Transposon display was carried out as previously described (Casa et al., 2000 *Proc. Natl. Acad. Sci. USA*, 93: 8524-8529) with the following modifications.

For amplification of Pong, the following primers were used: P1: CTT CGT TTC AGC TGA TGT G (SEQ ID NO:148), and P2: ATG TGG CGT CTG GGA AAC ACT G (SEQ ID NO:149). The temperature cycling parameters for pre-selective amplification were 72° C. for 2 minutes, 94° C. for 3 minutes, 94° C. for 45 seconds, 55° C. for 45 seconds, 72° C. for 45 seconds for 30 cycles, and a final cycle of 72° C. for 5 minutes. The temperature cycling parameters for selective amplification were 94° C. for 3 minutes, 94° C. for 45 seconds, 68-63° C. for 45 seconds, 72° C. for 45 seconds, touch-down, 94° C. for 45 seconds, 62° C. for 45 seconds, 72° C. for 45 seconds for 30 cycles, and a final cycle of 72° C. for 5 minutes.

As can be seen in FIG. 2, the results with the Pong primers mirror the mPing results. That is, the Pong band number increased dramatically in the *indica* cell line but remained virtually the same in Nipponbare.

The nature of the insertion sites and the inserted elements were determined in the same way as was done for mPing.

Nine out of ten insertion sites were located in single copy sequences (see FIG. 8). Eight newly inserted elements were successfully amplified by PCR and all were indistinguishable in size from Pong.

Figure 9:
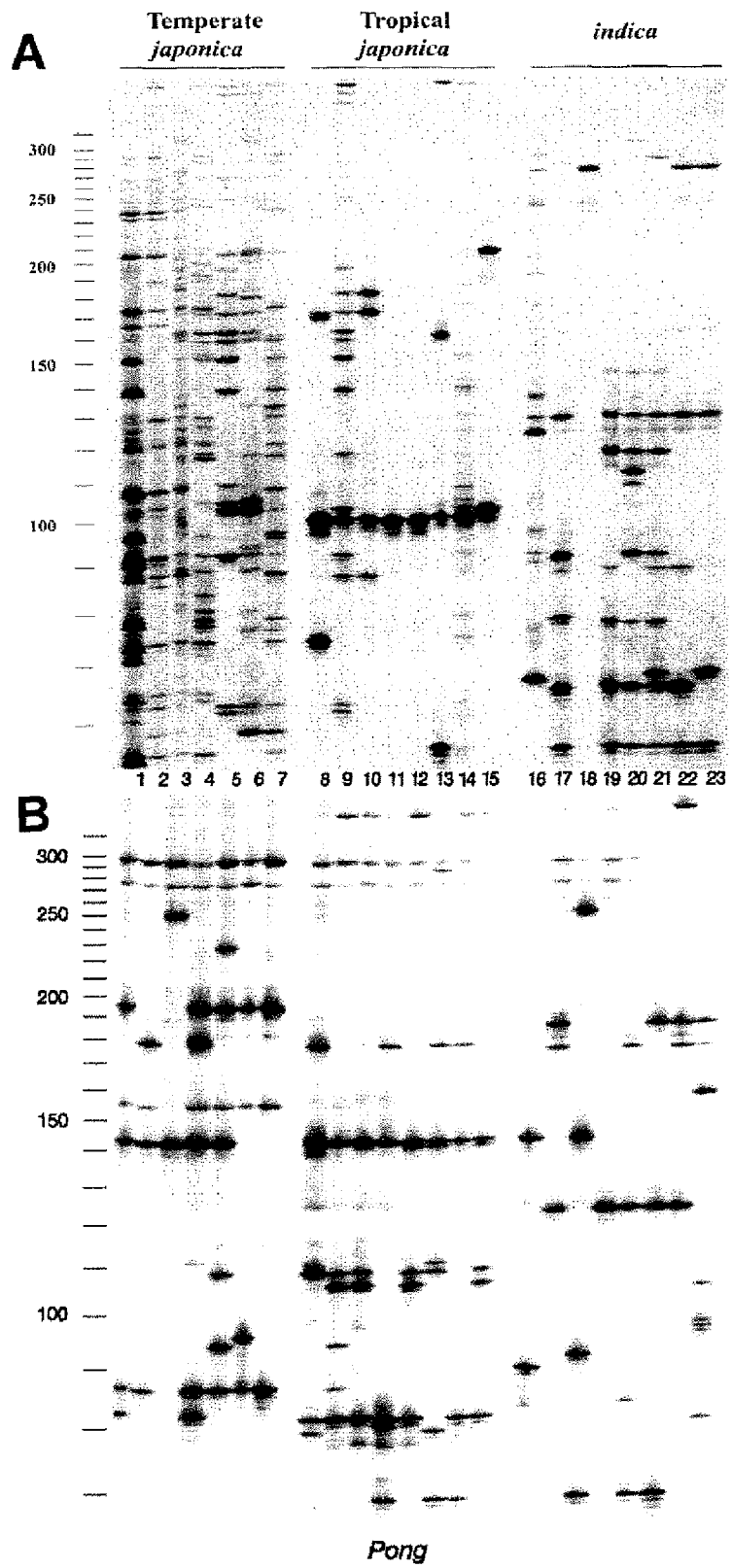
FIGS. 9A and B show autoradiographs of transposon display gels of mPing (A) and Pong (B). The genomic DNA in each respective lane is: 1, Nipponbare; 2, Gihobyeo; 3, JX 17; 4, Koshikari; 5, Calrose; 6, Early Wataribune; 7, Shinriki; 8, Azucena; 9, Lemont; 10, Jefferson; 11, Moroberekan; 12, Rexoro; 13, Wab56-104; 14, Carolina Gold; 15, Kaybonnet; 16, C5924; 17, IR64; 18, Kasalath; 19, GuangLuAi4; 20, 93-11; 21, Tequing; 22, IR36; 23, Bs125. The migration of DNA markers is on the left in base pairs.

The difference in the estimated copy number of mPing elements in a *japonica* (Nipponbare) and an *indica* (93-11) genome (70 vs. 14) suggested recent amplification of this MITE family, perhaps since domestication. To assess the timing of amplification, transposon display was undertaken with a panel of *O. sativa* DNAs to determine the approximate copy number of mPing and Pong elements. As can be seen in FIG. 9A, the temperate japonicas contain the largest number of different mPing-anchored amplicons while the tropical japonicas contain the fewest. This dramatic difference in mPing copy number between the two sub-groups of *japonica* is significant in light of evidence that the temperate and tropical cultivars are believed to have diverged since domestication (5000-7000 years ago) and are more closely related to each other than either is to indica (Ting, 1957 *Acta Agron. Sinica*, 8: 243-260; Glaszmann, 1987 *Theor. Appl. Genet.*, 74: 21-30; Wang, et al., 1992 *Theor. Appl. Genet.*, 83: 565-581; Kawakami, et al., 2000 *Proc. Natl. Acad. Sci. USA*, 97: 11403-11408; Matsuo, et al., 1997 *Science of the Rice Plant*, Ministry of Agriculture, Forest and Fisheries, Tokyo, Japan; Morishima & Oka, 1981 *Japan. J. Breed.*, 31: 402-413). The different amplicon patterns of Pong elements observed in these cultivars (see FIG. 9B) also suggest that this element has been active since domestication. However, the consistency of amplicon number across cultivars suggests that Pong elements have not significantly increased their copy number.

It is noted that although Ping appears to be dispensable for the transposition of mPing in the C5924 cell line, the fact that in temperate *japonica* cultivars the presence of Ping correlated with mPing amplification suggests that Ping may serve as a co-activator (with Pong, perhaps) to enhance transposition of mPing. Furthermore, the requirement for transposition of mPing in plants and in cell culture may be different. The data suggest that one reason for the success of MITEs is an ability to be cross-mobilized by related transposases.

Example 8

Recent and Explosive Amplification of Pong-Like Elements in *Brassica oleracea*

Figure 10:
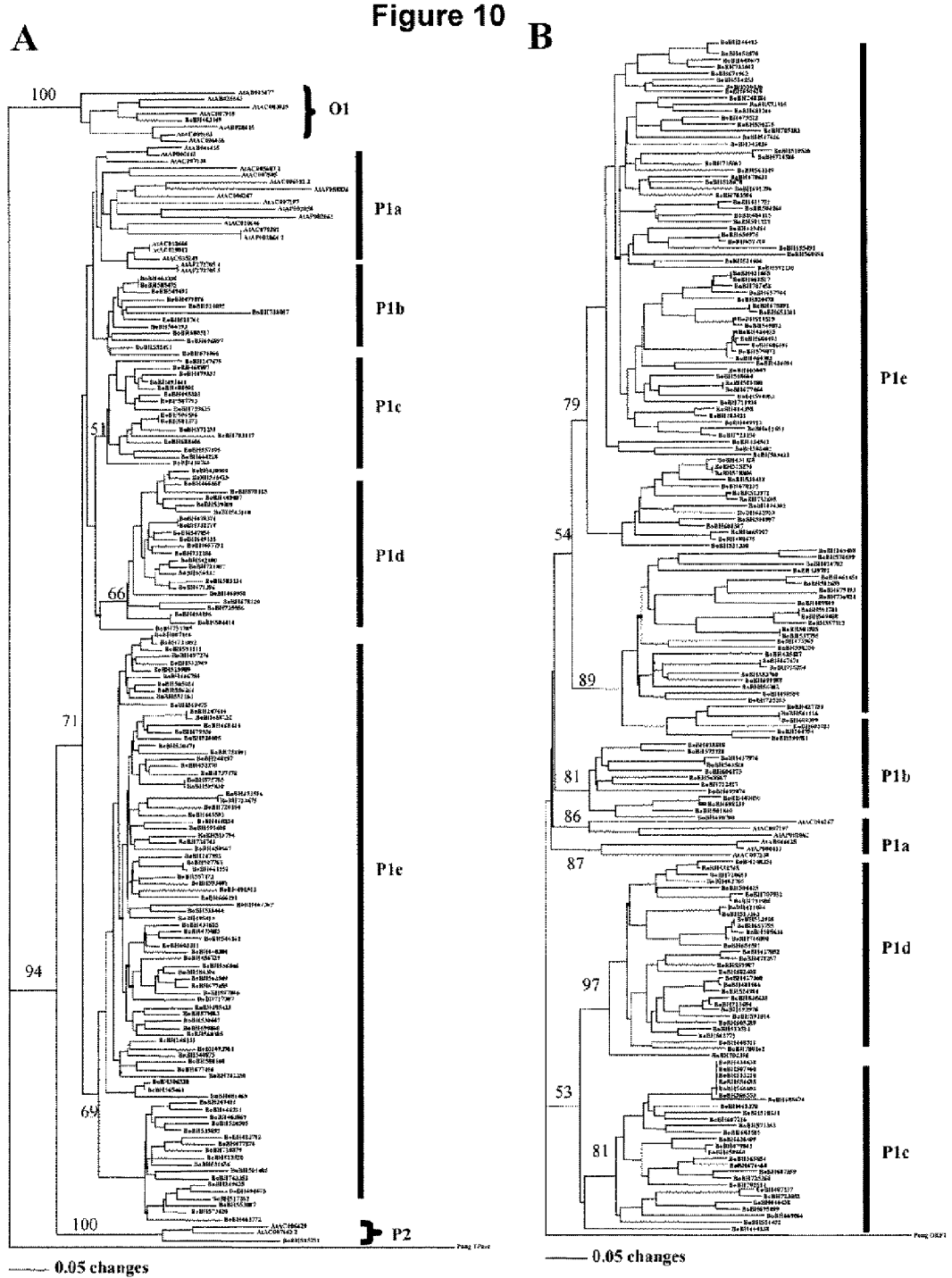
FIGS. 10A and B show the phylogeny of Pong-like transposable elements in B. oleracea and A. thaliana. (A) shows a neighbor-joining tree generated from a multiple alignment of the catalytic domains of 139 Pong-like transposases from B. oleracea and 28 from A. thaliana, rooted with the catalytic domain of Pong transposase (ORF2, SEQ ID NO, 13). (B) shows a neighbor-joining tree generated from a multiple alignment of 170 Pong-like ORF1s from B. oleracea and 6 from A. thaliana, rooted with the ORF1 of the rice Pong element (ORF2, SEQ ID NO; 12). Elements were named after the species initials, followed by GenBank accession numbers. Bootstrap values were calculated from 1,000 replicates.

The transposase of Pong (ORF2, SEQ ID NO:13) was used as query to blast the TIGR *Arabidopsis* and *Brassica oleracea* genomic databases. Pong-like transposase is significantly more abundant in *Brassica oleracea* (139 complete catalytic domains in 30% of its genomic sequences) than in its close relative *Arabidopsis thaliana* (34 in its entire genome). Considering these two species diverged fairly recently (~10-20 Mya), such a difference may indicate the recent amplification of Pong-like elements in the genome of Brass/ca oleracea. To explore this possibility. Pong-like transposases in *Arabidopsis* and *Brassica oleracea* were compared. A CLUSTALW multiple alignment was constructed from the catalytic domains of 167 Pong-like transposases (139 from *Brassica oleracea* and 28 from *Arabidopsis thaliana*) and used to generate a phylogenetic tree (FIGS. 10A and 10B), rooted with the catalytic domain of Pong transposase (ORF2, SEQ ID NO:13).

Three major lineages were observed in the phylogenetic tree. Two smaller lineages (O1 and P2) included sequences from both species and within each lineage no smaller cluster was found to be specific to either species. Therefore, O1 and P2 have clearly diverged prior to the divergence of the Brassicaceae family and neither has significantly amplified in either species. However, a dramatically different picture was observed for the P1 sublineage, which included the majority of the sequences from *Arabidopsis* and nearly all from *Brassica oleracea* (137 of 139). Inside P1, *Brassica oleracea* sequences clustered into four species-specific subgroups (P1b-P1e, P1b not strongly supported), indicating that several lineages of Pong-like elements have undergone recent and explosive amplifications in *Brassica oleracea*. Interestingly, the amplifications of Pong-like elements appeared to have occurred within a relatively short period of time and followed by a long period of extensive diversification with only sporadic increase in copy number. All sequences from *Arabidopsis* in P1 also clustered together (P1a). Although such grouping was not strongly supported by Bootstrap values, it suggested that a similar but less dramatic amplification might also have taken place in *Arabidopsis*.

In addition to the catalytic domains, over 1,000 *Brassica oleracea* entries in the TIGR *Brassica oleracea* database contained homology to various regions of the Pong transposase (ORF2, SEQ ID NO:13). Considering that only 30% of the *Brassica oleracea* genome was available for blast, and that each transposase sequence could have been hit 2-3 times because of the size of each entry in the database (average ~650 bp), it was roughly estimated that the relatively small genome of Brass/ca oleracea (~600 Mb) harbors at least 1,000 Pong-like elements, together contributing as high as 1% of its genome (assuming each element is, like the Pong element, ~5.0 kb in length). Such a copy number was surprisingly high for plant Class 2 elements and demanded further verification. For this reason homologs of Pong ORF1 in *Arabidopsis* and *Brassica oleracea* were also examined. Consistent with the recent amplification of Pong-like elements in *Brassica oleracea*, ORF1s were found to be significantly more abundant and homologous in its genome (>700 hits in ~30% genomic sequences, E value<e-10) than in *Arabidopsis* (21 hits, E value<e-5). In order to compare the phylogeny of ORF1s to that of the transposases, their pairwise association (i.e. a "pair" of ORF1 and transposase encoded by the same element) was first established. Fourteen of the 21 ORF1 hits from *Arabidopsis* were located within 2 kb of a transposase and, where element termini were defined, each "pair" was found to belong to the same element. A technical difficulty was encountered for *Brassica oleracea*. Since its sequences in the GSS database represented the end sequencing (~650 bp on average) of short genomic clones (~2.5 kb on average), the association between an ORF1 and a transposase could only be established when they happened to be located on two ends of the same clone, and there was not sufficient sequence information to define element termini. Nevertheless, a significant portion of ORF1 hits (over 200) were found to be associated with transposases, all arranged in the "tail-to-head pattern". One hundred and eighty five ORF1 hits (6 from *Arabidopsis*, 179 from *Brassica oleracea*) contained the entire conserved region, and their evolutionary relationships were determined. The phylogeny of ORF1s was strikingly similar to the phylogeny of their associated transposases. That is, both ORF1s and transposases in *Brassica oleracea* clustered into four large species-specific subgroups. In addition, based on the pairwise association between ORF1s and transposases, each ORF1 subgroup could be linked to a transposase subgroup, and corresponding subgroups exhibited very similar topology as well as similar numbers of sequences. Taken together, these results confirmed that Pong-like elements have indeed amplified recently and explosively in *Brassica oleracea*.

Example 9

Degree of Amino Acid Identity and Similarity of Pong-Like ORF1 and ORF2 in Rice and in *Brassica*

13 Pong-like elements in rice (*Oryza sativa*) were compared at the nucleotide and amino acid level to 188 Pong ORF1-like sequences from *Brassica oleracea*, and to 140

Pong ORE2-like sequences from *Brassica oleracea*. The chart below demonstrates the levels of identity and similarity within the rice sequences, within the *Brassica* sequences, and between rice and *Brassica* sequences for Pong-like ORF-1 and ORF-2 at the amino acid and nucleotide levels.

Multiple alignment was performed using the CLUSTALW program available at European Bioinformatics Institute with default parameters (gap opening penalty is 10 and gap extension penalty is 0.05 with blosum62 matrix). Average percentage of sequence similarity was the average of all possible pairwise sequence comparisons.

| Rice Pong-like ORF1 and ORF2 Average Amino Acid Identity in ORF1 | |
|---|---|
| Full length: | 27.76% |
| Conserved region (~110 a.a.): | 37.95% |
| Average Amino Acid Identity in ORF2 | |
| Full length: | 51.96% |
| Catalytic domain (~120 a.a.): | 65.63% |
| *Brassica* Pong-like ORF1 (~110 a.a. conserved region) | |
| Average Nucleotide Sequences Identity: | 59.52% |
| Average Amino Acid Sequences Identity: | 65.14% |
| *Brassica* Pong-like ORF2 (~120 a.a catalytic domain) | |
| Average Nucleotide Sequences Identity: | 79.24% |
| Average Amino Acid Sequences Identity: | 78.80% |

| Comparison between Rice and *Brassica* | |
|---|---|
| Average Amino Acid Identity in ORF1 (conserved region): | 29.03% |
| Average Amino Acid identity in ORF2 (catalytic domain): | 58.22% |

Example 10

Utility In Vivo

The invention provided herein describes the discovery of the first active DNA transposon system in rice and its activation in cell culture. This invention will be of primary value in the establishment of the first non-transgenic DNA transposable element tagging populations in rice. Such populations should be of value in gene discovery in rice as follows. The mPing/Pong transposable element family will be activated in cell culture and plants regenerated by established procedures. Large population of regenerants will be established and mutants identified by visual screening or by biochemical analysis. Mutants will be crossed to wild type plants and the F1 will be selfed. If the F2 population segregates for the mutant phenotype, cells from mutant and wild-type plants will be analyzed by transposon display using the procedures described above to identify mPing or Pong products that co-segregate with the mutant phenotype. These bands will be removed from the gel, reamplified, cloned and sequenced, by established procedures.

APPENDIX

```
Nucleotide sequence of mPingA in rice Nipponbare (SEQ ID NO: 1)
GGCCAGTCACAATGGGGTTTCACTGGTGTGTCATGCACATTTAATAGGGGTAAGACTGAATAAA

AAATGATTATTTGCATGAAATGGGGATGAGAGAGAAGGAAAGAGTTTCATGGTGCTGAAAGTGGT

GACGCTCGTTTGCAAGTCGTGGGTAACAGAGTGAAAGCCCCGTTGAGGCCGATTCGTTTCATTCA

GCGGATGTCTTGCCTCCGCCTCCGCCGTGCGACCTCCGGATTGTGGGCCGGCGCGCCGGATTTTC

CGTACAAATGATCCCAGCAAGTTGTATGAATTAAATCGTTTGGTTAGTCTTGGAAAGCTGAAAGT

GAAACGGGTCGACTGTGGGGATTGTTTCATAAAAGATTTGATTTGAGACAAGATCGTATAATATT

TTGGCTACCGGTGGAATGACAGTACGCATTCTGAGTGGCG

Nucleotide sequence of mPingB in rice Nipponbare (SEQ ID NO: 2)
GGCCAGTGAGAATGGCGCTTTGAGTGCTGTGTGATCCACATTTAATAGGGGTAAGAGTGAATAAA

AAATGATTATTTGCATGAAATGGGGATGAGAGAGAAGGAAAGAGTTTCATGGTGGTGAAACTGGT

CACGCTGGTTTGGAACTGCTCGGTAAGAGAGTGAAACCCCCGTTGACCGCGATTGGTTTGATTCA

CCGGATCTCTTGCGTCCGCCTCCGCCGTGCGACCTGGCGATTCACACCATTTTGGGTAGAAATCA

TGGGAGGAAGTTGTATGAATTAAATGGTTTGGTTAGTGTTCGAAAGGTGAAAGTGAAAGGGGTCG

AGTCTGGGGATTGTTTGATAAAAGATTTGATTTCACACAAGATCCTATAATATTTTGGGTAGGGG

TGGAATGAGAGTACGGATTGTGAGTGGCC

Nucleotide sequence of mPingC in rice 93-11 (SEQ ID NO: 3)
GGGGAGTGAGAATCCGCGTTTGAGTGGTGTGTGATGGAGATTTAATAGGGGTAACAGTGAATAAA

AAATGATTATTTCGATGAAATGGGGATGAGACAGAACGAAAGAGTTTGATGGTCGTGAAAGTGGT

CACGGTGGTTTCCAAGTGGTCGGTAACAGACTGAAAGGGCCGTTGAGGGTGATTCGTTTCATTGA

CCGGATCTGTTGGCTGGGCGTGCGCCGTGGGAGCTGGGGATTGTGGGCGTCGCTACAGGATTTTG

GGTAGAAATGATGGGAGGAACTTGTATCAATTAAATGGTTTGCTTAGTCTTGGAAACGTCAAAGT

GAAACCCCTCCACTGTGGGGATTCTTTGATAAAAGATTTCATTTGAGACAAGATGGTATAATATT

TTGGGTAGCCGTGGAATGAGAGTACCGATTGTGAGTGGCC
```

Nucleotide sequence of mPingD in rice C5924 (SEQ ID NO: 4)
GGCCAGTGAGAATGGGGGTTTCACTGGTCTCTGATCGAGATTTAATAGGGGTAACAGTGAATAAA

AAATGATTATTTGCATGAAATCCGGATGAGACACAAGGAAACACTTTGATGGTCCTGAAAGTGGT

GAGCGTGGTTTCGAAGTGCTGCCTAACAGAGTCAAACCCCCGTTGAGGGGGATTGGTTTCATTGA

GGGGATGTGTTCGGTGCGCCTGGGGGGTGCGAGGTGGGTACAGGAAGTTGTCTAAGTTTGTCTGA

CGCCTGGGTAGAGGATTTTGCCTACAAATGATGGGAGGAACTTGTATGAATTAAATCCTTTGGTT

AGTGTTGGAAAGGTGAAAGTCAAAGGGGTGGAGTGTGGGGATTGTTTCATAAAACATTTCATTTG

AGAGAAGATGGTATAATATTTTCGGTAGGGGTCGAATGACACTAGGGATTGTGACTGCGC

Nucleotide sequence of Ping in ap004236 in rice Nipponbare
(SEQ ID NO: 5)
GGCCAGTGAGAATGGAGCTTTCAGTGGTGTCTGATGGAGATTTAATAGCGGTAAGAGTCA

ATAAAAAATGATTATTTCGATGAAATGCGGATGAGAGAGAAGGAAAGAGTTTCATGGTCG

TGAAACTGGTCAGGCTGCTTTGGAAGTGCTCGGTAAGAGAGTCAAACCCCCGTTGAGGGG

GATTCCTTTGATTCACGCGATGTCTTGGGTCGGGGTGGGGGCTGGCACGTCCCGATTCTG

CCGCGCCGCGCCGCGCCACGCCTCCTTCCCGCGTGAACATTGGTCGTTCGCGGGGCAGGC

ATTCCACCATCTCCCCCCTCCGGCGCCTACGGAGTACACCGCAACCGGTCGCCCGAATCC

GGCCCCTAGACCGTGACCCACCCGCCATCTTCCGCAAGACCGAATCCCCAACCCACCCAC

CATCTTCCGCCGCCCCCGTCCCCGTCCCCGGCCATGGATCCGTCGCCGCCCGTGGATCCG

TGGCCGCCCGTGGATCGGTCGCCGGCTGCTCAAACCCCGCGGCGTGCAACCGGGAAAGGA

GCCAAACAGCGCGGGGCAAGCAACTAGGATTGAAGACCCCGCCGCCGATTTCTGTCCCG

GCCACCCCGCCTCCTGCTGCGACGTCTTCATCCCCTGCTGCGCCGACGGCCATCCCACCA

CGACCACCGCAATCTTCGCCGATTTTCGTCCCCGATTCGCCGAATCCGTCACCGGCTGCG

CCGACCTCCTCTCTTGCTTGGGGGACATCGACGGCAAGGCCACCCCAACCACAACGAGGA

GGATGGCGACCAACATCGACCATTTCCCCAAACTTTGGATCTTTCTTTGGAAACCAACAA

GACCCAAATTCATGGTACATGTATTTTCTTCTTTTTCTGTTACCTTCAACCTACGCTAAC

TCTAATTCATGGATGAGACTACTGCCATTGTGGAGTTCAATGCTTTTTCTTCATGTTATA

TTTCGTCCAGCTGTGAGTTATGGTTTGAAGATTGCTGTGGTTGTTTCATTGCTGACTATG

TGAAAGATAGATGGATGAAAGAGAGAATTATATTTTAGTCTGTAATCTTGCTCATGCAGT

TGCTCATGTATGACCTTGGTTCTAGAATGTTGCCCTGACTGTATCCTTAATGTTGAGAGA

AGTGATGCCTAAACCAGTCAGATCAGTGGGATCAGATTACCTATCGACATATAATATTAG

CTATCTCAGTTGTGAAAGACAGATGGGTGAAAAGGCACCCCTTGGATTAATTCTGTAGTA

TCAAATTCTGCACCTTGTCTGTCCATATGTTCTGCTTCGTTGGTGGGTGCAGTGCATTTG

TAAAAAATAGTTTGCETGTGATCCTTAATATATGTAACAGGGAATGAATTTTCACCCATC

TCAGTTGTAAAGGTACTGTCTTGCTATGCAATATGTGTAAATTGACAAACCTGAAAATAG

TCTGTTTGGAATTTGCAAAAGCAATTCGATAGTTTGGAATTTCCAAACCTCAGTCAGCAG

TAGGCAATCCATTTTAGTTCTTGCTATGCACAAAAACACTACACCTGATATGCTCATTTT

AATACAACTTTTTTGTCTCTGTTACACTTTGGTCAGGGGTTATCCTCCAGGAGGGTTTGT

CAATTTTATTCAACAAAATTGTCCGCCGCAGCCACAACAGCAAGGTGAAAATTTTCATTT

CGTTGGTCACAATATGGGATTCAACCCAATATCTCCACAGCCACCAAGTGCCTACGGAAC

ACCAACACCCCAAGCTACGAACCAAGGCACTTCAACAAACATTATCATTGATGAAGAGGA

CAACAATGATGACAGTAGGGCAGCAAAGAAAAGATGGACTCATGAAGAGGAAGAGAGACT

GGTATTCATCGGATACTTTTACATTTCCATATGTCTTTGTTTTGACTAATACTTGACAGG

```
-continued

TCATTAACTGATTCTTGTAGCCCAGTCCTTGGTTGAATGCTTCTAAAGACTCAATTCATG

GGAATGATAAGAAAGGTGATACATTTTGGAAGGAAGTCACTGATGAATTTAACAAGAAAG

GGAATGGAAAACGTAGGAGGGAAATTAACCAACTGAAGGTTCACTGGTCAAGGTTGAAGT

CAGCGATCTCTGAGTTCAATGACTATTGGAGTACGGTTACTCAAATGCATAGAAGCGGAT

ACTCCGACGAGATGCTTGAGAAAGAGGCACAGAGGCTGTATGCAAACAGCTTTGGAAAAC

CTTTTGCGTTGGTCCATTGGTGGAAGATACTCAAAGATGAGCCGAAATGGTGTGCTCAGT

TTGAATCAGAGAAAGACAACACCGAAATGGATGCTGTTCCAGAACAGCAGTCACGTCCTA

TTGCTAGAGAAGCAGCAAAGTCTGAGCGCAATGGAAAGCGCAAGAAAGAAAATGTTATGG

AAGGCATTGTGCTCCTAGGGGAGAATGTCCAGAAAATTATAAAGGTCCACCAAGACCGGA

GGGTGGATCGTGAAAAGCCCACCGAAGCACAGATTCAGATATCAAATGCAACATTGTTGG

CCGGTAAGGAGCAGAAGGAAGCAAAGATGTTCGATGTCTACAATACTCTATTAAGTAAGG

ATACAAGCAACATGTCTGAAGATCAAATGGCTAGCGACGAGAGGCCAATACGGAAATTAG

AGGAGAAGCTATTTGCGGATTAAGGTGAGTTTTATAAACTGACCACTATTTTCTGAAATG

TATGAATTCTGAAATTTATATACAATTGTGTAAACATGGAAAATTAGATAATCTATGCAT

GATGCACAACATGTGCGTGCAGCACTATTTAATGGCAGTTTCACAAGTGTGAAAACTGAC

GACTATAGTACTATTGTGGTGTGAAAACTGACCACTACTATTGTCGTGTGAATGCTACTG

TGGTGTGAAAACTGACCACTATAGTTTCACATTCCTGGATGCAGCCCTCCTCTATATATA

TAGATAGAGTCCTCATCTCTTCCTGGCATACACACAGCCCTCTTCTCTAATTCCTGGACG

CAGTCCTCATCTCTTCCTGGCATAGACGCAGCCCTTCTCTCTTCCTGTTTAGTTCAACAA

CATTGAGCTGATCTGCCTTTCTTTGAAGTTTCTATCTTTTTTGACTGCTGTGAATGATTA

TTTCTCTGCTGTGAATGATTATTTCTCCAATCTTCCTTTGTTCACCTTCTCTCTTTCTCT

GCTGTGAAGATGTCTGGAAATGAAAATCAGATTCCTGTGTCCTTGTTGGACGAGTTTCTC

GCTGAGGATGAGATCATGGATGAGATAATGGATGATGTTCTCCATGAAATGATGGTGTTA

TTGCAGTCCTGCATCGGAGATCTTGAAAGACACGCTGCTGACCATCCTTTGCATCCAAGG

AAGCACATCAAGAGGCCACGAGAGGAAGCACATCAAAATTTCGTGAATGATTATTTCTCT

GAAAATCCTCTATATCCTTCCAATATTTTTCGCCGAAGATTTCGTATGTACAGGCCGCTG

TTTTTACGTATTGTGGACGCATTAGGCCAGTGGTCAGATTACTTTACTCAGAGCGTAGAT

GCCGCTGGTAGGCAAGCGCTTAGTCCATTACAAAAGTGTACTGCAGCAATTCGCCAATTG

GCTACTGGTAGTGGTGCTGATGAACTAGATGAGTATTTGAAGATTGGAGAGAGTACTCCT

ATGGATGCTATGAAAAATTTTGTGAAACGAATTAGAGAAGTATTTGGTGAAAGATATCTC

ACGCGTCCCACTGTAGAAGATACTGAACGACTACTCGAGCTTGGTGAGAGACGCGGTTTT

CCTGGTATGTTCGGTAGCATTGACTGTATGCATTGGCAATGGGAAAGGTGCCCAACTGCG

TGGAAGGGTCAGTTCACTCGTGGTGATCAAAAAGTGCCAACGCTGATTCTTGACCCAGTG

GCATCAGATGATCTTTGGATTTGGCATGCGTTCTTTGGAGTAGCAGGTTCTAACAATGAT

ATCAATGTTTTGAGCCGATCTACTGTGTTTATCAATGAGCTGAAAGGACAAGCTCCTAGA

GTGCAGTACATGCTAAATGGGAATGAATACAACGAACGTTATTTTCTTCCTGATGGAATT

TACCCTGAATGGAAGCTATTTCCTAAGTGATATCGACTCCCTATGACTGACAAGGAGAAG

TTGTATGCACAACATCAAGAAGGGGCAAGAAACGATATCGAGAGACCATTTCGTGTTCTA

CAACGTCGATTCTGCATCTTAAAACGACCAGGCCGTCTATATGACCGAGGTCTACTCCCT

GATGTTGTCCTAGGTTGCATCATACTTCACAATATGATAGTTGAAGATGAGAAGGAAGCG
```

-continued

```
CGACTTATTGAAGAAAATGTAGATTTAAATGGGCCTCCTAGTTCATCAACGGTTCAGGCA

CCAGAATTCTCTCCTGACCAGCATGTTCCATTAGAAAGAATTTTAGAAAAGGATACTAGT

ATGAGAGATCGTTTGGCTCATCGCCGACTCAAGAATGATTTGGTGGAACATATATGGAAT

AAGTTTGGTGCTGGTGCACATTCATCTGGTAATTATGTTTTTATTTTGCATTATTAGTTA

TCTATGGTACTAAGATATGTACAAGTTTCTCTAAATTGCACTAAATCTGTGGTTCATATT

GGATATGTGTAAACTATGAATGTAGCCTCACTAAAACCATCATTCATGCTGAACTGGTTT

TTGTTTTGTATATCCACGATGAAACAAGGAACTAGGTTTCTGAACGCATTACGCACTGAA

GGTTGAGGGGCAGAATGATCCACCCACTTGCTTCTATCAGATCACTAAAGTTTCATTTCA

CTGTTTTATTTTGGACACTTGATGCTTGTGTGCATCCGATGAATGTTTAATTTGGTCACC

TGATGCTTGTGTGCATCCGATGAATGTTTAATTTGGTCACCTGATGCTTGTATGCAGTTA

TCTATCTTATTTGTTAATGTTGCTGCTACTGACGATTTTTAGAAGTGAAATGCACAAGTT

GCTGTCTTTTTTGACTGATCCTTGTCTGCACTTGACCTTGTATGTGACAAATGATGGTTC

CCAGTTGTGCACCTGATTCATGATTCAGTTATTCAGTTTAAATTGAGGTTGTTTGTGTGC

ACCTTTTGTCAGTTAGCCAGTTACGGCTGGAACTTGTGTAAGTTTGTGTGACGCCTGGCT

ACAGGATTTTGGGTACAAATGATCCCAGCAACTTGTATCAATTAAATGCTTTGCTTAGTC

TTGGAAACGTCAAAGTGAAACCCCTCCACTGTGGGGATTGTTTGATAAAAGATTTCATTT

GAGAGAAGATCGTATAATATTTTGGGTAGCCGTGCAATGACACTAGCCATTGTGACTGGC

C
```

Deduced amino acid sequence of ORF1 of Ping in ap004236 in
rice Nipponbare (SEQ ID NO: 6)
MHTSGYSDDMLEKEAQRLYANRFGKPFALVHWWKILKDEPKWCAQFESEKDKSEMDAVPE

QQSRPIGREAAKSERNGKRKKENVMEGIVLLGDNVQKIIKVHEDRRVDREKATEAQIQIS

NATLLAAKEQKEAKMFDVYNTLLSKDTSNMSEDQMASHQRAIRKLEEKLFAD

Deduced amino acid sequence of ORF2 of Ping in ap004236 in
rice Nipponbare (SEQ ID NO: 7)
MSGNENQIPVSLLDEFLAEDEIMDEIMDDVLHEMMVLLQSSIGDLEREAADHRLHPRKHI

KRPREEAHQNLVNDYFSENPLYPSNIFRRRFRMYRPLFLRIVDALGQWSDYFTQRVDAAG

RQGLSPLQKCTAAIRQLATGSGADELDEYLKIGETTAMDAMKNFVKGIREVFGERYLRRP

TVEDTERLLELGERRGFPGMFGSIDCMHWQWERCPTAWKGQFTRGDQKVPTLILEAVASH

DLWIWHAFFGVAGSNNDINVLSRSTVFINELKGQAPRVQYMVNGNQYNEGYFLADGIYPE

WKVFAKSYRLPITEKEKLYAQHQEGARKDIERAFGVLQRRFCILKRPARLYDRGVLRDVV

LGCIILHNMIVEDEKEARLIEENLDLNEPASSSTVQAPEFSPDQHVPLERILEKDTSMRD

RLAHRRLKNDLVEHIWNKFGGGAHSSGNYVFILHY

Nucleotide sequence of Pong in ap003714 in rice Nipponbare
(SEQ ID NO: 8)
GGCCAGTCACAATGGGTGTTTCATTTGAGTGTCATGCGCATTTAATACAGTGACAAGTCA

GCAAAAGAGCAATATTTGCATGAAATGGGTAGGAGAGAGAGTAAACTGGTTTCACCATCG

TGACACGAGATACCGCCCTTTCCCAGCTCCCTGAAACGCGGTGAAACAGCATTGAGAGTT

CATCGTTTCACCTCCGGGATCCCGTGCGAGGGCTGGGTTCGCCATCTTTCGCGCGCATCG

CCGGATTCTTCCCGCGCGAGTCCCCCATCTTCGCGCGCAGCACCTCCATGTTCCCCCCCC

CAAAGCACTGGCTCGAAGCTTTTTTCCCCAATCTCACCTGCAACGCTAGCGCCAGACTCA

GTCCCCATCGCCCCGTCCGTCCCATACCCTAGCGCAAGAACCACGAGCGGAGATTGCGGA

GCTGGATCCACAAGTAGGTGGTGAATCCTGTCGATCTGCCGCCGTCCGCCGTCCAGCAGC

CATGGATCCAGAAGGAGGTGGTGGATCCCGTCTGAGCGCCGCCGGCAGAGGAGGGAATAA
```

-continued

```
GCGTGGGCGCAAGGAGCTGGGCCTGAAGAGGTGGTCGGCCCCTGCTCGATCACCGCCAAG

AGCTCAGCCAGCGCTGCCTGCAAGTTCCGCTCGTGAAGCTGCATGCCCGCCAACAGTTCA

GCCGCCTACTCCATCGTCAAGTCCTGCTGTTGCTGCCCCCAGTTCATCCCCTCCTGTACC

GATGTGAACCATGCCCCCATGGCCACCGGAAGGAGCAGGATGGGGCTCTGTACCCCCCAA

TTTTGCTTTTCTGCAAGGAAACCAACAAGGCCCAAGTTCATGGTATTTTCTCCTTGTCAC

AGATTATTGACTGTACACTATGATACATGATATGACTCTCTTCTTCATGCATTAGTAATT

AGTTCCTGTTTATGCTCAATGAAATTTGTTAGAATGAGTATGTGAGTACATTGGTAATTT

GATATATGCCTGAGTAATGAATAGAAAAAATGTAGTATTCAGTATGGATTGCAGTAATAG

TTTGTTAGTGAAAATTCAGTATTCAGTATGCAGTATGGATTGCGGCTTGTATAACAGAAA

TTGAAAGCAAAAGATTCAGTTTGCAATCTGGACAGTGTACTGTACAACATGTAATTCACA

TACGTAAAGCTTCTTAAATATCTCCTTGTCAGTAGATTGCTAACAAATGCTTTGAGTGTA

AATGCCAAGGGTATCATCCTAACATTGCTATATATTTTTAGCCTTCTGTATGGAATGCAC

ACATGGTCTTCTTTGCAACCACAGCAACAGCTTGCGGTACACTCTGTGCTGTCGTCATAG

CTAACCAAATAACCTCTTAGTACTGATATATATGGTCTTCTTTGCAACCAGAGCAAGAGC

TTGCCCTACATGGTCTTCTGTATGCTTGACTAAACTTGTTACTTGACATATATGCTTGAC

TGAACTTGTTGCTTGACTGAATTATTCCTTACACATACTGTAGTACTTGCTTGACTGAAC

TATGTCAGGATCTTATTAAAAAAAATCTATGTCAGCACTGCTAGTATGTCAGGATCATGA

GTATGATGCTTAAGTAACGTGTTAGTATGTCAGTAGTTAGTATGTCAGGATGATGTTCTG

GAACTTACTATGTTTGATTTTGTTATGCTGCCATCGGTTTCAATTGGATTTGCTTCTTAT

GTTTTCAGGTTGTATCGTACAGAAGGCTTCGTAAATTTTCTCCAACAGAACTGTCTGCCG

CAGCCACAAGAAGGTGAAAATTTTCACCTTCTTGGTCAGACTACCAAGACAATGTCTACT

CCACCACCAAGACCCCAAGCTGCAGCTAACAATACAGTCCAAATTGATATTCATGAAGAT

GCAATCAATGATGCAAGTGCTAAAAAGAGAACTTTGAGATATTGGACTCATGATGAGGAA

GAGAGATTGGCTAGTGCTTGGTTGAATGCTTCTAAAGATCCCATTCATGGGAATGAAAAG

AAAGGTGATACGTTTTCGAAAGAGGTTACTGATGAGTTCAACAGAAAAGGGAATGGGAAG

CGTAGAAGGGAAATAAATCAATTGAAGGTTCATTGGTCACGCGTCAAATCATGGATTGGA

GAATTCAATGATTACTGGACTAAGGTAACTGAAATGAATAGAAGCGGATATGAGGATGAC

ATGCTGGAGAAGGAGGCACAACAGATGTATGCAAATACATTTGGAAAGCCTTTTCCACTT

GTGCATTGGTGGAAGATACTGAGAAAAGAGCCCAAGTGGTGTGCAATGATTGACAAGGAC

AAAAACAAGGCTGAAGTGGTTGATATTCCAGATGAACAAAAGCGTCGCATTGGTAGAGAA

GCAGCACAAGCCGAGCGCAATGGAAAACGGAAGAAGGACAGTATGTCAGAAGGAATTGTC

ATCCTAGGGGACAATATTGAAAAAATTATCAAAGTGACGCAAGATCGGAAGCTGGAGCGT

GAGAAGGTCACTGAAGCACAGATTCACATTTCAAACGTAAATTTGAAGGCACCAGAACAG

CAAAAAGAAGCAAAGATGTTTGAGCTATACAATTCCCTGCTCACTCAAGATACAAGTAAC

ATGTCTGAAGAACAGAAGGCTCGCCGAGACAAGGCATTACAAAAGCTGGAGGAAAAGTTA

TTTGCTGACTAAGGTTAGATATCTAATCTAATCTGAGCTGCACTATTATTTATAATAATT

AAAGAATGCTGCAATATTTAGTTATATTGTCTGTATATCTGTGCTGCAGTATGCAGTCAG

CTGCATATCACGAATTTGTCAAATCTGAGCTGCATATCTGTGAATGGTGCAATATTTAGT

TATATTAATTACCCACTGTGAATGATGTATTGCTGTCAGTTTCACATATACTATGAATGC

TGCACTATGCAGTCAGTTTCACATCGAGTGTGAATGCTGCACTAGGCAGTCAGTTTGACA
```

-continued
TGCAGTCGGCGCCTATTTATGCAGAGTTTACCCATCTCTCTACTCCTCTCAGAAACTCAT

TCCCTCTTTTCTCATACGAAGACGTCCTCCCTTTTATCTTTACTCTTTCTCTCTTCTTCA

AAGATGTCTGAGCAAAATACTGATGGAAGTCAAGTTCCACTGAACTTGTTGGATGAGTTC

CTGGCTGAGGATGAGATCATAGATGATCTTCTCACTGAAGCCACGCTGGTAGTACAGTCC

ACTATAGAAGGTCTTCAAAACGAGGCTTCTGACCATCGACATCATCCGAGGAAGCAGATC

AAGAGGCCACGAGAGGAAGCACATCAGCAACTAGTGAATGATTACTTTTCAGAAAATCCT

CTTTAGCCTTCCAAAATTTTTCGTCGAAGATTTCGTATGTCTAGGCCACTTTTTCTTGGC

ATCGTTGAGGCATTAGGCCAGTCGTCAGTGTATTTCACACAAAGGGTGGATGCTGTTAAT

CGGAAAGGACTCAGTCCACTGCAAAAGTGTACTGCAGCTATTCGCCAGTTGGCTACTGCT

AGTGGCGCAGATGAACTAGATGAATATCTCAAGATAGGAGAGACTACAGCAATGGAGGCA

ATGAAGAATTTTGTCAAAGGTCTTCAAGATGTGTTTCGTGAGAGGTATCTTAGGCGCCCC

ACCATGGAAGATACCGAACCGCTTGTCCAACTTGGTGAGAAACGTCGTTTTCCTGGAATG

TTCGGCAGCATTGAGTGCATGCACTCGCATTGGGAAAGATGCCCACTAGCATGGAAGGGT

CAGTTCACTCGTGGAGATCAGAAAGTGCCAACCCTGATTCTTGAGGCTGTGGCATCGCAT

GATCTTTGGATTGGCATGCATTTTTTGGAGCACCGGGTTCCAACAATGATATCAATCTA

TTGAACCAATCTACTGTATTTATCAAGGAGCTCAAAGGACAAGCTCCTAGAGTCCAGTAC

ATGGTAAATCGGAATCAATACAATACTGGGTATTTTCTTGCTGATGGAATCTACGGTGAA

TGGGCAGTGTTTGTTAAGTCAATACGACTCCCAAACACTGAAAAGGAGAAATTGTATGCA

GATATGCAAGAAGGGGCAAGAAAAGATATCGAGAGAGCCTTTGGTGTATTGCAGCGAAGA

TTTTGCATCTTAAAACGACCAGCTGGTGTATATGATCGAGGTGTACTGCGAGATGTTGTT

CTAGCTTGCATCATACTTCACAATATGATAGTTGAAGATGAGAAGGAAACCAGAATTATT

GAAGAAGATTTAGATCTAAATGTGCCTCCTACTTCATCAACCGTTCAGGAACCTGACTTG

TCTCCTGAACAGAACACACCATTTGATAGAGTTTTAGAAAAAGATATTTCTATCCGAGAT

CGAGCGGCTCATAACCGACTTAAGAAAGATTTGGTGGAACACATTTGGAATAAGTTTGGT

GGTGCTGCACATAGAACTGGAAATTGAGAATCAGTAAATGTAATTATTTTATTTTCTTG

TAATTTATATATCTATGGTCCACTTGTAAATTTCTGAATGCTCATCGCCATATTTTTAA

TCTCTGCAGGTTCCAATCTATTTACAGGTTCCGTAAAAAAAATCTATTTGCAGGTTCCA

GTCTGTTGTCTTCACAATGTAAGTTCTGAGAATCAAATGACTATGTTTTTCTCTTTTTG

GTACCTACAGGGTGTTAGAACATGTGTTATTTTCTTTACTATGCAATTGTGATCCTCCAA

TATTTATCTACTGCATGTGTAAACCTGTTTGTGATGTCTGAAGTAGTTTCATTTGTACAG

GGTGAAAGAATCAATGAAATCTATGGGTGCATCGTCAATTTGCCTCCAGTTACCTCCTTG

TCATCGTCATTTGTAGCTTAGTTCTGTCATATTTCACCTCGAGTTAACATCTATTCAGTT

ATCTAAACTTTGCTATGTAGTGAACTTGGTTGAATGGTCATTTAAATTTATCAAGTGAAC

AATCGTACGTATCTGTGCTGAATGCATGTATTTTGTTTTCTGTTCAAGTGGCTACACACG

TTTGTGTTACATACGATCCCACTATGTGGCTGGAATTAAATGCCTTGAATTTGCATTGGA

AACCCTAGAGTGAAACACAGCATTGAGAAGGTCTGTTTCATTGTACGTTTCAACTTGTTT

CATCTTCGTTTCAGGTGATCTGGCGTCTGGGAAACAGTGTAATGAAACACTGCATTGTGA

ATGGGC

Nucleotide sequence of Pong in ap004753 in rice Nipponbare
(SEQ ID NO: 9)
GCCCACTCACAATCGGTGTTTGATTTGACTGTCATCCCCATTTAATACAGTCACAAGTCA

GCAAAAGACCAATATTTCCATCAAATGGCTACCAGAGAGAGTAAACTCGTTTCACCATCG

-continued

```
TGACACGAGATACCGCCGTTTCCCAGCTCACTGAAACCGGGTGAAACAGCATTGAGAGTT

CATCGTTTCACCTCCCCCATCCCGTGCGAGCGCTCCTCTTCGCCATCTTCCCGCGCATCC

CCGGATTCTTCCCGCGCGAGTCCCCCATCTTCCCGCGCAGCACCTCCATGTTCCCGCCCC

CAAAGCACTCGCTCGAAGCTTTTTTCCCCGATCTCACGTGCAACCCTAGCGCCAGACTCA

GTCCCCATCGCCCCGTCCGTCCCATACCCTAGCGCAAGAACCACGAGCGGAGATTGCGGA

GCTGGATCCACAAGTAGGTGGTGAATCCTCTCCATCTGCCCCCGTCCCCCGTCCAGCAGC

CATGGATCCACAAGCACGTCCTGGATCCCGTCTGAGCGCCGCCGGCAGAGGAGGGAATAA

GCCTGGGGGCAACCAGCTCGGCCTCAAGAGGTCGTCGCCCCGTCCTCCATCACCGGCAAC

AGCTCACCCACCCCTGCCTCCAAGTTCCCCTCCTGAACCTCCATCGCCGGCAACAGTTCA

GCCGCCTACTCCATCGTCAACTCCTCCTGTTGCTGCCCCCACTTCATCCCCTGCTGTACC

GATCTCAACCATGCCCCATGCCCACCGCAAGGAGCACGATCCGGCTCTGTACCGCCCAA

TTTTGCTTTTCTCCAACGAAACCAACAAGCCCCAACTTCATCGTATTTTCTCCTTCTCAC

AGATTATTCATTGTACACTATGATACATGATATGACTCTCTTGTTCATGCATTAGTAATT

AGTTCCTGTTTATGCTCAATGAAATTTGTTAGAATCAGTATGTCAGTACATTGGTAATTT

GATATATCCCTGAGTAATCAATAGAAAAAATGTAGTATTCACTATGGATTGCAGTAATAC

TTTGTTACTGAAAATTCAGTATTCAGTATGCAGTATGGATTGCGGCTTGTATAACAGAAA

TTGAAAGCAAAGATTGAGTTTGCAATCTGGACAGTGTACTGTACAACATGTAATTCACA

TACGTAAAGCTTGTTAAATATCTCCTTGTCAGTACATTGGTAACAAATGCTTTGAGTGTA

AATGCCAACGGTATCATCCTAACATTGGTATATATTTTTAGCCTTCTGTATGGAATCCAG

ACATGGTCTTCTTTGCAACCACAGCAACAGCTTGCCCTACACTCTGTCTGTCGTCATTAG

CTAACCAAATAACCTGTTAGTACTGATATATATGCTCTTCTTTGCAACCACAGCAACAGC

TTGCCCTACATGGTCTTCTGTATGCTTGACTAAACTTCTTACTTGACATATATGCTTGAC

TGAACTTGTTCCTTCACTGAATTATTCCTTACACATACTGTAGTACTTGCTTGACTGAAC

TATGTCAGGATCTTATTAAAAAAAATCTATCTCAGCACTGCTACTATGTCAGGATCATCA

CTATCATGCTTAAGTAACCTCTTACTATGTCAGTACTTACTATGTCAGGATCATCTTCTG

GAACTTACTATGTTTCATTTTCTTATCCTGCCATCGCTTTCAATTGGATTTGCTTCTTAT

GTTTTCAGCTTGTATCCTACAGACCCTTCGTAAATTTTCTCCAACAGAACTGTCTGCCGG

CAGCCACAACAACGTGAAAATTTTCACCTTCTTCGTCAGACTACCAACACAATGTCTACT

CCACCACCAACACCCCAAGCTGCAGCTAACAATACAGTCCAAATTGATATTCATGAAGAT

GCAATCAATCATCCAAGTGCTAAAAAGAGAGTTTCAGATATTGGGACTCATGATGAGGAA

GAGACATTGGCTACTGCTTGGTTCAATGCTTCTAAACATCCCATTCATGGGAATGAAAAG

AAAGGTGATACGTTTTCGAAAGACGTTACTGATGAGTTCAACACAAAAGGGAATGGGAAG

CGTACAACCCAAATAAATCAATTGAAGGTTCATTGGTCACCCCTGAAATCATCCATTCGA

GAATTCAATGATTACTCCACTAAGGTAACTCAAATCAATACAACCGGATATGACGATGAC

ATGCTGGAGAAGGAGCCACAACACATGTATGCAAATACATTTGGAAAGCCTTTTGCACTT

GTGCATTCCTGGAAGATACTGAGAAAAGAGCCCAAGTGGTGTGCAATGATTGAGAAGGAC

AAAAACAACCCTGAAGTGGTTGATATTCCACATGAACAAAAGCGTCCCATTGGTAGAGAA

GCAGCACAACCCGAGCCAATGGAAAACGCAAGAAGGAACAGTATGTCAGAAGGAATTGTC

ATCCTAGGCGACAATATTCAAAAAATTATCAAAGTGACGCAAGATCGGAAGCTGGAGCGT

GAGAAGGTCACTGAAGCACAGATTCACATTTCAAACGTAAATTTGAAGGCAGCAGAACAG
```

-continued

```
GAAAAAGAAGCAAAGATGTTTGAGGTATACAATTCCCTGCTCACTCAAGATACAACTAAC
ATGTCTGAAGAACAGAAGGCTCGCCGAGACAAGGCATTACAAAAGCTGGAGGAAAAGTTA
TTTGCTGACTAAGGTTAGATATCTAATCTAATCTGAGCTGCACTATTATTTATAATAATT
AAAGAATGCTGCAATATTTAGTTATATTGTCTCTATATCTGTGCTGCACTATGGAGTCAG
CTGCATATCACGAATTTGTCAAATCTGAGCTGCATATGTGTGAATGCTGCAATATTTAGT
TATATTAATTACCCAGTGTGAATGATGTATTGCTGTCAGTTTCACATATAGTATGAATGC
TGCACTATGCAGTCAGTTTCAGATGCAGTGTGAATGCTGCACTACGCAGTCAGTTTCACA
TGCAGTGGGCGCCTATTTATCCACAGTTTAGCCATCTCTCTACTCCTCTCAGAAACTCAT
TCCCTCTTTTCTCATACGAACACCTCCTGCCTATTATCTTTACTCTTTCTCTCTTCTTGA
AAGATGTCTGAGCAAAATAGTGATGGAAGTCAAGTTGCAGTGAACTTGTTGGATGAGTTC
GTGGCTGAGGATGAGATCATAGATGATCTTCTCACTGAAGCCACGGTGCTAGTACAGTCC
ACTATAGAAGGTCTTCAAAACGAGGCTTCTGACCATCGACATCATCCGAGGAAGCACATC
AAGAGGCCACGAGAGGAAGCACATCAGCAACTAGTGAATGATTACTTTTCAGAAAATCCT
CTTTACCCTTCCAAAATTTTTCGTGGAAGATTTCGTATGTCTAGGCCACTTTTTCTTCGC
ATCGTTGAGGCATTACCCCAGTGGTCAGTGTATTTCACACAAAGCGTGGAAGCTGTTAAT
CGGAAACCACTCAGTCGACTGCAAAAGTGTAGTGCAGCTATTCGCGACTTGGCTAGTGGT
AGTGGCCCAGATGAACTAGATGAATATCTGAAGATAGGAGAGACTACAGCAATGGAGGCA
ATGAAGAATTTTGTCAAAGGTCTTCAAGATGTGTTTCCTGAGAGGTATCTTAGGCGCCCC
ACCATGGAAGATACCGAACGGCTTCTCCAACTTGGTGAGAAACGTGGTTTTCCTGGAATG
TTCGGCAGCATTGACTGCATGCACTGGCATTGGGAAAGATGCCCAGTAGCATGGAAGGGT
CAGTTCAGTCGTGGAGATGAGAAAGTGCCAACCCTGATTCTTCACGCTCTCGCATCGCAT
GATCTTTCGATTTGGCATGGATTTTTTGGAGCAGCCGGTTGCAAGAATGATATCAATGTA
TTGAACCAATCTACTGTATTTATCAAGGAGCTCAAAGGACAAGCTCCTAGAGTCCAGTAC
ATGGTAAATCGGAATCAATACAATACTGCGTATTTTCTTGCTGATGGAATCTACCCTGAA
TGGCCAGTGTTTGTTAAGTCAATACGACTCCCAAACACTGAAAAGGAGAAATTGTATGCA
GATATGCAAGAAGGGGCAAGAAAAGATATCGAGAGAGCCTTTGGTGTATTGCAGCGAAGA
TTTTGCATCTTAAAACGACCACCTGGTGTATATGATCGAGGTGTACTGCGAGATGTTGTT
CTAGCTTGCATCATACTTCACAATATGATAGTTGAAGATGAGAAGGAAACCAGAATTATT
GAAGAAGATTTAGATCTAAATGTGCCTCCTAGTTCATCAAGCGTTCAGGAACCTGAGTTC
TCTCCTGAACAGAACACACCATTTGATAGAGTTTTAGAAAAAGATATTTCTATCCGAGAT
CGAGCGGCTCATAACCGACTTAAGAAAGATTTGGTGGAACACATTTGGAATAAGTTTGGT
GGTGCTGCACATAGAACTGGAAATTGAGAATCAGTAAATGTAATTATTTTATTTTTCTTG
TAATTTATATATCTATGGTCCACTTGTAAATTTCTGAATGCTCATGGGCATATTTTTAA
TCTCTGCAGGTTCCAATCTATTTACTGGTTCCCTAAAAAAAAATGTATTTGCACGTTCCA
GTCTGTTGTCTTCACAATGTAAGTTCTGAGAATCAAATCACTATGTTTTTCTCTTTTTG
GTAGCTACAGGGTGTTAGAACATGTGTTATTTTCTTTACTATGCAATTGTGATCCTCCAA
TATTTATCTACTGCATCTGTAAACCTCTTTCTCATGTCTGAACTACTTTCATTTCTACAG
GGTGAAAGAATCAATGAAATCTATGCGTCCATCCTCAATTTGCCTCCACTTACCTCCTTC
TCATCGTCATTTGTAGCTTAGTTCTGTGATATTTCAGCTCGAGTTAACATCTATTCAGTT
ATCTAAACTTTGCTATGTAGTGAACTTGGTTGAATCGTCATTTAAATTTATGAAGTGAAC
AATCGTACCTATCTGTGCTGAATGCATGTATTTTGTTTTGTGTTCAAGTGGCTACACACG
```

-continued

TTTGTGTTACATAGGATCCGACTATGTGGCTGGAATTAAATGCCTTGAATTTGCATTGGA

AACGCTAGACTGAAAGAGAGGATTGAGAAGGTCTGTTTCATTGTACGTTTCAACTTGTTT

CATCTTCGTTTCAGCTGATGTGCCGTCTGGGAAACAGTGTAATGAAACAGTCCATTGTGA

ATGGCC

Nucleotide sequence of Pong in ap112208 in rice Nipponbare
(SEQ ID NO: 10)
GGCCAGTCACAATGGGTGTTTCATTTGAGTGTCATGCGCATTTAATAGAGTGACAAGTCA

GCAAAAGAGCAATATTTGCATGAAATGGGTAGGAGAGAGAGTAAACTCGTTTCACCATGG

TGACACGAGATAGCGCCGTTTCCCACGTCACTGAAACCGGGTGAAACAGCATTGAGAGTT

CATCGTTTCACGTCCGCGATCCCGTGCGACCGCTGCTCTTCGCCATCTTCGCCCGCATGC

CCGGATTCTTCCCGCGCGAGTCCCCCATCTTCCCGCGCAGCACCTCCATGTTGCCGCCCC

CAAAGCACTGGCTCGAAGCTTTTTTGCCCAATCTCACCTGCAACCCTAGCGCCAGACTCA

GTCCCCATCGCCCCGTCCGTCCCATACCCTAGCGCAAGAACCACGAGCGGAGATTGCGGA

GCTGGATCCACAACTAGGTGCTGAATCCTGTCCATCTGCCCCCGTCCGCCGTCCAGCAGC

CATGGATCCAGAAGGAGGTGGTGGATCCCGTCTGAGCGCCGCCGGCAGAGGAGGGAATAA

GCGTGGGGGCAAGCAGCTGGGCCTGAAGAGGTCGTCGGCGCCTCCTCCATCACCGGCAAC

AGCTCAGCCACCCCTGCCTGCAAGTTCCCCTCCTGTACCTCCATCGCCGGGAACAGTTCA

GCCGCCTACTCCATCGTCAAGTCCTGCTCTTGCTGCCCCCAGTTCATCCCGTCCTGTACC

GATGTCAACGATGCCCGCATGGCCACCGCAAGGAGCAGGATCCGGCTCTGTACCCCCCAA

TTTTGCTTTTCTCCAAGGAAAGCAACAAGGCCCAAGTTCATGGTATTTTCTCCTTGTCAC

AGATTATTCATTGTACACTATGATACATGATATGACTCTCTTCTTCATGCATTAGTAATT

AGTTCCTGTTTATGCTCAATGAAATTTGTTAGAATCAGTATGTGAGTACATTGGTAATTT

GATATATGCCTCAGTAATGAATACAAAAAATGTAGTATTCAGTATGGATTGCACTAATAC

TTTGTTAGTGAAAATTCAGTATTCAGTATGCAGTATGGATTGCGGCTTCTATAACAGAAA

TTGAAAGCAAAAGATTCACTTTGCAATCTGGACAGTGTACTGTACAACATGTAATTCACA

TACGTAAAGCTTCTTAAATATCTCCTTGTCAGTACATTGGTAACAAATGCTTTGAGTGTA

AATGCCAACCGTATCATCCTAACATTGGTATATATTTTTAGCCTTCTGTATGGAATGCAG

ACATGGTCTTCTTTGCAACCACAGCAACAGCTTGGCCTACACTCTGTGCTGTCGTCATAG

CTAACCAAATAACCTGTTAGTACTGATATATATCGTCTTCTTTGCAACCACAGCAACAGC

TTGCCCTACATGGTGTTCTGTATGCTTGACTAAACTTGTTACTTGACATATATGCTTGAC

TGAACTTGTTGCTTGACTGAATTATTCCTTACACATACTGTAGTAGTTGCTTGACTGAAC

TATGTCAGGATCTTATTAAAAAAAATCTATGTCAGCACTGCTACTATGTCAGGATCATCA

GTATGATGCTTAAGTAACCTGTTAGTATGTCAGTACTTACTATGTCAGGATCATCTTCTG

GAACTTACTATGTTTGATTTTCTTATGCTGCCATCCCTTTCAATTGGATTTGCTTCTTAT

GTTTTCAGGTTGTATCGTACAGAAGGCTTCGTAAATTTTCTCCAACAGAAGTGTCTGCCG

CAGCCACAAGAAGGTGAAAATTTTCACCTTGTTGGTCAGACTACCAACACAATGTCTAGT

CCACCACCAACACCCCAAGCTGCAGCTAACAATACAGTCCAAATTGATATTCATGAAGAT

GCAATCAATGATCCAAGTGGTAAAAAGAGAAGTTTGAGATATTGGACTCATGATGAGGAA

GAGAGATTGGCTAGTGCTTGGTTGAATGCTTCTAAAGATCCCATTCATGGGAATGAAAAC

AAAGGTGATACGTTTTGGAAAGAGGTTACTGATGAGTTCAACAGAAAAGGGAATGGGAAG

CGTACAAGGGAAATAAATCAATTGAACGTTCATTGGTCACGCCTCAAATCATCGATTGGA

-continued

```
GAATTCAATGATTACTGGACTAAGCTAACTCAAATGAATACAAGCGGATATGACGATGAC
ATGCTGGAGAAGGACGCACAACAGATGTATGCAAATACATTTGGAAAGCGTTTTGCACTT
GTGCATTCCTGGAAGATACTGAGAAAAGAGCCCAAGTGGTGTGCAATGATTGAGAAGGAC
AAAAACAAGGCTGAAGTGGTTGATATTCCAGATGAAGAAAAGCGTCCCATTGGTAGAGAA
CCAGCACAAGCCGAGCGCAATGGAAAACGCAAGAAGGACAGTATGTCAGAACGAATTGTC
ATCCTAGGGGACAATATTCAAAAAATTATCAAAGTGACGCAAGATCGGAAGCTGGAGCGT
GAGAAGGTCACTGAAGCACAGATTCACATTTCAAACGTAAATTTGAAGGCAGCAGAACAG
CAAAAAGAACCAAAGATGTTTGAGGTATACAATTCCCTGCTCACTCAAGATACAAGTAAC
ATGTCTGAAGAACAGAAGGCTCGCCCAGACAAGGCATTACAAAAGCTGGACGAAAAGTTA
TTTGCTGACTAAGGTTAGATATCTAATCTAATCTGAGCTGCACTATTATTTATAATAATT
AAAGAATGCTGCAATATTTAGTTATATTGTCTGTATATCTGTGCTGCACTATGCAGTCAG
CTGCATATCACGAATTTGTCAAATCTGAGCTGCATATCTGTGAATGGTGCAATATTTAGT
TATATTAATTACCCAGTGTGAATGATGTATTGCTGTCAGTTTGACATATAGTATGAATGC
TGCACTATGCAGTCAGTTTCACATGCAGTGTGAATGCTGCACTAGGCAGTCAGTTTCACA
TCCACTGGGGGCCTATTTATGCAGAGTTTAGCGATGTCTCTACTCCTCTGAGAAACTGAT
TCCCTCTTTTCTCATACGAAGACCTCCTCCCTTTTATCTTTACTGTTTCTCTCTTCTTCA
AAGATGTCTGAGCAAAATACTGATGGAAGTCAAGTTCCAGTGAACTTGTTGGATGAGTTC
CTGGCTGAGGATGAGATGATAGATGATCTTCTCAGTGAAGCCAGGGTGGTACTACACTCC
ACTATAGAAGGTCTTCAAAAGGAGGCTTCTGACCATCGACATCATCCGAGGAAGCACATC
AAGAGGCCACGAGAGGAAGCACATCAGCAACTACTGAATGATTACTTTTCAGAAAATCCT
CTTTACCCTTCCAAAATTTTTCGTCGAAGATTTCGTATGTCTAGGCCACTTTTTCTTCGC
ATCGTTGAGGCATTAGGCCAGTCGTCAGTGTATTTCACACAAAGGGTGGATCCTGTTAAT
CGGAAAGGACTCAGTCCACTGCAAAAGTGTACTGCAGCTATTCGCCAGTTGGCTACTGGT
AGTGGCGCAGATGAACTAGATGAATATCTGAAGATAGGAGAGACTACAGCAATGGAGGCA
ATGAAGAATTTTGTCAAAGGTCTTCAAGATGTGTTTGGTGAGAGGTATCTTAGGCGCCCC
ACCATGGAACATACCGAACGGGTTCTCCAACTTGCTCAGAAACCTGCTTTTCCTGGAATC
TTTCGCAGCATTGACTGCATGCACTCCCATTGGGAAAGATGCGCAGTACCATGGAAGCGT
CAGTTCACTCGTGGAGATCAGAAAGTGCCAACCCTGATTCTTGACGCTGTGCCATCCCAT
GATCTTTGGATTTGGCATGCATTTTTTGGAGCAGCGGGTTCCAACAATGATATCAATGTA
TTGAACCAATCTACTGTATTTATCAACGAGCTCAAAGGACAAGCTCCTAGAGTCCAGTAC
ATGGTAAATGGGAATCAATAGAATACTGGGTATTTTCTTGCTGATGCAATGTACCCTGAA
TGGGCAGTGTTTGTTAAGTCAATACCAGTCCCAAACACTGAAAAGGAGAAATTGTATGCA
GATATGCAAGAAGGCGCAAGAAAAGATATCGAGAGAGCCTTTGCTGTATTGCAGCGAAGA
TTTTGCATCTTAAAACGACCAGCTCGTCTATATGATCGAGGTGTACTCCGAGATGTTGTT
CTAGCTTGCATCATACTTCACAATATGATAGTTGAAGATTGAGAAGGAACCAGAATTATT
GAAGAAGATTTAGATCTAAATGTGCCTCCTAGTTCATCAACCGTTCAGGAACCTGAGTTC
TCTCCTGAACAGAACACACCATTTGATAGAGTTTTAGAAAAAGATATTTCTATCCGAGAT
CGAGCGCCTAATAACCGACTTAAGAAAGATTTGCTGGAACACATTTGGAATAAGTTTGGT
GGTGCTGCACATAGAACTGGAAATTGAGAATCAGTAAATGTAATTATTTTATTTTTCTTG
TAATTTATATATCTATGGTCCACTTGTAAATTTCTGAATGCTCATCGCCATATTTTTTAA
TCTCTCCAGGTTCCAATCTATTTACAGGTTCCCTAAAAAAAAATCTATTTGCAGGTTCCA
```

-continued

```
GTCTGTTGTCTTCAGAATGTAAGTTCTGAGAATCAAATCACTATGTTTTTCTCTTTTTG
GTAGCTACAGGGTGTTAGAACATGTGTTATTTTCTTTACTATGCAATTGTGATCCTCCAA
TATTTATCTACTGCATGTGTAAACCTGTTTGTCATGTCTGAACTACTTTCATTTGTACAG
GGTGAAAGAATCAATGAAATCTATGCGTGCATGGTCAATTTCCCTCCAGTTACCTGCTTG
TCATCGTCATTTGTAGCTTAGTTCTGTCATATTTCACCTCGAGTTAACATCTATTCAGTT
ATCTAAACTTTGCTATGTAGTGAACTTGGTTGAATGGTCATTTAAATTTATCAAGTGAAC
AATCGTAGCTATCTGTGCTGAATGCATGTATTTTCTTTTGTGTTCAAGTGGCTACACACG
TTTGTGTTACATACGATCCCACTATGTGGCTGGAATTAAATCCCTTGAATTTGCATTGGA
AACGCTAGAGTGAAAGACAGCATTGAGAAGGTCTGTTTCATTGTACGTTTCAACTTGTTT
CATCTTCGTTTCAGCTGATGTGGCGTCTGGGAAACAGTGTAATGAAACACTGCATTGTGA
ATGGCC
```

Nucleotide sequence of Pong in ap003543 in rice Nipponbare
(SEQ ID NO: 11)
```
GGCCAGTCACAATGGGTGTTTCATTTGAGTGTCATGCGCATTTAATACAGTGACAAGTCA
GCAAAAGAGCAATATTTGCATGAAATGGGTAGGAGAGAGAGTAAACTCGTTTCACCATGG
TGACACGAGATAGCGCCGTTTCCCAGCTCACTGAAACGGGGTGAAACAGCATTGAGACTT
CATCGTTTCACCTCCGGGATCCCGTGCGAGCGCTGCTCTTCGCCATCTTCGCGCGCATCG
CCGGATTCTTCCCCCGCGACTGCCCCATCTTCCGGCGGAGCACCTCCATGTTCCCGCCCC
CAAAGCACTCCCTCGAAGCTTTTTTCCCCAATCTCACCTGCAAGCCTAGCGCCAGACTGA
GTCCGCATCGCCCCGTCCGTCCCATACCCTAGCGCAAGAACCAGGAGCGGAGATTGCGGA
GGTGGATCCAGAAGTAGGTGGTGAATCCTGTCCATCTGCCGCCGTCCGCCGTCCAGCAGC
CATGGATCCACAAGGAGGTGGTGGATGCCGTCTGAGCGCCGCCGGCAGAGGAGGGAATAA
GCGTGGGGGCAAGCAGCTGGGCCTGAAGAGGTCGTCGGCGCCTGCTCCATCACCGGCAAC
AGCTCAGCCACCGCTGCCTGCAAGTTCCCCTCCTGAAGCTCCATCGCCGGCAACAGTTCA
GCCGCCTACTCCATCGTCAAGTGCTGCTGTTGCTGCCCCCAGTTCATCCCCTGCTGTACC
GATGTCAACCATGCCGCCATGGCCACCGCAAGGAGCAGGATCGGGCTCTGTACCCCCCAA
TTTTGCTTTTCTGCAAGGAAAGCAACAAGGCCCAAGTTCATGGTATTTTCTCCTTGTCAC
AGATTATTCATTGTACACTATGATACATCATATGACTCTCTTCTTCATGCATTAGTAAAT
TAGTTCCTGTTTATGCTGAATGAAATTTGTTAGAATCAGGTATGTTCAGTACATTGGGTA
ATTTTCATATATGCCTGAGTAATGAAATAGAAAAAAATGTAATATTCATATTTGGGATTG
CAGTAAATACTTTTGTAAATGGAAAATACAGTATTCCAAGAATGCAATATGGAATTGCTG
GTTTTTTTAACACAATTTCGAAAGCAAAAGAATTCAGTTTGCATTCTGGGCAGTGTATTG
TGAAACCTGGTAGTTTTACATTCTGTGAAACCTCGGTAAATATCCTCCTTTATACGTACC
TTTTGGTTACAAAAGGCTATCGAGTTGAAAAACACGAAGGGGATAGAATCGCCAATATTG
GTTATATTATTTTTAGNNNNNNNNNNNNNNNNNNNNNNNNNNNNNNNNNNNNNNNNNNNN
NNNNNNCCCAATTAAATGTTAAGTTGCAAGGGAACCCGGATTTTTGAAAAGGTTTAGATT
TAAATCGCCCCCTAGGTCACCAGGCGTGAGGACCTGAGTTTTTCCTGAACAGAACCCCCC
ATTTGATAAAGTTTTAAAAAAAAAATTTTCTATCCGAGATCGAGCGGCTCATAACCGAC
TAAAAAAGATTTGGGGGAACCCATTTGAATAAGTTTGGGGGTGCTGCACATAGAACTGGA
AAATTGAGAATCAGTAAATGAAATATTTTATTTTCCTGGTAATTTAAAAATCTATGGTCC
ACCTGAAATTTCTGAATGCTCATCGCCATATTTTTAATCTCTGCAGGTTCCAATCTATTT
```

-continued

```
ACAGCTTCCCTAAAAAAAAATCTATTTGCAGGTTCCAGTCTCTTGTCTTCACAATGTAAG

TTCTGAGAATCAAATCACTATGTTTTTCTGTTTTTTGGTAGCTACAGGGTGTTAGAACAT

GTGTTATTTTCTTTACTATGCAATTGTGATCGTCCAATATTTATCTACTGCATGTGTAAA

CCTGTTTGTCATGTCTGAACTACTTTCATTTGTACAGGGTGAAAGAATCAATGAAATCTA

TGGGTGCATCGTCAATTTGCCTCCAGTTACCTGCTTGTCATCGTCATTTGTAGCTTAGTT

CTGTCATATTTCACCTGGAGTTAACATGTATTCAGTTATCTAAACTTTGCTATGTAGTGA

ACTTCGTTGAATGGTCATTTAAATTTATCAAGTGAACAATCGTACCTATCTCTGCTGAAT

GCATGTATTTTGTTTTGTCTTCAAGTGGCTACACACGTTTGTGTTACATACGATCCCACT

ATGTGGCTGGAATTAAATGCCTTGAATTTGCATTGGAAACGCTAGAGTGAAACACAGCAT

TGAGAAGGTCTGTTTCATTGTACGTTTCAACTTGTTTCATCTTCGTTTCAGCTGATGTGG

CGTCTGGGAAACAGTGTAATGAAACACTGCATTGTGAATGGCCTAACACAAACGTCTGTA

GCCACTTGAACACAAAACAAATACATGCATTCACCACAGATAGCTACCATTGTTCACTT

GATAAATTTAAATGACCATTCAACGAAGTTCACTACATAGCAAAGTTTAGATAACTGAAT

AGATGTTAACTCGAGGTGAAATATGACAGAACTAAGCTACAAATGAGGATGACAAGCAGG

TAAGTGGAGGCAAATTGACGATGCACCCATAGATTTCATTGATTCTTTGACCCTGTACAA

ATGAAAGTAGTTCAGACATGACAAACAGGTTTACACATGCAGTAGATAAATATTGGAGGA

TCACAATTGCATAGTAAAGAAAATAACACATGTTCTAACACCCTCTACCTACCAAAAAAG

AGAAAAAGATAGTGATTTGATTCTGAGAACTTACATTGTGAAGACAACAGACTGGAACCT

GCAAATAGATTTTTTTTAGGGAACCTGTAAATAGATTGGAACCTGCAGAGATTAAAAAA

TATGGCGATGAGCATTCAGAAATTTACAAGTGGACCATAGATATATAAATTACAAGAAAA

ATAAAATAATTAGATTTACTGATTCTCAATTTCCAGTTCTATGTGCAGCACCAGCAAAGT

TATTCGAAATGTGTTGCACCAAATCTTTCTTAAGTGGGTTATGAGCCCCTCGATCTCGGA

TAGAAATATCTTTTTCTAAAACTCTATCAAATGGTGTGTTCTGTTCAGGAGAGAACTCAG

GTTCGTCAACGGTTGATGAACTAGGAGGCACATTTAGATCTAAATCTTCTTCAATAATTG

TGGTTTCCTTCTCATCTTCAACTATCATATTGTGAAGTATCATGCAAGCTAGAACAACAT

CTGGCAGTACACCTCGATCATATAGACGAGCTGGTCGTTTTAAGATGCAAAATCTTCGCT

GCAATACACCAAAGGCTCTCTCGATATCTTTTCTTGCCCCTTCTTGCATATCTGGATACA

ATTTCTCCTTTTCAGTGTTTGGGAGTGCTATTGACTTAACAAACACTGCCCATTCACGCT

AGATTCCATCAGCAAGAAAATACCCAGTATTGTATTGATTCGGATTTACCATGTACTGGA

GTCTAGCAGCTTGTCCTTTGAGCTCCTTGATAAATACAGTAGATTGGTTCAATACATTGA

TATCATTGTTGGAACCCGCTGCTCCAAAAAATGCATGCCAAATCGAAAGATCATGCGATC

CCACAGCCTCAAGAATCAGGGTTGGCACTTTCTGATCTCCACGAGTGAACTGACCCTTCC

ATGCTACTGGGCATCTTTCCCAATGCCACTGCATGCAGTCAATGCTCCCGAACATTCCAG

GAAACCACGTTTCTCACCAACTTCGAAGAAGCCGTTCCGTATCTTGCATGGTGGGCGCC

TAAGATACCTCTCACCAAAGACATCTTGAAGACCTTTGACAAAATTCTTCATTGCCTCCA

TTGCTGTAGTCTCTGCTATGTTCAGATATTCATCTAGTTCATCTGCGCCACTACCAGTAG

CCAACTGGCGAATAGCTGCAGTACACTTTTGCAGTGGACTGAGTCCTTTCCGATTAACAG

CATCCACCCTTTGTGTGAAATACACTGACCACTGGCCTAATGCCTCAACGATGCGAACAA

AAAGTGGCCTAGACATACGAAATCTTCGACGAAAAATTTTGGAAGGGTAAAGAGGATTTT

CTGAAAAGTAATCATTCACTAGTTGCTGATGTGCTTCCTGTCGTGGCCTCTTGATGTGCT

TCCTCGCATGATGTCGATGGTCAGAAGCCTCGTTTTGAAGACCTTCTATAGTGGACTGTA
```

-continued

```
CTACCACGGTCGCTTCAGTGAGAAGATGATCTATGATCTCATCCTCAGCCAGGAACTCAT

CCAACAAGTTCAGTGGAACTTGACTTCGATCAGTATTTTGCTCAGACATCTTTGAAGAAG

AGAGAAAGAGTAAAGATAAAAGGGAGGAGGTCTTCCTATGACAAAAGAGGGAATGAGTTT

CTGAGAGGAGTAGAGAGATGGCTAAACTCTGCATAAATAGGCGCCCACTGCATGTGAAAC

TGACTGCCTAGTGGAGGATTCACACTGCATGTGAAACTGACTGCATAGTGCAGCATTCAT

ACTATATGTGAAACTGACAGCAATACATCATTCACACTCGGTAATTAATATAACTAAATA

TTGCACCATTCACAGATATGCAGCTCAGATTTGACAAATTCGTGATATGCAGCTGACTGC

ATAGTGCAGCACAGATATACAGACAATATAACTAAATATTCCAGCATTCTTTAATTATTA

TAAATAATAGTGCAGCTCAGATTAGATTAGATATCTAACCTTACTCAGCAAATAACTTTT

CCTCCAGCTTTTCTAATGCCTTGTCTCGGCGAGCCTTGTGTTCTTCAGACATGTTACTTG

TATCTTGAGTGAGCAGGGAATTGTATAGCTCAAACATCTTTGCTTCTTTTTGCTGTTCTG

CTGCCTTCAAATTTAGGTTTGAAATCTGAATCTGTCCTTCAGTGACCTTCTGACGCTCCA

GCTTCCGATCTTGGGTCACTTTGATAATTTTTTCAATATTGTCCCCTAGGATGACAATTC

CTTCTGACATACTCTCCTTCTTGCGTTTTCCATTGCGCTCGGCTTGTGCTGCTTCTCTAC

CAATGGGACGCTTTTGTTCATCTGGAATATCAACCACTTCAGCCTTGTTTTTCTCCTTCT

CAATCATTGCACACCACTTGGGCTCTTTTCTCAGTATCTTCCACCAATGCACAAGTGCAA

AAGGCTTTCCAAATGTATTTGCATACATCTGTTGTGCCTCCTTCTCCAGCATGTCATCGT

CATATCCGCTTCTATTCATTTGAGTTACCTTAGTCCACTAATCATTGAATTCTCCAATCG

ATGATTTGAGGCGTGACCAATGAACCTTCAATTGATTTATTTCCCTTGTACGCTTCCCAT

TCCCTTTTCTGTTGAACTCATCAGTAACCTCTTTCCAAAACGTATCACCTTTGTTTTCAT

TCCCATGAATGGGATCTTTACAAGCATTCAAGCAAGCACTAGCCAATCTCTCTTCCTCAT

CATGAGTCCAATATCTCAAACTTCTCTTTTTAGCACTTGCATCATTGATTGCATCTTCAT

GAATATCAATTTGGACTGTATTGTTAGCTGCAGCTTGGGGTGTTGGTGGTGGAGTAGACA

TTGTCTTGGTAGTCTGACCAACAAGGTGAAAATTTTCACCTTCTTGTGCCTGCCGCACAC

AGTTCTGTTGGAGAAAATTTACGAAGCCTTCTGTAGGATACAACCTGAAAACATAAGAAG

CAAATCCAATTGAAACCGATGGCAGCATAAGAAAATCAAACATAGTAAGTTCCAGAAGAT

GATCCTGACATAGTAAGTACTGACATACTAACAGGTTACTTAAGCATCATACTGATGATC

CTGACATAGTAGCAGTGCTGAGATAGATTTTTTTAATAAGATCCTGAGATACTTGAGTC

AAGCAAGTACTACAGTATGTGTAAGGAATAATCAGTCAAGCAACAAGTTGCAGTCAAGCA

TATATGTCAAGTAACAAGTTTAGTCAAGCATACAGAAGACCATGTAGGGCAAGCTGTTGC

TGTGGTTGCAAAGAAGACCATATATATCAGTAGTAACAGGTTATTTGGTTAGCTATGACG

ACAGCAGAGAGTGTACGGCAAGCTGTTGCTGTGGTTGCAAAGAAGACGATGTCTGCATTC

CATACAGAAGGCTAAAAATATATACCAATGTTAGGATGATACCGTTGGCATTTACACTCA

AAGCATTTGTTACCAATGTACTGACAAGGAGATATTTAACAAGCTTTACGTATGTGAATT

ACATGTTGTACAGTACACTGTCCAGATTGCAAACTGAATGTTTTGCTTTCAATTTCTGTT

ATACAAGCCGCAATCCATACTGCATACTGAATACTGAATTTTCACTAACAAAGTATTACT

GCAATCCATACTGAATACTACATTTTTTCTATTCATTACTCAGGCATATATCAAATTAGC

AATGTACTGACATACTGATTCTAACAAATTTCATTGAGCATAAACACGAACTAATTACTA

ATGCATGAAGAAGAGTCATATCATGTATCATAGTGTACAATGAATAATGTGTGACAAG

GAGAAAATACCATGAACTTGGCCCTTGTTGGTTTGCTTGCAGAAAAGCAAAATTGGGGGG
```

-continued
```
TACAGAGCCCCATCCTGCTCGTTGCGGTGGCCATGCGGGCATGGTTGACATCGGTACAGC

AGGGGATGAACTGGGGGCAGCAACAGCAGGACTTGACGATGGAGTAGGCGGCTGAACTGT

TGCCGGCGATGGAGCTTCAGGAGGCGAACTTGCAGGCAGCGGTGGCTGAGCTGTTGCCCC

TGATGGAGCAGGCGCCGACGACCTCTTCAGGCCCAGCTGCTTGCCCCCACGCTTATTCCC

TCCTGTGCCCGCGCCGCTCAGACGGGATCCACCAGCTCCTTGTGGATCCATGGCTCCTGG

ACGGCGGACGGCGGCAGATGGACAGGATTCACCACCTACTTGTGGATCCAGCTCCCCAAT

CTCCGCTCGTGCTTCTTGCGCTACGGTATGGGACGGACGGCGCGATGGGGACTGAGTCTG

GCGCTAGGGTTGCAGGTGAGATTGGGGAAAAAAGCTTCGAGCGAGTGCTTTGGGGGCCCG

AAGATCGAGCTGCTGCCCGGGAAGATGGGGGACTCGCGCGGGAAGAATCCGGCGATGCGC

GCGAAGATGGCGAAGAGCAGCGCTCGCACGGCATCCCGGAGGTGAAACGATGAACTCTCA

ATGCTGTTTCACCCCGTTTCAGTGACCTGGGAAACGCCGCTATCTCGTGTCACCATGGTG

AAACGAGTTTACTCTCTCCTACGCATTTCATGCAAATATTGCTCTTTTGCTGACTTGT

CACTGTATTAAATGCGCATGACACTCAAATGAAACACCCATTGTGACTGGCCTTACATAC

GATCCGACTATGTGGCTGGAATTAAATGCCTTGAATTTGCATTGGAAACGCTAGACTGAA

ACACAGCATTGAGAACGTCTGTTTCATTGTACGTTTCAACTTGTTTCATCTTCCTTTCAG

CTGATGTGGCGTCTGGGAAACAGTGTAATGAAACACTGCATTGTGAATGGCC
```

Deduced amino acid sequence of Pong ORF-1 in rice Nipponbare
(SEQ ID NO: 12)
```
MFDFLMLPSVSIGFASYVFRLYPTEGFVNFLQQNCLPQPQEGENFHLVGQTTNTMSTPPP

TPQAAANNTVQIDIHEDAINDASAKKRSLRYWTHDEEERLASAWLNASKDPIHGNEKKGD

TFWKEVTDEFNRKGNGKRTREINQLKVHWSRLKSSIGEFNDYWTKVTQMNTSGYDDDMLE

KEAQQMYANTFGKPFALVHWWKILRKEPKWCAMIEKDKNKAEVVDIPDEQKRPIGREAAQ

AERNGKRKKDSMSEGIVILGDNIEKIIKVTQDRKLEREKVTEAQIHISNVNLKAAEQQKE

AKMFEVYNSLLTQDTSNMSEEQKARRDKALQKLEEKLFAD
```

Deduced amino acid sequence of Pong ORF-2 in rice Nipponbare
(SEQ ID NO: 13)
```
MQSLAISLLLSETHSLFSHTKTSSLLSLLFLSSSKMSEQNTDGSQVPVNLLDEFLAEDEI

IDDLLTEATVVVQSTIEGLQNEASDHRHHPRKHIKRPREEAHQQLVNDYFSENPLYPSKI

FRRRFRMSRPLFLRIVEALGQWSVYFTQRVDAVNRKGLSPLQKCTAAIRQLATGSGADEL

DEYLKIGETTAMEAMKNFVKGLQDVFGERYLRRPTMEDTERLLQLGEKRGFPGMFGSIDC

MHWHWERCPVAWKGQFTRGDQKVPTLILEAVASHDLWIWHAFFGAAGSNNDINVLNQSTV

FIKELKGQAPRVQYMVNGNQYNTGYFLADGIYPEWAVFVKSIRLPNTEKEKLYADMQEGA

RKDIERAFGVLQRRFCILKRPARLYDRGVLRDVVLACIILHNMIVEDEKETRIIEEDLDL

NVPPSSSTVQEPEFSPEQNTPFDRVLEKDISIRDRAAHNRLKKDLVEHIWNKFGGAAHRT

GN
```

Nucleotide sequence of PONG_LIKE_1 in AP004155 in *Oryza sativa*
(SEQ ID NO: 14)
```
GAGCAGGTACAATAGGGCTGACCCATCAGCTCCAATAATTGCCACGTCACATTATTTCTA

CGTGGAAGGGTAATGATTGAGCGGAAAGAGAAGAGCTGGCGACTAAATTGTCGCCAAGCT

ATAACCCATTTTTTGCGGGCATAGCGCCCGCTTGCAGCGCATTTAGATTGGATGACATGG

GGTAGGTATGTCACAAGGTGACATAGTGTAGATCTCAGTCCTTCGAAATAAATCCAGCGG

CTGAGATTCGTCCACGTCATTACAAGTTAAAATTTAACTCCAATAAAATTTTAACTCCTG

AAATTTTAACTACCAGTAAAATTTTTACTCATACGAGTTAAATTTTAACTCATGATGATC

TGAACGAATCTCAGCCGTTGGATTTATTTTGGAGAGCTGAGATCTACGCTATGTCACCTT
```

```
ATGACATGTCTATCGTATCTGACCCAATCTGAATCCGCTTGCAGCCGAGGCAGGCGCTAG

AAAACGCGGGTTGTGCGGCCCACGAACGGAAAAACTGATCATCTGCGCGCACCGCTCCTA

CGCGGCGGATCCACTGATCCGATCCCCTTTCCCCTTTCTCTTTCCGATGAGATCGATCCC

CGTGTCCGTCTTGGCGCGAGCGCGAGAAAGGACGCTGGCGCATCGATCTCTCCTTCCTGG

CGCATCGATCCCCTCCCGCCAAATCGATGGACAGATCTCCCACCCACCGCATCGATCGAT

CTCCTTCCCGCGCAGTATTCCCTCTCACTCACTCCTTTTTCTTCTCTCCCGGTCCTATAA

CTTCTCCGGCGCGCGCGAAATTCATTTTGCTGGCAGGTAGAACGATGCCAAAGCCCCAAA

ATCGCCCCTGAAATCCATCCCCCCGGTGAATTTGAGGGAGGGCGACTGCCCCCGGTCCTC

TTCGATAGTTCTACCGCACCAAAACCCTAGTTGCTTTTCACCATGTCTCGTCGGACGAAG

AGAGAGGTTGCACCACCGCAAACTCATTTGCAAGCTGGTGTGGTCCTCCCGGTGTTCATA

TCCCGCCGGCAACACCGTATCCATATCGAGGTCCTTTGTTCCCCACCCCACTGCCATCAT

GGTTTCCTTTTCCACCGTCACAAGGCATGGCCCGCTCATCTCCATATCGTCCTCCTACTG

ATGCCAAGACGGACGTGCAAGTTGATTTGGAACAATGGTACATTTATTATTTGGCTTTAT

CAGTTCTGATTTTGACATGCTTCTGTTTCCCTGTCTAATATTGAGAGTTTGATGGTCGTT

ATTGTTTTGATCCATAACAGCACTAGTGCAATGAATTCTTTAGGAAAAAGAGGTGATTT

TGGTCTGATAATCAGGTTACCGTAGTAACTTGGCGCATGTAATTTGGTCTGCAATGATTT

GTACCATGTATTTATGCAGCAATTTCGCTAAGTAAAAACAAGAGTCCAATGTTACATGTA

GGGTAACCATGCTAGGGTAATTAGCAGTGCTGGTAACCATGTATTTATGCAGTAATTTGG

CAAACTAAAAACAAGAGTCCAATGTTACATCTATTACTAATTTGTTTTAGATTCGAGCAC

TCATTTACGACTATGAACTGAAATAAAATAATTTTGACTGCACATATCAATATACCATTT

ATACTGGCGTAATATTGGGTTACCCCTTGCATTGATCAAGATTGGCTTGTTCATTCCTTT

TTATATATGGGACATAACTGATGAAGATTTTCATGTTCATGATTTTTATATAGGGGACTA

GAATCTCGCCCGCTCGGTGGTTTTGTTGATTTTATCAAAAACACCACGAACCTTATGCAC

CATGTGACTGAAGGGTGTCAGTTGCACCCAATTAATGTTGAGAATGGCAACAATGGAAAT

GCCACTAGGAGCGAGAAGCGCCTAGGCTGGTCAACTGAAGAACACTTGAGGCTGGTAAGT

GTCCTACGCGAGTTATTTATTTGGTAGTGGCATTCATAATAGATGCAATTTAAGAATAGT

GAAATATTTGGAAATTGTAGGTCAGGCTTGGTTAAACAACTCAAATGATCCAATAGAATC

GAATTTCAAAAGAATGATAAATATTGGGTGATGTTGCTGCTGCTTACAATAGCACTACT

CCGTCAAGCCGGTTTACTAAGATCAAGAAAAAAGTTAGGAATTTTTGTTGCCCTTGGAAC

GAGGCTAATTGATTATATGCTAGTGCGGAGTGTAATGTTGATCTCATGGACAACGCGCTG

AAAATGTATGAGAATGACTTCAAGGATGGGCGATTCTTGTTTATTGAGTGTTGGAATGAA

CTAAAAACCCAACCTAAATGGCATGCATATTTGGATCACCTTGACAAGTCGAATAAAAGG

AAGCGAGATTATGCTGATGGTACCCCCCTTGATGACGAGGAGATCCCACGTCCAATCCGA

GTCAAGGCAGCTAAGGCGAAGCGTATAGGCAAAGGAAAAGGCAAGGTTCAAGATTGTACT

GCTGAGCTAGAACATGACACCCACAACTTTATGGAAGCACATGAAGGAGCCAAGGAGCAG

TAAAGTGAATTGTTGGAGACCCAGCGACCTGTTGCTAGTGATAATCTTGAAGCGAAGAAC

GTGGGTCGCCAGACCGCTATGATTGCAGCATATAGAGAGTTACTGAACAAAGACACAAGA

GATATGCCTGATGATGTGAGGTCTGAGCTTGTTGCAATGTTGAAATGCATCAGAGAAGAT

ATATTTACAAAAAACCAGTGAGGTATGTGTCATGAAGTTCTTTGCAGTACTAAAACATGC

ATATATCTACCTTGATTTTCAGCAGTAGTCAAAGTATTGTACTGTATTCATAGCTCTAGT
```

-continued
```
TGCAAACAACGATGCAACCAGTCCCTGTTTTGTGATAATTAATAGCATTCAGTCCAAATA
ATCATGCATATAGTCTCATATTTTGTGCTGATTAACTGCCATTAGTCTAAATAAGCATGC
ACTCAACCCAAATTTTCATGATTATTGTAGCTGGTCTAAATTAAATTGCAGTCAATTGCC
AACCCATATTAAATTTCCATGGTTGTTGCAGCTGGTCCTAATTAAAATGCAGTCATAGTC
CAGACATATTAAATTTTTGATGGTTATTGCAGCTGGTCCTAATTAAAATGCAGTCATAGT
CCAGGCATATTAAAATTTGTATGCTTATTACAGCTAGTCCTTTGCAGCATCTATATATTA
CCTCTCATAACTTGAAACTGCCAACCCAATCTATCCTCCTCCTGCTCCAACCATGTC
GGACTCATCCTCCTATTCATCCTCTAACTCAGATGACCTAGACCCATCTAAAGTTCTAGA
CAAGTACATTTCTGAGCAGAATGTACTAGACTCATTTGCTTCTCGAATCATAGAGAAGAT
GAAGGGTAGGTTAGGAGCTGGGCGTTCGAAGCGCCAAGGTGGAACAAGGAAGACAATTCA
TAGGGATCATGTAGATGCCCACAGCCGTTTGGTGGCTGATTATTTTCCAGAGCATCCATT
GTACCCAGAGTGGATGTTTCGCACAAGGTTCCGCATGCACAAGCCACTCTTTCTACGTAT
TGTTGAAGCCTTAGGTCAGTGGTCACCATACTTTACTCAAAGGGAAGATTGCTCTAGCCG
CACAAGTCTCTCTCGACCTCAAAAGTGCACAGCAGCACTTCGTATGTTAGCATATGGCAC
ACCTGCTGATGCACTAGATGAATATTTAAAAATTGGCAAGAGCACAGCCTTAGAATGCTT
AGAAATGTTTTCACAACGGCTGATTCACGTATTTGCTGGGACGTACTTGAGACGCCCCAC
AAGGGAGGATCTAGAGCATATATTACATGTTAACGAGTCTCGTCCGTTTCCGCCTATGCT
AGGTAGTATTGATTGTATCCACTGGAGGTGCGAAAGTTGTCTGACGGCTTGGAAGGGTCA
ATTCACCCGTGGTGATTACAAAGTCCCAACAATTATCCTTGAAGCAGTTGCTTCACACGA
CCTATGGATTTGGCATGCCTTCTTTGGTGTCGCTGGTTCTAACAACGACATGAACGTGCT
GAATCAGTCCCCTCTTTTCCTTGACACAGTGAGAGGTGAGGCTTCTCGGGTGCATTATTA
TGTGAACCGGCAAGAGTACAACCATGCCTATTACCTACCTGATGCTATATATGCAGAATG
GGCTGTATTCCACAAGACTATACCACTTCGACAAACTGAGAAGCATAAGTTATATGCTAC
ACATCAACAGGGGGCAAGGAAAGATGTGGAGCGGGCTTTCCCGGTATTGTAAGCTCGTTT
CAAGATCGTACGTCGTCCGGCAAAGAAATGGAAGAGAAAGAGTGTTGGAAATATCATGCT
AACTTGCGTGATTCTCCACAATATGATTGTTGAAGACGAGGGCGAGGATGCAATATGTGA
CCTAGACGTCAATAGAATTGCTAGGACATCAATAGTACTGCCTCCAGAAGTAACCAGTGC
TGGTAACCAATGTTTTCGTGATGTGCTAAGTAGGAAAGCTACTATTTGTCCTCGTTCAAT
GGATACCCAGCTTAAAACTGATTTAATTTAGCAGATTTGGAACCGGTTCAGGAATACGCA
GCGTACATAACGATGGTAGGGTAATTAGCATATAATTTCCCCCTTTTTTGTCATATATAG
AGCCTTTTAATTTAGCCTTCTATATGTTTTATTTCAGGAACAATTAAGCTTTGATGTCTA
CTGTGTTGCACCTCTGCAACAGACCTCTTACAGGTATATTTCCATCATATGGTATATTTA
TCGTGTGAGTACTTTCAGCTGTAATGAACATCGAAATTTTTGTGTACATGAACCGATTTT
GTTCCTCCATATGCTATATATGTTGTATACATGAAGTGGTACCTTCATCATTGATCTTTT
TTACATCTCAGTTCAAAAATATGATTCATGAATCCATGTAACTATAGTGTAGGGACTGTG
ACAATCTTTCAAGAAAATTTATTGGAATGAGACACACCTAATTTTATAGTTTTAGGAAAA
GTTTACTGTAATTGGCAGAAATTTGACCATCACTAAGTAGTTAGATTTCTGGGATTAATA
TTGCATTTCTACTGTGATTGTTCTGCTCATAACATAATTTATATTCTGCAACAAATCAAG
ATGGCTGATGATGGTCCATATCGAGATCAAGAACTATCTCAGTTTATATCTATGTTTTCG
TTAACTGTTATTTTGTTATCCCTAAAAAGTTGCCTTGTGTAGCTTATTATTGTCTAGTTT
TTGTGGTCCTTTTGTTTGATGGCATGTTGCCAGGAGATTTGTGAATCATCGTATCTGTTT
```

-continued

CACTGTTTGGATTATTAATCCTCTATTTAACTAGCTCTGATGTGATTGTGTATATGTGGT

GCAACAAAATGGCCACAAATATGGATGTCAGGACTGATCCCAACAACTGCTATTGGCATG

CATGCATTAAATAGTTCAATGTATTAATCTCTGACATTTTACAGCTAATCTATTGTAGTT

GGTAAGCTATAAGCTAGCTCTTCCTGAGTTGGACAGAAAATTGGAGATCCCAGTGGCCTC

TCTATTGACCTTGCTC

Deduced amino acid sequence of PONG_LIKE_1 ORF1 in Oryza sativa
(SEQ ID NOs: 15-16)
MGLGCQLQPINVENGNNGNATRTEKRLGWSTEEDLRLVSVLREYLFGSGIHNTCNLTIVK

YLEIVGQAWLNNSNDPIESNFKKNDKYWDVAAAYNSTTPSSRFSKIKKKVRNFCCPWKEA

NSLYASGECNVDLMDKALKMYENDFKDGRFLFIECWNELKTQPKWHAYLDQLDKSNKRKR

DYADATPLDDEEIPRPMGVKAAKAKRIGKGKGKVQDCTAELEDDTHKFMEAHEAAKEQ*S

ELLETQRRVASDNLEAKKVGRQTAMIAAYRELLNKDTRDMPDDVRSELVAMLKCMREDIF

TKNQ*

Deduced amino acid sequence of PONG_LIKE_1 ORF2 in Oryza sativa
(SEQ ID NOs: 17-21)
MSDSSSYSSSNSDDLDPSKVLDKYISEQNVLDSFASRIIEKMKGRLGAGRSKRQGGTRKT

IHRDHVDAHSRLVADYFAEHPLYPEWMFRTRFRMHKPLFLRIVEALGQWSPYFTQREDCS

SRTSLSPPQKCTAALRMLAYGTPADALDEYLKIGKSTALECLEMFSQGVIEVFGGTYLRR

PTREDVEHILHVNESRGFPGMLGSIDCMHWRWESCLRAWKGQFTRGDYKVPTIILEAVAS

HDLWIWHAFFGVAGSNNDINVLNQSPLFLDTVRGEASRVHYYVNGEEYNHGYYLADGIYP

EWAVFQKTIPLPQTEKHKLYATHQEGARKDVERAFGVL*ARFNIVRRPAKKWKRKSVGNI

MTCVILHNMIVEDEGEDAICDLDLNRIPRTSIVLPPEVTSGGNQCFRDVLSRKAATICAR

SMHTQLKTDLI*HIWNRFRNTQRT*PW*GN

Nucleotide sequence of PONG_LIKE_2 in AP003684 in Oryza sativa
(SEQ ID NO: 22)
GGGCAAGCGAAATAATAGAGTAAACATCTTACTATTAGTATCCTCCACATCATCTATAGA

TGCTTTAACAGACGACATTTAGAATAAGATAGTACATCCTGTCTCTAAGCCGTCTCTAGC

AAACCAAGCTGCATTTAATTCTCTAATTGTATCTTTCAAGTTATGTAGGATCAACTGTAA

ACATCACTTGAGTAGCCACTTATATGTCAACCATAGATGGAAGACTATGTTCAATCAATA

AAAAAATAAATCATGTGATTTATCACAAAGCAGATGGATTTATGAACAACAATGGTCTAA

TATTCCTAATTCATTCGAACTAATTCATTCGAACTAAAGAGTACAATAGTGATTCAGATT

GTTACTTCATCGAAAGAATATTCAGAGATTCACAAATAACTAATTCATACACCGACAAAA

TAACTTAGTCTGTTGCAATGATCCATAGATCAACATTCGACAAAAGAAATTAGGCCATTA

CAACGATCCATACTGCCAATAGATGGTAACAACACAAGTGTTCTTACATGACACCACCGA

ATTACTAAAATTACTTTATAACTAGATTATCTTTCTCAAGCAGAACCAAAACAAGCTGC

CACCCTTCCAAATTGAGCATCTTCACTACCTGTCATTAAAGCAACATTATTTCCATGGAA

TATAGGAGGCTGATCATTATAGAACAATTGTACCATATAATCTGGATGCCAAAACAACTG

GAAGGAAGTAGTACTACTATTTTAACTAGACTATTAAAGGACTTATTTGATTATGTTGTT

CTTTGGACTGTACAGTGCAAGTAGACATGTACATACCTCTCAAAACCATAGCAGAAAGCA

CCAAAAAGCTAGCACCAAAGTTTTCCATTGTCCCTGAAATAAATAAAATGATAAGT

GAATTAAGATGCTTGCAATTGTAATTGAAAATGTGAAAACAAGATGCTTAATGTCCTACC

ACAACTAAGTACGACGGGTATTGCTAAACTTTTGCCAAATATGTTCAACCAGATCTTTTT

TTAGTTGGGAATGTGGTGCACGAGCACGTATTGCAGCTTTCCTACGCAGCACCTGATCAA

-continued

```
AGCATGGATTGTGCCCAGTAGTTACTTCAGGAGGAAGAGCAACCGATCCTCCAGCGTCCA

CATTCACATGAATAGGAATTTTAAACCCCCCCTCTCTCATTTTCAACTATCATATTATCG

AGAATAATACAAGCTTTCATGATTCTCCCAACACTCTTCCGCTTCCACGACCGTGCTGGG

TGGCGCACAATATTGAAAGGGGACTACAGGACCCCAAATGCACACTCCACGTCTTTCCTT

GCCCCTTCTTGATACTGTGCATATAGCTTGTGCTTCTCTGTTTGTGGAGCAGCTATTGAC

TTCACAAAGGTAGCCCATTTTGGATATATTCCATCAGCAAGGTAGTATCCTCTGTTATAC

TCATTACCATTGACAGAAAACTTTACTCTAGGAGCTTCCCCTTTCAGCACATCAAGAAAT

AGTGGCGATTGGTTCAGCACATTGATGTCATTATTTGACCCCGTGACACCGAAGAAAGCA

TGCCATATGCGGAGGTCAGGAGTAGCAACCGCTTCGAGGATAATTGTTGGCACTCCATAG

TCACCGCGGGTAAACTGCCCTCTCCATGCTGTTGGGCATTTTTCCCACCTCCAATGCATG

GAATCAATACTGCGTAGCATCCCACGGAAGCCCCTAGAGTCATTAACTTGAAGTATACGC

TCCACATCCTCATATGTGGGACGTCGCAAATACTCTGAACCAAATACCTCAATCAGCCCT

CGTGCGCACATATCCAAGCACTGCAAGGACGTGCTCTTGCCAATCTTAAGGTACTCATCT

AGGCTATCAGCAGCGCTGCCATACGCTAGCATGGGCATTGCAGCTGTGCACTTCTGTAAA

GGTGAGAGCCCTTGGCGACCACTGCAATCTACCTTTAGTGTAAAGTAAGGAGACCACCTT

CCAAGGGCACTCACTATGCGAAGAAAAAGGCGTCTTCCCATACGAAATCTTGTACCGAAC

ATGCTCTCAGGGTAAAGACGGTGTTCACTAAAGTAGTCAGCTATGAGACGATCATGTGCT

GCTGTGTGATCCCTCTTCATTGTCTTCCTTGTCACACTCTTCCTTCTGATTTTTCGAATT

CTAAGCTTGGTCTTCATCTTTTCCATGACCCTTCTTGCAAAAGAATCTATGAGGTTCTGC

TCACAATCTATTGCTGTATAATTTTGGAAGGATCTAATTCACCAGAATCATCTGGAAGAC

ATGGTGGAGACAAGGAGTGCAAGGAATGGGAAAGAAGTGTTGAAAGGAATGGGAAAGAAG

TGTTGAAAGGAATGGCAGAGGGATGGATAGTTAGCACCATTAGACCAATATATATATATA

TGGGCCAACAGTACACTGTTCGGAATGCATACTAGCTAGTAGCATGTTTATTTGAATTAC

CCTTAATTAGATTATTCGGAATCCATACACAGAGCATGTTTATTTGGATTACTATTAATT

AGACTATTGGGAATGCATACACAAAGCATGTTTATTTGGATTACTATTAACTAGAGTATT

GGGAATTCAAGAGTGCATGTTTATCTGCACATTGTTGACTTGACTGCATCTTAATTTTGC

AACTGCTGACTTGACTACATGTTTTTCTGGAAATAATAGCTACATGCTGATTATATTACA

AGTTAGATTAGATCAATATTTGCAACTCTTTGAATTGTGCAAGAAACATATATATGTTTG

CAGGAAGTTCAATTGCAGCAAGTAAAAAAAAATACAACAAGCTTTAATTAGAGACTGGAA

AGTGAAGATACCTTAGTATTACGGAAACAACTTCTCCCTCATACACTTCAATGCCATCAA

ATGCTCGGATCTAACATCATCAGGAATATCTTTTGTATCTTGTAACATGAGAGACCGATA

TGTTTCCAACATAACACCCTCCTTGTGCTCCATGGCTGCAAGGTGCGCTAACTTTTTGA

TTCAAGGTTATCACTAGCAACACGCCTCTGAGTCTCTAGTAGTTCATCACGACCTTTATT

TGCCATCTCCTGAACTTCTTTAAGCTTGTGAATTTCATCATCAGTATCTGATAGATAAAC

CTTTGCGTTCCTTTTGCGTCTGCCTTTACCATTACGTTGCGCCTTAGCAGTTTTTGTTCC

TATTGGACGTTTAATATCTTGAGGACTGTTAGGAGTGGACATTTGCTCCATCACTTCGAC

TTAATCATCCATCTTTGGTTTGTTGGCTTCTCAAGTTCGTCCAAGTAAGAATGCCACTT

TGGTTGGTCACGAAGAATGTTCCAACAATGCAGAAATGAAAATGGCCCTTCCTTGTAATC

TGCTTGATATGCTGCTTCAGCCTTTTCCCTGAGTTGCATATCATTTGTCCACTAACATA

TATGGATTTAACCTCTTTATAAACACAACAGAAACGGCCAACATTTTTCTTAATTTTATG

AAAACGGTCTTTGATTTGTTTTTCTTGCCTTGTCCTGTTTTTGGGAGTGGTGCTATTATA
```

-continued

```
CTCAGCAGTAACATCTCCCCAATAACGATCATTTTTCTTAAAATTACCACTGATCGAATC
ATTCGAGTTGTTTAGCCAACCACTCACCTATAATCAAAACAAAACAGGATTAGTCCTATA
CTAGAAATAAAGTAACAGTCAATGAGAAAAGACGATTCATTGCCTACATCCTTATTTACT
TACTAGTCTTATGTCCTCCTCTGTTGACCATGTCAACCGCTTCTCAGTCCTAACAGTGTG
GGCTTCTTCATCACCACTATCAATGTTGACAGGTTGTTGTGCTCCTGGACGTAATTTTGA
ACATGCTGCTACTTGTTCAGCACGATAATAATTTGGAGGCAGAAAAGGTCGATGATTCTG
TAAAATTGATGGATCCTGAAAGTAACTTAAGAAACCACCAGGCGGATGAAAGTCCATACC
ACTGCAAGAAAAAGAGAGTGATCCAAAATTATTGCCAGATAACATCCTTAGCACTTTTTT
TCTCTTCATCTGTAAATGAGTACATTAAAAATTGACAAAGCACACCCTATGATACTAATA
ATTCTCATGCCATATAAAATTACTATTTTTGTGTTTGTAGATAAGTTGATTTCTCTGTTC
ACTACCTATGTAGTAAGAGTTGTTGATTATTCAAGAGTAAAGTCCATCACCCGTCCCTAA
ACTTGTACCGCTGTGTCATCCTAGTCCCTAAACTCGCAAATCGACCGTTCAGGTCCTCAA
ACTTGTTCCACTGTGTCATCCCGGTCCCTAAACTTGCAGATCACTCATTTAGGTCATCCA
ACTTGTTCAATTCTGTCACCCCGGTCCCTAAATTTGGATTTGAATATCATCTGGGTCAAA
TAAAACGGTCTAAAGACTTTATATTTAAAAATAATTCATAACTTTTTCATGTGAATTATA
ATGAAGAGAAACTTTATATCAAACTTGTAGCCCTCGACGTCATCTACAACTTTGTAGTTG
ATTTTTTTAATTTAAGTCATTTTTTGTCCCAAAATGTAATTTTAAAATTAAAATTTCAA
AATCTATAAACATGCAACAATATTTTGGGACCATAAACAGTTTTAATTCAAAAACCTTTC
AACTACAAAGTTGTAGCTCGTGTCGAGGGCTAGAATTTTGATATAAAGTTTGTCTTCATT
AAAGTTGACATGAAAAAGTTATGAATTATTTTTATATAAAGTTTTAGACCGTCCTGT
TTAGAGACCGGGGTGACACAACTGAACAAGTTGGAGGACCTAAACGAGTGATCTGCAACT
TTAAGGACCGGGATGACACAGTCGAACAAGTTTGAGGACCTAAACGGTCGATTTATGAGT
TTAGGGACCAGGATGAGACAGCGGTACAAGTTTAGGGACCGGTGATGGAATTTACTCATT
ATTCAAAGTGTATGTGTAGATTAGTACAAAAAATTTGGCCATGCACTGACCTATGTACAC
TAGTTATTGCTATAAAATAAATCTATATGTATCTGTAGCCCTTGCTTACTATCAAGTTAT
TCTCTTGCCATAAAATTTTTTCCCTTTCCGAATATAGCAAGACTTAAGTTTAGTATGACA
AACATATGTACACGTTGATTCTTCAGATATTACCACGGGATATGCTAATCTGCTAGCAGC
AGATCAGATCGTGACCGGAAAACTAGAATACGGCAAGAATAAAACTTAGTTAGTCAACAC
CATTAATTTTGTAATCAAGATGGAGGTACACGGAACTTCCGGAGCAAATCAATCCAAAAC
CATTCAATATCAAAAGTACATACCGTTCTTGCAGATCTGACAAATCAATGGCACTACGAT
CCAATCCTTGCTTCATTTGGGCCATGGGAAAAGCAGAAGCAGCGGCGCCGTACGCGTAGA
GCAAAGGGTGCGGCGGCTGCGGTGGCGCCGGACCTTGCCAGGCACCACTGCCTAAGGATC
CCGGCAACATCATGCCAGATGCGAAGGATCCCGGCGAGGCTTGCGACGCAGATGCCCCCG
GCGGCGCCGCAACCTGCCGTTTCGAGGGACCCATTGTTTCAGCAGATTGAGTTGAGGGAT
TACTAACTAGATGGGGTATTTCAGTAGGAATTTGAGGCTTCCACTAAGTAATTTGGCGCG
TCAAGTGCGATTTTTTTCCCGCGGATGGGGATTTACCGCCAAATATACAGAGAAGGGAT
GAGCCATCGAGCATGGGATGCAAAAGGCCAAGAAAGCGCGTTATTGGTCGACGGCATCGG
CTCCTGCATGGTCTCCACGCCTACTCCATCCATCTTGTTGCTCGTGCCGAGCTGTCGATT
AAACATGCGCCCGCTTTCTTCTCTCTGTTCCTTTCTCTGTCCTCCAGCTTCTCTTCCTTT
```

-continued

```
CTCTGTCCTCCAGCTCAGATTGTGATGACCTGGACGGGCTAATAGTAGGTTCATTAGTGC

TTATTGTACTTGCCC
```

Deduced amino acid sequence of PONG_LIKE_2 ORF1 in *Oryza sativa*
(SEQ ID NOs: 23-24)
```
MKRKKVLRMLSGNNFGSLSFSCSGMDFHPPGGFLSYFQDPSILQNHRPFVPPNYYPAEQV

APCSKLRPGAQQPVNIDSGDEEAHTVRTEKRLTWSTEEDIRLVSAWLNNSNDSISGNFKK

NDRYWGDVTAEYNSTTPKNRTRQEKQIKDRFHKIKKNVGRFCCVYKEVKSIYVSGQNDMQ

LREKAEAAYQADYKEGPFSFLHCWNILRDQPKWHSYLEELEKPNKPKMDD*VEVMEQMST

PNSPEDIKRPIGTKTAKAQRNGKGRRKRKAKVYLSDTDDEIDKLKEVQEMANKGRDEELE

TQRRVASDNLESKKLAHLAAMEHKEAVMLETYRSLMLQDTKDIPDDVRSEHLMALKCMRE

KLFP*
```

Deduced amino acid sequence of PONG_LIKE_2 ORF2 in *Oryza sativa*
(SEQ ID NOs: 25-26)
```
MSPDDSGELDPSKIIDQYIVEQNLIDSFARRVMEKEKTKLRIGKIRRKSVTRKTIKRDHT

AAHHRLIADYFSEDPLYPESMFRTRFRMGRPLFLRIVSALGRWSPYFTLKVDCSGRQGLS

PLQKCTAAMRMLAYGSPADSLDEYLKIGKSTSLQCLDMCARGVIEVFGSEYLRRPTYEDV

ERILQVNESRGFPGMLGSIDCMHWRWEKCPTAWRGQFTRGDYGVPTIILEAVATRDLRIW

HAFFGVTGSNNDINVLNQSPLFLDVLKGEAPRVKFSVNGNEYNTGYYLADGIYPKWATFV

KSIAAPQTEKHKLYAQYQEGARKDVECAFGVL*SRFNIVRHPARSWKRKSVGRIMKACII

LHNMIVENERAKGGFKIPIDLNVDPGASVALPPEVTTGHNPCFDQVLRRKAAIRARAPHS

QLKKDLVEHIWQKFSNTRRT*
```

Nucleotide sequence of PONG_LIKE_3 in AC073393 in *Oryza sativa*
(SEQ ID NO: 27)
```
GGCCTCCTTCAAAGGTTGAGACAACTGTTAGCTCATAGATCCTACACATCATCTAAGAGA

TAGAACAAGAGATAGTTTCTCTAATGAACTGTCTGTAAGGTTATCTCTTCTTGCTTTTAT

GGCAGCATGGGTACTAAATGACATGGTGATAAACTACACAATATGTCTATGGTCCTTCAT

GTGATGCTATTCAAAAGATGTGTCGATTAAAAATGAACATCTCATCATAGTGTGAATATA

GATAAATAGCACAACATCGACTTAGAGTATATTTAGCATTAAGTGCAATTCTTCCAACTC

ACGGTCCACTACAGCAACCAGATAACATCATAGCCATATCATGGCACTTTAGTACAATCC

GGAAAAGAGCAATGAAGGGATAAAAAAAAAGACTGCATCACGTCACACAAGTGATAGAAG

AGTTCGACAACCACCAAAAGCTGGACAGGAACCACAAGTGCTTATCGCATTCCTTGAACA

AGATCAGCAAAAGCTGGACCGCAGCCACAAAAACAAGTGAAAGACATCGAATCTGTTCGC

CCCTGGTAGACAGAAAAACATGTACAGTAAGTGAAAGTGATGAATACAGTCAGTCTAAAA

TAAAATTACAATGAAATTGTACACTAGACCTTACATTATACTGAAATAACAGTGACTAAT

TATTTTGCCTAGTTTGAAACCGTTGCCAAATATGCTCAATTAAGTCATTTTTAAGCTGGC

TATGGATTGGTTTGGCTCGGATAGAACCATTTCTTTGCCGCACATCGCTGAAGCTTCGGT

GATCATTACTCCCTGCATGAACTTCTGGTGGAAGAACAATTGATCTTCCTGGGGCAGCAT

TCAAGTCAATAGGATCTTCTGCCATTTGTCCCTCATCTTCCACTATCATGTTGTGGAGAA

TTACACAAGCTTGCATGATTTTTCGAAGAACTTTTTGGCTCCATGATCGTGCTGGACGAT

GCACGATGTTGAAGCGAGCTTGCAACACCCCAAAAGCACGCTCAATATCTTTCCGTTTCC

CTTCTTGTTCCCTTGCAAATAGCTTGTGCTTGTCTAGTTAAGGAGATGTTATACACTTTA

CAAAGGCTGCCCATTCGGGATAAATTCCATCACCAAGATAATATCCCGTGTTGTATTGTG

TCCCATTGACAGTAAATTCGATTTGGGGAGCTTCACATTTTATTGCTTCAATAAACAGAG
```

-continued

```
GGGACTGATTGAGCACATTAATGTCATTCTTGGACCCAGGAATACCAAAGAATGGATGCC

AAATATGAAGGTCATATGAAGCTACAGCCTCAAGGATAATAGTTGGATACTTTTGGTCAC

CTCGGGTATATTGTCCCTTCCATGCGGTTGGGCAATTTTTCCATCGCCACTCCATGCAGT

CAATGCTTCCCAACATCCGAGGGAATCCACGAGACTCTCCAACTTGGAGCAAACGCTCGA

GATCCTCAGCCGTGGGGCGACCCACGTACCTACTAGTAAATACGTCGACGACACCTTGCA

CAAAATTTTCTAAGCACTGTAGAGCAGTACTCTGGGGAACCTTCAAGTACTCATCAAGAG

TGTCAGCAGCAGTGCCATATGCAAGCATACGGATCGCTGCAGTGCACTTCTCCAATGGTG

AGTGCCCAAGGCGTCCAGTACAATTTATTCTATGTGTAAAATAGGAAGACCACTTGCCTA

GTTCATCCACAATGTGTAGGAACACATGCCTTCTCATCCGGAACCTTCTACGGAATGTTC

CAGCAGAGTAGAGAGGATCTTTAGCAAAATAATCAGCAAATAGTTGATCATGGGTCCTT

CATGGTTCCTATTGATGTACTTCCTTGGACCACTTGTACGCCTAGATGTACGTCCTTCCA

GTCTGGCCTTAATCCTTTTGTGGATCCGCCCGGCAAAAGAGTTAAGGACACTATGCTCTG

CCATGAAGATATCTGTAGTGTAAACCTCGGCTGGGTCTATGGAATCGTCAGACTCATCCG

ACATGTTTTACTGGATGGAAGGGAACAGATGAGGCAGTGTTGGACTGGATGGAAGGAACA

GATGAGGAAGAATAGAATAGGAAGAATAGTACTGGATACAACGAACAGAGGAGGATAGTG

CTGGATTGTTTTCCTAGAGTGAATATAACAGAGCAATATATAGTCACATGGTATAGATTA

ATTTGTGGTACATTGACTAAGAATACAGATTATATTGTATGGTTATTTGTGGTACATTAA

CTAAGAATACAGATTACAATGTATGGTTGTTTGTGGTACATTAACTAAGAATACAGATTA

CAATGCATGGTTATTTGTGGTACATTGACTAATGATACAGATTACAATGCATGGTTATTT

GTGATATATTGACTAACAATACATATTACAATATATGGTCATTTGTGGAACATTGACTAA

AAATAAAGTGCATGGTGATTGACAGAAAATACCTTAGATTATATCACCAAGCAGTTTCTC

CCTCAACATCTTGAGACCGATCACGTGCTCAGCTTTCATCTCATCAGTCATTTGACTAGT

GTCCATGCTCATCATTTTTTCATATGATTCTGTCATGACAGCCTCTCTCCTAAGCCTTGC

TACTTCAACTTTTGCATCTGAAATACGGTGTTGAGTGCCTAAAAACTCTTCATGTCCTTT

GCTAGCTGCAGCTTGAACATCCATGTACTTCTTCATATCTTCACGTAAACTGTCATGATC

ATCCTTGCCTTTGCCTTTGCCTTTCCCATTGCGTTGTTTCTTAGCTTGATTCCTCCCTAT

TGGACGCTCCTTTTCTCCGATATCCTTTTGTGATAGTGTGTCACTTGCATCATCGAAGCT

CCGCTTGTGTCCCTTTTCAAGCTCCTCCAAAACAGCATGCCAGTTGGGTTCATCACGAAG

AACCTTCGAACAGTGCAAAACTGTGAATGCACCTTCGTTAGGATAGTCATCCAGATAAAA

CTGATTAGCAAACTCTCTCAACTGATCATCTGAATATCCACTAGTATAAACTAATGCAGC

CTTCTTCCAGGAGGCGCAGAAAAATCCCACCCATCTCTTAATCCTTTGCCATCGATCTTT

GAGATGCTTTACTTCCCTTTTCCGGTTAATAGGTGTAGTGCTGTTGTATAATTCAACTAC

ATCTCCCCAGTAGCTCTCATTCTTCTTGCCATTTCCATTGATCGGATCATTAGAGTGGTA

CAGCCATGCACTCACCTACATTTAGCATTATGTCTTAGTAAAGTTTCAGAATGATGGTAC

AAATCCCTCCAAGTTGTCTAAAATTTTACTCACCAACCGCAAGTCCTCATCTGATGCCCA

TGTAAGACGCTTAGCAGTCCTAACATCGTCACCATCATCTAAGTTGATGACACCTTTGGC

TTTTGACCTTGATCTAGCATGCGTACTGCCTGAATTAGTTGTTGGTGCCATAGGTCGCAT

AGGTGGCCATGTTGCTAGGAACAAAACATGAGGTGGGACTAATGGCTGTTCACCAGTTTG

TAACATGCTTAGGAAACCACCAGGTGGATGTATATCCATACCACTGAAATATCAGGAGCC

AAAATCATGACTATGAGCGAGGAAGAAACAACACATTTCCTATCTCTGCTAAAACATTAT

TAATTCTACAATCTAAATAGTCTCAACAAAAAGGAATTTGCTTGTTTCCTGCAGAAACAA
```

```
CACACAAGCAAATTGGTTTCTTACCAATGTGAGGATACAGGCCCAAAGGAGTTCGTGTGT

GGCAAAGATCCGTTCCACCACGCTGCACATGGTTGAGAGCATCATCAGCTTATTGTTCTA

CTCCAACATCCAGGAAGGAAGCAAGGCAGAGCCACTGCAATAAGCATGAGGTTTGAATGT

ACGGTACAGTACCTGGTTCGCCTCCTAGAGGAGGAGCGATTGCAAAACTGGCCTGAAAGA

AGGCACACGAGGCAGCGTCGAAGCACCCAGAGGCAGTCGCAGATCCGGATGGCGGCGATG

ATGGCGGCCGCGGCGGCCGCGAAGCTACTTGTCGTTTCGACCGCCGGCTCATCCTCCTGT

ACAGCTCCTCGTCGTTGGCAAGAGGAGTGGATTCATCGTTGGGCTCGTGGAAACGGATAC

GTCGACCCCGACGAGGAAGATTTCACACACTCGAGAAGAAAAGAGGAGGGAGGGTGCAAG

GGAAGGATTGGCGCGCGGGTGGGTGGAGCATTTGCGCGGGGGAGAGCAAATTGCCGCGCC

AGGGGGTGGGGGAGCGAATTGCAGCGCGCGGGATCGGCGGGAACGGCGTCCAGCGCGCG

GGGGTCGCCCGGACGTCCCCCGGGGCGATTTGGCCGAAGGGAGCAGGCGATCTGATTTTG

AGGGTGGAGAGTCGACTGCTGTCTCTTGCGCAGGCTCATACGGCATCGGTAACTGAGCGA

GATAGGCGTGGGAATAGGAGATAGATGGATTGATTTTTTGTCTTCTCTTTCCTGCACATA

GGATACATGATGATGTGCACATCTTATGAGATAGCTTACATGGCACCATTGGAGGAGGCC
```

Deduced amino acid sequence of PONG_LIKE_3 ORF1 in *Oryza sativa*
(SEQ ID NO: 28)
```
MDIHPPGGFLSMLQTGQQPLVPPHVLFLATWPPMPPMAPTTNSGTTHARSRSKAKPVINL

DDGDDVRTAKRLTWASDEDLRLVSAWLYHSNDPINGNGKKNESYWGDVVELYNSTTPINR

KREVKHLKDRWQRIKRWVGFFCASWKKAALVYTSGYSDDQLRDFANQFYVDDYPNEGPFT

VLHCWKVLRDEPKWHAVLEELEKPHKRSLDDGSDTLSQKDIGEKERPIGRNEAKKQRNGK

GKGKGKDDDDSLREDMKKYMDVQAAASKRHEEFLGTQHRISDAKVEVARLRREAVLTESY

QKMMSMDTSQMTDEMKAEHVMGLKMLREKLLGDII*
```

Deduced amino acid sequence of PONG_LIKE_3 ORF2 in *Oryza sativa*
(SEQ ID NOs: 29-30)
```
MSDESDDSIDPAEVYTTDMFMAEHSVLNSFAGRIDKRIKARLEGGTSRRTSGPRKYINRN

HEGAHDQLFADYFAKDPLYSAATFRRRFRMRRHVFLHIVDELGKWSSYFTHRINCTGRLG

HSPLQKCTAAIRMLAYGTAADTLDEYLKVPQSTALECLENFVEGVVEVFSSRYLRRPTAE

DLERLLQVGESRGFPRMLGSIDCMHWRWKNCPTAWKGQYTRGDQKYPTIILEAVASYDLH

IWHAFFGIPGSNNDINVLNQSPLFIEAIKCEAPQIQFTVNGTQYNTGYYLADGIYPEWAA

FVKSIRSP*LDKHKLFAREQEGKRKDIERAFGVLQARFNIVHRPARSWSQKVLRKIMQAC

VILHNMIVEDEGEMAEDPIDLNAAPGTSIVLPPEVHAGSNDHPSFSDVRQRNASIRAKPI

HSQLKNDLIEHIWQRFQTRQNN*
```

Nucleotide sequence of PONG_LIKE_4 in AP005053 in *Oryza sativa*
(SEQ ID NO: 31)
```
GGGCACTGGCAACCCTCCAGCTAGTGTCTAIAGAATTTATTAGGCTGCCACATAAGCAAA

AATATGATCTGTGTTCGCGGCTGTAAAATGTCGATTCTATACCGCCAACATGTACATAAA

GTTCGGATAATAAAACATCTAACATAGTGATAGGTGCTTAATCTCACATATTCCATAAGT

GTTCGTATATATTTGTATGCAGATGATAAACCCCGATGTTGGGAGGAAAATCAGAGTATA

GTGAGAGAAATGTGTATCCATATAAGGAGGGGTTGTGAACTTCATCAAACATCAGTGAA

TTAACCCAAAACTGCGAGAAATGGACAGAAGAGCCGAGGGAGTCCACAGATCGAAGGC

CAGGCTAGGAGGGCCGAGCCCACGTTCACCCGAACCCCTCTGATCACTGTTGATCCTTCC

GTTTGGCTTGGACGCTCGAGATCCTCTCCCAATGATGGTTGCGAGGCAATTGGGACATTT

CCCCTTACAATCGTCATACCTGTCCTATAAATAGACCTCACTTCATTCACTCTCACACAC
```

-continued

```
ACTTCCAAGCTTGAGCTGAATTATAAGAGGCTCTATTGTACTATATTGTATACTAGAATA
GAAAGAGAGTAGACTAGAAGAAGTCGGAAGAATTCCGGAGTTGTCGGTAATCTTCTCCTA
TTTTTCTTATTCTGTTTATAACTTTGAATTTAATATAATATTCTTCTCGAGTAATTTAGA
TTTATCTTGTGAGAATTATCTCTTGGTTAGTTCCTAAATAGCATACGTGATTATTGTTCA
CTATAATTAAGTGAAATATAGTGATTGCTTTGGTGAGTTATAAACACTAAAGTAGATAGT
AATTGCTTAGACGTGGTGTTTAGGTAATTGTTATCCACTAATTGATGTGTATCCCGCAGT
ACGTTTGAGGTGGGTGTAGAGGTGGTGATAGCCCTCAAGATCACTTGTAAGTCCTCCCTG
TCCGGGTAGATAGTAGAGCGACATCTGAGAACAGCGGGTTGCCAGTGCCTGAAGTATTGC
GTTAGGATTAAAATTAAGCTTTCCCTAGAGACTGTTTCTCACTAATAAATCCTCTCTATG
CTCGCCTATCATTTGCTTGGTGTCCTTGGATGAATCGGAGGAAGATCTGATCACACACGT
TCCCTTCGAATCGATACCCTTGGAATACTCCGTAAGGGAAACTGCTACATCGGTATATCT
GTGCACTTGCGGATTTTATCTGTGACCGTAAGAAATACCAAAAATCTCGCAAAGAAATTA
AAGAAGGGAGAGAAGAAAAAAGAGAGAAACCGTGTCTCATGCACGAGACGGGGTTGGGCG
CAAGCACCAAGACTAGGAAACGAGAGAAACTACCGTTGGGGGCAACTCATCGTTTCTTCC
GTCCGGATTTTCCTCAAGCTCCCGATCTGCTGCACCCGCCTCCATCCCACCGCCATGCCT
ACCACCATCCCAGCCTAAATCGTCACGATTTTTTGGCGTGTCCCCAATCGTCTTCGCGCC
AACAGCAACTCCTGCTTCCCTCTATCCATCTTGTTGCCTCCTTTTTTCCCCAATCACTTG
TCTTCTGCAATCTCTCTCGTGATACCTAGAATCAGCCAAAATCATCCCCAATCACTGATC
CCTGAGAAAGTAGTTCTCCCAAGCCATGTGCAAGGATGAATCCGACGGAATCGAAGAAGC
GTCGATCCAAATGCAATCAGCCTGCCGGTGAACCGACCGCCCTTGATCCACATGCCGCTA
CTGTTGTGGGAGCCGATGGTGCTCCAGATGCTACTGCTCTTCCTTGTGGTGCTCTACGAG
CTAGTGCTCCAGGCGCTGGCTTTCCTACCGCACGTGCTCATGCCCCCACTCCATGGTGGC
AAGAATCATCTCCTGATAGCTCCCAATGGTATGGTCCAAATTTTTGGGTGCAAAGATTTA
GGTTGATCAATGTTATTGGTGAATTAATGGGTTATATTAGACTGACAACTTTTTCCTTCA
AAGAATTGCTAATATATTGTTGTATAGCTGGTACTTTTTTGCTTCGAAGAATTTTTCGCT
AGGCTTGGTGGCAAGATGTATAGCTGGTACTGCTAATTACTTGTATTCACCTGATTAATC
TTAGTGAAGCTCATATATGCTAGTTTATGCGGACTGATTTTTTTCTGAAATATATTGCGC
TTGTATTTCACCACTTCTGTTCTTGTCATAGATATCATAATTTTTTATTGTTTTCTTTT
TCAGGATGTATCCACCAGGTGGTTTCCTGAATTATTTACAGAATAATAAGATCTCTCCAT
TTAGCCACACACATGCATTTGTGAACTATCATAATGCAAGTAAGCTTCCAGAAAATTTCC
ACTTTGTTGCTGCACCAATTACTTATTCTACAATGTTCTAAAGCGATACCGTCACCAACT
AGGACGTGTGCTGCAGCACAAATAGGTTCACAAGATAAAGAAACAATTGATATTGAGGAC
GATGACACCATTTAGCCTTTCCGATGCTAGGTCCGAGAAGCGATTGAATTGGTCAAATGA
AGAAGACATTAGATTGGTATGTTAATTTTCTTTGTTTCTTTTTAAAGATTTGAGTCTGTA
TGCTTTTAATTTTATTTGCACTTCATTAAACCTACCGTTTATTCTTGTCCTAATTGTAGG
CTAGTGCTTGGCTGCACAATTGATTTAACTGGATCGATGGAAATGATAAGAAGTCAAATC
AATATTGGTTAGATGTTACTGCTACATACAACAACACCAGTAAGAGTAACCGTATGACAA
ATTGTAATCAGTTGAACCAACGTTGAGACCGCATTAAGAAACCAGTCTCGGAATTCAACG
GTTTTTATGCAAGAATCACTAAAATACATCAAAGTGGTATGAGTGAAGACCAAAAGATGG
ACCAAGCATTCCAGCTATATGCCTCTCAACATAATGACAAGCGTTTCAGAATGGTGCATG
TAGGGAGGATATTACGACATGAGAAAAAGTGGTCTACATATTTGAAGAAAATTAAGAAGG
```

-continued

```
AAAAGGACAACAGTGTAAGTCCTAACCGAACTCATGTTGTGAATGTCAAAGATCCTCCAA

AAGAACGTCCTATTGGCCATAAGAACGCCAAAGATGAATGCAGTCGAAAACGTCTGACAT

CAGACCCTATTTCTGTTATTGACCACAAACTAGATAAATTCATTGAACCAAGCAGCAATG

CTGAGAAGATGGGAGAGGTACAACAAAGTTTGGCAAATAAGAAGCTAGAAGTAGCCAACC

TTAATCATAAAGCAGCTCAGGAACAAACAAAGGGTAAAATGATTGACCTTTACAAAGACT

TACTGCTAGCTCCCACAACTGATCTTAGTCAAGAAGCTTTGCCTGAGAGATCGAAAGCAT

TGGAGTGTATGAGATTCGGTTTGTTTGCTAAAGATAATTGACGTATGTTTTTAATATATT

GTTGCTAAACAAATTGTGTTGTGACAGTACCATTCAAATCTGAACAAGTGACAATTTTGT

CAATTGTGTGAACTCATTTTATTTTTCTAGTGCTTGTTTGAACATAATTAATTATGTGAA

CTCATTATTTTATACTGCATGTTGAACACAATTAATTTTGTGAACCCATTTTCTTTTTAT

ACTACAATTGAATACTATCAATTGTGTGAATCCATCCTGTTTTTATACTGCAAGTGACCA

CTATATATTGTGTGAACTGATTTTATTTTTCTAGTGCTTGTTTGAACACAATTAGTTATG

TGAACTCATTTTTTATACTGCAAGTGAACACCATTAATTGTGTGAACCTATTTGACTACC

CAAACATATTTATGTGTGTGTCTATATATATATATATATATATATATATATATATATATA

TATATATATATATATATATATATATATATATATATATATCCTCTAGCTCACACATTCTCC

CCCTCCCCTGCCTTCCACATTCTTTCTTCCCTCTTTACTCTTCCATCTTCTCTCATCCTT

AACACCATGTCGAACCAATCTGATGGTGATTCGGCTGCGCATGATGATTCTCTTGATGAG

GTGAGTAGCATAGATCCAATGGATCTGTACCCATTGGATGATATTAGGAGCATACTGGGT

GATCTTGCTAATCATGTAGTAGCCGAATTGAAGCCGAAGTTGAAGCTCTACAAGATATGA

GACCTACTATGCAGAGTGGTCCAAGGAGGTATGTTTAGGCCTTATGAAGAATCTTAAGG

GCTATTGAAAGATTACTTTGTACAGAATCCAGTCTATAATGATACAACCTTTTAGAGAAG

ATTCAGGATGAGAAAGCACCTCTTCTTACACATTGTTGAAGCCCTAGGGCAGTGGGATAA

ATATTTCACACTCAGAATCGATGCTCTTAACCGCCCAGGGTTATCTCCACTTAAGAAATC

TACATCGGCTATTCGCCAATTGGGAAATGGTAGCCCTGTAGATCAGCTTGATGAGTATCT

AAAGATTGGAGATAGTACTACAATGGAGTGCTTGAAGATCTGTGTGAAGGGTGTGATTGA

TGTATTCGGTGCAGAGTATTTGCGACGCCCCACGGTGCAAGATGTTGAACGCTTAGTGCA

GATTGATGAGCGCCGTGGTTTCCCTGGCATGTTAGGGAGCATTGACTGCATGCACTGACA

TTGGGAGAAATGCCCTCTTGCATGGTAGGGAATCTATACTCGTGGTGATCAACCTGTTCC

TATCGTCATTCTAGAAGCAGTACCTTCACATGATCGTTGGATATGGCATGCCTTCTTTGG

TCTTGCTGGATCCAACAATGATACTAACATGCTTAATCAATCACCATTGTTCATCCAGCA

ACTGAGAGGGAGGGTCCTCAAGTCTACTGCCATGTCAATCGAAGGCTATACAACAGAGG

TTACTAGCTTGCAAATGGCATATACCCATAATGGGTTGTCTTTGTTAAGTCAATACATCA

TCCACAATCTGAAAAGCGCAAGTTCTTTGCAAAACATGAAGAAGGGAAAAGGAAGGATGT

TGAATGTGCTTTTGGTATTTTGCAATCTCGCTTTGGTATTTTGAAACGACCTGCACATCT

ATATGATCAAGGTCATCTTGAGAATATCATGCTAGCTTGTATTATCCTTCACAACATGGT

AATCGAAGATGAGAAAGACATCGAGTAGCTTCCTCTTGATTTGAATGAGACATCAAGCAC

ATCAACTGTATTAGAAGCTACAATCTCGCATGGACCTAACCTAGAGATGGAAGAACTGAT

ACAAAGAAATGTTATTATTCATGATCGTACTACTCATAACCTACTTCAATCAGACTTGAT

TGAGCATATCTACCAAAACTTTAGGAATTCAAACTAATTAGGTGATTGTTAATCATTTAA

AGTGTAATTTACAATTTGTGTGTTGCCAATAACTAGTATGTTTCATTTTAAGTTGCAATC
```

```
-continued
TCTGTTACATTTTAGCCTAGCAGTACCAGTTTAGCTAAATATCTTATCTCTTATTTTCT

TGCTCTAAAGCTTCTGAATTATTTTGATATTGATTTGCCAACTATTTTCTTTTTTGTAGA

TCAAGTCCTGCTATTTTGGTGCTGCTGTGCTGCTGCAGGAAATGCTATGGATCAAGTTTG

GATGCTGTCCAAGCGTGTGGCAGACTTGTGGTTACATATGTTTGTTTGCTTTGCTGTTGC

AGTGCACCTAGAAGAACTGCTCATGTCATCAGAGACTAATTTGAGTCCAACTATTTCGGC

TACCAGTTTGCGTCCTACCATTTTGGCTACCTATATGTTTTTTTCCTTTTTATTGTACTG

AGATGGATGAACTTGAAAATTTGCTACTTCTTTATGCTCATATATGCACTGATATCTGCT

AGTTTCTACTCATATAATGTGATTTGCACTAATATATGTTCATGTTTTGATATTTCGCAC

TACAGTATTATGTAGATTGATATTCAAATTTGGATGTATCTATTCATGCGTCTCACATGG

ATGTATGTATTGATGCGTGTCACAGTTGATCCTTCGTTTACATCACATGCAAATAGTTAT

TAAATTTTCTTCTCTTAAGAAACTGCTATAGACAGTGTGCATTGGGGAGGTAGTGTCTAC

AAATACATTATTATTGTTTCTCTTCTTTTAGACACTACCTATAGACACCGTTGTTGGGA

GTGCCA

Deduced amino acid sequence of PONG_LIKE_4 ORF1 in Oryza sativa
(SEQ ID NOs: 32-36)
MLVYGD*FFSEIYCACISPLLFLS*ISNFFIVFFFRMYPPGGFLNYLQNNKISPFSQTHP

FVNYHNASKLPENFHFVGHQLVILQCSKAIPSPTRRCAAAQIGSQDKETIDIEDDDTI*P

SDARSEKRLNWSNEEDIRLASAWLHNSFNSIDGNDKKSNQYWLDVTATYNNTTKSNRMRN

CNQLKQR*ERIKKPVSEFNGFYARITKIHQSGNSEDQKMDQAFQLYASEHNDKRFTMVHV

GRILRHEKKWSTYLKKIKKEKDKSVTPNPTHVVNVKDAPKQRPIGHKKAKDECSGKRLTS

DAISVIDHKLDKFIEASSNAEKMGEVQQSLANKKLEVANLNHKAAQEQTKGKMIDLYKDL

LLAPTSDLSQEALAERSKALECMRLALFAKDN*

Deduced amino acid sequence of PONG_LIKE_4 ORF2 in Oryza sativa
(SEQ ID NOs: 37-46)
MSNQSDGDSPAHDDSLDEVSSIDPMDLYPLDHIRSILGDL*SCSSRIEAEVEALQDMRPT

MQSGPRRYICFRPYEES*GLLKDYFVQNPVYNDTTF*RRFRMRKHLFLHIVEALGQWDKY

FTLRMDALNRPGLSPLKKCTSAIRQLGNGSPVDQLDEYLKIGDSTTMECLKMCVKGVIDV

FGAEYLRRPTVQDVERLVQIDERRGFPGMLGSIDCMH*HWEKCPVAW*GMYTRGDQGVPM

VILEAVASHDRWIWHAFFGVAGSNNDTNMLNQSPLFIQQLRGEGPQV*CHVNGRLYNTGY

YLANGIYP*WVVFVKSIHHPQSEKRKLFAKHQEGKRKDVECAFGILQSRFGILKRPAHLY

DQGDLENIMLACIILHNMVIEDEKDIE*LPLDLNETSSTSTVLEATISHGPNLEMEEVIQ

RNVIIHDRTTHKLLQSDLIEHI*QNFRNSN*

Nucleotide sequence of PONG_LIKE_5a in AP004794 in Oryza sativa
(SEQ ID NO: 47)
GGGCATCCACAATCTACAGTCAAAGTAACCTTACACATTAAATACTGCTACAGTACAACC

CATTTAGCATTGTCGAGTCAGACCACAACTCCCATCCAACCAAAGTACACCTTAAGCTTA

AGGTGTACCAACAAAGCTATAAAATACAATACTTTTACTGTTTTTCTCTGCACACCAATA

AAATATACATGTCAGTTACTAAACATAGTAACCAGTACTACTAGCCGTTCCTCCTATTCC

ATTTGACTTGCTCATTTCGTCCCCTAGCCGTTCTCTTCCTCCACCATTCTTCTGCTGCCT

ACAAAAGGAGGAACAAGTGAGATGAACAACAATTTTTGATCTATTCAGTTTTCCCACATA

CTAAATGGAGCCTTTCAAAGGAAACTTCTGAAACGTCGTCAACCAAGCTTCCTCAAGCCA

AGCAACAAATAGTGAGGCCCAAAACTCCCTTTCTACCCAATTTCCCACAAGTTATCCCCA

AAACTTCAGACCTAGTTTTGTGCAAAATTTCCATCCTTTTGGTCCTCCAAGCAACTACCA

GCGATATCGACACCCTCCAATCTTTCAAGGTGCTCACCAACAAGAATATTATGGGCAACC
```

-continued

```
TACTCCAGGAAGCTTGGAAGGTTTTCAACTTCAAGAAAATCTGGTGCACTCATCTAACCA

AGCATTTGGATTTGCAGCCAATAGATCACAGTTTGGTATGCAATATAGTACTTCAATTAG

GGCTACAGCCAACACTTCTTCTCATGGATCAGCTTCTCCATGTCATACAAGACATAATGA

GAAAGAAGTAGTTGAGGTTGAACAGGCAAGTGATAGCAGTGAAGAAGGAAGGAGAGGGAC

ACGCATCAATTGGACTGTAGATGACAATATAGGACTAATGAGTTCTTGGTTGAACAATTC

AGTTGATCCCATCAAAGGCAATGACAAGAAATCAGAACAATATTGGTAGGCTGTAGCTAG

AGAGTTCAACAGCAATATGCCTAGCAATGGGAACAAAACGAACCCCAAGCAATGCAGAAC

ACATTGGGACAATGTCAAGAGAGATGTCACTAAGTTCTGTGGATTTTATTCTAAAGCTAG

AACTACTTTGAGAAGTGGGTATTCTGATGATATGATAATGGAGAAAGCCCGTGAATGGTA

CAAAAAGCACAACAACCAAAAACCTTTCACCTTGGACTATATGTGGAAAGATCTTAAAGA

TCAACCTAAATGGCGTAGAGTCCTTGAAGAGAGTAGCCATAATAAGAGGAGCAAGATTTC

TGAATCAGGAGCATATACTTCATCGTCGAACCAAGACACAGAGGAGGAAACAGAGCGCAA

AGAGAAGCGCCCTGAGGGGCAGAAGGCAGCAAACAGAGGCAAAAGGAAAAGGTGCACC

ATCACCTTTAGGGGATAAGCCAAGTCAAAATATGGTTCTCTTTCACGAAGCTATTACAAC

TAAAGCAGCAGCATTGCTAAAGCCAGCAGAAGCAACACTGATTGGAGCAGAAGCAAAAAA

AGAGAAGGCGATTGCAAAAAAAACAGAAGGCAAGGGCAGAAAAATACCAAATCTATTTAA

AACTGATGGAGAAGGATACATCAACCTCCAGTGAAGCAAAACTGAAGAGACATGAAAATG

TATTGGACCAATTAGCTAGAGAACTTGCTGAGGAATAAATGACTAGCAAGCAATGTTAGC

AATTATGCTTATTTTATAATGTCAGTATTCTTGTCATATATTAAAATTATGTACTGTCTT

GATGCTTGTACTGTGAACCTATTTGTATTGTAGTATGTTATGCTAATTTGTATAAATATT

GTGTATTACAGCTATGGAATGAAACTACAATATCCTTAGTACTTGAGAAATCACCTTTTG

ACATGGATCTAGTTGGTGTTGATGGTTTTTCTTCCATCCATGACCAATCTGTTTTTTTTT

CTCCACCTGAATACATATGAGCAATAATTAATAGAGAACAAAAGCAAGAGCGATGTTGAC

AAAACCTAGGAAAATATAGCTGTTGTAAAAGACTGACAAAAGCAAGAGCTAGCTGTTAGG

ATATTGACAAAACGGAGGAAAATATAGCTGTTGTAAAAATCTGACAAATCTAGTCGTTGT

AAAATCTATCATCTACAAATAGGTAATGTAGTTCAGCAGAACAACACCCATTCTCATTTT

GTTCAAGTTCATCTCAACAGCCTTCCCACTTTGAAAAAAAAAATGTCCAGCAAGTCACC

AGATCAATCTAGTGAGTCAGATGATTCTAGCTCTAGTGACTACCTTGAAGAGCTGATTTT

GGAAGAAATCAATGATGCTATGGAAGCTGAGATTGAAGATGAGATTGAAGCTCAACTTCA

ACCTCAAATGCAAGCAGAACAAACTGGTCATTCTAATCGTCGTGGGGCCTACAAACGAAG

GTACATCAATAGACATTACCAAGACGACCACAACAGATTGTTTGCAAAATACTATTCGGA

CAATCCTTTATATACCGATGATCACTTCCGTAGAAGATTTCGCATGAGAAAGCATCTATT

TTTGCACATTGTTGAAGCTCTTCGGCATTGGTCTCCATATTTTCGTTTCCGAAGAGATGC

ATTTGGCAAGGTTGGTCTATCACCGTTGCAAAAATGCACAGCTGCCATACGCATGTTGGC

ATATGGTACACCAGCTGACCTTATGGATGAAACTTTTGGCGTTGCAGAAAGCACAGCAAT

GGAATGCATGATAAATTTTGTTCAAGGTGTTAGACATATATTTGGTCAGCAATACCTTCG

CAAGCCTAATGAACAAGATATCCAGTGTTTACTTCAACAAGGAGAGGCTCATGGGTTCCC

TGCCATATTGGGTAGTGTTGAGTGCATCCATTGGGAGTGGCAAAATTGCCCGGTTGCATG

GAAGGGACAATTCACACGTGGTGATTATGGTGTACCCACTATCATGCTTGAAGCAGTTGC

ATCTGCTGACCTATGGTTTTGGCATGCATTTTTCCGTGCTGCTGGTTCAAACAATCATAT
```

-continued

CAATCTGTTGGATCAGTCACCATTGTTTAGTGCAGTGCTACAAGGAAGAGCTCCTAGTGT

TCAATTTACTGTCAATGCGACAGAATATAACATGGGATACTATTTAGCTGATAATATTTA

TCCAGAGTGGCCTGCATTTGCCAAATCAATTAGTAGACCTGAAAGTGACAAGGCTAAATT

GTATGCAGAACCCCAAGAATCAGCAAGGAAAGATGTCGAACGAGCATTTGGGGTTTTGCA

AAAACGTTGGGCCATAATTCGCGACCCAGCAGGGCTTTGGGAAACGGATGAACTAGCTGA

TATCATGTATGCATGTATTATTTTGCACAACATGATAGTTGAGGATAAGAGAGACGATTA

TGACATACCTGATGACAACACATATGAGCAATCACAATCTTCTGTACAACTAGCAGGACT

CGACCATCGCCCAATCCATGGATTTGCAGAGGTCCTACACGCAGAGATGAATATTGGCGA

TCGAACAACCCATGGACGTCTAAACTCAGATTTGATGGAGCACATTTGGCAGAAATATGG

TGGTCAACAACAACAAAACTAGAGTTTATTTGTGTTATGAAACTTGTGTTCTTTTTTCCA

TTTTTCTTTCAGTCGTCCAATTTATTCTTATTAGTAACTGAGACTCTTTACTTTTTCATG

CACTAAGAGTAATGTACCAGTACCATTGCCTTAATTAGTCAAGCACAAGTCATATTGAAA

ATATCATGTTTTTTTGGTCATTTTTTTTAATTTCAGATCTGTTGGAGCACAACTAAACAC

TCTATGAAAATTCCATCGGGATCGAAATCAACGATTCACATGATGCATACCTACAAACAC

AAAAAGAATCTGTAGTAGCAGCACTTGCACATATTTGATGACAAATTTAATCGTAGCAGC

AGGAGCACTTGCACAAACAGATATAAATTTAATGACCGGGCAAACCAAAAGCAAGTAGAG

ATTCCACAACACGGAAAGGAGAGGCCACGGAATCAATCACCTTGTCTCTAACCCAGAAC

TCACGGAGGATGTAGGCGAAGTTGAGGGCGGTGACCGTCTAGTAGGTGCTGATGGTTGAG

AGCAGCTTCAAGTTTGTGCCCCACACGAGACAGAGAAGCACGCGTCGGCAGCGTCGCGGC

CGGAGTAGTTCGCGCACGCAGCGTGATCGATGGGTCACCCCGCGCACGCCAACGTCGCAC

CGAAGCCACCGCACAGCGAGGTCACAGCCGAAGGAGGGGAGGGCGCGAGGAGCAGCGACG

TTGGCGCAGCCACGGGAGGAGCAATCGTCGGAGAAATTGGGGATCCAGTGCATGCGCTGT

GGGAGAATTTGGGGATCGAGCGGAGCGACGAAGAGAGGAATTGGGGATCTGAGGCCGAGC

AAATGGGGATCGAACAGAGTAACAGTGGATGAGGATTTTTTTTCACTCCCGCGAACAAGC

AGATGGTTACGAGTGATCTGTATTCTTTTTCTGCCGTGGGGCCCAGCGGGACCCACCTTA

TTTCCATCAAACAAACAGTATCATTGTAGAGATTTGGTTAATAACTATTGCTACCTGTAG

ATGGGCCCACTCTTGTTATGCATTTTACCATATACATTGGCCTTGCCC

Deduced amino acid sequence of PONG_LIKE_5a ORF1 in Oryza sativa
(SEQ ID NO: 48)
MEPFKGNFSNLLNQGSSSQATNSEAQNSLSTQFPTSYPQNFRPSFLQNFHPFGPPSNYQP

YRHPPIFQGAQQQEYYGQPTPGSLEGFQLQENLVHSSNQAFGFAANRSQFGMQYSTSIRA

TANTSSHGSASPCHTRHNEKEVVEVEEASDSSEEGRRGTRINWTEDDNIRLMSSWLNNSV

DPIKGNDKKSEQYWKAVAREFNSNMPSNGNKRNPKQCRTHWDNVKRDVTKFCGFYSKART

TFTSGYSDDMIMEKAREWYKKHNNQKPFTLEYMWKDLKDQPKWRRVLEESSHNKRSKISE

SGAYTSSSNQDTEEETERKEKRPEGQKAAKQRQKGKGAPSPLGDKPSQNMVLFHEAITTK

AAALLKAAEATLIGAEAKKEKAIAKKREGKGRKIPNVFKTDGEGYINLQ*

Deduced amino acid sequence of PONG_LIKE_5a ORF2 in Oryza sativa
(SEQ ID NO: 49)
MSSKSPHQSSESDDSSSSDYLEELILEEINDPMEAEIEDEIEAQLQAQMQAQQTGHSNRR

GGYKRRYINRDYQDDHNRLFAKYYSDNPLYTDDQFRRRFRMRKHLFLHIVEALGIWSPYF

RLRRDAFGKVGLSPLQKCTAAIRMLAYGTPADLMDETFGVAESTAMECMINFVQGVRHIF

GQQYLLRKPNEQDIQCLLQQGEAHGFPGILSLDCMHWEWQNCPVAWKGQFTRGDYGVPTI

MLEAVASADLWFWHAFFGAAGSNNDINVLDQSPLFTAVLQGRAPSVQFTVNGTEYNMGYY

LADNIYPEWAAFAKSITRPQSDKAKLYAQRQESARKDVERAFGVLQKRWAIIRHPARLWE

RDELADIMYACIILHNMIVEDKRDDYDIPDDNTYEQSQSSVQLAGLDHGPIHGFAEVLDA

DMIRDRTTHRRLKSDLMEHIWQKYGGQQQQN*

Nucleotide sequence of PONG_LIKE_5b in AL662995 in *Oryza sativa* (SEQ ID NO:50)
GGGCACCCACAATGTTGTAAAAAACCAGGTAGTAAGCATTAAATGGTTCCTTACTACCTG

GTATTAGTCATTGTCGGAGTAGTTCATTCTTAAAGCCACGAAGTAGCGCTGCTGCCGGCA

AGAACGGAATAAAAAATGAAATGTGTACAGTGGAGTTCTGACAAAAAATTTTAAATTCCA

AGTAGCCGTTGCTTCTTCCAACCGTTGCTCTCCTCCCCAGCCAACCGTTGCATGGAGTGT

TCTTCTTGCGATCTTCATCTCCTACAAAAACAGAGATGGCTCATAATTTCTTTGAATCAA

CACAAAGACATTCTGTGAAACTTAGCTAGCTGAGAGCTTGAGATGGATCCCTCCAAGAGA

GGTTTCATGAACTTGTTAAACCAAGGCTCTCCAAGCCAACAATCTAGCCAAAACTCCCCT

CCTACTCAATTCCCCTCAACTTTCTCCCAATCACAATTTCGCCAATCCCCACATTTTACC

CAACCCTCACGACCTAATTTCCAAACCTTCAACCCTTTTGGTCCTCCAGCCAACTATCAC

CTATATGGTAGTTCTCCTCCAAACTTTCAACGTTTTCTGCAGCAAGCAACCTGGTTACAA

TCTGCACCAATAAGCTTTCAAGGTTTTCCTCGCCAAGAAAGTTGGATGGACTCACCAAAT

CAAGTTGTCGGGTCCGCCTCATCTCATGCATCCAAATCAGCCTCTCAGTGCCCTGCAAGA

CAGGAACAGAACAATTTGGTTAACATCGAAGAGTCAAGTGACAATAGCCAAGAGACAGCG

AGAAGAGGGACACACGTCAACTGGACCGAAGAAGAAAAGTTACGACTCCTCAGCTCTTGG

TTGAATAACTCAGTAGATTCTATAAATGGCAATGACAAGAAGGGAGAATACTATTCCAGG

GATGTTGCTGCAGAGTTCAATGGTAATGCATCTAGCAATAACCGCAAAAGCACAGTCGTG

GAATGCAAGACACATTGGGGTGGTGTTAACAAGGACATTGCAAAATTTTGTGCAGCTTAT

TCTCGAGCTAGAAGAACCTGGAGGAGTGGATTCTCTGATGATATGATCATGGAGAAAGCC

CATGGATTATATAAATCAGAAAACAATGATAAAACTTTTACATTAGAGTATATGTGGAGA

GAATTAAAGGATCAACCAAAATGGCGACGGATACTTGAAGAGGACAGCAAGAACAAGAGG

ACTAAGATTTCTGAATCTCGTGCATATACATCATCATCCAACCAAGAAACTGAGGACGAG

ACCAGCCGAAAAGAGAAGCGTCCTGAAGGCCAGAAAAAAGCCAAAGCCAAGCTTAAAGGG

AAAGGAAAAAAACCTGCACCGTCTCGTTTGGCCGACCAGCCATCTGAAGATTTTGTTCTC

TTCAACGAAGCTGTAAAATTGAGAGCAGAAGCAGTGCTGAAATCTGCAGAACCAACCACC

AAATCAGCGGAAGCAAAGAACGAACAAACTAGGATGGAGAAGTATCAGACATATTTAAAG

TTGTTGGACAAAGACACTCCCAATTTTAGTGATGCAAAACTCAAGAGGCATGAAGCTGTC

CTCGAAAAGCTAGCTACAGAACTTGCAGAAGAATAGAAGATCCCTAAGTTATCTTTGTAC

CCCTAGTACTTAGTGTGTCACTGTTTCATTAAGTTTAACTTGCTAGTAATATTTAGACTT

GTGATAGGTTTGTAGGGCAAGTAATTGTTGTATTGTGAACTCAGTGAATGATGAATGTAA

TATTTCACTAGTGAGAAGGCATATGAAGTGATAATATTTGCCCACAATCATAATATGTCT

GAACCTTCTTCTCTGTAGTCTCTGATTTGTCCCATAACAACAGCAATTCGTTTCTTAAGC

AGCGTGCAGAAAAATATACATTGATAATAATTAGCACAAGATTTTATAATATGGTGGTTT

GAATAGATAGAAAACGAAGGTATGGTTGTTTAAAATCTAGCTGTTAGAATACATCGAAAA

AGCAAGACATGCTTGTTTAAAATCTAGCTGTTGGAATACATCCAAAAAGCAAGACACAGT

TGTCTAAAATTTAGCTGTTGGAATACATCCAAAAAGAAAGACATGGCTGTTCAGAATCTA

GCTGTTGGAAACTAGCCGTTGCAATGGAAGCAAAAGCAAGGCATCAATGTTACACATAGC

-continued
TAGCAGCATGAACCATATATAAATAAGACATGCACATCACCAAGGCAGCATTCCCCTTCC

TTTCCTTCAACTTGTTACCAACATAGCAACCCATGTCCAAAAAAGATGTGCACTGAGTCA

CAAGATAATTCTAGTCATTGCGATGAGTCCATCAGTAGTGAGAAGCTTGATGATATGACA

TGGGAAGAAATTAATGACCGTATGGAAGCTCAGCTTGAAGCTCGGTTGGAAGCTCAACTT

GAAGCGAGATTGATGGCTCACCTAGCTGGTAGCTCTAATCAGCTCGGGGGCTACACAAGG

ACCTACATTAGTAGAGATCATGAAGATGACCACAACACATTATTTGCTAAATATTTTTCT

GAGAGTCCATTGTACACCGATGATCAGTTTCCGAGGAGATTTCGCATGAGAAGGCATCTT

TTTTTCCGCATTGTACAAGCTCTTCGTGTTTGGTCTCCATATTTTCGTCTAAGGCGAGAT

GCATTTCGCAAGGTGGCTCTATCACGATTGCAAAATGCAGCGCTGCCATGCGAATGTTG

GCATATCGTACACCAGCTGATCTTATGGATGAGACCTTTGGGGTTGCAGAAAGTACACCA

ATGGAGTGCATGATCAATTTTGTTCAAGCTGTGCGGCATTTATTTGGTGAAGAATATTTG

CGCAGGCCTACCGTGGACGATATTCAACGTTTACTTCAATTTGGAGAGGCACATGGATTT

CCTGGGATGTTCGCGAGTATTGATTGCATGCATTGGGAATGGCAAAGTTGTCCGGTTGCA

TGGAAGGGCCAATTCACACGTGGTCACTATGGAGTACCCACTATTATGCTTGAAGCAGTT

GCTTCTTTAGATTTATGGATTTGGCATGCTTTCTTTGGTGCTGCTGGTTCAAACAATGAT

ATTAATGTATTCGACCAGTCTCCATTATTCACTGAAATGATACAAGGAAGAGCACCTCCT

GTTCACTTTACCATAAATGGTACACAATATAACATGGGATACTATTTAACTCATAGAATT

TATCCGGAGTGGGCTGCATTTGCCAAATCAATCACCAGGCCCCGAAGTGCTAAGCACAAA

TTATATGCCGAACGTCAAGAATCAGCAAGAAAGATGTGGAAAGAGCCTTTGGGGTTTTG

CAAAAACGTTCGGCCATCATACGTCACCCGGCGCGTATTTGCCAAACCGAAGAGCTTGCA

GATATAATGTATGCCTCCATTATTTTGCACAACATGATACTTGACGATGAGAGACGCTCA

TATGATATACCCGATGACAATACATATGAACAACGGGACTATTATCCTCAAATGACAGGG

CTTGAGCATCGACCAATATATGGATTTCAAGAAGTTTTAGAGCAAAACAAGGCTATCCAT

GACCGACAAACACATCGCCGTCTGAACGGAGATTTGATAGAGCACGTGTCGCAGAAATTT

AGTGGTGAGCAACAATAAGATTAGATTTTAATAATTCCATATCAACCTTGTATTTTACTA

GTTTAATTTGTCTTTACGAATTTAGAATCTAAATGTTTGCTTCCAAAAGTACTTGTATTT

GTATCTCAAATGTATTACTTTTTATCAGCTACCTATTCCAATAGGGACTATGTACACTAG

CTAGTTATCTTGCAATACCTACAAAAATCCATTGCCTTTTATTTCTGAAGAACTATATAT

ATGTTCTGTATACAGCTAGTAGACTGAAGAAAAAAGGAGAGCAAAACTACCAACAGAGAG

GCAAAATGTGGTTCCTTTTTCCTGAAAACATTTGAACAGGAAACAACTGTGTTGATACAT

AGCAACAAGGTTAGTTACACGAAGACCAATGCACTGGTGTCAAGTATAGTCCGCTGCAGC

TAGCTGATCGACAATCGAGAATCAGCTAGAGCCCTGACAGACATATACTCCAGTAGCTAT

ATCGAATACTATTGAAGTTTTCAGATTAATCAAACTCGGATGCTTACTTTTGATTAGTGT

TCTAAGAATTAAACATAATTATATCTCATCATCATGTAGCTTGTATTTTTGAGAAAAAAC

ACAGTCGGTTGCTGTTAAGAGCCCGGCAACATAGCAAATAGATATATTTTGGATGGCAAG

AGAGTTAAATTAAATTTTCTGCAACATAATATTTAGCAAGAACATAAAAGGTTAGTGCTA

GCTACATCCGTTCGTGATGTAGAACAGTAGAAGGTTAATGTAGCTACCTGTTTTAAACTG

CTGTATGCAGCGCTCTTATCGAGTGGGGAAACCTAGTGTTGTGTTCTTTACTTGGATAGA

AGCACGAACCATAACACAGATCAAACGGTAAACAAACTGACCGTGATTAAACAAAAAATC

TGTCCACATAGTTATAGCAACTCCGACCGTGATTAAACAAAAAAAAATCTGTCCACACA

GTTATGGCAACTCCGATTCTCATAAACTGAACTAGAAAATATAACATGCGCAACATCGAG

-continued

```
AGAGAGGTACATGGTACAATATTTATCATGCAAGCACATACGCTATTCTACTACTTAAAT

CACAAGCATAGGGGTTACTTGGAGTTACAGTTGGTCTTGCAGCTCCGTCGCAGATCTCAG

CAGGAGGATATGAACCCGAAGCTGATCACACACCAGAGAAGATGACCTCCTCAGTCTCCA

GCCGGGGTGAAGCACCAGTCCGCCATAATAAGGGAGGTCGCTTGCGGCGTCGGTCGGCGG

GGATAGGGGCGACGGATGAAGGGGAAAGCGTTCCCTGATTGCAGAGAAGGAAGGTTTGCG

GCGTCGATGGTGGGGGTGGAGCGGATGCGGCGCCGGGTGGTAGCGATACAGGGGATTGCG

TCCTTGGGTGGCGGAGAGGAACCCGCCGTCAGTGGAAGGGTGGAGGCGTTTGTGGCGTTG

ATTTCGGGGGGAGGGCGAGCGGATCGCCGCATGGATACTCCGGACGGAGGAGTTGGCGGC

GGCGAGTGGCCGGGTACGACCGGATTTTACGGCGGCGGGGAAGGAGAGGAGATTGCGGCG

CCGGTGGAAACAGCGAAAGAGGAATTGGGGATCGATCTGGCCGGAACTCGCGCGAAGGAA

CTGAGCGCCGATTTTTTTTATCCTGTGGACCCCACCTTTACTACCCTCTCGCCCAGATAA

GCATTGTGGATAGTGTCTTGTCCTATTACCGCCTGTGACTGGGTCCCACACTAATACTCA

TCTTGATAATATACATTGGTGTTGCCC
```

Deduced amino acid sequence of PONG_LIKE_5b ORF1 in Oryza sativa
(SEQ ID NO: 51)
```
MDPSKRGFMNLLNQGSPSQQSSQNSPPTQFPSTFSQSQFPQSPHFTQASPPNFQTFNPFG

PPANYHLYGSSPPNFQGFLQQASWLQSAPISFQGFRPQESWMHSPNQVVGSASSHGSKSA

SQCPARQEENNLVNIEESSDNSQETGRRGTHVNWTEEENLRLLSSWLNNSLDSINGNDKK

GEYYWRDVAAEFNGNASSNNRKRTVVQCKTHWGGVKKDIAKFCGAYSPARRTWSSGFSDD

MIMEKAHALYKSENNDKTFTLEYMWRELKDQPKWRRILEEDSKNKRTKISESGAYTSSSN

QETEEETSRKEKRPEGQKKAKAKLKGKGKKPAPSPLGDQPSQDFVLFNEAVKLRAEAVLK

SAEATTKSAEAKKEQTRMEKYQTYLKLLDKDTANFSDAKLKRHEAVLEKLATELAEE*
```

Deduced amino acid sequence of PONG_LIKE_5b ORF2 in Oryza sativa
(SEQ ID NO: 52)
```
MSTESQDNSSHSDESITSEKLDDMTWEEINDPMEAQLEARLEAQLEARLMAHLAGSSNQL

GGYTRRYISRDHEDDHNRLFAKYFSESPLYTDDQFRRRFRMRRHLFLRIVQALGVWSPYF

RLRRDAFGKVGLSPLQKCTAAMRMLAYGTPADLMDETFGVAESTAMECMINFVQGVRHLF

GEQYLRRPTVEDIQRLLQFGEAHGFPGMLGSIDCMHWEWQSCPVAWKGQFTRGDYGVPTI

MLEAVASLDLWIWHAFFGAAGSNNDINVLDQSPLFTEMIQGRAPPVQFTINGTQYNMGYY

LTDRIYPEWAAFAKSITRPRSAKHKLYAQRQESARKDVERAFGVLQKRWAIIRHPARIWE

REELADIMYACIILHNMIVEDERGSYDIPDDNTYEQGQYYPQMTGLDHPTIYGFQEVLEQ

NKAIHDRQTHRRLKGDLIEHVWQKFSGQQQ*
```

Nucleotide sequence of PONG_LIKE_5c in AP004859 in Oryza sativa
(SEQ ID NO: 53)
```
CGGCAACCACAATCTCCTTAAAAAGCAGCTAATAAACAATAAATGCACTCGTCCAAGCAG

GTAATAGCCATTGTGGCCCCAGATAACAGCAACAATCACCCACTAGTGTTACTGCCGGCA

ACACACAAATAAAATATAGCATGTGTACAGTGATTTTAGAGAGTTGCACTAAAATAATAG

ACTACCACTTAGCCGTTACATTTGTAGCAATTGTAACTTGTTGCAACAACGCTACAACCT

CATGCCTCTACAAATACAAACACAACTCAGTCATTTTCTGTATTTCATCAAATAAGATCG

ATCCTCCCAACAGAGCTTTTATCCACATGCTTAGCTACCCCTCCCAAACCCAAACTTCTC

CAAATGGTAGCCAAAACTCCACTTCTCCACACTTCCCCTCAATATTCTCCCAATCCCACT

TTTCTCAATCCTCAACACCCACTTTTCACAACTTCCATCCTTTTCCGGCTCCAAACAACT

ATCAACCATATGGCAATTCTACTCCAAGCTTCCACGGTTTTCAGCAGCAAGCACATTGGT
```

-continued

```
TACACTCTACACCACTCACTTTTCAACCTTTTCGTCCTCCGGAAAATTGCGTCTACTCAC

CTAATCAAATTACTGGGTCTGCTTCTTCCCACGCATCACAATCACCCTCTCAGTCCCCTC

CAAGATATCAACAGAACAATGTCCTTCATATCCAACACTCAACTGAGAAGACTCAAGACC

CAGGGAGGAGAGGACACGAGTCAACTGGACTGAAGAGGAAAACATAAGACTCCTTAAGCT

CTTGGCTGAATAATTGAGTGCATCCTATAAATCGTAATGATAACAACGGAGAATACTATT

GGAAGGCTGTAGCTGTAGACTTTAATACCAATACATCTAGAACTAACCCCAAAAGCACAG

TTGTCCAATCCAAGACACATTGGGGTGGTGTTAAGAAGGAAATTGGAAAATTTTGTGGAG

CTTATTCTCGAGCTAGAACCACCTTCAGTAGTGCATATTCTGATGATATCATCATCCAGA

AAGCTCATATTATGTTTAACTCACAAAACAATCAAAAACCTTTCACATTCCAGTATATGT

GGAGAGAACTGAAAGATCAACCAAAATGGCGAAGGGTCTTAGAAGAAGATAGTAAGAATA

AGAGGACTAAGATCTCTCAATCACCTGCATACACATCATCGTCCAACCAAGACACCCACC

AGGACAACAGACGCAAAAAGGACAACAGACGCAAAAAGAAGCGCCCTGAGGGACACAAAA

AAGCCAAAGCCAACTTAAAACCGAGAGGTAAAAATGTCGCACCTTCTCCTTTGGGAGACC

AGCCATGTCAAGACTTTGTTCTTTACAATCAAGCTATAAAAGTCAAACCAGAACCCATCC

TGAAATCTCCACAAGCAACATCGAAATCACCTGAAGCAAAGAAGGAATACACAAGAATGC

AGAAGTATCAGACATACTTAAAATTCTTGGACAAAGACACTTCAAATTTTAGTGATCCAA

AACTGAACACCCATCAAGCTCTCCTCCAAAAGCTAGCTACAGAACTTCCTGAAGAATAAA

TGATCACCAAGTGATGTTGTATCCCTCTTACTTAGTCTGCCACTATCTCCTCTATCATCA

ATTTCCTCCTAGGATTTAGACTTACCAATTATTACACTTGTCAACTCAGTGTTAAGTTTG

TAGGCTAAGTAAATGTTGGATTGTAAACTTAGTGAATGATCGTTGTATCTTTGTACCTGT

AGAAGATGTTATCTACTGATAATATGTAGCCCACAGTCTTAATTGAACTTATTTGAAGTT

GTTGGCCCATAATTTCTTAGCACTTGATTTAACACCAGCCTACAAAATACATATCTAGCA

CCAATAATTAGCACAATTATTTATAATCTTGCTGTTGTGATAGTTTAAAATAGTTGTAAA

GCAAGACATTGATGTTTATAAAAGTGTTGTTTCAATATATAAAAAGGAAGACATGGATGT

TTATAAAACTATTGTTTAAATATATAAAAAGCAAGACATGGCTACTAAGAATCTAGCTGT

TGGAATACATCCAAACAGCAAGGCATGCCTGCTGTGAATCTAGCTGTTCGAATACATCCA

AACAACAAGTCATGACATAGTTGTATGGAATATAGCTCTTCCAAACTAGCTGTTGGAACA

AAAGCAACACTGAGATGTTAGCACATATCCATTCAGTTCTATCTTCTATGAAACAGGGTA

TGCAGTTCACCAAGATATATACCATTGCGTTTAATTCAGTTCATTCTCAACAAAGCCACC

TAGTTCCCACAAAGATGTCTAGTGATTCACAACTCCATTCTAGTCATTCTGATGAGTCCA

TCACTAGTGAGAATTTGGAAGATATGATGTGGGAAGAAATTAATGATCCTACTGAAGCTC

AGCTAGAAGCCCGGCTTGAAGCTCAACTTGAGATGAAATTGATGGCACGCCTAGCTGGGA

ACTCTAATCAGCGTGGAGGCTACACACGCAGGTACATCACTAGAGATCATGAAGACGATC

ACAACAGGTTATTTGCTAAATATTTTTCAGACAATCCTTTGTACACGGATGATCAATTCC

GTAGGAGATTTCCCATGAGGAGGCATCTTTTTTTGCACATTGTACAACCTCTTGGCGAGT

GGTCTCCATATTTTTGTCTTAGGACAGATGCATTTGGAAAGGTGGGTCTTTCACCATTTC

AAAAATGCACTGCTGCCATGCGAATGTTGGCATATGGTACTCCAGCTGATCTTATGGATG

AGACTTTTGGGGTAGCTGAAAGGACAGCAATGGAGTGTATGATCAATTTTGTTCAAGGTC

TGACGCACATATTTGGTAAACAATATTTACGTAGGCCTACCGAAGAGCATATTCAACGCT

TACTTCAGTTTGGAGAGGCACATGGATTTGCTGGCATGTTGGGTAGTGTTGATTGCATGC

ATTGGGAATGGCAAAATTGTCCGGTTGCATGGAAGGCACAATTCACACGTGGTGATTATG
```

```
GGGTACCCACTATGATGCTTGAAGCGGTTGCCTGAAAAGACTTATGGATTTGGCATGCTT

TTTTTGGTGCCGCTGGTTCAAATAATGATATTAATGTGTTAGACCAATCCCCATTATTTA

CTGATGTCCTACAAGGAAGAGCACCTCCTGTTCAATATACTCTCAATGAGTCAGATTACA

ACATGGATACTATCTAGCTGATGGTATCTATCCAGAGTGGGCAACATTTGCCAAATCAA

TCATCAGACCACAGAGCGCTAACCATAAATTGTATGCACAAGATCAGGAATCAGCTAGAA

AAGATCTGGAAAGAGCCTTTGGGGTTCTACAGAAACGTTGGGCGATAATACGTCACCCCG

CAAGAGTTTGCGAAAGAGAAGAGCTAGCAGATATAATGTATAGTTGTATTATTTTGCCCA

ACATGATAGTTGAGGATGAGAAAGCTTCCTATGACATACCGGATGACAAAACATATGAAC

AAGGTGAATTCTCTGCTCAGATAACAGGACTTGACCACGGACCAATATATGGATTTGCAG

ACGTACTAGAGAAAAACAGGGCTATTCGTGATCGATCTACACATCGGCCTCTGAAGGAAC

ATTTGATAGAGCACATCTGCAGTAAATTTGGAGGTCAACCACAACAAGATTAGAGTGTAT

TAACTTACTATCAACCTTGTACTTTAGTATTTTCATATCAACCTTGTACTGTAATATTTT

CATCTCAAGAGATTTGGCTCAATTAGTTGTTTTTGCAATATACTTGTATTACTTTGCAAT

CTACCAGATTTGTCTCAAAGCACTTATCTTAATATGTCACATATTGAACCAGAACAAACA

AGAAACAAATAATCACACATGAACAGTGAGGCATAAAATACATGCAACTGCGTGAAAGGC

GGCTTACCAAATGGTCTACTTTGCAATCTAGACCGATCTTTCAGATCCGATGCACATAGG

CTCCGGATGAGGACTAGAAGCCCAAGCCGACGCCTCCCATGACCTATTCAGCCTCCACAA

CGATGGCGGAAATTTGGCGGGAAGAACCCGTGGATGCGCGTGAGGGGTGGGGTGGGGGTG

GTAGGGCAGCGGAGGGGGTAGTGGCGGCGATTAGGACGACATCAAGTCGGAGTCGGCCGG

AATCGATCGCGGCTTTGATGGAAGGATTTTGGATCGGGATCGGAAGAGAGTTGGATGGAG

AGGCGCTCCGGGATAGGGAGCTGCTCCTCCGCCGGCCTAGGCTGCTGCGCATTGAGGCCT

CGGAGGCCGGCCTGATGCCCCGGCCGACTGCTCCGGATCAAGCGATGCAAGCAGCGGCGA

CGATGGAGTCTCTTTCTCTTTTTTTTTCGATAAGCCAGCGATGGAGTCGAGACTGGGGA

TCGCATCGGCCGCGGGAGGAACTGAGAAAGTCACGGGAGGTTGGGGCTAGCGATTTGTTT

TATTCCGTGCGCCCCATCTTAATTCCTTCTCTCTATTCTCATACATTGTGATGGCTAATT

TAACTACTACTCACTGACAAATGGTCCCACACTAATACCCACTTCCATATTACACATTGC

TGTTGCGC
```

Deduced amino acid sequence of PONG_LIKE_5c ORF1 in *Oryza sativa*
(SEQ ID NOs: 54-55)
```
MDPPNRGFMHMLS*GSQSQTSGNGSQNSTSPQFPSIFSQSQFSQSSTPTFQNFHPFGAPN

NYQPYGNSTPSFHGFQQQAHWLHSTPVSFQGFRPPENWVYSPNQITGSASSHGSESASQC

PARYEENNVVDIEESSDNSQEAGRRGTRVNWTEEENIRLLSSWLNNSVDPINGNDKKAEY

YWKAVAVEFNSNTSRSNRKRTVVQCKTHWGGVKKEIGKFCGAYSPARSTFSSGYSDDMIM

EKAHIMFKSENNEKPFTLEYMWRELKDQPKWRRVLEEDSKNKRTKISESGAYTSSSNQDT

EEENRRKKENRRKKKRPEGQKKAKAKLKGRGKNVAPSPLGDQPCQDFVLYNEAIKVKAEA

MLKSAEATSKSAEAKKEYTRMEKYQTYLKLLDKDTSNFSDAKLKRHEAVLEKLATELAEE

*
```

Deduced amino acid sequence of PONG_LIKE_5c ORF2 in *Oryza sativa*
(SEQ ID NO: 56)
```
MLAHIHSVVSSMKQGMQFSKIYTIAFNSVHSQQSHLVPTMKSSDSQVHSSHSDESITSEN

LEDMMWEEINDPTEAQLEARLEAQLEMKLMARLAGNSNQRGGYTRRYISRDHEDDHNRLF

AKYFSDNPLYTDDQFRRRFRMRRHLFLHIVQALGEWSPYFCLRTDAFGKVGLSPFQKCTA
```

-continued

AMRMLAYGTPADLMDETFGVAESTAMECMINFVQGVRHIFGKQYLRRPTEEDIQRLLQFG

EAHGFPGMLGSVDCMHWEWQNCPVAWKGQFTRGDYGVPTIMLEAVASKDLWIWHAFFGAA

GSNNDINVLDQSPLFTDVLQGRAPPVQYTLNESDYNMGYYLADGIYPEWATFAKSIIRPQ

SAKHKLYAQHQESARKDVERAFGVLQKRWAIIRHPARVWEREELADIMYSCIILPNMIVE

DEKGSYDIPDDKTYEQGQFSAQITGLDHGPIYGFAEVLEKNRAIRDRSTHRRLKEDLIEH

IWQKFGGQPQQD*

Nucleotide sequence of PONG_LIKE_6 in AP004556 in *Oryza sativa*
(SEQ ID NO: 57)
GGCCTNTNACAGNGGCTCCTAGCTGGACTGTGGCTTACTAGCGCGACGTCTGTTTTTTGC

CTGCGTGTCGCTCGGCCCCGCGCCTCTGCTTGGCCGCTGGTGACCAAACTCCGATGCGCA

AAACCTCGCCTGGAAAAGGGGCCGGACGGAGGAATCGAGGGGAGGCGCGTGCACTGTGGG

TGTCGTTCCCTCGCCACCCGGTGCTCTCCCATGGGATTCGGCCGGCGAAATCGCCTATTC

ACCCTCGAAAACCCACCCGATTCCCCTCCTCCCGCCACTGATTTCGTAGCTCCCCCGCCG

GATTGGAGTCCGTCTTGCCTCAGCGCCGCTGTTCTTCCACCTCGACCTCGCCGCCCTGAA

GTCTCAATTCAGGACGGCCTCGCCATCCCCTCCGACGGCGCCGGAGGTGCCACTGCCGCG

CTCCGCTGTAGGATCTTCAGTCATCGTCGAGCTGTCGATGGCCATCGTGAGAGGTAGCGG

TCAGCAAACCCTCTCCCCAACTCATAGTTTGACCGATTTGCCAAGCCTTGGTTCCCTGAT

TCGATCTCTCCATCTGATGCAAACCCTAGTTGCAGATGGATCCGCGGCTAGCCGATGCTT

TTGCCCGTTTCCTCCAAGATCCGGCATCAGCGGCGGCGATATTGCAGTCCCTAAGCCAGC

CGTCGTCGGTCCCTCTATAGGATCAAGGCGGCGGACTAGAGGGGGGTGAATAGGCGGTTT

TTAAAACTTTTGGCTAAAACCAACTTTTGTATGCGGAAGCGTAAATCAAAATGGTTTTGC

ACAATTCAAAACCTAAATCAACTAGTGTCAAGTAAGTGCACAAAGAAGCTACCCTATGTT

GAGGTTTGCAAGCCTAGGGTAATAATAGCACAAATAAACTCTAGTATGTAAACTTGCTCA

AAGTAAATTTCGAGAAACTAAAGGAGACAAGAAATAAGGAATTTTTGACCGAGGTTCGGA

AACTTGCCAGTTTCCTAATCCCCGTTGAGGCCAGCCCAACTCGACCGCTCAACCACGAAG

CCACCGCACCCCCCCTTCGTCAAGGGGTGGCCAAGGCGGGAGTCGGCCGACGGAGAGGAC

TAGCAAAGCCTCGATCACTAGGGTAGTTCTTCCTTGACTCCGAAGGTGGTGAACCCCAAA

CCACTCACAACCCCGCCGGGCCTCCTCCACAATCTCCTCGGAGAGGTCACCGAGCAACA

CTTCGACAACCTGTCTAGGAGGCAGCAACCTGCAAGAGTAACAAGTCTAGGATGCTTGCC

GAGGATGATCAAGTGCCACACTAGCTATAACAATGAAGCAATGCACTTGGATTGGCTTAA

CTCACTCTCTAACACCTCACTAGATAAACTAAGTGCACAAGGGTGTGAGAGCTCTTGCAA

GGGTTCAAGATAATCAGGGGTGAAAACGGAGCGGATATTATCCGATCCGATCCGATCCGA

ATCCGTCCGATGTGAGGATATGGTAAGGGTTGTTAGATATCCGGCCCGATGCGGATGCCG

ATGCGGATTTTGTCATGCGGATGCGGATCCGGATGTCGTATCAATGATATGCGACACATT

CGGATTATCCGATTTTTTAATCAGATTATCCGATATAGTGTTTGGCGGATAATCCGCAAC

TTTCAGGCCCATCTAGCATTCTTGGCCAATAACCCATCTATTCTAACCCTAATCCTTCCT

CTCCTCCCCCTATCCCCAGATCGGCAGATCCCTCTCTCTCTCTGTGACTCTCTCTCT

TTCTCCCGTCAGCTCTCAGTCCTAGGGGAGTGGGCGAGTGGCGGCGCGACAGCGAGTCGA

CCCAGCGCGACGGCGACCCAGCGCCGGCCGGCCGCTCCTCCTTGGCTGCTAGCGCCGCCG

CCGCTCCTCGTCGGCTGCAGTACAGGCTGGTGGCGCCGCTGCCATTCGTCCTCGCCTCCT

CGGCTCCTCGGCGCCGCCACCACTCCGTCCACTGTCGCCCATCAGCACGTCTCGAGCGCC

GGCCCGCCAGCGCACCGTCGCATCCCCGTCACCAGCCCAGCCGCCATCGCTGTTGGCTGT

-continued

```
CGCGAGCAGCCATCCCCGTCGCCGCGTCGCCACTCGCCAGCCACCACTGTCGTCAGCCGT

GCCGTGTCGTCGTCGTGCTGTAACTGCTCGAGGCCTAGAGCTGCAGCTGCTGTTCCAGTC

CAACGACAAGTGGACGATAGATTAGGTATTCTTTTCTTCTACACTTGCAGTCCAATTTGA

AGTATCAAATTTGGGATTTACTGATTTAGAAATCTAGAGATGAGCTTTGCTTACGGAAAT

TAGGTGAATAGCAAGTTATAATTTGATTAATTGTTCATCATTGATTAGGATCGTAAAAAA

TGGCACCTAGAAAAGAGGGGCAAAAGCAGCAGCTGCTGCTACTGCTACTGAAAGTAGCA

TTGCTGCCTCGTCGCCAGCTGCAGCTGAAGGGGAAGAAGGGCCATCAACTGTGGGCAGTG

GCAATGAAAGTCCCAAGACTATTGTTGTTGTTGATGTGGATAACATTGGTGCAGAGCGGG

ATGGAGACCATGAAACCAATGATGAACCTGCAGCAAAGAAAGCAAAGAAGAGATAGTGGA

AGTGATGCAAGTGACTTGGATAAATATAAGGCTGAACCATGCCTGTTGGTTCCTAATCGA

GATAAATTTGATGTTTTGTCATGGTCGAAAGCTCACAAAGATGTATATCCAGTGCTATCT

CTTCTTGCCCGCGATGTCTTGTCCATTGAAGCTTCCACTGTTGCTTCAGAATCAGCTTTT

AGTGCTGGGCGACGTGTTCTTGATCCATTTCGTACTAAACTTGAACCTGAAATGGTAGAA

GCACTAGTCTGTACCAAGGATTGGATTGCTCGATATAGAAGAGGTGATCACTTGTGTCAT

TTTTCATTTATATTTTGTAAAAGGTATTCTTCTTAGTTGATTTTTATTAATAGTCTAA

TATAGCTTTCTTCCAAATTTTTCAGATTCTAATAAAAGGGTTGGATCTATTCTTAATGAT

CTCGAGGTTGCGGAGACCTTGGTTGCTAATATGACACTTGACGAGATTGATGATATGGTA

TGACATTTTATTGCATAAATTTTGTTGCAATACATTTTGTAGTCCTATCGTCAAAATAAA

TGTATATTGTTTGCTCATACTTATAGGAAAAGCAACAGAGCAGTGATGATGAAGAATAAG

TGATGAAGTGAGGTGTGAAGCCTTGAAGGGCATGTTGCTCTGTGGTTGTGTCTGCCTGTC

TGCCTGTGTGCATGTGCATCGTTCACTGCTATATGTGCGGTATGCTTGTATGCCTATTGA

ACAACTGTGTTGTGTGCTGTGCTGTATGAGATCTATGCTCTCTGCTGTATTGCTGGCTCA

TATGCTGCATGCAGCATGCATGTGGTACTGAACTACTGATGAGTGATGACTTATAAGTTA

TATTGTTAAATTTTAAGCAATGCAGTGACCAGTGACTAATGAGTGATGGATGTATGTTGG

ATTATTTTGTTGGATGTGTTCTATTAAGCAAAATTATATTATTGATGTGTTTTGGTTGGT

TTTTCCTAGAGAGCTGAGATCATGTTTAGATGTTATTTTGCCATCGTATTGCGGCTAATT

GTATTGGCGTCCACTTGTTGTATGGATTGAATACAAACTTGACATCCGACAACTTTTTGT

CCGTTTCCGAACCGACTCCGCACCCAATCCGACGTCCGAAATAATCCGCTCCCCATCCGC

ATCCGGACCTCATCCGCACCGGCTCCGCATCCGTTTAAAAAAAATGGTTTAGGATATGGT

ATAGCTATTATCCGTCGGAATCCGATCCGTTTTCACCCGTAAAGATAATGCAATGGGGTG

CCAAAACTTTACCCTTGCTGCTGGGGAGTGGGTATATATACCCCCAACCACCAAAACTAG

CCGTTGGAGTCGAAATCCCCAACTCCGTCAGACCGCCGTCGGCTCGGTCTGACCGGTTGC

GGCTCTGGCGGCTTTGTATCAGCACAAAAAACTAGACCAATGCAACAGACTAGTGGGGCC

GGTCGGACTGGCCTTACCACGCCAGTGAGACCGGCTAACAGGCCCGGTCAGACCGGCCTA

AGGCCAACGGTCAGACCGCAGGTCACTTTTCAGCTCAACCGACCGTTAGTAAAACGACGA

TATCTCTTGACTCGGGTCTCGGAATTTGGCGTTCTTGGACTATATGGAAAGCTTATTCAA

AGGCCCATCCAACCCATGAAAAAACCATCCAAGAAACACAACTTAACTCAAGGATAAAGG

GCTCACATTCCAAAGGATATCCACGGGACATACCCACAAGATGTCACTCACTCCTATTGG

ACATGCCCACTTCTCTCTTTGTTTAGGACTTGAGAAAACTCATCACACATGGCTAGACAA

GCCCACCAAATGCACCTATATGCATATGAACTAATATGGCACAAGGTCATCCACATGCTC
```

-continued

```
GCTTCATAGACCCGTCTTGATAGTACGACGCCTATCTAGCAAATCCGGTCTACACGAAAC

ACCAAGAGCGGAAAAAGACTAAGAAAACATTCTTAGTTCTATTATACCTTTGCCTTGCGC

CATCCAACTTGGGGTGAATGCTTGAGCCAAGATCAACACTCGTGACCATTTGCTTGAAGC

ATGTTTATCCCGAGGTCTTGAGCATCCTTTGTCAAGACTTTCTTCTCATCACAATCTTGA

CTTCACTATTGTCAACATGGCGATGTCCTTGTCTTGCTGACCATCAACCCATGTTCTCAT

CCATTAGCCTCATTACGGTGGAACCTATTCCTTTTCACATCTGAAAGGAGAACATTAGTC

TCAACAAATCGCTTGTAATCCTTCACTTGATGACCAACCGGTTGCATATGAAACATATGG

ATATGTTTGTTGAGTATTCATTTACACCTCAAGTGTCATATACCCGTATGCAAGCTCAAG

TGCAAAGATCCGATATAAATAATAGCTAAACAACATGGATCTAGAACATGCACAATAAAT

CTATAGGATTTGCTCCCCCTAAGTATATGCATACAAAGAAATATACAAGAGAGACAAGTG

TATGCATAAGTAAAGAAGAATCAACCGGGGTTTATCCTATACACATAGAGAATGCATATG

TAGTAATGATGTAGACCAATATAAAACATATACCTTCATGATCTCCATGTTCTTAATCTA

AATTAGACTAAATAAGATATGACTCGAGTAAAGATTAGTCTCACACTTATATAACAATAA

CATGAAAATGATACATATAAACCTATCAAAAAGGAGATAAGAAGTGGTAGATATCCTTTT

ATCTCCATGCATTTCATCCTTGTCATGATTAAGGTCCATCACCAAACAATGCATATCTAC

CACATCTCATCATCGGGAAATAACCTAGTTAACAACTTATGAAAAAGAGAGGTTAATCCC

ATAAACATCGATTTATCATCTATCACCAAAGCAACAATTACACAAATTGTTTAATCCAAG

ATCTTTCAATCTTTTCTGTCTTTTGTGATAGACAATAACCCGATATAAACAATAGAAAGA

GATGAGATGAAAGATAATTTCAAATCAAGGTAGAGATGTTATAATGAACAAAATATAGAA

TAAGCTCCCCCTCAAGATGTGCATACATATGGATATGAACGAATGCATATGCACATAATC

AATCAAGATCAATGAGGGAGCTCACACTATATTTTGGATCCACAAGAGAGACCAAATTAG

AATATGTGAAGTTTAATACATACCTCTCATCATTTTTACTTTCATATCCAAATAAGACTA

GTCAAAGAAAGGCTCATAAAAACGTTAGTCTCATATAATTAGATTTGTCATTAATCACTC

AAACCAAATTAAGGCAGTTGAACTTACACCCTCCTGTTCCGTCGTTCCCATACCGTCGTC

CACCATTCCCTCTCTTCTGCACGCAGCCGCCAACAGCAGCGCCGCCGCCACCTTCGGCCC

CAACGCGAACCAGTGAACCTTTGGCGGCCGAGGCAACTCTATGTTCGGCACCGGATGTAG

CCTTTGCAGCGACATGCAAGCGTTCATCGACCTCAAGACCTGGACGCTGACACTGTGTGA

CAACAGAGCCTGCCCCTATCCCTGCGTCTACCCCTGCCCCTCCCCCTGTCCGTGCCGATG

AGTCTATTGGCAAGGCCCCCAGGATGTTGTACAGTCATGAAGAAGACATTAGGCTGGTAA

GAATTTACTTGTTGATTTTAGTAAAAAATCGATCCTAGCAGTGTGGATGATTAATCTATG

CAAATAATAGAGGTACAGAGGTCTGTGTACCTGTGCTAGAGCATTTTAGTTAGGCAAAAT

GCGAAGAAACAACATCTGAATTTTGTAGAGGACATACTTGTGTACTACACTGAACATGCA

ATTAGATAAATAAGCATCATCTCAGTATTTGATTAGTGTTAAGCTAGAACTACAACCAGT

GTAAGAGTAATTAAGGTTCGGAATTAGAAGTGCCAATAGCTTGCTTTTTTGGTTTGCTCT

TCATAATTCTGTTTGCTATAAGAAGCAGAATGCTCTTCATCTTTTGTGCTGCCATCTATT

TGTACTATCCTGTTCATCTTTTGGTTTGTTGGATGTATACATTACTGCAAATATAGATTC

ATTGACCTAGTTATTTCCGGCAGGATGTTTCCATTTGGTTTGAGCGTCTCAATTATTTTT

CTTGTTTATCATGTATGACATTGCAGCTACCTAGGTAGGTACGATTAATTTAGGAGTAGG

TTATCATGCTGCGTTTTTGTAATGGTTGTAGGCAAGTGCTTGGCTCAAATGTTGAACAGA

TCCTATAGGAGTGAATAGGAAGGGTGAGACCTATTGGCTACATGTGGCCGAGACTTACAA

TGAGACAACTCTGGATGGAAGGAAGAGGGATCCCACCTGTCTCAAAGCGCATTGGCACAA
```

-continued

```
GATTACACCGAAGGTCACTTTATTCAATGGGTGTTGCGTGCAACTGAGGAATACACCTAT

CAGTGGGAGGAATGACGAGAAGCTCATGGATGATCCCTTGGCGCTCTACATCAACCGTTC

AAAGAAGCACAAGGCCTTCCTCTACCAATCGAGAAGTCTACCGCCGTGATGCGCATGTTG

GCCTATGGGTGTGTGCCGATCAAACCGATGAGTATGTTCGCATTCCTGGAACCACTGCG

TATGAATCCCTCGAAAGGTTCTGTGGAGGTGTTATTGCGGTGTTTGGTCGACAGTATTTG

AGGAAACCTACCTTGGATGATGTACAACGTCTCCTATATATGCATGAAGAACGTGGGTTT

CCTGGGATGTTGGGGAGCATCGACTGTATGCATTCGAGATGGATGAACTGCCCTAATGGT

TCGAAAGGGATGTACACACCCGGTGATTATGGTATAGCAACAATAATCCTCGAGGCAGTT

GCATCACGTGACAAATAGATGTGGAATTGATTTTTTGGTGTGACGGGGTCTAACAATGAT

ATTAACGTGCTCAATCAAAGCAATGTCTTCACCGATGTCATTATGGGTAGATCTCCCATT

GTGTGATACATGGTTAACGTGAATCAGTACGACTTGGGGTACTATCTTGCTGACGGGATA

TACCTGGAATGGGCAACGCTCATGAAGTGAATTCGTCATCCCCAATTGCCGAAAGATAAA

TTGTTCGCACAACGTGAAGAATCCGCAACAAAGCATGTTGAGTGTGCTTTTGGGATTTTG

AAGGCATGCTTCAGAGTGGTGGAAACTGCGAGGCATTTGTGGCTGATAGCTGACATTAGC

GATATAATGACGGCTTGTGTAATCATGCGCAACATGATCGTCGAGGACGAAGGACACGTT

TGGGATACTGAAGACTTGGAGTTTGAGGGTGACTACGAGATCGAACCTCCAGAACACACT

TTTGGGACAGCACAACATATTGCTAGATTACTTGAGCGTGACAGCCAACTTCAAAGTCGA

ACAATGCACAACCGTCTAAAAAATGATTTGGTGGAGCACATATGGGCAAGGTAGATCCTA

CACGTTCATGAACATTGATGTTTTAGGAAATAAGGTTATCTCGGAGGAGGATTGGTAGTT

GTTCGGAAATAAGGATGATTTGTCAAATCATCCAAGTTATCTAGGTGTAGGTGTAGTTTT

AAGAAAGAAGGAAGATTTCTCAAATGATCCAAATTATACAGGAGTAGGGGTAGTTTTAGG

AAGTAACGATGATTTCTCAAATCATCAAAGTTATCTAGGAGTAGAGGTAGTTTTAACAAA

GGATGATTTCTCAAATGTAGGCATTTACAAATATGAATGACCATTGTAAATAAATAAAGG

TGCTGTATCCCCAATTTGTGCATGCCATCTATATAAATAAATGAATTGCAATCGGTGCCA

TATAAAGTGCACAGGACAAAACAATTAGGAGATAATGAGCAACGGACCGACTAAGTTCAG

GAAGCCAACACAAAATAGGTCAGGTAGATACACCATCAACTAACCGAAACCCACAGACAT

ATTGCTTTGACACATGCCATCATCCACCTTACAGACACCATACATAACCCATATCACAAC

ATTACACAGTTGAGAGTGCTACCTAAATATATAAGCATGTTATATATCTGTTGCTTGCAT

ACTATCCATGTTGTCACGCCATGAACCTAACCCTGCAGGGAAAAAATACAGCATGTGAAA

AATGGTTGTGAATTTTAAATAGAGGGGGACATTATATGCACCCGTATAGTTAGCCTCAAC

CATTGCCATCAATACTTAGTTACAAACATAACTCATCCTTCAACTACAGTGACCTAATCA

TGCAGATTAGGCACATTGCAACTCATAATAGCAGAGATTTGAGATCCCAGAGCAATCGCG

GCTTTCAATTTTGGTAGTTAGAATTCACATGTTACTTCTTGCACATATCTGCATTACAAC

ATCTACTTCAGTCAACGAGTTCTGAAGTACAAACACTCTGTCCATCCCCCAATGATCATG

TCTAGGGGAAGTATCAAGAACCATGCACTAAACTAATCATACAGCCAATAACTAAACTTT

ATGAATTTGAGCAAACATGGCACATCCAACCTCTCCATATATTTTAACAAAGGAGCAGA

GCCCTCCATTCCAATATCTCAAATGACAACAAAATCATCCCACATCTCAAATTACAATAA

AATCATGAAACAGCTCAAATGACAAAGAAATTTGAAATGACATTCGAGTGAGATCCAAAA

CTTCTTGGCTGCTACAGTAGATGGAGAAGCCACTGGCGCGGGTGTAGCTGGAGCCAGCGC

CGCATTCACCTTCTCAAAACCTGCTGCCACCTCCGGGAAGCCTAAACCTCCCTGCGCCGC
```

-continued

```
ATCTGCCTCCCCCTCCACAGCGATGACCCCGAGATAGATGGACGACCCGACCCTCTCCCC

CCTCACCGGCGCCGGCGTAGATCACAGGCGCGAAGTACCTGCCCCTACCGCCGTTCCCCT

ATTCTTCTTCCCGCCATCCCTAGGCACTGTGGACGGGGTATAGCCCGGCGGGAGCAGCAC

AAGGCCACTACGGAGCTCAATCTGCGTGAACTTGGGGCGGTCGTCCATCGTTTCGGGCGG

ATCAGAGGACCCGCGGAGTGGGAGGATGAGACGACCACCGACGGGACTGAAGCGCGCCGA

GAGGCGGGCGAGGCGGACAGACTAGAGAGAGGGGATGGAATCGTCGAATGGTTACAGTCG

GTGGCGAGGGAACCGCAACGCCGTGTGTGCCGGAGTGCGAGGACGCGGTAGCGAGAGGAG

GGAAGGAGCCATGGCGACAGGTGGTCGAGGGCTCGAGGCGGAGAGCGAGAGGAATGGCC

GAATGGATAGGATCGGCATCGTCCAGCCAGGGTAGGTGGGGAAAAATTTTTGGGGCGGC

CCATGACCTCGCGCTAGCATAGGCATGCCCATTGTGGGCTTCGTACCCTTTACCAGTGCC

TCCATTGAATTAAGCTACACAACTACAGGTGCTTGCACTGTCGGATAAGTGTCTATGGAC

CAACTTTTTGGGCTAGGGGTACCGGCCCCATACCTTGCACTGTGAGAGGCC
```

Deduced amino acid sequence of PONG_LIKE_6 ORF1 in *Oryza sativa*
(SEQ ID NO: 58)
SAWLKCSTDPIGVNRKGETYWVHVAETYNETTLDGRKRDPTCLKGHWHKITPKVTLFNGC

CVQLRNTPISGRNDEKLMDDALALYIKRSKKHKPF

Deduced amino acid sequence of PONG_LIKE_6 ORF2 in *Oryza sativa*
(SEQ ID NOs: 59-61)
PIQKCTAVMRMLAYGVCADQTDEYVRIGGTTAYESLERFCGGVIAVFGPQYLRKPTLDDV

QRLLYMHEERGFPGMLGSIDCMHWRWMNCPNGWKGMYTRGDYGIATIILEAVASRDK*IW

NSFFGVTGSNNDINVLNQSNVFTDVIMGRSPIV*YMVNVNQYDLGYYLADGIYLEWATLM

KSIRHPQLPKDKLFAQRQESARKDVECAFGILKACFRVVETPTHLWLIADISDIMTACVI

MRNMIVEDEGHVWDTEDLEFEGDYEIEPPEHTFGTPQHIARLLERDSQVQSRTMHNRLKN

DLVEHIWAR*

Nucleotide sequence of PONG_LIKE_7 in AC097279 in *Oryza sativa*
(SEQ ID NO: 62)
```
GGGCACGTACAACGGCATTAATTAGCCGGCTCTCTCCAGTGCCACATAGACAAATAAGAT

GACGTGGAAGAGAGATGATAGATGAGAGAGAAACAACGATGCTATCTGTGACATCGCCGA

AGCATCGGCTCCTCTCGCGCAAAAAACGAGCAGAGTTGAGGAGAGCCCACCATTGTAGAA

TTGGTTTTTGCTGCAGAGCTGGGCCTCGAGATCCAATGTAAAAAAAGCGCGCGGAAGAAA

TTTGGCGCGGGTGAGGGATCGAGATACGGGACCGCGGGAATCGGAGCAGAGATCCGCGCC

ATCCAATTTCTTGGATCCCCAAATATGACGCTGAAATCCGCAGATGGGGTTCCAGTCCAA

TACATCGCTGCTACGCTCCTCCACCTCACTGCAGCCTTGGATCGTCCACCTCGCCACCAA

CGTTTCCCCTCCACCTCGCCGCCGACGTTGCTCCTCAACCACTCCCTCCATCGGCGTTGA

CTGTATGGCTGGGAGACGGACAAAGGTGGCATCGGTGCCTGAGACATCCTCTGGCGGTAC

CAACACTTCCGGCTTCCGCTTCACCTCAACTGATACCCCCGCTGCCACTGGTACCTTCCC

TCCCTATCTTCCAATACCTCCCTTCTCTGCATCTAGGATGAGCGCGGCTACGACCGGCAG

CCATATTTCCGCATCTCCTTCATGGATGCAGACCGACAAAAGCTCACATAAAGCTACTAC

GTCGGATTTGTCGTCACCAGATGCAAATATCCAGAGCTCGTAACCACAAATCCCACCAAT

AATCTCTGCTATGTTATGAAGATTCAGTTCTGCAAGTTTTCTGTTCTCTGAATGAAATTA

TTAAACGGTTGCCATGTTCTAGACTTGATATATTTTCTGAAATACAATGAGTAAAGCAAT

GCAAGATTTTCTGAAATACATCGTTTAAAGCAGTCCAAATAAATTGACATATAAATATTG

GTATATAATCCATAAGGTTACTGTTTGTTCAGATAGGTATATAAAGATTATGTTATTGTA

CATCTTTGGTCATGCTGAAACTGAAGAGACATATATTTCCAATGTTATGTTATTTCTCTG
```

-continued

```
TACAAACTAAGGTTTCTATATTTTTTGGGAGTAGGCATTTGTTTTTACAGATTATGAGGT

TGTTACATGTTGTTTCTTCATGTACGTGTGTGTTGTTTGTTATAGGTTTATCTTAATGAT

CAATTGGTTATGGCACTGAAATTGTGAGCTTCTTGCAGGGGAAATGGTACACACCCACCT

GGAGGATTCATGAGTTTTTTTCACAATCAGCCAAATATATCTGAACATTACAATTTTGTC

CCCGCGTCTTCGCACTACACACCATTACATGCTAATGGTTCTTCGCCACCGCTTCCTAAT

GGTGCTTCTATGCCGCTTGCGACACCCACTCCACCCCCACTTACTGGGAACCAGGACCAT

GTCAATGTTGATAGTGATGATGACACTGCGGTCGCTCGGACCAAATTGAAGCTAAATTGG

ACCCAAGAGGAGGATGTCAGACCACTGAGAATGATCCAAATTTTACTTGATTCGCATTCT

GAATCTCTGTCCATAATTACACTTTCTTTTGTTATCTTTGTAGATGACCGCTTGGTTGAA

GAATTCAATGGACCTAATTAATGGGAATGATAAGAAGGCTGAAAAATATTGGGGAGATGT

TGCTACAGAATACAATAAAACCACACCACAGAATAGATGGACAAGCCCAAAGCAAGCCAA

GGAGCGGTGGCACAAACTCAACACTCGGACGGATCTGTTCCAAGGCTGTTGGTTGAAGGC

TAAGCGCACATATACTACTGGTTACTCTGAACTAAATGTGGATTGACATGGCCCATAAGT

TCTATGAGGCTGATAAGAAAAAATTACGACGGTTCGTCCTAATAGATGTATGGTACGCAT

GCTCTCATCAGCCTAAGTGGAATGCATATAATGATGCACTCAAGAGAGATCGTAAAAGGA

AGTCGTCTGATAACAGAGAGATGCTTGGGCAAGCATCAGGACCTTCAGATGTTGAAGAAA

CCCCATGGCCAATCGGACAAAAGGCTGCTAAAACCGGTGCACGTGAAACCATGGGAAAGT

TGAACGATATTTCTGATGCTGAAGAGATACACAAGTTAGACGAAGTGCAATCTGATATTC

ACACAAGATGCATGAAGATGATGGAAATGCAAGAAGTTATGTACTCGTCAGGTTCAATGA

TGAAAGCTTTCTCAAGTTGCTGCACGGGAAAATAGATTAGTTGCAAAGGAAAATAAGGAT

GCCAAGATGTTCGAGACCTATAGTTGTCTACTCGCACAGGACACAACTGGGATGGCTGAT

GACATTAGAGCCGAGCATGTCACTGCCATAAGGTGTTTGACCAAGATCTTGTTTCCGGAC

TTATCTTGAGCTTAGTTAATAATTTACTGGAAATGATTTAATTGATTATGACCTAGATTA

CATATTAATCTACATATCATGTGACCTGAAATGTCATTTGATTATATATGATTTCATTGA

ACCTGAAATGTGGGCATGTTCTAGATGATATCTGTTCAAGTTGCTGAAATGATAATATAG

GCTATAATGTTAATAGCTTGCTGTATGGAGCAGTGTTTCTTTAAGCTTGCTATAGGACTG

TTATTGTATTCCCTATTATGTAGAAGTAATATTGAGCTCCGTGTCTTCAAAATTATTGCC

TAAGTGGACACTTTGGCAGACAACAAAACAAGCTCCAATTCTGACTTTAAGATCAGTATC

CGAAATTGAGCAGTGATTCAATCTGAAATTTGTGATTGTTGGGCATGTTTATCTTTTGAA

TTTGAATAGTATATATTGATATATTATCTCACTGAAGCTGAATCTGAAAATTTATATTTA

TGTAACTGAATCTATTTTTTTAGTATGTCAGGTAATAATATCTGGAAGATCTGTTCAATG

TGGATGACATCTATGCCATTGGAAGAATGCAATGTGATTTGCTGCTGCACATGCAACTGG

TCCATCTGATTGCGAAGCAAGGATAAATTTACTTCCTAGTTATATGAACATGTAATAATTC

AGTTTGTTCCTATCTGAACATGTCACCTGGACCATGATATTCATTCCCATGTGATTTTTA

TATCTTTTACCTTCCCTCAAATAATGACACATGTTCGTATTCTAATATAAATGATGATTT

TGTTTCCTTTATTCTGTCAACATGCTATCTGCATATCTGTATACATGTCGTTTAAAATTA

GAACGATAGAACCAGTACATGTCGAGTCCAACAAAGAAGTCCAATCTTCTAGATTGTCAG

ACCATACGATGTCTCCCAATAATATCGACCACCTCGATGATGATGTCGTCGTCGACGCTG

ACCTGGCATTGAGGATGATGCTGTCATCGACCTGGACCTCGACGATGATGCCGCCGTCG

ACGCCGACATGGACCTCGACCTCGACCTCGACGATGATGCCGTCGTCGACCTCGACCTCG
```

-continued

```
ACCTCGACGATGATGCCGCCATCGACCTTGACAACTTTCATCCTATGAATATATACAGCA
TGGATGACTTTATAGCTGAAGCAACCTTTTTCGATGAATATAGTGAACAGATTATTCTCA
GGTTGAAGGAGAACATAACATCTGAGCCACCTCGTCGTCTACATCAAACTGGTACAAGAC
GGTATATACCAAGAAACCGTGAAGCTAGCAATGCGGATCTTGTGGCCAACTACTTCTCCG
AGTCTCCAATCTACACAGATAAGATGTTCCGTAGGAGGTTTCGGATGAGGAAGCCTCTCT
TCCTACGAATTGTGAGTGCCCTTAGTGAATGGTCTCCTTATTTTACTAATAGATTGGATG
CCACTGGTAGAGCAGGACATTGACCACTTCAAAAGTGTACGGCTGCTATTCGTATGCTAG
CATATGGAACTCCTGCGGATCAACTTGATGAGCTATTAAAGATTGGTCCTAATACAGCTT
TGGAGTGTTTGGGAAAATTCGCTGAAGGAGTCATTCAAATATTTCGCAAAGAGTACTTAC
GAGCTCCTAGGACTGATGAGGTTGAAAGATTCCTACAGGTTGCTGACTCACGTGGTTTTC
CTGGCATGTTAGGAAATATAGATTGTATGCATTGGGCATGGAAAAATTGCGCGGTCTCAT
GGTGTGCCCAATTTACTCGTGGTGAGAAGGGAGTTCCTACCATGATTCTTGAAGCGGTAG
CATCGAAAGACCTTCGCATATGGCATGATTTTTTGCTACTGCAGGATCGAATAATGACA
TCAATGTCTTAAACAAGTCACCCTTGTTCATTGAAGCATTGAGAGGGGAAGCTCCTCGTG
TACAGTTTAGTGTAAATGGGAACCAATATAACACATGGTACTATGTTGCTGATGGAATTT
ATCCAGAGTGGGCGAGATTCGTGAAGACAATACAGCTTCCTCAAACAGACGAACATAAAT
TATATGCAGCTCGTGAAGAACGAACAAGGAAGGATGTTGAGCGACCCTTCGGTGTGTTGC
AGTCTCGCTTTAACATCGTTTGTCGTCTAGCTCGGATGTGCAGGCAGGCCGATGTTATCA
ATATAATCGAAGCTTGTGTTATTCTTCGCAATATGATAGTTGAAGATGAACAGGAAATGG
CTGAAATTCCTTTCGATTTAAATGAGAAGCCAGGAGCATCGTTCGTTCTACCACCTGAAG
TGACGAACTCATCTGACCCCAACCGTTGCTTTGCTGCGGTATTACGAAGAAATTCATCTA
TTCGTGATCGTGCGAAACATATGCAACTGAAGAAAGATTTAGTTGCACATATATGGCAGC
GTTTTGGGAAAAAGTACAACTACTTTATGTAATGAAATAATGTAATTTAGCTTATCATTT
GATTAAATAATAATTTCGGATGTGTGTGCTGGTAGGATCCACATCGTCTTCTTTTATATG
GTTATCATACCAGGATGTAGCCTTAGTTCTATAGAGAAGAAATACAAATATATGTGCTGC
TGAAATTTACATTTGATTACATGCAATGAATTTATTAGCTATTTATTACCTTGTATTAAT
AGAGAGTTGGTTAAAGAGACAGTTCTTTGTAGGTACGAGTTTCTTCGCTGATGTGGAGTA
TAGAGAGAGACCACACCCAGCTGTACCTTTGAACATGCCC
```

Deduced amino acid sequence of PONG_LIKE_7 ORF1 in *Oryza sativa*
(SEQ ID NOs: 63-77)
MSFFHNQPNISQHYNFVGASSHYTPLHANGSSPPLANGASMPLATPTPPPLTGNQDHVNV

DSDDDTAVARTKLKLNWTQEEDVRPMSAWLNNSMDLINGNDKKAEKYWGDVATEYNKTTP

QNRWRSPKQAKERWHKLNTRTDLFQGCWLKAKRTYTSGYSELNVD*HGP*VL*G**EKIR

TVRPNRCMVRML*SA*VECI**CTQERS*KEVV*TERCLGKHQDLQMLKKPHGQSDKRLL

KGLHVKAWES*TIFLMLKR*TS*TKSNLIFTQDA*R*WKCKKLSTRQVQSSKLSQLAARE

NRLVAKENKDAKMFETYSCLLAQDTTGMADDIRAEHVTAIRCLRKILFPDLS*

Deduced amino acid sequence of PONG_LIKE_7 ORF2 in *Oryza sativa*
(SEQ ID NO: 78)
MMILFPLLCEHAICISVYMWFKIRTIEPVHVESNKQVQSSTLSDHTMSPNNIDHLDDDVV

VDADLAIEDDAVIDLDLDDDAAVDADIDLDLDLDDDAVVDLDLDLDDDAAIDLDNFHPMN

IYSMDDFIAEATFLDEYSEQIILRLKENITSEPPRPLHQSGTRRYIPRNREASNADLVAN

YFSESPIYTDKMFRRRFRMRKPLFLRIVSALSEWSPYFTNRLDATGRAGHSPLQKCTAAI

RMLAYGTPADQLDEVLKIGPNTALECLGKFAEGVIEIFRKEYLRAPRSDEVERLLQVADS

RGFPGMLGNIDCMHWAWKNCPVSWCGQFTRGDKGVPTMILEAVASKDLRIWHDFFATAGS

NNDINVLNKSPLFIEALRGEAPRVQFSVNGNQYNTWYYLADGIYPEWATFVKTIQLPQTD

EHKLYAAREEGTRKDVERAFGVLQSRFNIVCRLARMWRQGDVINIMEACVILRNMIVEDE

QEMAEIPLDLNENPGASFVLPPEVRNSSDPNPCFAAVLRRNSSIRDRAKHMQLKKDLVAH

IWQRFGKK*

Nucleotide sequence of PONG_LIKE_8 in AC091774 in *Oryza sativa* (SEQ ID NO: 79)
GGGCAAGTACAACGGTTCACCGACACCCGTCCACATCCAGTCTTTTTTTGCCAAAACCCC

CCCCCACGCCGCTCGCTTCGGCCCATCCCTCCTCTCGTTCGTCGACGAGGCCAGCCCGTG

CTTCGAGGCCAAGCCACGGCGATGAACCCCATTGTACGACGCGATGCGCGGACGCGACCC

ACGCGCCGGATCAGCTCCACCGGATCAGCTCTCTCCCCCGCGGAACAGGTTCGCCCCTTC

CTCCCCCGCCAAAATCTCTCTCGCGCCTCTTGAAATAGCCCCCCCTGCCTTCCCCATCCA

ACCCTATTTCCATTTGCCCACCATCTCGCGGCAGGCACGCAAGGAGCCGCCGGCGGCGGC

GCAAGATATCCTGAAGTTGGATGCGGCTCACATGCCCAAGCCACCTGCATCGCAATCTCC

AAAGCCTGCCCCCCCGCCGATCCGCAAGCCCCAGCGAGGAGCTCGGGCGGCCTCGATGGT

CCCGGAGCAGAGCAGTTCACGCTTGGCGCCCCGTGTGCCAGAGCACCCCACTTCGAGATA

TGGCGCGCCTAGTCCACCACCAACCTCCTTCACCGACGGCACCTGCTTCTTCAACGGCAC

TGCCGGCGGCTTCTTCGGCAACGCCGGCCAAAGCCCTAGTGGTCAACCATGGAGTTCTTA

ATCTTCACATCCTGCAACATGGTACTATCTCTGAACTTTGCTTCTGTGATGAGCTCAATG

ATCCGAATCATATGGGTAGGAATTAATTTTAGATGTTATTTCCAGTTCCCTCCCTTATAC

AAGATTTGGGATACACTGTCATGAGTTTCACTATTGTGGTTGATCCAAAGATTGATTGCA

CTGGTGCAGATTTCTTTGATAGTTTAATAAAGCTATGTAACTAGTTTTTATCCACTGTAT

AACATCAAAGAGGATGAAGCACTGAAAGAAACATTAGTTCCTACTTTTACACATAACATT

AGTCCCTAGTTGCTTTCATTGCTCATATATATGTGTAAAATATGGCAGGGGAAACAATGC

AACACCTCTTCCAGCCTTCATAAACTTGATGCAGCCTAACTTGTCTCAACAATTTAATTT

TGTTGGAGACCAAAATCAGTCAGAAGATGATTACTCGACTCCTATTTCAGCTAGGGACAA

TAGATATGTTAATGTTGAGAGTGGTGATGAGACACCTAGGACTGAGAAAAGAATCTTTTG

GACTCAAGAAGAAGATGTTAGGATGGTGAGTCTCACTGTAAATTCACTGTGTTTATAGTT

TTTTTACTTACCATAACAGTCCAAGTGATAATATATGCTAATTAACATTTACAGATGAGC

TCTTGGCTGCTCAATTCAACGGACTCAACCGTTGCTGCTCATAGGAAGAATGAACAATAT

TGGACTGATGTTGAGGCTACTTACAATGAGACTACACCAAGTCATACGAGAAGAAATGCG

AAGCAAATCAAGGACCGCTTTGATAAGGTAAATAAGTGGACTGAGCTTTTCCATAGTGCT

TGGTTGAAGGCTAGAATGATTTATACAAGTGGCTATAATGATCAAATGTGGATTGAGAAG

GCCCATGTATTCTATATAAAAGACAATGAGAAACTCAATCTAGGTCCTTTTGTGTTGATG

GAAGTATCGAACACAGTTAAAACTGAAGCAAACTGGATCACATACAACAATGGCCTGAAA

GCAGCAAGAAAAGAATAGCAACAAAGGGGTTAGGCAAGGAGAAGGAAGGAGAGGATAGT

AGCCCTTTATATCTAGATGAACTTGATGAACAGGCAAGACGAATCCGGCAAAAAGAGCT

AAAAAACTAGAATATGGGCAAAGTAAGGAGCTGGACCATATTGATCTTGAGGAGCTAGAC

AAATTTAGTAAACTCCAGAATGAACAGAATGCAAATAGGCTGAAAGTATTGGAAATACAA

CAGAAGCTATCATCCGAGAAGATCGAACAAACAAAGATTTCCCATCTTGCAGCAAACCAG

CAAATGGAGGCAGCAAAGGTGCAAAGAGAGGCAAGAAAATTAGACCTTCAAGCTAGGATG

-continued

```
TATGAGACATATAACCGCCTTCTTGTAGTTGACACAAGTCTGATGTCCGATGAAGAGAAG

GTTGACGATGGAAATAGATTGAAGTTTTTGAAGAAGAAATTATTTACTGATAATTGACCT

GAGTTTCATGTTACTTCTCTGTCTAGCCTAACTTGTGTGAATTTTGCTATGTTCTATCA

ATTTTCCTCCATGTTATCAATGTTATATATCTGCATGTTATTTTGCTATGTTCTATCAAT

TCTGCTCATATTTACTATTTGTCTATCCTAAATTCTGTAATTGGGACCTAGTACTTTTGC

AGGTCTTGGAGAAGATTGCTTGCTATGTTACTGTAAGGGGTGAGAAGGCAATGCAGCTTC

TGGAGATTGGACTGAAGCTCAAACAATATGAACTAGTCTCTCTTTTCCTATGTTTTGGAA

TCCAGGAGCACATCAATTGCTAATTCGAAGTAGTCTCTGTTTTGCTATGTTCTGTTTCTG

GGATTGTTTTTTTTTGGCTATTGTGAACTGTTTTTTGTGAAGTGAAACCTCTCAATGGA

ATGTGAACTGATGGGTCATTGCAATGTGAACTGATATGATGTGAAATCGAATGTGAAATG

ATAAGGCAATGCCGTGTATGCATTTGTATATAAAATCAACTGCTCTGTGACTTGTATGCA

TCACAATTCTGGCGATCGAGGCCTCTGGTGCCTCTGGTGGCGACCATCCTGGTGGCGACG

ATGAGGGGTCTGGTGGCGAGTTCTTCGCCTCTGGTGGAGATGGAGGCGATGAAGATACTG

TCCTTGAAGAAATCGATCCAGCGGAAGTATATACACTTGAAGATTTTCTGGCCGAAGATG

AAATAATCGAATCATTTCGAAGGAAGATTGCCGATAAATTGAAGCCCAAAATCGAAGGAT

CTTCTTCTGGTCCACCTCGTCGTCGCCAGCCTCAAAGTGGACCTAGAAGGTACATACCTA

GGCCAAGAGAAAAGGGACATGAAGATTTAGTTGCTAATTATTTTTCAGCAAATCCTATCT

ATACTGATGAGCAGTTTCGGACGAGGTTTCCCATGAATAAGCCTTTGTTTCTTGGAATTG

TCAATGCCCTGTCTAACTGCGATCAATTTTTTACCCAAAGAGTTGATGCAACAGGTCGAG

ATAGCCACTCACCTCTCCAAAAGTGCACCGCTGCTATTCGAATGCTAGGATATGGCACAC

CAGCGGACGCACTAGATGAGGTACTCAAGATTGCAGCGACCACTTCTTTCGAATGTTTGG

GAAAATTTGCCGTAGGAATAATTGAATGTTTTGGTAGCGAGTACTTGGGTCGTCCGACAA

GTGATGAACTAGAAAAAATTTTACAAGAGAATGAAGCTCGTCGCTTTCCAGGCATGATAG

GAAGTATTGATTGTATCCATTGGCAATCCAAGAATTGTCCAAAAGGTTGGGCAGGAATGT

TTATCAATGGTTTCAAAGGTAAACCTACAATGATCCTTGAAGCGGTAGCATCTCGGGACC

TTCGTATATGGCATGCTTTTTTGGCAACGCGGGGTCTCAAAATGATATCCAAGTGTTAA

ACAAGTCACCATTGTTCATTGATGCGATTAAAGGAGAAGCCCCCCGAGTGAGTTATACTG

TAAATGGAAGGCAGTATGACACGCGGTATTATGTTCCCGATGGAATATATCCCGAGTGGG

CTGCCTTCGTGAAGACAATAAGAAAACCTGAAACGGAGAAACATAAATTATATGCACAAC

GACAAGAAGCGGCGAGAAAGGATGTCGAGTGTGCATTTGGGGTGTTGCAATCCCGTTTTG

ATATTGTCAACCGTCCAGCACGGTTGTGGAAAAGGAATGATGTTGTTAATATAATGCAAG

GTTGCGTTATCCTCCATAATATGATAGTGGAAGATGAAAAGGATTTGGTTAAAATCCCAT

TGGATTTGAATGAAAATCGAAGTGCAACCATTGTCCTACGACCGGAAGTGCAAACAAATG

ACAATCCTAATCCATGCTTTGTCGACGTGCTTAACAGAAACTCGGCTATCCGGGCTGCCT

CTACACATCGACAGCTCAAGAATGATTTAGTTGAGCACATATGGCAGCGATATGGGCGAA

GAGCAGGTTAGAGCCATGTGTCCAATGAAATGGTGACTTTATTATTATCTCACATCATGT

ATTTCTAAGATCATTTCATATATAAATATATATAATTATTATATACATGTTTAGTTTACA

AGTCATGCGGAATATTTAAATGTACTGTGCATTGTCTTATGTATCCAATAAAATGACTAC

AAAGATCAATTATACACTAGATCATCATGATTTGTGTGTCAAAGGATGAATTAAACACTC

CACAGACAGCCAAACCAACAACCCATTGTATAAGCTGTCTGTTTAAGCTGTCTATTTGTC

TAAAAAGACAGCAAGCTGTCTACACGGTTGTTACTTGCCC
```

-continued

Deduced amino acid sequence of PONG_LIKE_8 ORF1 in *Oryza sativa*
(SEQ ID NO: 80)
PLGGFINLIQPNLSQQFNFVGDQNQSEDDYSTPISARDNTYVNVDSGDETPRTEKRIFWT

QEEDVRMMSSWLLNSTDSTVGADRKNEQYWTDVEATYNETIPSHRRRNAKQIKDRFHKVN

KWTDLFHSAWLKARMIYTSGYNDQMWIEKAHVFYIKDNEKLNLGPFVLMEVWNTVKTEAK

WITYNNGLKAARKRIATKGLGKEKEGEDSSPLYVDELDEQPRPMGQKRAKKLQYAQSKEV

DHIDLEELDKFSKLQNEQNANRLKVLEIQQKLSSEKIEQTKISHLAAKEQMEAAKVQREA

RKLEVEARMYETYNRLLVVDTSLMSDEEKVDHGNTLKFLKKKLFTDN*

Deduced amino acid sequence of PONG_LIKE_8 ORF2 in *Oryza sativa*
(SEQ ID NO: 81)
MEASGASGGEHPGGDDEGSGGEFFASGGDGGDEDTVLEEIDPAEVYTLEDFLAEDEIMES

FRRKIGDKLKAKIEGSSSGPPRRRQRQSGPRRYIPRPREKGHEDLVANYFSANPIYTDEQ

FRRRFRMNKPLFLRIVNALSNWDQFFTQRVDATGRDSHSPLQKCTAAIRMLGYGTPADAL

DEVLKIAASTSLECLGKFAVGIIECFGSEYLRPPTSDELEKILQENEARGFPGMIGSIDC

MHWQWKNCPKGWAGMFINGFKGKPTMILEAVASRDLRIWHAFFGNAGSQNDIQVLNKSPL

FIHAIKGEAPRVSYTVNGTQYDTGYYLADGIYPEWAAFVKTIRKPQTEKHKLYAQRQEGA

RKDVECAFGVLQSRFDIVNRPARLWKRNDVVNIMQACVILHNMIVEDEKDLVKIPLDLNE

NPSATIVLPPEVQTNDNPNPCFVDVLNRNSAIRAASTHRQLKNDLVEHIWQRYGPRGG*

Nucleotide sequence of PONG_LIKE_9 in AP003199 in *Oryza sativa*
(SEQ ID NO: 82)
GGGCATGTACAACCCGTCTCCTCGCCCCGTCTCTCTCTTGGTGATTTTCCAAAAAAAACC

CGTCCACCCCCAGAGACGCCCAGCCCGCCCCCTCCCGACGCGACCAGTTCATCGCGTTCT

CCCACGTGGAGTCGACGCCACCCCACGCGCTGTAGAGCCCCGTCATCCCCACCCGACGGG

CGAACGGATCCCCCGTCCCGCCGCCCTCGCCCACAAATTTCCCAGGCAACCACGCCCCCT

GTTCTCCCCCGCTCTCCTCCCGACTTCCCCGAAATTTCTTCCCCCGCCCATCTGCGCCGC

CCCCATCTGCTCGCCCCCCATGTCGTATTCTCGCCGGACTTGCTCCGCCGGGATGTCCAC

GCCCGGCGCACCTTCCAGAAGCAATGGATCGAGGACATTGCATGCCGCCGCGACCGCCCC

AGGCCGAACCCTAGGTGTCGGGGCGGCGGCGGCGGCTCCCTCATTCGGTCGGCCTTCTTT

TGGTCACGCTGTCGGGCTACCACCCCCGCCCCGTTCTCGCGGACACGGTCGCGGGTGAGT

ACCGGCAGCGACGACCGTCCCCGCTTTCTCGATTGATGCTTCTGTCGGAGCTGACTTCAC

CAGGTCAATTGGTCCCCATCCATCGTGTCAACGTTGGTTTGATGCGCCCGGCGGTGATCC

CTCATCTCCTGGATCATGGTAAATCCTTGTTTCATTGCTGATTTTCTAGTTGATATTAGG

CATTGTGAATCTAGATAATTTTGTAGTTGATATTAAGCATTGTGAATCTGTAAATCCCAT

ACTGTTGTACCTGGATCCCTTTTATACCATATTTTAACAATCTCCAGAAGTGATTCATTG

AACTCTTTGTTAGATATTCAACTGATAAATGATTATGATAAAAATGAGCCCATCAAGCTT

CTGTGTCCAACATATTGTACTCTTTGTTAGTTGTTCTTAAAGAGTAAAAATACCCATCAA

GGTTCTGTGTCAACTGATCATTTTAAGCTAATTTCATATTTTAAGCTAATTTCATGTTAA

GCTTCTGTGCGGAAATCATTTTAAGCTAATTTTACCTTCTAACCGTTGATAAATACAGCG

ACAATAGTAGTAGTACTGCATCTGAATTTTATTTGTAGATGGACCATGGAAAATTTGATG

TTAATTGCAATTTCGTGCAGGGACCAAGATGTACGTCCACCTGGTGGTTTCATGAGCTAT

TTTGGAAATGAAGCACAGAACTCTCATTTCGTTGGTGCAGTTATTCACATGAGTCCTCTC

AATCAGGCACACAATGGTAGTTCACCGCGCGAAGTGGAAATATTACATGGCAATCACAGT

GTTAGAACCGAGAAGAGGATCATGTGGACTCCGGACGAGGATGTTAGAGTGATGAGCGCT

-continued

```
TGGTTAGAACATTCAACCGACTTTACCTGTGGTGCGGATAAGGGTGCTGTGCAATATTGG

GGTGAGGTTGTCGAAACGTACAACAAAACTACCCCTCCACTTCGAAGAAGAAATGCGAAG

CAATGCAAGGATAGATGGAACAAGATTAATAAATGGACAGACCTCTTTGAATGTGCTTAC

GCTAAGGCTCGTAGAGTATTTACAAGTGGATATTCGGCTGAAATGTGGCTTCATGCAGCA

CACAAGTTCTATGTGGATGACAACAAAGAATGCAAAGACGTCGTTGGACCTTATATGCTG

ACAGAGGTTTGGAAAATTTGCCGAGATGTGGCAAAGTGGAAAACATATAATGAAAACCTG

AAGAATGCACGTAAAAGGAAAGCATTCCATCTGGAAGGAGAATCTGAGGAAAATGAGGAC

ACTTGTGATCAGATGCCACAACGACCAATTGGTGAGAAGGCAGCTAAAAAGCCAGCTCTA

GCTGCTAAAAATGGCAAGTTAAACGGTTCCAGCAGTAGTGATGATGGTCACTCAAAGGAT

TCTCCTATTGAGCTAGACAAATTTGATAGATAGACTAAATTTTAGGAGGCAAACAATGAG

AAGCCTATGAAGCTATTGGACAGGCAAGAGAAGATAGCTTCTGAGAAGCTAGAGGCCACA

AAAATTCCCCACCTTACAGCACAACAGTAGAAAGAAGGAAAGAAGCTTGATAAAGAGACA

AAGATGATGGAGACTTATAACAACCTCGTTTGACAGGATACAAGTTCAATGTCCGATGAG

GAAAAGGCACAGCGAGCTATGATGATGAAGTGTCTTATGAAGGCCCTTTTTCCTGAAACT

GTTTGAGAAGGTATTTCTTATCTGTGTACTTCTGAAATTTAGCACTTGTAGTTCTGAAAT

TTAGCACTTGTAGTAGCCATATATGAACCTCACCCAGTTCTGGTATGAAGATATGAAGTT

TCTGCTTATTTAGTATTCTGTGACAAACTTGTTAAATTCTGAAATTCTGTGACAAACTTG

TTAAATTTACCACTTGTAGTAGCCATATATGAACCTCAGCCATATATGTTCAGTTTTCTG

CTCATTCATGCTTTTTTTTCTGAAATTCAGTTTTCTGCATATTCAGTAGCCATATATGA

ACCTCAGCCATATATGTTCAGTATCAATGTTCAGTATAGTGGTAGTTTTGCCGTGTTTTC

CCTTACTCAGTACCCAGCCATATATGAACCTCAGCCAAATTCAGTTTTCTGCTTATTCAG

TACCCATATATGTTCAGTTCTCCCTTACTCAGTTTTGCTCTATAGGCCATAATGTAAATT

CTGAAATTATGGTATCCTGGTAGTTTCAGTTTCAGGTATCCTGGTAATTAAATTCTGAAA

TGCAATTAAATGTGAAACTGCGCATGATTTTCTAAATGGTAATGACACTGCTTTGTGAAC

TTGACACTGTGTGTCAACTGAAACTGATCGCAGAGGATGATATTTTTACTGTGAACTG

AAACTGAAACTGTGTGTGAACTGAAACTGTGCTTTGTGAACTTGAATGTGAACTGAAA

CTGCGCATGATTTTCTGAATTGTGTGTGAACTTGAATGTGAATGGAATGGTCATCTTT

TTACTGGTGCCGGAGTTGATCAGTTTTCTGAAATTCAATGCTGAACTTGAATCTAAATGT

GAATGGTCATCTTTTAAGTGGTGCTGGAGTTGATCAGTTCATCAGTTTAGCCGCTGTAGT

GCGACGTTGATCTTTTTAGTAGCTTGAATGTGCCACTTGAATGTAAATGTAAATGCTGAA

TTTGAATGTAGCTTGAATGCTAGTAGTTGATCACTTTAGTGGTGCCGATCAGTTTTTGTA

AATATGAATCGTCATATTTTTTATTCTATAAAACATCGTTGTTCTGTGCGCTCCTCTGT

ACACTACTCCACCATCCAAACACTTGCATCAAAGAAGGTGTATCGTAACTCTTTGAATGG

AGCCGCACGAAGAAGATGAAGTCGAAGATGCCGAAGAGTTTGAAGAGGTGTTCACCGTGG

AAGACTTAATCGTAGAGGATGATATTTTTGAAGAAATAGTACCAGAGGGATTCAAGGCCG

ACATGGACAGAGAAGCATCGAAGCATCGACTGTACATCGCCGACGTCGACAGAGTGGACC

AAGGAGGTACATACCAAGGAATCGAGAACAAGGTCATGATGATCTTGTTGCTAATTATTT

TTCCCCAAATCTGCTAATTATTTTTCCGCAAATCCTATCTACACCGATGACATGTTCCGT

AGGAGATTTAGGATGAATAAGCCATTGTTCCTGCGTATCGTGCATGCACTTAGCCATTCG

TCCCGTTATTTCACCCAAAGAGTCGATCCTATTGCTAGAAATAGTCATTCAGCACTTCAA

AAGTGTACAGCGGCCATCACGATGTTACCTTATGGAACCTCGGCTGATGAACTTGATGAG
```

-continued

```
GTCTTGAAAATACCTGCAAGCACTTGTTTGGAGATTTTGGGAAAATTCGCTGAAGGTGTG

ATTGAAAGATTTGGTGAGGAATATCTAGCGCCTCCAAGAAGCGATGAACTTGAATAAATC

TTACAAGAAAATGAGGCTCGTGGTTTTCCTGGGTGCATGGGAAGCATCGATTACATGCAT

TGGCCATGGAAGAATTGTCCGAAAGGTTGGGCGGGTCAGTTTACAAGTGGTAAACAAGGT

GTTGCTACTATGATCCTTGAAGCAGTGGCATCAAAAAATCTTCGTATATGGCATGCTTTC

TTTGGTACCGCGGGGTCTCAGAATGACATTAACGTTTTAAACAACTCACCACTGTTAATT

CAAGCAATAAAACCCCAATCTCCTACGGTACACTATACTGTAATTGGAAATCAATATCAC

ATGGGTTACTATCTTGCCGATAAAATATATCCAGAATGGCCAGTATTCCTGAAGAGAGTT

AATGCCCCTCAATCAGCGGAAGATAAAACATTTTCGTTGAGCCAAGAAGGGGTGAGGAAA

GATGTCCAGTGTGCATTTGGTCTTCTGCAATCACGCTTTGATATTGTTCGTCGACCAGCA

CGCTTATGGAAGCAAGGAGACCTTATCAACATTATGCAAGCTTGTGTTATCCTTCACAAT

ATGATAGTTGAAGATGAGAAGGACTCAGTTAGGGATGTCTTCGATTTGAATCAAAATCCA

AGTGCGACGATAGTGATCCCAGCAGAAGTGCGTACAAATGATGAGCCTAATCGAAGCTTT

GCAGAGCCACTTCGTAGAAATTCCGCTATCAAAGCTCGACCAACACATAGGCAACTTAAG

AAGGATCTAATCGAGCACATATGGCAACGCTACGGAAACAAAGAAAATTAGACAAAAAGC

ATTGTAACTATATATAATATAATTATTATATATATGGTTTCTAAAAATTATTGTAATCGG

CTTTCTATTATTTAATCTTCATATTTATTCTATGGATTAGCCACACAATCGTACATAGAA

ATACATTTATAGTTGATCTAAGCTACATGCAAAGCATTAAACAGCTTACACATCGCCGCT

CTGTTTGTGGGTTGTATGAGCTGTCTTTATATCTATGTGTATGAGAATTTCGAGTTTCTG

CAGACGACCCACGGTCTGTGGGTTGTACATGCGC

Deduced amino acid sequence of PONG_LIKE_9 ORF1 in Oryza sativa
(SEQ ID NOs: 83-84)
MENFMLIAISCRDQDVRPPGGFMSYFGNEAQNSHLVGAVIHMSPLNQAHNGSSPPEVEIL

HGNDSVRTEKRIMWTPDEDVRVMSAWLEHSTDFTCGADKGGVQYWGEVVETYNKTTPPLR

RRNAKQCKDRWNKINKWTDLFECAYAKARRVFTSGYSAEMWLDAAHKFYVDDNKECKDVV

GPYMLTEVWKICRDVPKWKTYNENLKNARKRKAFHLEGESEENEDTCDQMPQRPIGQKAA

KKAALAAKNGKLKGSSSSDDGHSKDSPIELDKFDRYSKF*EANNEKRMKLLDRQEKIASE

KLEATKIAHLTAQEYKEGKKLDKETKMMETYNNLVSQDTSSMSDEEKAQRAMMMKCLMKA

LFPETV*

Deduced amino acid sequence of PONG_LIKE_9 ORF2 in Oryza sativa
(SEQ ID NOs: 85-86)
MEPHEEDEVEDAEEFEEVFTVEDLIVEDDIFEEIVAEGFKADMDREASKPVHRRRRQSGP

RRYIPRNREQGHDDLVANYFSESANYFSANPIYTDDMFRRRFRMNKPLFLRIVHALSDWS

PYFTQRVDAIGRNSHSPLQKCTAAIRMLAYGTSADQLDEVLKIAASTCLEILGKFAEGVI

ETFGDEYLRPPRSDELE*ILQENEARGFPGCMGSIDYMHWPWKNCPKGWAGQFTSGKQGV

PTMILEAVASKNLRIWHAFFGTAGSQNDINVLNKSPLLIQAIKGESPTVHYTVIGNQYDM

GYYLADKIYPEWAVFVKTVNAPQSAEDKTFSLRQEGVRKDVECAFGVLQSRFDIVRRPAR

LWKQGDVINIMQACVILHNMIVEDEKDSVRDVLDLNENPSATIVIPPEVRTNDDPNPSFA

EALRRNSAIKARPTHRQKLLDLIEHIWQRYGNKEN*

Nucleotide sequence of PONG_LIKE_10 in AP002093 in Oryza sativa
(SEQ ID NO: 87)
GAGCATCTCCAGTAGAGACCTCAAATCCAACCTCTAATCAAATTTTGAGAGTTAAGATAA

AAAAAAAACTAGATCCAGCAGGAACCCTACTACTAGAGCCCTAAAGTGAGGACGCCCTCA
```

-continued

```
AATCCTCCCCCCAAGGCCCCACTCCTGGGGACTCGGAGCACAGCCCCCATCGTCCTTTTT

TTTGCCGCGGAACAATTTTGCTTCGCGCGTTTTATTGTTACTCCCGCGCGCCTGCGACGA

GGGATCTTCTCCAGCGACCACCGACGAACTCCCACCACCTCCGCCAAAACTGCCCCAAAA

GGTAAGACTTTTCCATAACTTTCTTGCCTGTCGTCCACAATGCCGTCGGCGGCTGTCGAT

GCGCATCCCCGGTCGCCGACCTCCCGCCATCCGCCGGCCGTCGCGTGCTCTCCGAGACCA

CCCGCGCGCACGTCGCCCACCTGCACGGCGTCTGCCCCCATGCTGGCCTCTGCCCGCTCG

TATTTCCAGTTTTCACTGGCCCGACCCTGTACCCCGCCGCTGCCGCATTGATTTTTCTGG

AAAAAAAACTTGAAGTAGGTCATGTGGTCCCCTGGTTGAGTAGTACAGTAGCAGTCAATT

TTCTGAATAACTCCTTCTTCACTACAATTGGACATGCATGTGGTGCTAGATGGTTCTCGT

CTGGTGGAGACTGATTTGTTTTTAATTTTTTTTTGAGAATTGCAGTGGACTGTCAGCCAC

GAGAATCTAATTTTATCAACTAGTAGATATCACTGTACTTATAGTAGCACTGCATTGTGT

AGCACTGTACAATTGTTGCAATGGATCGATTAGAACCATATACATATATGTAACGCTCCG

CTTTTCGTGACCCGTTAAAAAACTAATTCGCTAAAATCCTAATTTCGAAAATTTTCGTTG

TTTGTGTCCGAGTCTAAGTCGTGCGAAGATCTCATTTCAAATCCCGTTGATCCCTCTCAT

CGAAATCAAAATCCTCCACCTGAAATTTCTCTTCCGATTCGAGTCTCTGAAATCAAGTTC

TGAAATTCAAATCCTTCCTGTAAATCCTCGCCAAATACTTCTACGAATCCAGAACTATTC

AGATGCCGCCTCGAATCCTTTCCTTGACTCCACCGTATGTTCCCGAAAACAAATACCCAA

GTATTCCTTTTGAATCCTTTCCATGACTTCTCCTTGAATCCCCCTTGATACATCCCTAAA

CCCTCGAGTTCGAATATCAAATTTGAATTTGAGTCCAAACCGTAAAATCTCTCCAATTCT

ATCCAAATCAGTTTTCTCTCTAAAAGTCTAGTTTACCTCCCTGTATTTTTGGATCGACCG

ATTTCCCTCCCGCGGCTCATCTCCCCTCCCAGCCCATCATCTTACCCCCCCTCGCACGTG

CGTTGCACGCATGCCAGCCGAGAGAGAGCTCTCTCGCTCTCTCGATTCTTTCTCTCTCCC

GTCTTCGCTCTCTCTGCTCTATCCCCTCCCGGCGCCGATTCCCGCCGTCGCCGCCCAA

AACCCGCCACCGCCTTCGCTCTTTCCCGCGCTCGCCCGCGCGTGCCACACCCCCGGGTCG

CCGCCGCATCAGCCCTGGCCGCCTGCCGCACAGCCCCGCATGCCGCCCTGCCGCTCGC

CCCCACCCTGTGCGCGCGTGCCTCCAAGACGTGGACGCAGCGCGTCTCTCTGCCTGACGC

GCTGTCCTCTCCCTCTCCGACCTGGTTTTTGCCAAACCGGCATGGTAAACCCCCCCCTTT

CCACCGTCGTCCCTTCTCTTTTTCCCTCCCAAGCAACGACGCCATGCCTCCACTCCTTGG

CGGCTAGCGCTCGGAGGCAGAGACGCAGACGCCAGCGCCGGCTCGCCACCCCCACCTTGA

CCGCGCCAGCCCGCGCTAATCCTCGCGCTCCCGCGGTTCGATTTTCCGACGCTCGATCCA

CCGCCTTCGCCGCCCAACGCATCCACACCGTCCCCGCCTTCGCACTGCCCACGAAACCGC

CGCTGCCGCCCGTGAACACGAGCACAGCTCCCTGTTCCCCCACCTTTTTCCTTTTGCCCG

ACACCGCCGGCGTCATCACCTGTCGCCGCCTTGGCTGCACGCGTCGATGACCGCCAGCTC

GCTCTCCTTGAGCGCCAATGTCGGTTCCCCCTCCCAAACCGCCTCTTTTCCATCTATAAA

GCCCGGGCCGAGCCTCCCTATCTTATTCTCTCTCGGCATCTGTGTTGCACCGCCATCGTG

CCTTTGTTGCCGCCTTGCAGCTGCCGACCTCGCCTCCCTTCCCTGTCGCGCGTGCTGGTC

AAGCCGGCGTGTGCGCGACGAGCCGAAGAGGACTCCGCCCACCCTTCTTCTTCCCCTTCC

CCGGCGCAAGGCCCGAGAGCTCGCCCCGCGCCGTCGACTGCCCATCACTGCCCGCCGGGC

TCGGTAGTGCCTCCTCCCGTTCCCCTTCCTCGCTCTCGGTCGTCCGCGCTAGCTTGCGTC

GTAGCTCGGTAGCCCTGCCGAACGCGCGTAGACGCCGCCCCAAGGACCGCCGCCACCCGG

CGTGGCCCCACCGCCATTGCCGCCCACCCCCGGAGGCCGCCTCTCGTCGCCGGACCTGCA
```

-continued

```
CGGCGCCGCTCAGAGCGATCCGACCCCGGAAATGAGTTCCTTGAACACCCGAGATGCTTC

CGCCGCCTTTAATTGAGTCCTCGTCGCCCCTCAGTGATTTCCCCTTTCTCTCGCCGCCGG

CCGCGACTGTCGAATTCCACCGCCGTCGAACTCCCTGCGGCGAATCCGAGCCGTTGGCTC

GCTCGTTCTCGACGCCCTCGTCACTCCCGTCTGCTCCGCGAAGACCAAATCCGTCGCGCT

TGCTCCGGTGAACACGGCCGCCCTCCGCCGTCCATCTCGGCCTCCCCTTCTTCCTCCTCC

CGCCGGCCCGCGTGGGTGCCACGTACGCCCCACGTCGGCGCCACCTCGGCTTTGACCGGG

CCAAGCCGGTCAGCCGTCGGCTCCCTCCGTCTTCCCTCCCGTGCGCGCAGTCCAGGGAAA

GCCGTGCGCCTGCATGTGGGCCCGCCGCCATCCGTCCAACCGGTGCACCGCTCCTAAGCC

ATGCCCACCCGAAACCCGTGCGCCGCACCTCGCGTGCGCCGATCGCACCGTGGGCCGTGC

CACCGACAAGCGGGCCCCACCCGGGACCGCGCGCCGTCGAATCCGTCCACCGGGCCGTCT

CTCTCTCCCCCGCGCCCCCTCTGTTGGGGOGCCTCCTCGCGCCCGCGCCCGGCCCAATGG

CTCGGCCGCGCCGTGCTTATCCCTTGGGCCATACCCGAGCCTCCCAAAGAACTCTAAATT

ACATCCCTGCACCGTTTTCTTTTTCAGGGATTTAATAAATCCTTTTTTTTTCCTTCCTT

TGTCCCATAAATCAATTCCTTATTCCCAAAATTCCACAAACGATTTCCTTTGGTCCCGCG

TGACAGTGACTATCAATAATATTTTTGAGAATATTATTTCTATAAATTCCATAAACCATT

TCTCCTATTCCAGAAACTCCAATTAAACTTCGAAAATTCATATCACCCAATTCGCAACTC

CGATTGACTCCGTTCAACTTCCAATATTCCCATAAAATTGAGATCTATTTAATGCCAGTA

CTAATTAGTCTAAATAGGATCTTTCTTTTCGTCTTTTGTTTAGGTTTTCAGTTGTTTCCG

TATAGTTGCGGTTATCGGATTTTCGTCGATCGCGTGTTTTCTCGAAGATTCGTGAAGCTT

CGTGAACACGTTGAGCAAGCCAAGTCACCCTTTGATCAATTCCCCCTATAATTGAAAAGT

CATTATTATTTTGTTTGCAACTTGCATTATTAGAATCACACACTTAACTTGCTTGGCCTC

GGTTTGCGTGCCAAACCGACGGACCTACCCAGTAGTCGCACTAATTTCCGTAGGTTGTAC

TACCCTGTTTCCTTGTCGCTCCACGCTTGTGGTACCTCCGTATTCGTGCTGTCTGACCCC

GTATACCAAATATCCCACATACACCGTTGTTTGTCGAAAACTTGGGAAATGGCTTTGTGA

AGCCTTCAAAACCCGACATGTCGTGTCGCTGTGTTTGAAAATAAAAATGAATTGTGAAAA

CTCGCGATGCGGGGGTTGTGCCTATGTGGCACTGTCCCGTATTCGCATATAAGGACCGAT

TCCTGTGGGAAACTCATCGAACATAATCAAAGTGCAACCACAAGGTGGAATGGGACACCG

TGGGTAAGTAACTAGTCGGTTCAGGGAAACGTCGCATGCCAATAGTTCGGAACACCGGGG

CGGCGTCGGTTGGAGCCAAACGCGGTTGCTGGTAATGCAAGAACCAGAAGCTTGCTGAAT

TACCGATCGAGGTGGTTGGAGTTTGATTTGTGAACGCCTAAAATGGCCTATGATTATGTG

AGGATTTGATCCTTCTATGTGGCATGAGGTATCCCTGGGTCGGCTTGGGAAAGGCTTTGT

CGCGAACCTCTGAGACGGCCCAGTGTCTGGAGTAAGTTGGTGTCTTGTGGGTAAAGTGTA

CCCCTCTACAGAGGTTAACTAACTGTTCGAACAACCGTGCCCACGGTCATGGGCGGATGT

GAGGTGGTTCCCGTTGCGTAGATTTCTTTGCCTCTGCTTTGTGAAAAGTTGTTGTGGTGT

GCGAATCGTAACCAGAATCACCCTATGTGGCAGATGGATGACCTGAGTGGTCAGAAACGA

ATCTGTGTGATTCGGGATGTCTGTGGGCATCATAGACTAGCCTTCCCGAGTGGAAGCGGA

TTGTTGTGCTGCTGGGCAGCTGGACTCTGGGAGTCCGAGAAAATGAAAAAGGCTCTGGGA

GCCGATTAATCAAGTGGAATGGCTCTGGGAGCGGAGAAGTAATGATCTGAGCCGGGAGGT

CGGTAGATTACCAATTGAGTTGTTGAAAAGCATCTCTTAAAGTCGAATTGAGATGCAAGT

GTCTCTTCGGCCCAAACTTAGAAAGAAATAAATCACTTAGTGATTTCAAAATGCCTTCAA
```

-continued

```
ATAAAAGATTTGTAAAACAACCTTGCCTCTCCTCCAAGCTTGCATCAAACAGCTAAGTTC

CCGTGACTTGCTGAGTACGAAAGTACTCACCCTTCCTCTATATAAATATATATATATAGT

TCCTCCGCCCTGAAGAGAAGATAAAGTGAAGAGAAGATTAGGGTTTCGTCCTGGTTCCCA

GCCGTGGCCTGTGGTGTTGGCTGTTAGTTCGTTGGTTCCGCTGCTGCTGCTGTTGTTGCT

GTTTCGTGATGCGTGTGGTGGGTTGCATTCTCGGGTTGTTCTGAGCTGCAACCTAAGTTA

AGGTAAATAAGTCCTCTATTTATTTTAAGGATTGCTATGATTCATATTTGTCACCGTGGG

AACTAGCACTATGTCCTGGGACTGGTACCGAGATCGCGGTTTCGTAGGAAACGGTTCACG

CCGTTTTCCCTACGACACGCTCCTGTCAGGTGCCGTTGTACGGCGGTATCAGATTCGGGT

GTGACAATATATATGCAGGAGTATGTGGTATTGTACTAGTACGATATCACTGCTTTTCAT

AGATTGAGTGTTGCATAGTGTATATGGGTATACTCTGTTCGATACGTGTGCATATGCTCT

AAATTTTCTTATTAATTTTATGATCCTGTGATGGCAGTGTTTTTTACATCGACTTCTACG

ACGACGACGACGACGACAATCTCATTACCGAATGCTGGGATCAAGAGGAGTTATCTGACG

ATGATGACTACTACATTGTAGCTGCTCTTCTTACGGACATAGAGCATAAGAGGACCAAAA

GAAAGCGTCGTGGTTCAGTCCCAGCTCGTGAGATAATTCATAGGGACAGGTTTGCTGGCA

ATTTGGGCATACTCGCTGATTATTTTGCAGATCCTCCTGTATATAATCCAAAATTATTTA

GGAGGAGGTTCAGAATGTGAAGGGAGCTCTTGTTGCGCATCGTGGCTAGTGTGGAGGCTC

AGGATGACTACTTCAGGCAGAGAGCGAATGCAATGGGTGTTCTCGGTGCTACTGCACTAC

AGAAGGTGTATGGTGCAATTCGCATCCTTGCATATGATATTGCAGCCGATAGTCTTGATG

AAGTCGTGAGGATTTCAGAGAGCACCATGATAGAAGCTTTTAAGCACTTTGTCAAGGCTG

TGGTAGATGTCTTTTCTGATCAGTAATTCAGGGCACCAACTGCTGAGGACACTGTGAAGC

ATCTAGGCGCCCGGTGTTAATTTTGGTAATTAATGACAAGCACTAATTGTGGACTAACCG

TTGTCTTTGAGTTATACATTTTTAAGTTAGGTCCACGTCATATGTGCGCATACATGATTA

TCGATGGATTAAAATTGACGGTCCAAACCAAAGGGAAAGAAGACGGTAAAACTAGCGCTT

TAATTTAGAATTGATCGAGGTGTAGGGCGATCAAATTTGCTAGTTTAATTTTAGTTTCGC

CGTACTATTAAGAGGGGTAATGACGTAGCAAAGAGATGATTTTAATTTCCACATTACGTC

ATTGCATTTTCATTTGTGCTCTCTTTTTCATTTCACACACATTCACTAATTCACTGGGTT

GCGCCTGACCAGGGAGGGTCAGACTGGCCACATAGTGGCGGTCTGACCGCCCTCCCCTGC

CCCGTTAGACGAGCTACATAGTCGGGGTCTGACCGGCGGCAGTTTCCCGCTCAGACCGGC

CCCCTGGAGGCCGAGATGATGCTGCTCGGGATGCCCGATACGGACCCGACGGAGCCGTAG

TCGGTCAGACCGAGCTGATGGTGGTCTGACCGAGCCGAGGCCCCTCTGACCGGCCGCCCC

ATGCCGGTCTGACCGGCTAGGCCGATGGGGCCCTCTGACAGGGCTACAACGGCTAGTTTT

CTAGCGGTTGCAGAGTAGCACGGTCTGACCGGCCACATACCTCCGGTCATACCGGTAGAG

CACAAAGTTGGGGGATTTCGCCCCCAACGGCTAGTTTTCGTGGGTGGGAGTATAAATACT

CCCGCACCAGCAGCAAGGGGGCTGTCTTGGCACGCAATTCAATTGCATAGACTGCTTGCA

CCTCTCTCACACTCACTTGAGCTTTGTGTTCATGCATCTAGTGTGTTAGAGCGTTCTTTA

GCCAAGAGTCAAGTGCATTTGCTTCCATTGTAGATCTAGTGTGGCACTTGATCATCTCCA

CACCGGGTCATTGCTTGTTACTCTTGGAGGTTCCCGCCTCCTAGACGGCTTGTGGAGGAG

TTGCCCGGTGACCTCTCCGAGAAGATTGTGGAGGAGGCCCGGCGCCGGTTTGTGAGTGGT

TTGGAGTTCACCACCTTCGGAGTGAAGGAAGAACTATCCCGAGTGATCGAGGCTTGGGTA

CTCCTCTCCGTGGGCCGGCTCCCGCCTTGCCCACCCCTTGACCAAGGGGCCGTGCGGTGG

GTTCGTCGTTGAGCGGTGGACTTGGGCTTGCCTCAACGGGGAGTAGGAAAGCCGCGAGTT
```

```
CTGGAACCTCGGTGAAAAATCTCTTGTCTCATTGTCTCATTTGATTGTCGCATTTACATT

TGTGCAATTTACATTTCTAGAGACACACTTGAGATCATATCACCCTAGGATTGCAAAACA

TTGACATAGGAGCGTGATTTACTTTCCTAGATATATAATTGAGCCAGTATCACCCTAGGT

TTGCAAAACATAATTTAGTTGCTTAGTTAGAGTTGACGCTCACCAAGCCTAGCAACTTAG

GTTAGATTTGATTAGCTGTTATTTAGTTTTAAATGGCCTATTCATCCCCCCTCTAGTCGA

CATCTCGATCCTACACACTGCAAGGTTGTTGGCTATAAACACTCCAAGCGGCTTCCCAGG

GATGCTAGGTTCTATTGACTGTATGCATTGGAGGTGGAAGAATTGCCCAACAGGCTGGAA

AGGACAATACTCAGGGCATGTGGATGGGCCAACCATGATTCTTGAAGCTGTTGCATCTAA

AGATTTGTGGATTTGGGATTCCTTCTTTGGACTAGCAGGTTTTCTTAATCATATCAATGT

ACTACAGAGATCACCACTCTTTCAAAGGCTTACATCAGGGACAGCTCCAGAGTTGGAGTT

TATGGTGAATGGAAAGAAATACACCATTCGTTACTATCTTGGTGATGGCATATACCCTTC

TCGGGCCACTTTTGTGAAGAGCATTTCCAATCCACAAGGTAATAAGAGAATACATTATGC

AAAAGTTCAAGAAGGAGTGAGAAAGGATGTTGAAAGAACATTTGGTGTTCTACAAGCGCG

CTTTGCAATGGTCAGAGGCCCTGCTAGATTTTGCGATACAGAGACCCTATCGTAGATAAT

GACAGCTTGTGTAATTATGCAGAACATGATGATTGAAAATGAGCGAGATGAAGATGTAGA

CTTTGACTAAGATCAGGAGGAGACTGAGGTGTTGAGGAAGGAGGAATAGCAACGACGTAA

TAAACATGTGTTAGAGAAGTTTCTAAAGATACATAAAGAAATTGAAGACCGGCAGGTACA

TGAGCAACTTCGAGATGATCTTGTCGAACATTGTGGGCGCTTCATGGTGCTCGGTAGTT

CAATTTTTGCATTTTCTATCATGTATTGGGTTATGTTCAATATTTGCTTGTAGGACATAT

CATTTTCATGTTTGAAATTTTTGAACTCAAATTTCAATTGTGGTGTTTGAAATTGCAAAT

TTGAATATGGTTGAATTCCACGCGCTAGAATTATTTATGTTTCAATTATTGTGTGTTAAA

CTGGATATAAATATAAATTCTATACTAAAATAAAAGAAAAAAAGAAATAGGCGCTAAGAT

ATGGAGGCTACTGCTAGACATAAAGACATATTTAGGATCCTAAAGCATTGGGGGCAGCTC

CCATTTAATCTTTGGGGACTCTAAAGTAGGGGCTACTACTGGAGATGCTG

Deduced amino acid sequence of PONG_LIKE_10 ORF2 in Oryza sativa
(SEQ ID NOs: 88-89)
MDFYDDDDDDNLITEWWDQEELSDDDDYYIVAALLTDIEHKRTKRKRRGSVPAREIIHRD

RFAGNLRIVADYFADPPVYNAKLFRRRFRMSRELFLRIVASVEAHDDYFRQRPNAMGLLG

ATALQKVYGAIRMLAYDIPADSLDEVVRISESTMIEAFKHFVKAVVDVFSDQ*LRAPTAE

DTAARLLAINTPRGFPGMLGSIDCMHWRWKNCPTGWKGQYSGHVDGPTMLLEAVASKDLW

IWHSFFGLPGFLNDINVLQRSPLFQRLTSGTAPELEFMVNGKKYTIGYYLADGIYPSRAT

FVKTISNPQGNKRIHYAKVQEGVRKDVERTFGVLQARFAMVRGPARFWDTETLWYIMTAC

VIMHNMIIENERDEDVDFD*

Nucleotide sequence of PONG_LIKE_12 in AP004231 in Oryza sativa
(SEQ ID NO: 90)
CAGCATCTCCAATAGATGACTAAAATTAAACTCCCAAAAATCCTGTATTCGGGAGAGCGA

AAAACATATTTAGCCTAAAATACACCCTCTTGTCCAATAGATGACTAAAATTTGGTTCCC

AAAAATTTAAAATTTTTCCACATGATCATTACTGGGCCCTTCCCAACTAATTTTCTACCT

GCTCGTTAAAATCACAGGCGAGACCGGACGGGAGATCGCGTCCCGCGTGAGAGGCGAGG

AGGAGATCCCGGCCTGCGGATGCGGAGGGGTATGGGCATGGTCGACGCGACCCACGCGGA

CGGAAGGAGATCGCTGCTCATCCTAGTCGCGCGCGAGATCGCAACTGATACCGTTGGCGA

GGTTATATATCAGACCCAGCGATATACCAAATTGATCGAAGGACACAGTGCTATAGACGC
```

-continued

```
ACATAGAGCTCTTCCTCTGTCAGCCCCGGCGGCGTTAGCACTTCACTCAATCAGAGCTCT
TCCTCTGTCAGGGCCGGCGACCTTAGCACCTCACTTAATCAGGCAACTGCAGCAAGCAGC
AACGATTGGTGACAGGCACAAGCTCTTGTGCAGTGCGTCACTAGCAAAATTTTGCTAGCA
ACCATGTTTTTTACTTTGTTCTATTTCCTTTTTTTATGTTTCTGATCTGACAATGTCTTG
ATGGAAAAAAAAACTTAATTTGATATGATGRATAAATATTTGGAAAAACGGAAGGCCAAT
CACATTTTTTTAATTTGATCTGACAACGTCGCAAGGGGAAAACTTAATTTATTGTGATG
AATAATGGTTTGGCAGTTGATTTGATCCAACATGAGTCGACCTCGCTCCTCGTTTCAACA
GCTCGTGGATGAATCATCGTCTGACGATGACGATGATTTTTTTTTTTGCCACGGCACAAA
TCGTCCATAGCTATTGCCACTCTGTCAATGCACCAAGACATCGTGGGTCAGTCATGGGAC
ATGAAGTGATTGATCGCAACAGAGAAGCACCCCACTTGAGATTATACCAAGACTACTTTT
CCAATAATCCTACCTATGGCCCAGTTTTATTGAGGCGCAGGTTTGTATAAGTAAATTTTA
TATAATTTATTTTTGTTATATCCATAGATATGCATGTCTCATTAGTTATGATTCGCAGGA
ATAGAATGAGCAGGCCTCTGTTTCTCCGCATAATGAATGCAATAGAGGATCACGATGACT
ATTTTGTGCAGAAGAGAAATGCAGCTGGTTTAATTGGGTTCAGTTGTCACCAAAAGGTCA
CTGCAGCAATGCGTCAGTTGGCTTATGGTATAGCAGCAGATGCTTTGGATGAATATCTCG
GTATTGCAGAAAGTACCGCTATAGAGACCCTGAGAAGGTTTGTGAAAGCAGTTCTACAAG
TTTTTGAACATGAATACTTAAGATCACCCAATGAGAACGATACAACTCGATTACTTGAAC
TTGGCGAGGACAGAGGTTTCCCCGGTATGTTAGGCTCCATAGATTGCATGCATTGGAAGT
GGAAGAACTGCCCTACAGAATTGCACCGTATCTACCAAGGGCACGTCCACGAGCCTACAA
TAATTTTAGAAGCCGTTGCTTCAAACGATCTCTGGATTTGCCACGCTTTTTTGGTATGC
CTGGGTGTCATAACGATATCAATGTACTTCATCGATCCCCGCTATTTGCAAAGCTAGCTG
AAGGCAAGCCTCCTGAAGTGAACTATAGTATAAATGGACACGATTATATCATGCGATATT
ATCTTGCTGATGGCATATATCCTTCTTGGGCCACATTTGTGAAGACCATACCACAACCAG
ATGGCAACAAGAGGAAATATTTTGCCAAAGGACAGGAACCACTAAGGAAGGATGTCGAAC
GAGCTTTTGGGGTTCTGCAAGCTCGATTTCCCATTGTTCGAGGGCCAGCTCGACATTGGG
ATGAAAAGACTCTGGGATACATCATGAAAGCTTGTGTTATCATGCATAACATGATTATTG
AAGATGAGGGAGAAGTTGATTGGGAAGAACGGTTCCCAGAGGGAGGAGAAAATGTCAGAG
TGTCCCACGATGAAATACCTGATCTTGATGATTTTATCCAGATGCACAAAAAAATAAGCG
AGGACGAAACTCACTATCAGCTACGTGAAGACCTAGTGGAGCACTTGTGGCAACATTATG
CTGATAAATATTGAGGTTTTATTTATATGTTTGAATTCCATGTAATAAATAGTATACATA
TGTGAGGATTTGCAAAATCATTTTAATTTGTTCTTCATGTATTGAATAAATGCTGTACTG
TTCGGTTTAAGAATAGTACAGGAGAATTAATAAAAGTCCACTTGCTTTATGCATTTTGTT
GAATATCTCCGCTGGCAGTGATAAATATGTCATGTGGTCTTCCTGTCAATCATGAAAAGC
CACAGATGAGCTAGAGGCCCGAGAAGCTTTTCAATCATGCCAGGAAACAATCAAACATCA
CGCTCTCAGTGAGAGACAATACAGATTACCACAGGTCAATAGCAACATCAGCCTCTCATA
AAGTCTGATTCATTACACAGACTAACACCAAGGGCATGATAAGGCAAGTACCCATCTACT
AACACCAACTTCGGACAAAACAAAAAGACACAATTCTGAATATAAATAGTTTGCATTGCA
GACTTAGTAAACCTAGATAAATTTCTAACAAACGACTGATCTAAACTGCAGCTACGATTG
CCATCTCTTTCCCTCCCATTCTCTGATCTGGTCACAATTTGTTCAGTTCCTTCTTCACAT
GTACCAAGGTCTCAGCGAGGTGGCTTCCCTGTTGATAGCAATAAGATGGAGTTCGAATTA
ACCATAATACATCTACAGAGTATAGACCTGCCAAGTTTTCTAGTCTATTTTAATTAGTAA
```

-continued

```
TGTACAATATTTGAAGCTACCTATATGTTTGTACTGTAAACAATAATTGAAGCTAGCTAG

TACTGCAAGTGATTTTTTTGACTGATCACTGTCGAAAATATGGATTGAGTAACCTATCAT

TCAAACTGAAATTGAATATGCACTCACATGGATCAGTTGATCATGCAGCAAGGTATTTGA

TCTTCGGCTCTTCGCTCTCTGTAGGTTCATTATCTTCATCAACATGATTGGTAGTATCAT

CATTTGTGGGTATACGTTTTCGCAAACCATCTGTGCTTGCCTTCTGTTTTTTGGTGGCAC

AGGGTTTTTCGGATGTTATTTGCTTCATCTTATCATGCCACTTGGATTGTGACCTCAAGA

GAGTCCAACAGTGCAGGAATTGGAACGGCTTATCTTCCAACTCCTTAAATACAGCAATGG

CCTGAGCAATCTGCAGATGTCAAGTCAAGTGAATGTGGTTAGCAAACATCATATCTTTTA

TTTATAAACTAACATAAAAACACAAGCTACATAACTATGTAGTACCTTGTCGTGTATACT

AACCCCGCTTTGTCTTCTACCCTCAATCTCGCTGAGATATCCACAAAACTTGTTGACATT

CTCTTGTATAGTTTTGCAACGATGCATAAGTGAATTCTGGCTGCGATCTGGTGTGGATTT

ACTTGTTTTGTATAAGTGCTCGTATATTCTAGTCCAATATGCAGCACGAGTTTGATTTGT

GCCTAGCACTGGATCCAAACTTACATGCAACCACGCCGACACAAGTATCTTATCTTCTTG

TTCACTAAAATTCTTCGATCTTTTTTGATTTGCTCTAGCCACGGTAGTCCTCTCAATAGT

GGGGAACTGTTGCCTGACAGGCTCGCTACTCATGCCATTCTCATCAAGCTGGTTACTCAT

ATCATCGTCCACAGGCATCGTACTCAAACTATCCCAATCTAAGGAATCGTTCCCCTCATT

CATCAAATTAGTATAGAATCCTTCTTCTTCCATTATCAGTAGGAGCTACAACCAATTATC

TCCATCATGTATGTTAAATGGAAGATGATTATTTTGTTTACATCTCTATCTAAGCAATGC

AATGTTGTCTGTCTGCCTAAAAAAACAAGATGATAGATGCTATTCAGATTTTTCGTTTGA

TATAATATTTTAGATTTGTAGACAGCAGCCTTTGAGGTGGTGTGCTGACTTAAGTGCACA

TGCACCATGCCAGATAGCATCCCACAGCTCAAGATGTAAAATATACTAACATTGTTCAAA

AAAATTTCGACCTTAATTTTGACCTTAATCATGATAGAAGTAAAAGTCGGCACAAGCATA

TGACACACAACAGATGGAACTGGTCAATGGAAACATACCTCAGATTAGGCGTCAGTGCAG

TGTGATACTGACTTTTATGAATACAACATTCAAAGCAAAGGAGTTCAGTGAAAAAAAAAC

TTAACTATAGCAGTTTAGGGAAAAAAAAAACTTATAGTAGTTCAGGGGAAAAAACCTCAA

CTATAGGAGTAAAGAAATAAAATGTTCAGTAGAATATGAAAGTAGGATGTGGCATTTGTC

TTGTTGAATAAAATAGTTTTAGTAGAATTAAGTGGAGTTGAATAGAAGTTTAGGGTGAGA

AGAATATGGTCTGTTAGGAACTTGTGAAGACTATTTTCGACATATTGATCTAAGAGTTGT

ATGAACGAAAGAAAGAAATACAGATAAGGAGGTTGTGAGTAGTAGGATATGAATGCGGA

TAATATGAGTGAGTCAAGGTCAATTGAAGAGAAAGAGAGTTAGATCGATGGAGAGAAGGA

GAAAATAAATGAGTTGTTAGTCTGAAATTAGGTGAAAGAAATCGAGTAGCAAGTGACGTG

GTTGAGAGGCGAGGTGGACGAAGGGGCACAGACTGCCGACGGTCCCTGGATTGACAGTCG

ATGGTGACTTGGACGGAGGCCGCTAGCGCTCTGGACGGAGGGGCGGCAGCGACCTAGATG

GGCTGCCGGCGACGCCCTGGACGGAGGGGCGGCAGCGACCTAGATGGGCTGCCGGCGGCG

CCCTGGACGGAGGGCCGGCGACGCCTTGGAGAACCTGCGGCGTCCCGGACGGACGGACGG

CTGGCGGCGCCCTGAACGGAGTTGGCGCGAGGAGAGGAAGCTGGCGCGAGGAGGGGAAGA

AAGGCGCGGCTCCTCCCGGCGAACGAAGAGACGGTGGTTGAGGGAAAGCGCGGGCGAGGA

AAAAAATTGGCGCCAGGAAAAGAAAAAACGGCGCGGGCAGGAACGATTGCTTCGATTGGG

AGCGCTTCTAGTTGCCCAATATTTGGTTCAGGTTGGTCCTGGTTTTGGAGGTGGCTAAAT
```

```
TTTGGGACCATGTTTAGGAGTCTGTTGGAGGGCTGATTTTCACCAAATTCCTAAAATTTA

TGTTTTAGTAACCTGTTTAGCATTCTCTTGGAGA

Deduced amino acid sequence of PONG_LIKE_12 ORF1 in Oryza sativa
(SEQ ID NO: 91)
MEEEGFYTNLMNEGNDSLDWDSLSTMPVEDDMSNQLDENGMSSEPVTQQFPTIERTTVAR

PNQKRSKNFSEQEDKILVSAWLHVSLDPVLGTNQTRAAYWTRIYEHLYKTSKSTPDRSQN

SLMHRWKTIQENVNKFCGYLSQIEGRRQSGIAQAIAVFKELEDKPFQFLHCWTLLRSQSK

WHDKMKQITSQKPCATKKQKASTDGLGKAIPTNDDTTNHVDEDNEPTETEEPKIKYLAA*

Deduced amino acid sequence of PONG_LIKE_12 ORF2 in Oryza sativa
(SEQ ID NO: 92)
MNHRLTMTMIFFFATAQIVHSYWHSVNAPRHGGSVMGHEVIDRNREARHLRLYQDYFSNN

PTYGPVLFRRRNRMSRPLFLRIMNAIEDHDDYFVQKRNAAGLIGFSCHQKVTAAMRQLAY

GIAADALDEYLGIAESTAIESLRRFVKAVVQVFEHEYLRSPNENDTTRLLELGEDRGFPG

MLGSIDCMHWKWKNCPTELHGMYQGHVHEPTIILEAVASKDLWIWHAFFGMPGSHNDINV

LHRSPLFAKLAEGKAPEVNYSINGHDYMMGYYLADGIYPSWATFVKTIPEPHGNKRKYFA

KAQEAVRKDVERAFGVLQARFAIVRGPARHWDEKTLGYIMKACVIMHNMIIEDEGEVDWE

ERFPEGGENVRVSHDEIPDLEDDFIQMHKKIRDDETHYQLREDLVEHLWQHYPDKY*

Nucleotide sequence of ORF2 in BH247993 in Brassica
(SEQ ID NO: 93)
GGAAGGATGGATTGTATGGATTGGGAGTGGAAGAATTGTGGGAGGGGTTGCAAAGCAGAATATT

GAGGGGGTTGGGGTAAAGGGAGAATGGTATTAGAGGGGGTTGGTTGGTAGGATGTATGGATATG

AGATGGGTTTTTTGGAGGTGGAGGTAGGTTAAATGATATGAATGTTGTTGATGGGTGAGGAGTT

TTTGATGAGATAATAAAGACTGAAGGTGGGGAAGTTAGTTTGTGTGTGAATGGAAAGGAGTATT

GTTGGGGTTAGTATGTGAGGGATAGTATTTATGGGAAATGGGGAAGTTTTGTGGAATGTATTTG

AGTAGGACAAGGTGGGAAAGGGAGTTTATTTGGTGAAGATCAA

Deduced amino acid sequence of ORF2 in BH247993 in Brassica
(SEQ ID NOs: 94-95)
GSIDCMHWEWKNCPTAWKGQYSRGSAKPTIVLEAVASYDLWI*HAFFGPPGTLNDINVLDRSPV

FDDIINSQAPQVTFSVNGNEYCWAYYLTDSIYPKWATFVQSISLPQGPKATLFAQHQ

Nucleotide sequence of ORF2 in BH248131 in Brassica
(SEQ ID NO: 96)
GGAAGCATCGATTGTATGCACTGGGAGTGGAAGAATTGTCCCACCGCTTGGAAAGGGCAATATT

CTCGTGGTTCGGGTAAACCAACAATCGTTTTAGAGGCTGTCGCTTCATATGATCTCTGGATATG

ACATGCATTTTTTGGACCTCCAGGTACATTAAATGATATCAATGTTCTTGACCGTTCTCCCGTT

TTTGATGACATAATAAACGGTAAAGCCCCGAATGTCACTTACTATGTCAATGGAAGAGAGTTCC

ATATGGCTTACTATCTCACCGATGGTATATATCCGAAATGGGCAACTTTTATCCAATCTATTTC

TATGCCACAAGGGCCGAAGGCAGTTTTATTTGCTCAACGGCAA

Deduced amino acid sequence of ORF2 in BH248131 in Brassica
(SEQ ID NOs: 97-98)
GSIDCMHWEWKNCPTAWKGQYSRGSGKPTIVLEAVASYDLWI*HAFFGPPGTLNDINVLDRSPV

FDDIINGKAPNVTYYVNGREFHMAYYLTDIYPKWATFIQSISMPQGPKAVLFAQRQ

Nucleotide sequence of ORF2 in BH249416 in Brassica
(SEQ ID NO: 99)
GGAACCATCGACTGTATGCATTGGGAGTGGAAGAATTGTCCCACCGCTTGGAAAGGAATGTATT

CACGGGGAACCAGAAAACCAACAATTGTGTTGGAGGCTGTTGCTTCAAAAGACCTCTGGATTTG

GCACGCTTTTTTTGGAGCTCCAGGTACTATGAACGATCTTAATATTCTTGATCGATCACCTGTT

TTTGATGACATTATTAACGGGGTCGCCCCACAAGTTAACTATTATCTCAACGGAACGGAGTACC
```

```
ATCTCGCATATTACCTAACAGATGCTATATATCCGAAATGAGCGACTTTTATTCAGTCAATCCG

ACTACCACAAACCGAAAAGCAGTCATTGTTTGCTACATACCAA
```

Deduced amino acid sequence of ORF2 in BH249416 in *Brassica*
(SEQ ID NOs: 100-101)
```
GSIDCMHWEWKNCPTAWKGMYSRGTRKPTIVLEAVASKDLWIWHAFFGAPGTMNDLNILDRSPV

FDDIINGVAPQVNYYVNGTEYHLAYYLTDGIYPK*ATFIQSIRLPQTEKQSLFATYQ
```

Nucleotide sequence of ORF2 in BH249435 in *Brassica*
(SEQ ID NO: 102)
```
GGAAGCATCGACTGTATGCATTGGGAGTGGAAGAATTGCCCCACGGCTTGGAAAGGAATGTACT

CACGAGCAACCGGAAAACCGACAATTGTGTTGGAGGCGGTAGCTTCGTATGACCTCTGGATATG

GCACGCATTTTTTGGAGCACCAGGTACTATGAACGATCTAAATATTCTTGATCGATCACCTGTT

TTTGACGACATTATTAATGGCATCGCGCCACAAGTAAACTTGTATGTTAATGATAATCGGTACC

ATTTCGGATATTATCTCACTGATGGTATTTATCCGAAATGGACGACTTTTATTCAATCTATCCG

ACTACCACAAAATCAGAAGCATTTATTATTTGCTCAAACCCAA
```

Deduced amino acid sequence of ORF2 in BH249435 in *Brassica*
(SEQ ID NO: 103)
```
GSIDCMHWEWKNCPTAWKGMYSRGTGKPTIVLEAVASYDLWIWHAFFGAPGTMNDLNILDRSPV

FDDIINGIAPQVNFYVNDNRYHFGYYLTDGIYPKWTTFIQSIRLPQNQKHLLFAQTQ
```

Nucleotide sequence of ORF2 in BH446750 in *Brassica*
(SEQ ID NO: 104)
```
CCAAGCATCCATTCTATCCATTCCCACTCCAACAATTCTCCCACCCCTTGGAAACCTCAATATT

CTTCTCCTTCCCCAAAACCCACAATCCTTTTACACCCCCTTCCATCCTATCATCTATCCATATC

ACATCCATTTTTTCCACCTCCACCTACCTAAATCATATCAATCTTCTTCATCCCTCACCTCTT

TTTCATCACATAATAAAACCTCAACCTCCCCAACTCACCTTCCATCTCAATCCAACACACTATC

ATATCCCTTACTATCTCACCCACCCTATTTACCCCAAATCCCCAACTTTTATCCAATCAATTTC

AATCCCACAACCCCCCAAACCCCTTTTATTTCCTCAACAACAA
```

Deduced amino acid sequence of ORF2 in BH446750 in *Brassica*
(SEQ ID NOs: 105-106)
```
GSIDCMHWEWKNCPTAWKGQYSCGSGKPTIVLEAVASYDLWI*HAFFGPPGTLNDINVLDRSPV

FDDIIKGEAPQVTFHVNGREYHMAYYLTDGIYPKWATFIQSISMPQGPKAVLFAQQQ
```

Nucleotide sequence of ORF2 in BH530471 in *Brassica*
(SEQ ID NO: 107)
```
CCAACCATCCATTCTATCCATTCCCACTCCAACAATTCTCCCACCCCTTCCAAACCCCAATATA

CTCCCCCTTTCCCTAAACCAACAATTCTTTTACACCCCCTTCCTTCATATCATCTCTCCATATC

CCATCCATTTTTTCCACCTCCACCTACCTAAATCATATCAATCTTCTTCATCCCTCACCTCTT

TTTCATCACATAATAAATCCTCAACCTCCCCAACTCACATACTCTCTCAACCCAACACACTATC

ATTTCCCTTACTATCTAACTCATCCTATCTATCCCAAATCCCCAACTTTTATCCAATCAATTCC

ATTACCACAACCCCCAAAACCCCTTTTATTTCCTCAACCTCAA
```

Deduced amino acid sequence of ORF2 in BH530471 in *Brassica*
(SEQ ID NO: 108)
```
GSIDCMHWEWKNCPTAWKGQYTRGLGKPTIVLEAVASYDLWIWHAFFGPPGTLNDINVLDRSPV

FDDIINGQAPQVTYSVNGREYHLAYYLTDGIYPKWATFIQSIPLPQGPKAVLFAQRQ
```

Nucleotide sequence of ORF2 in BH566193 in *Brassica*
(SEQ ID NO: 109)
```
CCAACCATTCATTCTATCCATTCCCACTCCAACAATTCCCCCACCCCATCCAAACCTCAATATA

CACCTCCATCACCAAACCCAACAATTCTTTTACACCCTCTACCTTCACCACATCTTTCCATATG

CCACCCCTTTTTCCCACCTCCACCTACATTAAACCATATCAATCTTCTTCATCCATCACCACTT

TTTCATCATATATTACAACCTCCACCTCCAAACCTTAATTACATTATCAACCAACACCACTACC

ATTTCCCTTACTATCTCACACATCCTATTTATCCAAAATCCCCTACTTTTCTCCAATCTATTCC
```

```
ACTTCCTCAAACTCCCAAACCAACCTTATTCCCTACCCATCAA
```

Deduced amino acid sequence of ORF2 in BH566193 in *Brassica*
(SEQ ID NO: 110)
```
GSIDCMHWEWKNCPTAWKGQYTRGSGKPTIVLEAVASADLWIWHAFFGPPGTLNDINVLDRSPV

FDDILQGRAPKVNYIINEHEYHLGYYLTDGIYPKWATFWVQSIPLPQSPKATLFATHQ
```

Nucleotide sequence of ORF2 in BH571259 in *Brassica*
(SEQ ID NO: 111)
```
CCCACCATTCACTCTATCCATTCCCAATCCAAAAATTCCCCCACCCCTTCCAAACCACACTACA

CACCTCCATCACCAAAACTGACAATTCTCTTAGAGGCTGTGGCTTCCCAAGACCTTTCCATATC

CCACCCTTTTTTCCTCCTCCACCTACCTTAAACCATATTAATCTCCTCCAACCCCCTCCTCTT

TTTCACCACATTATACAACCTCCACCTCCCACCCTAACCTACATCCTCAACCCACACATCTATA

ACTTGGCGTACTACCTCACTGACGGTATATATCCAAAATGGTCAACATTTATCCAATCTATCAC

ACTCCCTCAATGTCCTAAACAAGAGTTATTTGCCAAAGTTCAA
```

Deduced amino acid sequence of ORF2 in BH571259 in *Brassica*
(SEQ ID NO: 112)
```
GSIDCMHWEWKNCPSAWKGQYTRGSGKLTIVLEAVASQDLWIWHAFFGPPGTLNDINVLERGPV

FDDIIEGRAPRVRYMVNGHMYKLAYYLTDGIYPKWSTFIQSITLPQCPKQELFAKVQ
```

Nucleotide sequence of ORF2 in BH587793 in *Brassica*
(SEQ ID NO: 113)
```
GGAAGCATCGACTGTATGCATTGGGAGTGGAAAAATTGCCCAACCGCCTGGAAAGGACAGTACA

CACGTGGATCAGGAAAGCCAACAATTCTCTTCGAGGCTGTAGCTTCAGAAGATCTTTGGATATG

ACACGCTTTTTTGGTCCTCCAGGTACCTTAAACGATATTAACGTCCTCGATCGGTCTCCTGTT

TTTGATGACATTTTACAAGGTCGAGCTCCAAGGGTACAATATGTGGTCAACGGGCACCAGTATG

ATTTGGCATACTACCTCACAGACGGCATATATCCAAAATGGTCAACATTTATCCAATCTATCTC

AAACCCTCAACGTCCTGAAGCAGAGTTATTTGCTAAAGTTCAA
```

Deduced amino acid sequence of ORF2 in BH587793 in *Brassica*
(SEQ ID NOs: 114-115)
```
GSIDCMHWEWKNCPTAWKGQYTRGSGKPTIVLEAVASEDLWI*HAFFGPPGTLNDINVLDRSPV

FDDILQGRAPRVQYVVNGHQYDLAYYLTDGIYPKWSTFIQSISNPQRPEAELFAKVQ
```

Nucleotide sequence of ORF2 in BH649138 in *Brassica*
(SEQ ID NO: 116)
```
GGCTCCATCCACTCTATCCATTGGGAGTCGAAAAACTGCCCAACGCCTTCCAAACGCCACTACA

CACGTGGTTCACCCAACCCCACAATTGTCTTAGAAGCTGTGGCATCACAGCATCTTTCGATATG

GCACGCATTTTTTGGATTACCACCTTAACTCAATCATATCAATCTTCTTGATCGCTCACCAGTT

TTTGATCACATTTTACAAGGTCGAGCACCAAAAGTTAAGTTCAACCTCAACAACCACACATATC

GTATGGCATACTACCTTAATGACGCAATCTATCCAAACTGACCAACATTTATCCAATCCATCCC

ACTTCCTCAACCTCCTAAAGCAGAGCTATTTCCCCAACGTCAA
```

Deduced amino acid sequence of ORF2 in BH649138 in *Brassica*
(SEQ ID NOs: 117-119)
```
GSIDCMHWEWKNCPTAWKGQYTRGSGKPTIVLEAVASQDLWIWHAFFGLPG*LNDINVLDRSPV

FDDILQGRAPKVKFKVNNHTYRMAYYLNDGIYPN*ATFIQSIRLPQGPKAELFAERQ
```

Nucleotide sequence of ORF1 in BH431665 in *Brassica*
(SEQ ID NO: 120)
```
CTGATCACCTCGTGGTTAAACACGAGCAAAGATCCAGTTCTTAGCACCGACCAAAACTCACGCG

CTTTCTCGACAACAATACCAGCCTACTTTCCTCCAAGTCATCAAGATGGTCGCTCCCAATAGAC

ACCGGCTACTCATTGCAAGCACCCTTCCCAGAAGATCAATGATCTCCTTTGCAAATTCTGTGGA

CCCTATGAACCTCCAACCACACACAACACATCAGCTCAAAACGAAAACAATCTGCTCAAACTTG
```

-continued

CTCATCAAATATTTTTCAACAACCATAACAAGAAATTCCTCCTTCAACACCCGTGGAAGGAACT

GAGCCACCACCACAAGTCG

Deduced amino acid sequence of ORF1 in BH431665 in *Brassica*
(SEQ ID NO: 121)
LISSWLNTSKDPVVSTEQKSGAFWTRIAAYFAASHQDGGSE*RGASHCKHRWQKINDLVCKFCG

AYEAARREKTSGQNENNVLKLAHQIFFNNHKKKFLLEHAWKELRHDQKW

Nucleotide sequence of ORF1 in BH431721 in *Brassica*
(SEQ ID NOs: 122-123)
CTCATCAGCTCGTGGTTAAACACGAGCAAAGATGCAGTAGTAGGGAATGAGCAAAGGTTTAATA

CATTCTGGACAAGAATTGCTGCGTACTACAATGTTAGTCCTCAGGCTGCGGGCAGCGAGAAGAG

AGAGCCACGTCACTGTAAGAATCGTTGGCAGAAGATCAATGATCTGGTTTGTAAATTTTGTGGA

GCATTTGAAGCTGCGACCAGAGAGAAAACAAGTGGTCAAAACGAGAATGATGTTCTCAAACTAG

CCCACCACATCTTCTACACTAACCATAAAAAAATTTCACCCTTGAGCATGCTTGGAAAGAGTT

GCCTAATCACCAGAAGTGG

Deduced amino acid sequence of ORF1 in BH431721 in *Brassica*
(SEQ ID NO: 124)
LISSWLNTSKDAVVGNEQRFNTFWTRIAAYYNVSPQAAGSEKREPRHCKNRWQKINDLVCKFCG

AFEAATREKTSGQNENDVLKLAHHIFYTNHKKNFTLEHAWKELRNDQKW

Nucleotide sequence of ORF1 in BH481046 in *Brassica*
(SEQ ID NO: 125)
CTGATCAGTGCTTGGTTGAACACCAGCAATGATCCAATCCTCAGTAATGAGCAAAAGGCTTGCT

CATTTTCGAAGCGCATAGAGGAGTGTGTCAATGCAAGCCCTCTGCTCGTTGGCTCCGTTCCTAG

CCACTCCAGTCAATCTAAGCAGAGGTGGGGTACCGTTAATGAACAGGTTTGCAAGTTCGTGGCA

TCTCACGAAGCTGCTTTGAAGAAGCAACCCAGTGGACAAACTGAGAATGATGTCATGAAGGCGG

CTCATGACATCTTCTTTAATGACTACAATGCCAAGTTCACTCTTGAACATTGTTGCAGGGAGCT

TCGGTTTGATCAAAAATGG

Deduced amino acid sequence of ORF1 in BH481046 in *Brassica*
(SEQ ID NO: 126)
LISAWLNTSNDPIVSNEQKACSFWKRIEECVNASPLLVGSVPREWSQCKQRWGRVNEQVCKFVG

CHEAALKKQASGQTENDVMKAAHDIFFNDYNAKFTLEHCWRELRFDQKW

Nucleotide sequence of ORF1 in BH515274 in *Brassica*
(SEQ ID NO: 127)
CTCATTAGCGCCTGGTTAAACACCAGCAAGGACCCGGTGGTGGGCAATGACCAGAAAGCAGGGG

CGTTTTGGAGCCGCATTCCCGCTTACTTCGTAGCCAGTCCAACGGTCCAAACAGGTGCAAAGCG

TGAGGCTATTCAATCTAAGCAGCGATGGCAGAAGATGAACGATCTACTCTGTAAGTTTTGTGGA

TCCTATGCCCCTCCAACTACACAGAAGACAAGTGGTCAAAATCAGGCTGACACTGTGAAACTGG

CACACCACATCTTCTACAACGATCACAACATCAAATTTAACCTCCACCATGCTTCGGACCACCT

GACGAATGACCAGAAATGG

Deduced amino acid sequence of ORF1 in BH515274 in *Brassica*
(SEQ ID NO: 128)
LISAWLNTSKDPVVGNEQKAGAFWSRIAAYFVASPTVERGAKREAIQCKQRWQKMNDLVCKFCG

SYAAATRQKTSGQNEADTVKLAHEIFYNDHKIKFNLHHAWEELRNDQKW

Nucleotide sequence of ORF1 in BH556611 in *Brassica*
(SEQ ID NO: 129)
CTCATCACCTCCTGGCTCAACACAAGCAAGCATCCAGTAGTCCGAAATCAGCAACGCTCTGGCG

CATTCTCGAATAGGATCGCCGCTTACTTTGCGGCAAGTCCCAAGGTTCCAGCCACTCAACACCC

AGAATCAACTCATTGCAAGCAGCGTTGGCACAAGATCAATGATCAAGTCAACAAGTTTTGTGGG

GCTTTCGAAGCAGCAACCAGAGAGAACACAAGTGGGCAAAATGAGAATGATGTTCTCAACAGAG

```
CTCATGAAATCTTCTTCACCAACCACCGAAAAAAAATTATTCTTGAGCACGCTTGGAAGGAGCT

TCGGAATGATCAAAAATGG
```

Deduced amino acid sequence of ORF1 in BH556611 in *Brassica*
(SEQ ID NO: 130)
```
LISSWLNTSKDPVVGNEQRSGAFWNRIAAYFAASPKVAATEHRESTHCKQRWHKINDQVNKFCG

AFEAATREKTSGQNENDVLNRAHEIFFTNHRKKIILEHAWKELRNDQKW
```

Nucleotide sequence of ORF1 in BH566603 in *Brassica*
(SEQ ID NO: 131)
```
CTGATTGGGGCTTGGCTTAACACAAGCAAAGACGCTGTGGTGAGCAATGAGCACAAAGCTGACC

CTTTCTGGAAGAGAATCGTTGATTACTACAATGCAAGCCCTCTCTTGGTTGGGACAGCACCTAG

GGAGCTCGGTCAGTGCAAGCAGCGGTGGGCGAGGATTAACGAGGGCGTCTGTAAGTTCGTTGCC

TGCTACGACGCGGCTCTGAGGTGCCAGAGTAGTGGTCAAAACGAGGATGACGTGATGAAAGCTG

CCTTGGACTTCTACTACAACGACCACTCCATCAAGTTCAACCTCGAACATGCTTGGAGGGAGCT

CCGGCATGACAGTAAATGG
```

Deduced amino acid sequence of ORF1 in BH566603 in *Brassica*
(SEQ ID NO: 132)
```
LIGAWLNTSKDAVVSNEQKADAFWKRIVDYYNASPLLVGTAPRELGQCKQRWARINEGVCKFVG

CYDAALRCQSSGQNEDDVMKAALDFYYNDHSIKFNLEHAWRELRHDSKW
```

Nucleotide sequence of ORF1 in BH568867 in *Brassica*
(SEQ ID NO: 133)
```
CTAATAAGTGCTTGGTTAAACACTTCTAAAGACCCAGTAGTAGGAAATGAGCAGAAAGCAAATG

CGTTTTGGCAACGTATTGCTGCTTATTTCGCTGCGAGTCCTAAGCTAGCTGGTCTGCAAAAGAG

AGATCGAACGTGCTGTAAACAAAGGTGGGCGAAGATTAATGAGGCAGTGTCGAGGTTTGTGGGC

TGCTATGTCGCTGCAACGAAGCAGAGATCGAGTGGACAGAATGAGGATGACGTGTTGAAGATAG

CTCATCAGATTTTCTACAATGATTACAAGGTGAAGTTCACCATGGAGCATGCATGGTTGGAGCT

TCGCCATGATCAGAAATGG
```

Deduced amino acid sequence of ORF1 in BH568867 in *Brassica*
(SEQ ID NO: 134)
```
LISAWLNTSKDPVVGNEQKANAFWQRIAAYFAASPKLAGLQKRDRTCCKQRWAKINEAVSRFVG

CYVAATKQRSSGQNEDDVLKIAHQIFYNDYKVKFTMEHAWLELRHDQKW
```

Nucleotide sequence of ORF1 in BH583760 in *Brassica*
(SEQ ID NO: 135)
```
CTAATCAGTGCCTGCTTAAACACATCTAAGGATGCTGTTATTGGAAATGAACAAAAGTCAGGGA

CCTTCTGAAAACGACTAGAAGAATACTACGCAGCAAGTCCTCATGCTAGAGAGGGTGGTGAAAA

CAGAGAGCATATCCATTGTAAGCAGAGGTGGCACAAAATCAATGATCTGACGAACAAGTTCTGT

GGCGCATTCGGTGCTGCAGAGAGACAAAATAGCAGCGGTCAGAATGACAATGACGTTCTAAAGG

TGGCTCATGACATCTTCTACTCTGATCACAACATGAAGTTTATCCTTGAGCATGCGTGGTGTCT

GTTGACGTATGAACACAAATGG
```

Deduced amino acid sequence of ORF1 in BH583760 in *Brassica*
(SEQ ID NOs: 136-137)
```
LISAWLNTSKDAVIGNEQKSGTF*KRVEEYAASPHAREGGENREHIHCKQRWHKINDLTNKFC

GAFGAAERQNSSGQNDNDVLKVAHDIFYSDHNMKFILEHAWCLLRYEQKW
```

Nucleotide sequence of ORF1 in BH695499 in *Brassica*
(SEQ ID NO: 138)
```
CTTATTGGTGCGTGGCTTAACACAGTTAAGGACCCTGTCGTCAGCACTGACCAAAAAGCTGATG

CTTTCTGGAACCGTATTGTAGACTACTACAACGCAAGCCCTCACCTGGTGGGACTATACCGAG

AAACCTTCGTCCTTGCAAGCAGAGGTCGGCTCGGATTAACGAGCAAGTATCCAAGTTTGCTCGT

TGCCATGATGGGGCTCTGAGCGAGCAGAGGAGTGGGCAAAATGATGATGATGTCATGAAAGCTG
```

CATTAGAGATTTTCTTCAATAATAACGGCTACAAGTTCACTCTGGATCACTGCTGGAGGGAGCT

CAGGCACGACCAGAAATGG

Deduced amino acid sequence of ORF1 in BH695499 in *Brassica*
(SEQ ID NO: 139)
LIGAWLNTSKDPVVSTEQKADAFWNRIVDYYNASPHLVGTIPRKLRPCKQRWARINEQVSKFAG

CHDGALREQRSGQNDDDVMKAALDIFFNNNGYKFTLDHCWRELRHDQKW

Nucleotide sequence of ORF1 in BH720651 in *Brassica*
(SEQ ID NO: 140)
CTCATCAGTGGGTGGTTGAACACCAGTAAGGATCCCATAGTTAGTAACCAGCAGAAGTTAGGGT

CTTTTTGGAAAAGAATAGAGGATTACTTTAATTCAAGCGCTCAGCTCACTGGCTTTGCTCCCAG

AGAGTGGAGTCAGTGTAAGCAGAGGTGGGGAAGGGTTAATGAGCAGGTGTGTAAGTTTGTTGGA

AGCTATGAGGCGGCTTTGAAGGAGCAAGCTAGTGGCCAAAATGAGAACGATGTCATGAAGTCTG

CTCATGACATCTTTTTTGACGACTACGAGGCGAAGTTCACACTTGAACACGCGTGGAGGGAGCT

GAGGTTTGATCAAAAGTGG

Deduced amino acid sequence of ORF1 in BH720651 in *Brassica*
(SEQ ID NO: 141)
LISAWLNTSKDPIVSNQQKLGSFWKRIEDYFNSSAQLTGFAPREWSQCKQRWGRVNEQVCKFVG

SYEAALKEQASGQNENDVMKSAHDIFFDDYQAKFTLEHAWRELRFDQKW

Oligonucleotide sequence for the amplification of mPing
(SEQ ID NO: 142)
TGT GCA TGA CAC ACC AGT G Oligonucleotide sequence for the amplification of mPing
(SEQ ID NO: 143)
CAG TGA AAC CCC CAT TGT GAC Oligonucleotide sequence for the amplification of ID-1
(SEQ ID NO: 144)
TAT GCT GAC ATG GAT CTC Oligonucleotide sequence for the amplification of ID-1
(SEQ ID NO: 145)
CTC TTR TAG AGA GCC TAT AG Oligonucleotide sequence for the amplification of SZ-2
(SEQ ID NO: 146)
ACG TGG GCG ATT GCG TCT G Oligonucleotide sequence for the amplification of SZ-2
(SEQ ID NO: 147)
TCT GCC TCA AGC CTC TAG TC Oligonucleotide sequence for the amplification of Pong
(SEQ ID NO: 148)
CTT CGT TTC AGC TGA TGT G Oligonucleotide sequence for the amplification of Pong
(SEQ ID NO: 149)
ATG TGG CGT CTG GGA AAC AGT G

---

SEQUENCE LISTING

<160> NUMBER OF SEQ ID NOS: 149

<210> SEQ ID NO 1
<211> LENGTH: 430
<212> TYPE: DNA
<213> ORGANISM: Oryza sativa

<400> SEQUENCE: 1
ggccagtcac aatgggggtt tcactggtgt gtcatgcaca tttaataggg gtaagactga    60

| | |
|---|---|
| ataaaaaatg attatttgca tgaaatgggg atgagagaga aggaaagagt ttcatcctgg | 120 |
| tgaaactcgt cagcgtcgtt tccaagtcct cggtaacaga gtgaaacccc cgttgaggcc | 180 |
| gattcgtttc attcaccgga tctcttgcgt ccgcctccgc cgtgcgacct ccgcattctc | 240 |
| ccgcgccgcg ccggattttg ggtacaaatg atcccagcaa cttgtatcaa ttaaatgctt | 300 |
| tgcttagtct tggaaacgtc aaagtgaaac ccctccactg tggggattgt ttcataaaag | 360 |
| atttcatttg agagaagatg gtataatatt tgggtagcc gtgcaatgac actagccatt | 420 |
| gtgactggcc | 430 |

```
<210> SEQ ID NO 2
<211> LENGTH: 419
<212> TYPE: DNA
<213> ORGANISM: Oryza sativa

<400> SEQUENCE: 2
```

| | |
|---|---|
| ggccagtcac aatgggggtt tcactggtgt gtcatgcaca tttaataggg gtaagactga | 60 |
| ataaaaaatg attatttgca tgaaatgggg atgagagaga aggaaagagt ttcatcctgg | 120 |
| tgaaactcgt cagcgtcgtt tccaagtcct cggtaacaga gtgaaacccc cgttgaggcc | 180 |
| gattcgtttc attcaccgga tctcttgcgt ccgcctccgc cgtgcgacct ccgcattcac | 240 |
| aggattttgg gtacaaatga tcccagcaac ttgtatcaat taaatgcttt gcttagtctt | 300 |
| ggaaacgtca aagtgaaacc cctccactgt ggggattgtt tcataaaaga tttcatttga | 360 |
| gagaagatgg tataatattt gggtagccg tgcaatgaca ctagccattg tgactggcc | 419 |

```
<210> SEQ ID NO 3
<211> LENGTH: 430
<212> TYPE: DNA
<213> ORGANISM: Oryza sativa

<400> SEQUENCE: 3
```

| | |
|---|---|
| ggccagtcac aatgggggtt tcactggtgt gtcatgcaca tttaataggg gtaagactga | 60 |
| ataaaaaatg attatttgca tgaaatgggg atgagagaga aggaaagagt ttcatcctgg | 120 |
| tgaaactcgt cagcgtcgtt tccaagtcct cggtaacaga gtgaaacccc cgttgaggct | 180 |
| gattcgtttc attcaccgga tctcttgcgt ccgcctccgc cgtgcgacct ccgcattctc | 240 |
| cgcctggcta caggattttg ggtacaaatg atcccagcaa cttgtatcaa ttaaatgctt | 300 |
| tgcttagtct tggaaacgtc aaagtgaaac ccctccactg tggggattgt ttcataaaag | 360 |
| atttcatttg agagaagatg gtataatatt tgggtagcc gtgcaatgac actagccatt | 420 |
| gtgactggcc | 430 |

```
<210> SEQ ID NO 4
<211> LENGTH: 450
<212> TYPE: DNA
<213> ORGANISM: Oryza sativa

<400> SEQUENCE: 4
```

| | |
|---|---|
| ggccagtcac aatgggggtt tcactggtgt gtcatgcaca tttaataggg gtaagactga | 60 |
| ataaaaaatg attatttgca tgaaatgggg atgagagaga aggaaagagt ttcatcctgg | 120 |
| tgaaactcgt cagcgtcgtt tccaagtcct cggtaacaga gtgaaacccc cgttgaggcc | 180 |
| gattcgtttc attcaccgga tctcttgcgt ccgcctccgc cgtgcgacct ggctacagga | 240 |
| agttgtgtaa gtttgtgtga cgcctggcta caggattttg ggtacaaatg atcccagcaa | 300 |
| cttgtatcaa ttaaatgctt tgcttagtct tggaaacgtc aaagtgaaac ccctccactg | 360 |

-continued

| | |
|---|---|
| tggggattgt tcataaaag atttcatttg agagaagatg gtataatatt ttgggtagcc | 420 |
| gtgcaatgac actagccatt gtgactggcc | 450 |

<210> SEQ ID NO 5
<211> LENGTH: 5341
<212> TYPE: DNA
<213> ORGANISM: Oryza sativa

<400> SEQUENCE: 5

| | |
|---|---|
| ggccagtcac aatggaggtt tcactggtgt gtcatgcaca tttaataggg gtaagactga | 60 |
| ataaaaaatg attatttgca tgaaatgggg atgagagaga aggaaagagt ttcatcctgg | 120 |
| tgaaactcgt cagcgtcgtt tccaagtcct cggtaacaga gtgaaacccc cgttgaggcc | 180 |
| gattcgtttc attcaccgga tctcttgcgt ccgcctccgc cgtgcgacct ccgcattctc | 240 |
| ccgcgccgcg ccgcgccacg cctccttccc gcgtgaacat tcctccttcc cgcgcgagcg | 300 |
| attccaccat ctcccccgtc cggcgcctac ggagtacacc gcaaccggtc gccccaatcc | 360 |
| ggcgcctaga ccgtgaccca cccgccatct tccgcaagac cgaatcccca acccacccac | 420 |
| catcttccgc cgccccgtc cccgtccccg gccatggatc cgtcgccggc cgtggatccg | 480 |
| tcgccggccg tggatccgtc gccggctgct gaaacccggc ggcgtgcaac cgggaaagga | 540 |
| ggcaaacagc gcggggggcaa gcaactagga ttgaagaggc cgccgccgat ttctgtcccg | 600 |
| gccaccccgc ctcctgctgc gacgtcttca tcccctgctg cgccgacggc catcccacca | 660 |
| cgaccaccga atcttcgcc gattttcgtc cccgattcgc cgaatccgtc accggctgcg | 720 |
| ccgacctcct ctcttgcttc ggggacatcg acggcaaggc caccgcaacc acaaggagga | 780 |
| ggatggggac caacatcgac catttcccca aactttgcat cttctttggg aaaccaacaa | 840 |
| gacccaaatt catggtacat gtatttttct cttttttctgt tactttcaac ctacggtaac | 900 |
| tctaattcat ggatgagact actgccattg tgcagttcaa tgcttttttct tcatgttata | 960 |
| tttcgtccag ctgtgagtta tggtttgaag attgctgtgg ttgtttcatt gctgagtatg | 1020 |
| tgaaagatag atggatgaaa gagagaatta tattttagtc tgtaatcttg ctcatccagt | 1080 |
| tgctcatgta tgaccttggt tctagaatgt tgccctgact gtatgcttaa tgttcagaga | 1140 |
| agtgatgcct aaagcagtga gatcagtggg atcagattag ctatcgacat ataatattag | 1200 |
| ctatctcagt tgtgaaagag agatgggtga aaaggcaccc cttggattaa ttctgtagta | 1260 |
| tcaaattctg caccttgtct gtccatatgt tctgcttggt tggtgggtgc agtgcatttg | 1320 |
| taaaaaatag tttgcttctg atccttaata tatgtaacag ggaatgaatt ttcacccatc | 1380 |
| tcagttgtaa aggtactgtc ttgctatgca atatgtgtaa attgacaaac ctgaaaatag | 1440 |
| tctgtttgga atttgcaaaa gcaattcgat agtttggaat ttccaaacct cagtcagcag | 1500 |
| taggcaatcc attttagttc ttgctatgca caaaaacagt acacctgata tgctcatttt | 1560 |
| aatacaactt ttttgtctct gttacagttt ggtcaggggt tatcctccag gagggttgt | 1620 |
| caattttatt caacaaaatt gtccgccgca gccacaacag caaggtgaaa attttcattt | 1680 |
| cgttggtcac aatatgggat tcaacccaat atctccacag ccaccaagtg cctacggaac | 1740 |
| accaacaccc caagctacga accaaggcac ttcaacaaac attatgattg atgaagagga | 1800 |
| caacaatgat gacagtaggg cagcaaagaa aagatggact catgaagagg aagagagact | 1860 |
| ggtattcatc ggatactttt acatttccat atgtctttgt tttgactaat acttgacagg | 1920 |
| tcattaactg attcttgtag gccagtgctt ggttgaatgc ttctaaagac tcaattcatg | 1980 |
| ggaatgataa gaaaggtgat acattttgga aggaagtcac tgatgaattt aacaagaaag | 2040 |

```
ggaatggaaa acgtaggagg gaaattaacc aactgaaggt tcactggtca aggttgaagt    2100
cagcgatctc tgagttcaat gactattgga gtacggttac tcaaatgcat acaagcggat    2160
actccgacga catgcttgag aaagaggcac agaggctgta tgcaaacagg tttggaaaac    2220
cttttgcgtt ggtccattgg tggaagatac tcaaagatga gcccaaatgg tgtgctcagt    2280
ttgaatcaga gaaagacaag agcgaaatgg atgctgttcc agaacagcag tcacgtccta    2340
ttggtagaga agcagcaaag tctgagcgca atggaaagcg caagaaagaa aatgttatgg    2400
aaggcattgt cctcctaggg gacaatgtcc agaaaattat aaaggtccac gaagaccgga    2460
gggtggatcg tgaaaaggcc accgaagcac agattcagat atcaaatgca acattgttgg    2520
ccgctaagga gcagaaggaa gcaaagatgt tcgatgtgta caatactcta ttaagtaagg    2580
atacaagcaa catgtctgaa gatcaaatgg ctagccacca gagggcaata cggaaattag    2640
aggagaagct atttgcggat taaggtgagt tttataaact gaccactatt ttctgaaatg    2700
tatgaattct gaaatttata tacaattgtg taaacatgga aaattagata atgtatgcat    2760
gatgcacaac atgtgcgtgc agcactattt aatggcagtt tcacaagtgt gaaaactgac    2820
cactatagta ctattgtggt gtgaaaactg accactacta ttgtggtgtg aatgctactg    2880
tggtgtgaaa actgaccact atagtttcac attcctggat gcagccctcc tctatatata    2940
tagatacagt cctcatctct tcctggcata cacacagccc tcttctctaa ttcctggacg    3000
cagtcctcat ctcttcctgg catagacgca gcccttctct cttcctgttt agttcaacaa    3060
cattgaggtg atctgccttt ctttgaagtt tctatctttt ttcactgctg tgaatgatta    3120
tttctctgct gtgaatgatt atttctccaa tcttcctttg ttcaccttct ctctttctct    3180
gctgtgaaga tgtctggaaa tgaaaatcag attcctgtgt ccttgttgga cgagtttctc    3240
gctgaggatg agatcatgga tgagataatg gatgatgttc tccatgaaat gatggtgtta    3300
ttgcagtcct ccatcggaga tcttgaaaga gaggctgctg accatcgttt gcatccaagg    3360
aagcacatca gaggccacg agaggaagca catcaaaatt tggtgaatga ttatttctct    3420
gaaaatcctc tatatccttc caatattttt cgccgaagat ttcgtatgta caggccgctg    3480
tttttacgta ttgtggacgc attaggccag tggtcagatt actttactca gagggtagat    3540
gccgctggta ggcaagggct tagtccatta caaaagtgta ctgcagcaat tcgccaattg    3600
gctactggta gtggtgctga tgaactagat gagtatttga agattggaga gactactgct    3660
atggatgcta tgaaaaattt tgtgaaagga attagagaag tatttggtga agatatctc    3720 aggcgtccca ctgtagaaga tactgaacga ctactcgagc ttggtgagag acgcggtttt    3780
cctggtatgt tcggtagcat tgactgtatg cattggcaat gggaaaggtg cccaactgcg    3840
tggaagggtc agttcactcg tggtgatcaa aaagtgccaa cgctgattct tgaggcagtg    3900
gcatcacatg atctttggat ttggcatgcg ttctttggag tagcaggttc taacaatgat    3960
atcaatgttt tgagccgatc tactgtgttt atcaatgagc tgaaaggaca agctcctaga    4020
gtgcagtaca tggtaaatgg gaatcaatac aacgaaggtt attttcttgc tgatggaatt    4080
taccctgaat ggaaggtatt tgctaagtca tatcgactcc ctatcactga aaggagaag    4140 ttgtatgcac aacatcaaga aggggcaaga aaggatatcg agagagcatt tggtgttcta    4200
caacgtcgat tctgcatctt aaaacgacca gcccgtctat atgaccgagg tgtactccgt    4260
gatgttgtcc taggttgcat catacttcac aatatgatag ttgaagatga aaggaagcg    4320 cgacttattg aagaaaatct agatttaaat gagcctgcta gttcatcaac ggttcaggca    4380
ccagaattct ctcctgacca gcatgttcca ttagaaagaa ttttagaaaa ggatactagt    4440
```

```
atgagagatc gtttggctca tcgccgactc aagaatgatt tggtggaaca tatatggaat    4500
aagtttggtg gtggtgcaca ttcatctggt aattatgttt ttattttgca ttattagtta    4560
tctatggtac taagatatgt acaagtttct ctaaattgca ctaaatctgt ggttcatatt    4620
ggatatgtgt aaactatgaa tgtagcctga ctaaaaccat cattcatgct gaactggttt    4680
ttgttttgta tatgcaggat gaaacaagga actaggtttc tgaacgcatt acggactgaa    4740
ggttgagggg cagaatgatc cacccagttg cttctatcag atcactaaag tttcatttca    4800
ctgttttatt ttggacactt gatgcttgtg tgcatccgat gaatgtttaa tttggtcacc    4860
tgatgcttgt gtgcatccga tgaatgttta atttggtcac ctgatgcttg tatgcagtta    4920
tctatcttat ttgttaatgt tgctggtact gaggattttt agaagtgaaa tgcacaagtt    4980
gctgtgtttt ttgactgatc cttgtgtgca cttgacgttg tatgtgacaa atgatggttc    5040
ccagttgtgc acctgattca tgattcagtt attcagttta aattgacgtt gtttgtgtgc    5100
accttttgtc agttagccag ttacggctgg aagttgtgta agtttgtgtg acgcctggct    5160
acaggatttt gggtacaaat gatcccagca acttgtatca attaaatgct ttgcttagtc    5220
ttggaaacgt caaagtgaaa cccctccact gtggggattg tttcataaaa gatttcattt    5280
gagagaagat ggtataatat tttgggtagc cgtgcaatga cactagccat tgtgactggc    5340
c                                                                    5341
```

<210> SEQ ID NO 6
<211> LENGTH: 172
<212> TYPE: PRT
<213> ORGANISM: Oryza sativa

<400> SEQUENCE: 6

```
Met His Thr Ser Gly Tyr Ser Asp Asp Met Leu Glu Lys Glu Ala Gln
  1               5                  10                  15

Arg Leu Tyr Ala Asn Arg Phe Gly Lys Pro Phe Ala Leu Val His Trp
             20                  25                  30

Trp Lys Ile Leu Lys Asp Glu Pro Lys Trp Cys Ala Gln Phe Glu Ser
         35                  40                  45

Glu Lys Asp Lys Ser Glu Met Asp Ala Val Pro Glu Gln Gln Ser Arg
     50                  55                  60

Pro Ile Gly Arg Glu Ala Ala Lys Ser Glu Arg Asn Gly Lys Arg Lys
 65                  70                  75                  80

Lys Glu Asn Val Met Glu Gly Ile Val Leu Leu Gly Asp Asn Val Gln
                 85                  90                  95

Lys Ile Ile Lys Val His Glu Asp Arg Arg Val Asp Arg Glu Lys Ala
            100                 105                 110

Thr Glu Ala Gln Ile Gln Ile Ser Asn Ala Thr Leu Leu Ala Ala Lys
        115                 120                 125

Glu Gln Lys Glu Ala Lys Met Phe Asp Val Tyr Asn Thr Leu Leu Ser
    130                 135                 140

Lys Asp Thr Ser Asn Met Ser Glu Asp Gln Met Ala Ser His Gln Arg
145                 150                 155                 160

Ala Ile Arg Lys Leu Glu Glu Lys Leu Phe Ala Asp
                165                 170
```

<210> SEQ ID NO 7
<211> LENGTH: 455
<212> TYPE: PRT
<213> ORGANISM: Oryza sativa

<400> SEQUENCE: 7

```
Met Ser Gly Asn Glu Asn Gln Ile Pro Val Ser Leu Leu Asp Glu Phe
 1               5                  10                  15
Leu Ala Glu Asp Glu Ile Met Asp Glu Ile Met Asp Asp Val Leu His
            20                  25                  30
Glu Met Met Val Leu Leu Gln Ser Ile Gly Asp Leu Glu Arg Glu
        35                  40                  45
Ala Ala Asp His Arg Leu His Pro Arg Lys His Ile Lys Arg Pro Arg
    50                  55                  60
Glu Glu Ala His Gln Asn Leu Val Asn Asp Tyr Phe Ser Glu Asn Pro
 65                  70                  75                  80
Leu Tyr Pro Ser Asn Ile Phe Arg Arg Phe Arg Met Tyr Arg Pro
                85                  90                  95
Leu Phe Leu Arg Ile Val Asp Ala Leu Gly Gln Trp Ser Asp Tyr Phe
                100                 105                 110
Thr Gln Arg Val Asp Ala Ala Gly Arg Gln Gly Leu Ser Pro Leu Gln
        115                 120                 125
Lys Cys Thr Ala Ala Ile Arg Gln Leu Ala Thr Gly Ser Gly Ala Asp
    130                 135                 140
Glu Leu Asp Glu Tyr Leu Lys Ile Gly Glu Thr Thr Ala Met Asp Ala
145                 150                 155                 160
Met Lys Asn Phe Val Lys Gly Ile Arg Glu Val Phe Gly Glu Arg Tyr
                165                 170                 175
Leu Arg Arg Pro Thr Val Glu Asp Thr Glu Arg Leu Leu Glu Leu Gly
                180                 185                 190
Glu Arg Arg Gly Phe Pro Gly Met Phe Gly Ser Ile Asp Cys Met His
        195                 200                 205
Trp Gln Trp Glu Arg Cys Pro Thr Ala Trp Lys Gly Gln Phe Thr Arg
    210                 215                 220
Gly Asp Gln Lys Val Pro Thr Leu Ile Leu Glu Ala Val Ala Ser His
225                 230                 235                 240
Asp Leu Trp Ile Trp His Ala Phe Phe Gly Val Ala Gly Ser Asn Asn
                245                 250                 255
Asp Ile Asn Val Leu Ser Arg Ser Thr Val Phe Ile Asn Glu Leu Lys
                260                 265                 270
Gly Gln Ala Pro Arg Val Gln Tyr Met Val Asn Gly Asn Gln Tyr Asn
        275                 280                 285
Glu Gly Tyr Phe Leu Ala Asp Gly Ile Tyr Pro Glu Trp Lys Val Phe
    290                 295                 300
Ala Lys Ser Tyr Arg Leu Pro Ile Thr Glu Lys Glu Lys Leu Tyr Ala
305                 310                 315                 320
Gln His Gln Glu Gly Ala Arg Lys Asp Ile Glu Arg Ala Phe Gly Val
                325                 330                 335
Leu Gln Arg Arg Phe Cys Ile Leu Lys Arg Pro Ala Arg Leu Tyr Asp
                340                 345                 350
Arg Gly Val Leu Arg Asp Val Val Leu Gly Cys Ile Ile Leu His Asn
        355                 360                 365
Met Ile Val Glu Asp Glu Lys Glu Ala Arg Leu Ile Glu Glu Asn Leu
    370                 375                 380
Asp Leu Asn Glu Pro Ala Ser Ser Thr Val Gln Ala Pro Glu Phe
385                 390                 395                 400
Ser Pro Asp Gln His Val Pro Leu Glu Arg Ile Leu Glu Lys Asp Thr
                405                 410                 415
Ser Met Arg Asp Arg Leu Ala His Arg Arg Leu Lys Asn Asp Leu Val
```

```
                   420            425           430
Glu His Ile Trp Asn Lys Phe Gly Gly Gly Ala His Ser Ser Gly Asn
        435                 440                 445

Tyr Val Phe Ile Leu His Tyr
    450             455

<210> SEQ ID NO 8
<211> LENGTH: 5166
<212> TYPE: DNA
<213> ORGANISM: Oryza sativa

<400> SEQUENCE: 8
ggccagtcac aatgggtgtt tcatttgagt gtcatgcgca tttaatacag tgacaagtca      60
gcaaaagagc aatatttgca tgaaatgggt aggagagaga gtaaactcgt ttcaccatgg     120
tgacacgaga tagcgccgtt tcccaggtcg ctgaaacggg gtgaaacagc attgagagtt     180
catcgtttca cctccgggat cccgtgcgag cgctgctctt cgccatcttc gcgcgcatcg     240
ccggattctt cccgcgcgag tcccccatct tcccgcgcag cacctccatg ttcccgcccc     300
caaagcactg gctcgaagct ttttccccca atctcacctg caaccctagc gccagactca     360
gtccccatcg ccccgtccgt cccataccct agcgcaagaa ccacgagcgg agattgcgga     420
gctggatcca caagtaggtg gtgaatcctg tccatctgcc gccgtccgcc gtccagcagc     480
catggatcca aaggaggtg gtggatcccg tctgagcgcc gccggcagag gagggaataa     540
gcgtgggggc aagcagctgg gcctgaagag gtcgtcggcg cctgctccat caccggcaac     600
agctcagcca ccgctgcctg caagttcccc tcctgaagct ccatcgccgg caacagttca     660
gccgcctact ccatcgtcaa gtcctgctgt tgctgccccc agttcatccc ctgctgtacc     720
gatgtcaacc atgcccccat ggccaccgca aggagcagga tggggctctg taccccccaa     780
ttttgctttt ctgcaaggaa ccaacaaggg cccaagttca tggtattttc tccttgtcac     840
agattattca ctgtacacta tgatacatga atgactctc ttcttcatgc attagtaatt     900
agttcctgtt tatgctcaat gaaatttgtt agaatcagta tgtcagtaca ttggtaattt     960
gatatatgcc tgagtaatga atagaaaaaa tgtagtattc agtatggatt gcagtaatac    1020
tttgttagtg aaaattcagt attcagtatg cagtatggat tgcggcttgt ataacagaaa    1080
ttgaaagcaa aagattcagt ttgcaatctg acagtgtac tgtacaacat gtaattcaca    1140
tacgtaaagc ttgttaaata tctccttgtc agtacattgg taacaaatgc tttgagtgta    1200
aatgccaagg gtatcatcct aacattggta tatatttta gccttctgta tggaatgcag    1260
acatggtctt ctttgcaacc acagcaacag cttgccctac actctgtgct gtcgtcatag    1320
ctaaccaaat aacctgttag tactgatata tatggtcttc tttgcaacca cagcaacagc    1380
ttgccctaca tggtcttctg tatgcttgac taaacttgtt acttgacata tatgcttgac    1440
tgaacttgtt gcttgactga attattcctt acacatactg tagtacttgc ttgactgaac    1500
tatgtcagga tcttattaaa aaaaatctat gtcagcactg ctactatgtc aggatcatca    1560
gtatgatgct taagtaacct gttagtatgt cagtacttac tatgtcagga tcatcttctg    1620
gaacttacta tgttgatttt cttatgctg ccatcggttt caattggatt tgcttcttat    1680
gttttcaggt tgtatcctac agaaggcttc gtaaattttc tccaacagaa ctgtctgccg    1740
cagccacaag aaggtgaaaa ttttcacctt gttggtcaga ctaccaacac aatgtctact    1800
ccaccaccaa caccccaagc tgcagctaac aatacagtcc aaattgatat tcatgaagat    1860
gcaatcaatg atgcaagtgc taaaaagaga agtttgagat attggactca tgatgaggaa    1920
```

```
gagagattgg ctagtgcttg gttgaatgct tctaaagatc ccattcatgg gaatgaaaag    1980
aaaggtgata cgttttggaa agaggttact gatgagttca acagaaaagg gaatgggaag    2040
cgtacaaggg aaataaatca attgaaggtt cattggtcac gcctcaaatc atcgattgga    2100
gaattcaatg attactggac taaggtaact caaatgaata caagcggata tgacgatgac    2160
atgctggaga aggaggcaca acagatgtat gcaaatacat ttggaaagcc ttttgcactt    2220
gtgcattggt ggaagatact gagaaaagag cccaagtggt gtgcaatgat tgagaaggac    2280
aaaaacaagg ctgaagtggt tgatattcca gatgaacaaa agcgtcccat tggtagagaa    2340
gcagcacaag ccgagcgcaa tggaaaacgc aagaaggaca gtatgtcaga aggaattgtc    2400
atcctagggg acaatattga aaaaattatc aaagtgacgc aagatcggaa gctggagcgt    2460
gagaaggtca ctgaagcaca gattcacatt tcaaacgtaa atttgaaggc agcagaacag    2520
caaaaagaag caaagatgtt tgaggtatac aattccctgc tcactcaaga tacaagtaac    2580
atgtctgaag aacagaaggc tcgccgagac aaggcattac aaaagctgga ggaaaagtta    2640
tttgctgact aaggttagat atctaatcta atctgagctg cactattatt tataataatt    2700
aaagaatgct gcaatatttt agttatattgt ctgtatatct gtgctgcact atgcagtcag    2760
ctgcatatca cgaatttgtc aaatctgagc tgcatatctg tgaatggtgc aatatttagt    2820
tatattaatt acccagtgtg aatgatgtat tgctgtcagt ttcacatata gtatgaatgc    2880
tgcactatgc agtcagtttc acatgcagtg tgaatgctgc actaggcagt cagtttcaca    2940
tgcagtgggc gcctatttat gcagagttta gccatctctc tactcctctc agaaactcat    3000
tccctctttt ctcatacgaa gacctcctcc cttttatctt tactgtttct ctcttcttca    3060
aagatgtctg agcaaaatac tgatggaagt caagttccag tgaacttgtt ggatgagttc    3120
ctggctgagg atgagatcat agatgatctt ctcactgaag ccacggtggt agtacagtcc    3180
actatagaag gtcttcaaaa cgaggcttct gaccatcgac atcatccgag gaagcacatc    3240
aagaggccac gagaggaagc acatcagcaa ctagtgaatg attactttc agaaaatcct    3300 ctttaccctt ccaaaatttt tcgtcgaaga tttcgtatgt ctaggccact ttttcttcgc    3360
atcgttgagg cattaggcca gtggtcagtg tatttcacac aaagggtgga tgctgttaat    3420
cggaaaggac tcagtccact gcaaaagtgt actgcagcta ttcgccagtt ggctactggt    3480
agtggcgcag atgaactaga tgaatatctg aagataggag agactacagc aatggaggca    3540
atgaagaatt ttgtcaaagg tcttcaagat gtgtttggtg agaggtatct taggcgcccc    3600
accatggaag ataccgaacg gcttctccaa cttggtgaga acgtggtttt cctggaatg    3660 ttcggcagca ttgactgcat gcactggcat tgggaaagat gcccagtagc atggaagggt    3720
cagttcactc gtggagatca gaaagtgcca acctgattc ttgaggctgt ggcatcgcat    3780
gatctttgga tttggcatgc atttttttgga gcagcgggtt ccaacaatga tatcaatgta    3840
ttgaaccaat ctactgtatt tatcaaggag ctcaaaggac aagctcctag agtccagtac    3900
atggtaaatg ggaatcaata caatactggg tattttcttg ctgatggaat ctaccctgaa    3960
tgggcagtgt tgttaagtc aatacgactc ccaaacactg aaaaggagaa attgtatgca    4020
gatatgcaag aaggggcaag aaaagatatc gagagagcct tggtgtatt gcagcgaaga    4080 ttttgcatct taaaacgacc agctcgtcta tatgatcgag gtgtactgcg agatgttgtt    4140
ctagcttgca tcatacttca caatatgata gttgaagatg agaaggaaac cagaattatt    4200
gaagaagatt tagatctaaa tgtgcctcct agttcatcaa ccgttcagga acctgagttc    4260
tctcctgaac agaacacacc atttgataga gttttagaaa aagatatttc tatccgagat    4320
```

```
cgagcggctc ataaccgact taagaaagat ttggtggaac acatttggaa taagtttggt    4380
ggtgctgcac atagaactgg aaattgagaa tcagtaaatg taattatttt attttttcttg   4440 taatttatat atctatggtc cacttgtaaa tttctgaatg ctcatcgcca tattttttaa    4500
tctctgcagg ttccaatcta tttacaggtt ccctaaaaaa aaatctattt gcaggttcca    4560
gtctgttgtc ttcacaatgt aagttctgag aatcaaatca ctatgttttt ctctttttg    4620 gtagctacag ggtgttagaa catgtgttat tttctttact atgcaattgt gatcctccaa    4680
tatttatcta ctgcatgtgt aaacctgttt gtcatgtctg aactactttc atttgtacag    4740
ggtgaaagaa tcaatgaaat ctatgggtgc atcgtcaatt tgcctccagt tacctgcttg    4800
tcatcgtcat ttgtagctta gttctgtcat atttcacctc gagttaacat ctattcagtt    4860
atctaaactt tgctatgtag tgaacttggt tgaatggtca tttaaattta tcaagtgaac    4920
aatcgtacct atctgtgctg aatgcatgta ttttgttttg tgttcaagtg gctacacacg    4980
tttgtgttac atacgatccc actatgtggc tggaattaaa tgccttgaat ttgcattgga    5040
aacgctagag tgaaacacag cattgagaag gtctgtttca ttgtacgttt caacttgttt    5100
catcttcgtt tcagctgatg tggcgtctgg gaaacagtgt aatgaaacac tgcattgtga    5160
atggcc                                                              5166
```

<210> SEQ ID NO 9
<211> LENGTH: 5166
<212> TYPE: DNA
<213> ORGANISM: Oryza sativa

<400> SEQUENCE: 9

```
ggccagtcac aatgggtgtt tcatttgagt gtcatgcgca tttaatacag tgacaagtca      60
gcaaaagagc aatatttgca tgaaatgggt aggagagaga gtaaactcgt ttcaccatgg     120
tgacacgaga tagcgccgtt tcccaggtca ctgaaacggg gtgaaacagc attgagagtt     180
catcgtttca cctccgggat cccgtgcgag cgctgctctt cgccatcttc gcgcgcatcg     240
ccggattctt cccgcgcgag tcccccatct tcccgcgcag cacctccatg ttcccgcccc     300
caaagcactg gctcgaagct ttttttcccca atctcacctg caaccctagc gccagactca     360
gtccccatcg ccccgtccgt cccatacccct agcgcaagaa ccacgagcgg agattgcgga    420
gctggatcca caagtaggtg gtgaatcctg tccatctgcc gccgtccgcc gtccagcagc     480
catggatcca caaggaggtg gtggatcccg tctgagcgcc gccggcagag gagggaataa     540
gcgtgggggc aagcagctgg gcctgaagag gtcgtcggcg cctgctccat caccggcaac    600
agctcagcca ccgctgcctg caagttcccc tcctgaagct ccatcgccgg caacagttca     660
gccgcctact ccatcgtcaa gtcctgctgt tgctgccccc agttcatccc ctgctgtacc     720
gatgtcaacc atgcccccat ggccaccgca aggagcagga tggggctctg taccccccaa     780
ttttgctttt ctgcaaggaa accaacaagg cccaagttca tggtattttc tccttgtcac     840
agattattca ttgtacacta tgatacatga tatgactctc ttcttcatgc attagtaatt     900
agttcctgtt tatgctcaat gaaatttgtt agaatcagta tgtcagtaca ttggtaatttt     960 gatatatgcc tgagtaatga atagaaaaaa tgtagtattc agtatggatt gcagtaatac    1020
tttgttagtg aaaattcagt attcagtatg cagtatggat tgcggcttgt ataacagaaa    1080
ttgaaagcaa aagattcagt ttgcaatctg acagtgtac tgtacaacat gtaattcaca     1140
tacgtaaagc ttgttaaata tctccttgtc agtacattgg taacaaatgc tttgagtgta    1200
aatgccaagg gtatcatcct aacattggta tatattttta gccttctgta tggaatgcag    1260
```

```
acatggtctt ctttgcaacc acagcaacag cttgccctac actctgtgct gtcgtcatag   1320
ctaaccaaat aacctgttag tactgatata tatggtcttc tttgcaacca cagcaacagc   1380
ttgccctaca tggtcttctg tatgcttgac taaacttgtt acttgacata tatgcttgac   1440
tgaacttgtt gctgactga attattcctt acacatactg tagtacttgc ttgactgaac    1500
tatgtcagga tcttattaaa aaaaatctat gtcagcactg ctactatgtc aggatcatca   1560
gtatgatgct taagtaacct gttagtatgt cagtacttac tatgtcagga tcatcttctg   1620
gaacttacta tgtttgattt tcttatgctg ccatcggttt caattggatt tgcttcttat   1680
gttttcaggt tgtatcctac agaaggcttc gtaaattttc tccaacagaa ctgtctgccg   1740
cagccacaag aaggtgaaaa ttttcacctt gttggtcaga ctaccaacac aatgtctact   1800
ccaccaccaa cacccccaagc tgcagctaac aatacagtcc aaattgatat tcatgaagat  1860
gcaatcaatg atgcaagtgc taaaaagaga agtttgagat attggactca tgatgaggaa   1920
gagagattgg ctagtgcttg gttgaatgct tctaaagatc ccattcatgg gaatgaaaag   1980
aaaggtgata cgttttggaa agaggttact gatgagttca acagaaaagg gaatgggaag   2040
cgtacaaggg aaataaatca attgaaggtt cattggtcac gcctcaaatc atcgattgga   2100
gaattcaatg attactggac taaggtaact caaatgaata caagcggata tgacgatgac   2160
atgctgagaa aggaggcaca acagatgtat gcaaatacat ttggaaagcc ttttgcactt   2220
gtgcattggt ggaagatact gagaaaagag cccaagtggt gtgcaatgat tgagaaggac   2280
aaaaacaagg ctgaagtggt tgatattcca gatgaacaaa agcgtcccat ggtagagaa    2340
gcagcacaag ccgagcgcaa tggaaaacgc aagaaggaca gtatgtcaga aggaattgtc   2400
atcctagggg acaatattga aaaaattatc aaagtgacgc aagatcggaa gctggagcgt   2460
gagaaggtca ctgaagcaca gattcacatt tcaaacgtaa atttgaaggc agcagaacag   2520
caaaaagaag caaagatgtt tgaggtatac aattccctgc tcactcaaga tacaagtaac   2580
atgtctgaag aacagaaggc tcgccgagac aaggcattac aaaagctgga ggaaaagtta   2640
tttgctgact aaggttagat atctaatcta atctgagctg cactattatt tataataatt   2700
aaagaatgct gcaatattta gttatattgt ctgtatatct gtgctgcact atgcagtcag   2760
ctgcatatca cgaatttgtc aaatctgagc tgcatatctg tgaatggtgc aatatttagt   2820
tatattaatt acccagtgtg aatgatgtat tgctgtcagt ttcacatata gtatgaatgc   2880
tgcactatgc agtcagtttc acatgcagtg tgaatgctgc actaggcagt cagtttcaca   2940
tgcagtgggc gcctatttat gcagagttta gccatctctc tactcctctc agaaactcat   3000
tccctctttt ctcatacgaa gacctcctcc cttttatctt tactgtttct ctcttcttca   3060
aagatgtctg agcaaaatac tgatggaagt caagttccag tgaacttgtt ggatgagttc   3120
ctggctgagg atgagatcat agatgatctt ctcactgaag ccacggtggt agtacagtcc   3180
actatagaag gtcttcaaaa cgaggcttct gaccatcgac atcatccgag gaagcacatc   3240
aagaggccac gagaggaagc acatcagcaa ctagtgaatg attacttttc agaaaatcct   3300
ctttacccctt ccaaaatttt tcgtcgaaga tttcgtatgt ctaggccact ttttcttcgc   3360
atcgttgagg cattaggcca gtggtcagtg tatttcacac aaagggtgga tgctgttaat   3420
cggaaaggac tcagtccact gcaaaagtgt actgcagcta ttcgccagtt ggctactggt   3480
agtggcgcag atgaactaga tgaatatctg aagataggag agactacagc aatggaggca   3540
atgaagaatt ttgtcaaagg tcttcaagat gtgtttggtg agaggtatct taggcgcccc   3600
accatggaag ataccgaacg gcttctccaa cttggtgaga aacgtggttt tcctggaatg   3660
```

-continued

```
ttcggcagca ttgactgcat gcactggcat tgggaaagat gcccagtagc atggaagggt   3720
cagttcactc gtggagatca gaaagtgcca accctgattc ttgaggctgt ggcatcgcat   3780
gatctttgga tttggcatgc attttttgga gcagcgggtt ccaacaatga tatcaatgta   3840
ttgaaccaat ctactgtatt tatcaaggag ctcaaaggac aagctcctag agtccagtac   3900
atggtaaatg ggaatcaata caatactggg tattttcttg ctgatggaat ctaccctgaa   3960
tgggcagtgt ttgttaagtc aatacgactc ccaaacactg aaaaggagaa attgtatgca   4020
gatatgcaag aaggggcaag aaaagatatc gagagagcct ttggtgtatt gcagcgaaga   4080
ttttgcatct aaaacgacc agctcgtcta tgatcgag gtgtactgcg agatgttgtt   4140
ctagcttgca tcatacttca caatatgata gttgaagatg agaaggaaac cagaattatt   4200
gaagaagatt tagatctaaa tgtgcctcct agttcatcaa ccgttcagga acctgagttc   4260
tctcctgaac agaacacacc atttgataga gttttagaaa agatatttc tatccgagat   4320 cgagcggctc ataaccgact taagaaagat ttggtggaac acatttggaa taagtttggt   4380
ggtgctgcac atagaactgg aaattgagaa tcagtaaatg taattatttt attttcttg    4440 taatttatat atctatggtc cacttgtaaa tttctgaatg ctcatcgcca tatttttaa    4500 tctctgcagg ttccaatcta tttacaggtt ccctaaaaaa aaatctattt gcaggttcca   4560
gtctgttgtc ttcacaatgt aagttctgag aatcaaatca ctatgttttt ctcttttttg   4620
gtagctacag ggtgttagaa catgtgttat tttctttact atgcaattgt gatcctccaa   4680
tatttatcta ctgcatgtgt aaacctgttt gtcatgtctg aactactttc atttgtacag   4740
ggtgaaagaa tcaatgaaat ctatgggtgc atcgtcaatt tgcctccagt tacctgcttg   4800
tcatcgtcat ttgtagctta gttctgtcat atttccactc gagttaacat ctattcagtt   4860
atctaaactt tgctatgtag tgaacttggt tgaatggtca tttaaattta tcaagtgaac   4920
aatcgtacct atctgtgctg aatgcatgta ttttgttttg tgttcaagtg gctacacacg   4980
tttgtgttac atacgatccc actatgtggc tggaattaaa tgccttgaat ttgcattgga   5040
aacgctagag tgaaacacag cattgagaag gtctgtttca ttgtacgttt caacttgttt   5100
catcttcgtt tcagctgatg tggcgtctgg gaaacagtgt aatgaaacac tgcattgtga   5160
atggcc                                                             5166
```

<210> SEQ ID NO 10
<211> LENGTH: 5166
<212> TYPE: DNA
<213> ORGANISM: Oryza sativa

<400> SEQUENCE: 10

```
ggccagtcac aatgggtgtt tcatttgagt gtcatgcgca tttaatacag tgacaagtca     60
gcaaaagagc aatatttgca tgaaatgggt aggagagaga gtaaactcgt tcaccatgg    120 tgacacgaga tagcgccgtt tcccaggtca ctgaaacggg gtgaaacagc attgagagtt   180
catcgtttca cctccgggat cccgtgcgag cgctgctctt cgccatcttc gcgcgcatcg   240
ccggattctt cccgcgcgag tcccccatct tcccgcgcag cacctccatg ttcccgcccc   300
caaagcactg gctcgaagct ttttccccca atctcacctg caaccctagc gccagactca   360
gtccccatcg ccccgtccgt cccataccct agcgcaagaa ccacgagcgg agattgcgga   420
gctggatcca caagtaggtg gtgaatcctg tccatctgcc gccgtccgcc gtccagcagc   480
catggatcca caaggaggtg gtggatcccg tctgagcgcc gccggcagag gagggaataa   540
gcgtgggggc aagcagctgg gcctgaagag gtcgtcggcg cctgctccat caccggcaac   600
```

```
agctcagcca ccgctgcctg caagttcccc tcctgaagct ccatcgccgg caacagttca    660
gccgcctact ccatcgtcaa gtcctgctgt tgctgccccc agttcatccc ctgctgtacc    720
gatgtcaacc atgcccccat ggccaccgca aggagcagga tggggctctg tacccccccaa   780
ttttgctttt ctgcaaggaa accaacaagg cccaagttca tggtattttc tccttgtcac    840
agattattca ttgtacacta tgatacatga tatgactctc ttcttcatgc attagtaatt    900
agttcctgtt tatgctcaat gaaatttgtt agaatcagta tgtcagtaca ttggtaattt    960
gatatatgcc tgagtaatga atagaaaaaa tgtagtattc agtatggatt gcagtaatac   1020
tttgttagtg aaaattcagt attcagtatg cagtatggat tgcggcttgt ataacagaaa   1080
ttgaaagcaa aagattcagt ttgcaatctg gacagtgtac tgtacaacat gtaattcaca   1140
tacgtaaagc ttgttaaata tctccttgtc agtacattgg taacaaatgc tttgagtgta   1200
aatgccaagg gtatcatcct aacattggta tatattttta gccttctgta tggaatgcag   1260
acatggtctt ctttgcaacc acagcaacag cttgccctac actctgtgct gtcgtcatag   1320
ctaaccaaat aacctgttag tactgatata tatggtcttc tttgcaacca cagcaacagc   1380
ttgccctaca tggtcttctg tatgcttgac taaacttgtt acttgacata tatgcttgac   1440
tgaacttgtt gcttgactga attattcctt acacatactg tagtacttgc ttgactgaac   1500
tatgtcagga tcttattaaa aaaaatctat gtcagcactg ctactatgtc aggatcatca   1560
gtatgatgct taagtaacct gttagtatgt cagtacttac tatgtcagga tcatcttctg   1620
gaacttacta tgtttgattt tcttatgctg ccatcggttt caattggatt tgcttcttat   1680
gttttcaggt tgtatcctac agaaggcttc gtaaattttc tccaacagaa ctgtctgccg   1740
cagccacaag aaggtgaaaa ttttcacctt gttggtcaga ctaccaacac aatgtctact   1800
ccaccaccaa caccccaagc tgcagctaac aatacagtcc aaattgatat tcatgaagat   1860
gcaatcaatg atgcaagtgc taaaaagaga agtttgagat attggactca tgatgaggaa   1920
gagagattgg ctagtgcttg gttgaatgct tctaaagatc ccattcatgg gaatgaaaag   1980
aaaggtgata cgttttggaa agaggttact gatgagttca acagaaaagg gaatgggaag   2040
cgtacaaggg aaataaatca attgaaggtt cattggtcac gcctcaaatc atcgattgga   2100
gaattcaatg attactggac taaggtaact caaatgaata caagcggata tgacgatgac   2160
atgctggaga aggaggcaca acagatgtat gcaaatacat ttggaaagcc ttttgcactt   2220
gtgcattggt ggaagatact gagaaaagag cccaagtggt gtgcaatgat tgagaaggac   2280
aaaaacaagg ctgaagtggt tgatattcca gatgaacaaa agcgtcccat tggtagagaa   2340
gcagcacaag ccgagcgcaa tggaaaacgc aagaaggaca gtatgtcaga aggaattgtc   2400
atcctagggg acaatattga aaaaattatc aaagtgacgc aagatcggaa gctggagcgt   2460
gagaaggtca ctgaagcaca gattcacatt tcaaacgtaa atttgaaggc agcagaacag   2520
caaaaagaag caaagatgtt tgaggtatac aattccctgc tcactcaaga tacaagtaac   2580
atgtctgaag aacagaaggc tcgccgagac aaggcattac aaaagctgga ggaaaagtta   2640
tttgctgact aaggttagat atctaatcta atctgagctg cactattatt tataataatt   2700
aaagaatgct gcaatattta gttatattgt ctgtatatct gtgctgcact atgcagtcag   2760
ctgcatatca cgaatttgtc aaatctgagc tgcatatctg tgaatggtgc aatatttagt   2820
tatattaatt acccagtgtg aatgatgtat tgctgtcagt ttcacatata gtatgaatgc   2880
tgcactatgc agtcagtttc acatgcagtg tgaatgctgc actaggcagt cagtttcaca   2940
tgcagtgggc gcctatttat gcagagttta gccatctctc tactcctctc agaaactcat   3000
```

```
tccctcttt  ctcatacgaa  gacctcctcc  cttttatctt  tactgtttct  ctcttcttca   3060
aagatgtctg  agcaaaatac  tgatggaagt  caagttccag  tgaacttgtt  ggatgagttc   3120
ctggctgagg  atgagatcat  agatgatctt  ctcactgaag  ccacggtggt  agtacagtcc   3180
actatagaag  gtcttcaaaa  cgaggcttct  gaccatcgac  atcatccgag  gaagcacatc   3240
aagaggccac  gagaggaagc  acatcagcaa  ctagtgaatg  attacttttc  agaaaatcct   3300 ctttacccttt  ccaaaatttt  tcgtcgaaga  tttcgtatgt  ctaggccact  ttttcttcgc   3360
atcgttgagg  cattaggcca  gtggtcagtg  tatttcacac  aaagggtgga  tgctgttaat   3420
cggaaaggac  tcagtccact  gcaaaagtgt  actgcagcta  ttcgccagtt  ggctactggt   3480
agtggcgcag  atgaactaga  tgaatatctg  aagataggag  agactacagc  aatggaggca   3540
atgaagaatt  ttgtcaaagg  tcttcaagat  gtgtttggtg  agaggtatct  taggcgcccc   3600
accatggaag  ataccgaacg  gcttctccaa  cttggtgaga  aacgtggttt  tcctggaatg   3660
tttggcagca  ttgactgcat  gcactggcat  tgggaaagat  gcccagtagc  atggaagggt   3720
cagttcactc  gtggagatca  gaaagtgcca  accctgattc  ttgaggctgt  ggcatcgcat   3780
gatctttgga  tttggcatgc  attttttgga  gcagcgggtt  ccaacaatga  tatcaatgta   3840
ttgaaccaat  ctactgtatt  tatcaaggag  ctcaaaggac  aagctcctag  agtccagtac   3900
atggtaaatg  ggaatcaata  caatactggg  tattttcttg  ctgatggaat  ctaccctgaa   3960
tgggcagtgt  ttgttaagtc  aatacgactc  ccaaacactg  aaaaggagaa  attgtatgca   4020
gatatgcaag  aaggggcaag  aaaagatatc  gagagagcct  ttggtgtatt  gcagcgaaga   4080
ttttgcatct  taaaacgacc  agctcgtcta  tatgatcgag  gtgtactgcg  agatgttgtt   4140
ctagcttgca  tcatacttca  caatatgata  gttgaagatg  agaaggaaac  cagaattatt   4200
gaagaagatt  tagatctaaa  tgtgcctcct  agttcatcaa  ccgttcagga  acctgagttc   4260
tctcctgaac  agaacacacc  atttgataga  gttttagaaa  aagatatttc  tatccgagat   4320
cgagcggctc  ataaccgact  taagaaagat  ttggtggaac  acatttggaa  taagtttggt   4380
ggtgctgcac  atagaactgg  aaattgagaa  tcagtaaatg  taattatttt  attttctttg   4440
taatttatat  atctatggtc  cacttgtaaa  tttctgaatg  ctcatcgcca  tatttttaa   4500 tctctgcagg  ttccaatcta  tttacaggtt  ccctaaaaaa  aaatctattt  gcaggttcca   4560
gtctgttgtc  ttcacaatgt  aagttctgag  aatcaaatca  ctatgttttt  ctctttttg   4620 gtagctacag  ggtgttagaa  catgtgttat  tttcttact  atgcaattgt  gatcctccaa   4680
tatttatcta  ctgcatgtgt  aaacctgttt  gtcatgtctg  aactactttc  atttgtacag   4740
ggtgaaagaa  tcaatgaaat  ctatgggtgc  atcgtcaatt  tgcctccagt  tacctgcttg   4800
tcatcgtcat  ttgtagctta  gttctgtcat  atttcacctc  gagttaacat  ctattcagtt   4860
atctaaactt  tgctatgtag  tgaacttggt  tgaatggtca  tttaaattta  tcaagtgaac   4920
aatcgtacct  atctgtgctg  aatgcatgta  tttttgtttg  tgttcaagtg  gctacacacg   4980
tttgtgttac  atacgatccc  actatgtggc  tggaattaaa  tgccttgaat  ttgcattgga   5040
aacgctagag  tgaaacacag  cattgagaag  gtctgtttca  ttgtacgttt  caacttgttt   5100
catcttcgtt  tcagctgatg  tggcgtctgg  gaaacagtgt  aatgaaacac  tgcattgtga   5160
atggcc                                                                  5166
```

<210> SEQ ID NO 11
<211> LENGTH: 7492
<212> TYPE: DNA
<213> ORGANISM: Oryza sativa
<220> FEATURE:

<221> NAME/KEY: modified_base
<222> LOCATION: (1277)..(1326)
<223> OTHER INFORMATION: a, t, c, g, unknown or other

<400> SEQUENCE: 11

```
ggccagtcac aatgggtgtt tcatttgagt gtcatgcgca tttaatacag tgacaagtca      60
gcaaaagagc aatatttgca tgaaatgggt aggagagaga gtaaactcgt ttcaccatgg     120
tgacacgaga tagcgccgtt tcccaggtca ctgaaacggg gtgaaacagc attgagagtt     180
catcgtttca cctccgggat cccgtgcgag cgctgctctt cgccatcttc gcgcgcatcg     240
ccggattctt cccgcgcgag tcccccatct tcccgcgcag cacctccatg ttcccgcccc     300
caaagcactg gctcgaagct tttttcccca atctcacctg caaccctagc gccagactca     360
gtccccatcg ccccgtccgt cccataccct agcgcaagaa ccacgagcgg agattgcgga     420
gctggatcca caagtaggtg gtgaatcctg tccatctgcc gccgtccgcc gtccagcagc     480
catggatcca caaggaggtg gtggatcccg tctgagcgcc gccggcagag gagggaataa     540
gcgtggggggc aagcagctgg gcctgaagag gtcgtcggcg cctgctccat caccggcaac     600
agctcagcca ccgctgcctg caagttcccc tcctgaagct ccatcgccgg caacagttca     660
gccgcctact ccatcgtcaa gtcctgctgt tgctgccccc agttcatccc ctgctgtacc     720
gatgtcaacc atgcccccat ggccaccgca aggagcagga tggggctctg tacccccaa     780
ttttgctttt ctgcaaggaa accaacaagg cccaagttca tggtattttc tccttgtcac     840
agattattca ttgtacacta tgatacgatga tatgactctc ttcttcatgc attagtaaat     900
tagttcctgt ttatgctcaa tgaaatttgt tagaatcagg tatgttcagt acattgggta     960
attttgatat atgcctgagt aatgaaatac aaaaaaatgt aatattcata tttgggattg    1020
cagtaaatac ttttgtaaat ggaaaataca gtattccaag aatgcaatat ggaattgctg    1080
gttttttaa cagaatttgg aaagcaaaag aattcagttt gcattctggg cagtgtattg    1140
tgaaacctgg tagttttaca ttctgtgaaa cctcggtaaa tatcctcctt tatacgtacc    1200
ttttggttac aaaaggctat cgagttgaaa acacgaagg ggatagaatc gccaatattg    1260
gttatattat ttttagnnnn nnnnnnnnnn nnnnnnnnnn nnnnnnnnnn nnnnnnnnnn    1320
nnnnnnccca attaaatgtt aagttggaag ggaaccccga tttttgaaaa ggtttagatt    1380
taaatggccc cctaggtcac cacccgtcag gacctgagtt tttcctgaac agaaccccc    1440
atttgataaa gttttaaaaa aaaaatttt ctatccgaga tcgagcggct cataaccgac    1500
taaaaaagat ttgggggaac ccatttgaat aagtttgggg gtgctgcaca tagaactgga    1560
aaattgagaa tcagtaaatg aaatatttta ttttcctggt aatttaaaaa tctatggtcc    1620
acctgaaatt tctgaatgct catcgccata tttttaatct ctgcaggttc caatctattt    1680
acaggttccc taaaaaaaaa tctatttgca ggttccagtc tgttgtcttc acaatgtaag    1740
ttctgagaat caaatcacta tgttttctc tttttggta gctacagggt gttagaacat    1800
gtgttatttt ctttactatg caattgtgat cctccaatat ttatctactg catgtgtaaa    1860
cctgtttgtc atgtctgaac tactttcatt tgtacagggt gaaagaatca atgaaatcta    1920
tgggtgcatc gtcaatttgc ctccagttac ctgcttgtca tcgtcatttg tagcttagtt    1980
ctgtcatatt tcacctcgag ttaacatcta ttcagttatc taaactttgc tatgtagtga    2040
acttggttga atggtcattt aaatttatca agtgaacaat cgtacctatc tgtgctgaat    2100
gcatgtattt tgttttgtgt tcaagtggct acacacgttt tgttacata cgatcccact    2160
atgtggctgg aattaaatgc cttgaatttg cattggaaac gctagagtga aacacagcat    2220
```

```
tgagaaggtc tgtttcattg tacgtttcaa cttgtttcat cttcgtttca gctgatgtgg    2280
cgtctgggaa acagtgtaat gaaacactgc attgtgaatg gcctaacaca aacgtgtgta    2340
gccacttgaa cacaaaacaa atacatgca ttcagcacag ataggtacga ttgttcactt     2400
gataaattta atgaccatt caaccaagtt cactacatag caaagtttag ataactgaat     2460
agatgttaac tcgaggtgaa atatgacaga actaagctac aaatgacgat gacaagcagg    2520
taactggagg caaattgacg atgcacccat agatttcatt gattctttca ccctgtacaa    2580
atgaaagtag ttcagacatg acaaacaggt ttacacatgc agtagataaa tattggagga    2640
tcacaattgc atagtaaaga aaataacaca tgttctaaca ccctgtagct accaaaaaag    2700
agaaaaacat agtgatttga ttctcagaac ttacattgtg aagacaacag actggaacct    2760
gcaaatagat ttttttttag ggaacctgta aatagattgg aacctgcaga gattaaaaaa    2820
tatggcgatg agcattcaga aatttacaag tggaccatag atatataaat acaagaaaa     2880 ataaaataat tacattact gattctcaat ttccagttct atgtgcagca ccaccaaact     2940
tattccaaat gtgttccacc aaatctttct taagtcggtt atgagccgct cgatctcgga    3000
tagaaatatc ttttctaaa actctatcaa atggtgtgtt ctgttcagga gagaactcag     3060
gttcctgaac ggttgatgaa ctaggaggca catttagatc taaatcttct tcaataattc     3120
tggtttcctt ctcatcttca actatcatat tgtgaagtat gatgcaagct agaacaacat    3180
ctcgcagtac acctcgatca tatagacgag ctggtcgttt taagatgcaa aatcttcgct    3240
gcaatacacc aaaggctctc tcgatatctt ttcttgcccc ttcttgcata tctgcataca    3300
atttctcctt ttcagtgttt gggagtcgta ttgacttaac aaacactgcc cattcagggt    3360
agattccatc agcaagaaaa tacccagtat tgtattgatt cccatttacc atgtactgga    3420
ctctaggagc ttgtcctttg agctccttga taaatacagt agattggttc aatacattga    3480
tatcattgtt ggaacccgct gctccaaaaa atgcatgcca aatccaaaga tcatgcgatg    3540
ccacagcctc aagaatcagg gttggcactt tctgatctcc acgagtgaac tgacccttcc    3600
atgctactgg gcatctttcc caatgccagt gcatgcagtc aatgctgccg aacattccag    3660
gaaaaccacg tttctcacca agttggagaa gccgttcggt atcttccatg gtggggcgcc    3720
taagatacct ctcaccaaac acatcttgaa gacctttgac aaaattcttc attgcctcca    3780
ttgctgtagt ctctcctatc ttcagatatt catctagttc atctgcgcca ctaccagtag    3840
ccaactggcg aatagctgca gtacactttt gcagtggact gagtccttc cgattaacag     3900 catccaccct ttgtgtgaaa tacactgacc actggcctaa tgcctcaacg atgcgaagaa    3960
aaagtggcct agacatacga aatcttcgac gaaaaatttt ggaagggtaa agaggatttt    4020
ctgaaaagta atcattcact agttgctgat gtgcttcctc tcgtggcctc ttgatgtgct    4080
tcctcggatg atgtcgatgg tcagaagcct cgttttgaag accttctata gtggactgta    4140
ctaccaccgt ggcttcagtg agaagatcat ctatgatctc atcctcagcc aggaactcat    4200
ccaacaagtt cactggaact tgacttccat cagtattttg ctcagacatc tttgaagaag    4260
agagaaacag taaagataaa agggaggagg tcttcgtatg agaaaagagg gaatgagttt    4320
ctgagaggag tagagagatg gctaaactct gcataaatag gcgcccactg catgtgaaac    4380
tgactgccta gtgcagcatt cacactgcat gtgaaactga ctgcatagtg cagcattcat    4440
actatatgtg aaactgacag caatacatca ttcacactgg gtaattaata taactaaata    4500
ttgcaccatt cacagatatg cagctcgat ttgacaaatt cgtgatatgc agctgactgc     4560
atagtgcagc acagatatac agacaatata actaaatatt gcagcattct ttaattatta    4620
```

```
taaataatag tgcagctcag attagattag atatctaacc ttagtcagca aataactttt    4680
cctccagctt ttgtaatgcc ttgtctcggc gagccttctg ttcttcagac atgttacttg    4740
tatcttgagt gagcagggaa ttgtatacct caaacatctt tgcttctttt tgctgttctg    4800
ctgccttcaa atttacgttt gaaatgtgaa tctgtgcttc agtgaccttc tcacgctcca    4860
gcttccgatc ttgcgtcact ttgataattt tttcaatatt gtccctagg atgacaattc     4920
cttctgacat actgtccttc ttgcgttttc cattgcgctc ggcttgtgct gcttctctac    4980
caatgggacg cttttgttca tctggaatat caaccacttc agccttgttt ttgtccttct    5040
caatcattgc acaccacttg ggctcttttc tcagtatctt ccaccaatgc acaagtgcaa    5100
aaggctttcc aaatgtattt gcatacatct gttgtgcctc cttctccagc atgtcatcgt    5160
catatccgct tgtattcatt tgagttacct tagtccagta atcattgaat tctccaatcg    5220
atgatttgag gcgtgaccaa tgaaccttca attgatttat ttcccttgta cgcttcccat    5280
tcccttttct gttgaactca tcagtaacct cttttccaaaa cgtatcacct ttctttttcat   5340
tcccatgaat gggatcttta gaagcattca accaagcact agccaatctc tcttcctcat    5400
catgagtcca atatctcaaa cttctctttt tagcacttgc atcattgatt gcatcttcat    5460
gaatatcaat ttggactgta ttgttagctg cagcttgggg tgttggtggt ggagtagaca    5520
ttgtgttggt agtctgacca acaaggtgaa aattttcacc ttcttgtggc tgcggcagac    5580
agttctgttg gagaaaattt acgaagcctt ctgtaggata caacctgaaa acataagaag    5640
caaatccaat tgaaaccgat ggcagctaaa gaaaatcaaa catagtaagt tccagaagat    5700
gatcctgaca tagtaagtac tgacatacta acaggttact taagcatcat actgatgatc    5760
ctgacatagt agcagtgctg acatagattt ttttttaataa gatcctgaca tagttcagtc    5820
aagcaagtac tacagtatgt gtaaggaata attcagtcaa gcaacaagtt cagtcaagca    5880
tatatgtcaa gtaacaagtt tagtcaagca tacagaagac catgtagggc aagctgttgc    5940
tgtggttgca aagaagacca tatatatcag tactaacagg ttatttggtt agctatgacg    6000
acagcacaga gtgtagggca agctgttgct gtggttgcaa agaagaccat gtctgcattc    6060
catacagaag gctaaaaata tataccaatg ttaggatgat accccttggca tttacactca    6120
aagcatttgt taccaatgta ctgacaagga gatatttaac aagctttacg tatgtgaatt    6180
acatgttgta cagtacactg tccagattgc aaactgaatc ttttgctttc aatttctgtt    6240
atacaagccg caatccatac tgcatactga atactgaatt ttcactaaca aagtattact    6300
gcaatccata ctgaatacta catttttttct attcattact caggcatata tcaaattacc    6360
aatgtactga catactgatt ctaacaaatt tcattgagca taaacaggaa ctaattacta    6420
atgcatgaag aagagagtca tatcatgtat catagtgtac aatgaataat ctgtgacaag    6480
gagaaaatac catgaacttg ggccttgttg gtttccttgc agaaaagcaa aattgggggg    6540
tacagagccc catcctgctc cttgcggtgg ccatgggggc atggttgaca tcggtacagc    6600
aggggatgaa ctgggggcag caacagcagg acttgacgat ggagtaggcg gctgaactgt    6660
tgccggcgat ggagcttcag gagggaact tgcaggcagc ggtggctgag ctgttgccgg    6720
tgatggagca ggcgccgacg acctcttcag gcccagctgc ttgcccccac gcttattccc    6780
tcctctgccg gcgcgctca gacgggatcc accacctcct tgtggatcca tggctgctgg    6840
acggcggacg gcggcagatg gacaggattc accacctact tgtggatcca gctccgcaat    6900
ctccgctcgt ggttcttgcg ctagggtatg ggacggacgg ggcgatgggg actgagtctg    6960
gcgctagggt tgcaggtgag attggggaaa aaagcttcga gccagtgctt tgggggcggg    7020
```

```
aacatggagg tgctgcgcgg gaagatgggg gactcgcgcg ggaagaatcc ggcgatgcgc   7080
gcgaagatgg cgaagagcag cgctcgcacg ggatcccgga ggtgaaacga tgaactctca   7140
atgctgtttc accccgtttc agtgacctgg gaaacggcgc tatctcgtgt caccatggtg   7200
aaacgagttt actctctctc ctacccattt catgcaaata ttgctctttt gctgacttgt   7260
cactgtatta aatgcgcatg acactcaaat gaaacaccca ttgtgactgg ccttacatac   7320
gatcccacta tgtggctgga attaaatgcc ttgaatttgc attggaaacg ctagagtgaa   7380
acacagcatt gagaaggtct gtttcattgt acgtttcaac ttgtttcatc ttcgtttcag   7440
ctgatgtggc gtctgggaaa cagtgtaatg aaacactgca ttgtgaatgg cc           7492
```

<210> SEQ ID NO 12
<211> LENGTH: 340
<212> TYPE: PRT
<213> ORGANISM: Oryza sativa
<400> SEQUENCE: 12

```
Met Phe Asp Phe Leu Met Leu Pro Ser Val Ser Ile Gly Phe Ala Ser
  1               5                  10                  15

Tyr Val Phe Arg Leu Tyr Pro Thr Glu Gly Phe Val Asn Phe Leu Gln
                 20                  25                  30

Gln Asn Cys Leu Pro Gln Pro Gln Glu Gly Glu Asn Phe His Leu Val
             35                  40                  45

Gly Gln Thr Thr Asn Thr Met Ser Thr Pro Pro Thr Pro Gln Ala
     50                  55                  60

Ala Ala Asn Asn Thr Val Gln Ile Asp Ile His Glu Asp Ala Ile Asn
 65                  70                  75                  80

Asp Ala Ser Ala Lys Lys Arg Ser Leu Arg Tyr Trp Thr His Asp Glu
                 85                  90                  95

Glu Glu Arg Leu Ala Ser Ala Trp Leu Asn Ala Ser Lys Asp Pro Ile
            100                 105                 110

His Gly Asn Glu Lys Lys Gly Asp Thr Phe Trp Lys Glu Val Thr Asp
        115                 120                 125

Glu Phe Asn Arg Lys Gly Asn Gly Lys Arg Thr Arg Glu Ile Asn Gln
    130                 135                 140

Leu Lys Val His Trp Ser Arg Leu Lys Ser Ser Ile Gly Glu Phe Asn
145                 150                 155                 160

Asp Tyr Trp Thr Lys Val Thr Gln Met Asn Thr Ser Gly Tyr Asp Asp
                165                 170                 175

Asp Met Leu Glu Lys Glu Ala Gln Met Tyr Ala Asn Thr Phe Gly
            180                 185                 190

Lys Pro Phe Ala Leu Val His Trp Trp Lys Ile Leu Arg Lys Glu Pro
        195                 200                 205

Lys Trp Cys Ala Met Ile Glu Lys Asp Lys Asn Lys Ala Glu Val Val
    210                 215                 220

Asp Ile Pro Asp Glu Gln Lys Arg Pro Ile Gly Arg Glu Ala Ala Gln
225                 230                 235                 240

Ala Glu Arg Asn Gly Lys Arg Lys Lys Asp Ser Met Ser Glu Gly Ile
                245                 250                 255

Val Ile Leu Gly Asp Asn Ile Glu Lys Ile Ile Lys Val Thr Gln Asp
            260                 265                 270

Arg Lys Leu Glu Arg Glu Lys Val Thr Glu Ala Gln Ile His Ile Ser
        275                 280                 285

Asn Val Asn Leu Lys Ala Ala Glu Gln Gln Lys Glu Ala Lys Met Phe
    290                 295                 300
```

```
Glu Val Tyr Asn Ser Leu Leu Thr Gln Asp Thr Ser Asn Met Ser Glu
305                 310                 315                 320

Glu Gln Lys Ala Arg Arg Asp Lys Ala Leu Gln Lys Leu Glu Glu Lys
                325                 330                 335

Leu Phe Ala Asp
            340

<210> SEQ ID NO 13
<211> LENGTH: 482
<212> TYPE: PRT
<213> ORGANISM: Oryza sativa

<400> SEQUENCE: 13

Met Gln Ser Leu Ala Ile Ser Leu Leu Ser Glu Thr His Ser Leu
  1               5                  10                  15

Phe Ser His Thr Lys Thr Ser Ser Leu Leu Ser Leu Phe Leu Ser
                 20                  25                  30

Ser Ser Lys Met Ser Glu Gln Asn Thr Asp Gly Ser Gln Val Pro Val
            35                  40                  45

Asn Leu Leu Asp Glu Phe Leu Ala Glu Asp Glu Ile Ile Asp Asp Leu
 50                  55                  60

Leu Thr Glu Ala Thr Val Val Val Gln Ser Thr Ile Glu Gly Leu Gln
 65                  70                  75                  80

Asn Glu Ala Ser Asp His Arg His Pro Arg Lys His Ile Lys Arg
                85                  90                  95

Pro Arg Glu Glu Ala His Gln Gln Leu Val Asn Asp Tyr Phe Ser Glu
            100                 105                 110

Asn Pro Leu Tyr Pro Ser Lys Ile Phe Arg Arg Phe Arg Met Ser
                115                 120                 125

Arg Pro Leu Phe Leu Arg Ile Val Glu Ala Leu Gly Gln Trp Ser Val
130                 135                 140

Tyr Phe Thr Gln Arg Val Asp Ala Val Asn Arg Lys Gly Leu Ser Pro
145                 150                 155                 160

Leu Gln Lys Cys Thr Ala Ala Ile Arg Gln Leu Ala Thr Gly Ser Gly
                165                 170                 175

Ala Asp Glu Leu Asp Glu Tyr Leu Lys Ile Gly Glu Thr Thr Ala Met
            180                 185                 190

Glu Ala Met Lys Asn Phe Val Lys Gly Leu Gln Asp Val Phe Gly Glu
            195                 200                 205

Arg Tyr Leu Arg Arg Pro Thr Met Glu Asp Thr Glu Arg Leu Leu Gln
210                 215                 220

Leu Gly Glu Lys Arg Gly Phe Pro Gly Met Phe Gly Ser Ile Asp Cys
225                 230                 235                 240

Met His Trp His Trp Glu Arg Cys Pro Val Ala Trp Lys Gly Gln Phe
                245                 250                 255

Thr Arg Gly Asp Gln Lys Val Pro Thr Leu Ile Leu Glu Ala Val Ala
            260                 265                 270

Ser His Asp Leu Trp Ile Trp His Ala Phe Phe Gly Ala Ala Gly Ser
            275                 280                 285

Asn Asn Asp Ile Asn Val Leu Asn Gln Ser Thr Val Phe Ile Lys Glu
290                 295                 300

Leu Lys Gly Gln Ala Pro Arg Val Gln Tyr Met Val Asn Gly Asn Gln
305                 310                 315                 320

Tyr Asn Thr Gly Tyr Phe Leu Ala Asp Gly Ile Tyr Pro Glu Trp Ala
                325                 330                 335
```

```
Val Phe Val Lys Ser Ile Arg Leu Pro Asn Thr Glu Lys Glu Lys Leu
            340                 345                 350
Tyr Ala Asp Met Gln Glu Gly Ala Arg Lys Asp Ile Glu Arg Ala Phe
            355                 360                 365
Gly Val Leu Gln Arg Arg Phe Cys Ile Leu Lys Arg Pro Ala Arg Leu
            370                 375                 380
Tyr Asp Arg Gly Val Leu Arg Asp Val Val Leu Ala Cys Ile Ile Leu
385                 390                 395                 400
His Asn Met Ile Val Glu Asp Glu Lys Glu Thr Arg Ile Ile Glu Glu
            405                 410                 415
Asp Leu Asp Leu Asn Val Pro Pro Ser Ser Thr Val Gln Glu Pro
            420                 425                 430
Glu Phe Ser Pro Glu Gln Asn Thr Pro Phe Asp Arg Val Leu Glu Lys
            435                 440                 445
Asp Ile Ser Ile Arg Asp Arg Ala Ala His Asn Arg Leu Lys Lys Asp
            450                 455                 460
Leu Val Glu His Ile Trp Asn Lys Phe Gly Ala Ala His Arg Thr
465                 470                 475                 480
Gly Asn

<210> SEQ ID NO 14
<211> LENGTH: 5536
<212> TYPE: DNA
<213> ORGANISM: Oryza sativa
<400> SEQUENCE: 14
gagcaggtac aatagggctg acccatcagc tccaataatt gccacgtcac attatttcta      60
cgtggaaggg taatgattga ggggaaagag aagagctggc gactaaattg tcgccaagct     120
ataacgcatt ttttgggggc atagcgcccg cttgcagcgc atttagattg gatgacatgg     180
ggtaggtatg tcacaaggtg acatagtgta gatctcagtc cttcgaaata aatccagcgg     240
ctgagattcg tccacgtcat tacaagttaa aatttaactc caataaaatt ttaactcctg     300
aaattttaac taccagtaaa attttactc atacgagtta aattttaact catgatgatg     360
tgaacgaatc tcagccgttg gatttatttt ggagagctga gatctacgct atgtcacctt     420
atgacatgtc tatcctatct cacccaatct gaatccgctt gcagccgagg caggcgctag     480
aaaacgcggg ttgtggggcc cacgaacgga aaaactgatc atgtgcgcgc accgctccta     540
ggccgccgat ccactgatcc gatccccttt ccccttcctc tttgccatga gatcgatccc     600
cctctcccct ttggcgcgag cgcgagaaag gaggctggcg catcgatctc tccttcctgg     660
cgcatcgatc ccctcccgcc aaatcgatgg acagatctcc cacccaccgc atcgatcgat     720
ctccttcccg cgcagtattc cctctcactc actccttttt cttctctccc ggtcctataa     780
cttctcccgc gcgcgcgaaa ttcattttgc tggcaggtag aacgatgcca agcccaaa      840
atcgcccctg aaatccatcc ccccggtgaa tttcagggag ggccactgcc cccgtcctc      900
ttccatagtt ctaccgcacc aaaacccta ttccttttca ccatgtctcg tcggacgaag     960
agagaggttg caccaccgca aactcatttg caagctcgtc tggtcctccc ggtgttcata    1020
tcccgccggc aacaccgtat ccatatggag gtcctttgtt ccccacccca ctgccatcat    1080
ggtttccttt tccaccgtca caagccatgg cgggctcatc tgcatatcgt cctcctactg    1140
atgccaagac ggacgtccaa gttgatttgg aacaatggta catttattat ttggctttat    1200
cagttctgat tttgacatgc ttctgtttcc ctgtctaata ttgagagttt catggtcgtt    1260
```

```
attgttttga tccataacag cactagtgca atgaattgtt taggaaaaaa gaggtgattt    1320
tggtctgata atcaggttac cgtagtaact tgggcccatgt aatttggtct gcaatgattt   1380
gtaccatgta tttatgcagc aatttggcta agtaaaaaca agagtccaat gttacatgta    1440
gggtaaccat ggtagggtaa ttagcagtgg tggtaaccat gtatttatgc agtaatttgg   1500
caaagtaaaa acaagagtcc aatgttacat ctattactaa tttgttttag attcgagcac   1560
tcatttacca ctatgaactg aaataaaata attttgactg cacatatcaa tataccattt    1620
atactggggt aatattgggt taggccttgc attgatcaag attggcttgt tcattccttt    1680
ttatatatgg gacataactg atcaagattt tcatgttcat gattttata tagggggacta   1740 gaatctcgcc cgctcggtgg ttttgttgat tttatcaaaa acaccacgaa ccttatgcac    1800
catgtgactg aagggtgtca gttgcagcca attaatgttg agaatggcaa caatggaaat   1860
gccactagga ccgagaagcg cctaggctgg tcaactgaag aagacttgag gctggtaagt    1920
gtcctacgcg agttatttat ttggtagtgg cattcataat acatgcaatt taacaatagt    1980
gaaatatttg gaaattgtag gtcaggcttg gttaaacaac tcaaatgatc caatagaatc    2040
gaatttcaaa aagaatgata aatattggct gatgttgctg ctgcttacaa tagcactact   2100
ccgtcaagcc ggtttagtaa gatcaagaaa aaagttagga attttttgttg cccttggaag   2160 gaggctaatt cattatatgc tagtggggag tgtaatgttg atctcatgga caaggcgctg    2220
aaaatgtatg agaatgactt caaggatggg cgattcttgt ttattgagtg ttggaatgaa   2280 ctaaaaccc  aacctaaatg gcatgcatat ttggatcagc ttgacaagtc gaataaaagg    2340
aagcgagatt atgctgatgc tacccccctt gatgacgagg agatcccacg tccaatggga    2400
gtcaaggcag ctaaggcgaa gcgtataggc aaaggaaaag gcaaggttca agattgtact    2460
gctgagctag aagatgacac ccacaagttt atggaagcac atgaagcagc caaggagcag   2520
taaagtgaat tgttggagac ccagcgacgt gttgctagtg ataatcttga agcgaagaag    2580
gtgggtcgcc agaccgctat gattgcagca tatagagagt tactgaacaa agacacaaga    2640
gatatgcctg atgatgtgag gtctgagctt gttgcaatgt tgaaatgcat gagagaagat    2700
atatttacaa aaaaccagtg aggtatgtgt catgaagttc tttgcagtag taaaacatgc    2760
atatatctac gttgattttg agcagtagtc aaactattgt actgtattca tagctctagt    2820
tccaaacaac catgcaacca gtccctgttt tgtgataatt aatagcattc agtccaaata    2880
atcatgcata tagtctcata ttttgtgctg attaactgcc attagtctaa ataaccatgc    2940
agtcaaccca aattttcatg attattgtag ctggtctaaa ttaaattgca gtcaattgcc    3000
aacccatatt aaatttccat ggttgttgca gctggtccta attaaaatgc agtcatagtc    3060
cagacatatt aaatttttca tggttattgc agctggtcct aattaaaatg cagtcatagt    3120
ccagccatat taaaatttgt atggttatta cagctagtcc tttgcagcat ctatatatta    3180
cctctcataa cttgaaactg ccaacccaat ctatcctcct cctcctcctc caaccatgtc    3240
ggactcatcc tcctattcat cctctaactc agatgaccta gacccatcta aagttctaga   3300
caagtacatt tctgagcaga atgtactaga ctcatttgct tctcgaatca tagagaagat    3360
gaagggtagg ttaggagctg ggcgttcgaa gcgccaaggt ggaacaagga agacaattca    3420
tagggatcat gtagatgccc acagccgttt ggtggctgat tattttgcag agcatccatt    3480
gtacccagag tggatgtttc gcacaaggtt ccgcatgcac aagccactct ttctacgtat    3540
tgttgaagcc ttaggtcagt ggtcaccata ctttactcaa agggaagatt gctctagccg    3600
cacaagtctc tctccacctc aaaagtgcac agcagcactt cgtatgttag catatggcac    3660
```

```
acctgctgat gcactagatg aatatttaaa aattggcaag agcacagcct tagaatgctt    3720
agaaatgttt tcacaagggg tgattgaggt atttggtggg acgtacttga gacgccccac    3780
aagggaggat gtagagcata tattacatgt taacgagtct cgtgggtttc cgggtatgct    3840
aggtagtatt gattgtatgc actggaggtg ggaaagttgt ctgagggctt ggaagggtca    3900
attcacccgt ggtgattaca aagtcccaac aattatcctt gaagcagttg cttcacacga    3960
cctatggatt tggcatgcct tctttggtgt cgctggttct aacaacgaca tcaacgtgct    4020
gaatcagtcc cctcttttcc ttgacacagt gagaggtgag gcttctcggg tccattatta    4080
tgtcaacggg gaagagtaca accatgggta ttacctagct gatggtatat atccagaatg    4140
ggctgtattc cagaagacta taccacttcc acaaactgag aagcataagt tatatgctac    4200
acatcaagag ggggcaagga aagatgtgga gcgggctttc ggggtattgt aagctcgttt    4260
caacatcgta cgtcgtccgg caaagaaatg aagagaaag agtgttggaa atatcatgct    4320
aacttgcgtg attctccaca atatgattgt tgaagacgag ggcgaggatg caatatgtga    4380
cctagacctc aatagaattc ctaggacatc aatagtactg cctccagaag taaccagtgg    4440
tggtaaccaa tgttttcgtg atgtgctaag taggaaagct actatttgtg ctcgttcaat    4500
gcatacccag cttaaaactg atttaattta gcacatttgg aaccggttca ggaatacgca    4560
gcgtacataa ccatggtagg gtaattagca tataatttcc cccttttttg tcatatatag    4620
agccttttaa tttacccttc tatatgtttt atttcaggaa caattaagct ttgatgtcta    4680
ctgtgttgca cctctgcaac acacctctta caggtatatt tccatcatat ggtatattta    4740
tcgtgtgagt actttcagct gtaatgaaca tcgaaatttt tgtgtacatg aaccgatttt    4800
gttcctccat atgctatata tgttgtatac atgaactgct agcttcatca ttgatctttt    4860
ttacatctca gttcaaaaat atgattcatg aatccatgta actatagtgt agggactgtg    4920
acaatctttc aagaaaattt attggaatga gacacaccta attttatagt tttaggaaaa    4980
gtttactgta attggcagaa atttgaccat cactaagtag ttagatttct gggattaata    5040
ttgcatttgt actgtgattg ttctgctgat aacataattt atattctgca acaaatcaag    5100
atggctgatg atggtccata tggagatcaa gaactatctc agtttatatc tatgttttcg    5160
ttaactgtta ttttgttatc cctaaaaagt tgccttgtgt agcttattat tgtctagttt    5220
ttgtggtcct tttgtttgat ggcatgttgc caggagattt gtgaatcatc gtatctgttt    5280
cactgtttgg attattaatc ctctatttaa ctagctctga tgtgattgtg tatatgtggt    5340
gcaacaaaat ggccacaaat atggatgtca ggactgatcc caacaactgc tattggcatg    5400
catgcattaa atagttcaat gtattaatct ctgacatttt acagctaatc tattgtactt    5460
ggtaagctat aagctagctc ttcctgagtt ggacagaaaa ttggagatgg cagtgggctc    5520
tctattgacc ttgctc                                                    5536
```

<210> SEQ ID NO 15
<211> LENGTH: 238
<212> TYPE: PRT
<213> ORGANISM: Oryza sativa

<400> SEQUENCE: 15

```
Met Gly Leu Gly Cys Gln Leu Gln Pro Ile Asn Val Glu Asn Gly Asn
  1               5                  10                  15

Asn Gly Asn Ala Thr Arg Thr Glu Lys Arg Leu Gly Trp Ser Thr Glu
             20                  25                  30

Glu Asp Leu Arg Leu Val Ser Val Leu Arg Glu Tyr Leu Phe Gly Ser
         35                  40                  45
```

```
Gly Ile His Asn Thr Cys Asn Leu Thr Ile Val Lys Tyr Leu Glu Ile
    50                  55                  60

Val Gly Gln Ala Trp Leu Asn Asn Ser Asn Asp Pro Ile Glu Ser Asn
 65                  70                  75                  80

Phe Lys Lys Asn Asp Lys Tyr Trp Asp Val Ala Ala Tyr Asn Ser
                 85                  90                  95

Thr Thr Pro Ser Ser Arg Phe Ser Lys Ile Lys Lys Val Arg Asn
             100                 105                 110

Phe Cys Cys Pro Trp Lys Glu Ala Asn Ser Leu Tyr Ala Ser Gly Glu
             115                 120                 125

Cys Asn Val Asp Leu Met Asp Lys Ala Leu Lys Met Tyr Glu Asn Asp
130                 135                 140

Phe Lys Asp Gly Arg Phe Leu Phe Ile Glu Cys Trp Asn Glu Leu Lys
145                 150                 155                 160

Thr Gln Pro Lys Trp His Ala Tyr Leu Asp Gln Leu Asp Lys Ser Asn
                165                 170                 175

Lys Arg Lys Arg Asp Tyr Ala Asp Ala Thr Pro Leu Asp Asp Glu Glu
            180                 185                 190

Ile Pro Arg Pro Met Gly Val Lys Ala Lys Ala Lys Arg Ile Gly
            195                 200                 205

Lys Gly Lys Gly Lys Val Gln Asp Cys Thr Ala Glu Leu Glu Asp Asp
210                 215                 220

Thr His Lys Phe Met Glu Ala His Glu Ala Ala Lys Glu Gln
225                 230                 235

<210> SEQ ID NO 16
<211> LENGTH: 65
<212> TYPE: PRT
<213> ORGANISM: Oryza sativa

<400> SEQUENCE: 16

Ser Glu Leu Leu Glu Thr Gln Arg Arg Val Ala Ser Asp Asn Leu Glu
  1               5                  10                  15

Ala Lys Lys Val Gly Arg Gln Thr Ala Met Ile Ala Ala Tyr Arg Glu
             20                  25                  30

Leu Leu Asn Lys Asp Thr Arg Asp Met Pro Asp Asp Val Arg Ser Glu
         35                  40                  45

Leu Val Ala Met Leu Lys Cys Met Arg Glu Asp Ile Phe Thr Lys Asn
     50                  55                  60

Gln
 65

<210> SEQ ID NO 17
<211> LENGTH: 338
<212> TYPE: PRT
<213> ORGANISM: Oryza sativa

<400> SEQUENCE: 17

Met Ser Asp Ser Ser Ser Tyr Ser Ser Ser Asn Ser Asp Asp Leu Asp
  1               5                  10                  15

Pro Ser Lys Val Leu Asp Lys Tyr Ile Ser Glu Gln Asn Val Leu Asp
             20                  25                  30

Ser Phe Ala Ser Arg Ile Ile Glu Lys Met Lys Gly Arg Leu Gly Ala
         35                  40                  45

Gly Arg Ser Lys Arg Gln Gly Gly Thr Arg Lys Thr Ile His Arg Asp
     50                  55                  60
```

His Val Asp Ala His Ser Arg Leu Val Ala Asp Tyr Phe Ala Glu His
 65                  70                  75                  80

Pro Leu Tyr Pro Glu Trp Met Phe Arg Thr Arg Phe Arg Met His Lys
             85                  90                  95

Pro Leu Phe Leu Arg Ile Val Glu Ala Leu Gly Gln Trp Ser Pro Tyr
            100                 105                 110

Phe Thr Gln Arg Glu Asp Cys Ser Ser Arg Thr Ser Leu Ser Pro Pro
        115                 120                 125

Gln Lys Cys Thr Ala Ala Leu Arg Met Leu Ala Tyr Gly Thr Pro Ala
    130                 135                 140

Asp Ala Leu Asp Glu Tyr Leu Lys Ile Gly Lys Ser Thr Ala Leu Glu
145                 150                 155                 160

Cys Leu Glu Met Phe Ser Gln Gly Val Ile Glu Val Phe Gly Gly Thr
                165                 170                 175

Tyr Leu Arg Arg Pro Thr Arg Glu Asp Val Glu His Ile Leu His Val
            180                 185                 190

Asn Glu Ser Arg Gly Phe Pro Gly Met Leu Gly Ser Ile Asp Cys Met
        195                 200                 205

His Trp Arg Trp Glu Ser Cys Leu Arg Ala Trp Lys Gly Gln Phe Thr
    210                 215                 220

Arg Gly Asp Tyr Lys Val Pro Thr Ile Ile Leu Glu Ala Val Ala Ser
225                 230                 235                 240

His Asp Leu Trp Ile Trp His Ala Phe Phe Gly Val Ala Gly Ser Asn
                245                 250                 255

Asn Asp Ile Asn Val Leu Asn Gln Ser Pro Leu Phe Leu Asp Thr Val
            260                 265                 270

Arg Gly Glu Ala Ser Arg Val His Tyr Tyr Val Asn Gly Glu Glu Tyr
        275                 280                 285

Asn His Gly Tyr Tyr Leu Ala Asp Gly Ile Tyr Pro Glu Trp Ala Val
    290                 295                 300

Phe Gln Lys Thr Ile Pro Leu Pro Gln Thr Glu Lys His Lys Leu Tyr
305                 310                 315                 320

Ala Thr His Gln Glu Gly Ala Arg Lys Asp Val Glu Arg Ala Phe Gly
                325                 330                 335

Val Leu

<210> SEQ ID NO 18
<211> LENGTH: 92
<212> TYPE: PRT
<213> ORGANISM: Oryza sativa

<400> SEQUENCE: 18

Ala Arg Phe Asn Ile Val Arg Arg Pro Ala Lys Lys Trp Lys Arg Lys
  1               5                  10                  15

Ser Val Gly Asn Ile Met Leu Thr Cys Val Ile Leu His Asn Met Ile
             20                  25                  30

Val Glu Asp Glu Gly Glu Asp Ala Ile Cys Asp Leu Asp Leu Asn Arg
         35                  40                  45

Ile Pro Arg Thr Ser Ile Val Leu Pro Pro Glu Val Thr Ser Gly Gly
     50                  55                  60

Asn Gln Cys Phe Arg Asp Val Leu Ser Arg Lys Ala Thr Ile Cys Ala
 65                  70                  75                  80

Arg Ser Met His Thr Gln Leu Lys Thr Asp Leu Ile
             85                  90

```
<210> SEQ ID NO 19
<211> LENGTH: 12
<212> TYPE: PRT
<213> ORGANISM: Oryza sativa

<400> SEQUENCE: 19

His Ile Trp Asn Arg Phe Arg Asn Thr Gln Arg Thr
 1               5                  10

<210> SEQ ID NO 20
<211> LENGTH: 2
<212> TYPE: PRT
<213> ORGANISM: Oryza sativa

<400> SEQUENCE: 20

Pro Trp
 1

<210> SEQ ID NO 21
<211> LENGTH: 2
<212> TYPE: PRT
<213> ORGANISM: Oryza sativa

<400> SEQUENCE: 21

Gly Asn
 1

<210> SEQ ID NO 22
<211> LENGTH: 5955
<212> TYPE: DNA
<213> ORGANISM: Oryza sativa

<400> SEQUENCE: 22
gggcaaggga aataatagag taaacatctt actattagta tcctccacat catctataga      60
tggtttaaca gacgacattt acaataagat agtacatgct gtctctaagc cgtctctagc     120
aaagcaagct gcatttaatt ctctaattgt atctttcaag ttatgtagga tcaactgtaa     180
acatcacttg agtagccact tatatgtcaa ccatagatgg aagactatgt tcaatcaata     240
aaaaaataaa tcatgtgatt tatcacaaag cagatggatt tatcaacaac aatggtgtaa     300
tattcctaat tcattcgaac taattcattc gaactaaaca gtacaatagt gattcagatt     360
gttacttgat cgaaagaata ttcacagatt gacaaataac taattcatag accgacaaaa     420
taacttagtc tgttgcaatg atccatacat caacattcga caaaagaaat taggccatta     480
caacgatcca tactgccaat agatggtaac aacacaagtg ttcttacatg acaccagcga     540
attactaaaa attactttat aactagatta tctttctcaa gcagaaccaa aacaagctgc     600
cagccttcca aattgagcat cttcactacc tgtcattaaa gcaacattat tccatggaa      660 tataggaggc tgatcattat agaacaattg tagcatataa tctggatggc aaaacaactg     720
gaaggaagta gtactactat tttaagtaga ctattaaagg acttatttga ttatgttgtt     780
ctttggactg tacagtgcaa gtagacatgt acatacctct caaaaccata gcagaaagca     840
ccaaaaagct agcaccaaag ttttccattg tccctgaaat aaataaataa aatgataagt     900
gaattaagat gcttgcaatt gtaattgaaa atgtgaaaac aagatgctta atgtcctacc     960
acaactaagt acgacgggta ttgctaaact tttgccaaat atgttcaacc agatcttttt    1020
ttagttggga atgtggtgca cgagcacgta ttgcagcttt cctacgcagc acctgatcaa    1080
agcatggatt gtgcccagta gttacttcag gaggaagagc aaccgatgct ccagggtcca    1140
cattcagatc aataggaatt ttaaaccccc cctctctcat tttcaactat catattatgg    1200
```

```
agaataatac aagctttcat gattctccca acactcttcc gcttccacga ccgtgctggg    1260
tggcgcacaa tattgaaacg ggactacagg accccaaatg cacactccac gtctttcctt    1320
gccccttctt gatactgtgc atatagcttg tgcttctctg tttgtggagc agctattgac    1380
ttcacaaagg tagcccattt tggatatatt ccatcagcaa ggtagtatcc tgtgttatac    1440
tcattaccat tgacagaaaa ctttactcta ggagcttccc ctttcagcac atcaagaaat    1500
agtggggatt ggttcagcac attgatgtca ttatttgacc ccgtgacacc gaagaaagca    1560
tgccatatgc ggaggtcacg agtagcaacc gcttcgagga taattgttgg cactccatag    1620
tcaccgcggg taaactgccc tctccatgct gttgggcatt tttcccacct ccaatgcatg    1680
caatcaatac tgcctagcat cccagggaag cccctagact cattaacttg aagtatacgc    1740
tccacatcct catatgtggg acgtcgcaaa tactctgaac caaataccte aatcaccect    1800 cgtgcgcaca tatccaagca ctgcaaggac gtgctcttgc caatcttaag gtactcatct    1860
aggctatcag cagggctgcc atacgctagc atgcgcattg cagctgtgca cttctgtaaa    1920
ggtgagagcc cttggcgacc actgcaatct acctttagtg taaagtaagg agaccacctt    1980
ccaagggcac tcactatgcg aagaaaaagg ggtcttccca tacgaaatct tgtacggaac    2040
atgctctcag ggtaaagagg gtcttcacta agtagtcag ctatgagacg atgatgtgct    2100
gctgtgtgat ccctcttgat tgtcttcctt gtcacactct tccttctgat ttttccaatt    2160
ctaagcttgg tcttgatctt ttccatgacc cttcttgcaa agaatctat gaggttctgc    2220 tcaacaatgt attggtctat aattttggaa ggatctaatt caccagaatc atctggagac    2280
atggtggaga caaggagtgc aaggaatggg aaagaagtgt tgaaaggaat gggaagaag    2340 tgttgaaagg aatggcagag ggatggatag ttagcaccat tagaccaata tatatatata    2400
tgggccaaca gtacactgtt gggaatgcat actagctagt agcatgttta tttgaattac    2460
ccttaattag attattggga atgcatacac agagcatgtt tatttggatt actattaatt    2520
agactattgg gaatgcatac acaaagcatg tttatttgga ttactattaa ctagactatt    2580
gggaattcaa gactgcatgt ttatctgcac attgttgact tgactgcatg ttaattttgc    2640
aactgctgac ttgactacat gttttctgg aaataatagc tacatgctga ttatattaca    2700
agttagatta catcaatatt tgcaactctt tgaattgtgc aagaaacata tatatgtttg    2760
caggaagttc aattgcagca agtaaaaaaa aatacaacaa gctttaatta gagactggaa    2820
agtgaagata ccttagtatt acggaaacaa cttctccctc atacacttca atgccatcaa    2880
atgctcggat ctaacatcat caggaatatc ttttgtatct tgtaacatga gagaccgata    2940
tgtttccaac ataacagcct ccttgtgctc catggctgca aggtgcgcta acttttttga    3000
ttcaaggtta tcactagcaa cacgcctctg agtctctagt agttcatcac gacctttatt    3060
tgccatctcc tgaacttctt taagcttgtc aatttcatca tcagtatctg atagataaac    3120
ctttgccttc cttttgcgtc tgcctttacc attacgttgc gccttagcag ttttttgttcc    3180 tattggacgt ttaatatctt caggactgtt aggagtggac atttgctcca tcacttccac    3240
ttaatcatcc atctttggtt tgtttggctt ctcaagttcc tccaagtaag aatgccactt    3300
tggttggtca cgaagaatgt tccaacaatg cagaaatgaa aatgggcctt ccttgtaatc    3360
tgcttgatat gctgcttcag cctttttccct gagttgcata tcattttgtc cactaacata    3420
tatggattta acctctttat aaacacaaca gaaacggcca acatttttct taattttatg    3480
aaaacggtct ttgatttgtt tttcttgcct tgtcctgttt ttgggagtgg tgctattata    3540
ctcagcagta acatctcccc aataacgatc attttttctta aaattaccac tgatcgaatc    3600
```

```
attcgagttg tttagccaag cactcaccta taatcaaaac aaaacaggat tagtcctata    3660
ctagaaataa agtaacagtc aatgagaaaa cacgattcat tgcctacatc cttatttact    3720
tactagtctt atgtcctcct ctgttgacca tgtcaaccgc ttctcagtcc taacagtgtg    3780
ggcttcttca tcaccactat caatgttgac aggttgttgt gctcctggac gtaattttga    3840
acatggtgct acttgttcag caggataata atttggaggc acaaaaggtc gatgattctg    3900
taaaattgat ggatcctgaa agtaacttaa gaaaccacca ggcggatgaa agtccatacc    3960
actgcaagaa aaagacagag atccaaaatt attgccagat aacatcctta gcacttttt     4020 tctcttcatc tgtaaatgag tacattaaaa attgacaaag cacagcctat gatactaata    4080
attctcatgc catataaaat tactatttt gtgtttgtag ataagttgat ttgtctgttc     4140
actacctatg tagtaagagt tcttgattat tcaagagtaa agtccatcac cggtccctaa    4200
acttgtaccg ctgtgtcatc ctagtcccta aactcgcaaa tcgaccgttc aggtcctcaa    4260
acttgttcga ctgtgtcatc ccggtcccta aacttgcaga tcactcattt aggtcatcca    4320
acttgttcaa ttgtgtcacc ccggtcccta aatttggatt tgaatatcat ctgggtcaaa    4380
taaaacggtc taaagacttt atatttaaaa ataattcata acttttttcat gtgaattata    4440 atgaagacaa actttatatc aaacttgtag ccctcgacgt gatctacaac tttgtagttg    4500 attttttta atttaagtca tttttttgtcc caaaatgtaa tttaaaatt aaaatttcaa     4560 aatctataaa catgcaacaa tattttggga ccataaacag ttttaattca aaaccttc      4620 aactacaaag ttgtaggtcg tgtcgagggc tagaattttg atataaagtt tgtcttcatt    4680
aaagttcaca tgaaaaagt tatgaattat tttttatata aagttttag accgtcctgt      4740 ttagagaccg gggtgacaca actgaacaag ttggaggacc taaacgagtg atctgcaagt    4800
ttaaggaccg ggatgacaca gtcgaacaag tttgaggacc taaacggtcg atttatgagt    4860
ttagggacca ggatgacaca gcggtacaag tttagggacc ggtgatggaa tttactcatt    4920
attcaaagtg tatgtgtaga ttagtacaaa aaatttggcc atgcactgac ctatgtacac    4980
tagttattgc tataaaataa atctatatgt atctgtagcc cttgcttact atcaagttat    5040
tctcttgcca taaaatttt tccctttccg aatatagcaa gacttaactt tagtatgaga     5100
aacatatgta cacgttgatt cttgacatat tagcagggga tatgctaatc tgctagcagc    5160
agatcagatc gtgaggggaa aactagaata cggcaagaat aaaacttagt tagtcaacac    5220 cattaattt ctaatcaaca tggaggtaca cggaacttcc ggagcaaatc aatccaaaac     5280
cattcaatat caaaagtaca taccgttctt gcagatctga caaatcaatg gcactacgat    5340
ccaatccttg cttcatttgg gccatgggaa aagcagaagc agcggcgccg tacgcgtaga    5400
gcaaagggtg cggcggctgc ggtggcgccg gaccttgcca ggcaccactg cctaaggatc    5460
ccggcaacat catgccagat gcgaaggatc ccggcgaggc ttgcgacgga gatggcggcg    5520
gcggcggcgc aacctcccgt ttcgagcgac ccattgtttc agcagattga gttgagggat    5580
tactaactag atggggtatt tcagtaggaa tttgacgctt cgactaacta atttggcgcg    5640
tgaagtgcga ttttttttcc cgcggatggg gatttaccgc caaatataca gagaagggat    5700
gagccatgga gcatgggatg caaaaggcca agaaagcgcg ttattggtcg acggcatcgg    5760
ctcctgcatc gtctccacgc ctactccatc catcttgttg ctcgtgccga gctgtcgatt    5820
aaacatgcgc ccgctttctt ctctctcttc ctttctctgt cctccagctt ctcttccttt    5880
ctctgtcctc cagctcagat tgtgatgacc tggacgggct aatagtaggt tgattagtcc    5940
ttattgtact tgccc                                                      5955
```

<210> SEQ ID NO 23
<211> LENGTH: 230
<212> TYPE: PRT
<213> ORGANISM: Oryza sativa

<400> SEQUENCE: 23

Met Lys Arg Lys Lys Val Leu Arg Met Leu Ser Gly Asn Asn Phe Gly
1               5                   10                  15

Ser Leu Ser Phe Ser Cys Ser Gly Met Asp Phe His Pro Pro Gly Gly
            20                  25                  30

Phe Leu Ser Tyr Phe Gln Asp Pro Ser Ile Leu Gln Asn His Arg Pro
        35                  40                  45

Phe Val Pro Pro Asn Tyr Tyr Pro Ala Glu Gln Val Ala Pro Cys Ser
    50                  55                  60

Lys Leu Arg Pro Gly Ala Gln Gln Pro Val Asn Ile Asp Ser Gly Asp
65                  70                  75                  80

Glu Glu Ala His Thr Val Arg Thr Glu Lys Arg Leu Thr Trp Ser Thr
                85                  90                  95

Glu Glu Asp Ile Arg Leu Val Ser Ala Trp Leu Asn Asn Ser Asn Asp
            100                 105                 110

Ser Ile Ser Gly Asn Phe Lys Lys Asn Asp Arg Tyr Trp Gly Asp Val
        115                 120                 125

Thr Ala Glu Tyr Asn Ser Thr Thr Pro Lys Asn Arg Thr Arg Gln Glu
    130                 135                 140

Lys Gln Ile Lys Asp Arg Phe His Lys Ile Lys Lys Asn Val Gly Arg
145                 150                 155                 160

Phe Cys Cys Val Tyr Lys Glu Val Lys Ser Ile Tyr Val Ser Gly Gln
                165                 170                 175

Asn Asp Met Gln Leu Arg Glu Lys Ala Glu Ala Ala Tyr Gln Ala Asp
            180                 185                 190

Tyr Lys Glu Gly Pro Phe Ser Phe Leu His Cys Trp Asn Ile Leu Arg
        195                 200                 205

Asp Gln Pro Lys Trp His Ser Tyr Leu Glu Glu Leu Glu Lys Pro Asn
    210                 215                 220

Lys Pro Lys Met Asp Asp
225                 230

<210> SEQ ID NO 24
<211> LENGTH: 133
<212> TYPE: PRT
<213> ORGANISM: Oryza sativa

<400> SEQUENCE: 24

Val Glu Val Met Glu Gln Met Ser Thr Pro Asn Ser Pro Glu Asp Ile
1               5                   10                  15

Lys Arg Pro Ile Gly Thr Lys Thr Ala Lys Ala Gln Arg Asn Gly Lys
            20                  25                  30

Gly Arg Arg Lys Arg Lys Ala Lys Val Tyr Leu Ser Asp Thr Asp Asp
        35                  40                  45

Glu Ile Asp Lys Leu Lys Glu Val Gln Glu Met Ala Asn Lys Gly Arg
    50                  55                  60

Asp Glu Leu Leu Glu Thr Gln Arg Arg Val Ala Ser Asp Asn Leu Glu
65                  70                  75                  80

Ser Lys Lys Leu Ala His Leu Ala Ala Met Glu His Lys Glu Ala Val
                85                  90                  95

Met Leu Glu Thr Tyr Arg Ser Leu Met Leu Gln Asp Thr Lys Asp Ile

-continued

```
            100                 105                 110
Pro Asp Asp Val Arg Ser Glu His Leu Met Ala Leu Lys Cys Met Arg
        115                 120                 125

Glu Lys Leu Phe Pro
        130

<210> SEQ ID NO 25
<211> LENGTH: 332
<212> TYPE: PRT
<213> ORGANISM: Oryza sativa

<400> SEQUENCE: 25

Met Ser Pro Asp Asp Ser Gly Glu Leu Asp Pro Ser Lys Ile Ile Asp
  1               5                  10                  15

Gln Tyr Ile Val Glu Gln Asn Leu Ile Asp Ser Phe Ala Arg Arg Val
             20                  25                  30

Met Glu Lys Ile Lys Thr Lys Leu Arg Ile Gly Lys Ile Arg Arg Lys
         35                  40                  45

Ser Val Thr Arg Lys Thr Ile Lys Arg Asp His Thr Ala Ala His His
     50                  55                  60

Arg Leu Ile Ala Asp Tyr Phe Ser Glu Asp Pro Leu Tyr Pro Glu Ser
 65                  70                  75                  80

Met Phe Arg Thr Arg Phe Arg Met Gly Arg Pro Leu Phe Leu Arg Ile
                 85                  90                  95

Val Ser Ala Leu Gly Arg Trp Ser Pro Tyr Phe Thr Leu Lys Val Asp
            100                 105                 110

Cys Ser Gly Arg Gln Gly Leu Ser Pro Leu Gln Lys Cys Thr Ala Ala
        115                 120                 125

Met Arg Met Leu Ala Tyr Gly Ser Pro Ala Asp Ser Leu Asp Glu Tyr
    130                 135                 140

Leu Lys Ile Gly Lys Ser Thr Ser Leu Gln Cys Leu Asp Met Cys Ala
145                 150                 155                 160

Arg Gly Val Ile Glu Val Phe Gly Ser Glu Tyr Leu Arg Arg Pro Thr
                165                 170                 175

Tyr Glu Asp Val Glu Arg Ile Leu Gln Val Asn Glu Ser Arg Gly Phe
            180                 185                 190

Pro Gly Met Leu Gly Ser Ile Asp Cys Met His Trp Arg Trp Glu Lys
        195                 200                 205

Cys Pro Thr Ala Trp Arg Gly Gln Phe Thr Arg Gly Asp Tyr Gly Val
    210                 215                 220

Pro Thr Ile Ile Leu Glu Ala Val Ala Thr Arg Asp Leu Arg Ile Trp
225                 230                 235                 240

His Ala Phe Phe Gly Val Thr Gly Ser Asn Asn Asp Ile Asn Val Leu
                245                 250                 255

Asn Gln Ser Pro Leu Phe Leu Asp Val Leu Lys Gly Glu Ala Pro Arg
            260                 265                 270

Val Lys Phe Ser Val Asn Gly Asn Glu Tyr Asn Thr Gly Tyr Tyr Leu
        275                 280                 285

Ala Asp Gly Ile Tyr Pro Lys Trp Ala Thr Phe Val Lys Ser Ile Ala
    290                 295                 300

Ala Pro Gln Thr Glu Lys His Lys Leu Tyr Ala Gln Tyr Gln Glu Gly
305                 310                 315                 320

Ala Arg Lys Asp Val Glu Cys Ala Phe Gly Val Leu
                325                 330
```

<210> SEQ ID NO 26
<211> LENGTH: 107
<212> TYPE: PRT
<213> ORGANISM: Oryza sativa

<400> SEQUENCE: 26

Ser Arg Phe Asn Ile Val Arg His Pro Ala Arg Ser Trp Lys Arg Lys
 1               5                  10                  15

Ser Val Gly Arg Ile Met Lys Ala Cys Ile Ile Leu His Asn Met Ile
            20                  25                  30

Val Glu Asn Glu Arg Ala Lys Gly Gly Phe Lys Ile Pro Ile Asp Leu
        35                  40                  45

Asn Val Asp Pro Gly Ala Ser Val Ala Leu Pro Pro Glu Val Thr Thr
    50                  55                  60

Gly His Asn Pro Cys Phe Asp Gln Val Leu Arg Arg Lys Ala Ala Ile
65                  70                  75                  80

Arg Ala Arg Ala Pro His Ser Gln Leu Lys Lys Asp Leu Val Glu His
                85                  90                  95

Ile Trp Gln Lys Phe Ser Asn Thr Arg Arg Thr
            100                 105

<210> SEQ ID NO 27
<211> LENGTH: 4500
<212> TYPE: DNA
<213> ORGANISM: Oryza sativa

<400> SEQUENCE: 27
ggcctccttc aaaggttgag acaactgtta gctcatagat cgtacacatc atctaagaga      60
tagaacaaga gatagtttct ctaatgaact gtctctaagg ttatctcttc ttgctttat     120 ggcagcatgg gtagtaaatg acatggtgat aaactacaca atatctctat ggtccttcat    180
gtgatgctat tcaaaagatc tgtcgattaa aaatgaacat ctcatcatag tgtgaatata    240
gataaatagc acaacatcga cttagagtat atttagcatt aagtgcaatt cttccaactc    300
acggtccact acagcaacca gataacatca tagccatatc atggcacttt agtacaatgc    360
ggaaaagagc aaactgaagg gaaaaaaaaa gactgcatca cgtcacacaa gtgatagaag    420
agttcgacaa ccaccaaaag ctggacagca accagaagtg cttatcccat tccttgaaca    480
agatcaccaa aagctggacc gcagccacaa aaacaagtga agacatcga atctgttcgc     540 ccctggtaga gagaaaaaca tgtacagtaa gtgaaagtga tgaatacagt cagtctaaaa    600
taaaattaca atgaaattgt acactagagc ttacattata ctgaaataac agtgactaat    660
tattttgcct agtttgaaac cgttgccaaa tatgctcaat taagtcattt ttaagctggc    720
tatggattgg tttggctcgg atagaagcat ttctttgccg cacatcgctg aagcttgggt    780
gatcattact ccctgcatga acttctggtg gaagaacaat tgatgttcct ggggcagcat    840
tcaagtcaat aggatcttct gccatttctc cctcatcttc cactatcatg ttgtggagaa    900
ttacacaagc ttgcatgatt tttcgaagaa cttttggct ccatgatcgt gctggacgat      960
gcacgatgtt gaagcgagct tgcaacaccc caaaagcacg ctcaatatct ttccgtttcc    1020
cttcttgttc ccttgcaaat agcttgtgct tgtctagtta aggagatctt atagacttta    1080
caaaggctgc ccattccgga taattccat cagcaagata atatcccgtg ttgtattgtg      1140
tcccattgac agtaaattgg atttggggag cttcacattt tattgcttca ataaacagag    1200
gggactgatt gagcacatta atgtcattgt tggacccagg aataccaaag aatgcatgcc    1260
aaatatgaag gtcatatgaa gctacagcct caaggataat agttggatac ttttggtcac    1320

```
ctcgggtata ttgtcccttc catgcggttg ggcaattttt ccatcgccag tgcatgcagt    1380
caatgcttcc caacatccga gggaatccac gagactctcc aacttggagc aaacgctcga    1440
gatcctcagc cgtggggcga cgcaggtacc tactactaaa tacctcgacg acaccttcca    1500
caaaattttc taagcactct agagcagtac tctggggaac cttcaagtac tcatcaagag    1560
tgtcagcagc agtcccatat gcaagcatac ggatcgctgc agtgcacttc tgcaatggtg    1620
agtgcccaag gcgtccagta caatttattc tatgtgtaaa ataggaagac cacttgccta    1680
gttcatccac aatgtgtagg aacacatgcc ttctcatccg gaaccttcta cggaatgttg    1740
cagcagagta gagaggatct ttagcaaaat aatcagcaaa tagttgatca tgggctcctt    1800
catggttcct attgatgtac ttccttggac cacttgtacg cctagatgta cctccttcca    1860
gtctggcctt aatccttttg tcgatccgcc cggcaaaaga gttaaggaca ctatgctctg    1920
ccatgaacat atctgtagtg taaacctcgg ctgggtctat ggaatcgtca gactcatccg    1980
acatgtttta ctggatggaa gggaacagat gaggcagtgt tggactggat ggaaggaaca    2040
gatgaggaag aatagaatag gaagaatagt actggataga aggaacagag gaggatagtg    2100
ctggattgtt tgctagact gaatataaca gagcaatata tagtcacatg gtatagatta    2160
atttgtggta cattgactaa gaatacagat tatattgtat ggttatttgt ggtacattaa    2220
ctaagaatac agattacaat gtatggttgt ttgtggtaca ttaactaaga atacagatta    2280
caatgcatgg ttatttgtgg tacattgact aataatacag attacaatgc atggttattt    2340
gtgatatatt gactaagaat acatattaca atatatggtc atttgtggaa cattgactaa    2400
aaataaagtg catggtgatt gacagaaaat accttagatt atatcaccaa gcagtttctc    2460
cctcaacatc ttgagaccca tcacgtgctc agctttcatc tcatcagtca tttgactagt    2520
gtccatgctc atcatttttt gatatgattc tgtcaagaca gcctctctcc taagccttgc    2580
tacttcaact tttgcatctg aaatacggtg ttgagtccct aaaaactctt catgtcgttt    2640
gctagctgca gcttgaacat ccatgtactt cttcatatct tcacgtaaac tgtcatcatc    2700
atccttgcct ttgcctttgc ctttgccatt gcgttgtttc ttagcttcat tcctccctat    2760
tggacgctcc ttttctccga tatcctttg tgatagtgtg tcacttccat catccaagct    2820
ccgcttgtgt ggcttttcaa gctcctccaa aacagcatgc cacttgggtt catcacgaag    2880
aaccttccaa cagtgcaaaa ctgtgaatgg accttcgtta ggatagtcat ccacataaaa    2940
ctgattagca aagtctctca actgatcatc tgaatatcca ctagtataaa ctaatgcagc    3000
cttcttccag gaggcgcaga aaaatcccac ccatctctta atccttgcc atcgatcttt    3060 gagatgcttt acttcccttt tccggttaat aggtgtagtg ctgttgtata attcaactac    3120
atctccccag tagctctcat tcttcttgcc atttccattg atcggatcat tagagtggta    3180
cagccatgca ctcacctaca tttagcatta tgtgttagta aagtttcaga atgatggtac    3240
aaatccctgc aagttgtcta aaattttact caccaaccgc aagtcctcat ctgatgccca    3300
tgtaagacgc ttagcagtcc taacatcgtc accatcatct aagttgatga caggtttggc    3360
ttttgacctt gatctagcat gcgtagtgcc tgaattagtt gttggtgcca taggtggcat    3420
aggtggccat gttgctagga acaaaacatg aggtgggact aatggctgtt gaccagtttg    3480
taacatgctt aggaaaccac caggtggatg tatatcccata ccactgaaat atcaggagcc    3540
aaaatcatga ctatgagcga ggaagaaaca acacatttcc tatctgtgct aaaacattat    3600
taattctaca atctaaatag tctcaacaaa aaggaatttg cttgtttcct gcagaaacaa    3660
cacacaagca aattggtttc ttaccaatct gaggatacag ggccaaagga gttggtgtgt    3720
```

-continued

```
ggcaaagatc cgttccacca ccctgcacat cgttgagagc atcatcagct tattgttcta   3780
ctccaacatc caggaagcaa gcaaggcaga gccactgcaa taaccatcag gtttgaatgt   3840
acggtacagt acctggttgg cctcctagag gaggagccat tgcaaaactg gcctgaaaga   3900
aggcagacga ggcagcgtcg aagcacccag aggcagtcgc agatcccgat ggcggcgatg   3960
atggcggccg cggcggccgc gaagctactt gtcgtttgga ccggcggctc atcctgctct   4020
acagctcgtc gtcgttggca agaggagtgg attcatcgtt gggctcgtgg aaacggatac   4080
gtcgacgccg acgaggaaga tttcacacac tggagaagaa aagaggaggg agggtgcaag   4140
ggaaggattg gcgcgcgggt ggctggagga tttgcgcggg ggagagcaaa ttggcgcgcc   4200 aggggggtggg ggagcgaatt gcagcgcgcg ggatcgggcg ggaacggggt gcagcgcgcg   4260
ggggtgggcg ggaggtgcgg cggggcgatt tggggaagg gagcacggga tctgattttg    4320
gcgtggaaga gtcgactgct gtctcttgcg caggctcata cggcatcggt aactgagcga   4380
gataggcgtg ggaataggag atagatggat tgattttttg tcttctcttt cctccacata   4440
ggatacatga tgatgtggac atgttatgag atagcttaca tggcaccatt ggaggaggcc   4500
```

<210> SEQ ID NO 28
<211> LENGTH: 335
<212> TYPE: PRT
<213> ORGANISM: Oryza sativa

<400> SEQUENCE: 28

```
Met Asp Ile His Pro Pro Gly Gly Phe Leu Ser Met Leu Gln Thr Gly
  1               5                  10                  15

Gln Gln Pro Leu Val Pro Pro His Val Leu Phe Leu Ala Thr Trp Pro
                 20                  25                  30

Pro Met Pro Pro Met Ala Pro Thr Thr Asn Ser Gly Thr Thr His Ala
             35                  40                  45

Arg Ser Arg Ser Lys Ala Lys Pro Val Ile Asn Leu Asp Asp Gly Asp
         50                  55                  60

Asp Val Arg Thr Ala Lys Arg Leu Thr Trp Ala Ser Asp Glu Asp Leu
 65                  70                  75                  80

Arg Leu Val Ser Ala Trp Leu Tyr His Ser Asn Asp Pro Ile Asn Gly
                 85                  90                  95

Asn Gly Lys Lys Asn Glu Ser Tyr Trp Gly Asp Val Val Glu Leu Tyr
            100                 105                 110

Asn Ser Thr Thr Pro Ile Asn Arg Lys Arg Glu Val Lys His Leu Lys
        115                 120                 125

Asp Arg Trp Gln Arg Ile Lys Arg Trp Val Gly Phe Phe Cys Ala Ser
    130                 135                 140

Trp Lys Lys Ala Ala Leu Val Tyr Thr Ser Gly Tyr Ser Asp Asp Gln
145                 150                 155                 160

Leu Arg Asp Phe Ala Asn Gln Phe Tyr Val Asp Tyr Pro Asn Glu
                165                 170                 175

Gly Pro Phe Thr Val Leu His Cys Trp Lys Val Leu Arg Asp Glu Pro
            180                 185                 190

Lys Trp His Ala Val Leu Glu Glu Leu Glu Lys Pro His Lys Arg Ser
        195                 200                 205

Leu Asp Asp Gly Ser Asp Thr Leu Ser Gln Lys Asp Ile Gly Glu Lys
    210                 215                 220

Glu Arg Pro Ile Gly Arg Asn Glu Ala Lys Lys Gln Arg Asn Gly Lys
225                 230                 235                 240

Gly Lys Gly Lys Gly Lys Asp Asp Asp Asp Ser Leu Arg Glu Asp Met
```

```
                245                 250                 255
Lys Lys Tyr Met Asp Val Gln Ala Ala Ser Lys Arg His Glu Glu
            260                 265                 270

Phe Leu Gly Thr Gln His Arg Ile Ser Asp Ala Lys Val Glu Val Ala
        275                 280                 285

Arg Leu Arg Arg Glu Ala Val Leu Thr Glu Ser Tyr Gln Lys Met Met
        290                 295                 300

Ser Met Asp Thr Ser Gln Met Thr Asp Glu Met Lys Ala Glu His Val
305                 310                 315                 320

Met Gly Leu Lys Met Leu Arg Glu Lys Leu Leu Gly Asp Ile Ile
            325                 330                 335

<210> SEQ ID NO 29
<211> LENGTH: 308
<212> TYPE: PRT
<213> ORGANISM: Oryza sativa

<400> SEQUENCE: 29

Met Ser Asp Glu Ser Asp Asp Ser Ile Asp Pro Ala Glu Val Tyr Thr
1               5                   10                  15

Thr Asp Met Phe Met Ala Glu His Ser Val Leu Asn Ser Phe Ala Gly
            20                  25                  30

Arg Ile Asp Lys Arg Ile Lys Ala Arg Leu Glu Gly Gly Thr Ser Arg
        35                  40                  45

Arg Thr Ser Gly Pro Arg Lys Tyr Ile Asn Arg Asn His Glu Gly Ala
    50                  55                  60

His Asp Gln Leu Phe Ala Asp Tyr Phe Ala Lys Asp Pro Leu Tyr Ser
65                  70                  75                  80

Ala Ala Thr Phe Arg Arg Arg Phe Arg Met Arg Arg His Val Phe Leu
                85                  90                  95

His Ile Val Asp Glu Leu Gly Lys Trp Ser Ser Tyr Phe Thr His Arg
            100                 105                 110

Ile Asn Cys Thr Gly Arg Leu Gly His Ser Pro Leu Gln Lys Cys Thr
        115                 120                 125

Ala Ala Ile Arg Met Leu Ala Tyr Gly Thr Ala Ala Asp Thr Leu Asp
    130                 135                 140

Glu Tyr Leu Lys Val Pro Gln Ser Thr Ala Leu Glu Cys Leu Glu Asn
145                 150                 155                 160

Phe Val Glu Gly Val Val Glu Val Phe Ser Ser Arg Tyr Leu Arg Arg
                165                 170                 175

Pro Thr Ala Glu Asp Leu Glu Arg Leu Leu Gln Val Gly Glu Ser Arg
            180                 185                 190

Gly Phe Pro Arg Met Leu Gly Ser Ile Asp Cys Met His Trp Arg Trp
        195                 200                 205

Lys Asn Cys Pro Thr Ala Trp Lys Gly Gln Tyr Thr Arg Gly Asp Gln
    210                 215                 220

Lys Tyr Pro Thr Ile Ile Leu Glu Ala Val Ala Ser Tyr Asp Leu His
225                 230                 235                 240

Ile Trp His Ala Phe Phe Gly Ile Pro Gly Ser Asn Asn Asp Ile Asn
                245                 250                 255

Val Leu Asn Gln Ser Pro Leu Phe Ile Glu Ala Ile Lys Cys Glu Ala
            260                 265                 270

Pro Gln Ile Gln Phe Thr Val Asn Gly Thr Gln Tyr Asn Thr Gly Tyr
        275                 280                 285

Tyr Leu Ala Asp Gly Ile Tyr Pro Glu Trp Ala Ala Phe Val Lys Ser
```

```
                   290                 295                 300

Ile Arg Ser Pro
305

<210> SEQ ID NO 30
<211> LENGTH: 133
<212> TYPE: PRT
<213> ORGANISM: Oryza sativa

<400> SEQUENCE: 30

Leu Asp Lys His Lys Leu Phe Ala Arg Glu Gln Glu Gly Lys Arg Lys
  1               5                  10                  15

Asp Ile Glu Arg Ala Phe Gly Val Leu Gln Ala Arg Phe Asn Ile Val
             20                  25                  30

His Arg Pro Ala Arg Ser Trp Ser Gln Lys Val Leu Arg Lys Ile Met
         35                  40                  45

Gln Ala Cys Val Ile Leu His Asn Met Ile Val Glu Asp Glu Gly Glu
     50                  55                  60

Met Ala Glu Asp Pro Ile Asp Leu Asn Ala Ala Pro Gly Thr Ser Ile
 65                  70                  75                  80

Val Leu Pro Pro Glu Val His Ala Gly Ser Asn Asp His Pro Ser Phe
                 85                  90                  95

Ser Asp Val Arg Gln Arg Asn Ala Ser Ile Arg Ala Lys Pro Ile His
            100                 105                 110

Ser Gln Leu Lys Asn Asp Leu Ile Glu His Ile Trp Gln Arg Phe Gln
        115                 120                 125

Thr Arg Gln Asn Asn
        130

<210> SEQ ID NO 31
<211> LENGTH: 6126
<212> TYPE: DNA
<213> ORGANISM: Oryza sativa

<400> SEQUENCE: 31
gggcactccc aaccctccac ctagtgtcta tagaatttat taggctgcca cataagcaaa    60
aatatgatct gtgttggcgg ctgtaaaatg tcgattctat accgccaaca tctacataaa   120
gttcggataa taaacatctc aacatagtga taggtgctta atctcacata ttccataagt   180
gttggtatat atttgtatgc agatgataaa ccccgatgtt gggaggaaaa tcagagtata   240
gtgagagaaa tgtgtatcca taaggaggg gttgtgaac ttcatcaaaa catcagtgaa    300
ttaacccaaa actgcgagaa atggacagag aagagcccag ggagtccaca gatcgaaggc   360
caggctagga gggcccagcc caggttcagc cgaacccctc tgatcactgt tgatccttgg   420
gtttggcttg gacgctccag atgctctccc aatgatggtt gcgaggcaat tcggacattt   480
ccccttacaa tcgtcatacc tgtcctataa atagacctca cttcattcac tctcacacac   540
acttccaagc ttgagctgaa ttataagagg ctctattgta ctatattgta tactagaata   600
gaaagagagt agagtagaag aagtcggaag aattccggag ttgtcggtaa tcttctccta   660 ttttttcttat tctgtttata actttgaatt taatataata ttcttctcga gtaatttaga   720
tttatcttgt gagaattatc tcttggttag ttcctaaata gcatacgtga ttattgttca   780
ctataattaa ctgaaatata gtgattgctt tggtgagtta taaacactaa agtagatagt   840
aattgcttag acgtggtgtt taggtaattg ttatccagta attgatgtgt atcccgcagt   900
acgtttgagg tgggtgtaga ggtggtgata gccctcaaga tcacttgtaa gtcctccctg   960
```

```
tccgggtaca tagtagagcg acatctgaga acagcgggtt gccagtgcct gaagtattgc    1020
gttaggatta aaattaagct ttccctagac actgtttctc actaataaat cctctctatc    1080
ctggcctatc atttgcttgg tgtccttgga tgaatcggag gaagatctga tcacacacgt   1140
tcccttggaa tcgatacccct tggaatactc cgtaagggaa agtgctacat cggtatatct    1200
gtgcacttgc ggattttatc tgtgaccgta agaaatacca aaaatctggc aaagaaatta    1260
aagaagggag agaagaaaaa agagagaaac cgtgtctcat gcacgagacg gggttgggcg    1320
caagcaccaa gactaggaaa cgagagaaac tagcgttggg ggcaactcat cgtttcttcc    1380
gtccggattt tcctcaagct cccgatctgc tgcacccgcc tccatcccac cgccatgcct    1440
accaccatcc cacgctaaat cctcacgatt ttttggcgtg tccccaatcc tcttcgcgcc    1500
aacaccaact cgtgcttccc tctatccatc ttgttgcctc cttttttccc caatcacttg    1560
tcttctccaa tctctctcgt gatagctaga atcagccaaa atcatcccca atcactcatc    1620
cctgagaaag tagttctccc aagccatgtg caaggatgaa tccgacggaa tcgaagaagc    1680
gtcgatccaa atccaatcag gctgccggtg aaccgaccgc ccttgatcca gatgccgcta    1740
gtgttgtggg agccgatggt gctccagatg ctactgctgt tgcttgtggt gctctacgag    1800
ctagtgctcc aggcgctggc tttcctaccg caggtgctca tgccgccagt ccatggtggc    1860
aagaatcatc tcctgatagc tcggaatggt atggtgcaaa tttttgggtg caaagattta    1920
ggttgatcaa tgttattggt gaattaatgg gttatattag actgacaact ttttgcttca    1980
aagaattgct aatatattgt tgtatagctg gtactttttt gcttcaaaga attttttcgct    2040 aggcttggtg gcaagatgta tagctggtac tgctaattac ttgtattcac ctgattaatc    2100
ttagtcaagc tcatatatgc tagttttatgg ggactgattt ttttctgaaa tatattgcgc    2160
ttgtatttca ccacttctgt tcttgtcata gatatcataa ttttttttatt gttttctttt    2220 tcaggatgta tccaccaggt ggtttcctga attatttaca gaataataag atctctccat    2280
ttagccagac acatccattt gtgaactatc ataatgcaag taagcttcca gaaaatttcc    2340
actttgttgg tgcaccaatt agttattcta caatgttcta aagcgatacc gtcaccaact    2400
aggaggtgtg ctgcagcaca aataggttca caagataaag aaacaattga tattgaggac    2460
gatgacacca tttagccttt ccgatgctag gtccgagaag cgattgaatt ggtcaaatga    2520
agaagacatt agattggtat gttaattttc tttgtttctt tttaaagatt tgagtctgta    2580
tgcttttaat tttatttgca cttcattaaa ggtacggttt attcttctcc taattgtagg    2640
ctagtgcttg gctgcacaat tcatttaact cgatcgatgg aaatgataag aagtcaaatc    2700
aatattggtt agatgttact gctacataca acaacaccac taagagtaac cgtatgagaa    2760
attgtaatca gttgaagcaa cgttgagagc gcattaagaa accagtctcc gaattcaacg    2820
gtttttatgc aagaatcact aaaatacatc aaagtggtat gagtgaagac caaaagatgg    2880
accaagcatt ccagctatat gcctctgaac ataatgacaa cgtttcaca atggtgcatg    2940 tagggaggat attacgacat gagaaaaagt ggtctacata tttgaagaaa attaagaagg    3000
aaaaggacaa gagtgtaact cctaacccaa ctcatgttgt gaatgtcaaa gatgctccaa    3060
aacaacgtcc tattgggcat aagaaggcca agatgaatg cagtggaaaa cgtctgacat    3120
cagacgctat ttctgttatt gaccacaaac tagataaatt cattgaagca agcagcaatg    3180
ctgagaagat gggagaggta caacaaagtt tggcaaataa gaagctagaa gtagccaacc    3240
ttaatcataa agcagctcag gaacaaacaa agggtaaaat gattgacctt tacaaagact    3300
tactgctagc tcccacaagt gatcttagtc aagaagcttt ggctgagaga tccaaagcat    3360
```

```
tggagtgtat gagattggct tgtttgcta aagataattg aggtatgttt ttaatatatt    3420
gttggtaaac aaattgtgtt gtgacagtac cattcaaatc tgaacaagtg acaatttgt    3480 caattgtgtg aactcatttt attttttctag tgcttgtttg aacataatta attatgtgaa  3540
ctcattattt tatactgcat gttgaacaca attaattttg tgaacccatt ttcttttat    3600 actacaattg aatactatca attgtgtgaa tgcatcctct ttttatactg caactgacca   3660
ctatatattg tgtgaactca ttttattttt ctagtgcttg tttgaacaca attagttatg   3720
tgaactcatt ttttatactg caactgaaca ccattaattg tgtgaaccta tttgactacc   3780
caaacatatt tatgtgtgtg tctatatata tatatatata tatatatata tatatatata   3840
tatatatata tatatatata tatatatata tatatatc ctctagctca cacattctcc     3900
ccctcccctg ccttccacat tctttcttcc ctctttactc ttccatcttc tctcatcctt   3960
aacaccatgt cgaaccaatc tgatggtgat tcccctgcgc atgatgattc tcttgatgag   4020
gtgagtagca tagatccaat ggatctgtac ccattggatc atattaggag catactgggt   4080
gatcttgcta atcatgtagt agccgaattg aagccgaagt tgaagctcta caagatatga   4140
gacctactat gcagagtggt ccaaggaggt atgttttagg ccttatgaag aatcttaagg   4200
gctattgaaa gattactttg tacagaatcc agtctataat gatacaacct tttagagaag   4260
attcaggatg agaaagcacc tcttcttaca cattgttgaa gccctagggc agtgggataa   4320
atatttcaca ctgagaatgg atgctcttaa ccgcccaggg ttatctccac ttaagaaatg   4380
tacatcggct attcgccaat tgggaaatgg tagccctgta gatcagcttg atgagtatct   4440
aaagattgga gatagtacta caatggagtg cttgaagatg tgtgtgaagg gtgtgattga   4500
tgtattcggt gcagagtatt tgcgacgccc cacggtgcaa gatgttgaac gcttagtgca   4560
gattgatgag cgccgtggtt tccctggcat gttagggagc attgactgca tgcactgaca   4620 ttggagaaa tgccctgttg catggtaggg aatgtatact cgtggtgatc aaggtgttcc   4680
tatggtcatt ctagaagcag tagcttcaca tgatcgttgg atatggcatg ccttctttgg   4740
tgttgctgga tccaacaatg atactaacat gcttaatcaa tcaccattgt tcatccagca   4800
actgagaggg gagggtcctc aagtgtagtg ccatgtcaat ggaaggctat acaacacagg   4860
ttactacctt gcaaatggca tatacccata atgggttgtc tttgttaagt caatacatca   4920
tccacaatct gaaaagcgca agttgtttgc aaaacatcaa gaagggaaaa ggaaggatgt   4980
tgaatgtgct tttggtattt tgcaatctcg ctttggtatt tgaaacgac ctgcacatct    5040 atatgatcaa ggtgatcttg agaatatcat gctagcttgt attatccttc acaacatggt   5100
aatcgaagat gagaaagaca tcgagtagct tcctcttgat ttgaatgaga catcaagcac   5160
atcaactgta ttagaagcta caatctcgca tggacctaac ctagagatgg aagaagtgat   5220
acaaagaaat gttattattc atgatcgtac tactcataag ctacttcaat cagacttgat   5280
tgagcatatc tagcaaaact ttaggaattc aaactaatta ggtgattgtt aatcatttaa   5340
agtctaattt acaatttgtg tgttgccaat aactagtatg tttcatttta agttgcaatc   5400
tctgttacat tttagcctag cagtaccagt ttagctaaat atgttatctc ttattttct    5460 tgctctaaag cttctgaatt attttgatat tgatttgcca actattttct tttttgtaga   5520
tcaagtcctg ctattttggt gctgctgtgc tgctggagga aatgctatgg atcaagtttg   5580
gatgctgtcg aagcgtgtgg cagacttgtg gttacatatg tttctttggt ttgctgttgc   5640
agtgcaccta gaagaactgc tcatgtcatc agagactaat ttgagtccaa ctatttcggc   5700
taccagtttg ggtcctacca ttttggctac ctatatgttt ttttccttt tattgtactg    5760
```

```
agatggatga acttgaaaat tgctacttc tttatgctca tatatgcact gatatctgct      5820
agtttctact catataatgt gatttgcact aatatatgtt catgttttga tatttggcac      5880
tacagtatta tgtagattga tattcaaatt tggatgtatg tattgatgcg tgtcacatgg      5940
atgtatgtat tgatgcgtgt cacagttgat ccttcgttta catgacatgc aaatagttat      6000
taaattttct tctcttaaga aactgctata gacactgtgc attggggagg tagtgtctac      6060
aaatacattt attattgttt ctctcttta gacactacct atagacaccg tgggttggga       6120
gtgcca                                                                  6126
```

<210> SEQ ID NO 32
<211> LENGTH: 6
<212> TYPE: PRT
<213> ORGANISM: Oryza sativa

<400> SEQUENCE: 32

Met Leu Val Tyr Gly Asp
 1               5

<210> SEQ ID NO 33
<211> LENGTH: 17
<212> TYPE: PRT
<213> ORGANISM: Oryza sativa

<400> SEQUENCE: 33

Phe Phe Ser Glu Ile Tyr Cys Ala Cys Ile Ser Pro Leu Leu Phe Leu
 1               5                  10                  15

Ser

<210> SEQ ID NO 34
<211> LENGTH: 93
<212> TYPE: PRT
<213> ORGANISM: Oryza sativa

<400> SEQUENCE: 34

Ile Ser Asn Phe Phe Ile Val Phe Phe Arg Met Tyr Pro Pro Gly
 1               5                  10                  15

Gly Phe Leu Asn Tyr Leu Gln Asn Asn Lys Ile Ser Pro Phe Ser Gln
                20                  25                  30

Thr His Pro Phe Val Asn Tyr His Asn Ala Ser Lys Leu Pro Glu Asn
            35                  40                  45

Phe His Phe Val Gly His Gln Leu Val Ile Leu Gln Cys Ser Lys Ala
        50                  55                  60

Ile Pro Ser Pro Thr Arg Arg Cys Ala Ala Ala Gln Ile Gly Ser Gln
 65                  70                  75                  80

Asp Lys Glu Thr Ile Asp Ile Glu Asp Asp Thr Ile
                85                  90

<210> SEQ ID NO 35
<211> LENGTH: 68
<212> TYPE: PRT
<213> ORGANISM: Oryza sativa

<400> SEQUENCE: 35

Pro Ser Asp Ala Arg Ser Glu Lys Arg Leu Asn Trp Ser Asn Glu Glu
 1               5                  10                  15

Asp Ile Arg Leu Ala Ser Ala Trp Leu His Asn Ser Phe Asn Ser Ile
                20                  25                  30

Asp Gly Asn Asp Lys Lys Ser Asn Gln Tyr Trp Leu Asp Val Thr Ala
            35                  40                  45

Thr Tyr Asn Asn Thr Thr Lys Ser Asn Arg Met Arg Asn Cys Asn Gln
            50                  55                  60

Leu Lys Gln Arg
 65

<210> SEQ ID NO 36
<211> LENGTH: 204
<212> TYPE: PRT
<213> ORGANISM: Oryza sativa

<400> SEQUENCE: 36

Glu Arg Ile Lys Lys Pro Val Ser Glu Phe Asn Gly Phe Tyr Ala Arg
 1               5                  10                  15

Ile Thr Lys Ile His Gln Ser Gly Met Ser Glu Asp Gln Lys Met Asp
            20                  25                  30

Gln Ala Phe Gln Leu Tyr Ala Ser Glu His Asn Asp Lys Arg Phe Thr
        35                  40                  45

Met Val His Val Gly Arg Ile Leu Arg His Glu Lys Lys Trp Ser Thr
    50                  55                  60

Tyr Leu Lys Lys Ile Lys Lys Glu Lys Asp Lys Ser Val Thr Pro Asn
 65                  70                  75                  80

Pro Thr His Val Val Asn Val Lys Asp Ala Pro Lys Gln Arg Pro Ile
                85                  90                  95

Gly His Lys Lys Ala Lys Asp Glu Cys Ser Gly Lys Arg Leu Thr Ser
            100                 105                 110

Asp Ala Ile Ser Val Ile Asp His Lys Leu Asp Lys Phe Ile Glu Ala
        115                 120                 125

Ser Ser Asn Ala Glu Lys Met Gly Glu Val Gln Gln Ser Leu Ala Asn
    130                 135                 140

Lys Lys Leu Glu Val Ala Asn Leu Asn His Lys Ala Ala Gln Glu Gln
145                 150                 155                 160

Thr Lys Gly Lys Met Ile Asp Leu Tyr Lys Asp Leu Leu Leu Ala Pro
                165                 170                 175

Thr Ser Asp Leu Ser Gln Glu Ala Leu Ala Glu Arg Ser Lys Ala Leu
            180                 185                 190

Glu Cys Met Arg Leu Ala Leu Phe Ala Lys Asp Asn
        195                 200

<210> SEQ ID NO 37
<211> LENGTH: 40
<212> TYPE: PRT
<213> ORGANISM: Oryza sativa

<400> SEQUENCE: 37

Met Ser Asn Gln Ser Asp Gly Asp Ser Pro Ala His Asp Ser Leu
 1               5                  10                  15

Asp Glu Val Ser Ser Ile Asp Pro Met Asp Leu Tyr Pro Leu Asp His
            20                  25                  30

Ile Arg Ser Ile Leu Gly Asp Leu
        35                  40

<210> SEQ ID NO 38
<211> LENGTH: 36
<212> TYPE: PRT
<213> ORGANISM: Oryza sativa

<400> SEQUENCE: 38

Ser Cys Ser Ser Arg Ile Glu Ala Glu Val Glu Ala Leu Gln Asp Met

```
                1               5              10              15

Arg Pro Thr Met Gln Ser Gly Pro Arg Arg Tyr Ile Cys Phe Arg Pro
                         20                  25                  30

Tyr Glu Glu Ser
             35

<210> SEQ ID NO 39
<211> LENGTH: 18
<212> TYPE: PRT
<213> ORGANISM: Oryza sativa

<400> SEQUENCE: 39

Gly Leu Leu Lys Asp Tyr Phe Val Gln Asn Pro Val Tyr Asn Asp Thr
 1               5                  10                  15

Thr Phe

<210> SEQ ID NO 40
<211> LENGTH: 120
<212> TYPE: PRT
<213> ORGANISM: Oryza sativa

<400> SEQUENCE: 40

Arg Arg Phe Arg Met Arg Lys His Leu Phe Leu His Ile Val Glu Ala
 1               5                  10                  15

Leu Gly Gln Trp Asp Lys Tyr Phe Thr Leu Arg Met Asp Ala Leu Asn
             20                  25                  30

Arg Pro Gly Leu Ser Pro Leu Lys Lys Cys Thr Ser Ala Ile Arg Gln
         35                  40                  45

Leu Gly Asn Gly Ser Pro Val Asp Gln Leu Asp Glu Tyr Leu Lys Ile
     50                  55                  60

Gly Asp Ser Thr Thr Met Glu Cys Leu Lys Met Cys Val Lys Gly Val
 65                  70                  75                  80

Ile Asp Val Phe Gly Ala Glu Tyr Leu Arg Arg Pro Thr Val Gln Asp
                 85                  90                  95

Val Glu Arg Leu Val Gln Ile Asp Glu Arg Arg Gly Phe Pro Gly Met
            100                 105                 110

Leu Gly Ser Ile Asp Cys Met His
        115                 120

<210> SEQ ID NO 41
<211> LENGTH: 9
<212> TYPE: PRT
<213> ORGANISM: Oryza sativa

<400> SEQUENCE: 41

His Trp Glu Lys Cys Pro Val Ala Trp
 1               5

<210> SEQ ID NO 42
<211> LENGTH: 59
<212> TYPE: PRT
<213> ORGANISM: Oryza sativa

<400> SEQUENCE: 42

Gly Met Tyr Thr Arg Gly Asp Gln Gly Val Pro Met Val Ile Leu Glu
 1               5                  10                  15

Ala Val Ala Ser His Asp Arg Trp Ile Trp His Ala Phe Phe Gly Val
             20                  25                  30

Ala Gly Ser Asn Asn Asp Thr Asn Met Leu Asn Gln Ser Pro Leu Phe
         35                  40                  45
```

```
Ile Gln Gln Leu Arg Gly Glu Gly Pro Gln Val
    50                  55

<210> SEQ ID NO 43
<211> LENGTH: 20
<212> TYPE: PRT
<213> ORGANISM: Oryza sativa

<400> SEQUENCE: 43

Cys His Val Asn Gly Arg Leu Tyr Asn Thr Gly Tyr Tyr Leu Ala Asn
 1               5                  10                  15

Gly Ile Tyr Pro
         20

<210> SEQ ID NO 44
<211> LENGTH: 78
<212> TYPE: PRT
<213> ORGANISM: Oryza sativa

<400> SEQUENCE: 44

Trp Val Val Phe Val Lys Ser Ile His His Pro Gln Ser Glu Lys Arg
 1               5                  10                  15

Lys Leu Phe Ala Lys His Gln Glu Gly Lys Arg Lys Asp Val Glu Cys
             20                  25                  30

Ala Phe Gly Ile Leu Gln Ser Arg Phe Gly Ile Leu Lys Arg Pro Ala
         35                  40                  45

His Leu Tyr Asp Gln Gly Asp Leu Glu Asn Ile Met Leu Ala Cys Ile
     50                  55                  60

Ile Leu His Asn Met Val Ile Glu Asp Glu Lys Asp Ile Glu
 65                  70                  75

<210> SEQ ID NO 45
<211> LENGTH: 54
<212> TYPE: PRT
<213> ORGANISM: Oryza sativa

<400> SEQUENCE: 45

Leu Pro Leu Asp Leu Asn Glu Thr Ser Ser Thr Ser Thr Val Leu Glu
 1               5                  10                  15

Ala Thr Ile Ser His Gly Pro Asn Leu Glu Met Glu Glu Val Ile Gln
             20                  25                  30

Arg Asn Val Ile Ile His Asp Arg Thr Thr His Lys Leu Leu Gln Ser
         35                  40                  45

Asp Leu Ile Glu His Ile
     50

<210> SEQ ID NO 46
<211> LENGTH: 7
<212> TYPE: PRT
<213> ORGANISM: Oryza sativa

<400> SEQUENCE: 46

Gln Asn Phe Arg Asn Ser Asn
 1               5

<210> SEQ ID NO 47
<211> LENGTH: 4608
<212> TYPE: DNA
<213> ORGANISM: Oryza sativa

<400> SEQUENCE: 47
```

```
gggcatccac aatgtacact gaaagtaacc ttagacatta aatactgcta cagtacaacg    60
catttagcat tgtggagtca gaccacaagt ccgatgcaac caaagtacac cttaagctta   120
aggtgtagca acaaagctat aaaatacaat acttttactg tttttctgtg cacaccaata   180
aaatatacat gtcagttact aaacatagta acgagtacta ctagccgttg ctgctattcc   240
atttgagttg ctcatttggt cccctagccg ttgtcttcct ccagcattct tctgctgcct   300
acaaaaggag gaacaagtga gatgaacaac aattttgat ctattcagtt ttcccacata    360
ctaaatggag cctttcaaag gaaacttctc aaacctcctc aaccaaggtt cctcaagcca   420
agcaacaaat agtgaggccc aaaactccct ttctacccaa tttcccacaa gttatcccca   480
aaacttcaga cctagttttc tccaaaattt ccatccttt ggtcctccaa gcaactacca    540
gccatatcga caccctccaa tctttcaagg tgctcagcaa caagaatatt atgggcaacc   600
tactccagga agcttggaag ttttcaact tcaagaaaat ctggtgcact catctaacca    660
agcatttgga tttgcagcca atagatcaca gtttggtatg caatatagta cttcaattag   720
ggctacagcc aacacttctt ctcatggatc agcttctcca tgtcatacaa gacataatga   780
gaaagaagta gttgaggttg aagaggcaag tgatagcagt gaagaaggaa gaagagggac   840
acgcatcaat tggactgaag atgacaatat acgactaatg agttcttggt tgaacaattc   900
agttgatccc atcaaaggca atgacaagaa atcagaacaa tattggaagg ctgtagctag   960
agagttcaac agcaatatgc ctagcaatgg gaacaaaagg aaccccaagc aatgcagaac  1020
acattgggac aatgtcaaga gagatgtcac taagttctgt ggattttatt ctaaagctag  1080
aactactttc acaagtgggt attctgatga tatgataatg gagaaagccc gtgaatggta  1140
caaaaagcac aacaaccaaa aacctttcac cttggagtat atgtggaaag atcttaaaga  1200
tcaacctaaa tggcgtagag tccttgaaga gagtagccat aataagagga gcaagatttc  1260
tgaatcagga gcatatactt catcgtcgaa ccaagacaca gaggaggaaa cagagcgcaa  1320
agagaagcgc cctgagggc agaaggcagc aaaacagagg caaaaggaa aaggtgcacc    1380 atcacctta ggggataagc caagtcaaaa tatggttctc tttcacgaag ctattacaac    1440
taaagcagca gcattgctaa aggcagcaga agcaacactg attggagcag aagcaaaaaa   1500
agagaaggcg attgcaaaaa aagagaagg caagggcaga aaaataccaa atgtatttaa    1560
aactgatgga gaaggataca tcaacctcca gtgaagcaaa actgaagaga catgaaaatg   1620
tattggacca attagctaga gaacttgctg aggataaat gactagcaag caatgttagc    1680
aattatgctt attttataat gtcagtattc ttgtcatata ttaaaattat gtactgtgtt   1740
gatgcttgta ctgtgaacct atttgtattg tactatgtta tggtaatttg tataaatatt   1800
gtgtattaca gctatggaat gaaactacaa tatccttagt acttgagaaa tcacctttc    1860 acatggatct agttggtgtt gatggttttt cttccatcca tgaccaatct gtttttttt    1920 ctccacctga atacatatga gcaataatta atagagaaca aaagcaagag ggatgttgac   1980
aaaacctagg aaaatatagc tgttgtaaaa gactgacaaa agcaagagct agctgttagg   2040
atattgacaa aacccaggaa aatatagctg ttgtaaaaat ctgacaaatc tagtcgttgt   2100
aaaatgtatc atctacaaat aggtaatgta gttcagcaga acaacaccca ttctcatttt   2160
gttcaacttc atctcaacag ccttcccact ttcaaaaaaa aaaatgtcca gcaagtcacc   2220
acatcaatct agtgagtcag atgattctag ctctagtgac taccttgaag agctgatttt   2280
ggaagaaatc aatgatccta tggaagctga gattgaagat gagattgaag ctcaacttca   2340
agctcaaatg caagcacaac aaactggtca ttctaatcgt cgtgggggct acaaacgaag   2400
```

```
gtacatcaat agagattacc aagacgacca caacagattg tttgcaaaat actattccga   2460
caatccttta tataccgatg atcagttccg tagaagattt cgcatgagaa agcatctatt   2520
tttgcacatt gttgaagctc ttggcatttg gtctccatat tttcgtttgc gaagagatgc   2580
atttggcaag gttggtctat caccgttgca aaaatgcaca gctgccatac gcatgttggc   2640
atatggtaca ccagctgacc ttatggatga aacttttggg gttgcagaaa gcacagcaat   2700
ggaatgcatg ataaattttg ttcaaggtgt tagacatata tttggtcagc aataccttcg   2760
caagcctaat gaacaagata tccagtgttt acttcaacaa ggagaggctc atgggttccc   2820
tggcatattg ggtagtcttg actgcatgca ttgggagtgg caaaattgcc cggttgcatg   2880
gaagggacaa ttcacacgtg gtgattatgg tgtacccact atcatgcttg aagcagttgc   2940
atctgctgac ctatggtttt ggcatgcatt tttcggtgct gctggttcaa caatgatat    3000 caatgtgttg gatcagtcac cattgtttac tgcagtgcta caaggaagag ctcctagtgt   3060
tcaatttact gtcaatggga cagaatataa catgggatac tatttagctg ataatattta   3120
tccagagtgg gctgcatttg ccaaatcaat tactagacct caaagtgaca aggctaaatt   3180
gtatgcacaa cgccaagaat cagcaaggaa agatgtggaa cgagcatttg gggttttgca   3240
aaaacgttgg gccataattc gccacccagc acggctttgg gaaagggatg aactagctga   3300
tatcatgtat gcatgtatta ttttgcacaa catgatagtt gaggataaga gagacgatta   3360
tgacatacct gatgacaaca catatgagca atcacaatct tctgtacaac tagcaggact   3420
cgaccatggg ccaatccatg gatttgcaga ggtcctagac gcagacatga atattcgcga   3480
tcgaacaacc catcgacgtc taaagtcaga tttgatggag cacatttggc agaaatatgg   3540
tggtcaacaa caacaaaact agagtttatt tgtgttatga aacttgtgtt ctttttttcca  3600 tttttctttc agtcgtccaa tttattctta ttagtaactg agactcttta cttttttcatg  3660 cactaagagt aatgtaccag taccattgcc ttaattagtc aagcacaagt catattgaaa   3720
atatcatgtt tttttggtca tttttttttaa tttcagatct gttggagcac aactaaacac   3780
tctatgaaaa ttccatcggg atcgaaatca acgattcaca tgatgcatac gtacaaacag   3840
aaaaagaatc tgtagtagca gcacttgcac atatttgatg acaaatttaa tcgtagcagc   3900
agcagcactt gcacaaacag atataaattt aatcaccggg caaaccaaaa gcaagaagag   3960
attccacaac acgaaaaagg agaggccacg gaatcaatca ccttgtctct aacgcagaac   4020
tcacggacga tgtaggcgaa gttgagggcg gtgaccgtct agtaggtgct gatggttgag   4080
agcagcttca gtttgtggc gcagacgaga cagagaagca cgcgtcggca gcgtcgcggc    4140
cggagtagtt cgcgcacgca gcgtcatcga tgggtgaggc cgcgcacggc aacgtggcac   4200
cgaagccacg gcacagcgag gtcacagccg aaggagggga ggccgggagg agcagcgacg   4260
ttggcgcagc cacgggagga gcaatcgtcg gagaaattgg ggatccagtg catgcgctgt   4320
gggagaattt ggggatcgag cggagcgacg aagagaggaa ttggggatct gaggcggagg   4380
aaatggggat cgaacagagt aacagtggat gaggattttt tttcactcgc gcgaacaagc   4440
agatggttag gagtgatctg tattctttt ctcccgtggg gcccagcggg acccaccttta   4500 tttccatcaa acaaacagta tcattgtaga gatttcctta ataactattg ctacctgtag   4560
atgggcccac tcttgttatg cattttacca tatacattgg ccttgccc                4608

<210> SEQ ID NO 48
<211> LENGTH: 409
<212> TYPE: PRT
<213> ORGANISM: Oryza sativa
```

<400> SEQUENCE: 48

```
Met Glu Pro Phe Lys Gly Asn Phe Ser Asn Leu Leu Asn Gln Gly Ser
 1               5                  10                  15

Ser Ser Gln Ala Thr Asn Ser Glu Ala Gln Asn Ser Leu Ser Thr Gln
             20                  25                  30

Phe Pro Thr Ser Tyr Pro Gln Asn Phe Arg Pro Ser Phe Leu Gln Asn
         35                  40                  45

Phe His Pro Phe Gly Pro Ser Asn Tyr Gln Pro Tyr Arg His Pro
     50                  55                  60

Pro Ile Phe Gln Gly Ala Gln Gln Glu Tyr Tyr Gly Gln Pro Thr
 65                  70                  75                  80

Pro Gly Ser Leu Glu Gly Phe Gln Leu Gln Glu Asn Leu Val His Ser
             85                  90                  95

Ser Asn Gln Ala Phe Gly Phe Ala Ala Asn Arg Ser Gln Phe Gly Met
            100                 105                 110

Gln Tyr Ser Thr Ser Ile Arg Ala Thr Ala Asn Thr Ser Ser His Gly
        115                 120                 125

Ser Ala Ser Pro Cys His Thr Arg His Asn Glu Lys Glu Val Val Glu
130                 135                 140

Val Glu Glu Ala Ser Asp Ser Ser Glu Glu Gly Arg Arg Gly Thr Arg
145                 150                 155                 160

Ile Asn Trp Thr Glu Asp Asp Asn Ile Arg Leu Met Ser Ser Trp Leu
                165                 170                 175

Asn Asn Ser Val Asp Pro Ile Lys Gly Asn Asp Lys Lys Ser Glu Gln
            180                 185                 190

Tyr Trp Lys Ala Val Ala Arg Glu Phe Asn Ser Asn Met Pro Ser Asn
        195                 200                 205

Gly Asn Lys Arg Asn Pro Lys Gln Cys Arg Thr His Trp Asp Asn Val
210                 215                 220

Lys Arg Asp Val Thr Lys Phe Cys Gly Phe Tyr Ser Lys Ala Arg Thr
225                 230                 235                 240

Thr Phe Thr Ser Gly Tyr Ser Asp Asp Met Ile Met Glu Lys Ala Arg
                245                 250                 255

Glu Trp Tyr Lys Lys His Asn Asn Gln Lys Pro Phe Thr Leu Glu Tyr
            260                 265                 270

Met Trp Lys Asp Leu Lys Asp Gln Pro Lys Trp Arg Val Leu Glu
        275                 280                 285

Glu Ser Ser His Asn Lys Arg Ser Lys Ile Ser Glu Ser Gly Ala Tyr
290                 295                 300

Thr Ser Ser Ser Asn Gln Asp Thr Glu Glu Thr Glu Arg Lys Glu
305                 310                 315                 320

Lys Arg Pro Glu Gly Gln Lys Ala Ala Lys Gln Arg Gln Lys Gly Lys
                325                 330                 335

Gly Ala Pro Ser Pro Leu Gly Asp Lys Pro Ser Gln Asn Met Val Leu
            340                 345                 350

Phe His Glu Ala Ile Thr Thr Lys Ala Ala Leu Leu Lys Ala Ala
        355                 360                 365

Glu Ala Thr Leu Ile Gly Ala Glu Ala Lys Lys Glu Lys Ala Ile Ala
    370                 375                 380

Lys Lys Arg Glu Gly Lys Gly Arg Lys Ile Pro Asn Val Phe Lys Thr
385                 390                 395                 400

Asp Gly Glu Gly Tyr Ile Asn Leu Gln
                405
```

<210> SEQ ID NO 49
<211> LENGTH: 452
<212> TYPE: PRT
<213> ORGANISM: Oryza sativa

<400> SEQUENCE: 49

```
Met Ser Ser Lys Ser Pro His Gln Ser Ser Glu Ser Asp Asp Ser Ser
 1               5                  10                  15

Ser Ser Asp Tyr Leu Glu Glu Leu Ile Leu Glu Ile Asn Asp Pro
             20                  25                  30

Met Glu Ala Glu Ile Glu Asp Glu Ile Glu Ala Gln Leu Gln Ala Gln
             35                  40                  45

Met Gln Ala Gln Gln Thr Gly His Ser Asn Arg Arg Gly Gly Tyr Lys
 50                  55                  60

Arg Arg Tyr Ile Asn Arg Asp Tyr Gln Asp Asp His Asn Arg Leu Phe
 65                  70                  75                  80

Ala Lys Tyr Tyr Ser Asp Asn Pro Leu Tyr Thr Asp Asp Gln Phe Arg
                 85                  90                  95

Arg Arg Phe Arg Met Arg Lys His Leu Phe Leu His Ile Val Glu Ala
                100                 105                 110

Leu Gly Ile Trp Ser Pro Tyr Phe Arg Leu Arg Arg Asp Ala Phe Gly
            115                 120                 125

Lys Val Gly Leu Ser Pro Leu Gln Lys Cys Thr Ala Ala Ile Arg Met
130                 135                 140

Leu Ala Tyr Gly Thr Pro Ala Asp Leu Met Asp Glu Thr Phe Gly Val
145                 150                 155                 160

Ala Glu Ser Thr Ala Met Glu Cys Met Ile Asn Phe Val Gln Gly Val
                165                 170                 175

Arg His Ile Phe Gly Gln Gln Tyr Leu Arg Lys Pro Asn Glu Gln Asp
            180                 185                 190

Ile Gln Cys Leu Leu Gln Gln Gly Glu Ala His Gly Phe Pro Gly Ile
        195                 200                 205

Leu Gly Ser Leu Asp Cys Met His Trp Glu Trp Gln Asn Cys Pro Val
210                 215                 220

Ala Trp Lys Gly Gln Phe Thr Arg Gly Asp Tyr Gly Val Pro Thr Ile
225                 230                 235                 240

Met Leu Glu Ala Val Ala Ser Ala Asp Leu Trp Phe Trp His Ala Phe
                245                 250                 255

Phe Gly Ala Ala Gly Ser Asn Asn Asp Ile Asn Val Leu Asp Gln Ser
            260                 265                 270

Pro Leu Phe Thr Ala Val Leu Gln Gly Arg Ala Pro Ser Val Gln Phe
        275                 280                 285

Thr Val Asn Gly Thr Glu Tyr Asn Met Gly Tyr Tyr Leu Ala Asp Asn
290                 295                 300

Ile Tyr Pro Glu Trp Ala Ala Phe Ala Lys Ser Ile Thr Arg Pro Gln
305                 310                 315                 320

Ser Asp Lys Ala Lys Leu Tyr Ala Gln Arg Gln Glu Ser Ala Arg Lys
                325                 330                 335

Asp Val Glu Arg Ala Phe Gly Val Leu Gln Lys Arg Trp Ala Ile Ile
            340                 345                 350

Arg His Pro Ala Arg Leu Trp Glu Arg Asp Glu Leu Ala Asp Ile Met
        355                 360                 365

Tyr Ala Cys Ile Ile Leu His Asn Met Ile Val Glu Asp Lys Arg Asp
370                 375                 380
```

```
Asp Tyr Asp Ile Pro Asp Asp Asn Thr Tyr Glu Gln Ser Gln Ser Ser
385                 390                 395                 400

Val Gln Leu Ala Gly Leu Asp His Gly Pro Ile His Gly Phe Ala Glu
            405                 410                 415

Val Leu Asp Ala Asp Met Asn Ile Arg Asp Arg Thr Thr His Arg Arg
        420                 425                 430

Leu Lys Ser Asp Leu Met Glu His Ile Trp Gln Lys Tyr Gly Gly Gln
    435                 440                 445

Gln Gln Gln Asn
    450

<210> SEQ ID NO 50
<211> LENGTH: 5367
<212> TYPE: DNA
<213> ORGANISM: Oryza sativa

<400> SEQUENCE: 50
```

| | | | | | |
|---|---|---|---|---|---|
| gggcacccac | aatgttgtaa | aaaccaggt | agtaagcatt | aaatggttgc | ttactacctg | 60 |
| gtattagtca | ttgtgggagt | agttcattct | taaagccagg | aagtagcgct | gctgccggca | 120 |
| agaagggaat | aaaaaatgaa | atgtgtacag | tggagttctg | acaaaaaatt | ttaaattgca | 180 |
| agtagccgtt | gcttcttcca | accgttgctc | tcctccccag | ccaaccgttg | catggactgt | 240 |
| tcttcttgcc | atcttcatct | cctacaaaaa | cagagatggc | tcataatttc | tttgaatcaa | 300 |
| cacaaacaca | ttctgtgaaa | cttagctagc | tgagagcttg | agatggatcc | ctccaagaga | 360 |
| ggtttcatga | acttgttaaa | ccaaggctct | ccaagccaac | aatctagcca | aaactcccct | 420 |
| cctactcaat | tcccctcaac | tttctcccaa | tcacaatttc | cccaatcccc | acattttacc | 480 |
| caagcctcac | cacctaattt | ccaaaccttc | aacccttttg | gtcctccagc | caactatcac | 540 |
| ctatatggta | gttctcctcc | aaactttcaa | ggttttctgc | agcaagcaag | ctggttacaa | 600 |
| tctgcaccaa | taagctttca | aggttttcgt | ccccaagaaa | gttggatgca | ctcaccaaat | 660 |
| caagttgtcg | ggtccgcctc | atctcatgga | tccaaatcag | cctctcagtg | ccctgcaaga | 720 |
| caggaagaga | acaatttggt | taacatcgaa | gagtcaagtg | acaatagcca | agagacaggg | 780 |
| agaagaggga | cacacgtcaa | ctggaccgaa | gaagaaaact | tacgactcct | cagctcttgg | 840 |
| ttgaataact | cactgattc | tataaatggc | aatgacaaga | agggagaata | ctattggagg | 900 |
| gatgttgctg | cagagttcaa | tggtaatgca | tctagcaata | accgcaaaag | gacagtcgtg | 960 |
| caatgcaaga | cacattgggg | tggtgttaag | aaggacattg | caaaattttg | tggagcttat | 1020 |
| tctcgagcta | gaagaacctg | gagcagtgga | ttctctgatg | atatgatcat | ggagaaagcc | 1080 |
| catgcattat | ataaatcaga | aaacaatgat | aaaactttta | cattagagta | tatgtggaga | 1140 |
| gaattaaagg | atcaaccaaa | atggcgacgg | atacttgaag | aggacagcaa | gaacaagagg | 1200 |
| actaagattt | ctgaatctgg | tgcatataca | tcatcatcca | accaagaaac | tgaggaggag | 1260 |
| accagccgaa | aagagaagcg | tcctgaaggg | cagaaaaaag | ccaaagccaa | gcttaaaggg | 1320 |
| aaaggaaaaa | aacctgcacc | gtctcctttg | ggggaccagc | catctcaaga | ttttgttctc | 1380 |
| ttcaacgaag | ctgtaaaatt | gagagcagaa | gcagtgctga | atctgcaga | agcaaccacc | 1440 |
| aaatcagcgg | aagcaaagaa | ggaacaaact | aggatggaga | agtatcagac | atatttaaag | 1500 |
| ttgttggaca | aagacactgc | caattttagt | gatgcaaaac | tcaagaggca | tgaagctgtc | 1560 |
| ctcgaaaagc | tagctacaga | acttgcagaa | gaatagaaga | tccctaagtt | atgtttgtac | 1620 |
| ccctagtact | tagtgtgtca | ctgtttcatt | aagtttaact | tgctagtaat | atttagactt | 1680 |
| gtgataggtt | tgtagggcaa | gtaattgttg | tattgtgaac | tcagtgaatg | atgaatgtaa | 1740 |

```
tatttcacta gtgagaaggc atatgaagtg ataatatttg cccacaatca taatatgtct   1800
gaaccttctt ctctgtagtc tctgatttgt cccataacaa cagcaattcg tttcttaagc   1860
agcctgcaga aaaatataca ttgataataa ttagcacaac attttataat atggtggttt   1920
gaatagatag aaaaggaagg tatggttgtt taaaatctag ctgttagaat acatccaaaa   1980
agcaagacat ggttgtttaa aatctagctg ttggaataca tccaaaaagc aagacacagt   2040
tgtctaaaat ttagctgttg gaatacatcc aaaaagaaag acatggctgt tcagaatcta   2100
gctgttggaa actagccgtt gcaatggaag caaaagcaag gcatcaatgt tacacatagc   2160
tagcaggatg aaccatatat aaataagaca tgcacatcac gaaggcagca ttccccttcc   2220
tttccttcaa cttcttacca acatagcaac ccatctccaa aaagatgtc cactgagtca    2280 caagataatt ctagtcattc cgatgagtcc atcactagtg agaagcttga tgatatgaca   2340
tgggaagaaa ttaatgaccc tatggaagct cagcttgaag ctcggttgga agctcaactt   2400
gaagcgagat tgatggctca cctagctggt agctctaatc agctgggggg ctacacaagg   2460
aggtacatta gtagagatca tgaagatgac cacaacagat tatttgctaa atattttct    2520 gagagtccat tgtacaccga tgatcagttt cggaggagat ttcgcatgag aaggcatctt   2580
tttttgcgca ttgtacaagc tcttggtgtt tggtctccat attttcgtct aaggcgagat   2640
gcatttggca aggtgggtct atcaccattg caaaaatgca ccgctgccat gcgaatgttg   2700
gcatatggta caccagctga tcttatggat gagacctttg gggttgcaga agtacagca    2760 atggagtgca tgatcaattt tgttcaaggt gtgcggcatt tatttggtga acaatatttg   2820
cgcaggccta ccgtggagga tattcaacgt ttacttcaat ttggagaggc acatggattt   2880
cctgggatgt tggggagtat tgattgcatg cattgggaat ggcaaagttg tccggttgca   2940
tggaagggcc aattcacacg tggtgactat ggagtaccca ctattatgct tgaagcagtt   3000
gcttctttag atttatggat ttggcatgct ttctttggtg ctgctggttc aaacaatgat   3060
attaatgtat tggaccagtc tccattattc actgaaatga tacaaggaag agcacctcct   3120
gttcagttta ccataaatgg tacacaatat aacatgggat actatttaac tgatagaatt   3180
tatccggagt gggctgcatt tgccaaatca atcaccaggc cccgaagtgc taagcacaaa   3240
ttatatgccc aacgtcaaga atcagcaaga aaagatgtgg aaagagcctt tggggttttg   3300
caaaaacgtt gggccatcat acgtcacccg gcgcgtattt gggaaaggga agagcttgca   3360
gatataatgt atgcctgcat tattttgcac aacatgatag ttgaggatga gagaggctca   3420
tatgatatac cggatgacaa tacatatgaa caagggcagt attatcctca aatgacaggg   3480
cttgaccatg gaccaatata tggatttcaa gaagttttag agcaaaacaa ggctatccat   3540
gaccgacaaa cacatcggcg tctgaaggga gatttgatag agcacgtgtg gcagaaattt   3600
agtggtcagc aacaataaga ttagatttta ataattccat atcaaccttg tattttacta   3660
gtttaatttg tctttaccaa tttagaatct aaatgtttgc ttccaaaagt acttgtattt   3720
gtatgtcaaa tgtattactt tttatcagct acgtattcca ataggacta tgtacactag    3780 ctagttatct tgcaatacct acaaaaatgg attgccttt atttctgaag aactatatat    3840
atgttctgta tacagctagt agactgaaga aaaaaggaga gcaaaactac caacagagag   3900
gcaaaatgtg gttcctttt cctgaaaaca tttgaacagg aaacaactgt gttgatacat    3960
agcaacaagg ttacttacac caacaccaat gcactggtgt caagtatact ccctgcagc    4020 tagctgatcg agaatcgaga atcagctaga gccctgacaa acatatactc cagtagctat   4080
atcgaatact attgaagttt tcagattaat caaactccga tgcttacttt tgattagtgt   4140
```

```
tgtaagaatt aaacataatt atatctcatc atcatgtagc ttgtatttt gagaaaaaag    4200
acagtcggtt gctgttaaca ggccggcaac atagcaaata gatatatttt ggatggcaag    4260
agagttaaat taaattttct gcaacataat atttagcaag aacataaaag gttagtgcta    4320
gctacatccg ttcgtgatgt agaacagtag aaggttaatg tagctacctg ttttaaactg    4380
ctgtatgcag ggctcttatg gagtggggaa acctagtgtt gtgttcttta cttggataga    4440
agcacgaacc ataacacaga tcaaacggta aaacaactga ccgtgattaa acaaaaaatc    4500
tgtccacata gttatagcaa ctccgaccgt gattaaacaa aaaaaaatc tgtccacaca    4560
gttatggcaa ctccgattct cataaactga actagaaaat ataacatgcg caacatcgac    4620
agagaggtac atggtacaat atttatcatg caagcacata cgctattcta ctacttaaat    4680
cacaagcata ggggttagtt ggacttacag ttggtcttgc agctccgtcg cagatctcag    4740
caggaggata tgaagccgaa gctgatcaca caccagagaa gatgacctcc tcagtctcca    4800
gccgggctga agcaccagtc cgccataata agggaggtgg cttgcggcgt cggtcggcgg    4860
ggatagcggc gacggatgaa ggggaaagcg ttgcctgatt gcagagaagg aaggtttgcg    4920
gcgtcgatgg tggggtgga gcggatgcgg cgccgggtgg tagcgataga ggggattgcg    4980
tcgttgggtg gcggagagga acccggcgtc agtggaaggg tggaggggtt tgtggcgttg    5040
atttcggggg gaggggagc ggatcgccgc atggatagtg gggacggagg agttggcggc    5100
ggcgagtggc ggggtaggag cggattttac ggcggcgggg aaggagagga gattgcggcg    5160
ccggtggaaa cagcgaaaga ggaattgggg atcgatctgg ccggaactcg cgcgaaggaa    5220
ctgagcgccg atttttttta tcctgtggac cccacctta ctaccctctc gccgagataa     5280
gcattgtgga tagtgtcttc tcctattacc gcctgtgact gggtcccaca ctaatactca    5340
tcttgataat atacattggt gttgccc                                         5367
```

<210> SEQ ID NO 51
<211> LENGTH: 417
<212> TYPE: PRT
<213> ORGANISM: Oryza sativa

<400> SEQUENCE: 51

```
Met Asp Pro Ser Lys Arg Gly Phe Met Asn Leu Leu Asn Gln Gly Ser
  1               5                  10                  15

Pro Ser Gln Gln Ser Gln Asn Ser Pro Thr Gln Phe Pro Ser
             20                  25                  30

Thr Phe Ser Gln Ser Gln Phe Pro Gln Ser Pro His Phe Thr Gln Ala
         35                  40                  45

Ser Pro Pro Asn Phe Gln Thr Phe Asn Pro Phe Gly Pro Pro Ala Asn
     50                  55                  60

Tyr His Leu Tyr Gly Ser Ser Pro Asn Phe Gln Gly Phe Leu Gln
 65                  70                  75                  80

Gln Ala Ser Trp Leu Gln Ser Ala Pro Ile Ser Phe Gln Gly Phe Arg
                 85                  90                  95

Pro Gln Glu Ser Trp Met His Ser Pro Asn Gln Val Val Gly Ser Ala
            100                 105                 110

Ser Ser His Gly Ser Lys Ser Ala Ser Gln Cys Pro Ala Arg Gln Glu
        115                 120                 125

Glu Asn Asn Leu Val Asn Ile Glu Glu Ser Ser Asp Asn Ser Gln Glu
    130                 135                 140

Thr Gly Arg Arg Gly Thr His Val Asn Trp Thr Glu Glu Glu Asn Leu
145                 150                 155                 160
```

```
Arg Leu Leu Ser Ser Trp Leu Asn Asn Ser Leu Asp Ser Ile Asn Gly
                165                 170                 175

Asn Asp Lys Lys Gly Glu Tyr Tyr Trp Arg Asp Val Ala Ala Glu Phe
            180                 185                 190

Asn Gly Asn Ala Ser Ser Asn Asn Arg Lys Arg Thr Val Val Gln Cys
            195                 200                 205

Lys Thr His Trp Gly Gly Val Lys Lys Asp Ile Ala Lys Phe Cys Gly
    210                 215                 220

Ala Tyr Ser Arg Ala Arg Arg Thr Trp Ser Ser Gly Phe Ser Asp Asp
225                 230                 235                 240

Met Ile Met Glu Lys Ala His Ala Leu Tyr Lys Ser Glu Asn Asn Asp
                245                 250                 255

Lys Thr Phe Thr Leu Glu Tyr Met Trp Arg Glu Leu Lys Asp Gln Pro
            260                 265                 270

Lys Trp Arg Arg Ile Leu Glu Glu Asp Ser Lys Asn Lys Arg Thr Lys
            275                 280                 285

Ile Ser Glu Ser Gly Ala Tyr Thr Ser Ser Ser Asn Gln Glu Thr Glu
    290                 295                 300

Glu Glu Thr Ser Arg Lys Glu Lys Arg Pro Glu Gly Gln Lys Lys Ala
305                 310                 315                 320

Lys Ala Lys Leu Lys Gly Lys Gly Lys Lys Pro Ala Pro Ser Pro Leu
                325                 330                 335

Gly Asp Gln Pro Ser Gln Asp Phe Val Leu Phe Asn Glu Ala Val Lys
            340                 345                 350

Leu Arg Ala Glu Ala Val Leu Lys Ser Ala Glu Ala Thr Thr Lys Ser
            355                 360                 365

Ala Glu Ala Lys Lys Glu Gln Thr Arg Met Glu Lys Tyr Gln Thr Tyr
    370                 375                 380

Leu Lys Leu Leu Asp Lys Asp Thr Ala Asn Phe Ser Asp Ala Lys Leu
385                 390                 395                 400

Lys Arg His Glu Ala Val Leu Glu Lys Leu Ala Thr Glu Leu Ala Glu
                405                 410                 415

Glu

<210> SEQ ID NO 52
<211> LENGTH: 450
<212> TYPE: PRT
<213> ORGANISM: Oryza sativa

<400> SEQUENCE: 52

Met Ser Thr Glu Ser Gln Asp Asn Ser Ser His Ser Asp Glu Ser Ile
1               5                   10                  15

Thr Ser Glu Lys Leu Asp Asp Met Thr Trp Glu Glu Ile Asn Asp Pro
                20                  25                  30

Met Glu Ala Gln Leu Glu Ala Arg Leu Glu Ala Gln Leu Glu Ala Arg
            35                  40                  45

Leu Met Ala His Leu Ala Gly Ser Ser Asn Gln Leu Gly Gly Tyr Thr
    50                  55                  60

Arg Arg Tyr Ile Ser Arg Asp His Glu Asp Asp His Asn Arg Leu Phe
65                  70                  75                  80

Ala Lys Tyr Phe Ser Glu Ser Pro Leu Tyr Thr Asp Asp Gln Phe Arg
                85                  90                  95

Arg Arg Phe Arg Met Arg Arg His Leu Phe Leu Arg Ile Val Gln Ala
            100                 105                 110
```

```
Leu Gly Val Trp Ser Pro Tyr Phe Arg Leu Arg Arg Asp Ala Phe Gly
            115                 120                 125

Lys Val Gly Leu Ser Pro Leu Gln Lys Cys Thr Ala Ala Met Arg Met
        130                 135                 140

Leu Ala Tyr Gly Thr Pro Ala Asp Leu Met Asp Glu Thr Phe Gly Val
145                 150                 155                 160

Ala Glu Ser Thr Ala Met Glu Cys Met Ile Asn Phe Val Gln Gly Val
                165                 170                 175

Arg His Leu Phe Gly Glu Gln Tyr Leu Arg Arg Pro Thr Val Glu Asp
            180                 185                 190

Ile Gln Arg Leu Leu Gln Phe Gly Glu Ala His Gly Phe Pro Gly Met
        195                 200                 205

Leu Gly Ser Ile Asp Cys Met His Trp Glu Trp Gln Ser Cys Pro Val
210                 215                 220

Ala Trp Lys Gly Gln Phe Thr Arg Gly Asp Tyr Gly Val Pro Thr Ile
225                 230                 235                 240

Met Leu Glu Ala Val Ala Ser Leu Asp Leu Trp Ile Trp His Ala Phe
                245                 250                 255

Phe Gly Ala Ala Gly Ser Asn Asn Asp Ile Asn Val Leu Asp Gln Ser
            260                 265                 270

Pro Leu Phe Thr Glu Met Ile Gln Gly Arg Ala Pro Pro Val Gln Phe
        275                 280                 285

Thr Ile Asn Gly Thr Gln Tyr Asn Met Gly Tyr Tyr Leu Thr Asp Arg
290                 295                 300

Ile Tyr Pro Glu Trp Ala Ala Phe Ala Lys Ser Ile Thr Arg Pro Arg
305                 310                 315                 320

Ser Ala Lys His Lys Leu Tyr Ala Gln Arg Gln Glu Ser Ala Arg Lys
                325                 330                 335

Asp Val Glu Arg Ala Phe Gly Val Leu Gln Lys Arg Trp Ala Ile Ile
            340                 345                 350

Arg His Pro Ala Arg Ile Trp Glu Arg Glu Leu Ala Asp Ile Met
        355                 360                 365

Tyr Ala Cys Ile Ile Leu His Asn Met Ile Val Glu Asp Glu Arg Gly
370                 375                 380

Ser Tyr Asp Ile Pro Asp Asp Asn Thr Tyr Glu Gln Gly Gln Tyr Tyr
385                 390                 395                 400

Pro Gln Met Thr Gly Leu Asp His Gly Pro Ile Tyr Gly Phe Gln Glu
                405                 410                 415

Val Leu Glu Gln Asn Lys Ala Ile His Asp Arg Gln Thr His Arg Arg
            420                 425                 430

Leu Lys Gly Asp Leu Ile Glu His Val Trp Lys Phe Ser Gly Gln
        435                 440                 445

Gln Gln
    450

<210> SEQ ID NO 53
<211> LENGTH: 4568
<212> TYPE: DNA
<213> ORGANISM: Oryza sativa

<400> SEQUENCE: 53
gggcaaccac aatgtgctta aaaagcaggt aataaacaat aaatgcactc gtccaaccag    60
gtaatagcca ttgtgggggc agataacagc aagaatcagg cagtagtgtt actgccggca   120
agagacaaat aaaatatagc atgtgtacag tgatttagaa gagttgcact aaaataatag   180
```

```
agtagcagtt agccgttaca tttgtagcaa ttgtaacttg ttgcaacaac gctacaacct    240
catccctcta caaatacaaa cacaactcag tcattttctg tatttcatca aataagatgg    300
atcctcccaa cagaggtttt atgcacatgc ttagctaggg ctcccaaagc caaacttctg    360
gaaatggtag ccaaaactcc acttctccac agttccnctc aatattctcc caatcccagt    420
tttctcaatc ctcaacaccc acttttcaga acttccatcc ttttggggct ccaaacaact    480
atcaaccata tggcaattct actccaagct tccacggttt tcagcagcaa gcacattggt    540
tacactctac accagtgagt tttcaaggtt ttcgtcctcc ggaaaattgg gtgtactcac    600
ctaatcaaat tactgggtct gcttcttccc acggatcaga atcagcctct cagtgccctg    660
caagatatga agagaacaat gtggttgata tcgaagagtc aagtgacaac agtcaagagg    720
cagggaggag aggaacacga gtcaactgga ctgaagagga aaacataaga ctccttagct    780
cttggctgaa taattcagtg gatcctataa atggtaatga taagaaggca gaatactatt    840
ggaaggctgt agctgtagag tttaatagca atacatctag aagtaaccgc aaaaggacag    900
ttgtgcaatg caagacacat tggggtggtg ttaagaagga aattggaaaa ttttgtggag    960
cttattctcg agctagaagc accttcagta gtggatattc tgatgatatg atcatggaga   1020
aagctcatat tatgtttaag tcagaaaaca atgaaaaacc tttcacattg gagtatatgt   1080
ggagagaact gaaagatcaa ccaaaatggc aagggtcttt agaagaagat agtaagaata   1140
agaggactaa gatctctgaa tcaggtgcat acacatcatc gtccaaccaa gacacggagg   1200
aggagaacag acgcaaaaag gagaacagac gcaaaaagaa gcgccctgag ggacagaaaa   1260
aagccaaagc caagttaaaa gggagaggta aaaatgtcgc accttctcct ttgggagacc   1320
agccatgtca agactttgtt ctttacaatg aagctataaa agtgaaagca gaagcgatgc   1380
tgaaatctgc agaagcaaca tcgaaatcag ctgaagcaaa gaaggaatac acaagaatgg   1440
agaagtatca gacatactta aaattgttgg acaaagacac ttcaaatttt agtgatgcaa   1500
aactgaagag gcatgaagct gtcctcgaaa agctagctac agaacttgct gaagaataaa   1560
tgatcaccaa gtgatgttgt atccctgtta cttagtgtgc cactatgtgg tctatgatca   1620
atttgctgct aggatttaga cttagcaatt attagacttg tgaactcagt gttaagtttg   1680
taggctaagt aaatgttgga ttgtaaactt agtgaatgat ggttgtatct ttgtacctgt   1740
agaagatgtt atgtactgat aatatgtagc ccacagtctt aattgaactt atttgaagtt   1800
gttggcccat aatttcttag cacttgattt aacagcagcc tacaaaatac atatgtagca   1860
gcaataatta gcacaattat ttataatctt gctgttgtga tagtttaaaa tagttgtaaa   1920
gcaagacatt gatgtttata aaactgttgt ttcaatatat aaaaagcaag acatggatgt   1980
ttataaaact attgtttaaa tatataaaaa gcaagacatg gctactaaga atctagctgt   2040
tggaatacat ccaaacagca aggcatgcct gctgtgaatc tagctgttgg aatacatcca   2100
aacaacaagt catgacatag ttgtatggaa tatagctgtt ggaaactagc tgttggaaca   2160
aaagcaacac tgagatgtta gcacatatcc attcagttgt atcttctatg aaacagggta   2220
tgcagttcag caagatatat accattgcct ttaattcagt tcattctcaa caaagccacc   2280
tagttcccac aaagatgtct agtgattcac aagtccattc tagtcattct gatgagtcca   2340
tcactagtga gaatttggaa gatatgatgt gggaagaaat taatgatcct actgaagctc   2400
agctagaagc ccggcttgaa gctcaacttg agatgaaatt gatggcacgc ctagctggga   2460
actctaatca gcgtggaggc tacacacgca ggtacatcag tagagatcat gaagacgatc   2520
acaacaggtt atttgctaaa tatttttcag acaatccttt gtacaccgat gatcaattcc   2580
```

```
gtaggagatt tcgcatgagg aggcatctttt ttttgcacat tgtacaagct cttggcgagt    2640
ggtctccata tttttgtctt aggacagatg catttggaaa ggtgggtctt tcaccatttc    2700
aaaaatgcac tgctgccatg cgaatgttgg catatggtac tccagctgat cttatggatg    2760
agacttttgg ggtagctgaa agcacagcaa tggagtgtat gatcaatttt gttcaaggtg    2820
tgaggcacat atttggtaaa caatatttac gtaggcctac cgaagaggat attcaacgct    2880
tacttcagtt tggagaggca catggatttc ctggcatgtt gggtagtgtt gattgcatgc    2940
attgggaatg gcaaaattgt ccggttgcat ggaagggaca attcacacgt ggtgattatg    3000
gggtacccac tatcatgctt gaagcggttg cctcaaaaga cttatggatt tggcatgctt    3060
tttttggtgc cgctggttca aataatgata ttaatgtgtt agaccaatcc ccattattta    3120
ctgatgtcct acaaggaaga gcacctcctg ttcaatatac tctcaatgag tcagattaca    3180
acatgggata ctatctagct gatggtatct atccagagtg ggcaacattt gccaaatcaa    3240
tcatcagacc acagagcgct aagcataaat tgtatgcaca acatcaggaa tcagctagaa    3300
aagatgtgga aagagccttt ggggttctac agaaacgttg ggccataata cgtcacccgg    3360
caagagtttg ggaaagagaa gagctagcag atataatgta tagttgtatt atttttgccca   3420
acatgatagt tgaggatgag aaaggttcct atgacatacc ggatgacaaa acatatgaac    3480
aaggtcaatt ctctgctcag ataacaggac ttgaccacgg accaatatat ggatttgcag    3540
aggtactaga gaaaaacagg gctattcgtg atcgatctac acatcggcgt ctcaaggaag    3600
atttgataga gcacatctgg cagaaatttg gaggtcaacc acaacaagat tagagtgtat    3660
taacttacta tcaaccttgt actttactat tttcatatca accttgtact gtaatatttt    3720
catgtcaaca gatttggctc aattacttgt ttttgcaata tacttgtatt actttgcaat    3780
ctaccagatt tgtctcaaag cacttatctt aatatgtcac atattgaacc agaacaaaca    3840
agaaacaaat aatcacacat gaacagtgag gcataaaata catgcaagtg ggtgaaaggg    3900
ggcttaccaa atggtctact ttgcaatcta caccgatctt tcagatccga tgcacatagc    3960
ctccggatga ggactagaag ccgaagccga cgcctcccat gacctattca gcctccacaa    4020
cgatggcgga aatttggggg gaagaacccg tcgatgcgcc tgaggggtgg ggtgggggtg    4080
gtagggagg ggaggggta gtggcggcga ttaggacgac atcaagtcgg agtcggccgg    4140
aatcgatggc ggctttgatg gaaggatttt ggatcgggat cggaagagag ttggatggag    4200
aggcgctccg ggatagggag ctgctcctcc gccggcctag gctgctgggc attgaggcct    4260
cggaggccgg cctgatgcgg cggccgactg ctccggatca agcgatgcaa gcagcggcga    4320
cgatggagtc tctttctctt ttttttttgg ataaggcagc gatggagtcg agactgggga    4380
tcgcatcggc cgcgggagga actgagaaag tcacggagg ttgggggtag cgatttgttt    4440
tattccgtgg gccccatctt aattccttct ctctattctc atacattgtg atggctaatt    4500
taactactac tcactgacaa atggtcccac actaatacco acttccatat tacacattgc    4560
tgttgccc                                                              4568
```

<210> SEQ ID NO 54
<211> LENGTH: 13
<212> TYPE: PRT
<213> ORGANISM: Oryza sativa

<400> SEQUENCE: 54

Met Asp Pro Pro Asn Arg Gly Phe Met His Met Leu Ser
 1               5                  10

<210> SEQ ID NO 55
<211> LENGTH: 406
<212> TYPE: PRT
<213> ORGANISM: Oryza sativa

<400> SEQUENCE: 55

Gly Ser Gln Ser Gln Thr Ser Gly Asn Gly Ser Gln Asn Ser Thr Ser
 1               5                  10                  15

Pro Gln Phe Pro Ser Ile Phe Ser Gln Ser Gln Phe Ser Gln Ser Ser
            20                  25                  30

Thr Pro Thr Phe Gln Asn Phe His Pro Phe Gly Ala Pro Asn Asn Tyr
        35                  40                  45

Gln Pro Tyr Gly Asn Ser Thr Pro Ser Phe His Gly Phe Gln Gln Gln
    50                  55                  60

Ala His Trp Leu His Ser Thr Pro Val Ser Phe Gln Gly Phe Arg Pro
65                  70                  75                  80

Pro Glu Asn Trp Val Tyr Ser Pro Asn Gln Ile Thr Gly Ser Ala Ser
                85                  90                  95

Ser His Gly Ser Glu Ser Ala Ser Gln Cys Pro Ala Arg Tyr Glu Glu
            100                 105                 110

Asn Asn Val Val Asp Ile Glu Glu Ser Ser Asp Asn Ser Gln Glu Ala
        115                 120                 125

Gly Arg Arg Gly Thr Arg Val Asn Trp Thr Glu Glu Asn Ile Arg
    130                 135                 140

Leu Leu Ser Ser Trp Leu Asn Asn Ser Val Asp Pro Ile Asn Gly Asn
145                 150                 155                 160

Asp Lys Lys Ala Glu Tyr Tyr Trp Lys Ala Val Ala Val Glu Phe Asn
                165                 170                 175

Ser Asn Thr Ser Arg Ser Asn Arg Lys Arg Thr Val Val Gln Cys Lys
            180                 185                 190

Thr His Trp Gly Gly Val Lys Lys Glu Ile Gly Lys Phe Cys Gly Ala
        195                 200                 205

Tyr Ser Arg Ala Arg Ser Thr Phe Ser Ser Gly Tyr Ser Asp Asp Met
    210                 215                 220

Ile Met Glu Lys Ala His Ile Met Phe Lys Ser Glu Asn Asn Glu Lys
225                 230                 235                 240

Pro Phe Thr Leu Glu Tyr Met Trp Arg Glu Leu Lys Asp Gln Pro Lys
                245                 250                 255

Trp Arg Arg Val Leu Glu Glu Asp Ser Lys Asn Lys Arg Thr Lys Ile
            260                 265                 270

Ser Glu Ser Gly Ala Tyr Thr Ser Ser Ser Asn Gln Asp Thr Glu Glu
        275                 280                 285

Glu Asn Arg Arg Lys Lys Glu Asn Arg Lys Lys Lys Arg Pro Glu
    290                 295                 300

Gly Gln Lys Lys Ala Lys Ala Lys Leu Lys Gly Arg Gly Lys Asn Val
305                 310                 315                 320

Ala Pro Ser Pro Leu Gly Asp Gln Pro Cys Gln Asp Phe Val Leu Tyr
                325                 330                 335

Asn Glu Ala Ile Lys Val Lys Ala Glu Ala Met Leu Lys Ser Ala Glu
            340                 345                 350

Ala Thr Ser Lys Ser Ala Glu Ala Lys Glu Tyr Thr Arg Met Glu
        355                 360                 365

Lys Tyr Gln Thr Tyr Leu Lys Leu Asp Lys Asp Thr Ser Asn Phe
    370                 375                 380

Ser Asp Ala Lys Leu Lys Arg His Glu Ala Val Leu Glu Lys Leu Ala

```
            385                 390                 395                 400
Thr Glu Leu Ala Glu Glu
                405

<210> SEQ ID NO 56
<211> LENGTH: 492
<212> TYPE: PRT
<213> ORGANISM: Oryza sativa

<400> SEQUENCE: 56

Met Leu Ala His Ile His Ser Val Val Ser Ser Met Lys Gln Gly Met
1               5                   10                  15

Gln Phe Ser Lys Ile Tyr Thr Ile Ala Phe Asn Ser Val His Ser Gln
            20                  25                  30

Gln Ser His Leu Val Pro Thr Lys Met Ser Ser Asp Ser Gln Val His
        35                  40                  45

Ser Ser His Ser Asp Glu Ser Ile Thr Ser Glu Asn Leu Glu Asp Met
    50                  55                  60

Met Trp Glu Glu Ile Asn Asp Pro Thr Glu Ala Gln Leu Glu Ala Arg
65                  70                  75                  80

Leu Glu Ala Gln Leu Glu Met Lys Leu Met Ala Arg Leu Ala Gly Asn
                85                  90                  95

Ser Asn Gln Arg Gly Gly Tyr Thr Arg Arg Tyr Ile Ser Arg Asp His
            100                 105                 110

Glu Asp Asp His Asn Arg Leu Phe Ala Lys Tyr Phe Ser Asp Asn Pro
        115                 120                 125

Leu Tyr Thr Asp Asp Gln Phe Arg Arg Arg Phe Arg Met Arg Arg His
    130                 135                 140

Leu Phe Leu His Ile Val Gln Ala Leu Gly Glu Trp Ser Pro Tyr Phe
145                 150                 155                 160

Cys Leu Arg Thr Asp Ala Phe Gly Lys Val Gly Leu Ser Pro Phe Gln
                165                 170                 175

Lys Cys Thr Ala Ala Met Arg Met Leu Ala Tyr Gly Thr Pro Ala Asp
            180                 185                 190

Leu Met Asp Glu Thr Phe Gly Val Ala Glu Ser Thr Ala Met Glu Cys
        195                 200                 205

Met Ile Asn Phe Val Gln Gly Val Arg His Ile Phe Gly Lys Gln Tyr
    210                 215                 220

Leu Arg Arg Pro Thr Glu Glu Asp Ile Gln Arg Leu Gln Phe Gly
225                 230                 235                 240

Glu Ala His Gly Phe Pro Gly Met Leu Gly Ser Val Asp Cys Met His
                245                 250                 255

Trp Glu Trp Gln Asn Cys Pro Val Ala Trp Lys Gly Gln Phe Thr Arg
            260                 265                 270

Gly Asp Tyr Gly Val Pro Thr Ile Met Leu Glu Ala Val Ala Ser Lys
        275                 280                 285

Asp Leu Trp Ile Trp His Ala Phe Phe Gly Ala Ala Gly Ser Asn Asn
    290                 295                 300

Asp Ile Asn Val Leu Asp Gln Ser Pro Leu Phe Thr Asp Val Leu Gln
305                 310                 315                 320

Gly Arg Ala Pro Pro Val Gln Tyr Thr Leu Asn Glu Ser Asp Tyr Asn
                325                 330                 335

Met Gly Tyr Tyr Leu Ala Asp Gly Ile Tyr Pro Glu Trp Ala Thr Phe
            340                 345                 350

Ala Lys Ser Ile Ile Arg Pro Gln Ser Ala Lys His Lys Leu Tyr Ala
```

```
                355                 360                 365
Gln His Gln Glu Ser Ala Arg Lys Asp Val Glu Arg Ala Phe Gly Val
    370                 375                 380
Leu Gln Lys Arg Trp Ala Ile Ile Arg His Pro Ala Arg Val Trp Glu
385                 390                 395                 400
Arg Glu Glu Leu Ala Asp Ile Met Tyr Ser Cys Ile Ile Leu Pro Asn
                405                 410                 415
Met Ile Val Glu Asp Glu Lys Gly Ser Tyr Asp Ile Pro Asp Asp Lys
            420                 425                 430
Thr Tyr Glu Gln Gly Gln Phe Ser Ala Gln Ile Thr Gly Leu Asp His
        435                 440                 445
Gly Pro Ile Tyr Gly Phe Ala Glu Val Leu Glu Lys Asn Arg Ala Ile
    450                 455                 460
Arg Asp Arg Ser Thr His Arg Arg Leu Lys Glu Asp Leu Ile Glu His
465                 470                 475                 480
Ile Trp Gln Lys Phe Gly Gly Gln Pro Gln Gln Asp
                485                 490

<210> SEQ ID NO 57
<211> LENGTH: 10011
<212> TYPE: DNA
<213> ORGANISM: Oryza sativa
<220> FEATURE:
<221> NAME/KEY: modified_base
<222> LOCATION: (6)
<223> OTHER INFORMATION: a, t, c, g, unknown or other
<220> FEATURE:
<221> NAME/KEY: modified_base
<222> LOCATION: (8)
<223> OTHER INFORMATION: a, t, c, g, unknown or other
<220> FEATURE:
<221> NAME/KEY: modified_base
<222> LOCATION: (13)
<223> OTHER INFORMATION: a, t, c, g, unknown or other

<400> SEQUENCE: 57
ggcctntnac agnggctcct agctggactg tggcttagta gcgccacgtc tgttttttgc      60
ctgcgtgtcg ctcggccccg cgcctctgct tgggcgctcg tgaccaaact cggatgcgca    120
aaacctggcc tggaaaaggg gccgcacgga ggaatcgagg ggaggcgcgt gcactgtggg    180
tgtcgttccc tcgccacccg gtgctctcgc atgggattcg gccggcgaaa tcccctattc    240
accctcgaaa agccacccga ttcccctcct cccgccactg atttcgtagc tcccgcgccg    300
gattggagtg cctcttgcct cagcgccgct gttcttccac ctcgacctcg ccgccctgaa    360
gtctcaattc aggacggcct cgccatcgcc tccgacggcg ccggaggtgc cactgccgcg    420
ctccgctcta ggatcttcag tcatcgtcga ggtctccatc gccatcgtga gaggtagcgg    480
tcagcaaacc ctctccccaa ctcatagttt gaccgatttg ccaagccttg gttcgctgat    540
tcgatctctc catgtgatgc aaaccctagt tgcagatgga tccgcggcta gccgatgctt    600
ttgcccgttt cctccaagat ccggcatcag cggcggcgat attgcagtcc ctaagccagc    660
cgtcgtcggt ccctctatag gatcaaggcg gccgactaga gggggtgaa taggcggttt     720 ttaaaacttt tggctaaaac caagttttgt atgcggaagc gtaaatcaaa atggttttgc    780
acaattcaaa acctaaatca actagtctca agtaagtgca caaagaagct agcctatgtt    840
gaggtttgca agcctagggt aataatagca caaataaact ctagtatgta aacttgctca    900
aagtaaattt gcacaaacta aaggagacaa gaaataagga atttttcacc gaggttcgga    960
aacttgccag tttcctaatc cccgttgagg cgagcccaac tccaccgctc aaccacgaag   1020
```

```
ccaccgcacg ccccccttcgt caaggggtgg gcaaggcggg agtcggccca cggagaggac   1080
taccaaagcc tcgatcacta gggtagttct tccttcactc cgaaggtggt gaaccccaaa   1140
ccactcacaa ccggcgccgg gcctcctcca caatctcctc ggagaggtca ccgagcaaca   1200
cttccacaag ctgtctagga ggcagcaacc tccaagagta acaagtctag gatgcttgcc   1260
gaggatgatc aagtgccaca ctagctataa caatgaagca atgcacttgg attggcttaa   1320
ctcactctct aacacctcac tagataaact aagtgcacaa gggtgtgaga gctcttgcaa   1380
gggttcaaga taatcagggg tgaaaacgga gcggatatta ccgatccga tccgatccga   1440 atccgtccga tgtgaggata tggtaagggt tgttagatat ccggccggat gcggatgcgg   1500
atgcggattt tgtcatgcgg atgcggatgc ggatgtggta tcaatgatat ccgacagatt   1560
cggattatcc gattttttaa tcagattatc cgatatagtt tttggcggat aatccgcaac   1620
tttcaggccc atctagcatt cttgcccaat aacccatcta ttctaaccct aatccttcct   1680
ctcctccccc tatcccccag atcggcagat ccctctctct ctctctctga ctctctctct   1740
ttctcccgtc agctctcagt cgtaggggag tgggcgagtg gcggcgcgac agcgagtcga   1800
cccagcgcga cggcgaccca gcgccggccg gccgctcctc cttggctgct agcgccgccg   1860
ccgctcctcc tcggctgcag tacaggctgg tggcgccgct gccattcgtc ctcgcctcct   1920
cggctcctcg gcgccgccac cactccgtcc actgtcgccc atcagcacgt ctccagcgcc   1980
gggccgccag cgcaccgtcg catccccgtc accagcccag ccgccatccc tgttggctgt   2040
cgccagcagc catccccgtc gcggcgtcgc cactcgccag ccaccactgt cgtcagccgt   2100
gccgtgtcgt cgtcgtgctg taactgctcg aggcctagag ctgcagctgc tgttccagtc   2160
caacgacaag tcgacgatag attaggtatt gttttcttgt acacttgcag tccaatttga   2220
agtatcaaat ttgggattta ctgatttaga aatgtagaga tgagctttgc ttacggaaat   2280
tacgtcaata gcaagttata atttgattaa ttgttcatca ttcattagga tcgtaaaaaa   2340
tggcacctag aaaaagaggg gcaaaagcag cagctgctgc tactgctact gaaagtagca   2400
ttgctgcctc gtcgccagct ccagctgaag gggaagaagg gccatcaact gtgggcagtg   2460
gcaatgaaag tcccaacact attgttgttg ttgatgtgga taacattggt gcagaggggg   2520
atggagacca tgaaaccaat gatgaacctg cagcaaagaa agcaaagaag agatagtgga   2580
agtgatgcaa gtgacttgga taaatataag gctgaaccat ccctgttggt tcctaatgga   2640
gataaatttg atgttttgtc atggtggaaa gctcacaaag atgtatatcc agtgctatct   2700
cttcttgccc gcgatgtctt gtccattcaa gcttccactg ttgcttcaga atcagctttt   2760
agtgctgggg gacgtgttct tgatccattt cgtactaaac ttgaacctga aatggtagaa   2820
gcactagtct gtaccaagga ttggattgct ggatatagaa gaggtgatca cttgtgtcat   2880
ttttcattta tattttgta aaaggtattc ttgttagttg attttttatt aatagtctaa   2940
tatagctttc ttccaaattt ttcagattct aataaaaggg ttggatctat tcttaatgat   3000
ctcgaggttg cggagaccct tggttgctaat atgacacttg acgagattga tgatatggta   3060 tgacattta ttgcataaat tttgttgcaa tacatttttgt agtcctatcg tcaaaataaa   3120
tgtatattgt ttgctcatac ttataggaaa agcaacagag cagtgatgat gaagaataag   3180
tgatgaagtg aggtgtgaag gcttgaaggg catgttggtg tgtggttgtg tgtgcctgtc   3240
tgcctgtgtg catgtgcatc gttcactgct atatctgccg tatgcttgta tgcctattga   3300
acaactgtgt tgtgtgctgt gctgtatgag atgtatgctc tgtgctgtat tgctggctca   3360
tatgctgcat gcagcatgca tgtcgtactg aactactgat gagtgatgac ttataagtta   3420
```

```
tattgttaaa ttttaagcaa tgcagtgacc agtgactaat gagtgatgga tgtatcttgg    3480
attattttgt tggatgtgtt ctattaagca aaattatatt attgatgtgt tttggttggt    3540
ttttcctaga gagctgagat catgtttaga tgttattttg ccatcgtatt gcggctaatt    3600
gtattggcgt ccacttgttg tatggattga atacaaactt gacatccgac aactttttgt    3660
ccgtttccga accgactccg caccgaatcc gacgtccgaa ataatccgct ccgcatccgc    3720
atccgcacgt catccgcacc cgctccgcat ccgtttaaaa aaaatggttt aggatatggt    3780
atagctatta tccgtccgaa tccgatccgt tttcacccct aaagataatg caatggggtg    3840
ccaaaacttt acccttgctg ctggggagtg ggtatatata cccccaacca ccaaaactag    3900
ccgttggagt cgaaatcccc aactcggtca gaccgccgtc ggctcggtct gaccggttgc    3960
ggctctggcg gctttgtatc accacaaaaa actagaccaa tgcaacagac tagtggggcc    4020
ggtcggactg gccttaccac gccagtcaga ccggctaaca ggcccggtca gaccggccta    4080
aggccaacgg tcagaccgca ggtcactttt cagctcaacc gaccgttagt aaaacgacga    4140
tatctcttga ctcgggtctc ggaatttggc gttcttggac tatatggaaa gcttattcaa    4200
agggccatcc aacccatgaa aaaccatcc aagaaacaca acttaagtca aggataaagg     4260
gctcacattc caaaggatat ccaccggaca tacccacaag atgtcactca ctcctattgg    4320
acatgcccac ttctctcttt gtttaggact tgagaaaact catcacacat ggctagacaa    4380
gcccaccaaa tgcacctata tgcatatgaa ctaatatggc acaaggtcat ccacatgctc    4440
gcttcataga cccctcttga tagtacgacg cctatctagc aaatccggtc tacaccaaac    4500
accaagaccg gaaaaagact aagaaaacat tcttagttct attatacctt tgccttgcgc    4560
catccaactt ggggtcaatg cttgagccaa gatcaacact cgtgaccatt tgcttgaacc    4620
atgtttatcc cgaggtcttg agcatccttt gtcaagactt tcttctcatc acaatcttga    4680
cttcactatt gtcaacatgg cgatgtcctt gtcttggtga ccatcaaccc atgttgtcat    4740
ccattagcct cattacggtg gaacctattc cttttcacat ctcaaaggag aacattagtc    4800
tcaacaaatc ggttgtaatc cttcacttga tgaccaaccg gttgcatatg aaagatatgg    4860
atatgtttgt tgagtattca tttacacctc aagtgtcata tacccgtatg caagctcaag    4920
tgcaaagatc cgatataaat aataggtaaa caacatggat ctagaacatg cacaataaat    4980
gtataggatt tgctccccct aagtatatgc atacaaagaa atatcaaga gagacaagtg     5040 tatgcataag taaagaagaa tcaacggggg tttatcctat acacatagag aatgcatatg    5100
tagtaatgat gtagaccaat ataaaacata taccttcatg atctccatgt tcttaatgta    5160
aattagacta aataagatat gactcgagta aacattagtc tcacacttat ataacaataa    5220
catgaaaatc atacatataa acctatcaaa aaggagataa gaagtggtac atatcgttt    5280 atctccatgc atttcatcct tgtcatgatt aaggtccatc accaaagaat gcatatctac    5340
cacatctcat catcgggaaa taacctagtt aacaacttat gaaaaagaga ggttaatccc    5400
ataaacatcg atttatcatc tatcaccaaa gcaacaatta cacaaattgt ttaatccaag    5460
atctttcaat cttttctctc ttttgtgata gacaataacc cgatataaac aatacaaaga    5520
gatgagatga aagataattt caaatcaagg tagagatctt ataatgaaca aaatatagaa    5580
taagctcccc ctcaagatgt gcatacatat ggatatgaag gaatgcatat gcacataatc    5640
aatcaagatc aatgagggag ctcacactat attttggatc cacaagagag accaaattag    5700
aatatgtgaa gtttaataca tacctctcat cattttact ttcatatcca aataagacta     5760
gtcaaagaaa ggctcataaa aacgttagtc tcatataatt agatttgtca ttaatcactg    5820
```

```
aaaccaaatt aaggcacttg aacttacacc ctcctcttcc gtcgttccca taccctcctc   5880
caccattccc tctcttctgc acgcagccgc caacagcagc gccgccgcca ccttcggccc   5940
caacggcaag cactgaacct ttggcggccc aggcaactct atgttcggca ccggatgtag   6000
gctttgcagc gacatgcaag ccttcatcga cctcaagacc tggacgctga cactgtgtga   6060
caacagagcc tgcccctatc cctgcctcta cccctgcccc tgccctgtc cgtgccgatg   6120
agtctattgg caaggccggc aggatgttgt acagtcatga agaagacatt aggctggtaa   6180
gaatttactt gttgatttta gtaaaaaatc gatgctagca gtgtggatga ttaatctatg   6240
caaataatag aggtacagag gtctgtgtag ctgtgctaga gcattttagt taggcaaaat   6300
gcgaagaaac aacatctgaa ttttgtagag gacatacttg tgtactacac tgaacatgca   6360
attacataaa taagcatcat gtcagtattt gattagtgtt aagctagaac tacaaccagt   6420
gtaagagtaa ttaaggttcg caattagaag tgccaatagg ttgctttttt ggtttgctgt   6480
tcataattct gtttgctata agaagcagaa tgctcttcat cttttgtgct gccatgtatt   6540
tgtactatgc tcttcatctt ttggtttgtt gcatgtatac attactgcaa atatagattc   6600
attgacctag ttatttccgg caggatgttt ccatttggtt tgagggtctc aattattttt   6660
gttgtttatc atgtatgaca ttgcagctac ctaggtaggt accattaatt taggagtagg   6720
ttatcatgct gccttttgt aatggttgta ggcaagtgct tggctcaaat gttcaacaga   6780
tcctatagga gtgaatagga agggtgagac ctattgggta catgtggccg agacttacaa   6840
tgagacaact ctggatggaa ggaagaggga tcccacctgt ctcaaagggc attggcacaa   6900
gattacaccg aaggtcactt tattcaatgg gtgttgcgtg caactgagga atacacctat   6960
cagtgggagg aatgacgaga agctcatgga tgatgccttg gcgctctaca tcaagcgttc   7020
aaagaagcac aagcccttcc tctaccaatc cagaagtgta ccgccgtgat gcgcatgttg   7080
gcctatgggg tgtgtgcgga tcaaaccgat gagtatgttc gcattggtgg aaccactgcg   7140
tatgaatccc tcgaaaggtt ctgtggaggt gttattgcgg tgtttggtcc acagtatttg   7200
aggaaaccta ccttggatga tgtacaacgt ctcctatata tgcatgaaga acgtgggttt   7260
cctgggatgt tggggagcat cgactgtatg cattggagat ggatgaactg ccctaatggt   7320
tggaaaggga tgtacacacg gggtgattat ggtatagcaa caataatcct cgaggcagtt   7380
gcatcacgtg acaaatagat ctggaattca ttttttggtg tgacggggtc taacaatgat   7440
attaacgtgc tgaatcaaag caatgtcttc acggatgtca ttatgggtag atctcccatt   7500
gtgtgataca tggttaacgt gaatcagtac gacttgggga actatcttgc tgacgggata   7560
tacctggaat gggcaacgct catgaagtca attcgtcatc cccaattgcc gaaagataaa   7620
ttgttcgcac aacgtcaaga atccgcaaga aaggatgttg agtgtgcttt tgggattttg   7680
aaggcatgct tcagagtggt ggaaactccc acgcatttgt ggctgatagc tgacattagc   7740
gatataatga cggcttgtgt aatcatgcgc aacatgatcg tcgaggacga aggacacgtt   7800
tgggatactg aagacttgga gtttgagggt gactacgaga tcgaacctcc agaacacact   7860
tttgggacac cacaacatat tgctagatta cttgagcgtg acagccaagt tcaaagtcga   7920
acaatgcaca accgtctaaa aaatgatttg gtggagcaca tatgggcaag gtagatccta   7980
cacgttcatg aacattgatg ttttaggaaa taaggttatc tcggaggagg attggtagtt   8040
gttcggaaat aaggatgatt tctcaaatca tccaagttat ctaggtgtag gtgtagttttt   8100
aagaaagaag gaagatttct caaatcatcc aaattataca ggagtagggg tagttttagg   8160
aagtaaggat gatttctcaa atcatcaaag ttatctagga gtagaggtag ttttaacaaa   8220
```

```
ggatgatttc tcaaatgtag gcatttacaa atatgaatga ccattgtaaa taaataaagg    8280
tgctgtatcc ccaatttgtg catgccatgt atataaataa atgaattgca atcggtgcca    8340
tataaagtgc acaggacaaa acaattagga gataatcagc aacggaccga ctaagttcag    8400
caagccaaca caaataggt caggtacata caccatcaac taaccgaaac ccacagacat     8460
attgctttga cacatgccat catccacctt acagacacca tacataaccc atatcacaac    8520
attacacagt tcacagtcct agctaaatat ataagcatgt tatatatctg ttgcttccat    8580
actatccatg ttgtcacgcc atgaacctaa ccctgcaggg aaaaaataca gcatgtcaaa    8640
aatggttgtg aattttaaat agaggggggac attatatgca gccgtatagt taggctcaag   8700
cattggcatc aatacttagt tacaaacata actcatgctt caactacagt gacctaatca    8760
tgcagattag gcacattgca actcataata gcacagattt gagatcccag agcaatcgcg    8820
gctttcaatt ttgctagtta gaattcacat gttacttctt gcacatatct gcattacaac    8880
atctacttca gtcaaccagt tctgaagtac aaacactctg tccatcgccc aatgatcatc    8940
tctacgggaa gtatcaagaa ccatgcacta aactaatcat acagccaata actaaacttt    9000
atgaatttga gcaaacatgg cacatccaac ctgtccataa atttttaaca aaggagcaga    9060
gccctccatt ccaatatctc aaatgacaac aaaatcatcc cacatctcaa attacaataa    9120
aatcatgaaa cagctcaaat gacaaacaaa tttgaaatga cattcgagtg agatccaaaa    9180
cttcttggct gctacagtag atggagaagc cactggcgcg ggtgtagctg gagccagcgc    9240
cgcattcacc ttctcaaaac ctggtggcac ctccggaag cctaaacctc cctgcgccgc     9300
atctgcctcc ccctccacag cgatgacccc gagatagatc gacgagccga cgctctccgc    9360
cctcaccggc gccggcgtag atcacaggcg cgaagtacct gcccctaccg ccgttcccct    9420
attcttcttc ccgccatccc tagccactgt ggacggggta tagcccggcg ggagcagcac    9480
aaggccacta cggagctcaa tctgcgtgaa cttgggcgg tcgtccatgg tttcgggcgg     9540
atcagaggag cggcggagtg ggaggatgag acgacgaccg acgggagtga agcgcggcga    9600
gaggcgggcg aggcggacag actagagaga ggggatggaa tggtcgaatg gttacagtcg    9660
gtggcgaggg aagggcaacg gcgtgtgtgg cggagtggga ggaggcggta gcgagaggag    9720
ggaaggaggc atggcgacag gtggtcgagg gctcgaggcg gagagacgag aggaatggcc    9780
gaatggatag gatcggcatc gtccagccag ggtaggtggg gaaaaatttt tgggggcggc    9840
ccatgacctc gcgctagcat aggcatgccc attgtgggct tcgtacccctt taccagtgcc   9900
tccattgaat taagctacac aactagaggt gcttgcactg tgggataagt gtctatgac     9960
caacttttg ggctaggggt acgggcccca tagcttgcac tgtgagaggc                10011
```

```
<210> SEQ ID NO 58
<211> LENGTH: 95
<212> TYPE: PRT
<213> ORGANISM: Oryza sativa

<400> SEQUENCE: 58

Ser Ala Trp Leu Lys Cys Ser Thr Asp Pro Ile Gly Val Asn Arg Lys
  1               5                  10                  15

Gly Glu Thr Tyr Trp Val His Val Ala Glu Thr Tyr Asn Glu Thr Thr
                 20                  25                  30

Leu Asp Gly Arg Lys Arg Asp Pro Thr Cys Leu Lys Gly His Trp His
             35                  40                  45

Lys Ile Thr Pro Lys Val Thr Leu Phe Asn Gly Cys Cys Val Gln Leu
         50                  55                  60
```

Arg Asn Thr Pro Ile Ser Gly Arg Asn Asp Glu Lys Leu Met Asp Asp
 65                  70                  75                  80

Ala Leu Ala Leu Tyr Ile Lys Arg Ser Lys His Lys Pro Phe
             85                  90                  95

<210> SEQ ID NO 59
<211> LENGTH: 117
<212> TYPE: PRT
<213> ORGANISM: Oryza sativa

<400> SEQUENCE: 59

Pro Ile Gln Lys Cys Thr Ala Val Met Arg Met Leu Ala Tyr Gly Val
 1               5                  10                  15

Cys Ala Asp Gln Thr Asp Glu Tyr Val Arg Ile Gly Gly Thr Thr Ala
                 20                  25                  30

Tyr Glu Ser Leu Glu Arg Phe Cys Gly Gly Val Ile Ala Val Phe Gly
             35                  40                  45

Pro Gln Tyr Leu Arg Lys Pro Thr Leu Asp Asp Val Gln Arg Leu Leu
         50                  55                  60

Tyr Met His Glu Glu Arg Gly Phe Pro Gly Met Leu Gly Ser Ile Asp
 65                  70                  75                  80

Cys Met His Trp Arg Trp Met Asn Cys Pro Asn Gly Trp Lys Gly Met
                 85                  90                  95

Tyr Thr Arg Gly Asp Tyr Gly Ile Ala Thr Ile Ile Leu Glu Ala Val
            100                 105                 110

Ala Ser Arg Asp Lys
        115

<210> SEQ ID NO 60
<211> LENGTH: 35
<212> TYPE: PRT
<213> ORGANISM: Oryza sativa

<400> SEQUENCE: 60

Ile Trp Asn Ser Phe Phe Gly Val Thr Gly Ser Asn Asp Ile Asn
 1               5                  10                  15

Val Leu Asn Gln Ser Asn Val Phe Thr Asp Val Ile Met Gly Arg Ser
                 20                  25                  30

Pro Ile Val
        35

<210> SEQ ID NO 61
<211> LENGTH: 155
<212> TYPE: PRT
<213> ORGANISM: Oryza sativa

<400> SEQUENCE: 61

Tyr Met Val Asn Val Asn Gln Tyr Asp Leu Gly Tyr Tyr Leu Ala Asp
 1               5                  10                  15

Gly Ile Tyr Leu Glu Trp Ala Thr Leu Met Lys Ser Ile Arg His Pro
             20                  25                  30

Gln Leu Pro Lys Asp Lys Leu Phe Ala Gln Arg Gln Glu Ser Ala Arg
         35                  40                  45

Lys Asp Val Glu Cys Ala Phe Gly Ile Leu Lys Ala Cys Phe Arg Val
     50                  55                  60

Val Glu Thr Pro Thr His Leu Trp Leu Ile Ala Asp Ile Ser Asp Ile
 65                  70                  75                  80

Met Thr Ala Cys Val Ile Met Arg Asn Met Ile Val Glu Asp Glu Gly
                 85                  90                  95

```
His Val Trp Asp Thr Glu Asp Leu Glu Phe Glu Gly Asp Tyr Glu Ile
            100                 105                 110

Glu Pro Pro Glu His Thr Phe Gly Thr Pro Gln His Ile Ala Arg Leu
        115                 120                 125

Leu Glu Arg Asp Ser Gln Val Gln Ser Arg Thr Met His Asn Arg Leu
    130                 135                 140

Lys Asn Asp Leu Val Glu His Ile Trp Ala Arg
145                 150                 155

<210> SEQ ID NO 62
<211> LENGTH: 5140
<212> TYPE: DNA
<213> ORGANISM: Oryza sativa

<400> SEQUENCE: 62
gggcacgtac aacggcatta attagccggc tctctccagt gccacataga caaataagat      60
gacgtggaag agagatgata gatgagagag aaacaacgat gctatctgtg acatcgccga     120
agcatcggct cctctcgcgc aaaaaacgag cagagttgag gagagcccac cattgtagaa     180
ttggttttg ctgcagagct gggcctccag atccaatgta aaaaaagcgc gcggaagaaa      240
tttggcgcgg gtgagggatc gagatacggg agggcgggaa tcggagcaga gatgcgcgcc     300
atccaatttc ttcgatcccc aaatatgacg ctgaaatcgg cagatcgggt tccagtccaa     360
tacatcgctg ctacgctcct ccacctcact gcagccttgg atcgtccacc tcgccaccaa     420
cgtttcccct ccacctcgcc gccgacgttg ctcctcaacc actcgctcca tcggcgttga     480
ctgtatggct gggagacgga caaaggtggc atcggtgcct gagacatcct ctgccggtac     540
caacacttcc ggcttccgct tcacctcaac tgataccccc gctgccactg gtaccttccc     600
tccctatctt ggaataccte ccttctctgc atctaggatg agcgcggcta cgaccggcag     660
ccatatttcc ccatctcctt catggatgca gacggacaaa agctcacata agctactac      720
gtcggatttg tcgtcaccac atgcaaatat gcagagctgg taaccacaaa tcccagcaat     780
aatctctgct atcttatgaa gattcagttc tgcaagtttt ctgttctctg aatgaaatta     840
ttaaacggtt gccatgttct agacttgata tattttctga aatacaatga gtaaagcaat     900
ccaagatttt ctgaaataca tcgtttaaag cagtccaaat aaattgacat ataaatattg     960
gtatataatc cataaggtta ctgtttgttc agataggtat ataagatta tgttattgta     1020
catctttggt catgctgaaa ctgaagagac atatatttcc aatgttatgt tatttctctg    1080
tacaaactaa ggtttctata ttttttggga gtaggcattt gttttacag attatgaggt     1140
tgttacatgt tgtttcttca tgtacgtgtg tgttgtttct tataggttta tcttaatgat    1200
caattggtta tggcactgaa attgtgagct tcttgcaggg gaaatggtac acacccacct    1260
ggaggattca tgagtttttt tcacaatcag ccaaatatat ctcaacatta caattttgtc    1320
ggcgcgtctt cgcactacac accattacat gctaatggtt cttcgccacc gcttgctaat    1380
ggtgcttcta tgccgcttgc gacacccact ccacccccac ttactgggaa ccaggaccat    1440
gtcaatgttg atagtgatga tgacactgcg gtcgctcgga ccaaattgaa gctaaattgg    1500
acccaagagg aggatgtcag accagtgaga atgatgcaaa ttttacttga ttcgcattgt    1560
gaatctgtgt gcataattac actttctttt gttatctttg tagatgagcg cttggttgaa    1620
caattcaatg gacctaatta atgggaatga taagaaggct gaaaaatatt ggggagatgt    1680
tgctacagaa tacaataaaa ccacaccaca gaatagatgg agaagcccaa agcaagccaa    1740
ggagcggtgg cacaaactca acactcggac ggatctgttc caaggctgtt ggttgaaggc    1800
```

```
taagcgcaca tatactagtg gttactctga actaaatgtg gattgacatg gcccataagt      1860
tctatgaggc tgataagaaa aaattaggac ggttcgtcct aatagatgta tggtacgcat      1920
gctgtgatca gcctaagtgg aatgcatata atgatgcact caagagagat cgtaaaagga      1980
agtcgtctga taacagagag atgcttgggc aagcatcagg accttcagat gttgaagaaa      2040
ccccatggcc aatcggacaa aaggctgcta aagggctgc acgtgaaagc atgggaaagt       2100
tgaacgatat ttctgatgct gaagagatag acaagttaga ccaagtccaa tctgatattc      2160
acacaagatg catgaagatg atggaaatgc aagaagttat ctactcgtca ggttcaatca      2220
tcaaagcttt ctcaacttgc tgcacgggaa aatagattag ttgcaaagga aaataaggat      2280
gccaagatgt tcgagaccta tagttgtcta ctcgcacagg acacaactgg gatggctgat      2340
gacattagag ccgagcatgt cactgccata aggtgtttga ggaagatctt gtttccggac      2400
ttatcttgag gttagttaat aatttactgg aaatgattta attgattatg acctagatta      2460
catattaatc tacatatcat gtgacctgaa atgtgatttg attatatatg atttcattga      2520
acctgaaatg tgggcatgtt ctagatgata tctcttcaag ttgctgaaat gataatatag      2580
gctataatgt taatagcttg ctgtatggag cagtgttct  ttaagcttgc ataggactg       2640
ttattctatt ccctattatg tagaagtaat attgagctcc gtgtcttcaa aattattgcc      2700
taagtggaca ctttggcaga caacaaaaca agctccaatt ctgactttaa gatcagtatc      2760
cgaaattgag cagtgattca atctgaaatt tgtgattgtt gggcatgttt atcttttgaa      2820
tttgaatagt atatattgat atattatctc actgaagctg aatctgaaaa tttatattta      2880
tgtaactgaa tctatttttt tagtatgtca ggtaataata tctggaagat ctgttcaatg      2940
tggatcacat ctatgccatt ggaagaatgc aatgtgattt gctgctgcac atgcaactgg      3000
tcgatctcat tgccaagcaa ggataattta cttcctagtt atatgaacat gtaataattc      3060
actttgttgc tatctgaaca tgtcacctgg accatgatat tcattgccat gtgattttta     3120
tatcttttac cttgcctcaa ataatgatac atgttcctat tctaatataa atgatgattt      3180
tgtttccttt attgtgtgaa catgctatct gcatatctgt atacatgtgg tttaaaatta     3240
gaacgataga accagtacat gtcgagtcca acaaacaagt ccaatcttct acattgtcag      3300
accatacgat gtctcccaat aatatcgacc acctcgatga tgatgtcgtc gtcgacgctg      3360
accttgccat tgaggatgat gctgtcatcg acctcgacct cgacgatgat gccgccgtcg      3420
acgccgacat cgacctcgac ctcgacctcg acgatgatgc cgtcgtcgac ctcgacctcg      3480
acctcgacga tgatgccgcc atcgaccttg acaactttca tcctatgaat atatacagca      3540
tggatgactt tatagctgaa gcaaccttt tggatgaata tagtgaacag attattctca       3600
ggttgaagga gaacataaca tctgagccac ctcgtcgtct acatcaaagt ggtacaagac      3660
ggtatatacc aagaaaccgt gaagctagca atgcggatct tgtggccaac tacttctccg      3720
agtctccaat ctacacagat aagatgttcc gtaggaggtt tcggatgagg aagcctctct      3780
tcctacgaat tgtgagtgcc cttagtgaat ggtctcctta ttttactaat agattggatg      3840
ccactggtag agcaggacat tcaccacttc aaaagtgtac ggctgctatt cgtatgctag      3900
catatggaac tcctgcggat caacttgatg aggtattaaa gattggtcct aatacagctt      3960
tggagtgttt gggaaaattc gctgaaggag tcattgaaat atttcgcaaa gagtacttac      4020
gagctcctag gagtgatgag gttgaaagat tgctacaggt tgctgactca cgtggttttc      4080
ctggcatgtt aggaaatata gattgtatgc attgggcatg gaaaaattgc ccggtctcat      4140
ggtgtggcca atttactcgt ggtgacaagg gagttcctac catgattctt gaagcggtag      4200
```

```
catcgaaaga ccttcgcata tggcatgatt tttttgctac tgcaggatcc aataatgaca   4260
tcaatgtgtt aaacaagtca cccttgttca ttgaagcatt gagagggaa gctcctcgtg    4320 tacagtttag tgtaaatggg aaccaatata acacatggta ctatcttgct gatggaattt   4380
atccagagtg ggcgacattc gtgaagacaa tacagcttcc tcaaacagac gaacataaat   4440
tatatgcagc tcgtgaagaa ggaacaagga aggatgttga gcgagccttc ggtgtgttgc   4500
agtctcgctt taacatcgtt tgtcgtctag ctcggatgtg gaggcagggc gatgttatca   4560
atataatgga agcttgtgtt attcttcgca atatgatagt tgaagatgaa caggaaatgg   4620
ctgaaattcc tttggattta aatgagaacc caggagcatc gttcgttcta ccacctgaag   4680
tgaggaactc atctgacccc aaccctttgct ttgctgcggt attacgaaga aattcatcta   4740
ttcgtgatcg tgcgaaacat atgcaactca agaaagattt agttgcacat atatggcagc   4800
gttttgggaa aaagtagaac tactttatgt aatgaaataa tgtaatttag cttatcattt   4860
gattaaataa taatttcgga tgtgtgtgct ggtaggatgc acatcgtctt cttttatatg   4920
gttatgatag cacgatgtag cgttagttct atagagaaga aatacaaata tatgtgctgc   4980
tgaaatttac atttgattac atgcaatgaa tttattagct atttattacc ttgtattaat   5040
agagagttgg ttaaagagac agttctttgt aggtaggagt ttcttcgctg atgtggagta   5100
tagagagaga ccacaccgag ctctaccttt gaacatgccc                         5140
```

<210> SEQ ID NO 63
<211> LENGTH: 165
<212> TYPE: PRT
<213> ORGANISM: Oryza sativa

<400> SEQUENCE: 63

```
Met Ser Phe Phe His Asn Gln Pro Asn Ile Ser Gln His Tyr Asn Phe
  1               5                  10                  15

Val Gly Ala Ser Ser His Tyr Thr Pro Leu His Ala Asn Gly Ser Ser
             20                  25                  30

Pro Pro Leu Ala Asn Gly Ala Ser Met Pro Leu Ala Thr Pro Thr Pro
         35                  40                  45

Pro Pro Leu Thr Gly Asn Gln Asp His Val Asn Val Asp Ser Asp Asp
     50                  55                  60

Asp Thr Ala Val Ala Arg Thr Lys Leu Lys Leu Asn Trp Thr Gln Glu
 65                  70                  75                  80

Glu Asp Val Arg Pro Met Ser Ala Trp Leu Asn Asn Ser Met Asp Leu
                 85                  90                  95

Ile Asn Gly Asn Asp Lys Lys Ala Glu Lys Tyr Trp Gly Asp Val Ala
            100                 105                 110

Thr Glu Tyr Asn Lys Thr Thr Pro Gln Asn Arg Trp Arg Ser Pro Lys
        115                 120                 125

Gln Ala Lys Glu Arg Trp His Lys Leu Asn Thr Arg Thr Asp Leu Phe
    130                 135                 140

Gln Gly Cys Trp Leu Lys Ala Lys Arg Thr Tyr Thr Ser Gly Tyr Ser
145                 150                 155                 160

Glu Leu Asn Val Asp
            165
```

<210> SEQ ID NO 64
<211> LENGTH: 3
<212> TYPE: PRT
<213> ORGANISM: Oryza sativa

-continued

```
<400> SEQUENCE: 64

His Gly Pro
  1

<210> SEQ ID NO 65
<211> LENGTH: 2
<212> TYPE: PRT
<213> ORGANISM: Oryza sativa

<400> SEQUENCE: 65

Val Leu
  1

<210> SEQ ID NO 66
<211> LENGTH: 1
<212> TYPE: PRT
<213> ORGANISM: Oryza sativa

<400> SEQUENCE: 66

Gly
  1

<210> SEQ ID NO 67
<211> LENGTH: 16
<212> TYPE: PRT
<213> ORGANISM: Oryza sativa

<400> SEQUENCE: 67

Glu Lys Ile Arg Thr Val Arg Pro Asn Arg Cys Met Val Arg Met Leu
  1               5                  10                  15

<210> SEQ ID NO 68
<211> LENGTH: 2
<212> TYPE: PRT
<213> ORGANISM: Oryza sativa

<400> SEQUENCE: 68

Ser Ala
  1

<210> SEQ ID NO 69
<211> LENGTH: 4
<212> TYPE: PRT
<213> ORGANISM: Oryza sativa

<400> SEQUENCE: 69

Val Glu Cys Ile
  1

<210> SEQ ID NO 70
<211> LENGTH: 6
<212> TYPE: PRT
<213> ORGANISM: Oryza sativa

<400> SEQUENCE: 70

Cys Thr Gln Glu Arg Ser
  1               5

<210> SEQ ID NO 71
<211> LENGTH: 4
<212> TYPE: PRT
<213> ORGANISM: Oryza sativa

<400> SEQUENCE: 71

Lys Glu Val Val
```

-continued

<210> SEQ ID NO 72
<211> LENGTH: 36
<212> TYPE: PRT
<213> ORGANISM: Oryza sativa

<400> SEQUENCE: 72

Thr Glu Arg Cys Leu Gly Lys His Gln Asp Leu Gln Met Leu Lys Lys
1               5                   10                  15

Pro His Gly Gln Ser Asp Lys Arg Leu Leu Lys Gly Leu His Val Lys
            20                  25                  30

Ala Trp Glu Ser
        35

<210> SEQ ID NO 73
<211> LENGTH: 8
<212> TYPE: PRT
<213> ORGANISM: Oryza sativa

<400> SEQUENCE: 73

Thr Ile Phe Leu Met Leu Lys Arg
1               5

<210> SEQ ID NO 74
<211> LENGTH: 2
<212> TYPE: PRT
<213> ORGANISM: Oryza sativa

<400> SEQUENCE: 74

Thr Ser
1

<210> SEQ ID NO 75
<211> LENGTH: 11
<212> TYPE: PRT
<213> ORGANISM: Oryza sativa

<400> SEQUENCE: 75

Thr Lys Ser Asn Leu Ile Phe Thr Gln Asp Ala
1               5                   10

<210> SEQ ID NO 76
<211> LENGTH: 1
<212> TYPE: PRT
<213> ORGANISM: Oryza sativa

<400> SEQUENCE: 76

Arg
1

<210> SEQ ID NO 77
<211> LENGTH: 75
<212> TYPE: PRT
<213> ORGANISM: Oryza sativa

<400> SEQUENCE: 77

Trp Lys Cys Lys Lys Leu Ser Thr Arg Gln Val Gln Ser Ser Lys Leu
1               5                   10                  15

Ser Gln Leu Ala Ala Arg Glu Asn Arg Leu Val Ala Lys Glu Asn Lys
            20                  25                  30

Asp Ala Lys Met Phe Glu Thr Tyr Ser Cys Leu Leu Ala Gln Asp Thr
        35                  40                  45

```
Thr Gly Met Ala Asp Asp Ile Arg Ala Glu His Val Thr Ala Ile Arg
    50                  55                  60

Cys Leu Arg Lys Ile Leu Phe Pro Asp Leu Ser
65                  70                  75

<210> SEQ ID NO 78
<211> LENGTH: 548
<212> TYPE: PRT
<213> ORGANISM: Oryza sativa

<400> SEQUENCE: 78

Met Met Ile Leu Phe Pro Leu Leu Cys Glu His Ala Ile Cys Ile Ser
1               5                   10                  15

Val Tyr Met Trp Phe Lys Ile Arg Thr Ile Glu Pro Val His Val Glu
                20                  25                  30

Ser Asn Lys Gln Val Gln Ser Thr Leu Ser Asp His Thr Met Ser
            35                  40                  45

Pro Asn Asn Ile Asp His Leu Asp Asp Val Val Asp Ala Asp
    50                  55                  60

Leu Ala Ile Glu Asp Asp Ala Val Ile Asp Leu Asp Leu Asp Asp Asp
65                  70                  75                  80

Ala Ala Val Asp Ala Asp Ile Asp Leu Asp Leu Asp Leu Asp Asp
                85                  90                  95

Ala Val Val Asp Leu Asp Leu Asp Leu Asp Asp Ala Ala Ile Asp
                100                 105                 110

Leu Asp Asn Phe His Pro Met Asn Ile Tyr Ser Met Asp Asp Phe Ile
            115                 120                 125

Ala Glu Ala Thr Phe Leu Asp Glu Tyr Ser Glu Gln Ile Ile Leu Arg
        130                 135                 140

Leu Lys Glu Asn Ile Thr Ser Glu Pro Pro Arg Arg Leu His Gln Ser
145                 150                 155                 160

Gly Thr Arg Arg Tyr Ile Pro Arg Asn Arg Glu Ala Ser Asn Ala Asp
                165                 170                 175

Leu Val Ala Asn Tyr Phe Ser Glu Ser Pro Ile Tyr Thr Asp Lys Met
            180                 185                 190

Phe Arg Arg Arg Phe Arg Met Arg Lys Pro Leu Phe Leu Arg Ile Val
        195                 200                 205

Ser Ala Leu Ser Glu Trp Ser Pro Tyr Phe Thr Asn Arg Leu Asp Ala
    210                 215                 220

Thr Gly Arg Ala Gly His Ser Pro Leu Gln Lys Cys Thr Ala Ala Ile
225                 230                 235                 240

Arg Met Leu Ala Tyr Gly Thr Pro Ala Asp Gln Leu Asp Glu Val Leu
                245                 250                 255

Lys Ile Gly Pro Asn Thr Ala Leu Glu Cys Leu Gly Lys Phe Ala Glu
            260                 265                 270

Gly Val Ile Glu Ile Phe Arg Lys Glu Tyr Leu Arg Ala Pro Arg Ser
        275                 280                 285

Asp Glu Val Glu Arg Leu Leu Gln Val Ala Asp Ser Arg Gly Phe Pro
    290                 295                 300

Gly Met Leu Gly Asn Ile Asp Cys Met His Trp Ala Trp Lys Asn Cys
305                 310                 315                 320

Pro Val Ser Trp Cys Gly Gln Phe Thr Arg Gly Asp Lys Gly Val Pro
                325                 330                 335

Thr Met Ile Leu Glu Ala Val Ala Ser Lys Asp Leu Arg Ile Trp His
            340                 345                 350
```

```
Asp Phe Phe Ala Thr Ala Gly Ser Asn Asn Asp Ile Asn Val Leu Asn
        355                 360                 365

Lys Ser Pro Leu Phe Ile Glu Ala Leu Arg Gly Glu Ala Pro Arg Val
    370                 375                 380

Gln Phe Ser Val Asn Gly Asn Gln Tyr Asn Thr Trp Tyr Tyr Leu Ala
385                 390                 395                 400

Asp Gly Ile Tyr Pro Glu Trp Ala Thr Phe Val Lys Thr Ile Gln Leu
                405                 410                 415

Pro Gln Thr Asp Glu His Lys Leu Tyr Ala Ala Arg Glu Glu Gly Thr
            420                 425                 430

Arg Lys Asp Val Glu Arg Ala Phe Gly Val Leu Gln Ser Arg Phe Asn
        435                 440                 445

Ile Val Cys Arg Leu Ala Arg Met Trp Arg Gln Gly Asp Val Ile Asn
    450                 455                 460

Ile Met Glu Ala Cys Val Ile Leu Arg Asn Met Ile Val Glu Asp Glu
465                 470                 475                 480

Gln Glu Met Ala Glu Ile Pro Leu Asp Leu Asn Glu Asn Pro Gly Ala
                485                 490                 495

Ser Phe Val Leu Pro Pro Glu Val Arg Asn Ser Ser Asp Pro Asn Pro
            500                 505                 510

Cys Phe Ala Ala Val Leu Arg Arg Asn Ser Ser Ile Arg Asp Arg Ala
        515                 520                 525

Lys His Met Gln Leu Lys Lys Asp Leu Val Ala His Ile Trp Gln Arg
    530                 535                 540

Phe Gly Lys Lys
545

<210> SEQ ID NO 79
<211> LENGTH: 4479
<212> TYPE: DNA
<213> ORGANISM: Oryza sativa

<400> SEQUENCE: 79
gggcaagtac aacggttcag cgagacccgt cgacatgcac tgttttttg cgaaaacccc      60 cccgcacggc gctcgcttcg gcccatccgt cgtctcgttc gtcgacgagg ccagcgcgtg     120
cttccaggcg aagcgacggc gatgaagccc attgtacgac gcgatgcggg gaggcgacgg     180
aggcgcggga tcagctgcac gggatcagct ctctcgcgcg cggaacaggt tcgcgccttc     240
ctcgcccgcc aaaatctctc tcgcgcgtgt tgaaatagcc cccctgcgt tccccatcca     300 accctatttc gatttggcca ccatgtcgcg gcaggcacgg aaggaggcgg cggcggcggc     360
gcaagatatg ctgaagttgg atgcggctca gatgcgcaag ccagctgcat cgcaatctcg     420
aaagggtgcg gcggcgccga tgcggaaggc ccagggagga gctcgggcgg cgtcgatggt     480
gccggagcag agcagttcag ggttggcggc gcgtgtgcca gagcaccgga gttcgagata     540
tggcgcggct agtccaccac caagctcctt caccgacggc agctgcttct tcaacggcag     600
tgccggcggc ttcttcggca acgcggccaa agccctagt ggtcaaccat ggagttctta     660
atcttcagat cctgcaacat ggtactatct ctgaactttg cttctgtgat gagctcaatg     720
atgggaatca tatggctagg aattaatttt agatgttatt tgcacttccc tcgcttatac     780
aagatttggg atacactgtc atgagtttca gtattgtggt tgatgcaaag attgattgca     840
ctggtgcaga tttctttgat agtttaataa agctatgtaa ctagttttta tccactgtat     900
aacatcaaag aggatgaagc actgaaacaa acattagttc ctactttac acataacatt     960 agtccctagt tgctttcatt gctcatatat atgtgtaaaa tatggcaggg gaaacaatgc    1020
```

```
aacacctctt ggaggcttca taaacttgat ccagcctaac ttgtctcaac aatttaattt      1080
tgttggagac caaaatcagt cagaagatga ttactcgact cctatttcag ctagggacaa      1140
tacatatgtt aatgttgaca gtggtgatga gacacctagg actgagaaaa gaatcttttg      1200
gactcaagaa gaagatgtta ggatggtgag tctcactgta aattcactgt gtttatagtt      1260
tttttactta ccataacagt ccaagtgata atatatgcta attaacattt acagatgagc      1320
tcttggctgc tcaattcaac ggactcaacc gttggtgctg ataggaagaa tgaacaatat      1380
tggactgatg ttgaggctac ttacaatgag actacaccaa gtcataggag aagaaatgcc      1440
aagcaaatca aggaccgctt tcataaggta aataagtgga ctgacctttt ccatagtgct      1500
tggttgaagg ctagaatgat ttatacaagt ggctataatg atcaaatgtg gattgagaag      1560
gcccatgtat tctatataaa agacaatgag aaactcaatc taggtccttt tgtgttgatg      1620
gaagtatgga acacagttaa aactgaagca aagtggatca catacaacaa tggcctgaaa      1680
gcagcaagaa aaagaatagc aacaaagggg ttaggcaagg agaaggaagg agaggatagt      1740 agcccttat atgtagatga acttgatgaa cagccaagac caatggggca aaaaagagct       1800
aaaaaactac aatatgccca agtaaggag gtggaccata ttgatcttga ggagctagac        1860
aaatttagta aactccagaa tgaacagaat gcaaataggc tgaaagtatt ggaaatacaa      1920
cagaagctat catccgagaa gatcgaacaa acaaagattt cccatcttgc agcaaaggag      1980
caaatggagg cagcaaaggt gcaaagagag gcaagaaaat tagaggttga agctaggatg      2040
tatgagacat ataaccgcct tcttgtagtt gacacaagtc tgatgtccga tgaagagaag      2100
gttgaccatg gaaatacatt gaagtttttg aagaagaaat tatttactga taattgaggt      2160
gagtttcatg tttacttctc tgtctagcct aacttgtctg aattttgcta tgttctatca      2220
attttcctgc atgttatcaa tgttatatat ctgcatgtta ttttgctatg ttctatcaat      2280
tctgctcata tttactattt gtctatccta aattctgtaa ttgggaccta gtacttttgc      2340
aggtcttgga gaagattgct tgctatgtta ctgtaagggg tgagaaggca atgcagcttc      2400
tggagattgg actgaaggtc aaagaatatg aactagtctc tgttttgcta tgttttggaa      2460
tccaggagca catcaattgc taattggaag tagtctctgt tttgctatgt tctgtttctg      2520
ggattgtttt ttttttggct attgtgaact gtttttttgtg aactgaaacg tgtcaatgga     2580
atgtgaactg atgggtcatt gcaatgtgaa ctgatatgat gtgaaatgga atgtgaaatg      2640
ataaggcaat gccgtgtatg catttgtata taaaatcaac tgctctgtga cttgtatgca      2700
tcacaattgt ggcgatggag gcctctggtg cctctggtgg cgagcatcct ggtggcgacg      2760
atgaggggtc tggtggcgag ttcttcgcct ctggtggaga tggaggcgat gaagatactg      2820
tccttgaaga aatcgatcca gcggaagtat atacacttga agattttctc gccgaagatg      2880
aaataatgga atcatttcga aggaagattg gcgataaatt gaaggccaaa atcgaaggat      2940
cttcttctgg tccacctcgt cgtcgccagc gtcaaagtgg acctagaagg tacataccta      3000
ggccaagaga aaagggacat gaagatttag ttgctaatta ttttttcagca aatcctatct     3060 atactgatga gcagtttcgg aggaggtttc ggatgaataa gcctttgttt cttcgaattg      3120
tcaatgccct gtctaactgg gatcaatttt ttacccaaag agttgatgca acaggtcgag      3180
atagccactc acctctccaa aagtgcaccg ctgctattcg aatgctagga tatggcacac      3240
cagcggacgc actagatgag gtactcaaga ttgcagcgag cacttctttg gaatgtttgg      3300
gaaaatttgc cgtaggaata attgaatgtt ttggtagcga gtacttgcgt cctccgacaa      3360
gtgatgaact agaaaaaatt ttacaagaga atgaagctcg tggctttcca ggcatgatag      3420
```

```
gaagtattga ttgtatgcat tggcaatgga agaattgtcc aaaaggttgg gcaggaatgt      3480
ttatcaatgg tttcaaaggt aaacctacaa tgatccttga agcggtagca tctcgggacc      3540
ttcgtatatg gcatgctttt tttggcaacg ccgggtctca aaatgatatc caagtgttaa      3600
acaagtcacc attgttcatt catgcgatta aggagaagc cccccgagtg agttatactg        3660
taaatggaac gcagtatgac acggggtatt atcttgccga tgaatatat cccgagtggg        3720 ctgccttcgt gaagacaata agaaaacctc aaacggagaa acataaatta tatgcacaac      3780
gacaagaagg ggccagaaag gatgtcgagt gtgcattgg cgtgttgcaa tcccgttttg        3840
atattgtcaa ccgtccagca cggttgtgga aaggaatga tgttgttaat ataatgcaag        3900
cttgcgttat cctccataat atgatagtgg aagatgaaaa ggatttggtt aaaatcccat      3960
tggatttgaa tgaaaatcca agtgcaacca ttgtcctacc accggaagtg caaacaaatg      4020
acaatcctaa tccatgcttt gtcgacgtgc ttaacagaaa ctcggctatc cgggctgcct      4080
ctacacatcg acagctcaag aatgatttag ttgagcacat atggcagcga tatgggccaa      4140
gaggaggtta gagccatgtg tccaatgaaa tggtgacttt attattatct cacatcatgt      4200
atttctaaga tcatttcata tataaatata tataattatt atatacatgt ttagtttaca      4260
agtcatgcgg aatatttaaa tgtactgtgc attgtcttat gtatgcaata aaatgactac      4320
aaagatcaat tatacactag atcatcatga tttgtgtgtc aaaggatgaa ttaaacactc      4380
cacagacagc caaaccaaca acccattgta taagctgtct gtttaagctg tctatttgtg      4440
taaaaagaca gcaagctgtc tacacggttg tacttgccc                             4479
```

<210> SEQ ID NO 80
<211> LENGTH: 347
<212> TYPE: PRT
<213> ORGANISM: Oryza sativa

<400> SEQUENCE: 80

```
Pro Leu Gly Gly Phe Ile Asn Leu Ile Gln Pro Asn Leu Ser Gln Gln
  1               5                  10                  15

Phe Asn Phe Val Gly Asp Gln Asn Gln Ser Glu Asp Asp Tyr Ser Thr
                 20                  25                  30

Pro Ile Ser Ala Arg Asp Asn Thr Tyr Val Asn Val Asp Ser Gly Asp
             35                  40                  45

Glu Thr Pro Arg Thr Glu Lys Arg Ile Phe Trp Thr Gln Glu Glu Asp
         50                  55                  60

Val Arg Met Met Ser Ser Trp Leu Leu Asn Ser Thr Asp Ser Thr Val
 65                  70                  75                  80

Gly Ala Asp Arg Lys Asn Glu Gln Tyr Trp Thr Asp Val Glu Ala Thr
                 85                  90                  95

Tyr Asn Glu Thr Thr Pro Ser His Arg Arg Asn Ala Lys Gln Ile
                100                 105                 110

Lys Asp Arg Phe His Lys Val Asn Lys Trp Thr Asp Leu Phe His Ser
            115                 120                 125

Ala Trp Leu Lys Ala Arg Met Ile Tyr Thr Ser Gly Tyr Asn Asp Gln
        130                 135                 140

Met Trp Ile Glu Lys Ala His Val Phe Tyr Ile Lys Asp Asn Glu Lys
145                 150                 155                 160

Leu Asn Leu Gly Pro Phe Val Leu Met Glu Val Trp Asn Thr Val Lys
                165                 170                 175

Thr Glu Ala Lys Trp Ile Thr Tyr Asn Asn Gly Leu Lys Ala Ala Arg
            180                 185                 190
```

```
Lys Arg Ile Ala Thr Lys Gly Leu Gly Lys Glu Lys Glu Gly Glu Asp
            195                 200                 205
Ser Ser Pro Leu Tyr Val Asp Glu Leu Asp Glu Gln Pro Arg Pro Met
210                 215                 220
Gly Gln Lys Arg Ala Lys Lys Leu Gln Tyr Ala Gln Ser Lys Glu Val
225                 230                 235                 240
Asp His Ile Asp Leu Glu Glu Leu Asp Lys Phe Ser Lys Leu Gln Asn
            245                 250                 255
Glu Gln Asn Ala Asn Arg Leu Lys Val Leu Glu Ile Gln Gln Lys Leu
            260                 265                 270
Ser Ser Glu Lys Ile Glu Gln Thr Lys Ile Ser His Leu Ala Ala Lys
            275                 280                 285
Glu Gln Met Glu Ala Ala Lys Val Gln Arg Glu Ala Arg Lys Leu Glu
            290                 295                 300
Val Glu Ala Arg Met Tyr Glu Thr Tyr Asn Arg Leu Leu Val Val Asp
305                 310                 315                 320
Thr Ser Leu Met Ser Asp Glu Lys Val Asp His Gly Asn Thr Leu
            325                 330                 335
Lys Phe Leu Lys Lys Leu Phe Thr Asp Asn
            340                 345

<210> SEQ ID NO 81
<211> LENGTH: 478
<212> TYPE: PRT
<213> ORGANISM: Oryza sativa

<400> SEQUENCE: 81

Met Glu Ala Ser Gly Ala Ser Gly Gly Glu His Pro Gly Gly Asp Asp
1               5                   10                  15
Glu Gly Ser Gly Gly Glu Phe Phe Ala Ser Gly Gly Asp Gly Gly Asp
            20                  25                  30
Glu Asp Thr Val Leu Glu Glu Ile Asp Pro Ala Glu Val Tyr Thr Leu
            35                  40                  45
Glu Asp Phe Leu Ala Glu Asp Glu Ile Met Glu Ser Phe Arg Arg Lys
        50                  55                  60
Ile Gly Asp Lys Leu Lys Ala Lys Ile Glu Gly Ser Ser Ser Gly Pro
65              70                  75                  80
Pro Arg Arg Arg Gln Arg Gln Ser Gly Pro Arg Arg Tyr Ile Pro Arg
                85                  90                  95
Pro Arg Glu Lys Gly His Glu Asp Leu Val Ala Asn Tyr Phe Ser Ala
            100                 105                 110
Asn Pro Ile Tyr Thr Asp Glu Gln Phe Arg Arg Arg Phe Arg Met Asn
            115                 120                 125
Lys Pro Leu Phe Leu Arg Ile Val Asn Ala Leu Ser Asn Trp Asp Gln
        130                 135                 140
Phe Phe Thr Gln Arg Val Asp Ala Thr Gly Arg Asp Ser His Ser Pro
145                 150                 155                 160
Leu Gln Lys Cys Thr Ala Ala Ile Arg Met Leu Gly Tyr Gly Thr Pro
                165                 170                 175
Ala Asp Ala Leu Asp Glu Val Leu Lys Ile Ala Ala Ser Thr Ser Leu
            180                 185                 190
Glu Cys Leu Gly Lys Phe Ala Val Gly Ile Ile Glu Cys Phe Gly Ser
            195                 200                 205
Glu Tyr Leu Arg Pro Pro Thr Ser Asp Glu Leu Glu Lys Ile Leu Gln
            210                 215                 220
```

```
Glu Asn Glu Ala Arg Gly Phe Pro Gly Met Ile Gly Ser Ile Asp Cys
225                 230                 235                 240

Met His Trp Gln Trp Lys Asn Cys Pro Lys Gly Trp Ala Gly Met Phe
            245                 250                 255

Ile Asn Gly Phe Lys Gly Lys Pro Thr Met Ile Leu Glu Ala Val Ala
        260                 265                 270

Ser Arg Asp Leu Arg Ile Trp His Ala Phe Phe Gly Asn Ala Gly Ser
    275                 280                 285

Gln Asn Asp Ile Gln Val Leu Asn Lys Ser Pro Leu Phe Ile His Ala
290                 295                 300

Ile Lys Gly Glu Ala Pro Arg Val Ser Tyr Thr Val Asn Gly Thr Gln
305                 310                 315                 320

Tyr Asp Thr Gly Tyr Tyr Leu Ala Asp Gly Ile Tyr Pro Glu Trp Ala
                325                 330                 335

Ala Phe Val Lys Thr Ile Arg Lys Pro Gln Thr Glu Lys His Lys Leu
            340                 345                 350

Tyr Ala Gln Arg Gln Glu Gly Ala Arg Lys Asp Val Glu Cys Ala Phe
        355                 360                 365

Gly Val Leu Gln Ser Arg Phe Asp Ile Val Asn Arg Pro Ala Arg Leu
    370                 375                 380

Trp Lys Arg Asn Asp Val Val Asn Ile Met Gln Ala Cys Val Ile Leu
385                 390                 395                 400

His Asn Met Ile Val Glu Asp Glu Lys Asp Leu Val Lys Ile Pro Leu
                405                 410                 415

Asp Leu Asn Glu Asn Pro Ser Ala Thr Ile Val Leu Pro Pro Glu Val
            420                 425                 430

Gln Thr Asn Asp Asn Pro Asn Pro Cys Phe Val Asp Val Leu Asn Arg
        435                 440                 445

Asn Ser Ala Ile Arg Ala Ala Ser Thr His Arg Gln Leu Lys Asn Asp
    450                 455                 460

Leu Val Glu His Ile Trp Gln Arg Tyr Gly Pro Arg Gly Gly
465                 470                 475

<210> SEQ ID NO 82
<211> LENGTH: 5014
<212> TYPE: DNA
<213> ORGANISM: Oryza sativa

<400> SEQUENCE: 82
gggcatgtac aacccgtctc ctcgccccgt ctgtgtgttg gtgattttgc aaaaaaaacc     60
cgtgcacgcg cagagacggg cagcccggcg cctcccgacg cgacgagttc atcccgttct    120
cccaggtgga gtcgacgcga gcccacgcgc tgtagagcgc cgtcatcccc aggcgacggg    180
cgaacggatc ccgcgtgcgg ccgcgctcgc ccacaaattt cccaggcaac acgcgcgct    240 gttctcccgc gctctgctcg cgacttgccc caaatttctt cgcccgccca tctgcgcggc    300
cgccatctgc tcgccccca tctggtattc tcgccggagt tggtgcggcg ggatgtccac    360
gcccggcgca gcttggagaa ggaatggatc gaggacattg gatgcggcgg cgacggcccc    420
aggccgaacc ctaggtgtcg gggcggcggc ggcggctccc tcattcggtc ggggttcttt    480
tggtcacgct gtcgggctac caccgccgcc ccgttctcgc ggacacggtc gcgggtcagt    540
agcggcagcg acgaccgtcc cggctttctc cattgatggt tctgtcggag gtgacttcac    600
cagctcaatt ggtccccatg catcgtctca accttggttt gatgcggccg gcggtgatcc    660
ctcatctcct ggatcatggt aaatccttgt ttcattgctg attttgtagt tgatattagg    720
```

```
cattgtgaat ctagataatt ttgtagttga tattaagcat tgtgaatctg taaatcccat      780
actgttgtac ctggatccct tttataccat attttaacaa tgtccagaag tgattcattg      840
aactctttgt tagatattca actgataaat gattatcata aaaatgagcc catcaagctt      900
ctgtgtccaa catattgtac tctttgttag ttgttcttaa agagtaaaaa tacccatcaa      960
gcttctgtgt caactgatca ttttaagcta atttcatatt ttaagctaat ttcatgttaa     1020
gcttctgtgc cgaaatcatt ttaagctaat tttaccttct aacccttcat aaatacagcc     1080
acaatagtac tactactgca tctgaatttt atttgtagat ggaccatgga aaatttcatg     1140
ttaattgcaa tttcctgcag ggaccaagat gtacgtccac ctggtggttt catgagctat     1200
tttggaaatg aagcacagaa ctctcatttg gttggtgcag ttattcacat gagtcctctg     1260
aatcaggcac acaatggtag ttcaccgccc gaagtggaaa tattacatgg caatgacagt     1320
gttagaaccg agaagaggat catgtggact ccggacgagg atgttagagt gatgagcgct     1380
tggttagaac attcaaccga ctttacctgt ggtgcggata agggtggtgt ccaatattgg     1440
ggtgaggttg tcgaaacgta caacaaaact accctccac ttcgaagaag aaatgcgaag     1500
caatgcaagg atagatggaa caagattaat aaatggacag acctctttga atgtgcttac     1560
gctaaggctc gtagagtatt tacaagtgga tattcggctg aaatgtggct tgatgcagca     1620
cacaagttct atgtggatga caacaaagaa tgcaaagacg tggttggacc ttatatgctg     1680
acagaggttt ggaaaatttg ccgagatgtg ccaaagtgga aacatataa tgaaaacctg     1740 aagaatgcac gtaaaaggaa agcattccat ctggaaggag aatctgagga aaatgaggac     1800
acttgtgatc agatgccaca acgaccaatt ggtcagaagg cagctaaaaa ggcagctcta     1860
gctgctaaaa atggcaagtt aaagggttcc agcagtagtg atgatggtca ctcaaaggat     1920
tctcctattg agctagacaa atttgataga tacagtaaat tttaggaggc aaacaatgag     1980
aagcgtatga agctattgga caggcaagag aagatagctt ctgagaagct agaggccaca     2040
aaaattgccc accttacagc acaagagtac aaagaaggaa agaagcttga taaagagaca     2100
aagatgatgg agacttataa caacctcgtt tcacaggata caagttcaat gtccgatgag     2160
gaaaaggcac agcgagctat gatgatgaag tgtcttatga aggccctttt tcctgaaact     2220
gtttgagaag gtatttctta tctgtgtagt tctgaaattt agcacttgta gttctgaaat     2280
ttagcacttg tagtagccat atatgaacct cagccagttc tggtatgaag atatgaagtt     2340
tctgcttatt tagtattctg tgacaaactt gttaaattct gaattctgt gacaaacttg     2400 ttaaatttag cacttgtagt agccatatat gaacctcagc catatatgtt cagttttctg     2460
ctcattcatg cttttttttt ctgaaattca gttttctgca tattcagtag ccatatatga     2520
acctcagcca tatatgttca gtatcaatgt tcagtatact ggtagttttg ccgtgttttc     2580
ccttactcag tacccagcca tatatgaacc tcagccaaat tcagttttct gcttattcag     2640
tacccatata tgttcagttc tcccttactc agttttgctc tataggccat aatgtaaatt     2700
ctgaaattat ggtatcctgg tagtttcagt ttcaggtatc ctggtaatta aattctgaaa     2760
tccaattaaa tgtgaaactg cgcatgattt tctaaatggt aatgacagtg ctttgtgaac     2820
ttgacactgt gtgtgtgaac tgaaactgat cgcagaggat gatattttta gtgtgaactg     2880
aaactgaaac tgtgtgtgtg aactgaaact gtgcttgtg aacttgaatg tgaactgaaa     2940
ctgcgcatga ttttctgaat tgtgtgtgtg aacttgaatg tgaatggaat ggtcatcttt     3000
ttagtggtgc cggagttgat cagttttctg aaattcaatg ctgaacttga atgtaaatgt     3060
gaatggtcat cttttaagtg gtgctggagt tgatcagttg atcagtttag ccgctgtagt     3120
```

```
gcgacgttga tcttttagt agcttgaatg tgccacttga atgtaaatgt aaatgctgaa      3180
tttgaatgta gcttgaatgc tagtagttga tcagtttagt ggtgccgatc agttttgta       3240 aatatgaatg gtcatatttt tttattctat aaaacatcgt tgttctgtgc gctcctctgt      3300
acactactcc accatccaaa cacttgcatc aaacaaggtg tatcgtaact ctttgaatgg      3360
agccgcacga agaagatgaa gtcgaagatg ccgaagagtt tgaagaggtg ttcaccgtgg      3420
aagacttaat cgtagaggat gatattttg aagaaatagt agcagaggga ttcaaggccg       3480
acatggacag agaagcatcg aagcatcgac tgtacatcgc cgacgtcgac agagtggacc      3540
aaggaggtac ataccaagga atcgagaaca aggtcatgat gatcttgttg ctaattattt     3600
ttccgcaaat ctgctaatta ttttccgca atcctatct acaccgatga catgttccgt       3660
aggagattta ggatgaataa gccattgttc ctgcgtatcg tgcatgcact tagcgattgg    3720
tccccttatt tcacccaaag agtcgatgct attggtagaa atagtcattc accacttcaa    3780
aagtgtacag cggccatcag gatgttagct tatggaacct cggctgatca acttgatgag    3840
gtcttgaaaa tagctgcaag cacttgtttg gagattttgg gaaaattcgc tgaaggtgtg    3900
attgaaacat ttggtgacga atatctacgg cctccaagaa gcgatgaact tgaataaatc    3960
ttacaagaaa atgaggctcg tggttttcct gggtgcatgg gaagcatcga ttacatgcat    4020
tggccatgga agaattgtcc gaaaggttgg gcgggtcagt ttacaagtgg taaacaaggt    4080
gttcctacta tgatccttga agcagtggca tcaaaaaatc ttcgtatatg gcatgctttc   4140
tttggtaccg cggggtctca gaatgacatt aacgttttaa acaagtcacc actgttaatt    4200
caagcaataa aaggggaatc tcctacggta cactatactg taattggaaa tcaatatgac    4260
atgggttact atcttgccga taaaatatat ccagaatggg cagtattcgt gaagacagtt    4320
aatgcccctc aatcagcgga agataaaaca ttttcgttga ggcaagaagg ggtgaggaaa    4380
gatgtcgagt gtgcatttgg tgttctgcaa tcacgctttg atattgttcg tcgaccagca    4440
cgcttatgga agcaaggaga cgttatcaac attatgcaag cttgtgttat ccttcacaat    4500
atgatagttg aagatgagaa ggactcagtt agggatgtct tggatttgaa tgaaaatcca    4560
agtgcgacga tagtgatccc accagaagtg cgtacaaatg atgaccctaa tccaagcttt    4620
gcagaggcac ttcgtagaaa ttcggctatc aaagctcgac caacacatag caacttaag     4680 aaggatctaa tcgagcacat atggcaacgc tacggaaaca agaaaatta gacaaaaagc     4740 attgtaacta tatataatat aattattata tatgtgtttt ctaaaaatta ttgtaatcgc    4800
gtttctatta tttaatcttc atatttattc tatcaattag ccacacaatg gtacatacaa    4860 atacattat agtgatcta agctacatgc aaagcattaa acagcttaca gatggcccct       4920
ctgtttgtgg gttgtatgag ctgtctttat atctatctgt atgagaattt cgagtttctg    4980
cagacgaccc accgtctgtg ggttgtacat gccc                                5014
```

<210> SEQ ID NO 83  
<211> LENGTH: 279  
<212> TYPE: PRT  
<213> ORGANISM: Oryza sativa

<400> SEQUENCE: 83

Met Glu Asn Phe Met Leu Ile Ala Ile Ser Cys Arg Asp Gln Asp Val
 1               5                  10                  15

Arg Pro Pro Gly Gly Phe Met Ser Tyr Phe Gly Asn Glu Ala Gln Asn
            20                  25                  30

Ser His Leu Val Gly Ala Val Ile His Met Ser Pro Leu Asn Gln Ala

```
                35                  40                  45
His Asn Gly Ser Ser Pro Pro Glu Val Glu Ile Leu His Gly Asn Asp
    50                  55                  60

Ser Val Arg Thr Glu Lys Arg Ile Met Trp Thr Pro Asp Glu Asp Val
65                  70                  75                  80

Arg Val Met Ser Ala Trp Leu Glu His Ser Thr Asp Phe Thr Cys Gly
                85                  90                  95

Ala Asp Lys Gly Gly Val Gln Tyr Trp Gly Glu Val Val Glu Thr Tyr
            100                 105                 110

Asn Lys Thr Thr Pro Pro Leu Arg Arg Asn Ala Lys Gln Cys Lys
        115                 120                 125

Asp Arg Trp Asn Lys Ile Asn Lys Trp Thr Asp Leu Phe Glu Cys Ala
    130                 135                 140

Tyr Ala Lys Ala Arg Arg Val Phe Thr Ser Gly Tyr Ser Ala Glu Met
145                 150                 155                 160

Trp Leu Asp Ala Ala His Lys Phe Tyr Val Asp Asp Asn Lys Glu Cys
                165                 170                 175

Lys Asp Val Val Gly Pro Tyr Met Leu Thr Glu Val Trp Lys Ile Cys
            180                 185                 190

Arg Asp Val Pro Lys Trp Lys Thr Tyr Asn Glu Asn Leu Lys Asn Ala
        195                 200                 205

Arg Lys Arg Lys Ala Phe His Leu Glu Gly Glu Ser Glu Glu Asn Glu
    210                 215                 220

Asp Thr Cys Asp Gln Met Pro Gln Arg Pro Ile Gly Gln Lys Ala Ala
225                 230                 235                 240

Lys Lys Ala Ala Leu Ala Ala Lys Asn Gly Lys Leu Lys Gly Ser Ser
                245                 250                 255

Ser Ser Asp Asp Gly His Ser Lys Asp Ser Pro Ile Glu Leu Asp Lys
            260                 265                 270

Phe Asp Arg Tyr Ser Lys Phe
        275

<210> SEQ ID NO 84
<211> LENGTH: 86
<212> TYPE: PRT
<213> ORGANISM: Oryza sativa

<400> SEQUENCE: 84

Glu Ala Asn Asn Glu Lys Arg Met Lys Leu Leu Asp Arg Gln Glu Lys
1               5                   10                  15

Ile Ala Ser Glu Lys Leu Glu Ala Thr Lys Ile Ala His Leu Thr Ala
            20                  25                  30

Gln Glu Tyr Lys Glu Gly Lys Lys Leu Asp Lys Glu Thr Lys Met Met
        35                  40                  45

Glu Thr Tyr Asn Asn Leu Val Ser Gln Asp Thr Ser Ser Met Ser Asp
    50                  55                  60

Glu Glu Lys Ala Gln Arg Ala Met Met Met Lys Cys Leu Met Lys Ala
65                  70                  75                  80

Leu Phe Pro Glu Thr Val
                85

<210> SEQ ID NO 85
<211> LENGTH: 197
<212> TYPE: PRT
<213> ORGANISM: Oryza sativa

<400> SEQUENCE: 85
```

```
Met Glu Pro His Glu Glu Asp Glu Val Glu Asp Ala Glu Phe Glu
  1               5                  10                 15

Glu Val Phe Thr Val Glu Asp Leu Ile Val Glu Asp Ile Phe Glu
               20                  25                 30

Glu Ile Val Ala Glu Gly Phe Lys Ala Asp Met Asp Arg Glu Ala Ser
           35                  40                  45

Lys Pro Val His Arg Arg Arg Gln Ser Gly Pro Arg Arg Tyr Ile
 50                  55                  60

Pro Arg Asn Arg Glu Gln Gly His Asp Asp Leu Val Ala Asn Tyr Phe
 65              70                  75                  80

Ser Glu Ser Ala Asn Tyr Phe Ser Ala Asn Pro Ile Tyr Thr Asp Asp
                 85                  90                  95

Met Phe Arg Arg Arg Phe Arg Met Asn Lys Pro Leu Phe Leu Arg Ile
            100                 105                 110

Val His Ala Leu Ser Asp Trp Ser Pro Tyr Phe Thr Gln Arg Val Asp
            115                 120                 125

Ala Ile Gly Arg Asn Ser His Ser Pro Leu Gln Lys Cys Thr Ala Ala
        130                 135                 140

Ile Arg Met Leu Ala Tyr Gly Thr Ser Ala Asp Gln Leu Asp Glu Val
145                 150                 155                 160

Leu Lys Ile Ala Ala Ser Thr Cys Leu Glu Ile Leu Gly Lys Phe Ala
                165                 170                 175

Glu Gly Val Ile Glu Thr Phe Gly Asp Glu Tyr Leu Arg Pro Pro Arg
                180                 185                 190

Ser Asp Glu Leu Glu
        195

<210> SEQ ID NO 86
<211> LENGTH: 257
<212> TYPE: PRT
<213> ORGANISM: Oryza sativa

<400> SEQUENCE: 86

Ile Leu Gln Glu Asn Glu Ala Arg Gly Phe Pro Gly Cys Met Gly Ser
  1               5                  10                  15

Ile Asp Tyr Met His Trp Pro Trp Lys Asn Cys Pro Lys Gly Trp Ala
             20                  25                  30

Gly Gln Phe Thr Ser Gly Lys Gln Gly Val Pro Thr Met Ile Leu Glu
         35                  40                  45

Ala Val Ala Ser Lys Asn Leu Arg Ile Trp His Ala Phe Phe Gly Thr
 50                  55                  60

Ala Gly Ser Gln Asn Asp Ile Asn Val Leu Asn Lys Ser Pro Leu Leu
 65                  70                  75                  80

Ile Gln Ala Ile Lys Gly Glu Ser Pro Thr Val His Tyr Thr Val Ile
                 85                  90                  95

Gly Asn Gln Tyr Asp Met Gly Tyr Tyr Leu Ala Asp Lys Ile Tyr Pro
            100                 105                 110

Glu Trp Ala Val Phe Val Lys Thr Val Asn Ala Pro Gln Ser Ala Glu
            115                 120                 125

Asp Lys Thr Phe Ser Leu Arg Gln Glu Gly Val Arg Lys Asp Val Glu
        130                 135                 140

Cys Ala Phe Gly Val Leu Gln Ser Arg Phe Asp Ile Val Arg Arg Pro
145                 150                 155                 160

Ala Arg Leu Trp Lys Gln Gly Asp Val Ile Asn Ile Met Gln Ala Cys
                165                 170                 175
```

```
Val Ile Leu His Asn Met Ile Val Glu Asp Glu Lys Asp Ser Val Arg
            180                 185                 190

Asp Val Leu Asp Leu Asn Glu Asn Pro Ser Ala Thr Ile Val Ile Pro
        195                 200                 205

Pro Glu Val Arg Thr Asn Asp Asp Pro Asn Pro Ser Phe Ala Glu Ala
    210                 215                 220

Leu Arg Arg Asn Ser Ala Ile Lys Ala Arg Pro Thr His Arg Gln Leu
225                 230                 235                 240

Lys Lys Asp Leu Ile Glu His Ile Trp Gln Arg Tyr Gly Asn Lys Glu
                245                 250                 255

Asn

<210> SEQ ID NO 87
<211> LENGTH: 8870
<212> TYPE: DNA
<213> ORGANISM: Oryza sativa

<400> SEQUENCE: 87
gagcatctcc agtagagacc tcaaatccaa cctctaatca aatttgaga gttaagataa        60 aaaaaaaact agatccagca ggaaccctac tactagagcc ctaaagtgag gaggccctca      120
aatcctcccc ccaaggcccc agtcctgggg actccgagca cagcccccat cgtccttttt      180
tttggcgcgg aacaattttg cttcgcgcgt tttattgtta ctcccgcgcg gctgcgacga      240
gggatcttct ccagcgacca ccgacgaact cccagcacct ccgccaaaac tgccccaaaa      300
ggtaagactt ttccataact tgttgcctg tcgtccacaa tgccgtcggc ggctgtccat       360
gcgcatgccc ggtcgccgac ctcccgccat ccgccggccg tcgcgtgctc tccgagacca     420
cccgcgcgca cgtcgcccac ctgcacggcg tctgccccca tgctggcctc tgcccgctcg     480
tatttccagt tttcactggc cggagcctgt acgccgccgc tgccccattg attttttctgg    540 aaaaaaaact tgaagtaggt catgtggtgc ggtggttgag tagtacagta gcagtcaatt     600
ttctgaataa ctcgttcttg actacaattg gacatgcatg tggtgctaga tggttctcgt     660
ctggtggaga ctgatttgtt tttaatttttt ttttgagaat tgcagtggac tgtcagccag    720
gagaatctaa ttttatcaac tagtagatat cactgtactt atagtagcac tgcattgtgt     780
agcactgtac aattgttgca atggatcgat tagaaccata tacatatatg taacgctccg     840
cttttcgtga ggcgttaaaa aactaattcg gtaaaatcct aatttcgaaa attttcgttc    900
tttgtgtgcg agtctaagtc gtgccaagat ctcatttcaa atcccgttga tccctctcat    960
cgaaatcaaa atcctccacc tcaaatttct cttccgattc gagtctctga aatcaagttc   1020
tgaaattcaa atccttcctc taaatcctcg ccaaatactt ctacgaatcc agaactattc   1080
agatcccgcc tcgaatcctt tccttgactc caccctatgt tcccgaaaac aaatacccaa   1140
gtattccttt tgaatccttt ccatgacttc tccttgaatc cccttgata catccctaaa    1200 ccctcgagtt cgaatatcaa atttgaattt gagtccaaac cctaaaatct ctccaattct   1260
atccaaatca gttttctctg taaaagtcta ctttacctcc ctgtattttt ggatggaccg    1320
atttccctcc cccggctcat ctcccctccc agcccatcat cttacccccc ctcgcacgtg   1380
cgttgcacgc atgcgagccg agagagagct ctctcgctct ctcgattctt tctctctccc    1440
gtcttcgctc tctctctgct ctatccctc ccggcgccga ttcccgccgt cgccgcccaa    1500
aacccgccac cgccttcgct cttttcccgcg ctcgcccgcg cgtggcagac cgccggtcg    1560 ccgccgcatc agccctggcc gcctgcgccg cacagccgcc catgccgccc tgccgctcgc   1620
```

```
ccccaccctg tgcgcgcgtg cgtccaagac gtggaggcag cgcgtctctc tgcctcacgc   1680
gctctcctct ccctctccca cctccttttt cccaaaccgg catggtaaag cccccccttt   1740
ccaccgtcct cccttctctt tttccctccc aagcaacgac gccatgcctc cactccttgg   1800
ccgctagcgc tcggaggcag agacgcagac gccagcgccg gctcgccacc cccaccttga   1860
ccgcgccagc ccgcgctaat cctcccgctc ccgcggttcg attttccgac gctcgatcca   1920
ccgccttcgc cgcccaacgc atccacaccg tcgccgcctt cgcactgccc acgaaaccgc   1980
cgctgccgcc cgtgaacacc agcagagctc cctgttcccc cacctttttc cttttgcccg   2040
acaccgccgg cgtcatcacc tgtcgccgcc ttggctgcac gcgtcgatga ccgccagctc   2100
gctctccttg accgccaatg tcggttcccc ctcccaaacc gcctcttttc catctataaa   2160
gcccgggccg agcctcccta tcttattctc tctcggcatc tctcttccac cgccatcgtg   2220
cctttgttgc cgccttgcag ctgccgacct cgcctccctt cgctgtcgcg cgtgctggtg   2280
aagccggcgt gtgcgcgagg agccgaagag gactccggcc acccttcttc ttcccccttcc   2340
ccggcccaag gccggagagc tcgccccgcg ccgtcgactg cccatcactg cccgcccggc   2400
tcggtagtgc ctcctcccgt tcccttcct cgctctccct cgtccccgct agcttgcgtg   2460
gtagctcggt agccctgccg aacgcgcgta gacgccgccc caaggaccgc cgccacccgg   2520
cgtggcccca ccgccattgc cgcccacccc cggaggccgc ctctcgtcgc cggacctcca   2580
cggcgccgct cagacccatc cgaccccgga aatgagttcc ttgaacaccg gagatgcttc   2640
cgccgccttt aattgagtcc tcgtcgcccc tcagtgattt ccccttctc tcgccgccgg   2700
ccgccactgt cgaattccac cgccgtcgaa ctccctccgg cgaatccgag ccgttggctc   2760
gctccttctc gacgccctcg tcactccggt gtgctcccg aagaccaaat ccgtcgcgct   2820
tgctccggtg aacacggccg ccgtccgccg tccatctcgg cctcccttc ttcctcctcc   2880
cgccggcccg cgtggctgcc acgtaggcgc cacgtcggcg ccactcggc tttgaccggg   2940
ccaagccggt cagccgtccc ctccctccgt ctttcctccc gtgcgcgcag tccacggaaa   3000
gccgtgcggc tgcatgtggg cccgccgcca tccgtccaac cggtgcaccg ctcctaagcc   3060
atgcgcaccc gaaaccgtg cgccgcacct cgcgtgcgcc catcccaccg tgggccgtgc   3120
caccgacaag cgggccccac ccgggacccc gcgcggtgga atcggtccac cgggccgtct   3180
ctctctcccc cgccgcccct ctgttgggcc gcctcctcgc gcccgcgccc ggcccaatgg   3240
ctcggccgcg ccgtgcttat cccttgggcc atacccgagc ctcccaaaga agtctaaatt   3300
acatccctcc acccttttct ttttcaggga tttaataaat ccttttttt ttccttcctt   3360
tgtcccataa atcaattcct tattcccaaa attccacaaa ccatttcctt tggtcccgcg   3420
tgacagtgac tatcaataat atttttgaga atattatttc tataaattcc ataaaccatt   3480
tctcctattc cagaaactcc aattaaactt ccaaaattca tatcacccaa ttcgcaactc   3540
cgattgactc cgttcaactt ccaatattcc cataaaattg agatctattt aatggcacta   3600
ctaattagtc taaataggat cttttcttttg gtcttttgtt taggttttca gttgtttgcg   3660
tatagttgcg gttatcggat tttcgtcgat cgcgtgtttt ctcgaagatt cgtgaagctt   3720
cgtgaagacc ttgagcaagg caagtcaccc tttgatcaat gcccctata attgaaaagt   3780
cattattatt ttgttttgcaa cttgcattat tagaatcaca cacttaactt gcttggcctc   3840
ggtttgcgtg ccaaaccgac ggacctaccc agtagtcgca ctaatttccg taggttgtac   3900
taccctgttt ccttgtcgct ccaccttgt ggtacctcgg tattcgtgct ctctgagcgc   3960
gtataccaaa tatcccacat acaccgttgt ttgtcgaaaa cttgggaaat gggtttgtga   4020
```

```
agccttcaaa acccgacatg tggtgtcggt gtgtttgaaa ataaaaatga attgtgaaaa    4080
ctcgcgatgc gggggttgtg cctatgtggc actgtcccgt attcgcatat aaggaccgat    4140
tcctgtggga aactcatcga acataatcaa agtgcaacca caaggtggaa tgggacaccc    4200
tggctaagta actagtcggt tcagggaaac ctcgcatgcc aatagttggg aacaccgggg    4260
cggggtcggt tggagccaaa ccgggttcct ggtaatgcaa gaacgagaag cttgctgaat    4320
taccgatcga ggtggttgga gtttgatttg tgaacgccta aaatggccta tgattatgtg    4380
aggatttgat ccttctatgt ggcatgaggt atccctgggt cggcttggga aaggctttgt    4440
cgcgaacctc tgacaccggc cagtgtctgg agtaagttcg tgtcttgtgg gtaaagtgta    4500
cccctctaca gaggttaact aactgttcga acaaccgtgc ccacggtcat gggcggatgt    4560
gaggtggttc ccgttgcgta gatttgtttg cctgtgcttt gtgaaaagtt gttgtggtgt    4620
gggaatcgta accagaatca gcctatgtgg cagatggatg acctgagtgg tcagaaacga    4680
atctgtgtga ttcgggatgt ctgtgggcat catagactag gcttcccgag tggaagcgga    4740
ttgttgtgct gctgggcagc tggactctgg gagtccgaga aaatgaaaaa ggctctggga    4800
gccgattaat caagtggaat ggctctggga gccgagaagt aatgatctga cccgggaggt    4860
cggtacatta ccaattgagt tgttgaaaag catctcttaa agtcgaattg agatgcaagt    4920
ctctcttcgg cccaaactta gaaagaaata aatcacttag tgatttcaaa atgccttcaa    4980
ataaaagatt tgtaaaacaa ccttgcctct cctccaagct tgcatcaaac acctaagttc    5040
ccgtgacttg ctgagtacga aagtactcac ccttgctcta tataaatata tatatatagt    5100
tcctccgccc tgaagagaag ataaagtgaa gagaagatta gggtttcgtc ctggttccca    5160
gccgtcgcct gtggtgttgg gtgttagttc gttggttccg ctgctgctgc tgttgttggt    5220
gtttcctcat ccgtgtcgtc ggttgcattc tcgggttgtt ctgagctgca acctaagtta    5280
aggtaaataa gtcctctatt tattttaagg attgctatga ttcatatttg tcaccgtggg    5340
aactagcact atgtcctggg actggtaccg agatcgcggt ttcgtaggaa acggttcacg    5400
ccgtttttccc tacgcacgc tcctgtcagg tgccgttgta cggcggtatc agattggggt    5460
gtgacaatat atatgcagga gtatgtggta ttgtactagt acgatatcac tgcttttcat    5520
agattgagtg ttgcatagtg tatatgggta tactctgttg gatacgtgtg catatgctct    5580
aaattttctt attaatttta tgatcctgtg atggcagtgt tttttacatg gacttctacg    5640
acgacgacga cgacgacaat ctcattaccg aatggtggga tcaagaggag ttatctgacg    5700
atgatgacta ctacattgta gctgctcttc ttacggacat agagcataag aggaccaaaa    5760
gaaagcgtcg tggttcagtc ccagctcgtg agataattca tagggacagg tttgctggca    5820
atttgcgcat agtggctgat tattttgcag atcctcctgt atataatgca aaattattta    5880
ggaggaggtt cagaatgtca agggagctct tcttgcgcat cgtggctagt gtggaggctc    5940
acgatgacta cttcaggcag agaccgaatg caatgggtct tctcggtgct actgcactac    6000
agaaggtgta tggtgcaatt cgcatgcttg catatgatat tccagccgat agtcttgatg    6060
aagtcgtgag gatttcagag agcaccatga tagaagcttt taagcacttt gtcaaggctg    6120
tggtagatgt gttttctgat cagtaattga gggcaccaac tgctgaggac actgtgaagc    6180
atctaggccc ccggtgttaa ttttggtaat taatgacaag cactaattgt ggactaaccg    6240
ttgtctttga gttatacatt tttaagttag gtccacgtca tatgtgcgca tagatgatta    6300
tcgatggatt aaaattgacg gtgcaaagca aagggaaaga agacggtaaa actagcgctt    6360
taatttagaa ttgatcgagg tgtagggcga tcaaatttgc tagtttaatt ttagtttcgc    6420
```

```
cgtactatta agaggggtaa tgacctagca aagagatgat tttaatttcc acattaggtc    6480 attgcattt  catttgtgct ctcttttca  tttcacacac attcactaat tcactgggtt    6540
cggcctgacc agggacggtc agactggcca catagtggcg gtctgaccgg cgtgccctgg    6600
ccggttagac cagctacata gtggcggtct gaccggcggc actttcccgg tcagaccggc    6660
cccctggagg ccgagatgat gctgctcggg atggccgata cggagccgac ggagccgtag    6720
tcggtcagac cgagctgatg gtggtctgac cgagccgagg ccgtctgac  cggccgcccc    6780 atgccggtct gaccggctag gccgatgggg ccctctgaca gggctacaac ggctagtttt    6840
ctagccgttg cagagtagca cggtctgacc ggccacatac ctccggtcat accggtagag    6900
cacaaagttg ggggatttcg cccccaacgg ctagttttgg tgggtgggag tataaatact    6960
cccccaccag cagcaagggg gctctcttgg cacccaattc aattgcatac actccttgca    7020
cctctctcac actcacttga gctttgtgtt catccatcta gtgtgttaga gggttgttta    7080
gccaagagtc aagtgcattt gcttccattg tagatctagt gtggcacttg atcatctcca    7140
caccgggtca ttgcttgtta ctcttggagg ttgccgcctc ctagacggct tgtggaggag    7200
ttgcccggtg acctctccga gaagattgtg gaggaggccc ggcgccggtt tgtgagtggt    7260
ttggagttca ccaccttcgg agtgaaggaa gaactatccc gagtgatcga ggcttgggta    7320
gtcctctccg tgggccggct cccgccttgc ccaccccttg acgaaggggg cgtgcggtgg    7380
cttcgtggtt gagcggtgga gttgggcttg cctcaacggg gagtaggaaa ccggcgagtt    7440
ctcgaacctc ggtgaaaaat ctcttgtctc attgtctcat ttgattgtcg catttacatt    7500
tgtgcaattt acatttctag agacacactt gagatcatat caccctagga ttgcaaaaca    7560
ttgacatagg agcgtgattt actttcctag atatataatt gagccactat caccctaggt    7620
ttgcaaaaca taatttagtt gcttagttag agttcaccct caccaagcct agcaacttag    7680
gttagatttg attaggtgtt atttagtttt aaatcgccta ttcatccccc ctctagtcga    7740
catctcgatc ctacacactg caaggttgtt ggctataaac actccaaggg ggttcccagg    7800
gatgctaggt tctattgact gtatgcattg gaggtggaag aattgcccaa caggctggaa    7860
aggacaatac tcagggcatg tggatgggcc aaccatgatt cttgaagctg ttgcatctaa    7920
agatttgtgg attggcatt  ccttctttgg actaccaggt tttcttaatg atatcaatgt    7980
actacagaga tcaccactct ttcaaaggct tacatcaggg acagtccag  agttggagtt    8040 tatggtgaat ggaaagaaat acaccattgg ttactatctt gctgatggca tatacccttc    8100
tcgggccact tttgtgaaga ccatttccaa tccacaaggt aataagagaa tacattatgc    8160
aaaagttcaa gaaggagtga aaaggatgt  tgaaagaaca tttggtgttc tacaagcccg    8220
ctttgcaatg gtcagaggcc ctgctagatt tgggataca  gagaccctat ggtacataat    8280
gacagcttgt gtaattatgc acaacatgat cattgaaaat gagcgagatg aagatgtaga    8340
ctttgactaa gatcaggagg acagtgaggt gttgaggaag gaggaatagc aacgacgtaa    8400
taaacatgtg ttagagaagt ttctaaagat acataagaa  attgaagacc ggcaggtaca    8460
tgagcaactt cgagatgatc ttgtggaaca tttgtgggcg cttcatggtg ctcggtagtt    8520 caattttgc  attttctatc atgtattggg ttatgttcaa tatttgcttg taggacatat    8580
cattttcatg tttgaatttt tgaactcaa  atttgaattg tggtgtttga aattgcaaat    8640
ttgaatatgg ttgaattcca cgcgctagaa ttatttatgt ttcaattatt gtgtgttaaa    8700
ctggatataa atataaattc tatactaaaa taaagaaaaa aagaaatag  gggctaagat    8760 atggaggcta ctgctagaca taagacata  tttaggatcc taaagcattg ggggcagctc    8820
```

```
ccatttaatc tttggggact ctaaagtagg ggctactact ggagatgctg          8870
```

<210> SEQ ID NO 88
<211> LENGTH: 172
<212> TYPE: PRT
<213> ORGANISM: Oryza sativa

<400> SEQUENCE: 88

Met Asp Phe Tyr Asp Asp Asp Asp Asn Leu Ile Thr Glu Trp
1               5                   10                  15

Trp Asp Gln Glu Glu Leu Ser Asp Asp Asp Tyr Tyr Ile Val Ala
                20                  25                  30

Ala Leu Leu Thr Asp Ile Glu His Lys Arg Thr Lys Arg Lys Arg Arg
            35                  40                  45

Gly Ser Val Pro Ala Arg Glu Ile Ile His Arg Asp Arg Phe Ala Gly
        50                  55                  60

Asn Leu Arg Ile Val Ala Asp Tyr Phe Ala Asp Pro Pro Val Tyr Asn
65                  70                  75                  80

Ala Lys Leu Phe Arg Arg Arg Phe Arg Met Ser Arg Glu Leu Phe Leu
                85                  90                  95

Arg Ile Val Ala Ser Val Glu Ala His Asp Asp Tyr Phe Arg Gln Arg
            100                 105                 110

Pro Asn Ala Met Gly Leu Leu Gly Ala Thr Ala Leu Gln Lys Val Tyr
        115                 120                 125

Gly Ala Ile Arg Met Leu Ala Tyr Asp Ile Pro Ala Asp Ser Leu Asp
130                 135                 140

Glu Val Val Arg Ile Ser Glu Ser Thr Met Ile Glu Ala Phe Lys His
145                 150                 155                 160

Phe Val Lys Ala Val Val Asp Val Phe Ser Asp Gln
                165                 170

<210> SEQ ID NO 89
<211> LENGTH: 206
<212> TYPE: PRT
<213> ORGANISM: Oryza sativa

<400> SEQUENCE: 89

Leu Arg Ala Pro Thr Ala Glu Asp Thr Ala Ala Arg Leu Leu Ala Ile
1               5                   10                  15

Asn Thr Pro Arg Gly Phe Pro Gly Met Leu Gly Ser Ile Asp Cys Met
                20                  25                  30

His Trp Arg Trp Lys Asn Cys Pro Thr Gly Trp Lys Gly Gln Tyr Ser
            35                  40                  45

Gly His Val Asp Gly Pro Thr Met Ile Leu Glu Ala Val Ala Ser Lys
        50                  55                  60

Asp Leu Trp Ile Trp His Ser Phe Phe Gly Leu Pro Gly Phe Leu Asn
65                  70                  75                  80

Asp Ile Asn Val Leu Gln Arg Ser Pro Leu Phe Gln Arg Leu Thr Ser
                85                  90                  95

Gly Thr Ala Pro Glu Leu Glu Phe Met Val Asn Gly Lys Lys Tyr Thr
            100                 105                 110

Ile Gly Tyr Tyr Leu Ala Asp Gly Ile Tyr Pro Ser Arg Ala Thr Phe
        115                 120                 125

Val Lys Thr Ile Ser Asn Pro Gln Gly Asn Lys Arg Ile His Tyr Ala
130                 135                 140

Lys Val Gln Glu Gly Val Arg Lys Asp Val Glu Arg Thr Phe Gly Val
145                 150                 155                 160

```
Leu Gln Ala Arg Phe Ala Met Val Arg Gly Pro Ala Arg Phe Trp Asp
            165                 170                 175

Thr Glu Thr Leu Trp Tyr Ile Met Thr Ala Cys Val Ile Met His Asn
        180                 185                 190

Met Ile Ile Glu Asn Glu Arg Asp Glu Asp Val Asp Phe Asp
        195                 200                 205

<210> SEQ ID NO 90
<211> LENGTH: 5314
<212> TYPE: DNA
<213> ORGANISM: Oryza sativa

<400> SEQUENCE: 90
gagcatctcc aatagatgac taaaattaaa ctcccaaaaa tcctgtattg gggacagcca      60
aaaacatatt tagcctaaaa tacaccctct tctccaatag atgactaaaa tttggttccc     120
aaaaatttaa aattttttcca catcatcatt agtgggccct tcccaactaa ttttctacct    180
gctcgttaaa atcacaggcg agagcggagg gggagatcgc gtcgcgcgtg agaggcgagg    240
aggagatcgc ggcgtgcgga tgcggagggg aatgggcatg gtcgacgcga cgcacgcgga    300
cggaaggaga tggctgctca tcctagtcgc gcgcgagatc gcaactgata ccgttggcga    360
ggttatatat cagacgcagc gatatacgaa attgatcgaa ggacacagtg ctatagacgc    420
acatagagct cttcctctgt cagcgccggc ggcgttagca cttcactcaa tcagagctct    480
tcctctgtca gggccggcga cgttagcacc tcacttaatc aggcaactgc agcaagcagc    540
aacgattggt gacaggcaca agctcttgtg cagtgcgtga gtagcaaaat tttgctagca    600
accatgtttt ttactttgtt ctatttcctt ttttatgtt tctgatctga caatgtcttg      660
atggaaaaaa aaacttaatt tgatatgatg aataaatatt tggaaaaacg gaaggccaat    720 cacattttt ttaatttgat ctgacaacgt cgcaagggga aaacttaatt tattgtgatg     780
aataatggtt tggcagttga tttgatccaa gatgagtcga cctcgctcct cgtttcaaca    840
gctcgtggat gaatcatcgt ctgacgatga cgatgatttt ttttttgcc acggcacaaa     900 tcgtccatag ctattggcac tctgtcaatg caccaagaca tggtgggtca gtcatgggac    960
atgaagtgat tgatcgcaac agagaagcac ggcacttgag attataccaa gactactttt   1020
ccaataatcc tacctatggc ccagtttat tcaggcgcag gttgtataa gtaaatttta      1080 tataatttat ttttgttata tgcatagata tgcatgtctc attagttatg attcgcagga    1140
atagaatgag caggcctctg tttctccgca taatgaatgc aatagaggat cacgatgact    1200
attttgtgca gaagagaaat gcagctggtt taattgggtt cagttgtcac caaaaggtca    1260
ctgcagcaat gcgtcagttg gcttatggta tagcagcaga tgctttggat gaatatctcg    1320
gtattgcaga aagtaccgct atagagagcc tgagaaggtt tgtgaaagca gttgtacaag    1380
tttttgaaca tgaatactta agatcaccca atgagaacga tacaactcga ttacttgaac    1440
ttggggagga cagaggtttc cccggtatgt taggctccat agattgcatg cattggaagt    1500
ggaagaactg ccctacagaa ttgcacggta tgtaccaagg gcacgtgcac gagcctacaa    1560 taatttaga agccgttgct tcaaaggatc tctggatttg gcacgctttt tttggtatgc     1620
ctgggtctca taacgatatc aatgtacttc atcgatcccc gctatttgca aagctagctg    1680
aaggcaaggc tcctgaagtg aactatagta taaatggaca cgattatatg atgggatatt    1740
atcttgctga tggcatatat ccttcttggg ccacatttgt gaagaccata ccagaaccac    1800
atggcaacaa gaggaaatat tttgccaaag cacaggaagc agtaaggaag gatgtcgaac    1860
```

```
gagcttttgg ggttctgcaa gctcgatttg ccattgttcg agggccagct cgacattggg   1920
atgaaaagac tctgggatac atcatgaaag cttgtgttat catgcataac atgattattg   1980
aagatgaggg agaagttgat tgggaagaac ggttcccaga gggaggagaa atgtcagag    2040
tgtcccacga tgaaatacct gatcttgatg attttatcca gatgcacaaa aaataaggg    2100
acgacgaaac tcactatcag ctacgtgaag acctagtgga gcacttgtgg caacattatc   2160
ctgataaata ttgaggtttt atttatatgt ttgaattcca tgtaataaat agtatacata   2220
tgtgaggatt tgcaaaatca ttttaatttg ttcttcatgt attgaataaa tggtgtactg   2280
ttcggtttaa gaatagtaca ggagaattaa taaaagtgca cttcctttat gcattttgtt   2340
gaatatgtcg gctggcagtg ataaatatgt catgtggtct tcctgtcaat catgaaaagc   2400
cacagatgag gtagaggccc cagaagcttt tcaatcatgc caggaaacaa tcaaacatca   2460
ggctctcagt gagagacaat acagattacc acaggtcaat agcaacatca ggctctcata   2520
aagtctgatt cattacacag actaacacca agggcatgat aagggaagta cccatctact   2580
aacaccaact tcggacaaaa caaaaagaca caattctgaa tataaatagt ttgcattgca   2640
gacttagtaa acctagataa atttctaaca aaccactgat ctaaactgca gctacgattg   2700
ccatctcttt ccctcccatt ctctgatctg gtcacaattt gttcagttgc ttcttcacat   2760
gtacgaaggt ctcagcgagg tggcttccct gttgatagca ataagatgga gttcgaatta   2820
accataatac atgtacagag tatagagctg ccaagttttc tagtctattt taattagtaa   2880
tgtacaatat ttgaagctac ctatatgttt gtactgtaaa caataattga agctagctag   2940
tactgcaagt gattttttttg actgatcact gtcgaaaata tggattcagt aacctatcat   3000
tcaaactgaa attgaatatg cactcacatg gatcagttga tcatgcagca aggtatttga   3060
tcttcggctc ttcggtctct gtaggttcat tatcttcatc aacatgattg gtagtatcat   3120
catttgtggg tatagctttt cccaaaccat ctgtgcttgc cttctgtttt ttggtggcac   3180
agggttttttg ggatgttatt tgcttcatct tatcatgcca cttggattgt gacctcaaga   3240
gagtccaaca gtgcaggaat tggaagggct tatcttccaa ctccttaaat acagcaatgg   3300
cctgagcaat ctgcacatgt caagtcaagt gaatgtggtt agcaaacatc atatctttta   3360
tttataaact aacataaaaa cacaagctac ataactatgt agtaccttgt cgtgtatact   3420
aaccccgctt tgtcttctac cctcaatctg gctcagatat ccacaaaact tgttgacatt   3480
ctcttgtata gttttccaac gatgcataag tgaattctgg ctgcgatctg gtgtggattt   3540
acttgttttg tataagtgct cgtatattct agtccaatat gcagcacgag tttgatttgt   3600
gcctagcact ggatccaaac ttacatgcaa ccacgccgac acaagtatct tatcttcttg   3660
ttcactaaaa ttcttcgatc tttttttgatt tggtctagcc acggtagtcc tctcaatagt   3720
ggggaactgt tgcgtgacag gctcgctact catgccattc tcatcaagct ggttactcat   3780
atcatcctcc acaggcatcg tactcaaact atcccaatct aaggaatcgt tccectcatt   3840
catcaaatta gtatagaatc cttcttcttc cattatcagt aggacctaca agcaattatc   3900
tccatcatgt atgttaaatg gaagatgatt attttgttta catgtctatc taagcaatgc   3960
aatgttgtct gtctgcctaa aaaaacaaga tgatagatgc tattcagatt tttcgtttga   4020
tataatattt tagatttgta gacagcagcc tttcaggtgg tgtgctgact taagtgcaca   4080
tgcaccatgg cagatagcat gccacacctg aagatctaaa atatactaac attgttcaaa   4140
aaaatttcga ccttaatttt gaccttaatc atgatagaag taaagtgggg cacaagcata   4200
tgacacacaa cagatggaac tggtcaatgg aaacatacct cagattaggc ctcagtgcag   4260
```

-continued

```
tgtgatactg actttatga atacaacatt caaagcaaag cagttcagtg aaaaaaaaac    4320
ttaactatag cagtttaggg aaaaaaaaaa cttatactag ttcagggaa aaaacctcaa     4380 ctataccagt aaagaaataa aatcttcagt agaatatgaa actagcatgt cccatttgtc    4440
ttcttgaata aaatagtttt agtacaatta agtggacttc aatagaactt tagggtgaga    4500
agaatatggt ctgttagcaa cttgtgaaga ctattttgga catattcatc taagacttgt    4560
atcaacgaaa acaaagaaat acacataagg accttgtcag tactaggata tcaatgggga    4620
taatatcagt gagtcaacct caattgaaca caaagagagt tagatccatg gagagaagca    4680
gaaaataaat gagttgttac tctgaaatta cctcaaacaa atccagtagc aactcacgtc    4740
gttgagaggc gaggtggacg aaggggcaca gactgccgac ggtccctgga ttgacagtcg    4800
atggtgactt ggacggaggc cgctagcgct ctggacggag gggcggcagc gacctagatg    4860
ggctgccggc gacgccctgg acggaggggc ggcagcgacc tagatgggct gccggcggcg    4920
ccctggacgg agggccggcg acgccttgga gaacctgcgg cgtcccggac ggacggacgg    4980
ctggcggcgc cctgaacgga gttggcgcga ggagaggaag ctggcgcgag gagggggaaga    5040 aaggcgcggc tcctcccggc gaacgaagag acggtggttg agggaaagcg cgggcgagga    5100
aaaaaattgg cgccaggaaa agaaaaaacg cgcgggcag gaacgattgc ttcgattggg     5160
agcgcttcta gttgcccaat atttggttca ggttggtcct ggttttggag gtggctaaat    5220
tttgggacca tgtttaggag tctgttggag ggctgatttt caccaaattc ctaaaattta    5280
tgttttagta acctgtttag cattctcttg gaga                               5314
```

<210> SEQ ID NO 91
<211> LENGTH: 239
<212> TYPE: PRT
<213> ORGANISM: Oryza sativa

<400> SEQUENCE: 91

```
Met Glu Glu Gly Phe Tyr Thr Asn Leu Met Asn Glu Gly Asn Asp
 1               5                  10                  15

Ser Leu Asp Trp Asp Ser Leu Ser Thr Met Pro Val Glu Asp Asp Met
                 20                  25                  30

Ser Asn Gln Leu Asp Glu Asn Gly Met Ser Ser Glu Pro Val Thr Gln
             35                  40                  45

Gln Phe Pro Thr Ile Glu Arg Thr Thr Val Ala Arg Pro Asn Gln Lys
         50                  55                  60

Arg Ser Lys Asn Phe Ser Glu Gln Glu Asp Lys Ile Leu Val Ser Ala
     65                  70                  75                  80

Trp Leu His Val Ser Leu Asp Pro Val Leu Gly Thr Asn Gln Thr Arg
                 85                  90                  95

Ala Ala Tyr Trp Thr Arg Ile Tyr Glu His Leu Tyr Lys Thr Ser Lys
            100                 105                 110

Ser Thr Pro Asp Arg Ser Gln Asn Ser Leu Met His Arg Trp Lys Thr
        115                 120                 125

Ile Gln Glu Asn Val Asn Lys Phe Cys Gly Tyr Leu Ser Gln Ile Glu
    130                 135                 140

Gly Arg Arg Gln Ser Gly Ile Ala Gln Ala Ile Ala Val Phe Lys Glu
145                 150                 155                 160

Leu Glu Asp Lys Pro Phe Gln Phe Leu His Cys Trp Thr Leu Leu Arg
                165                 170                 175

Ser Gln Ser Lys Trp His Asp Lys Met Lys Gln Ile Thr Ser Gln Lys
            180                 185                 190
```

-continued

Pro Cys Ala Thr Lys Lys Gln Lys Ala Ser Thr Asp Gly Leu Gly Lys
        195                 200                 205

Ala Ile Pro Thr Asn Asp Asp Thr Thr Asn His Val Asp Glu Asp Asn
    210                 215                 220

Glu Pro Thr Glu Thr Glu Glu Pro Lys Ile Lys Tyr Leu Ala Ala
225                 230                 235

<210> SEQ ID NO 92
<211> LENGTH: 415
<212> TYPE: PRT
<213> ORGANISM: Oryza sativa

<400> SEQUENCE: 92

Met Asn His Arg Leu Thr Met Thr Met Ile Phe Phe Ala Thr Ala
 1               5                  10                  15

Gln Ile Val His Ser Tyr Trp His Ser Val Asn Ala Pro Arg His Gly
            20                  25                  30

Gly Ser Val Met Gly His Glu Val Ile Asp Arg Asn Arg Glu Ala Arg
        35                  40                  45

His Leu Arg Leu Tyr Gln Asp Tyr Phe Ser Asn Asn Pro Thr Tyr Gly
    50                  55                  60

Pro Val Leu Phe Arg Arg Arg Asn Arg Met Ser Arg Pro Leu Phe Leu
65                  70                  75                  80

Arg Ile Met Asn Ala Ile Glu Asp His Asp Asp Tyr Phe Val Gln Lys
                85                  90                  95

Arg Asn Ala Ala Gly Leu Ile Gly Phe Ser Cys His Gln Lys Val Thr
            100                 105                 110

Ala Ala Met Arg Gln Leu Ala Tyr Gly Ile Ala Ala Asp Ala Leu Asp
        115                 120                 125

Glu Tyr Leu Gly Ile Ala Glu Ser Thr Ala Ile Glu Ser Leu Arg Arg
    130                 135                 140

Phe Val Lys Ala Val Val Gln Val Phe Glu His Glu Tyr Leu Arg Ser
145                 150                 155                 160

Pro Asn Glu Asn Asp Thr Thr Arg Leu Leu Glu Leu Gly Glu Asp Arg
                165                 170                 175

Gly Phe Pro Gly Met Leu Gly Ser Ile Asp Cys Met His Trp Lys Trp
            180                 185                 190

Lys Asn Cys Pro Thr Glu Leu His Gly Met Tyr Gln Gly His Val His
        195                 200                 205

Glu Pro Thr Ile Ile Leu Glu Ala Val Ala Ser Lys Asp Leu Trp Ile
    210                 215                 220

Trp His Ala Phe Phe Gly Met Pro Gly Ser His Asn Asp Ile Asn Val
225                 230                 235                 240

Leu His Arg Ser Pro Leu Phe Ala Lys Leu Ala Glu Gly Lys Ala Pro
                245                 250                 255

Glu Val Asn Tyr Ser Ile Asn Gly His Asp Tyr Met Met Gly Tyr Tyr
            260                 265                 270

Leu Ala Asp Gly Ile Tyr Pro Ser Trp Ala Thr Phe Val Lys Thr Ile
        275                 280                 285

Pro Glu Pro His Gly Asn Lys Arg Lys Tyr Phe Ala Lys Ala Gln Glu
    290                 295                 300

Ala Val Arg Lys Asp Val Glu Arg Ala Phe Gly Val Leu Gln Ala Arg
305                 310                 315                 320

Phe Ala Ile Val Arg Gly Pro Ala Arg His Trp Asp Glu Lys Thr Leu
                325                 330                 335

```
Gly Tyr Ile Met Lys Ala Cys Val Ile Met His Asn Met Ile Ile Glu
                340                 345                 350

Asp Glu Gly Glu Val Asp Trp Glu Arg Phe Pro Glu Gly Gly Glu
            355                 360                 365

Asn Val Arg Val Ser His Asp Glu Ile Pro Asp Leu Asp Asp Phe Ile
370                 375                 380

Gln Met His Lys Lys Ile Arg Asp Asp Glu Thr His Tyr Gln Leu Arg
385                 390                 395                 400

Glu Asp Leu Val Glu His Leu Trp Gln His Tyr Pro Asp Lys Tyr
                405                 410                 415

<210> SEQ ID NO 93
<211> LENGTH: 363
<212> TYPE: DNA
<213> ORGANISM: Brassica oleracea

<400> SEQUENCE: 93
ggaagcatcg attgtatgca ttgggagtgg aagaattgtc ccaccgcttg gaaaggacaa      60
tattcacgcg gttcggctaa acccacaatc gtattagagg cggttgcttc gtacgatcta     120
tggatatgac atgcgttttt tggacctcca ggtaccttaa atgatatcaa tgttcttgat     180
cgctcaccag tttttgatga cataataaac agtcaagctc cgcaagttac tttctctgtc     240
aatggaaacg agtattgttg ggcttactat ctcaccgata gtatttatcc gaaatgggca     300
acttttgtcc aatctatttc actaccacaa ggtccgaaag cgactttatt tgctcaacat     360
caa                                                                  363

<210> SEQ ID NO 94
<211> LENGTH: 42
<212> TYPE: PRT
<213> ORGANISM: Brassica oleracea

<400> SEQUENCE: 94

Gly Ser Ile Asp Cys Met His Trp Glu Trp Lys Asn Cys Pro Thr Ala
1               5                   10                  15

Trp Lys Gly Gln Tyr Ser Arg Gly Ser Ala Lys Pro Thr Ile Val Leu
                20                  25                  30

Glu Ala Val Ala Ser Tyr Asp Leu Trp Ile
            35                  40

<210> SEQ ID NO 95
<211> LENGTH: 78
<212> TYPE: PRT
<213> ORGANISM: Brassica oleracea

<400> SEQUENCE: 95

His Ala Phe Phe Gly Pro Pro Gly Thr Leu Asn Asp Ile Asn Val Leu
1               5                   10                  15

Asp Arg Ser Pro Val Phe Asp Asp Ile Ile Asn Ser Gln Ala Pro Gln
                20                  25                  30

Val Thr Phe Ser Val Asn Gly Asn Glu Tyr Cys Trp Ala Tyr Tyr Leu
            35                  40                  45

Thr Asp Ser Ile Tyr Pro Lys Trp Ala Thr Phe Val Gln Ser Ile Ser
        50                  55                  60

Leu Pro Gln Gly Pro Lys Ala Thr Leu Phe Ala Gln His Gln
65                  70                  75

<210> SEQ ID NO 96
<211> LENGTH: 363
```

```
<212> TYPE: DNA
<213> ORGANISM: Brassica oleracea

<400> SEQUENCE: 96
ggaagcatcg attgtatgca ctgggagtgg aagaattgtc ccaccgcttg gaaagggcaa      60
tattctcgtg gttcgggtaa accaacaatc gttttagagg ctgtcgcttc atatgatctc     120
tggatatgac atgcattttt tggacctcca ggtacattaa atgatatcaa tgttcttgac     180
cgttctcccg tttttgatga cataataaac ggtaaagccc cgaatgtcac ttactatgtc     240
aatggaagag agttccatat ggcttactat ctcaccgatg gtatatatcc gaatgggca      300 acttttatcc aatctatttc tatgccacaa gggccgaagg cagttttatt tgctcaacgg     360
caa                                                                   363

<210> SEQ ID NO 97
<211> LENGTH: 42
<212> TYPE: PRT
<213> ORGANISM: Brassica oleracea

<400> SEQUENCE: 97

Gly Ser Ile Asp Cys Met His Trp Glu Trp Lys Asn Cys Pro Thr Ala
 1               5                  10                  15

Trp Lys Gly Gln Tyr Ser Arg Gly Ser Gly Lys Pro Thr Ile Val Leu
             20                  25                  30

Glu Ala Val Ala Ser Tyr Asp Leu Trp Ile
         35                  40

<210> SEQ ID NO 98
<211> LENGTH: 78
<212> TYPE: PRT
<213> ORGANISM: Brassica oleracea

<400> SEQUENCE: 98

His Ala Phe Phe Gly Pro Pro Gly Thr Leu Asn Asp Ile Asn Val Leu
 1               5                  10                  15

Asp Arg Ser Pro Val Phe Asp Asp Ile Ile Asn Gly Lys Ala Pro Asn
             20                  25                  30

Val Thr Tyr Tyr Val Asn Gly Arg Glu Phe His Met Ala Tyr Tyr Leu
         35                  40                  45

Thr Asp Gly Ile Tyr Pro Lys Trp Ala Thr Phe Ile Gln Ser Ile Ser
     50                  55                  60

Met Pro Gln Gly Pro Lys Ala Val Leu Phe Ala Gln Arg Gln
 65                  70                  75

<210> SEQ ID NO 99
<211> LENGTH: 363
<212> TYPE: DNA
<213> ORGANISM: Brassica oleracea

<400> SEQUENCE: 99
ggaagcatcg actgtatgca ttgggagtgg aagaattgtc ccaccgcttg gaaaggaatg      60
tattcacggg gaaccagaaa accaacaatt gtgttggagg ctgttgcttc aaaagacctc     120
tggatttggc acgctttttt tggagctcca ggtactatga cgatcttaa tattcttgat      180 cgatcacctg tttttgatga cattattaac ggggtcgccc acaagttaa ctattatgtc      240 aacggaacgg agtaccatct cgcatattac ctaacagatg gtatatatcc gaatgagcg     300 acttttattc agtcaatccg actaccacaa accgaaaagc agtcattgtt tgctacatac    360
caa                                                                   363
```

<210> SEQ ID NO 100
<211> LENGTH: 98
<212> TYPE: PRT
<213> ORGANISM: Brassica oleracea

<400> SEQUENCE: 100

Gly Ser Ile Asp Cys Met His Trp Glu Trp Lys Asn Cys Pro Thr Ala
1               5                   10                  15

Trp Lys Gly Met Tyr Ser Arg Gly Thr Arg Lys Pro Thr Ile Val Leu
            20                  25                  30

Glu Ala Val Ala Ser Lys Asp Leu Trp Ile Trp His Ala Phe Phe Gly
        35                  40                  45

Ala Pro Gly Thr Met Asn Asp Leu Asn Ile Leu Asp Arg Ser Pro Val
    50                  55                  60

Phe Asp Asp Ile Ile Asn Gly Val Ala Pro Gln Val Asn Tyr Tyr Val
65                  70                  75                  80

Asn Gly Thr Glu Tyr His Leu Ala Tyr Tyr Leu Thr Asp Gly Ile Tyr
                85                  90                  95

Pro Lys

<210> SEQ ID NO 101
<211> LENGTH: 22
<212> TYPE: PRT
<213> ORGANISM: Brassica oleracea

<400> SEQUENCE: 101

Ala Thr Phe Ile Gln Ser Ile Arg Leu Pro Gln Thr Glu Lys Gln Ser
1               5                   10                  15

Leu Phe Ala Thr Tyr Gln
            20

<210> SEQ ID NO 102
<211> LENGTH: 363
<212> TYPE: DNA
<213> ORGANISM: Brassica oleracea

<400> SEQUENCE: 102
ggaagcatcg actgtatgca ttgggagtgg aagaattgcc ccacggcttg gaaaggaatg      60
tactcacgag gaaccggaaa accgacaatt gtgttggagg cggtagcttc gtatgacctc     120
tggatatggc acgcattttt tggagcacca ggtactatga cgatctaaa tattcttgat     180 cgatcacctg tttttgacga cattattaat ggcatcgcgc acaagtaaa cttctatgtt      240 aatgataatc ggtaccattt cggatattat ctcactgatg gtatttatcc gaaatggacg     300 actttattc aatctatccg actaccacaa aatcagaagc atttattatt tgctcaaacc      360
caa                                                                   363

<210> SEQ ID NO 103
<211> LENGTH: 121
<212> TYPE: PRT
<213> ORGANISM: Brassica oleracea

<400> SEQUENCE: 103

Gly Ser Ile Asp Cys Met His Trp Glu Trp Lys Asn Cys Pro Thr Ala
1               5                   10                  15

Trp Lys Gly Met Tyr Ser Arg Gly Thr Gly Lys Pro Thr Ile Val Leu
            20                  25                  30

Glu Ala Val Ala Ser Tyr Asp Leu Trp Ile Trp His Ala Phe Phe Gly

```
                35                  40                  45
Ala Pro Gly Thr Met Asn Asp Leu Asn Ile Leu Asp Arg Ser Pro Val
            50                  55                  60

Phe Asp Asp Ile Ile Asn Gly Ile Ala Pro Gln Val Asn Phe Tyr Val
65                  70                  75                  80

Asn Asp Asn Arg Tyr His Phe Gly Tyr Tyr Leu Thr Asp Gly Ile Tyr
                85                  90                  95

Pro Lys Trp Thr Thr Phe Ile Gln Ser Ile Arg Leu Pro Gln Asn Gln
            100                 105                 110

Lys His Leu Leu Phe Ala Gln Thr Gln
        115                 120

<210> SEQ ID NO 104
<211> LENGTH: 363
<212> TYPE: DNA
<213> ORGANISM: Brassica oleracea

<400> SEQUENCE: 104
ggaagcatcg attgtatgca ttgggagtgg aagaattgtc ccaccgcttg gaaaggtcaa    60
tattcttgtg gttcgggaaa acccacaatc gttttagagg cggttgcatc gtatgatcta   120
tggatatgac atgcatttt tggacctcca ggtaccttaa atgatatcaa tgttcttgat   180
cgctcacctg tttttgatga cataataaaa ggtgaagctc cgcaagtcac cttccatgtc   240
aatggaagag agtatcatat ggcttactat ctcaccgacg gtatttaccc gaaatgggca   300
acttttatcc aatcaatttc aatgccacaa gggccgaaag cggttttatt tgctcaacaa   360
caa                                                                 363

<210> SEQ ID NO 105
<211> LENGTH: 42
<212> TYPE: PRT
<213> ORGANISM: Brassica oleracea

<400> SEQUENCE: 105

Gly Ser Ile Asp Cys Met His Trp Glu Trp Lys Asn Cys Pro Thr Ala
1               5                   10                  15

Trp Lys Gly Gln Tyr Ser Cys Gly Ser Gly Lys Pro Thr Ile Val Leu
            20                  25                  30

Glu Ala Val Ala Ser Tyr Asp Leu Trp Ile
        35                  40

<210> SEQ ID NO 106
<211> LENGTH: 78
<212> TYPE: PRT
<213> ORGANISM: Brassica oleracea

<400> SEQUENCE: 106

His Ala Phe Phe Gly Pro Pro Gly Thr Leu Asn Asp Ile Asn Val Leu
1               5                   10                  15

Asp Arg Ser Pro Val Phe Asp Asp Ile Ile Lys Gly Glu Ala Pro Gln
            20                  25                  30

Val Thr Phe His Val Asn Gly Arg Glu Tyr His Met Ala Tyr Tyr Leu
        35                  40                  45

Thr Asp Gly Ile Tyr Pro Lys Trp Ala Thr Phe Ile Gln Ser Ile Ser
    50                  55                  60

Met Pro Gln Gly Pro Lys Ala Val Leu Phe Ala Gln Gln Gln
65                  70                  75
```

```
<210> SEQ ID NO 107
<211> LENGTH: 363
<212> TYPE: DNA
<213> ORGANISM: Brassica oleracea

<400> SEQUENCE: 107
ggaagcatcg attgtatgca ttgggagtgg aagaattgtc ccaccgcttg gaaagggcaa      60
tatactcggg gtttgggtaa accaacaatt gttttagagg cggttgcttc atatgatctc     120
tggatatggc atgcattttt tggacctcca ggtaccttaa atgatatcaa tgttcttgat     180
cgctcacctg tttttgatga cataataaat ggtcaagctc cgcaagtcac atactctgtc     240
aacggaagag agtatcattt ggcttactat ctaactgatg gtatctatcc gaaatgggca     300
acttttatcc aatcaattcc attaccacaa ggcccaaaag cggttttatt tgctcaacgt     360
caa                                                                   363

<210> SEQ ID NO 108
<211> LENGTH: 121
<212> TYPE: PRT
<213> ORGANISM: Brassica oleracea

<400> SEQUENCE: 108

Gly Ser Ile Asp Cys Met His Trp Glu Trp Lys Asn Cys Pro Thr Ala
  1               5                  10                  15

Trp Lys Gly Gln Tyr Thr Arg Gly Leu Gly Lys Pro Thr Ile Val Leu
             20                  25                  30

Glu Ala Val Ala Ser Tyr Asp Leu Trp Ile Trp His Ala Phe Phe Gly
         35                  40                  45

Pro Pro Gly Thr Leu Asn Asp Ile Asn Val Leu Asp Arg Ser Pro Val
     50                  55                  60

Phe Asp Asp Ile Ile Asn Gly Gln Ala Pro Gln Val Thr Tyr Ser Val
 65                  70                  75                  80

Asn Gly Arg Glu Tyr His Leu Ala Tyr Tyr Leu Thr Asp Gly Ile Tyr
                 85                  90                  95

Pro Lys Trp Ala Thr Phe Ile Gln Ser Ile Pro Leu Pro Gln Gly Pro
            100                 105                 110

Lys Ala Val Leu Phe Ala Gln Arg Gln
        115                 120

<210> SEQ ID NO 109
<211> LENGTH: 363
<212> TYPE: DNA
<213> ORGANISM: Brassica oleracea

<400> SEQUENCE: 109
ggaagcattg attgtatgca ttgggagtgg aagaattgcc cgaccgcatg gaaaggtcaa      60
tatacacgtg gatcaggaaa gccaacaatt gttttagagg ctgtagcttc agcagatctt     120
tggatatggc acgcgttttt cggacctcca ggtacattaa cgatatcaa tgttcttgat      180 cgatcaccag tttttgatga tatattacaa ggtcgagctc caaaggttaa ttacattatc     240
aacgaacacg agtaccattt gggttactat ctcacagatg gtatttatcc aaaatgggct     300
acttttgtcc aatctattcc acttcctcaa agtccgaaag caaccttatt cgctacgcat     360
caa                                                                   363

<210> SEQ ID NO 110
<211> LENGTH: 121
<212> TYPE: PRT
<213> ORGANISM: Brassica oleracea
```

<400> SEQUENCE: 110

| Gly | Ser | Ile | Asp | Cys | Met | His | Trp | Glu | Trp | Lys | Asn | Cys | Pro | Thr | Ala |
|---|---|---|---|---|---|---|---|---|---|---|---|---|---|---|---|
| 1 | | | | 5 | | | | | 10 | | | | | 15 | |

| Trp | Lys | Gly | Gln | Tyr | Thr | Arg | Gly | Ser | Gly | Lys | Pro | Thr | Ile | Val | Leu |
|---|---|---|---|---|---|---|---|---|---|---|---|---|---|---|---|
| | | | 20 | | | | | 25 | | | | | 30 | | |

| Glu | Ala | Val | Ala | Ser | Ala | Asp | Leu | Trp | Ile | Trp | His | Ala | Phe | Phe | Gly |
|---|---|---|---|---|---|---|---|---|---|---|---|---|---|---|---|
| | | | 35 | | | | | 40 | | | | | 45 | | |

| Pro | Pro | Gly | Thr | Leu | Asn | Asp | Ile | Asn | Val | Leu | Asp | Arg | Ser | Pro | Val |
|---|---|---|---|---|---|---|---|---|---|---|---|---|---|---|---|
| | 50 | | | | | 55 | | | | | 60 | | | | |

| Phe | Asp | Asp | Ile | Leu | Gln | Gly | Arg | Ala | Pro | Lys | Val | Asn | Tyr | Ile | Ile |
|---|---|---|---|---|---|---|---|---|---|---|---|---|---|---|---|
| 65 | | | | | 70 | | | | | 75 | | | | | 80 |

| Asn | Glu | His | Glu | Tyr | His | Leu | Gly | Tyr | Tyr | Leu | Thr | Asp | Gly | Ile | Tyr |
|---|---|---|---|---|---|---|---|---|---|---|---|---|---|---|---|
| | | | | 85 | | | | | 90 | | | | | 95 | |

| Pro | Lys | Trp | Ala | Thr | Phe | Val | Gln | Ser | Ile | Pro | Leu | Pro | Gln | Ser | Pro |
|---|---|---|---|---|---|---|---|---|---|---|---|---|---|---|---|
| | | | | 100 | | | | | 105 | | | | | 110 | |

| Lys | Ala | Thr | Leu | Phe | Ala | Thr | His | Gln |
|---|---|---|---|---|---|---|---|---|
| | | | 115 | | | | | 120 |

<210> SEQ ID NO 111
<211> LENGTH: 363
<212> TYPE: DNA
<213> ORGANISM: Brassica oleracea

<400> SEQUENCE: 111

```
gggagcattg actgtatgca ttgggaatgg aaaaattgcc cgagcgcttg gaaaggacag      60
tacacacgtg gatcaggaaa actgacaatt gtcttagagg ctgtggcttc gcaagacctt     120
tggatatggc acgcttttt tggtcctcca ggtaccttaa cgatattaa tgtcctcgaa      180
cggggtcctg ttttgacga cattatagaa ggtcgagctc ccagggtaag gtacatggtc     240
aacggacaca tgtataagtt ggcgtactac ctcactgacg gtatatatcc aaaatggtca    300
acatttatcc aatctatcac actccctcaa tgtcctaaac aagagttatt tgccaaagtt    360
caa                                                                   363
```

<210> SEQ ID NO 112
<211> LENGTH: 121
<212> TYPE: PRT
<213> ORGANISM: Brassica oleracea

<400> SEQUENCE: 112

| Gly | Ser | Ile | Asp | Cys | Met | His | Trp | Glu | Trp | Lys | Asn | Cys | Pro | Ser | Ala |
|---|---|---|---|---|---|---|---|---|---|---|---|---|---|---|---|
| 1 | | | | 5 | | | | | 10 | | | | | 15 | |

| Trp | Lys | Gly | Gln | Tyr | Thr | Arg | Gly | Ser | Gly | Lys | Leu | Thr | Ile | Val | Leu |
|---|---|---|---|---|---|---|---|---|---|---|---|---|---|---|---|
| | | | 20 | | | | | 25 | | | | | 30 | | |

| Glu | Ala | Val | Ala | Ser | Gln | Asp | Leu | Trp | Ile | Trp | His | Ala | Phe | Phe | Gly |
|---|---|---|---|---|---|---|---|---|---|---|---|---|---|---|---|
| | | | 35 | | | | | 40 | | | | | 45 | | |

| Pro | Pro | Gly | Thr | Leu | Asn | Asp | Ile | Asn | Val | Leu | Glu | Arg | Gly | Pro | Val |
|---|---|---|---|---|---|---|---|---|---|---|---|---|---|---|---|
| | 50 | | | | | 55 | | | | | 60 | | | | |

| Phe | Asp | Asp | Ile | Ile | Glu | Gly | Arg | Ala | Pro | Arg | Val | Arg | Tyr | Met | Val |
|---|---|---|---|---|---|---|---|---|---|---|---|---|---|---|---|
| 65 | | | | | 70 | | | | | 75 | | | | | 80 |

| Asn | Gly | His | Met | Tyr | Lys | Leu | Ala | Tyr | Tyr | Leu | Thr | Asp | Gly | Ile | Tyr |
|---|---|---|---|---|---|---|---|---|---|---|---|---|---|---|---|
| | | | | 85 | | | | | 90 | | | | | 95 | |

| Pro | Lys | Trp | Ser | Thr | Phe | Ile | Gln | Ser | Ile | Thr | Leu | Pro | Gln | Cys | Pro |
|---|---|---|---|---|---|---|---|---|---|---|---|---|---|---|---|
| | | | | 100 | | | | | 105 | | | | | 110 | |

| Lys | Gln | Glu | Leu | Phe | Ala | Lys | Val | Gln |
|---|---|---|---|---|---|---|---|---|
| | | | 115 | | | | | 120 |

<210> SEQ ID NO 113
<211> LENGTH: 363
<212> TYPE: DNA
<213> ORGANISM: Brassica oleracea

<400> SEQUENCE: 113
ggaagcatcg actgtatgca ttgggagtgg aaaaattgcc caaccgcctg gaaaggacag      60
tacacacgtg gatcaggaaa gccaacaatt gtcttggagg ctgtagcttc agaagatctt     120
tggatatgac acgcttttt tggtcctcca ggtaccttaa cgatattaa cgtcctcgat      180 cggtctcctg tttttgatga catttacaa ggtcgagctc caagggtaca atatgtggtc     240
aacgggcacc agtatgattt ggcatactac ctcacagacg gcatatatcc aaaatggtca     300
acatttatcc aatctatctc aaaccctcaa cgtcctgaag cagagttatt tgctaaagtt     360
caa                                                                    363

<210> SEQ ID NO 114
<211> LENGTH: 42
<212> TYPE: PRT
<213> ORGANISM: Brassica oleracea

<400> SEQUENCE: 114

Gly Ser Ile Asp Cys Met His Trp Glu Trp Lys Asn Cys Pro Thr Ala
1               5                   10                  15

Trp Lys Gly Gln Tyr Thr Arg Gly Ser Gly Lys Pro Thr Ile Val Leu
            20                  25                  30

Glu Ala Val Ala Ser Glu Asp Leu Trp Ile
        35                  40

<210> SEQ ID NO 115
<211> LENGTH: 78
<212> TYPE: PRT
<213> ORGANISM: Brassica oleracea

<400> SEQUENCE: 115

His Ala Phe Phe Gly Pro Pro Gly Thr Leu Asn Asp Ile Asn Val Leu
1               5                   10                  15

Asp Arg Ser Pro Val Phe Asp Asp Ile Leu Gln Gly Arg Ala Pro Arg
            20                  25                  30

Val Gln Tyr Val Val Asn Gly His Gln Tyr Asp Leu Ala Tyr Tyr Leu
        35                  40                  45

Thr Asp Gly Ile Tyr Pro Lys Trp Ser Thr Phe Ile Gln Ser Ile Ser
    50                  55                  60

Asn Pro Gln Arg Pro Glu Ala Glu Leu Phe Ala Lys Val Gln
65                  70                  75

<210> SEQ ID NO 116
<211> LENGTH: 363
<212> TYPE: DNA
<213> ORGANISM: Brassica oleracea

<400> SEQUENCE: 116
ggctcgatcg actgtatgca ttgggagtgg aaaaactgcc caacggcttg gaaaggccag      60
tacacacgtg gttcagggaa gccgacaatt gtcttagaag ctgtggcatc acaggatctt     120
tggatatggc acgcattttt tggattacca ggttaactca atgatatcaa tgttcttgat     180
cggtcaccag tttttgatga catttacaa ggtcgagcac caaaagttaa gttcaaggtc     240
aacaaccaca catatcgtat ggcatactac cttaatgacg gaatctatcc aaactgagca     300

```
acatttatcc aatccatccg acttcctcaa ggtcctaaag cagagctatt tgccgaacgt       360
caa                                                                    363
```

<210> SEQ ID NO 117
<211> LENGTH: 51
<212> TYPE: PRT
<213> ORGANISM: Brassica oleracea

<400> SEQUENCE: 117

```
Gly Ser Ile Asp Cys Met His Trp Glu Trp Lys Asn Cys Pro Thr Ala
  1               5                  10                  15

Trp Lys Gly Gln Tyr Thr Arg Gly Ser Gly Lys Pro Thr Ile Val Leu
                 20                  25                  30

Glu Ala Val Ala Ser Gln Asp Leu Trp Ile Trp His Ala Phe Phe Gly
         35                  40                  45

Leu Pro Gly
     50
```

<210> SEQ ID NO 118
<211> LENGTH: 46
<212> TYPE: PRT
<213> ORGANISM: Brassica oleracea

<400> SEQUENCE: 118

```
Leu Asn Asp Ile Asn Val Leu Asp Arg Ser Pro Val Phe Asp Asp Ile
  1               5                  10                  15

Leu Gln Gly Arg Ala Pro Lys Val Lys Phe Lys Val Asn Asn His Thr
                 20                  25                  30

Tyr Arg Met Ala Tyr Tyr Leu Asn Asp Gly Ile Tyr Pro Asn
         35                  40                  45
```

<210> SEQ ID NO 119
<211> LENGTH: 22
<212> TYPE: PRT
<213> ORGANISM: Brassica oleracea

<400> SEQUENCE: 119

```
Ala Thr Phe Ile Gln Ser Ile Arg Leu Pro Gln Gly Pro Lys Ala Glu
  1               5                  10                  15

Leu Phe Ala Glu Arg Gln
                 20
```

<210> SEQ ID NO 120
<211> LENGTH: 339
<212> TYPE: DNA
<213> ORGANISM: Brassica oleracea

<400> SEQUENCE: 120

```
ctgatcagct cgtggttaaa cacgagcaaa gatccagttg ttagcaccga gcaaaagtca       60
ggcgctttct ggacaagaat agcagcctac tttgctgcaa gtcatcaaga tggtggctcc      120
gaatagagag gggctagtca ttgcaagcac cgttggcaga agatcaatga tctcgtttgc      180
aaattctgtg gagcctatga agctgcaagg agagagaaga catcaggtca aaacgaaaac      240
aatgtgctca aacttgctca tcaaatattt ttcaacaacc ataagaagaa attcctcctt      300
gaacacgcgt ggaaggaact gaggcacgac cagaagtgg                             339
```

<210> SEQ ID NO 121
<211> LENGTH: 41
<212> TYPE: PRT

<213> ORGANISM: Brassica oleracea

<400> SEQUENCE: 121

Leu Ile Ser Ser Trp Leu Asn Thr Ser Lys Asp Pro Val Val Ser Thr
1               5                   10                  15

Glu Gln Lys Ser Gly Ala Phe Trp Thr Arg Ile Ala Ala Tyr Phe Ala
            20                  25                  30

Ala Ser His Gln Asp Gly Gly Ser Glu
        35                  40

<210> SEQ ID NO 122
<211> LENGTH: 71
<212> TYPE: PRT
<213> ORGANISM: Brassica oleracea

<400> SEQUENCE: 122

Arg Gly Ala Ser His Cys Lys His Arg Trp Gln Lys Ile Asn Asp Leu
1               5                   10                  15

Val Cys Lys Phe Cys Gly Ala Tyr Glu Ala Ala Arg Arg Glu Lys Thr
            20                  25                  30

Ser Gly Gln Asn Glu Asn Asn Val Leu Lys Leu Ala His Gln Ile Phe
        35                  40                  45

Phe Asn Asn His Lys Lys Lys Phe Leu Leu Glu His Ala Trp Lys Glu
    50                  55                  60

Leu Arg His Asp Gln Lys Trp
65                  70

<210> SEQ ID NO 123
<211> LENGTH: 339
<212> TYPE: DNA
<213> ORGANISM: Brassica oleracea

<400> SEQUENCE: 123
ctcatcagct cgtggttaaa cacgagcaaa gatgcagtag tagggaatga gcaaggttt      60 aatacattct ggacaagaat tgctgcgtac taatgttaa gtcctcaggc tgcgggcagc    120
gagaagagag agccacgtca ctgtaagaat cgttggcaga gatcaatga tctggtttgt    180 aaattttgtg gagcatttga agctgcgacc agagagaaaa caagtggtca aaacgagaat    240
gatgttctca actagcccca ccacatcttc tacactaacc ataaaaaaaa tttcacccct    300
gagcatgctt ggaaagagtt gcgtaatgac cagaagtgg                           339

<210> SEQ ID NO 124
<211> LENGTH: 113
<212> TYPE: PRT
<213> ORGANISM: Brassica oleracea

<400> SEQUENCE: 124

Leu Ile Ser Ser Trp Leu Asn Thr Ser Lys Asp Ala Val Val Gly Asn
1               5                   10                  15

Glu Gln Arg Phe Asn Thr Phe Trp Thr Arg Ile Ala Ala Tyr Tyr Asn
            20                  25                  30

Val Ser Pro Gln Ala Ala Gly Ser Glu Lys Arg Glu Pro Arg His Cys
        35                  40                  45

Lys Asn Arg Trp Gln Lys Ile Asn Asp Leu Val Cys Lys Phe Cys Gly
    50                  55                  60

Ala Phe Glu Ala Ala Thr Arg Glu Lys Thr Ser Gly Gln Asn Glu Asn
65                  70                  75                  80

Asp Val Leu Lys Leu Ala His His Ile Phe Tyr Thr Asn His Lys Lys

```
                85                  90                  95
Asn Phe Thr Leu Glu His Ala Trp Lys Glu Leu Arg Asn Asp Gln Lys
            100                 105                 110

Trp

<210> SEQ ID NO 125
<211> LENGTH: 339
<212> TYPE: DNA
<213> ORGANISM: Brassica oleracea

<400> SEQUENCE: 125
ctgatcagtg cttggttgaa caccagcaat gatccaatcg tgagtaatga gcaaaaggct      60
tgctcatttt ggaagcgcat agaggagtgt gtgaatgcaa gccctctgct cgttggctcc     120
gttcctaggg agtggagtca atgtaagcag aggtggggta gggttaatga acaggtttgc     180
aagttcgtgg gatgtcacga agctgctttg aagaagcaag ccagtggaca aactgagaat     240
gatgtcatga aggcggctca tgacatcttc tttaatgact acaatgccaa gttcactctt     300
gaacattgtt ggagggagct tcggtttgat caaaaatgg                            339

<210> SEQ ID NO 126
<211> LENGTH: 113
<212> TYPE: PRT
<213> ORGANISM: Brassica oleracea

<400> SEQUENCE: 126

Leu Ile Ser Ala Trp Leu Asn Thr Ser Asn Asp Pro Ile Val Ser Asn
  1               5                  10                  15

Glu Gln Lys Ala Cys Ser Phe Trp Lys Arg Ile Glu Glu Cys Val Asn
             20                  25                  30

Ala Ser Pro Leu Leu Val Gly Ser Val Pro Arg Glu Trp Ser Gln Cys
         35                  40                  45

Lys Gln Arg Trp Gly Arg Val Asn Glu Gln Val Cys Lys Phe Val Gly
     50                  55                  60

Cys His Glu Ala Ala Leu Lys Lys Gln Ala Ser Gly Gln Thr Glu Asn
 65                  70                  75                  80

Asp Val Met Lys Ala Ala His Asp Ile Phe Phe Asn Asp Tyr Asn Ala
                 85                  90                  95

Lys Phe Thr Leu Glu His Cys Trp Arg Glu Leu Arg Phe Asp Gln Lys
            100                 105                 110

Trp

<210> SEQ ID NO 127
<211> LENGTH: 339
<212> TYPE: DNA
<213> ORGANISM: Brassica oleracea

<400> SEQUENCE: 127
ctcattagcg cctggttaaa caccagcaag acccggtgg tgggcaatga gcagaaagca       60
ggggcgtttt ggagccgcat tgcggcttac ttcgtagcca gtccaacggt ggaaagaggt     120
gcaaagcgtg aggctattca atgtaagcag cgatggcaga agatgaacga tctagtctgt     180
aagttttgtg gatcctatgc ggctgcaact agacagaaga caagtggtca aaatgaggct     240
gacactgtga aactggcaca cgagatcttc tacaacgatc acaagatcaa atttaacctc     300
caccatgctt gggaggagct gaggaatgac cagaaatgg                            339

<210> SEQ ID NO 128
```

```
<211> LENGTH: 113
<212> TYPE: PRT
<213> ORGANISM: Brassica oleracea

<400> SEQUENCE: 128

Leu Ile Ser Ala Trp Leu Asn Thr Ser Lys Asp Pro Val Val Gly Asn
  1               5                  10                  15

Glu Gln Lys Ala Gly Ala Phe Trp Ser Arg Ile Ala Ala Tyr Phe Val
             20                  25                  30

Ala Ser Pro Thr Val Glu Arg Gly Ala Lys Arg Glu Ala Ile Gln Cys
         35                  40                  45

Lys Gln Arg Trp Gln Lys Met Asn Asp Leu Val Cys Lys Phe Cys Gly
     50                  55                  60

Ser Tyr Ala Ala Thr Arg Gln Lys Thr Ser Gly Gln Asn Glu Ala
 65                  70                  75                  80

Asp Thr Val Lys Leu Ala His Glu Ile Phe Tyr Asn Asp His Lys Ile
                 85                  90                  95

Lys Phe Asn Leu His His Ala Trp Glu Glu Leu Arg Asn Asp Gln Lys
            100                 105                 110

Trp

<210> SEQ ID NO 129
<211> LENGTH: 339
<212> TYPE: DNA
<213> ORGANISM: Brassica oleracea

<400> SEQUENCE: 129
ctcatcagct cctggctcaa cacaagcaag gatccagtag tgggaaatga gcaacggtct      60
ggggcattct ggataggat cgccgcttac tttgcggcaa gtcccaaggt tgcagccact      120
gaacaccgag aatcaactca ttgcaagcag cgttggcaca agatcaatga tcaagtcaac      180
aagttttgtg gggcttttcga agcagcaacc agagagaaga caagtgggca aaatgagaat      240
gatgttctca acagagctca tgaaatcttc ttcaccaacc accgaaaaaa aattattctt      300
gagcacgctt ggaaggagct tcggaatgat caaaaatgg                             339

<210> SEQ ID NO 130
<211> LENGTH: 113
<212> TYPE: PRT
<213> ORGANISM: Brassica oleracea

<400> SEQUENCE: 130

Leu Ile Ser Ser Trp Leu Asn Thr Ser Lys Asp Pro Val Val Gly Asn
  1               5                  10                  15

Glu Gln Arg Ser Gly Ala Phe Trp Asn Arg Ile Ala Ala Tyr Phe Ala
             20                  25                  30

Ala Ser Pro Lys Val Ala Ala Thr Glu His Arg Glu Ser Thr His Cys
         35                  40                  45

Lys Gln Arg Trp His Lys Ile Asn Asp Gln Val Asn Lys Phe Cys Gly
     50                  55                  60

Ala Phe Glu Ala Ala Thr Arg Glu Lys Thr Ser Gly Gln Asn Glu Asn
 65                  70                  75                  80

Asp Val Leu Asn Arg Ala His Glu Ile Phe Phe Thr Asn His Arg Lys
                 85                  90                  95

Lys Ile Ile Leu Glu His Ala Trp Lys Glu Leu Arg Asn Asp Gln Lys
            100                 105                 110

Trp
```

<210> SEQ ID NO 131
<211> LENGTH: 339
<212> TYPE: DNA
<213> ORGANISM: Brassica oleracea

<400> SEQUENCE: 131

```
ctgattgggg cttggcttaa cacaagcaaa gacgctgtgg tgagcaatga gcagaaagct    60
gacgctttct ggaagagaat cgttgattac tacaatgcaa ccctctctt ggttgggaca    120
gcacctaggg agctcggtca gtgcaagcag cggtgggcga ggattaacga gggcgtctgt    180
aagttcgttg gctgctacga cgcggctctg aggtgccaga gtagtggtca aaacgaggat    240
gacgtgatga agctgccctt ggacttctac tacaacgacc actccatcaa gttcaacctc    300
gaacatgctt ggagggagct ccggcatgac agtaaatgg                           339
```

<210> SEQ ID NO 132
<211> LENGTH: 113
<212> TYPE: PRT
<213> ORGANISM: Brassica oleracea

<400> SEQUENCE: 132

```
Leu Ile Gly Ala Trp Leu Asn Thr Ser Lys Asp Ala Val Val Ser Asn
  1               5                  10                  15
Glu Gln Lys Ala Asp Ala Phe Trp Lys Arg Ile Val Asp Tyr Tyr Asn
             20                  25                  30
Ala Ser Pro Leu Leu Val Gly Thr Ala Pro Arg Glu Leu Gly Gln Cys
         35                  40                  45
Lys Gln Arg Trp Ala Arg Ile Asn Glu Gly Val Cys Lys Phe Val Gly
     50                  55                  60
Cys Tyr Asp Ala Ala Leu Arg Cys Gln Ser Ser Gly Gln Asn Glu Asp
 65                  70                  75                  80
Asp Val Met Lys Ala Ala Leu Asp Phe Tyr Tyr Asn Asp His Ser Ile
                 85                  90                  95
Lys Phe Asn Leu Glu His Ala Trp Arg Glu Leu Arg His Asp Ser Lys
            100                 105                 110
Trp
```

<210> SEQ ID NO 133
<211> LENGTH: 342
<212> TYPE: DNA
<213> ORGANISM: Brassica oleracea

<400> SEQUENCE: 133

```
ctaatcagtg cctggttaaa cacatctaag gatgctgtta ttggaaatga acaaagtca     60
gggaccttct gaaaacgagt agaagaatac tacgcagcaa gtcctcatgc tagagagggt    120
ggtgaaaaca gagagcatat ccattgtaag cagaggtggc acaaaatcaa tgatctgacg    180
aacaagttct gtggcgcatt cggtgctgca gagagacaaa atagcagcgg tcagaatgac    240
aatgacgttc taaaggtggc tcatgacatc ttctactctg atcacaacat gaagtttatc    300
cttgagcatg cgtggtgtct gttgaggtat gaacagaaat gg                       342
```

<210> SEQ ID NO 134
<211> LENGTH: 113
<212> TYPE: PRT
<213> ORGANISM: Brassica oleracea

<400> SEQUENCE: 134

```
Leu Ile Ser Ala Trp Leu Asn Thr Ser Lys Asp Pro Val Val Gly Asn
```

```
                1               5              10              15
Glu Gln Lys Ala Asn Ala Phe Trp Gln Arg Ile Ala Tyr Phe Ala
                  20              25              30

Ala Ser Pro Lys Leu Ala Gly Leu Gln Lys Arg Asp Arg Thr Cys Cys
         35              40              45

Lys Gln Arg Trp Ala Lys Ile Asn Glu Ala Val Ser Arg Phe Val Gly
     50              55              60

Cys Tyr Val Ala Ala Thr Lys Gln Arg Ser Ser Gly Gln Asn Glu Asp
 65              70              75              80

Asp Val Leu Lys Ile Ala His Gln Ile Phe Tyr Asn Asp Tyr Lys Val
             85              90              95

Lys Phe Thr Met Glu His Ala Trp Leu Glu Leu Arg His Asp Gln Lys
             100             105             110

Trp

<210> SEQ ID NO 135
<211> LENGTH: 342
<212> TYPE: DNA
<213> ORGANISM: Brassica oleracea

<400> SEQUENCE: 135
ctaatcagtg cctggttaaa cacatctaag gatgctgtta ttggaaatga acaaaagtca      60
gggaccttct gaaaacgagt agaagaatac tacgcagcaa gtcctcatgc tagagagggt     120
ggtgaaaaca gagagcatat ccattgtaag cagaggtggc acaaaatcaa tgatctgacg     180
aacaagttct gtggcgcatt cggtgctgca gagagacaaa atagcagcgg tcagaatgac     240
aatgacgttc taaaggtggc tcatgacatc ttctactctg atcacaacat gaagtttatc     300
cttgagcatg cgtggtgtct gttgaggtat gaacagaaat gg                       342

<210> SEQ ID NO 136
<211> LENGTH: 23
<212> TYPE: PRT
<213> ORGANISM: Brassica oleracea

<400> SEQUENCE: 136

Leu Ile Ser Ala Trp Leu Asn Thr Ser Lys Asp Ala Val Ile Gly Asn
 1               5              10              15

Glu Gln Lys Ser Gly Thr Phe
             20

<210> SEQ ID NO 137
<211> LENGTH: 90
<212> TYPE: PRT
<213> ORGANISM: Brassica oleracea

<400> SEQUENCE: 137

Lys Arg Val Glu Glu Tyr Tyr Ala Ala Ser Pro His Ala Arg Glu Gly
 1               5              10              15

Gly Glu Asn Arg Glu His Ile His Cys Lys Gln Arg Trp His Lys Ile
             20              25              30

Asn Asp Leu Thr Asn Lys Phe Cys Gly Ala Phe Gly Ala Ala Glu Arg
         35              40              45

Gln Asn Ser Ser Gly Gln Asn Asp Asn Asp Val Leu Lys Val Ala His
     50              55              60

Asp Ile Phe Tyr Ser Asp His Asn Met Lys Phe Ile Leu Glu His Ala
 65              70              75              80

Trp Cys Leu Leu Arg Tyr Glu Gln Lys Trp
             85              90
```

<210> SEQ ID NO 138
<211> LENGTH: 339
<212> TYPE: DNA
<213> ORGANISM: Brassica oleracea

<400> SEQUENCE: 138
cttattggtg cgtggcttaa caccagtaag gaccctgtgg tgagcactga gcaaaaagct      60
gatgctttct ggaaccgtat tgtagactac tacaacgcaa gccctcacct ggttgggact     120
ataccgagaa agcttcgtcc ttgcaagcag aggtgggctc ggattaacga gcaagtatcc     180
aagtttgctg gttgccatga tggggctctg agggagcaga ggagtgggca aaatgatgat     240
gatgtcatga aagctgcatt agacattttc ttcaataata acggctacaa gttcactctg     300
gatcactgct ggagggagct caggcacgac cagaaatgg                            339

<210> SEQ ID NO 139
<211> LENGTH: 113
<212> TYPE: PRT
<213> ORGANISM: Brassica oleracea

<400> SEQUENCE: 139

Leu Ile Gly Ala Trp Leu Asn Thr Ser Lys Asp Pro Val Val Ser Thr
 1               5                  10                  15

Glu Gln Lys Ala Asp Ala Phe Trp Asn Arg Ile Val Asp Tyr Tyr Asn
            20                  25                  30

Ala Ser Pro His Leu Val Gly Thr Ile Pro Arg Lys Leu Arg Pro Cys
        35                  40                  45

Lys Gln Arg Trp Ala Arg Ile Asn Glu Gln Val Ser Lys Phe Ala Gly
    50                  55                  60

Cys His Asp Gly Ala Leu Arg Glu Gln Arg Ser Gly Gln Asn Asp Asp
65                  70                  75                  80

Asp Val Met Lys Ala Ala Leu Asp Ile Phe Phe Asn Asn Asn Gly Tyr
                85                  90                  95

Lys Phe Thr Leu Asp His Cys Trp Arg Glu Leu Arg His Asp Gln Lys
            100                 105                 110

Trp

<210> SEQ ID NO 140
<211> LENGTH: 339
<212> TYPE: DNA
<213> ORGANISM: Brassica oleracea

<400> SEQUENCE: 140
ctcatcagtg cctggttgaa caccagtaag gatcccatag ttagtaacca gcagaagtta      60 gggtctttt ggaaaagaat agaggattac tttaattcaa gcgctcagct cactggcttt     120
gctcccagag agtggagtca gtgtaagcag aggtggggaa gggttaatga gcaggtgtgt     180
aagtttgttg gaagctatga ggcggctttg aaggagcaag ctagtggcca aaatgagaac     240
gatgtcatga agtctgctca tgacatcttt tttgacgact accaggcgaa gttcacactt     300
gaacacgcgt ggagggagct gaggtttgat caaaagtgg                            339

<210> SEQ ID NO 141
<211> LENGTH: 113
<212> TYPE: PRT
<213> ORGANISM: Brassica oleracea

<400> SEQUENCE: 141

Leu Ile Ser Ala Trp Leu Asn Thr Ser Lys Asp Pro Ile Val Ser Asn
1               5                   10                  15

Gln Gln Lys Leu Gly Ser Phe Trp Lys Arg Ile Glu Asp Tyr Phe Asn
            20                  25                  30

Ser Ser Ala Gln Leu Thr Gly Phe Ala Pro Arg Glu Trp Ser Gln Cys
        35                  40                  45

Lys Gln Arg Trp Gly Arg Val Asn Glu Gln Val Cys Lys Phe Val Gly
    50                  55                  60

Ser Tyr Glu Ala Ala Leu Lys Glu Gln Ala Ser Gly Gln Asn Glu Asn
65                  70                  75                  80

Asp Val Met Lys Ser Ala His Asp Ile Phe Phe Asp Tyr Gln Ala
                85                  90                  95

Lys Phe Thr Leu Glu His Ala Trp Arg Glu Leu Arg Phe Asp Gln Lys
            100                 105                 110

Trp

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 142
tgtgcatgac acaccagtg                                            19

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 143
cagtgaaacc cccattgtga c                                         21

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 144
tatgctgaca tggatctc                                             18

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 145
ctcttrtaga gagcctatag                                           20

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Primer

```
<400> SEQUENCE: 146
acgtgggcga ttgcgtctg                                                19

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 147
tctgcctcaa gcctctagtc                                               20

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 148
cttcgtttca gctgatgtg                                                19

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 149
atgtggcgtc tgggaaacag tg                                            22
```

We claim:

1. A method of modifying a nucleic acid in a plant cell comprising transforming said plant cell with an isolated nucleic acid comprising a transposable element, wherein the transposable element comprises the nucleic acid sequence of SEQ ID NO:1, SEQ ID NO:2, SEQ ID NO:3, or SEQ ID NO:4, wherein the plant cell comprises a transposase that transposes the transposable element, wherein said transposase comprises the amino acid sequence of SEQ ID NO:7.

2. The method of claim 1, wherein an isolated nucleic acid encoding a functional transposase is inserted into an expression vector, and wherein expression of said functional transposase from said expression vector in the plant cell results in increased transposition of the transposable element as compared to a wild type variety of the plant cell.

3. A method of producing a transgenic plant cell comprising:
   i) transforming a plant cell genome with an isolated nucleic acid comprising a transposable element that is actively transposed in said plant cell genome, wherein the transposable element comprises the nucleic acid sequence of SEQ ID NO:1, SEQ ID NO:2, SEQ ID NO:3, or SEQ ID NO:4, wherein the plant cell comprises a functional transposase that transposes the transposable element, wherein said transposase comprises the amino acid sequence of SEQ ID NO:7; and
   ii) generating said transgenic plant cell comprising said transposable element in the genome of said transgenic plant cell.

4. The method of claim 3, wherein an isolated nucleic acid encoding a functional transposase is inserted into an expression vector, and wherein expression of said functional transposase from said expression vector in the plant cell results in increased transposition of the transposable element as compared to a wild type variety of the plant cell.

5. A method of producing a transgenic plant comprising producing transformed transgenic cells of claim 3, and generating said transgenic plant from said transformed transgenic cells.

6. The method of claim 5, wherein said transgenic plant is a monocot.

7. The method of claim 5, wherein said transgenic plant is a dicot.

8. The method of claim 5, wherein said transgenic plant produces transgenic seeds.

* * * * *